(12) United States Patent
Flasinski et al.

(10) Patent No.: US 12,060,564 B2
(45) Date of Patent: Aug. 13, 2024

(54) PLANT REGULATORY ELEMENTS AND USES THEREOF

(71) Applicant: Monsanto Technology LLC, St. Louis, MO (US)

(72) Inventors: Stanislaw Flasinski, Ballwin, MO (US); Barrett C. Foat, St. Louis, MO (US); Mohammed Oufattole, Wildwood, MO (US); Randall W. Shultz, St. Louis, MO (US); Xiaoping Wei, St. Louis, MO (US); Wei Wu, Chesterfield, MO (US); Shiaw-Pyng Yang, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 488 days.

(21) Appl. No.: 17/229,604

(22) Filed: Apr. 13, 2021

(65) Prior Publication Data

US 2021/0310015 A1    Oct. 7, 2021

Related U.S. Application Data

(62) Division of application No. 16/549,573, filed on Aug. 23, 2019, now Pat. No. 11,046,966, which is a division of application No. 15/802,843, filed on Nov. 3, 2017, now Pat. No. 10,550,401, which is a division of application No. 14/117,342, filed as application No. PCT/US2012/037561 on May 11, 2012, now Pat. No. 9,845,477.

(60) Provisional application No. 61/485,876, filed on May 13, 2011.

(51) Int. Cl.
C12N 15/82    (2006.01)

(52) U.S. Cl.
CPC ................. *C12N 15/8216* (2013.01)

(58) Field of Classification Search
None
See application file for complete search history.

(56) References Cited

U.S. PATENT DOCUMENTS

| | | | |
|---|---|---|---|
| 5,489,520 A | 2/1996 | Adams et al. | |
| 5,500,365 A | 3/1996 | Fischhoff et al. | |
| 6,462,258 B1 | 10/2002 | Fincher et al. | |
| 6,642,438 B1 | 11/2003 | Clendennen et al. | |
| 6,660,911 B2 * | 12/2003 | Fincher et al. | C12N 15/8221 800/278 |
| 9,845,477 B2 | 12/2017 | Flasinski et al. | |
| 10,550,401 B2 | 2/2020 | Flasinski et al. | |
| 11,046,966 B2 | 6/2021 | Flasinski et al. | |
| 11,180,768 B2 | 11/2021 | Flasinski et al. | |
| 2003/0182690 A1 | 9/2003 | Clendennen et al. | |
| 2004/0055039 A1 | 3/2004 | Hiroshi et al. | |
| 2007/0006335 A1 | 1/2007 | Cook et al. | |
| 2007/0204367 A1 * | 8/2007 | Flasinski et al. | C12N 15/8216 536/23.6 |
| 2008/0000405 A1 | 1/2008 | Wu et al. | |
| 2010/0058495 A1 | 3/2010 | Abbitt | |
| 2012/0084885 A1 | 4/2012 | Alexandrov et al. | |
| 2020/0056195 A1 | 2/2020 | Flasinski et al. | |
| 2022/0090108 A1 | 3/2022 | Flasinski et al. | |

FOREIGN PATENT DOCUMENTS

| | | |
|---|---|---|
| CN | 101880657 | 11/2010 |
| CN | 101952435 | 1/2011 |
| CN | 102016049 | 4/2011 |
| JP | 2001-346580 A | 12/2001 |
| WO | 2000037662 | 6/2000 |
| WO | WO 01/44457 | 6/2001 |
| WO | WO 01/44457 A2 * | 6/2001 |
| WO | WO 2005/098007 | 10/2005 |
| WO | WO 2006/039449 | 4/2006 |

OTHER PUBLICATIONS

Saha et al. (2007) In Silico Biol 7(1):7-19.*
Rose (2008) Curr Top Microbial Immunol, 326:277-90.*
Potenza et al. (2004) In Vitro Cell Dev Biol Plant 40:1-22.*
Dolferus et al. (1994) Plant Physiol 105:1075-87.*
Donald & Cashmore (1990) EMBO J 9:1717-26.*
Liu et al. (2013) Nat Rev Genet 14:781-93, 782.*
Cho & Cosgrove (2002) Plant Cell 14:3237-53.*
Wang & Oard (2003) Plant Cell Rep 22:129-34.*
Kim et al. (1994) Plant Mol Biol 24:105-17.*
Joung & Kama (2006) Plant Cell Rep 25:1081-88.*
Rose, Intron-mediated regulation of gene expression, Current Topics in Microbiology and Immunology, 326:277-290, 2008.
GenBank Accession No. XM_008459007, dated Jun. 7, 2016.
Odell et al., Identification of DNA sequences required for activity of the cauliflower mosaic virus 35S promoter, Nature 313:810-12, 1985.
Callis et al., "Introns increase gene expression in cultured maize cells," *Genes Dev.* 1:1183-1200, 1987.
Chee et al., "Expression of a bean storage protein 'phaseolin minigene' in foreign plant tissues," *Gene* 41:47-57, 1986.
Cho et al., *Plant Cell* 14:3237-53 (2002).
Christiansen et al., "Maize polyubiquitin genes: structure, thermal perturbation of expression and transcript splicing, and promoter activity following transfer to protoplasts by electroporation," *Plant Mol. Biol.* 18:675-689, 1992.
Clancy et al., "Splicing of the maize Sh1 first intron is essential for enhancement of gene expression, and a T-rich motif increases expression without affecting splicing," *Plant Physiol.* 130(2):918-929, 2002.
Dean et al., "Sequences downstream of translation start regulate quantitative expression of two petunia rbcS genes," *Plant Cell* 1(2):201-208, 1989.

(Continued)

*Primary Examiner* — Russell T Boggs
(74) *Attorney, Agent, or Firm* — Dentons US LLP; Judith Koehler

(57) ABSTRACT

The invention provides DNA molecules and constructs, including their nucleotide sequences, useful for modulating gene expression in plants and plant cells. Transgenic plants, plant cells, plant parts, seeds, and commodity products comprising the DNA molecules operably linked to heterologous transcribable polynucleotides are also provided, as are methods of their use.

19 Claims, 6 Drawing Sheets

Specification includes a Sequence Listing.

(56) References Cited

OTHER PUBLICATIONS

Dolferus et al., *Plant Physiol.* 105:1075-87 (1994).
Donald & Cashmore, EMBO J. 9:1717-26 (1990).
International Preliminary Report on Patentability regarding PCT Application No. PCT/US2012/037561, dated Nov. 19, 2013.
International Search Report regarding PCT Application No. PCT/US2012/037561, dated Sep. 12, 2012.
Jeon et al., "Tissue-preferential expression of a rice alpha-tubulin gene, OsTubA1, mediated by the first intron," *Plant Physiol.* 123(3):1005-1014, 2000.
Kim et al., Plant Mol. Biol. 24:105-17 (1994).
Kuhlemeier et al., "Upstream sequences determine the difference in transcript abundance of pea rbcS genes," *Mol. Gen. Genet.* 212:405-411, 1988.
Lasserre et al., "Differential activation of two ACC oxidase gene promoters from melon during plant development and in response to pathogen attack," *Mol. Gen. Genet.* 256(3):211-222, 1997.
Leon et al., "Transient gene expression in protoplasts of *Phaseolus vulgaris* isolated from a cell suspension culture," *Plant Physiol.* 95(3):968-972, 1991.
Li et al., Advanced genetic tools for plant biotechnology, *Nat Rev Genet* 14:781-93 (2013).
Loganantharaj, *Int. J. Bioinf. Res. Appl.* 2:36-51 (2006).
Mascarenhas et al., "Intron-mediated enhancement of heterologous gene expression in maize," *Plant Mol. Biol.* 15(6):913-920, 1990.
Mcelroy et al., "Isolation of an efficient actin promoter for use in rice transformation," *Plant Cell* 2(2):163-171, 1990.
Norris et al., "The intron of *Arabidopsis thaliana* polyubiquitin genes is conserved in location and is a quantitative determinant of chimeric gene expression," *Plant Mol. Biol.* 21(5):895-906, 1993.
Piechulla et al., Plant Mol. Biol. 38:655-62 (1998).
Potenza et al., *In Vitro Cell Dev. Biol. Plant* 40:1-22 (2004).
Rose et al., "Introns act post-transcriptionally to increase expression of the *Arabidopsis thaliana* tryptophan pathway gene PAT1," *Plant J.* 11(3):455-464, 1997.
Rose et al., "Intron-mediated enhancement of gene expression independent of unique intron sequences and splicing," *Plant Physiol.* 122(2):535-542, 2000.
Saha et al., *In Silico. Biol.* 7(1):7-19 (2007).
Sherf et al., "Dual-luciferase reporter assay: an advanced co-reporter technology integrating firefly and Renilla luciferase assays," *Promega Notes Magazine* No. 57, p. 2, 1996.
Sinibaldi et al., "Intron splicing and intron-mediated enhanced expression in monocots," *Prog. Nucleic Acid Res. Mol. Biol.* (42):229-257, 1992.
Vancanneyt et al., "Construction of an intron-containing marker gene: splicing of the intron in transgenic plants and its use in monitoring early events in Agrobacterium-mediated plant transformation," *Mol. Gen. Genet.* 220(2):245-250, 1990.
Vasil et al., "Increased gene expression by the first intron of maize shrunken-1 locus in grass species," *Plant Physiol.* 91(4):1575-1579, 1989.
Welsch et al., Planta 216:523-34 (2003).

Xu et al., "Rice triosephosphate isomerase gene 5' sequence directs β-glucuronidase activity in transgenic tobacco but requires an intron for expression in rice," *Plant Physiol.* 106(2):459-467, 1994.
Yamagata et al., "TGTCACA motif is a novel cis-regulatory enhancer element involved in fruit-specific expression of the cucumisin gene," *J. Biol. Chem.* 227(13):11582-11590, 2002.
GenBank Accession No. HN314561, dated Nov. 24, 2010.
GenBank Accession No. JG468661, dated Mar. 16, 2011.
GenBank Accession No. HN298588, dated Nov. 24, 2010.
GenBank Accession No. JG469358, dated Mar. 16, 2011.
GenBank Accession No. HN327993, dated Nov. 24, 2010.
GenBank Accession No. JG467489, dated Mar. 16, 2011.
GenBank Accession No. HN319913, dated Nov. 24, 2010.
GenBank Accession No. JG480182, dated Mar. 16, 2011.
Office Action regarding Chilean Application No. 201601540, dated Jun. 14, 2017.
GenBank Accession No. LN713263, dated Mar. 5, 2015.
Office Action regarding Eurasian Application No. 201690416, dated Jul. 28, 2017.
GenBank Accession No. HN320890, dated Nov. 23, 2010.
USPTO Written Description Guidelines. (2008).
Wang et al., (2003) Plant Cell Rep 22:129-34.
Joung & Karna (2006) Plant Cell Rep 25:1081-88.
Hondred et al., "Use of Ubiquitin Fusions to Augment Protein Expression in Transgenic Plants," Plant Physiology 119:713-723, 1999.
Yuebing et al., "UBI1 intron-mediated enhancement of the expression of Bt cry1 ah gene in transgenic maize (*Zea mays* L.)," Chinese Science Bulletin 53(20):3185-3180, 2008.
Clepet et al., "Analysis of expressed sequence tags generated from full-length enriched cDNA libraries of melon" BMC Genomics (2011), 12:252.
China Office Action and Search Report regarding China Application No. 201710186179.8, dated Nov. 7, 2019, 13 pages.
Australia Office Action regarding Australia Application No. 2019246918, dated Jan. 15, 2020, 7 pages.
GenBank Accession No. AM740200, Sep. 27, 2007.
GenBank Accession No. HN296636, Nov. 23, 2010.
Gonzalez-Ibeas et al., "Melogen: an EST database for melon functional genomics", BMC Genomics (2007), 8:306.
Gonzalez et al., "Genome-wide BAC-end sequencing of Cucumis melo using two BAC libraries", BMC Genomics (2010), 11:618.
GenBank Accesion No. HN305077, dated Nov. 23, 2010.
GenBank Accession No. JG553522, dated Jun. 13, 2011.
U.S. Appl. No. 17/488,189, filed Sep. 28, 2021, Flasinski et al.
GenBank Accession No. LN713260, dated Mar. 5, 2015.
European Search Report and Written Opinion regarding European App. No. 22199610.1, dated Feb. 23, 2023.
GenBank Accession No. LN713255, dated Mar. 5, 2015.
GenBank Accession No. HN316421, dated Nov. 24, 2010.
Eurasian Office Action regarding Eurasian App. No. 202092524, dated Sep. 13, 2023.

* cited by examiner

| | | |
|---|---|---|
| P-CUCme.Ubq1-1:1:15 | (SEQ ID NO: 2) | ATCTGAAAGGAACACCTAGCAAGGGGCTACTCTACAAGCATACTAAGTCTACAAAGCTAG |
| P-CUCme.Ubq1-1:1:16 | (SEQ ID NO: 6) | ------------------------------------------------------------ |
| P-CUCme.Ubq1-1:1:17 | (SEQ ID NO: 8) | ------------------------------------------------------------ |
| P-CUCme.Ubq1-1:1:18 | (SEQ ID NO: 10) | ------------------------------------------------------------ |
| P-CUCme.Ubq1-1:1:19 | (SEQ ID NO: 12) | ------------------------------------------------------------ |
| | | |
| P-CUCme.Ubq1-1:1:15 | (SEQ ID NO: 2) | AGTTGTATGGTTATGCAGAAGACCTGGACAAAAGAAGATCACTCGCTGCTTTTACTTTTA |
| P-CUCme.Ubq1-1:1:16 | (SEQ ID NO: 6) | ------------------------------------------------------------ |
| P-CUCme.Ubq1-1:1:17 | (SEQ ID NO: 8) | ------------------------------------------------------------ |
| P-CUCme.Ubq1-1:1:18 | (SEQ ID NO: 10) | ------------------------------------------------------------ |
| P-CUCme.Ubq1-1:1:19 | (SEQ ID NO: 12) | ------------------------------------------------------------ |
| | | |
| P-CUCme.Ubq1-1:1:15 | (SEQ ID NO: 2) | TCCTAAGGAGGAAATGTGATTTTATGGAAGTTTAACCTATAGCCTGTAGTGGCACTATTCA |
| P-CUCme.Ubq1-1:1:16 | (SEQ ID NO: 6) | ------------------------------------------------------------ |
| P-CUCme.Ubq1-1:1:17 | (SEQ ID NO: 8) | ------------------------------------------------------------ |
| P-CUCme.Ubq1-1:1:18 | (SEQ ID NO: 10) | ------------------------------------------------------------ |
| P-CUCme.Ubq1-1:1:19 | (SEQ ID NO: 12) | ------------------------------------------------------------ |
| | | |
| P-CUCme.Ubq1-1:1:15 | (SEQ ID NO: 2) | CAACAAAAGTAAAGTTTATAGCCATGACTGAAGTTGTTAAAGAAGTCGTCTGGCTAAAAG |
| P-CUCme.Ubq1-1:1:16 | (SEQ ID NO: 6) | ------------------------------------------------------------ |
| P-CUCme.Ubq1-1:1:17 | (SEQ ID NO: 8) | ------------------------------------------------------------ |
| P-CUCme.Ubq1-1:1:18 | (SEQ ID NO: 10) | ------------------------------------------------------------ |
| P-CUCme.Ubq1-1:1:19 | (SEQ ID NO: 12) | ------------------------------------------------------------ |
| | | |
| P-CUCme.Ubq1-1:1:15 | (SEQ ID NO: 2) | GACTACTTGAAGAACTTGGCTTCTTTTAACAGTCAGTAAACATCATGTGTGATAGTTAAA |
| P-CUCme.Ubq1-1:1:16 | (SEQ ID NO: 6) | ------------------------------------------------------------ |
| P-CUCme.Ubq1-1:1:17 | (SEQ ID NO: 8) | ------------------------------------------------------------ |
| P-CUCme.Ubq1-1:1:18 | (SEQ ID NO: 10) | ------------------------------------------------------------ |
| P-CUCme.Ubq1-1:1:19 | (SEQ ID NO: 12) | ------------------------------------------------------------ |
| | | |
| P-CUCme.Ubq1-1:1:15 | (SEQ ID NO: 2) | GTGCAATACACTTGTCTAAAAATCTGCAATATCACGAAAGAACTAAGCATATTGATGTGA |
| P-CUCme.Ubq1-1:1:16 | (SEQ ID NO: 6) | ------------------------------------------------------------ |
| P-CUCme.Ubq1-1:1:17 | (SEQ ID NO: 8) | ------------------------------------------------------------ |
| P-CUCme.Ubq1-1:1:18 | (SEQ ID NO: 10) | ------------------------------------------------------------ |
| P-CUCme.Ubq1-1:1:19 | (SEQ ID NO: 12) | ------------------------------------------------------------ |

FIG. 1a

```
P-CUCme.Ubq1-1:1:15  (SEQ ID NO: 2)   AGCTATATGTCATTAGAGAAGTCATAGCAAAGAGAAAAGTAACAGTATCAAAGGTTCAGA
P-CUCme.Ubq1-1:1:16  (SEQ ID NO: 6)   ------------------------------------------------------------
P-CUCme.Ubq1-1:1:17  (SEQ ID NO: 8)   ------------------------------------------------------------
P-CUCme.Ubq1-1:1:18  (SEQ ID NO: 10)  ------------------------------------------------------------
P-CUCme.Ubq1-1:1:19  (SEQ ID NO: 12)  ------------------------------------------------------------

P-CUCme.Ubq1-1:1:15  (SEQ ID NO: 2)   CAAAAGAAAATGCAGCAGATATGTTGACTAAAATAGTTACTAATGCTAAACTCGAGCACT
P-CUCme.Ubq1-1:1:16  (SEQ ID NO: 6)   ------------------------------------------------------------
P-CUCme.Ubq1-1:1:17  (SEQ ID NO: 8)   ------------------------------------------------------------
P-CUCme.Ubq1-1:1:18  (SEQ ID NO: 10)  ------------------------------------------------------------
P-CUCme.Ubq1-1:1:19  (SEQ ID NO: 12)  ------------------------------------------------------------

P-CUCme.Ubq1-1:1:15  (SEQ ID NO: 2)   GCCTACAGTTGCTCAAGGTAATAGACTACTTAAAAGAATAGAATCAGAAGAAATAGTCAT
P-CUCme.Ubq1-1:1:16  (SEQ ID NO: 6)   ------------------------------------------------------------
P-CUCme.Ubq1-1:1:17  (SEQ ID NO: 8)   ------------------------------------------------------------
P-CUCme.Ubq1-1:1:18  (SEQ ID NO: 10)  ------------------------------------------------------------
P-CUCme.Ubq1-1:1:19  (SEQ ID NO: 12)  ------------------------------------------------------------

P-CUCme.Ubq1-1:1:15  (SEQ ID NO: 2)   TGGTAGCAATAAAATTCAAGGTGGAGGATTGTTAAAAGAAGAGTGAATTTTATTACTTA
P-CUCme.Ubq1-1:1:16  (SEQ ID NO: 6)   ------------------------------------------------------------
P-CUCme.Ubq1-1:1:17  (SEQ ID NO: 8)   ------------------------------------------------------------
P-CUCme.Ubq1-1:1:18  (SEQ ID NO: 10)  ------------------------------------------------------------
P-CUCme.Ubq1-1:1:19  (SEQ ID NO: 12)  ------------------------------------------------------------

P-CUCme.Ubq1-1:1:15  (SEQ ID NO: 2)   AAGAAAAATCTCGGTGAAACTCGAAAGATCTCGATTCGAAACTCTATTGCTTAAGAACCTG
P-CUCme.Ubq1-1:1:16  (SEQ ID NO: 6)   -TCGGTGAAACTCGAAAGATCTCGATTCGAAACTCTATTGCTTAAGAACCTG
P-CUCme.Ubq1-1:1:17  (SEQ ID NO: 8)   ------------------------------------------------------------
P-CUCme.Ubq1-1:1:18  (SEQ ID NO: 10)  ------------------------------------------------------------
P-CUCme.Ubq1-1:1:19  (SEQ ID NO: 12)  ------------------------------------------------------------

P-CUCme.Ubq1-1:1:15  (SEQ ID NO: 2)   GTGAAGCTCGAGAGATCTTGATACAATCCCAGTGCCCTAACTCTTCAACAAGCTAAGCAA
P-CUCme.Ubq1-1:1:16  (SEQ ID NO: 6)   GTGAAGCTCGAGAGATCTTGATACAATCCCAGTGCCCTAACTCTTCAACAAGCTAAGCAA
P-CUCme.Ubq1-1:1:17  (SEQ ID NO: 8)   ------------------------------------------------------------
P-CUCme.Ubq1-1:1:18  (SEQ ID NO: 10)  ------------------------------------------------------------
P-CUCme.Ubq1-1:1:19  (SEQ ID NO: 12)  ------------------------------------------------------------
```

FIG. 1b

```
P-CUCme.Ubq1-1:1:15  (SEQ ID NO: 2)   GTTGTACTGTGGGGCTCAATCTCGGTTCAATCTCGACGCACCTGATGCTTTGTTCCCTGT
P-CUCme.Ubq1-1:1:16  (SEQ ID NO: 6)   GTTGTACTGTGGGGCTCAATCTCGGTTCAATCTCGACGCACCTGATGCTTTGTTCCCTGT
P-CUCme.Ubq1-1:1:17  (SEQ ID NO: 8)   ------------------------------------------------------------
P-CUCme.Ubq1-1:1:18  (SEQ ID NO: 10)  ------------------------------------------------------------
P-CUCme.Ubq1-1:1:19  (SEQ ID NO: 12)  ------------------------------------------------------------

P-CUCme.Ubq1-1:1:15  (SEQ ID NO: 2)   CTACTCGATGAAGAAGCAATTACTTCTCAGGACAACTCGGTACCCCTAAATACAGATTTT
P-CUCme.Ubq1-1:1:16  (SEQ ID NO: 6)   CTACTCGATGAAGAAGCAATTACTTCTCAGGACAACTCGGTACCCCTAAATACAGATTTT
P-CUCme.Ubq1-1:1:17  (SEQ ID NO: 8)   ------------------------------------------------------------
P-CUCme.Ubq1-1:1:18  (SEQ ID NO: 10)  ------------------------------------------------------------
P-CUCme.Ubq1-1:1:19  (SEQ ID NO: 12)  ------------------------------------------------------------

P-CUCme.Ubq1-1:1:15  (SEQ ID NO: 2)   GAGCTTCGTGATCCTACAACTGAAATCAAATAGAAAAACTAATAAGTTAGTTAGAGTTTG
P-CUCme.Ubq1-1:1:16  (SEQ ID NO: 6)   GAGCTTCGTGATCCTACAACTGAAATCAAATAGAAAAACTAATAAGTTAGTTAGAGTTTG
P-CUCme.Ubq1-1:1:17  (SEQ ID NO: 8)   ------------------------------------------------------------
P-CUCme.Ubq1-1:1:18  (SEQ ID NO: 10)  ------------------------------------------------------------
P-CUCme.Ubq1-1:1:19  (SEQ ID NO: 12)  ------------------------------------------------------------

P-CUCme.Ubq1-1:1:15  (SEQ ID NO: 2)   TTATATTTACTGCCATTAAATAACTCTGTAATGTAAATAATAAACCATTTAACTCAATAT
P-CUCme.Ubq1-1:1:16  (SEQ ID NO: 6)   TTATATTTACTGCCATTAAATAACTCTGTAATGTAAATAATAAACCATTTAACTCAATAT
P-CUCme.Ubq1-1:1:17  (SEQ ID NO: 8)   ------------------------------------------------------------
P-CUCme.Ubq1-1:1:18  (SEQ ID NO: 10)  ------------------------------------------------------------
P-CUCme.Ubq1-1:1:19  (SEQ ID NO: 12)  ------------------------------------------------------------

P-CUCme.Ubq1-1:1:15  (SEQ ID NO: 2)   GAAATATAGAATGAGAAAAAGAAAAAGAAAAAGAAAAAGTTAAAGAGAGAGGAAGAAACTCAT
P-CUCme.Ubq1-1:1:16  (SEQ ID NO: 6)   GAAATATAGAATGAGAAAAAGAAAAAGAAAAAGAAAAAGTTAAAGAGAGAGGAAGAAACTCAT
P-CUCme.Ubq1-1:1:17  (SEQ ID NO: 8)   ------------------------------------------------------------
P-CUCme.Ubq1-1:1:18  (SEQ ID NO: 10)  ------------------------------------------------------------
P-CUCme.Ubq1-1:1:19  (SEQ ID NO: 12)  ------------------------------------------------------------

P-CUCme.Ubq1-1:1:15  (SEQ ID NO: 2)   TTTCAAATTCTCTATACTTGTTTGATCCTTGAATAAGTTGAATAAAGCTCTATGGCGGC
P-CUCme.Ubq1-1:1:16  (SEQ ID NO: 6)   TTTCAAATTCTCTATACTTGTTTGATCCTTGAATAAGTTGAATAAAGCTCTATGGCGGC
P-CUCme.Ubq1-1:1:17  (SEQ ID NO: 8)   ------------------------------------------------------------
P-CUCme.Ubq1-1:1:18  (SEQ ID NO: 10)  ------------------------------------------------------------
P-CUCme.Ubq1-1:1:19  (SEQ ID NO: 12)  ------------------------------------------------------------
```

FIG. 1c

| | | |
|---|---|---|
| P-CUCme.Ubq1-1:1:1:15 | (SEQ ID NO: 2) | TTCAAAGTGGATGTAGGCACTATTAGTCGAACCACAATAAATTGTTATGTTCTTTTGCT |
| P-CUCme.Ubq1-1:1:1:16 | (SEQ ID NO: 6) | TTCAAAGTGGATGTAGGCACTATTAGTCGAACCACAATAAATTGTTATGTTCTTTTGCT |
| P-CUCme.Ubq1-1:1:1:17 | (SEQ ID NO: 8) | ---------------AGTCGAACCACCAATAAATTGTTATGTTCTTTGCT |
| P-CUCme.Ubq1-1:1:1:18 | (SEQ ID NO: 10) | ------------------------------------------------------------ |
| P-CUCme.Ubq1-1:1:1:19 | (SEQ ID NO: 12) | ------------------------------------------------------------ |
| | | |
| P-CUCme.Ubq1-1:1:1:15 | (SEQ ID NO: 2) | ATTCCTTGTAATCTCCATAAATATTTCTTACTAAGCTCTAGAAATCTGCTTGTCAAGAG |
| P-CUCme.Ubq1-1:1:1:16 | (SEQ ID NO: 6) | ATTCCTTGTAATCTCCATAAATATTTCTTACTAAGCTCTAGAAATCTGCTTGTCAAGAG |
| P-CUCme.Ubq1-1:1:1:17 | (SEQ ID NO: 8) | ATTCCTTGTAATCTCCATAAATATTTCTTACTAAGCTCTAGAAATCTGCTTGTCAAGAG |
| P-CUCme.Ubq1-1:1:1:18 | (SEQ ID NO: 10) | ------------------------------------------------------------ |
| P-CUCme.Ubq1-1:1:1:19 | (SEQ ID NO: 12) | ------------------------------------------------------------ |
| | | |
| P-CUCme.Ubq1-1:1:1:15 | (SEQ ID NO: 2) | ATTAGGTATCATTTATGCCTTTTATATTTCCTTCGGTTGCATATCTTGAGCTAGTTAAG |
| P-CUCme.Ubq1-1:1:1:16 | (SEQ ID NO: 6) | ATTAGGTATCATTTATGCCTTTTATATTTCCTTCGGTTGCATATCTTGAGCTAGTTAAG |
| P-CUCme.Ubq1-1:1:1:17 | (SEQ ID NO: 8) | ATTAGGTATCATTTATGCCTTTTATATTTCCTTCGGTTGCATATCTTGAGCTAGTTAAG |
| P-CUCme.Ubq1-1:1:1:18 | (SEQ ID NO: 10) | ------------------------------------------------------------ |
| P-CUCme.Ubq1-1:1:1:19 | (SEQ ID NO: 12) | ------------------------------------------------------------ |
| | | |
| P-CUCme.Ubq1-1:1:1:15 | (SEQ ID NO: 2) | ATCGAGAGGTTACTGTTGTTGAAACCGAGATTAGTATCTTTGGATTAACACGTGCCTACC |
| P-CUCme.Ubq1-1:1:1:16 | (SEQ ID NO: 6) | ATCGAGAGGTTACTGTTGTTGAAACCGAGATTAGTATCTTTGGATTAACACGTGCCTACC |
| P-CUCme.Ubq1-1:1:1:17 | (SEQ ID NO: 8) | ATCGAGAGGTTACTGTTGTTGAAACCGAGATTAGTATCTTTGGATTAACACGTGCCTACC |
| P-CUCme.Ubq1-1:1:1:18 | (SEQ ID NO: 10) | ------------------------------------------------------------ |
| P-CUCme.Ubq1-1:1:1:19 | (SEQ ID NO: 12) | ------------------------------------------------------------ |
| | | |
| P-CUCme.Ubq1-1:1:1:15 | (SEQ ID NO: 2) | AAAATTTGAAATTTGTATTTACCCCATTCATTGGATAATAAGCAATTCTTATAGTGTTA |
| P-CUCme.Ubq1-1:1:1:16 | (SEQ ID NO: 6) | AAAATTTGAAATTTGTATTTACCCCATTCATTGGATAATAAGCAATTCTTATAGTGTTA |
| P-CUCme.Ubq1-1:1:1:17 | (SEQ ID NO: 8) | AAAATTTGAAATTTGTATTTACCCCATTCATTGGATAATAAGCAATTCTTATAGTGTTA |
| P-CUCme.Ubq1-1:1:1:18 | (SEQ ID NO: 10) | ------------------------------------------------------------ |
| P-CUCme.Ubq1-1:1:1:19 | (SEQ ID NO: 12) | ------------------------------------------------------------ |
| | | |
| P-CUCme.Ubq1-1:1:1:15 | (SEQ ID NO: 2) | TCAATTAAACTCCTATAAAGTGTAATAATTGAATCCATGAACTATTTCATATGTAATCT |
| P-CUCme.Ubq1-1:1:1:16 | (SEQ ID NO: 6) | TCAATTAAACTCCTATAAAGTGTAATAATTGAATCCATGAACTATTTCATATGTAATCT |
| P-CUCme.Ubq1-1:1:1:17 | (SEQ ID NO: 8) | TCAATTAAACTCCTATAAAGTGTAATAATTGAATCCATGAACTATTTCATATGTAATCT |
| P-CUCme.Ubq1-1:1:1:18 | (SEQ ID NO: 10) | ------------------------------------------------------------ |
| P-CUCme.Ubq1-1:1:1:19 | (SEQ ID NO: 12) | ------------------------------------------------------------ |

FIG. 1d

```
P-CUCme.Ubq1-1:1:15 (SEQ ID NO: 2)   TAATAAAAATGAATTAGAAGTTTAATTAAAATAATATATTTTGTATGCTATTTTTCAAAG
P-CUCme.Ubq1-1:1:16 (SEQ ID NO: 6)   TAATAAAAATGAATTAGAAGTTTAATTAAAATAATATATTTTGTATGCTATTTTTCAAAG
P-CUCme.Ubq1-1:1:17 (SEQ ID NO: 8)   TAATAAAAATGAATTAGAAGTTTAATTAAAATAATATATTTTGTATGCTATTTTTCAAAG
P-CUCme.Ubq1-1:1:18 (SEQ ID NO: 10)  ------------------------------------------------------------
P-CUCme.Ubq1-1:1:19 (SEQ ID NO: 12)  ------------------------------------------------------------

P-CUCme.Ubq1-1:1:15 (SEQ ID NO: 2)   TTTGAAGAAGTGTTAATTGATACACATACAAAAAATCTAGGTTTTACATGAAAAACTAT
P-CUCme.Ubq1-1:1:16 (SEQ ID NO: 6)   TTTGAAGAAGTGTTAATTGATACACATACAAAAAATCTAGGTTTTACATGAAAAACTAT
P-CUCme.Ubq1-1:1:17 (SEQ ID NO: 8)   TTTGAAGAAGTGTTAATTGATACACATACAAAAAATCTAGGTTTTACATGAAAAACTAT
P-CUCme.Ubq1-1:1:18 (SEQ ID NO: 10)  ------------------------------------------------------------
P-CUCme.Ubq1-1:1:19 (SEQ ID NO: 12)  ------------------------------------------------------------

P-CUCme.Ubq1-1:1:15 (SEQ ID NO: 2)   GGAAGTGAAAGATAGCATCTAATATTTTATGACACAAAATGCAAACTAATATATAAAGGA
P-CUCme.Ubq1-1:1:16 (SEQ ID NO: 6)   GGAAGTGAAAGATAGCATCTAATATTTTATGACACAAAATGCAAACTAATATATAAAGGA
P-CUCme.Ubq1-1:1:17 (SEQ ID NO: 8)   GGAAGTGAAAGATAGCATCTAATATTTTATGACACAAAATGCAAACTAATATATAAAGGA
P-CUCme.Ubq1-1:1:18 (SEQ ID NO: 10)  ---------------------TGACACAAAATGCAAACTAATATATAAAGGA
P-CUCme.Ubq1-1:1:19 (SEQ ID NO: 12)  ------------------------------------------------------------

P-CUCme.Ubq1-1:1:15 (SEQ ID NO: 2)   TTTAATTAATTTTATAGGTTTCAAATTGTTAGACTTGTCAAATACAAAATTTATTGA
P-CUCme.Ubq1-1:1:16 (SEQ ID NO: 6)   TTTAATTAATTTTATAGGTTTCAAATTGTTAGACTTGTCAAATACAAAATTTATTGA
P-CUCme.Ubq1-1:1:17 (SEQ ID NO: 8)   TTTAATTAATTTTATAGGTTTCAAATTGTTAGACTTGTCAAATACAAAATTTATTGA
P-CUCme.Ubq1-1:1:18 (SEQ ID NO: 10)  TTTAATTAATTTTATAGGTTTCAAATTGTTAGACTTGTCAAATACAAAATTTATTGA
P-CUCme.Ubq1-1:1:19 (SEQ ID NO: 12)  ------------------------------------------------------------

P-CUCme.Ubq1-1:1:15 (SEQ ID NO: 2)   ACCAAATACATACACAAACATCAAAATTAAGAACAGAAAATCTAAATTCAAATGAAATTTAT
P-CUCme.Ubq1-1:1:16 (SEQ ID NO: 6)   ACCAAATACATACACAAACATCAAAATTAAGAACAGAAAATCTAAATTCAAATGAAATTTAT
P-CUCme.Ubq1-1:1:17 (SEQ ID NO: 8)   ACCAAATACATACACAAACATCAAAATTAAGAACAGAAAATCTAAATTCAAATGAAATTTAT
P-CUCme.Ubq1-1:1:18 (SEQ ID NO: 10)  ACCAAATACATACACAAACATCAAAATTAAGAACAGAAAATCTAAATTCAAATGAAATTTAT
P-CUCme.Ubq1-1:1:19 (SEQ ID NO: 12)  ------------------------------------------------------------

P-CUCme.Ubq1-1:1:15 (SEQ ID NO: 2)   TAATAGAAAAATTAGAAAAAAAAGAAAAATAAAAGGAATCGTATTGTTTTTCCTTC
P-CUCme.Ubq1-1:1:16 (SEQ ID NO: 6)   TAATAGAAAAATTAGAAAAAAAAGAAAAATAAAAGGAATCGTATTGTTTTTCCTTC
P-CUCme.Ubq1-1:1:17 (SEQ ID NO: 8)   TAATAGAAAAATTAGAAAAAAAAGAAAAATAAAAGGAATCGTATTGTTTTTCCTTC
P-CUCme.Ubq1-1:1:18 (SEQ ID NO: 10)  TAATAGAAAAATTAGAAAAAAAAGAAAAATAAAAGGAATCGTATTGTTTTTCCTTC
P-CUCme.Ubq1-1:1:19 (SEQ ID NO: 12)  TAATAGAAAAATTAGAAAAAAAAGAAAAATAAAAGGAATCGTATTGTTTTTCCTTC
```

FIG. 1e

```
P-CUCme.Ubq1-1:1:1:15 (SEQ ID NO: 2)   CTTTTTCCCATTGAGAGGTGAATAAAGCTAATTGAGCTGCTCTAACTTCCTAATCTTTA
P-CUCme.Ubq1-1:1:1:16 (SEQ ID NO: 6)   CTTTTTCCCATTGAGAGGTGAATAAAGCTAATTGAGCTGCTCTAACTTCCTAATCTTTA
P-CUCme.Ubq1-1:1:1:17 (SEQ ID NO: 8)   CTTTTTCCCATTGAGAGGTGAATAAAGCTAATTGAGCTGCTCTAACTTCCTAATCTTTA
P-CUCme.Ubq1-1:1:1:18 (SEQ ID NO: 10)  CTTTTTCCCATTGAGAGGTGAATAAAGCTAATTGAGCTGCTCTAACTTCCTAATCTTTA
P-CUCme.Ubq1-1:1:1:19 (SEQ ID NO: 12)  ---------------------------------------------------------

P-CUCme.Ubq1-1:1:1:15 (SEQ ID NO: 2)   TGCTTTCCCATAAAGCTTTCCCAACTGCGCGTAATCGTATAAATGGAAAATTGACCTTT
P-CUCme.Ubq1-1:1:1:16 (SEQ ID NO: 6)   TGCTTTCCCATAAAGCTTTCCCAACTGCGCGTAATCGTATAAATGGAAAATTGACCTTT
P-CUCme.Ubq1-1:1:1:17 (SEQ ID NO: 8)   TGCTTTCCCATAAAGCTTTCCCAACTGCGCGTAATCGTATAAATGGAAAATTGACCTTT
P-CUCme.Ubq1-1:1:1:18 (SEQ ID NO: 10)  TGCTTTCCCATAAAGCTTTCCCAACTGCGCGTAATCGTATAAATGGAAAATTGACCTTT
P-CUCme.Ubq1-1:1:1:19 (SEQ ID NO: 12)  ----------------------TCGTATAAATGGAAAATTGACCTTT

P-CUCme.Ubq1-1:1:1:15 (SEQ ID NO: 2)   CCAACTAGATCTTCCAGAACTAAACAATACGTAACACGCAAGTAATCAAAGACACGTTT
P-CUCme.Ubq1-1:1:1:16 (SEQ ID NO: 6)   CCAACTAGATCTTCCAGAACTAAACAATACGTAACACGCAAGTAATCAAAGACACGTTT
P-CUCme.Ubq1-1:1:1:17 (SEQ ID NO: 8)   CCAACTAGATCTTCCAGAACTAAACAATACGTAACACGCAAGTAATCAAAGACACGTTT
P-CUCme.Ubq1-1:1:1:18 (SEQ ID NO: 10)  CCAACTAGATCTTCCAGAACTAAACAATACGTAACACGCAAGTAATCAAAGACACGTTT
P-CUCme.Ubq1-1:1:1:19 (SEQ ID NO: 12)  CCAACTAGATCTTCCAGAACTAAACAATACGTAACACGCAAGTAATCAAAGACACGTTT

P-CUCme.Ubq1-1:1:1:15 (SEQ ID NO: 2)   CATTTCCTATAGAATATTATAGTTATTCGTGATTAACGGAAGTCGGCAATTTTAGTAT
P-CUCme.Ubq1-1:1:1:16 (SEQ ID NO: 6)   CATTTCCTATAGAATATTATAGTTATTCGTGATTAACGGAAGTCGGCAATTTTAGTAT
P-CUCme.Ubq1-1:1:1:17 (SEQ ID NO: 8)   CATTTCCTATAGAATATTATAGTTATTCGTGATTAACGGAAGTCGGCAATTTTAGTAT
P-CUCme.Ubq1-1:1:1:18 (SEQ ID NO: 10)  CATTTCCTATAGAATATTATAGTTATTCGTGATTAACGGAAGTCGGCAATTTTAGTAT
P-CUCme.Ubq1-1:1:1:19 (SEQ ID NO: 12)  CATTTCCTATAGAATATTATAGTTATTCGTGATTAACGGAAGTCGGCAATTTTAGTAT

P-CUCme.Ubq1-1:1:1:15 (SEQ ID NO: 2)   AAATACGTGAATTCTCGAGCGCTAATTT
P-CUCme.Ubq1-1:1:1:16 (SEQ ID NO: 6)   AAATACGTGAATTCTCGAGCGCTAATTT
P-CUCme.Ubq1-1:1:1:17 (SEQ ID NO: 8)   AAATACGTGAATTCTCGAGCGCTAATTT
P-CUCme.Ubq1-1:1:1:18 (SEQ ID NO: 10)  AAATACGTGAATTCTCGAGCGCTAATTT
P-CUCme.Ubq1-1:1:1:19 (SEQ ID NO: 12)  AAATACGTGAATTCTCGAGCGCTAATTT
```

FIG. 1f

```
                       SEQUENCE LISTING

<160> NUMBER OF SEQ ID NOS: 212

<210> SEQ ID NO 1
<211> LENGTH: 2611
<212> TYPE: DNA
<213> ORGANISM: Cucumis melo

<400> SEQUENCE: 1
atctgaaagg aacacctagc aagggctac  tctacaagca tactaagtct acaaagctag      60
agttgtatgg ttatgcagaa gacctggaca aaagaagatc actcgctgct tttacttta      120 tcctaagagg aaatgtgatt ttatggaagt ttaacctata gcctgtagtg gcactattca     180
caacaaaagt aaagtttata gccatgactg aagttgttaa agaagtcgtc tggctaaaag     240
gactacttga agaacttggc ttcttttaac agtcagtaaa catcatgtgt gatagttaaa     300
gtgcaataca cttgtctaaa aatctgcaat atcacgaaag aactaagcat attgatgtga     360
agctatatgt cattagagaa gtcatagcaa agagaaaagt aacagtatca aaggttcaga     420
caaaagaaaa tgcagcagat atgttgacta aaatagttac taatgctaaa ctcgagcact     480
gcctacagtt gctcaaggta atagactact taaaagaata gaatcagaag aaatagtcat     540
tggtagcaat aaaattcaag gtggaggatt gttaaaaaga agagtgaatt ttattactta     600
aagaaaatct cggtgaaact cgaaagatct cgattcgaaa ctctattgct taagaacctg     660
gtgaagctcg agagatcttg atacaatccc agtgccctaa ctcttcaaca agctaagcaa     720
gttgtactgt ggggctcaat ctcggttcaa tctcgacgca cctgatgctt tgttccctgt     780
```

-continued

```
ctactcgatg aagaagcaat tacttctcag acaactcgg tacccctaaa tacagatttt       840
gagcttcgtg atcctacaac tgaaatcaaa tagaaaaact aataagttag ttagagtttg       900
ttatatttac tgccattaaa taactctgta atgtaaataa taaaccattt aactcaatat       960
gaaatataga atgagaaaaa gaaaagaaa aagttaaaga gagagaggaa gaaaactcat      1020
tttcaaattc tctatacttg tttgatcctt gaataagttg aataaaagct ctatggcggc      1080
ttcaaagtgg atgtaggcac tattagtcga accacaataa atttgttatg ttcttttgct      1140
attccttgta atctccataa atattttctt actaagctct agaaatctgc ttgtcaagag      1200
attaggtatc atttatgcct tttatatttc ctttcggttg catatcttga gctagttaag      1260
atcgagaggt tactgttgtt gaaaccgaga ttagtatctt tggattaaca cgtgcctacc      1320
aaaatttgaa attttgtatt taccccattc attggataat aagcaattct tatagtgtta      1380
tcaattaaac tcctataaag tgtaataatt gaatccatga actattttca tatgtaatct      1440
taataaaatg aatttagaag tttaattaaa ataatatatt ttgtatgcta tttttcaaag      1500
tttgaagaat gtgttaattg atacacatac aaaaaatcta ggttttacat gaaaaactat      1560
ggaagtgaaa gatagcatct aatattttat gacacaaaat gcaaactaat atataaagga      1620
tttaattaat ttttataggt ttcaaatttg ttagacttgt caaatacaaa attttattga      1680
accaaataca tacaaacatc aaaattaaga acagaaaatc taaattcaaa tgaaatttat      1740
taatagaaaa attagaaaaa agaaaaagaa aataaaagga atcgtattgt ttttttcttc      1800 cttttttccca tttgagaggt gaataaagct aattgagctg ctctaacttc ctaatctta      1860 tgctttcccc ataaagcttt cccaactgcg cgtaatcgta taaatggaaa attgacctt      1920 ccaactagat tcttccagaa ctaaacaata cgtaacacgc aagtaatcaa agacacgttt      1980
cattttccta tagaatatta tagttattcg tgattaacgg aagtcggcaa ttttaggtat      2040
aaatacgtga attctcgagc gctaattttc catacagact cgaaatactc taaactttct      2100
catcgcgctt tattcctatt tcgtaattcg ctcttcttca acctctcaag gttttcatct      2160
tttctctatc ttctgttttc agattgcatc ttttccccct cctgttcgat taattgatgt      2220
ttgaattttc gagaaacgat ttgaagtctt tgttgtattt ttcatttctg ttcgttaggt      2280
aggtcgattt ttaatcgtga tgtccgacgt tgttcggatg attcacattt ggttttgtc      2340 atcttcttttc tatgttgtga ttatcatgat ttttatcttt ttttcttctc aagatttgta      2400
atttatcgat tccccatggt tcttggtttt ttatacatgt attgaatctg gttactagaa      2460
ttatgttctt cgacggacgt ctttcagatt taaattgcat tgtaggaaat atgatttgct      2520
atctgagtaa cgttttttcca gagtattctt gattgcgcga tctatcttca attgttaaat      2580
tgtttttgtt taattggggt catgacaggt g                                     2611
```

<210> SEQ ID NO 2  
<211> LENGTH: 2068  
<212> TYPE: DNA  
<213> ORGANISM: Cucumis melo
<400> SEQUENCE: 2

```
atctgaaagg aacacctagc aaggggctac tctacaagca tactaagtct acaaagctag        60
agttgtatgg ttatgcagaa gacctggaca aaagaagatc actcgctgct tttactttta       120
tcctaagagg aaatgtgatt ttatggaagt ttaacctata gcctgtagtg gcactattca       180
caacaaaagt aaagtttata gccatgactg aagttgttaa agaagtcgtc tggctaaaag       240
```

```
gactacttga agaacttggc ttcttttaac agtcagtaaa catcatgtgt gatagttaaa        300
gtgcaataca cttgtctaaa aatctgcaat atcacgaaag aactaagcat attgatgtga        360
agctatatgt cattagagaa gtcatagcaa agagaaaagt aacagtatca aaggttcaga        420
caaaagaaaa tgcagcagat atgttgacta aaatagttac taatgctaaa ctcgagcact        480
gcctacagtt gctcaaggta atagactact aaaagaata gaatcagaag aaatagtcat         540
tggtagcaat aaaattcaag gtggaggatt gttaaaaaga agagtgaatt ttattactta        600
aagaaaatct cggtgaaact cgaaagatct cgattcgaaa ctctattgct taagaacctg       660
gtgaagctcg agagatcttg atacaatccc agtgccctaa ctcttcaaca agctaagcaa       720
gttgtactgt ggggctcaat ctcggttcaa tctcgacgca cctgatgctt tgttccctgt       780
ctactcgatg aagaagcaat tacttctcag gacaactcgg taccccctaaa tacagatttt      840 gagcttcgtg atcctacaac tgaaatcaaa tagaaaaact aataagttag ttagagtttg       900
ttatatttac tgccattaaa taactctgta atgtaaataa taaaccatttt aactcaatat      960 gaaatataga atgagaaaaa gaaaagaaa aagttaaaga gagagaggaa gaaaactcat       1020
tttcaaattc tctatacttg tttgatcctt gaataagttg aataaaagct ctatggcggc      1080
ttcaaagtgg atgtaggcac tattagtcga accacaataa atttgttatg ttctttttgct    1140 attccttgta atctccataa atatttttctt actaagctct agaaatctgc ttgtcaagag     1200
attaggtatc atttatgcct tttatatttc ctttcggttg catatcttga gctagttaag     1260
atcgagaggt tactgttgtt gaaaccgaga ttagtatctt tggattaaca cgtgcctacc      1320
aaaatttgaa attttgtatt taccccattc attggataat aagcaattct tatagtgtta     1380
tcaattaaac tcctataaag tgtaataatt gaatccatga actattttca tatgtaatct     1440
taataaaatg aatttagaag tttaattaaa ataatatatt ttgtatgcta tttttcaaag    1500
tttgaagaat gtgttaattg atacacatac aaaaaatcta ggttttacat gaaaaactat    1560
ggaagtgaaa gatagcatct aatatttat gacacaaaat gcaaactaat atataaagga     1620
tttaattaat ttttataggt ttcaaatttg ttagacttgt caaatacaaa attttattga    1680
accaaataca tacaaacatc aaattaagga acagaaaatc taaattcaaa tgaaatttat    1740
taatagaaaa attagaaaaa agaaaaagaa aataaaagga atcgtattgt tttttccttc    1800 cttttttccca tttgagaggt gaataaagct aattgagctg ctctaacttc ctaatcttta    1860 tgcttttcccc ataaagcttt cccaactgcg cgtaatcgta taaatggaaa attgacctt    1920 ccaactagat tcttccagaa ctaaacaata cgtaacacgc aagtaatcaa agacacgttt    1980
cattttccta tagaatatta tagttattcg tgattaacgg aagtcggcaa ttttaggtat    2040
aaatacgtga attctcgagc gctaattt                                        2068

<210> SEQ ID NO 3
<211> LENGTH: 82
<212> TYPE: DNA
<213> ORGANISM: Cucumis melo

<400> SEQUENCE: 3
tccatacaga ctcgaaatac tctaaacttt ctcatcgcgc tttattccta tttcgtaatt        60
cgctcttctt caacctctca ag                                                82

<210> SEQ ID NO 4
<211> LENGTH: 461
<212> TYPE: DNA
<213> ORGANISM: Cucumis melo
```

<400> SEQUENCE: 4

```
gttttcatct tttctctatc ttctgttttc agattgcatc ttttcccect cctgttcgat    60
taattgatgt ttgaattttc gagaaacgat ttgaagtctt tgttgtattt ttcatttctg   120
ttcgttaggt aggtcgattt ttaatcgtga tgtccgacgt tgttcggatg attcacattt   180
ggttttgtc atcttctttc tatgttgtga ttatcatgat ttttatcttt ttttcttctc   240
aagatttgta atttatcgat tccccatggt tcttggtttt ttatacatgt attgaatctg   300
gttactagaa ttatgttctt cgacggacgt ctttcagatt taaattgcat tgtaggaaat   360
atgatttgct atctgagtaa cgttttttcca gagtattctt gattgcgcga tctatcttca   420
attgttaaat tgttttgtt taattggggt catgacaggt g                        461
```

<210> SEQ ID NO 5
<211> LENGTH: 2002
<212> TYPE: DNA
<213> ORGANISM: Cucumis melo

<400> SEQUENCE: 5

```
tcggtgaaac tcgaaagatc tcgattcgaa actctattgc ttaagaacct ggtgaagctc    60
gagagatctt gatacaatcc cagtgcccta actcttcaac aagctaagca agttgtactg   120
tggggctcaa tctcggttca atctcgacgc acctgatgct tgttccctg tctactcgat    180
gaagaagcaa ttacttctca ggacaactcg gtaccctaa atacagattt tgagcttcgt   240
gatcctacaa ctgaaatcaa atagaaaaac taataagtta gttagagttt gttatattta   300
ctgccattaa ataactctgt aatgtaaata ataaccatt taactcaata tgaaatatag   360
aatgagaaaa agaaaagaa aaagttaaag agagagagga agaaaactca ttttcaaatt   420
ctctatactt gtttgatcct tgaataagtt gaataaaagc tctatggcgg cttcaaagtg   480
gatgtaggca ctattagtcg aaccacaata aatttgttat gttcttttgc tattccttgt   540
aatctccata aatattttct tactaagctc tagaaatctg cttgtcaaga gattaggtat   600
catttatgcc ttttatattt cctttcggtt gcatatcttg agctagttaa gatcgagagg   660
ttactgttgt tgaaaccgag attagtatct ttggattaac acgtgcctac caaaatttga   720
aattttgtat ttaccccatt cattggataa taagcaattc ttatagtgtt atcaattaaa   780
ctcctataaa gtgtaataat tgaatccatg aactattttc atatgtaatc ttaataaaat   840
gaatttagaa gtttaattaa aataatatat tttgtatgct attttcaaa gtttgaagaa   900
tgtgttaatt gatacacata caaaaaatct aggttttaca tgaaaaacta tggaagtgaa   960
agatagcatc taatatttta tgacacaaaa tgcaaactaa tatataaagg atttaattaa  1020
tttttatagg tttcaaattt gttagacttg tcaaatacaa aattttattg aaccaaatac  1080
atacaaacat caaaattaag aacagaaaat ctaaattcaa atgaaattta ttaatagaaa  1140
aattagaaaa aagaaaaaga aaataaaagg aatcgtattg ttttttcctt cctttttccc  1200
atttgagagg tgaataaagc taattgagct gctctaactt cctaatcttt atgctttccc  1260
cataaagctt tcccaactgc gcgtaatcgt ataaatggaa aattgacctt tccaactaga  1320
ttcttccaga actaaacaat acgtaacacg caagtaatca aagacacgtt tcatttttcct 1380
atagaatatt atagttattc gtgattaacg gaagtcggca attttaggta taaatacgtg  1440
aattctcgag cgctaatttt ccatacagac tcgaaatact ctaaactttc tcatcgcgct  1500
ttattcctat ttcgtaattc gctcttcttc aacctctcaa ggttttcatc ttttctctat  1560
```

```
cttctgtttt cagattgcat cttttccccc tcctgttcga ttaattgatg tttgaatttt    1620
cgagaaacga tttgaagtct tgttgtatt tttcatttct gttcgttagg taggtcgatt     1680
tttaatcgtg atgtccgacg ttgttcggat gattcacatt tggttttgt catcttcttt    1740 ctatgttgtg attatcatga tttttatctt tttttcttct caagatttgt aatttatcga   1800
ttccccatgg ttcttggttt tttatacatg tattgaatct ggttactaga attatgttct   1860
tcgacggacg tctttcagat ttaaattgca ttgtaggaaa tatgatttgc tatctgagta   1920 acgttttttcc agagtattct tgattgcgcg atctatcttc aattgttaaa ttgttttttgt 1980 ttaattgggg tcatgacagg tg                                            2002

<210> SEQ ID NO 6
<211> LENGTH: 1459
<212> TYPE: DNA
<213> ORGANISM: Cucumis melo

<400> SEQUENCE: 6
tcggtgaaac tcgaaagatc tcgattcgaa actctattgc ttaagaacct ggtgaagctc      60
gagagatctt gatacaatcc cagtgcccta actcttcaac aagctaagca agttgtactg     120
tggggctcaa tctcggttca atctcgacgc acctgatgct ttgttccctg tctactcgat     180
gaagaagcaa ttacttctca ggacaactcg gtacccctaa atacagattt tgagcttcgt    240
gatcctacaa ctgaaatcaa atagaaaaac taataagtta gttagagttt gttatatttta   300 ctgccattaa ataactctgt aatgtaaata ataaccatt taactcaata tgaaatatag     360
aatgagaaaa agaaaaagaa aaagttaaag agagagagga agaaaactca ttttcaaatt    420
ctctatactt gtttgatcct tgaataagtt gaataaaagc tctatggcgg cttcaaagtg    480
gatgtaggca ctattagtcg aaccacaata aatttgttat gttcttttgc tattccttgt   540
aatctccata atatttctct tactaagctc tagaaatctg cttgtcaaga gattaggtat    600
catttatgcc ttttatattt cctttcggtt gcatatcttg agctagttaa gatcgagagg    660
ttactgttgt tgaaaccgag attagtatct ttggattaac acgtgcctac caaaatttga    720
aattttgtat ttaccccatt cattggataa taagcaattc ttatagtgtt atcaattaaa    780
ctcctataaa gtgtaataat tgaatccatg aactattttc atatgtaatc ttaataaaat   840
gaatttagaa gttaattaa aataatatat tttgtatgct attttttcaaa gtttgaagaa    900 tgtgttaatt gatacacata caaaaaatct aggttttaca tgaaaaacta tggaagtgaa    960
agatagcatc taatatttta tgacacaaaa tgcaaactaa tatataaagg atttaattaa   1020
tttttatagg tttcaaattt gttagacttg tcaaatacaa aattttattg aaccaaatac   1080
atacaaacat caaaattaag aacagaaaat ctaaattcaa atgaaattta ttaatagaaa   1140
aattagaaaa agaaaaaga aataaaagg aatcgtattg ttttttcctt cctttttccc     1200
atttgagagg tgaataaagc taattgagct gctctaactt cctaatcttt atgctttccc   1260
cataaagctt tcccaactgc gcgtaatcgt ataaatggaa aattgacctt tccaactaga   1320
ttcttccaga actaaacaat acgtaacacg caagtaatca aagacacgtt tcattttcct   1380
atagaatatt atagttattc gtgattaacg gaagtcggca attttaggta taaatacgtg   1440
aattctcgag cgctaatttt                                                1459

<210> SEQ ID NO 7
<211> LENGTH: 1507
<212> TYPE: DNA
<213> ORGANISM: Cucumis melo
```

<400> SEQUENCE: 7

```
agtcgaacca caataaattt gttatgttct tttgctattc cttgtaatct ccataaatat    60
tttcttacta agctctagaa atctgcttgt caagagatta ggtatcattt atgcctttta   120
tatttccttt cggttgcata tcttgagcta gttaagatcg agaggttact gttgttgaaa   180
ccgagattag tatctttgga ttaacacgtg cctaccaaaa tttgaaattt tgtatttacc   240
ccattcattg gataataagc aattcttata gtgttatcaa ttaaactcct ataaagtgta   300
ataattgaat ccatgaacta ttttcatatg taatcttaat aaaatgaatt tagaagttta   360
attaaaataa tatattttgt atgctatttt tcaaagtttg aagaatgtgt taattgatac   420
acatacaaaa aatctaggtt ttacatgaaa aactatggaa gtgaaagata gcatctaata   480
tttatgaca caaaatgcaa actaatatat aaaggattta attaattttt ataggtttca   540
aatttgttag acttgtcaaa tacaaaattt tattgaacca aatacataca aacatcaaaa   600
ttaagaacag aaaatctaaa ttcaaatgaa atttattaat agaaaaatta gaaaaaagaa   660
aaagaaaata aaaggaatcg tattgttttt tccttccttt ttcccatttg agaggtgaat   720
aaagctaatt gagctgctct aacttcctaa tctttatgct ttccccataa agctttccca   780
actgcgcgta atcgtataaa tggaaaattg acctttccaa ctagattctt ccagaactaa   840
acaatacgta acacgcaagt aatcaaagac acgtttcatt ttcctataga atattatagt   900
tattcgtgat taacggaagt cggcaatttt aggtataaat acgtgaattc tcgagcgcta   960
attttccata cagactcgaa atactctaaa ctttctcatc gcgctttatt cctatttcgt  1020
aattcgctct tcttcaacct ctcaaggttt tcatcttttc tctatcttct gttttcagat  1080
tgcatctttt ccccctcctg ttcgattaat tgatgtttga attttcgaga aacgatttga  1140
agtctttgtt gtatttttca tttctgttcg ttaggtaggt cgatttttaa tcgtgatgtc  1200
cgacgttgtt cggatgattc acatttggtt tttgtcatct tctttctatg ttgtgattat  1260
catgattttt atcttttttt cttctcaaga tttgtaattt atcgattccc catggttctt  1320
ggttttttat acatgtattg aatctggtta ctagaattat gttcttcgac ggacgtcttt  1380
cagatttaaa ttgcattgta ggaaatatga tttgctatct gagtaacgtt tttccagagt  1440
attcttgatt gcgcgatcta tcttcaattg ttaaattgtt tttgtttaat tggggtcatg  1500
acaggtg                                                            1507
```

<210> SEQ ID NO 8
<211> LENGTH: 964
<212> TYPE: DNA
<213> ORGANISM: Cucumis melo

<400> SEQUENCE: 8

```
agtcgaacca caataaattt gttatgttct tttgctattc cttgtaatct ccataaatat    60
tttcttacta agctctagaa atctgcttgt caagagatta ggtatcattt atgcctttta   120
tatttccttt cggttgcata tcttgagcta gttaagatcg agaggttact gttgttgaaa   180
ccgagattag tatctttgga ttaacacgtg cctaccaaaa tttgaaattt tgtatttacc   240
ccattcattg gataataagc aattcttata gtgttatcaa ttaaactcct ataaagtgta   300
ataattgaat ccatgaacta ttttcatatg taatcttaat aaaatgaatt tagaagttta   360
attaaaataa tatattttgt atgctatttt tcaaagtttg aagaatgtgt taattgatac   420
acatacaaaa aatctaggtt ttacatgaaa aactatggaa gtgaaagata gcatctaata   480
```

```
ttttatgaca caaaatgcaa actaatatat aaaggattta attaattttt ataggtttca      540
aatttgttag acttgtcaaa tacaaaattt tattgaacca atacataca aacatcaaaa       600 ttaagaacag aaaatctaaa ttcaaatgaa atttattaat agaaaaatta gaaaaagaa       660 aaagaaaata aaaggaatcg tattgttttt tccttccttt ttcccatttg agaggtgaat      720
aaagctaatt gagctgctct aacttcctaa tctttatgct ttccccataa agctttccca     780
actgcgcgta atcgtataaa tggaaaattg acctttccaa ctagattctt ccagaactaa     840
acaatacgta acacgcaagt aatcaaagac acgtttcatt ttcctataga atattatagt     900
tattcgtgat aacggaagt cggcaatttt aggtataaat acgtgaattc tcgagcgcta      960
attt                                                                 964

<210> SEQ ID NO 9
<211> LENGTH: 1022
<212> TYPE: DNA
<213> ORGANISM: Cucumis melo

<400> SEQUENCE: 9
tgacacaaaa tgcaaactaa tatataaagg atttaattaa ttttatagg tttcaaattt      60 gttagacttg tcaaatacaa aattttattg aaccaaatac atacaaacat caaaattaag   120
aacagaaaat ctaaattcaa atgaaattta ttaatagaaa aattagaaaa agaaaaga     180 aaataaaagg aatcgtattg ttttttcctt ccttttccc atttgagagg tgaataaagc     240
taattgagct gctctaactt cctaatcttt atgctttccc cataaagctt tcccaactgc    300
gcgtaatcgt ataatggaa aattgacctt tccaactaga ttcttccaga actaaacaat    360
acgtaacacg caagtaatca agacacgtt tcatttttcct atagaatatt tagttattc    420 gtgattaacg gaagtcggca attttaggta taaatacgtg aattctcgag cgctaatttt   480
ccatacagac tcgaaatact ctaaactttc tcatcgcgct ttattcctat ttcgtaattc    540
gctcttcttc aacctctcaa ggttttcatc ttttctctat cttctgtttt cagattgcat    600
ctttcccccc tcctgttcga ttaattgatg tttgaatttt cgagaaacga tttgaagtct    660
ttgttgtatt tttcatttct gttcgttagg taggtcgatt tttaatcgtg atgtccgacg    720
ttgttcggat gattcacatt tggtttttgt catcttcttt ctatgttgtg attatcatga   780
tttttatctt tttttcttct caagattgt aatttatcga ttccccatgg ttcttggttt    840
tttatacatg tattgaatct ggttactaga attatgttct tcgacggacg tctttcagat    900
ttaaattgca ttgtaggaaa tatgatttgc tatctgagta acgttttttcc agagtattct    960 tgattgcgcg atctatcttc aattgttaaa ttgtttttgt ttaattgggg tcatgacagg   1020
tg                                                                  1022

<210> SEQ ID NO 10
<211> LENGTH: 479
<212> TYPE: DNA
<213> ORGANISM: Cucumis melo

<400> SEQUENCE: 10
tgacacaaaa tgcaaactaa tatataaagg atttaattaa ttttatagg tttcaaattt      60 gttagacttg tcaaatacaa aattttattg aaccaaatac atacaaacat caaaattaag   120
aacagaaaat ctaaattcaa atgaaattta ttaatagaaa aattagaaaa agaaaaga     180 aaataaaagg aatcgtattg ttttttcctt ccttttccc atttgagagg tgaataaagc     240
taattgagct gctctaactt cctaatcttt atgctttccc cataaagctt tcccaactgc    300
```

| | |
|---|---|
| gcgtaatcgt ataaatggaa aattgacctt tccaactaga ttcttccaga actaaacaat | 360 |
| acgtaacacg caagtaatca aagacacgtt tcatttccct atagaatatt atagttattc | 420 |
| gtgattaacg gaagtcggca attttaggta taaatacgtg aattctcgag cgctaattt | 479 |

<210> SEQ ID NO 11
<211> LENGTH: 716
<212> TYPE: DNA
<213> ORGANISM: Cucumis melo

<400> SEQUENCE: 11

| | |
|---|---|
| tcgtataaat ggaaaattga cctttccaac tagattcttc cagaactaaa caatacgtaa | 60 |
| cacgcaagta atcaaagaca cgtttcattt tcctatagaa tattatagtt attcgtgatt | 120 |
| aacggaagtc ggcaatttta ggtataaata cgtgaattct cgagcgctaa ttttccatac | 180 |
| agactcgaaa tactctaaac tttctcatcg cgctttattc ctatttcgta attcgctctt | 240 |
| cttcaacctc tcaaggtttt catcttttct ctatcttctg ttttcagatt gcatctttc | 300 |
| cccctcctgt tcgattaatt gatgtttgaa ttttcgagaa acgatttgaa gtctttgttg | 360 |
| tattttcat ttctgttcgt taggtaggtc gattttaat cgtgatgtcc gacgttgttc | 420 |
| ggatgattca catttggttt ttgtcatctt ctttctatgt tgtgattatc atgattttta | 480 |
| tctttttttc ttctcaagat ttgtaattta tcgattcccc atggttcttg gttttttata | 540 |
| catgtattga atctggttac tagaattatg ttcttcgacg gacgtctttc agatttaaat | 600 |
| tgcattgtag gaaatatgat ttgctatctg agtaacgttt ttccagagta ttcttgattg | 660 |
| cgcgatctat cttcaattgt taaattgttt ttgtttaatt ggggtcatga caggtg | 716 |

<210> SEQ ID NO 12
<211> LENGTH: 173
<212> TYPE: DNA
<213> ORGANISM: Cucumis melo

<400> SEQUENCE: 12

| | |
|---|---|
| tcgtataaat ggaaaattga cctttccaac tagattcttc cagaactaaa caatacgtaa | 60 |
| cacgcaagta atcaaagaca cgtttcattt tcctatagaa tattatagtt attcgtgatt | 120 |
| aacggaagtc ggcaatttta ggtataaata cgtgaattct cgagcgctaa ttt | 173 |

<210> SEQ ID NO 13
<211> LENGTH: 2000
<212> TYPE: DNA
<213> ORGANISM: Cucumis melo

<400> SEQUENCE: 13

| | |
|---|---|
| cttattcagc gctttcctgt aaaattaaag acttgatgag ggagaaaaag aaaaccggtt | 60 |
| cgcagcttca agaagacggc ttccgaataa gaatcagata ctcgatgatg gggaaacaat | 120 |
| aacaaagata tcaaaagaaa tcatgaaaca tagcataaga acgaaaaccc agaggtgaag | 180 |
| aacagtgccc aaacgcaact ttacccaaag aacatgtata aacgtcttc cagacgttca | 240 |
| aaataagaaa gtggacaaaa tcaaagctac aaacgatctc caataactag atggaaaaca | 300 |
| ctaattgcac tagagatttt gaatgctttg ttgttgattt ataatcctcg acttccaaga | 360 |
| aaaagtaaca agtagaaatg aacgaatcag atccgcaatc gaagatctga aggcaagata | 420 |
| aggtaaggct aaagaaccat aggaaaacgg taaaaacgtc caaacagtg tgagaaatat | 480 |
| cgcagattca aaggtccgaa ccctaagaac ggtgttatgc agctataaag gtgagaatca | 540 |

```
aaaccctcta tccataacgt ggacggcgcg gttgaatcat tgtcttgttc cttgaaactg      600
aaggtatgcg agacatagaa ttcgatctca ctattatctt ctaatcaacg acgaagtaaa      660
gaagtgaaat ccagaacaaa gaatggagaa ttggaaatga caagaaaaac ggcagaggaa      720
agtggaaaag tgaaagcgga ctcacctaga tcaatgccct tggctggtcg agcttcagga      780
acctgtcgtc ggagagaaag agaagagaa aagagcaaga gagagagaga gagagcacaa       840
ggagaagaga acgaggacaa tggaggcttt tgtttcgata ctccctgatc tggaattcta      900
taataacata actataaact tctctgggtt ggcccatcat cacgtatatt gggcttttag      960
cccaattatt tgttcactgc tcatgggccg tgattttgg gctttcttct gggccttggt      1020
acataacaac ccagtatatg acgtattttc ggtgatagct atttcaaga acaccaactt      1080
ttttgttcaa caatgtggag atcaaataac agtatgtata tatacacaaa catatgctca     1140
tttatgaaaa atagaaagaa aaagaatgtt ggtaatttgt tacaaaatta taatttctct     1200
ctctttgttt gatttcatga acggtgtgtt ctatataaaa caatgaaata acataattat     1260
taaaatgatt cttaaaacat gatgatttca atattcatgg tttacatttg gtgggatgat    1320
tcgtttaatt attattgata atgtatagtt attgtgtgtc ccgttttctt tttctttggt    1380
ggaagaaaag aaaaaagtag gaaggcatgt aatattgcga tccttcacgg acagatcca     1440
ttttccaatg tgatcgagta ctagttaggt ggagagtgga agaatcttcg tgcatgcata    1500
aatcaagtca caacttgcca atttggaaag aatcatgtta tattctacct ttactttcaa   1560
gtagggttaa gtgaattaga ccacaacgaa gcaatcaagt ccaaccaaac tcacttaggt   1620
caagcagttt agtgatatag acaggtcagt ggtcgttttt ttaatactaa gaaatgtcaa   1680
ttctatctag ttgactatta ttcatataga aggagaaaaa tgataactat gattgtccca   1740
caaacaacaa ctaccgatcg atctaaacca acaagtcgat gattggtgcc actttaaatt   1800
taaatctgac gccactcaat tgatgatcac ccctattcaa gcacacaaga acgcatgctc   1860
ttaaaacatt tggtaatatg attggaatta gtacaaaatg tttattcgat ctatacaaac   1920
aactcctttt taacacaaat gttttattgt actttcccgt gaaatggggt tagtaaaact   1980
atggagttaa taaaacataa                                                2000

<210> SEQ ID NO 14
<211> LENGTH: 2000
<212> TYPE: DNA
<213> ORGANISM: Cucumis melo

<400> SEQUENCE: 14
tataacaaaa tatgtgaaat tagccattat gtttgtcctt tcgttcttct tattcacttc       60
gttgcgattt ctttctatcg tctatcgtct ttcttctttt ttctgttgaa atttattttc      120
atcgtttttc ttctttttcc atcgtgaaaa aaatagtcaa atctaaatga tcgtgtataa     180
agaataaacg atcgtgtaga caaatctaaa tggtcgaata ttaagaaaat tgataggaaa     240
atttattcat tagaaaaatt ttagtaagaa aaattagaaa tgaaagggtt gaaccagaaa     300
gaaataaaag taatagacaa atgaaaattt taaataaaaa gaaatttggg atgggtgcat    360
ttactattta gtcttgagtt ttaattcttt tattacttta cataagatgt attaaattaa    420
agaggtaaga tagaattttt ttttaaaaaa aactatcatt agtaaattta acaaaagtga    480
catagcacca ttttcgttaa aagaataatt gttttatgta gtaaaattgg tagaaatatt    540
ttttaagtat agcaaaatat ctttgtcttt ttatatcttt cactgacaga taataataat   600
ttattaatat atcatttata tagtcccatt ttcggtaaat tttaatattt gaacataaaa    660
```

```
cactatttaa aataatgaaa aaaaacttta caaactttt tattttat atatttgtaa     720 atatttctaa aaaattttac atttaaaata atattttcaa ggttaataca gaagaaaaaa     780
aacaaaaaaa gaggaaaagg caatttaaga agaatgacaa gaaaatcggg aggtggtgtg     840
gctaagagga agaagggacc ggttcttcaa gatccaacgc tccacattca atctcacttc     900
cttcttcaat tccgtcttct ccgtttcctc ctttatatgc ttctctcttt ccctcccttt     960
ctttctctcc ttcaatcaat caatcaatca atcaatcaat cctcccattc ccattacatt    1020
gccaaaaggt tctattctca ttctctacat ccatttccct ttctttcctt cttcttcctc    1080
tgtttcttct tcgtttcctt gattcatttc tctttgtacg ttccttcctt ccttctgcat    1140
tttgattatt ttcttttgtt ttacgtccgg aattgcaatg tggtttatct ttatttctgt    1200
ttttggacgt caagatgcct gttgttttta acattttgat ttgattcatc gttcatggcg    1260
taatcatgtc ttttggaatt gtttgaaatc caaggatcac attgatttca ctattgtttc    1320
atttgttctt ttttgttaat tttgtataat gaatcgtata ggggatcatt tttccattgg    1380
ttctcttgaa aatctttaag agttgcatta tgtatactaa gtctctctta tggcgtctgt    1440
ttgagtgaga attgataaaa gatccatggg aggaagaagt tttcttcat gaggcttggt    1500 tttattcagc tgtttcttct cgttgcaatt tgttgaagaa gggacatggg tatcttttac    1560
atcaaagtat aactaactat ataattcaat ttggttgata agtagatac atgtaggagt    1620 caaccgattt gagtgtataa taatgttgtt atgtcccttg caacttaatg tagtgcatat    1680
ttgggagtga ttataaaatt gtataaatca tttatgttt agaatcatct tgaaacacgt    1740
tttttagtat ttaaaaacta atttaatatt tagttttgca cttttaaatg aaattttgt    1800 ttcactaata ttagttttga ttcattaaat gcatgctcca tcgtaatatt aaaagtaact    1860
agtgatttta acatttat aatcacatgt ctgtgatata gtgaagtgta cggctgcctt    1920
gttgagaatt gttacccttt agaagaaaca caggatgtat ttgatgttta acttgcattt    1980
tcttctggca ggcttagaaa                                                2000

<210> SEQ ID NO 15
<211> LENGTH: 1990
<212> TYPE: DNA
<213> ORGANISM: Cucumis melo

<400> SEQUENCE: 15
tatttgtaca atgaaaatat ttatttcttt tctcgattct ttaacaaaag ttcaaaatct     60
tttatcataa atacaaatat ttagtaattt aagtttagac taggtgtatc agatgtgcac    120
caagtgtata ttacgtgcat caagtatata tcaaatgtgt accaaacgta tatcacgtgt    180
atcaagtgtg tatcaagtgt ctatttgaag tcaagtgcat taagaatata tcacatgtgt    240
accaaatata tcaaaataaa tactgattga gcatcaagta tgtctattag tagtgtatca    300
agtgtattaa ttaagtttgt agcaaaggtg tatcatgatg tataacgtgt attatgtggg    360
ttggtttttt tttttttttg tcattttgc aaaagtaatt aagtttgtgt tatgaaccta    420
attttttaaa tttctttttg tcacgtataa gagacttgaa aataggttta aaaggtctta    480
agggtatttt agtttgactt ttttaaaaag tatttatatg atatttaaaa attagaattt    540
tttagaaaga ataggagttt tataaattat tcttttaaga aaaattgcat cagatgacaa    600
aaaaaattta gaataagca gcccataata actctttaaa tttgctatca gacgactatc    660
cgagggttat catcttttaa atttgctact tttacaattt agaaaatgta gtgacatgga    720
```

| | |
|---|---:|
| ccctattatc ataagattttt tttttgctat ttttgcaaac acatgttctt ttaaaatgac | 780 |
| ataattattt aaaataaaaa tataaagtta tttgatggat cttttgaacc tatttttaaa | 840 |
| agctaaagta ctaaaaagat acatattgaa aacttgaggt caaatgggct attattataa | 900 |
| atatgtggac taaaaatgta catttctaaa acttagagac taaatgcaca tatttaaaaa | 960 |
| agcatgtgaa ctaaaaagt cgttttccct aatattttt tacaacaatg actaaattga | 1020 |
| acctcaaatt tgaagggtgg aaaaccatac taattattca ctaatgaact aaactcattt | 1080 |
| gatgatttca agacatatga ggttcattga gtagttgggt ttgagggat gaaatgagtg | 1140 |
| gtggaagaaa gttatgtaa cgacccaacg aaataggaag gtcatcccaa ggaagtcgca | 1200 |
| catccaatga gtaattacca caaaacaacc tctccttttt tctcaaattc ccttttaata | 1260 |
| aataatttga ttccccattc cttccttct cccttggcag ccttctcctt ttttcaaagg | 1320 |
| tttttgtttt ttcttttctt ttttaaattt cattcctttg tttctctctt tctttcttca | 1380 |
| ttaacattct tcttatttcc tcattactga tcatctcctt ttcttggtat tattcttctt | 1440 |
| tcttttctca aagttttgtt tttcattgat gtagatgttt ttgtatcaat caatggaaat | 1500 |
| ttgagttttt cttatctcat tgtatcatca ttgagtgtgt gtttatgtta gggatccatt | 1560 |
| attaggatgg atgagaatca taatttcatt gctaatctat gaaccatgaa taagaaaatc | 1620 |
| taaatccaac atagaagata gaacatttgc attgtgttat gagtaaccag ctctgtcact | 1680 |
| tcaattggtt cttctacaca tttgatggca atggctttgt ttgatattcg tgatggcatc | 1740 |
| taagcattgg ttcttcctat gttttttcgtt ggctcttggt ttgatttgca attagtgaag | 1800 |
| agcatgtttg gaatgaatga gttgaaatca cctttaacat tttaaaaatc actttaaata | 1860 |
| ttaaattaat tttgagtgat aaaagtaatt ttaacaatga taaaattact ttcaaatgtg | 1920 |
| ggccgaatca aattgtctag aatgtttagg gttctccaac taatagcaat ttatccaaac | 1980 |
| agggtaaaaa | 1990 |

<210> SEQ ID NO 16
<211> LENGTH: 2005
<212> TYPE: DNA
<213> ORGANISM: Cucumis melo

<400> SEQUENCE: 16

| | |
|---|---:|
| ttgttagagg agttagcttt tcagggagtc ggttacaact tacaagacag acaaccatac | 60 |
| tgtacaatca atcactactg cctcaaagtc gaaaccattt aataccagtt gagcctcatt | 120 |
| gtgactgcat aattttgacc cctaccacga ggtaattca gttcaaatca attgtatctc | 180 |
| tcttctggat atcagtcaag aatctcatgt tctcaagtta tagtacattg ataattactg | 240 |
| tgcatttttta ttaatttatg agttaaaatc ctgctgatta attcaactaa aggaataaaa | 300 |
| tagttattgg catttggatg agaatagaat gtgaatccca tcattcatcg ctagattgga | 360 |
| ccgtaattat aagtgagagg gagaaacttc tgttgctatt cccttttat ttcttaattc | 420 |
| atttataaat tgttttagg ccttttatat atatatattt ctaccatttt tacatttaaa | 480 |
| attctttaa ctttattatg tatggactca aactaacaag ctttattgta taaaattgtt | 540 |
| caaactatta tattagtttt atatttgtaa accataaac aaatccataa aattccacct | 600 |
| gcatcactca ctcatgttgt tgaatggtac gaaataaaca atacatgtga aagatgaaaa | 660 |
| taagaattgt tctcttatta aatctaaaat ctagattttc tttttagtac atttaacact | 720 |
| tcaatgaaag gtctaaaaca ttattgaatg acgtcacgaa ctattacaaa agattattcc | 780 |
| gatttatctc aaaagggggtc tatttcacta attttggtgt cccacatctg taaagagaat | 840 |

```
tttcgtgata tgtgtagata tttaaatata attgaattcg atgaaagcaa agcaagaatc      900
gatatccgta gttattttga tatagatcgg tgataaataa aagacaatat gcataaagtt      960
tgtgggtaca gagtcggcta gttgcaatga ggggtatggc cccaagactt ttccccaacc     1020
ccaacggtca attaatcacc ccaatggggc atcgaatctt ccccaccatt ttcctttttct    1080
tcgccgactc ttctacccat ctcttttgcc gactctttct cacaggtttg attaaatccc    1140
attcatattc agatacacta tttcaaaata actcgcaaat taatttgttt tttaaatatt    1200
ggtataataa taaaattaat tataaattgt gacctaaaaa gtactttgtg aagaggggga    1260
tatagtctgt ctaatatatt attgattaaa tatataatag aaccataaat gcaaaccact    1320
agaattgtta ataaaaatca acgctctttt aagtctttcc atagaaagaa aggcaaagac    1380
gcgcaacgtc tagaattttc tttataacgg aagctaactc tgttataacg gccgtccaca    1440
taatatggta gatttaaaat gacgtcagca tgtcgcttct aaatttgggt ccaaagggggg   1500
gattcattta tagggaaggg aaacggcaaa tgcaagcata gtgagtaaat acgtggcggc    1560
aaagtaatgg ataattctgc ctctgccgtg acgacattgc ccttccattt cactataaat    1620
acacctcctc tatccctcga tttcttcgca attgaatttc tcttctcatc tctgtcgtag    1680
caaaccaaat cgatttcttc aaaggtattt cttcctttcc tttttttttt tttttttttt    1740
ttttaaatc atgttgttca aactttgaga gatgaaatga ttaggggctt tcaaagtggt    1800
tttcgtttga tatgtttctt agatcgatag ggtttagaat cgagcatcct tgtaggtatc    1860
ctgaggtttg gtggttggat ctgcttaatt tttatgtggt tgcatggaaa attgggattt    1920
tttttttcta attacgtgat tctggaaata ttgatctgtg gttcagatgg aattgaatct    1980
gatctttctg ttttgttctg tatag                                          2005

<210> SEQ ID NO 17
<211> LENGTH: 2004
<212> TYPE: DNA
<213> ORGANISM: Cucumis melo

<400> SEQUENCE: 17
tagaaaaaaa ttgaagatct tcttaatgct aataataaaa gcatatataa aaaggcttca       60
tattacacaa gcatcttaaa accaaaccga acttgatttg aaattatccc actaattctg      120
tagatttcac caaagtcctt aacctttata ctaacatctg catttgactc tttcatttga      180
cctccaacat attctttctc attttccttc cattcaccac aaaaaccaac aaatacaaaa      240
aaccacaaat acatagaaaa ttaataaaaa aatcaaaatt tcgagatgaa atcattataa      300
actcatccga taactttgag atttgaaacc ttacactata taagaaact catccgataa      360
ctttgaattc gcatcgaaat tacgtaagtg aagacgaaaa tgtaaatgat tagatgcgaa      420
taacaaaaaa aacataattt ctaaacgtaa aacactatat tcaccttatt atacttgatt      480
attttggaaa agtatgaaat ttgagtgtgg gagaggagcc aaagaattgg aaacttgtta      540
ttaggagtcg ttatgaaaca ttttcaacaa gccaatattc tttcacatac tataatgata      600
tacatagaaa taatacaata atattttgaa aattgaggca ttttgtcgt aatttatcta      660
aaaatgtcag ggtagattca tcatgtatac aaatctctcg ctatcaaaac tatataaaaa      720
tcttgtgaat gatttcaatc gaaatggacc gagaaaaaac atcgtaacca cctctaaaat      780
cgataaattt gtttcaattt caaatcccta aaactaaagg tgctactttg tacaatttcc      840
cctgattagg gtgctaaagt taaaccctaa ataaaggtgt gtacgtttcc ggaagtttct      900
```

```
agaatcccca gcgaagttct ccaaatcgtg gcttgcagac caaggacccc cattaaaatt      960
cgtttcttcc tctaaacctc ctcccttaat tttggcattt tggtattttg gctcctataa     1020
attcaccccc tccttatccc taatcctttg tcttccaaat tttccttcaa agcctgcttt     1080
tcccatttcg tcgtgctttt tcttcatcta aggtatatt tcagttctag ttttctttct      1140
ctgttgatct cttggatttg agggacgttt gaagttggct ttgtttaatt ctttgttatt     1200
caatctcttt ttttgttaga gttgttgttt aatcgtttcc cttgtgtttt ttctcccttc     1260
tagttcgatt ttagaacgct ttttgtgggt tgattttaat ttctccgttt tcttacatct     1320
ttcacaaaga aacgattgaa atcgtgtttg ttttttttcc cacggcatac gttattagat     1380
cttgtagata atgatctcaa tctattgttt agttttgca aataagaagt tggttttta      1440 tctccaactt ttatatattc gattcgatga gatgttctac accgttagga tggaaccaag     1500
aagtgaggta agggtgtttg attgaaaaat tgaactgaga agttaaagtt ccttcctaac     1560
tttttaatgg attgtataat tcgttcaatt ccttgtcgtt ccatttttat ttctgtttcg     1620
tttttcgtgt tgctgcgtat cgcttcccct gttgttttcc tccctatt atttgcgtt       1680 tcttggagtt tctctgtttt ctctcttcat ttttctacaa aaatcaattc tattttt at    1740 cgttttcaat tcccgagctc cttggaatgt tatccttttc tcctgtgtaa ataagaaccc    1800
gtattcaatc ccagttcata gtttggcttt cccaaataag agcaaaaaga ttgtactgag    1860
aagttgaaga tttcaaaatt ttgtacatga tttcttctaa tttatcaatt tgattggact    1920
ttttgtatat agatttggtt cttgagctat ttatgttatg acgttttcat attgaggcca    1980
tgcgttgaat tggtttctta acag                                            2004

<210> SEQ ID NO 18
<211> LENGTH: 1935
<212> TYPE: DNA
<213> ORGANISM: Cucumis melo

<400> SEQUENCE: 18
tatacaaatg acaaaatatc gttgaagtcc aaaaaagatt tattgttggt aaatatcgtt       60
aaagttagta aatagatttt agagaaagga gatatagccc ttgtagtaga aacacacaca      120
caaattgaat tagatgtgtt taatgtttaa ttaaattaga tatgagtcaa cttatatcta      180
atataggaca ttattaaaca aataagaaat aagaaacatg aaacaagaaa aacaagaaat      240
agaaacaata tcaaacacat tcctatttct tgttctaaaa aaagaaaaaa catggtacaa      300
gaaataggaa acgaaaaga ggaaacaagg aacaaatgct accaaacggg cctaagtttc       360
taacaaaatg agctaggtgt agtttattgg tatagatagt gactttcaat tatttttaaat     420 ttttttatcc atacctccac gtctttagaa tctttcttat ttatatgtga tcttaattca      480
ttcatgtctc aatcttaaaa ttagaacatt acatgttcat cattttttcc ttttgttact      540
gtgtttaatc tttcctaaca agacaaatag tttaaccttta atccacacat tattataacc     600
aaattaaaat aatctaccttt caagaaaac attattataa tcttatatta accacaaatt      660
ataataccaa actctaacgc tccaacccaa cctaggaaga atgacaaggc tgtcataatt       720
tagttggttt ggcacgttgt tggaagttct caaaattatg gaatatttta ttccttctt      780 ctttatccat catcctcctt ggagggtga atttgtgtta aaaagaata gaaactaaag        840 tctaagtggc aggacttaca ttatgtgtgt atgtggaagt aaaattgcag taacagttta      900 caaaacaac tcatccatga ttcataacca acttaaatga atataatttt ttgcctaaag       960
attttaaatt aatatataag cggaagaatt aacctataac ttcaagttta acaacacaaa     1020
```

| | |
|---|---|
| tattatatca tactgattaa ttattggaat gatgtttagg ctttaaacat aaagtattga | 1080 |
| gaggctaatt tgagtttaac tcactaaact atcattaccc tttcaaaata gatccaatca | 1140 |
| tccatttatt ataatactca atgaaataaa gcaaaagatg agtaaaataa ttcaccatga | 1200 |
| acattgataa ttaattttcc cactaagata aactactact cctcaaatct tcatatgtgt | 1260 |
| ttttcctttt tgagttgcac tcaaattttc atagttgaaa tttacccatc aaaacaacca | 1320 |
| acaatctttc aaattcaaca aacatttgac cttacaccct tgatgccaa atccttaccc | 1380 |
| tctccctctt ccataaaaat tcttatataa accaccatca ctctcacttc tcaattcact | 1440 |
| ctcttctcta ctcccaatca cctgacttgc ctcttactcc accgccaggt tccgccccaa | 1500 |
| cttccccggt aagttccagt tcttcagatc tggttaccac atttgatttc ttgcttgtat | 1560 |
| ttgacgtggg aattttcata tcggcgtttt ttcgaactgg gttttgcttt atgatcatat | 1620 |
| tcttgtagta aaatgccatg aatctgttat ttgattccgt ttttttggga gatcggtcta | 1680 |
| gctttatggc catattctgg catttaaatg ccatgaatcc gtgatttggt tgaatttcac | 1740 |
| ttccgatcca atgtttatgc tgatattgac atctttgcat tcaatgcaga ggagttttgt | 1800 |
| ttcgatttat tactgatctc atcacactga tcttgaattt tttatacttt tatgtgtgtg | 1860 |
| tgtgtatttt ctttaatatc tatgccaatt gaactatgtg gttaacttca gagtgttctt | 1920 |
| gtgggcagtg agaag | 1935 |

<210> SEQ ID NO 19
<211> LENGTH: 1606
<212> TYPE: DNA
<213> ORGANISM: Cucumis melo

<400> SEQUENCE: 19

| | |
|---|---|
| atatattgta tcgattcttt agttgctcta tgttttgtt tgcttcattt gtcgattaaa | 60 |
| ctgtaaaatt aatttctttg acaaggaaaa agatataatt taattctata atttattaca | 120 |
| atctaatcca tatggtttaa taaaacactg aaaattgttt atgaaaattt tatcgaacta | 180 |
| caagaactat taataaagtt ttttttaaacc gtaaattgaa tgaattttct ccacggtgta | 240 |
| aatttgaaaa cattaattaa ttaattaatt aattttaatt tcaaggtttt ttctgaccca | 300 |
| tgaacctatt ttatgatata agttgttcag gggttgcaat agtaaccaaa taaagttgat | 360 |
| cagaaaaggt taacaactca tgaaaacttc caaatgcatt tgtgtttcaa ttattttctt | 420 |
| aaccctcttt ttttggtaat tttagtttaa aaagtgagtc ggttgatcat tattgttctt | 480 |
| taatttcttg ggagaaaaat attaatgttg attatggtga tgagttaagt ccaattcttc | 540 |
| atcaaatcat accaaattag gaacaaaaaa acatcaatt ttaaggtgca aatccatttc | 600 |
| taatggctaa aatgtcaagc atcccaccaa accaacaatc tctaaaccca ttttactcc | 660 |
| actaatctaa tgtttaataa taatcaacaa ggttttgctc attcctttt tagttaataa | 720 |
| tcatttaaca ccaaagctca aaagtaccca cccaatggat caaaatcgag aatatatagc | 780 |
| atttaaggat ataaagacta gagataataa taacctagct tagagcttaa agggatacac | 840 |
| tagccatcaa gtcaatttgg tagacaatct aaaaacaaat aattcgatga aaataaagtt | 900 |
| gtattttgt gttttcaaac atgttttaag acgaaggttt tgataaaatt tgatctcaat | 960 |
| aggtaaacaa tggtaattac tcgattataa ttactcacta ataccaaat cgaatataaa | 1020 |
| ttattactaa ttaattatga acatgtttta cattttaaaa aatgaataat ttttttttta | 1080 |
| gaatttgtgt tattgaaaat aattttcaaa acaatattga atgaatctta agtgaaatca | 1140 |

| | |
|---|---|
| atgtattaaa agaacataaa acataatcta gatggtctat cgaacaagct agaaaatatc | 1200 |
| ttccataaat ccaatgatta agacaggcag gcaggcatga agataagagg attggattaa | 1260 |
| ttggtgattt taagttatga ataaagacac aagaactagc agctctcctc ttcttgtcac | 1320 |
| cttcctttgt catccagctc acacaactcc aacttggaat tgacaggtc tctcttcact | 1380 |
| catacattcc cacatgaaat tattaattga atcttcaaca ttgtctttga ttcttcagct | 1440 |
| gcactgtcct ttttccaccat tttttttcttc aagataaaga ctaataaact ccttatatat | 1500 |
| tcctctcttc ccattcacct gtgcatactc acaaagcaac tgccatttcc ttcttgttta | 1560 |
| tctctgtttt tttcttacac atttgttgaa ctttccctct gaaaaa | 1606 |

<210> SEQ ID NO 20
<211> LENGTH: 1487
<212> TYPE: DNA
<213> ORGANISM: Cucumis melo

<400> SEQUENCE: 20

| | |
|---|---|
| taatgaattt gtatttgtta gtggattgag tttatatgat attaattttg acccaaacag | 60 |
| ttgagtacgt aattaatgtg gcttgcattg aaagtgatat gggcatatag tatgtgtaga | 120 |
| atgtagctga cacaacacat taacaaaacc caattttaac ttttttcttt tcttttctt | 180 |
| ttaattttat atggatcaga tcacatgtca ttttccatta caactcactc tctaccaatc | 240 |
| atcccatccc ataggccata ccccataaca tcccttttcta aatatctaaa tcatctccct | 300 |
| aaattattac attttttttc tctcaaatat aactattcaa ttcataaata ttattctttt | 360 |
| tttagctctt attatttcaa ttatgatttt aaatattcct tttcaattta cgaccttttta | 420 |
| tttaccatat caacatttta attctactca attaaagatc attataatga aatttcaggt | 480 |
| ataacaaaat aaataggtgt gatataatga tggactacta atttcactaa tttcgtcatc | 540 |
| tgaaataagg acaagttcca actatcacta ttgtgaaaac ctcataactc ctaaaagtgt | 600 |
| taaaattgga ccctcaagtt tataataatt ttgcaaattg aatcccaaaa ttaaataatc | 660 |
| agtataattt atacgttttg agagtcaaat ttaatatttg aataagcttg aatacttaac | 720 |
| ttctaatttt gaaaatttaa aaatgcaact gcgagagtaa cttttgcaat tagccgtcga | 780 |
| aacaattaat tatattggtt aatttatgtc tcattctctt ttgatgacca taaagataaa | 840 |
| cccatttata atataaatat caagcaaagc taaaacaaaa tcttttttttt ttcaaattag | 900 |
| atctaaatat gaataaaagc agaactttct agaagtacaa atttgattat ttttcttgag | 960 |
| ataaaattt cgctatgaac ctttttataa taggaaaaag agaaaaagga tggttttata | 1020 |
| taaatgtatg ataaaaaggt aataatatcc attgtaatag taaaaaagaa aaaagaaaa | 1080 |
| aaagaaaaag caattttctt tttcatgatt aggaaatata aaaacaaaaa ttggctccca | 1140 |
| attgacatct ttaatcttct ttttctttttt cttagaaaat aaaattagtg agagaaggaa | 1200 |
| aaaaacgaag ggttgagaga tagagagaga aaaaattgat tttttaattta gtttatttc | 1260 |
| ctttttttgga gcacaaaata aatagataaa taaaatatta gtttgcaaaa aagcccctcg | 1320 |
| agtttatctt atttgctcaa aaaagcaagg ataaatacct cccgacatcc ctgtttatcc | 1380 |
| ctctcagttt cataattcca ttggttcgat aagaaaacaa ttctcccaat attcccgctg | 1440 |
| tagatctcgt cgattttccg tttgtttccc gggaagatca atcaaag | 1487 |

<210> SEQ ID NO 21
<211> LENGTH: 1448
<212> TYPE: DNA
<213> ORGANISM: Cucumis melo

<400> SEQUENCE: 21

```
ggtgtcttgt tgtaaggaaa tggaaagaaa agagaaaggc tcttgttgtt gtccttgttc      60
tgtgtatcga tgaaaatgga tcgacgcgaa gaagatgaag gacgagagtg gggattataa     120
gacagagaaa ctccgaaatt tgagggctaa tatggtaata caaatggcg  ggatactttc     180
aatggacgtg gacccattgc ttctttaact caccgtctga tctttatttt acggtcatga     240
tttccctctt tccccaatat ttttggggag gaaaaccaac tttgtttttg taattttaat     300
cattttttcct caaatcgtaa aaaaaaaatt atagattttt tcaaaaatag aaaaaattca    360
tataagaaaa ccaagataaa atattttgaa aaatatccta tttttttactt cttaaaaata    420
attcataaaa gaattattat aaatattaaa aaatatcagt accactatag caactatttt    480
atatagcaca tatagatata tttgttggtt tttctattta gtatttgaaa caactccaa     540
aaacaataca tttcaatata cctacgaagc atacaaatat aattattaat tttaataagt    600
tcaaaaatat ctaatggcat ccttatttaa tcaattttt catcgacgtt atacacggta     660
aggatgtcct aatccttgac cattgaaaga cgtttgtttt gataattata tcttttgata    720
tatacaaaca tttatctcat gattagaata gtcacctttt tatttgattt aacgattata    780
cataatatttt gaaaattttt aaatccatca acacaatcaa accaaaaatt tcctaactac    840
ataatctaca agagatttac catcttcttt aaacaattgg tcattacgtt tgttaatgtt    900
taaaattaaa tgcaaccata ttgggtgtaa aagccaaaca ttgatttgat tattaaagtt    960
ttttctatat agacttgatg tgtaaaccta ataaccaact tgagctaaat aactttaatt   1020
tctaaaattc attaaactgt cctcatccaa attataatat caaagatttt tgaaatattt   1080
aaaaattccg aacatgggaa ctactggaac ttggcaataa attcaagcaa gaaagaggaa   1140
aacgatataa tcaaacaatt aaaaaacaac agaaatttat ttaatcaaag gaataatctc   1200
atctttattt tattgggttt tactttaat actgtgagtg atgattggaa cattaattaa   1260
catttaagac attaatttgc aacaatcaat caaaattgta taaatccact tgttttgatt   1320
tatttgaacc atcacttttt tttttatata tatatataat atgggagtga aagatcaaac   1380
gtataatcat gaaatgaaag atgggatatc attgaactta attaaaatatc attgaactgc   1440
aatttttt                                                            1448
```

<210> SEQ ID NO 22
<211> LENGTH: 1235
<212> TYPE: DNA
<213> ORGANISM: Cucumis melo

<400> SEQUENCE: 22

```
aaatttttaat aattaaaatg aacaattttt caagagtaat agagtttgag agatgtcaga    60
gaagtttgag gaagaagata acaagtggga gaagagaata agtttgttgt gtgaaagaga   120
aggggaaatt tcattcaagg gtatattgaa cttttttactc aaattttgta agtctatttt   180
ttccgatcaa tcctaaaatc acacacaccc ttaaaaaatg gattatattt ggcaattttc    240
catgataaac tcattttaaa tttagagtta ttttttcaac gagatattaa cagttttagt    300
tcatatacta attgtaagaa tagttttcttt taagttgaat agaattttttg aaacttttaa  360
tagttcaaaa ggtatttttg aaacaaaata agaatgtttt tgaactttttt ataaaaagaa   420
ttgagatttt tttgaaattt ttgataaaga gaaagaaaaa gaagaaagaa aaagaaaaa    480
caagtttgta gaactccgtg ggaaaatcgt cgagggccct gtgaaggaat tttgaaatta    540
```

```
taatgagggt attttcgtca acaagggaat ttagacatcg tatataagca tcctcaaacc    600
ctataattaa gcccttcaat ccaattgcca ttctccatct ctcgccgcaa gggtttaaga    660
gcagcttctc tcctcaggtt gggtttccc cctatcttct tcattcttcc tcttctcgat     720
ttctttcttc tatttgctcg atagtctctt atttcttgag cttttgctgt ttttctcctg    780
tacatcctaa catgaattat aacttggttt tgattttgtc tttacttct gtattaaaca     840 acttttctta ccctttattt cttctcttct cttcgtgtc cctgcccttt tgttttatg      900 ctaattttat gtttctgttt atcaatctat cgaggcgtga cctgtcgttc ttccaatagc    960
gtagatctgc acttaatcta ttctagctga ttggattggt cgttttcgt ttttttaatt    1020 tattttctct gttctagttc cgataaattt ttttatatat aattaacaag ttctccagcc   1080
aaaagggtta atattgcgtt ggatatttta attttacgt tatttagatg tgtgaatcta    1140
ataaaattag ggttattcat aaatttcagt aatgatattt tggttatctg ttcttgctgt   1200
tcctgtttcg cagttctttt acctaatatt caagc                              1235

<210> SEQ ID NO 23
<211> LENGTH: 2003
<212> TYPE: DNA
<213> ORGANISM: Cucumis melo

<400> SEQUENCE: 23
ctagacattt ttgtctaacc tttcaaatgt tttgttttaa tcttccctct cccaaatagt     60
gaaggacatc cagtgtcaac cgtgaacgca tactgtgtca ttcatgaaac aaatcttttt    120
tgtagtgggc attgtcagca tacatagcat gtagaagcta tagacagatg ttgctttgag    180
ttgtatttag ttctctttaa aggaactttg tacaaagtac tgaatgtact ctgttatttg    240
aaatatcaat gaagtcctct taattctttt gagttcccat tccacgttta agttgttagt    300
tgtattcatt ttcgcttact aggtgttctg catgtatctc acagagagac tcacgtgaaa    360
tgtttaggcg gtcacatccc taatgacttt tgaaggggtg tgacacgatc atttgaatat    420
atcacttatc taatagtgac agtggtctat atctttgtct atctgtatag atcattggtt    480
gtttagatat tggtacacta ttgtgtagtg aaaaaagaag aagaagaaga aaatataat    540 acttgataat gagaaaagaa taagaaaaaa tattgtcttt atgaaagatg aaaaaatgat    600
gctgaagacg agaaatgacg gaaaaggaat aaattctaga tgaagagatg aagaaattct    660
agaagaacaa atctagaatt tataaatggg ataacaataa agataaatgg ataacaaag    720 aaaaaaaatc aagaaattac ctaaatgttt caatcttgct acgccttaat tagaaaaga    780 aagaaacaa aaagaaaat gcacaaaaat atctatatat atatacacac acaagcacaa     840
gaaaaaaatg aatattggaa aaagacgaaa atgcattatt ttttatttgc gttagcgagt    900
tgttgtgatt ttgtgagcaa gaaaaggata tgcaggagaa ttaagataaa taaggaagat   960
tgaatagaga ttaaaagaga aatatgggaa tagagtgggg atgaaaggtt taagatagg   1020 gagggaggga gcgagagaga ggagaaacaa acataccttg agaaagggag aatgagagag  1080
ataataaata aatacggtga tttggaactc ataaaaagat taaaaaaaa aaccttagag   1140 taaagacttt tccatgcatt tcgagaaaat ggaaagaat attctattct atttgcttgg   1200
acaccaagtt ccttttttgtc gcatgcatac gtctatttat ttctgcttgc ttgcataggc   1260 agttttttgtc caaggaaatt cagcaaaggc ggtatcaatt tcgtcaactt agaatccact   1320
cagtactatt tgaagttcct cactaccaat ttgcaccatc caatctcttc tctctccaac   1380
ttcctgccag ggcttaaccct ctcttaattc cttatcctta cttgttacct tacctggttc   1440
```

-continued

```
cactcttcac gtctctctat tctatattgt ttttttttca ttcataattt tgttactctc      1500
ttctctgtcc cctttgtctt ggattttatc tctccatata ttcattggaa taatttaagt      1560
tctttgtaga ttttatgaaa ttaccaattt aattttcaa acagttttg gatttgttta       1620 atttctcctt ctctaaatcg cgttgacttt atgttatttc gcccttgctc tgttttctct     1680
gatcataaag tatgtacttg attttatggt gaatgctttc ttgatttaac aaccctggtg     1740
ctgaaatctt ttttaaatcc tacttttgtt gttttacata tgttcttact ctaaaatgag     1800
cgacttattt ccttttattc ttccttcttg attaaggatt taatcgttga agtatgctta     1860
tattgtggaa atttggtttt aattgatcat acgagctagt attactagct tctcggtttc     1920
tttggatgag ttatatgcat atgatgattt caattccaat tttatttg caacagattg     1980 tttttttgtgg ctgaaattca agt                                              2003

<210> SEQ ID NO 24
<211> LENGTH: 2015
<212> TYPE: DNA
<213> ORGANISM: Cucumis melo

<400> SEQUENCE: 24
gatcagagta gcagttgagc aaacccaaac caaacccttt atctatacaa tcctctcaaa      60
ataaaattat tgtttaatta ttcccatatc tattatcatt tttccataat tgcattgaga      120
gaaaaaaaaa aaattctagg agacctaaat acaacaacaa ctatttaata atagccccat     180
gtcacattaa ataaaactaa caaaaagttt aatacgtcaa gaaacgatac ttgtggatat     240
tgaggcatgg gtccctcctt ctttgtatat tcaaatctgt ggtctgccat cagataaggc     300
ctttaccata taataagttt tcaaaaaagt aagcaccact tgctgctttt ttaatttaat     360
tatatttaat ctaattattg aaacttatag ttgttttcta tccttattct tttcttctct     420
tcaaacaccc tcctattaat ttaaaataac caaacaacct ttttctttac atagacaaac     480
ttaattagat taaatataac ttgtaattag attaataata tagtttaaaa agaatttat     540 tttaagtaga attattagta aaatgaatt ttgtggatag atacttggaa tttaagagaa     600
agttaaaaga gagaaaaata tgaaaaggaa ttaaatgatt aaagttgaat gtaagaaatc     660
aataaacata aattccatgt attaaatttt tgtcggtgtg tgaataaata aatatctatt     720
actattagat tacccagctt tgtttataaa aagaaaaaga aaaagttttt aaaatattgg     780 aaaatttgt ataattattg aagaaattgc gtggtctttg caatttgggc atcgttctta      840
tcgcttccaa tgaaggggcc gtttacctcc accactattt ccaacttgtt tttgtaccat     900
tctctatatt tctttgacac ctatattaca cgtgtcttta atccattgga ccttcgtcct     960 actatattt tacccgaaat gacgaatctg tccttctcat ccacctataa attcacctct     1020
ccggctcctt ccctttcatt cagttttcct ctattcttct ctctatacgt catattcatt     1080
tcttccaagg ttcgtcctcc ttttatcttt cttcttct tcactttttt tcgcttttt      1140 cttttctttc ggttttgtt cttttaattt cattcgtttc ttttgttat atggtatgtg     1200 gtatttgttg aattgagatg tttagggtt tcgatttagg ttttattct tatcctactt     1260 aagggctatt gtgattttgg agaaggagt tcttatttgt ttttttttt ttccttttc     1320 ttatctggca gatgcaaatc ttcgttaaaa ccctaaccgg taagacaatc accttgagg     1380 ttgagtcgtc tgatacgatc gacaacgtca aggccaagat ccaggacaag gaagggattc     1440
ccccggatca gcaacgtctc atcttcgccg gtaaacaact cgaggatggc cgtaccttgg     1500
```

-continued

| | |
|---|---|
| ccgactacaa catccagaag gagtccaccc tccaccttgt cctccgtctt cgtggtggca | 1560 |
| tgcagatttt cgtgaagacc ctgaccggaa agaccatcac ccttgaggtt gagtcgtctg | 1620 |
| acaccattga caacgtgaag gccaagatcc aggacaaaga aggcattccc ccagaccaac | 1680 |
| agcgtcttat cttcgctgga aagcaactcg aggatggccg cactttggcc gactacaaca | 1740 |
| tccagaagga gtctacccte cacttggtcc tccgtcttcg tggtggtatg caaattttcg | 1800 |
| ttaagaccct gacgggtaaa accatcaccc tcgaggtcga atcctctgat accatcgata | 1860 |
| acgtcaaggc aaagatccag gacaaggagg gaattccccc agaccaacaa agactcatct | 1920 |
| ttgctggtaa gcaattagag gacggccgta cccttgccga ttacaacatc cagaaggagt | 1980 |
| ccaccctcca ccttgtgttg cgtcttcgtg gtggt | 2015 |

<210> SEQ ID NO 25
<211> LENGTH: 2006
<212> TYPE: DNA
<213> ORGANISM: Cucumis melo

<400> SEQUENCE: 25

| | |
|---|---|
| accaccacga agacgcaaca caaggtggag ggtggactcc ttctggatgt tgtaatcggc | 60 |
| aagggtacgg ccgtcctcta attgcttacc agcaaagatg agtctttgtt ggtctggggg | 120 |
| aattccctcc ttgtcctgga tctttgcctt gacgttatcg atggtatcag aggattcgac | 180 |
| ctcgagggtg atggttttac ccgtcagggt cttaacgaaa atttgcatac caccacgaag | 240 |
| acggaggacc aagtggaggg tagactcctt ctggatgttg tagtcggcca agtgcggcc | 300 |
| atcctcgagt tgctttccag cgaagataag acgctgttgg tctgggggaa tgccttcttt | 360 |
| gtcctggatc ttggccttca cgttgtcaat ggtgtcagac gactcaacct caagggtgat | 420 |
| ggtcttttccg gtcagggtct tcacgaaaat ctgcatgcca ccacgaagac gcaacacaag | 480 |
| gtggagggtg gactccttct ggatgttgta atcggcaagg gtacggccgt cctctaattg | 540 |
| cttaccagca aagatgagtc tttgttggtc tggggggaatt ccctccttgt cctggatctt | 600 |
| tgccttgacg ttatcgatgg tatcagagga ttcgacctcg agggtgatgg ttttacccgt | 660 |
| cagggtctta acgaaatttg cataccacca cgaagacgga ggaccaagtg gagggtagac | 720 |
| tccttctgga tgttgtagtc ggccaaagtg cggccatcct cgagttgctt ttccagcgaa | 780 |
| gataagacgc tgtttggtct ggggaatgc ctttctttgt cctggatct tggccttaaa | 840 |
| agaacaaaaa ccgaaagaaa agaaaaaagc gaaaaaaagt gaaagaaaga agaaagataa | 900 |
| aaggaggacg aaccttggaa gaaatgaata tgacgtatag agagaagaat agaggaaaac | 960 |
| tgaatgaaag ggaaggagcc ggagaggtga atttataggt ggatgagaag gacagattcg | 1020 |
| tcatttcggg taaaaatata gtaggacgaa ggtccaatgg attaaagaca cgtgtaatat | 1080 |
| aggtgtcaaa gaaatataga gaatggtaca aaaacaagtt ggaaatagtg gtggaggtaa | 1140 |
| acggccccctt caattggaaa gcgataagaa cgatgcccaa aattgcaaaa gacccacgca | 1200 |
| atttcttcaa taattataca aaattttccc aatattaaaa actttcttt tcttttat | 1260 |
| aaacaaagct gggtaatcta atagtaatag atatttattt attcacacac cgacaaaaat | 1320 |
| ttaatacatg gaatttatgt ttattgattt cttacattca actttaatca tttaattcct | 1380 |
| tttcatattt ttctctcttt taactttctc ttaaattcca agtatctatc cacaaaattc | 1440 |
| atttttacta ataattctac ttaaaataaa attcttttta aactatatta ttaatctaat | 1500 |
| tacaagttat atttaatcta attaagtttg tctatgtaaa gaaaaaggtt gtttggttat | 1560 |
| tttaaattaa taggagggtg tttgaagaga agaaaagaat aaggatagaa aacaactata | 1620 |

| | | |
|---|---|---|
| agtttcaata attagattaa atataattaa attaaaaaag cagcaagtgg tgcttacttt | 1680 | |
| tttgaaaact tattatatgg taaaggcctt atctgatggc agaccacaga tttgaatata | 1740 | |
| caaagaagga gggacccatg cctcaatatc cacaagtatc ggtttcttga cgtattaaac | 1800 | |
| tttttgttag ttttatttaa tgtgacatgg ggctattatt aaatagttgt tgttgtattt | 1860 | |
| aggtctccta gaatttttt tttttctctc aatgcaatta tggaaaaatg ataatagata | 1920 | |
| tgggaataat taaacaataa ttttatttg agaggattgt atagataaag ggtttggttt | 1980 | |
| gggtttgctc aactgctact ctgatc | 2006 | |

<210> SEQ ID NO 26
<211> LENGTH: 2017
<212> TYPE: DNA
<213> ORGANISM: Cucumis melo

<400> SEQUENCE: 26

| | | |
|---|---|---|
| atggataagg cagagcttac cactaacctt ctaagatatt ttcgtcgctc ggcatttatt | 60 | |
| cttggaggga accacaccaa ctccaaaata cccatgaaac ataggaaaaa atggttcata | 120 | |
| gtctaagttt ccatttcgat tcggtttggt tcggtctttt attttaaaaa caataaaatat | 180 | |
| aaacctacta atttgatgat gacaagttta ctaatgttaa gtaagaattc atcaataccct | 240 | |
| aagaatttgc aagttttct taagtttgat ggtaaggatt tcgtaatcct tgaaatacaa | 300 | |
| caattgtata gaaatgaagc gttgcatttt taacgtctat ataggaacac tattttactc | 360 | |
| caatcaagtt gtaatttgat agataatagt ttgtataact taatgatgaa gagctttttt | 420 | |
| ttttatatat aattttttatt aatacgtata gttcaaaatt ggaattagct atcactaaca | 480 | |
| cgtgcttgcg atagaaacaa caataaaattc aattagtgtc gcatgtattt catatggtat | 540 | |
| tgatgacata agagtagttt gatacgatgg gttacatgga gtgacatgat aattgtatta | 600 | |
| aatttcaata gttatgatct caagtttggg ttgtgtctca ctttgagctt tttgagaaat | 660 | |
| tggcctcaag actcgcctaa tttaatgttg cttcaagcta tagatgctta catcgtgtgt | 720 | |
| atgaaacata ttgcactttg atgcttaaag ttaatatagt gagtaactaa ccagatatta | 780 | |
| cacgctactc ttttaaaatg gtcaaataag aacatttatt agtatgtgat ataacacgta | 840 | |
| ccctccaatt acatacaata attgatcaac ccaaatcttg aggtatttaa taataacaaa | 900 | |
| tacaaaatag atggattata tatctgaata gctaaagaat aaagaatatg tgttatgttg | 960 | |
| tagttacata gtacaataag tcctctcaaa attagaatgg tataataaaa aataagaggt | 1020 | |
| acattcttaa agaaaatgtt atcaaaactg ttgcatcata ggcattttgg caggaagaat | 1080 | |
| agtggaagaa aattcttaaa cctaaattct atcgatatta aatagatttt ataagggata | 1140 | |
| attgcaaatg tagcaattat atttaaaata attagtata tagcaacatt ttaaaaaaat | 1200 | |
| ggcaaatata gcaaatttg tcaaaatcta tcgatgaccg atagatcatg taagtctatc | 1260 | |
| actgataaac cataggagtt tatcaacgat agaagtctat caccgataaa ttttgttata | 1320 | |
| tttataattt ttttaaaata ttgctacata gttaataatt attctaaaaa ttgctattac | 1380 | |
| caccggtttt taaataggac ctaaatttaa ggtatttgac ataaattttg atgaaccaaa | 1440 | |
| ctagcccaaa tcaagaagt ttgggcccaa agcccaacga atccacaaca aacaaagccc | 1500 | |
| acacaacact tcatgaaaat gatttttca aattttagaa aaaggttata aaatataaaa | 1560 | |
| aaaataatca aactatccct ggtagctaag tagttattat tatttttatg gatacgaatt | 1620 | |
| gagtagtatt tattttaaaa taggataatt gatcttagtt tcacttgtga tgaactattt | 1680 | |

| cactttatta tttgtttgta attcaataaa attagggttt gattgtcaat gataattatt | 1740 |
| acaacctcaa tattatactc agtaaagaaa aataaaaatt taaaattgag aaattaatac | 1800 |
| caattttttt tgtgaaataa aaggaaaagt aagtaaatat tataaaattt tggacttgga | 1860 |
| aattaaaatg cattaataat aatatttagt attattgaat taaaatggac accggaaacc | 1920 |
| ctaaaagagg gagtggccac ctataaaagg gaagcactca tctcacccaa acccttgtta | 1980 |
| ttcccaattg gccgtgcggc aaagaagcct ctcaacc | 2017 |

<210> SEQ ID NO 27
<211> LENGTH: 1353
<212> TYPE: DNA
<213> ORGANISM: Cucumis melo

<400> SEQUENCE: 27

| tgagggtcaa aggaggagga agaacaagaa gtaaatgaag tggagtcatg ggaaaaggaa | 60 |
| aacaaatgtg agaaaagaaa gaaagccaga gagggaacat aaaattatta gtcagaatta | 120 |
| caacagaaaa tttctgaaga attgagtttg tatgcagcaa taatatattg aacaaataag | 180 |
| gagagaagga ggaggggaaa ttcaataaac agcagaggaa gaagaatggc gaaaacccaa | 240 |
| tatctaaaac tagttaattc aacaagaagc aacacaatca tttcattaaa aaaagaaaag | 300 |
| gtaaagagaa attcccagat tcgttactct agattggtcc aatggagtgg aaagggatgc | 360 |
| aatgaaatca gtaatagaaa agaaaagagt taaagtagta ttggtaggta ccgattaaaa | 420 |
| atggaaggcg tcggaaggaa acggagagtt caataaaagg aagattcttt gcttcctccg | 480 |
| gccatttgat gagaaacaaa aactccgcac ctccaagttc cttccggggg aaggagaaga | 540 |
| ctcttctatt ctggggtaca caccctccct tcctgctaca gaatcaaatc taaattattt | 600 |
| tggattggaa tggcatggga ttggtctaac ttccaatttc tcgacacaca accccaatct | 660 |
| acccgccacc tgtacccagt tttcccaaaa cgcaactcac attgcaattg caattcttgt | 720 |
| ctttaataaa tacaaattga tttttctttt tcttttttttt ttttttttaat aacgattaac | 780 |
| cctaaaaaaa ataagaaaaa gaaagccgat cctaaaagta gaattacttt ttttttgttt | 840 |
| ttcaaggttc acgtctgtgt ttgcatagac gtgttgtagt cggtgggtgt gtaaattaga | 900 |
| gtttgttttt ctcatctctt gttcttttta acgaaatttc aaagatacaa aagcataatg | 960 |
| aagaaaagta tacaaagcaa cgtaaactta gcattttgca catgtacaaa atttagtcaa | 1020 |
| actcaaaccc tggacaacct agcactctct tgggcacgtg gtagatttat gtgaatttcc | 1080 |
| ctattttttct tttgaactca caaatgggca aataataata ataaaattta ttgttgattt | 1140 |
| ttcttatatt tcaatttatt acctctagtt ttaacctaaa gtttagatgt atataattat | 1200 |
| aaatgagcgg tgaaacgggc actgattgat gaatatattg ggccttgggt tggcccaaca | 1260 |
| aacctaatgc ccaaatataa aactttggca accatagtta accctaatct gtcaatctac | 1320 |
| tctcctcgac tcggtaaacc tgcgactccc aca | 1353 |

<210> SEQ ID NO 28
<211> LENGTH: 2005
<212> TYPE: DNA
<213> ORGANISM: Cucumis melo

<400> SEQUENCE: 28

| cagtgtgctg gaattcgccc ttatccaagg agattaatgt cgagagatta ttatcgaggt | 60 |
| ttgaatttat tttgtccaat catatgattc caagagctga ccatcaattc aacagaacat | 120 |
| gaaccggaac ctcatacccta ttgtaatggt tcacagcatc ctaatacaga acatgaaccg | 180 |

| | | |
|---|---|---|
| aaacctctta cccattgtaa tggttcacag catctttata cgtattatag gtagtaccat | 240 | |
| tgaagatgca tttaaatgct gtccatgctc tgttctctaa aaagttggac ttggacttgg | 300 | |
| acgtcagctg aaagtatgaa atgcactgta gccaacgaag ctatgttttc aggcttcaac | 360 | |
| atggttttag gaaagtggag gctctttggt tgaagggttg aatgaatgct tttctaattc | 420 | |
| cagcatgatc ttcaaatttc gacacaaaaa gcttaagtat tttgttccgt tattctttta | 480 | |
| atccttgtat tgttatatat tctttctct gaactgaatg tacgatgatt gcaggggtcg | 540 | |
| agagcaagtc cgatataatg aaacacgtaa ggacgtgatt gaatgaaaaa ctatgagcag | 600 | |
| agatacaaag tctaacttac gggatgaacg atgagaggtt tgaccaagag ctgtgacgcc | 660 | |
| tgtatatttc aacaaagtt gatgactaac atcacatgtc agagtaatca agaaatgca | 720 | |
| gccgcacata tatatctta tatatatc gtttagtttt ttttttttt ttttattttt | 780 | |
| tttttttatc taattatatt ttaattctat tttcctctgc cctcctcccc ctcctcttcc | 840 | |
| cccacccttc ttctgcacat agtagccaag gattgatcgg tttctttttga ttcgggggga | 900 | |
| aaatgttgta caatttttgc ttccatagaa gcttgaaagt tttgcagatt atgttgtaaa | 960 | |
| attacccttg tgtactcaca ctagttcttc tcgtggaaac ttatattaca atggttgagt | 1020 | |
| tttaaggggc atattcacac tggtaactac cattttctaa tttatgaatg ccgagtttct | 1080 | |
| ctccatgaaa gacctttcaa atgcccttc ctccgcggtg cgtttgttgt tgtaaatgtg | 1140 | |
| cagtgtcgtt ggatacacga ttgtgtgaaa gggaaaaggg aatacgatta actcttaaat | 1200 | |
| tcaaccccta tctccatcag tatcaatcac atttcagcaa ctagctcttg aataacattg | 1260 | |
| agattcttgt ttaatccacg tactactact actattacta ctatttgaca gccgatatct | 1320 | |
| caaataacat ccatatttat caaattggta ttttaaggac ttttaatttc ttcgtacata | 1380 | |
| tttcattata atttaactac tctgaccatc attgaaaatt tcacaagaa gacattttaa | 1440 | |
| attgaattga gttgaattaa gttgatataa tggttgaacg ttggatttaa tttataattt | 1500 | |
| agtggtgtat gggtccattg taataattct taaaaaaaat atcatattct gaattctaaa | 1560 | |
| gaaccatcta agaccaaaac taaggggtca ccaatgagta tggtaaagtc aacaaagttt | 1620 | |
| gtctactttt cttatcctta tcatcaagag tgcaatatga tatcaaagat aaattgtacg | 1680 | |
| tgggcgtcat ccattgggta agaccaagaa gcaaatatc atagagaagt tgttttagta | 1740 | |
| gccataggaa ggaaggaagc aaaataataa tatagatttg aaattgtgga tgataaactg | 1800 | |
| ccaaatggga attcaaaata aactaaataa ataaaataaa aagagaaatc ttgggagttt | 1860 | |
| ccattttagc caatgaggaa acagatagag atctcatcaa gataaggacc ctattctctt | 1920 | |
| cttcatctat aaaacaaaaa caaatcaaac cctcatttca ctcattcaaa acaaaaagta | 1980 | |
| ctccaaagtc aaactaacaa atacg | 2005 | |

<210> SEQ ID NO 29
<211> LENGTH: 1445
<212> TYPE: DNA
<213> ORGANISM: Cucumis melo

<400> SEQUENCE: 29

| | | |
|---|---|---|
| tcccttcagc cacttaacac ttaaaaatct taggaaactc cattggctcc tctttctcca | 60 | |
| atgaaatttt gacatctgtg ttgttgatag ctcctatatc ctttgagaat ttgatataca | 120 | |
| cctgtcattt gctgatttgt ggataactgt tagccttttg atattgatac gttcctttt | 180 | |
| tatgaatttt tgtaaatcca ttcaatttta atgctgtcgt aaatgaaaag ccctttcatt | 240 | |

```
aatgttgttt atatacatat tttaaaatta attcaataac aagtttagtt ctgttagctt      300
ctaggtttgt atctatttta tctattaaag gtatgtttgg gcttcaggtt ggaatggagt      360
agaattgaat gggttgggga gtaaattttc cattcaacaa gttcaatttc aaaatggcta      420
ataagttttg aactcaattt tattttcaat aaattcctta attttttgtt ccttgtttgt      480
aaactattga cttattcgat atattttaaa attgaggtat tttaaaaaaa taatacaata      540
ttaaaattat tttataaaata taacaaaatt tatgtatagt ttatttgaaa atttactat      600 agtttcattt ttatattatt cctaaccatt tccatttaaa attatttcaa ttatttcttt      660
tattaatata attgaaattt catggattta ttagacacat gatttgaaat tttatgggtt      720
tattaagtat tttctaacac aaaatcgctt ccgcatcgtt ttcaattcat tcagtaatag      780
aagtaatttt ttaaaagaac caaatttgcc aaattttgag ttccataagg actctgaaaa      840
ctcattatgt ctattactct tcactaattg tagagactta aattcaagat aagagacact      900
aattgatgat aattgcccaa aaaataaaaa taaaaatgtt tcttccccat cctcaacctc      960
catgaattca cagagcccaa agattaatta ttgggcccca attcctactc atatatacct     1020
tacagtccct caaagaaatc ttaggaagta atcaatttct gtttattcaa gatgtagcct     1080
cccaaaagaa aaatacatca catcaaattc aaacaaaaat atctacagct agcaaaacct     1140
caaaccgtta aaatttcaag ccacataaat gaaattttca tctgaaaaaa ggacaatcta     1200
tctagacgtt agatttcagc cctaatatga atctgaagca tttggtggac gagaaagagc     1260
catgtaggaa tgcatcaaac aaaggaaaaa tctttgaact ccaatgggat tgaagataca     1320
gataccaatg gataagaatc tgttctcttt gcccactatt taaactcacc aaacccacca     1380
gtatcttcct caccacaaaa tacattccac cgttgatcac aagccttatt ccaccacctc     1440
caaca                                                                 1445

<210> SEQ ID NO 30
<211> LENGTH: 1282
<212> TYPE: DNA
<213> ORGANISM: Cucumis melo

<400> SEQUENCE: 30
tgcaattaag aataagctaa tcttaatgaa gaaagaaaaa tgttctttgt atttgataaa       60
tggtggcgtt ttgggggact ttatatgctt ttttttttccc atgagattgg ttatcttcat      120
ttccgtcatg atgtcgccaa gtggcgcttc attgatgata tcttaaaatc tataatgatc      180
atcctctttg ccaatggtgt ggtgacacgt ggaaggactc tccatcttct aaaagattct      240
tcaaataaaa ataaataaat aaagaaaaaa cttgtaagaa gatacatatg tacatttttta      300 tatgaaatta atatgagaaa taatcgactt tacagtgact tgatcaaact ttcttatttg      360
tttcatatgt taggttaaat tactaatcaa ttcacgtact ttactagatg agatttcacg      420
tactttactc attgagtcca acggttgatt aacttatttc aagaaaattg attcattcaa      480
ggatgtttcc aactctcata taatttccat gttgttccac ttctatcaag tacaatccta      540
tcgaacacaa gtttgtttaa ctgaagttca ataatcgaga tcaagatagg ccttattatt      600
tcttctagag gttcaagtga tcaatcaaaa aaggttatc acatgattca ttccaattca       660
actaagctaa taagtggtgt tgcatgatag agtatcggac tagctcgaac ccctatcaat      720
atgataaatg tctatgtata taaataggta cttaacccaa cgaacaatgt gtcttacgtg      780
agaaagcttt tttctaatat acataaaaag cttgcatgac ttttttgatga attgtgtttt      840 gataaaacat atttgtgagt atattatctt tataaattta agttataaca acaatgtata      900
```

```
ggtgtgagta tgcttttaaa cttaataaaa aaattagaaa aaattacctt tttagtatga    960
aagttttaat gatatatcaa tttgtgtctt tatgatcaaa atgtatactt ttagtctcaa   1020
atgtttataa gaattaactc cttaataatt atcctaaaca atcatgttca aacttggatt   1080
cttattgaca catatttcat tttaatctaa gtttagaaat gaagataatt aggataagga   1140
tctttagctt atgatatctt atccaatatc ttaaataaat cttcaacacc aagaaatttc   1200
cctattgcgg atatttcaat atcgaatgcc ttggagtatc aaaggcattg gataacaagt   1260
gggacataat tgcgataaaa aa                                            1282
```

<210> SEQ ID NO 31
<211> LENGTH: 2002
<212> TYPE: DNA
<213> ORGANISM: Cucumis melo

<400> SEQUENCE: 31

```
ccgtagattg aacttatggc ttcggtcagt tattgagatt ttaattctct ttaacattag     60
gctaatccat gagtttacgt gtgctaacat gttaatatga aaagtatagt agaaaagtaa    120
aataatataa ataaataaat tggattgttt tgaaaagttg aaagattaga atatacataa    180
gattctgaaa tatctcaaat ttttgaccca gcaaactgaa attagccaaa gtaggttgtg    240
ttgtaaataa ttatacttta tattgttctt tttgtataag cttttatgtg tcaatgacaa    300
ttttaacagc taaataattt aaacagaata ttgccaagat gggtggctac aaaaataatt    360
gtaaatagaa cccaataata attagtttaa tcaattatgt ttttattaac ttgtaaatta    420
aatttacact gaaaagttga agagtttggg aaaatatttt atttgaataa atcaaacaat    480
tgaatactaa tttgcgtaaa atacgtagtt taaaatatat atatatgtat atatatatat    540
atagtgtaat tttcaagtaa taaataaaat gaaaattaaa ggtttaaaaa taagctaatg    600
ggtgcttaaa gtatctacgg aaacgagatt gcattcgact cacgtacgac atgaaaaaga    660
tataaatgaa ttttacatta aaactattaa attgcacata tgattgtcca acaagtaaga    720
agaatcacaa tcaaagtaaa aagaatcaca atcaaaagag aatgtatcta atggatgatg    780
acaatttact taagatttaa gaattaatct aaaaatttag agagaggggt aaagatatca    840
acttttattt accagaacta aaaattatcc ttaggcctca attgctttag taatggatat    900
atatatatat atatacacat ctacctaaca aagctttaat aatagtaata ataaaaattt    960
aaataataaa taaagaaat cgaccaatat aaaaacatat aaaaaatgta tagttaaaaa    1020
gaaagagaga aagagagaaa gagagaagag tacatgcaag agatttgatt tggaaggagc   1080
acataatagg acaagagaag ggtaattttg gaatttgggt caattattct tagtccaagg   1140
gttacactac aaaaacctaa cagccttcac aaatttttcc ctctttcgct cgcttcgctt   1200
tgcccaaaca ctcgcctcca actccacgga tcagatccga agagtttggc aaaccctagc   1260
ttcctctctt caatctccat cttttttcttc tctaacaatc cacaggtttg tttttcattc   1320
ctttctcttt cgattttgcc ttcctcttct acttattcga ctgcacgaat atggttgtat   1380
gtatgtttcc gccctctttt catatcccctt tttgttcctt tagccttgaa ctactctggg   1440
ttttcttttc ttttttttact tttttctatt attgtatatc tcaagatttg acgctaatct   1500
ggtctgtggt tgtgggttga gttcgttttt attcgtttgt ttgtttgttt gtttatggcc   1560
atggcttgta attgcttctg taatctacgt gaatctgttt ttgctttgga acgttttgt   1620 tgttcaactc atacgagaat cgtcgtctat agttgggttg ggttttttt ttcagtagca   1680
```

```
tcttgctttg ggaaaaggtt aatgcggtgt ctttttttt tttttggaga aaaaaagtta      1740
ttagacatcc ctcaactcct tttcctacat tgagacagaa gtttaatgct tgttttcctc     1800
tttatctgga ttgcaagttt ggcttttctg ttacagattt cctttctcag gatagctttg    1860
aacagatttg taatgttgtt ctgtttattc cttggtgggg ttgataaaat ggttatgatt     1920
ttttgtttgt tggcggcata attctggata tttttatctg tttggtctgt gttcatattt     1980
gcattgtttt ccacttacag ct                                              2002
```

<210> SEQ ID NO 32
<211> LENGTH: 2003
<212> TYPE: DNA
<213> ORGANISM: Cucumis melo

<400> SEQUENCE: 32

```
tggatcgacc atgacattca aaacccttta agatatggat cttataaaat aaatgtaaag      60
ggtaaacaat tcttccttgc ttaacccaag ctatatattt tatgcactaa tttaggtatt     120
agagtatatt cagctgaaca ccacctacca atgctagtac tttaatcagt caattctaac    180
ttcgataata tatctcaacc aaattagtga aaaagagtcg taaatgaaaa actatgtacc    240
aagatattct atttgttttt tttatgttta aatatctcaa agataatacc taaaacgttt    300
tctcctcgta caaagattcc tcatttactt tttattgtcg taaactctaa tacaataaac    360
taaaacaagt acaaatacac tagctttaga aatctacttt ttattgaaac caaaccaat     420
aattcaacat ttcattttca ccgacaaacc tttgtaaaca attgaagtaa tttttgttgg    480
tactatgaat agtaacatca agtcttcaag tgcatcatat caaccaagac atgttcttaa    540
aagcgacact aaaagattta aaccaaaag catttatgaa atccgaactt aatcaaatcc     600
taaatatttt tcacttaaaa aaaaaaaaat aggaagaaaa attgacataa atgggatatt    660
ttcgttttca aactggcaag ccagcatgca ccacgttgtt gacgtgtcct tccacgtcgg    720
aaaaaaaaat attaccacag taaaagaga ataaaatgaa agtcgttgac tctcccttag     780
tcggaggaag cgcgtgaagc tgaagccgga ttagaaatcg gcaataaccc cgacacgtca    840
tcgaaatgct agtatcaaat attgtccgtt ggatcttcct tcaccaactc tatttgaacg    900
gccacgatct tccaggtcca acggttcgga agaatctttt cgaaattcca tggctagtcc    960
ctacactcct ccctattggc tcccctaggc atcccgaccg ttattccgg ttgccgggaa     1020
ggtggctgga cgctataaat acccgctttg ttcatctcgt agtccttgta ccgttgagct    1080
tcgccttcta atagagctct ggttcggttg gcgtattagc tcgaattctt tctctcttcc    1140
agatctacgc tgccgatttc atcaggtttg cgagctctgt tccaccattt ttcttttcct    1200
gaagctttga gcatgcttgt gattcttcat ttcctcattt cttgatggt ttatgaaga      1260
atttagggga attttctctt tttgtattct agtggtactg gtagatttgt ttgaagtttg    1320
tttctcttct tctgagaagt gaattcttcc agatctgaca gttgcttttg atttttctt     1380
tgggaattag tgaatgatac ttcgatactg tttttttgctc tctgagattc tggatctcgg   1440
gccttggggt tttctattgt cttttggtag ctatgtttcg tttgtcagct tgtatttgtc   1500
attgttgaat ggttcgatcc ggtttgtaaa taaatataat tttgtaggcg cacttgtttt   1560
ccacggtttt cgtgttacgg tttcatgatt ccctagatct ctggttagaa ctaagttttt   1620
tgtcggtaat tggatttggt aagggactgt tactgtggtt gaattgtaga tccagtcatc   1680
ttctacatga gtgtagggtt ccttagggca gatcttgtgt tttataattt taattttgtt   1740
gtttccctga ttttgaacct gtttggttgt tcagattcgt cgagtcattt ccattcatta   1800
```

| | | | | |
|---|---|---|---|---|
| aaagtttcta | taattttatt | tgaatcttct | gaatctgtgc | ttgtattacc cagatttcta | 1860 |
| taaacctatc | ttgatttcaa | gtgtgctatg | tggtaactgt | tgatattttc aagcttaagc | 1920 |
| aatactgatg | tgactaaaac | ttaactaatg | aactgaatgt | tttttgtaca cgaactaata | 1980 |
| tggtgttttg | ttatgtttca | gag | | | 2003 |

<210> SEQ ID NO 33
<211> LENGTH: 1372
<212> TYPE: DNA
<213> ORGANISM: Cucumis melo

<400> SEQUENCE: 33

| | | | | | |
|---|---|---|---|---|---|
| aaataaaacg | cggagacaaa | cttggacttc | cattcccttc | ttcttccttt ttcttgtagg | 60 |
| aattcttctt | tcttccttat | aaaattctcg | gaccctttt | ttttccttt taattttatt | 120 |
| tttccttctg | tagttcgttt | cttgatttag | attttcgaca | aaggtacctt ttacaggttt | 180 |
| gttccttctc | ttcatcgttt | actccgattg | atgcatttcc | tctatttca cttttggatt | 240 |
| ggaattatta | cgatctatgt | tcaatatcgt | ttgatccatt | ccctagatgg aaattatgtc | 300 |
| tctgtaatta | tacatagtgt | ttgatttgtt | tgggaaattt | tgtttctttg tgataatgtc | 360 |
| ttcatcgatt | tgatgatgta | tttgtttttt | ttttttggt | ggaatcgata tgatttatga | 420 |
| tttgggtgtt | tttttgcttt | tgagaattat | gatttgatca | gagttttct tattatttct | 480 |
| gttgttttgt | ttcatttcct | gccgttttta | aagatgtgtt | tagattctgg ttgtttttgt | 540 |
| ccttttgatt | atgttttat | ttttcatgta | gttggaaatc | ataggatttt cagataattc | 600 |
| atttggttgc | atagggattt | gaggattgga | agttcggcac | tctataactt tgcagtgaat | 660 |
| gatttgggtg | aagttttcc | tcttgtttgt | gctttcatgc | ttcagttgcc tcaaccaata | 720 |
| tcgcttttg | gaagtcttga | aaatctgtag | ctttgagctt | gtgtttagtt cgcaactgaa | 780 |
| gcttcaagga | aaaagtaatt | tctttcgatt | ttcgtaaaag | gggggaaaaa ggaagtaatt | 840 |
| ctactaaaat | tttctcctat | gaactcgtag | gtcacatagt | tgttatttgg tcagttgaca | 900 |
| ctctagacta | tcttgttacc | attccacata | actcaaaggt | tttaagaata aactcaatat | 960 |
| gggaatggtt | tcattaggat | tgcagagtca | ggaacaagag | aggttgcttt gcacaagtta | 1020 |
| catactttct | attcttaggg | agaaaagcca | gttgtcattg | ttcagggaga agattaattt | 1080 |
| ggttggaaag | atttattgtc | cttctgtctt | taggttgtca | ttggtttgtt ataattaaag | 1140 |
| tttcttgttt | cctagaaaat | agaagttttt | ccctatgagt | aatgttatac ttcattgtct | 1200 |
| tttattttgt | gacaagcaaa | cagtgattta | ttggatgaac | tacagttaaa ttctgaatcc | 1260 |
| attaattttt | ctgaaatcca | ttgtgattag | aatcatgcaa | tgccaactga agaaattttc | 1320 |
| accaattatt | aaatgaatat | gtttatttgc | agggtgtttt | aaatagatca ag | 1372 |

<210> SEQ ID NO 34
<211> LENGTH: 1122
<212> TYPE: DNA
<213> ORGANISM: Cucumis melo

<400> SEQUENCE: 34

| | | | | | |
|---|---|---|---|---|---|
| atatatttat | tgctagggtt | ttccggttcc | tgtttgctcc | actatttcag ccgcctaggg | 60 |
| ttgaaacaac | tcattcctcc | gatttcagga | ttactatctt | cctcctcgac cttctccggt | 120 |
| aatactttct | cttcacaccc | cttttgttgt | ttgtgatttt | taacttcctt tggattgaaa | 180 |
| tgcgagatct | gtgtgtttct | accactcttc | tttcttaact | tttcgatagt attgcatgtt | 240 |

| | |
|---|---|
| ccttacttat ggagaggata atgtgtactt agggatatca attttcgttc acagtattca | 300 |
| atattcatga cttactgagg tgtgaggagt tttcatttca tagaccgact gatgctatga | 360 |
| tctcaagccg agtttgaccc ctgttttttct ttttatattc tttttcttat ttttgtgtca | 420 |
| atatattagg tgatcaatga catcctaatc tattattagt gaattgagta ataagaagta | 480 |
| aagtcttgtt tatccaattt tttggtttgg atttattact attttgttgg aatgcttgaa | 540 |
| tgaattctaa tggagtccgt agaaatttgt tcaggcgtg cgccttttct tctcactaaa | 600 |
| tttttcatta ggaatgggtg tatttatttt caggagaatt tgtcgattgg cgatagttgt | 660 |
| cttgttcttt tcatttcct ttataaattc tttatggaaa aaatgtattt gctgcaacct | 720 |
| ctgtcttatt accctatt gaatcaatag agttcctgat ccttcctacg atgtggtttc | 780 |
| tggggatttc tctctgggtt cgtgtgatag atgggtgacc gagggaacac cctttattgg | 840 |
| aaatgctcct attcttcaga gtcggtttct cattttctca cctttacgct tgctgctgc | 900 |
| tctcattgac agtcgaaccg ttttggaatt cgtgatattg tgtgtatttt ggggatgaaa | 960 |
| gttttcttta ataagactag tgacagttca ttattgattg tggagaaatt tatgaccatc | 1020 |
| taattttaat ttgaacaagg gaggatgaaa atgattgggc gcattgcatg ttttatccaa | 1080 |
| ctagtactca tttttttcttt gttctgatat tcttcaggaa ca | 1122 |

<210> SEQ ID NO 35
<211> LENGTH: 2017
<212> TYPE: DNA
<213> ORGANISM: Cucumis melo

<400> SEQUENCE: 35

| | |
|---|---|
| actattggag acgacgaagg aaaactctaa tgtgagctta gaattgaaga tggtgaacaa | 60 |
| ttgggagtct ttttttaaaaa tctttcgtcg gtatattgaa atttccttt acactcaaat | 120 |
| aaccccccctt ttcacgcgtt caacgtcttc aaaccttcct ttttcaatta ttttttcgtt | 180 |
| tacattaatg acatttaggt aataagataa attagtggat tcttttgtga aaaatgttag | 240 |
| cccatttaag acttttatga aatatattag aaaaaaatca tatagcaatt tatattattc | 300 |
| tagttaaaag cccataatag aaactaaccc aacctaaagt aacgtaaaca ttcaataaga | 360 |
| gagacaaatt ttaaaataat ttctaattaa aaaaaaatt gtcaagaccg tccgggtcgg | 420 |
| atccaaaata taacccgaac cggccggttt agcatctata taaatacacc tttagggttt | 480 |
| ttattctctc aagacttcac cgcatttcca cttctctgag gccacggtca gccattggag | 540 |
| cagctcaata atcctttgac tccctactac ggtaagtcga ccttactgct ttcggcttct | 600 |
| agttttttca atcctgtcat tagtccttg gagttcttct gtacatttat gacgttttcg | 660 |
| gctcgtgttt tgtttcgcct gtatgtagtg gttttcga gttttgtttt tactttttt | 720 |
| tatacttgca ggaattagtt gaaatctatg tacttcatgc cttggataat actcttgatc | 780 |
| tgttgtgtta ttcaaaaatg aattgtttta agatggtatt tgagaatggt catgtgagtt | 840 |
| ttgcctactt ggttattaaa atgaattgtt ttaggatggt atttgagaat ggtcttctgg | 900 |
| gtatttggtt ggaacctttg tgctctgcta tgaattaggg tgttctcccc gttttttttt | 960 |
| tttttttct tttggttatt aatatatctt ttatgactac ttattcatat atgatatctt | 1020 |
| ttactcgtaa attttgactc atttgaaagt tttatcctta gtcctttctc attcagggtg | 1080 |
| taaaggtatg ttgttagggt taaaatagcc tatgcaggaa agttctgtat tgttctaat | 1140 |
| tattgcattt gtgtgcattt gtatctagtt tatttcttgc tgagagtatg cttcatttt | 1200 |
| tagtacacat cacttgtgcc actttattat agttgcacat ttttgtttat ggagaggatg | 1260 |

```
aatagcattt agggatgtca atttttatt gagaaaaccc tctctcctac ttaagcttgg    1320 ggaattttg ttctaaatgt ggtaaacata atacttcttc ttatttaat ttgaatggaa    1380 ggggaagacg aatactaata ttttcaacga accttcacaa cttttttc ttatttagga    1440 agccatgttt ttcaaaattg tactgtgtga tccacatatt tatcgattat tagtgaatcg    1500
aataataatt agagttttat tggtataatt ttgaagttca gacttattac atttgtggaa    1560
agtttggtta caattttcaa ttttattgga atcctaagaa ctttgtgtta acatatattg    1620
agttttcttc tctttttttt tactcattaa gttctctatt aggaatgttt ggttcaatgt    1680
cacatagtcg atagctaaga ccagtgaccc acaaagctat gattgaacga aaacaagcc    1740 tttcacatct tggtaggaat ttgttatttc tcaatagatt tacagagctg tttcatgtga    1800
tcacaatttt tttctatttt tctgaagttc tctattagga atgggctatc tggttagttg    1860
cttttgagag aacatgtgga ttggtgttgc tcggtttcct tgcctttgta attttgtcct    1920
tggaaaaagc aaaatgatta ggtatcctga tatgcataac atgtttaagc caactagttc    1980 tcacttttt agtgcaaata attgatcttc aggaatc                            2017

<210> SEQ ID NO 36
<211> LENGTH: 2000
<212> TYPE: DNA
<213> ORGANISM: Cucumis melo

<400> SEQUENCE: 36
aagttgttga ggctttcaat ccaaccaaat aattgtttcg ttttccacta caatttccta      60
gtactaaggt agcaatggat cgatccatag agaaccattt gattttcac taaaatcaat     120 ggttgctaag taaccaaggg aggattggtt gaattgattc ctaatttcac ttcaataatt     180
aaagcaatgg caataaaaca aaaattggaa gattgttgaa ttaaatttag caatgagata     240 aataccctagg ccaagactta cgtaggttac tttagattca caactcaatt attgattcat     300
aatgatatta gattccttgc aacatatgaa caaaatctta gttgaccacg tctagagaag     360
ctaatgtgat gttctataaa tcaaatcaat ccttatgtct agattaaaag catcctagag     420
atgaaaatca attggcatta aggtttgagg ctaaagctaa gtcgatcaaa caatttggag     480
ttgtctaatt gattgttcga tgtgatacaa ttctaaacta gttagataaa cgtaattaga     540
atggaattgt caattcaata aatgattcta acttagctta tgttatcttg cagtctaaaa     600
ataacaatta catattagat ctagatctat aacaattaat taaacatgct tggaaaatcg     660
ccaatatttc cgaacacact caatcaaaga aataagtcca aggaaagaat tcattaaatc     720
ttaagattca caggatgaaa atgttcataa catcacacaa gtgtgtgaat caaaagataa     780
gactagaatc tcgagataat agtaccttag ctatgataca tcctcgaaaa catccaacaa     840
aatcaatgaa agtcttgagt caattcgtct agtaaaatac gaagagttca agagaaaatg     900
cctaaaattt agtgccaaaa attgtgtaaa aagtgttggc ggctagggta ataatgcaaa     960
attaagtcac agcaccgcaa caacgtgcaa aacacatgtg ctatactctc gaaaaactct    1020
atagcatcgc agtcaacacg ataccgctac acaacacgtt gtagggctga ggtgtttgca    1080
tgaaattaga ccattctacc ttacagcatc gtgccttctt cgttccattt caattttctt    1140
gccccagttg acacactaaa cctccaatta atctcgttta atataaaaga taattatgat    1200
tttctttatc tacgaacaac attattgtga aaagatataa ggatgatata tcacaatttt    1260
tagggaaaaa aggaaaatat attggcattt attatctcta tcaaatagat gatttacaa    1320
```

```
ttatatgtta agatgtttta atccttgcta atgtgaatat ttattttatt tttgttcaca    1380
tgaaacaatg gtattttgta cactccaagt acaatagttt ctttaaaaaa atttaaaatg    1440
atacgtaaat tatctaaatt gacatcttaa ctaagcaaac aaaaatagtt gtttgaaaac    1500
tagacttatt tagtttacaa aaacatgcac cagatatcct cacttaatca ctagctctac    1560
acccaaaata tagactaaat aacttcacat ataatataca aatttaccaa actcaattcg    1620
gcatctcaat tggcgaaaga tcttttaac ccaaaagaag acgttggggc attaacttt     1680 caaaatgaac tttggcttca tagtaggaaa ttgggagtga acatgaggc tgaaaaggg     1740 ctaacaaaga gagcgatcgt ccacgtggtt ggcagtcaag aggtctttat agaagaggat   1800
gaagaacttg tttcccattg gtccgaaatc tatccaacac cctcctatta gatttcccttt  1860 ccagattctc atcttcatga ttcctacttg gctccattta aacccacaat tcaattcaca   1920
atatctccca cacatcctct tcttcatcat atcataaaac acagtccgtt acatacctga   1980
aatcttccat ctcaaaaacc                                               2000

<210> SEQ ID NO 37
<211> LENGTH: 1760
<212> TYPE: DNA
<213> ORGANISM: Cucumis melo
<220> FEATURE:
<221> NAME/KEY: misc_feature
<222> LOCATION: (1)..(1760)
<223> OTHER INFORMATION: n=g, a, t or c.
<220> FEATURE:
<221> NAME/KEY: unsure
<222> LOCATION: (1)..(1760)
<223> OTHER INFORMATION: unsure at all n locations

<400> SEQUENCE: 37
ataatgaata gcaaactacg taagttaagt tttggttact caaatttaaa cgacgtaaaa     60 aaagaagaa gaaagaaaa aatacgatgg aagaaatca cagagaaaaa agaaaggaa       120 aaaagaaag acgatggaaa gattaaacga cgtatagaaa gaagaagaaa agaagaaann   180 nnnnnnnnn nnnngcagc gaaaaaaaaa gaggaaaaca ataaagatga caaaagaaat    240
cggagcgaag agaagaaaaa gatggaagaa taaacttgaa ttggacaaat tttatggact  300
ttttacatag acactaattt ggttttttg ttagcttcct acaaattttc ctcttttatt   360
ttatttttgt aaaagtaaat aaatatgtgt cattagtcta atttttttgaa cttattttgg 420 gagagataga ggaagacttt aaaaaattat tattactctc cattttaatt ttgagaagag  480
attgtgttgt accattcctc ttattgcttc caatttcttt gagggcagcc ctagcctttg   540
tacaacgcaa gcttcctgta gtatctctat ctctctctct ccctcttccg acggtgatct   600
cttttctctc tctcacattc atcacccgcc gccgccggta gcttctcttt ctctgacgcc   660
accgccgccg gtaatctctc actcgtcgct ctcaacacag agaaatttct gattgagcat   720
caccaggtcc ggcaactaac attccttgct tctgcatctc tttttcttca atttctggta   780
tagttttgat ggatggattg tgtgtattca atcatttatt gtgttttgat ggatgaaccc   840
gtttattatt cttttttatg acttcaagta attgcaactg ggtacttcta tctgcaactt   900
cttggctgaa gtaattttta gttaagtgca aacggacggg ctgggaccga gccaatctaa   960
cgcttatttt atcgaatttt gaggagttgg ttttgtttgg gtttatagct taggaagggt  1020
ttttggtttc gaagaaccta ccatttgaag ggttgggtct aaaatgtcgc ttaattcgac  1080
ccaatatgac tctgaatgtt aaatattgaa tagaaaagaa atgaaatact atccctaacc  1140
tgtctgccaa tttcgtgcaa aaaagcctaa tagccagttt tttctcgccg gcagtacatt  1200
```

```
cgccttcccc ttccaagcgc tacggactgt tgctcaatct ccagaatctc tcaattcgca    1260
gggggcaagt tctttccatc aatcatttta tgtattttg cttctgccct agatcgttca     1320
tctaaagttc tttaccttt tcttctgttt tgttttttgg tgtataactt atttgatggt    1380
gatggattat gattcagtat cattttctta ttttatatca gcaacaaatt tggatttgaa    1440 atcattttt aaataccttt tgatgttaag ggtttaggct tattattatg attcagagtc    1500
attttctacg tgttaaatta gtttactttc caagtatgca gttatgttca agcagttatg    1560
cagtcatttt ctgatgtggg atagtgct gttttcctta aatgttttct atttaaacca     1620
ttgtgcgctt ggttggtggc cgtgcagata attgcatttc ttttttgga ttggggcagg    1680 ttggttactc tctggtttaa ctttcacaaa gaaccaagac agacatccgt aacttgtttg    1740
cataaagaca ttcaaccaag                                                1760

<210> SEQ ID NO 38
<211> LENGTH: 1767
<212> TYPE: DNA
<213> ORGANISM: Cucumis melo
<220> FEATURE:
<221> NAME/KEY: misc_feature
<222> LOCATION: (1)..(1767)
<223> OTHER INFORMATION: n=g, a, t or c.
<220> FEATURE:
<221> NAME/KEY: unsure
<222> LOCATION: (1)..(1767)
<223> OTHER INFORMATION: unsure at all n locations

<400> SEQUENCE: 38
aatataaata aatctcatta ctctttatga gctagaaagg atgcctaatg gacctacaga     60
ctagaagcta caacgatatg agattaattg gctaaactca ttaaccacat tatgatatat    120
ttgttaactg tgtgtacact ccactaaaga ctcgcagctg aactcttctc actgtagata    180
tatttatgtg tccacggata tagaccaata ccaataagtt agtccttcac aagtgttcat    240
aacactagct gggtcaaatt actgttttcc ccttgggtta cttctagtcc ttaaatacca    300
atgctcctct aatgaacaac ctgtttaatg tccaaccact aaacagaatc ctttctcatg    360
ccatagagag ggtaagacct tcaagtcctg gatacaccat ttaaaggagc gcttatctat    420
ttaccataaa gtcaagaagg agtgaattcc atcttnnnng attatgttcc cagctcccca    480
cccggttttg tcctcaaaat gataaatata ttgagttgac aatctgacca ctctcacccg    540
tacaaatcaa aagacaatcc ctcgcgaata ggagttcata atatactcat aattaagact    600
aagttatcca tgtcattcta atgaaataga aacccaacta gttaatggag ttacatcttg    660
tggttactat ttcgtggtcg ggtcttatgc aaactcatta catacgatac cctcactcgc    720
atgtcgctta cttgaacatg ttgaataaat gcatttatat tagatacaaa gtaagtcgta    780
tccatagtgt taccaggata agttacctag ccttaaccct atactataga cnnnttaagc    840
tgatcttgaa cattgtttcc tgtatgtctc tacatactgt tcaagactca tcaaacaact    900
caagatgtta atttattgga tttaggttat taagataaaa cgaataatat aattaataac    960
acttcttgaa attataataa tataacactt tattaataac taccaatgaa ttatatttac    1020
tatatacgag ttttaagaca taaaatccaa tataagggtg tatgaactgt taagatgat    1080 gtgctattct tgttggatat tataggaggt atttagtgga ttatttgtga aagaataagg   1140
aggtacttat gggaagactg ctggaggtta gggaggatct ttgaaaatta ggaagtaggg   1200
atcaacaaaa aaaacgaaag ggaaagctta agcttaaaa aagaaacgaa ataagaaaa    1260
```

```
atgatttaga ccagcatact aaaatggcaa tgtaatctga ggctaatgta tcaattgaga    1320
actttgtagt cataatgatt aatcccaaac aaattagttt tcaagaaatc aaccccaaat    1380
aaaatgactt aaatattgaa gagtttaaat ggtctaaaat tattgttact gttttttatt    1440
tttggaaaag agacgaaaaa ggaaaaataa gaaacgccca ccgtggggct cgaacccacg    1500
accacaaggt taagagcctt gcgctctacc gactgagcta gacgggcttg gtgtccaaaa    1560
atccaataat attgaaaata ccatatagtt taatgaactg gcaattggaa ataggcccaa    1620
tatattagat atagcgaccc aattgttagg cgtgtcttct tccaaaaatt ggaggcaaaa    1680
cacaaaccct agcatccgct tctgctcctt tatcgtttct ctcggcgatc aattttcacg    1740
gagctaggtt taatcaagct tcaagca                                       1767

<210> SEQ ID NO 39
<211> LENGTH: 2000
<212> TYPE: DNA
<213> ORGANISM: Cucumis melo

<400> SEQUENCE: 39
tttaaataaa aataaaaacc atctctttat tttaagtagt taaatgattg tcgtttacta     60
aattaactct agcctatttt aagacggtct ggtcaaaaaa tcgattacga ccgaccaata    120
ttcatctaac ggtcttatta tttttaaaag atatagaaat gtatctcgtt aataaagcca    180
cgacggtctt tttctaataa aaattcaact aaaccatata caaaattat tgtaccatga     240 aaaacacttt catacataat gcaaacaac aatagcaaaa accaaagag gaaggggaca     300 atttggggaa aagtaatctc aaatttccct ttttgacttt gttctaaatt agtttattga    360
aataaaatct actaatttcc catttccaaa ttaaaatgct taatctttgt ctcattagca    420
ttgctagaac aaattgtctt ctcaaaataa aaataaaaat acaatatcaa ctatttatac    480
ttaattatct aacatttctc caacataaaa agagttatat atatatccta ttttgttctc    540 taattttttcc tcttttttg gtaattaatt ataaatattgt cctaacatat tatattagat    600
agcttcgaca aaccgttgct taaaaaaga aaagagaaat ccaacctaac tcaatccgaa    660
aatatacaaa gtacaaaata attataataa ggtagatggt atatgcatca atgaaataat    720
attgtcaact ttcctcgatg atgatggtaa taataataat aattttatat ttattaggcg    780
taatattttc ctcaattttta gtgtttgtat atactttcat atgtttaatt taagttttaa    840
aatttagtcc ctcaattaac ttgaaattaa ttaaagaatg tgaaaatgtt aatgggtgaa    900
ataaataatt tagagaaaaa ccaaaataaa ttagaggtag ggagtaattt tagaagttca    960
aaaaaaaaaa aaaaataaat tagatgtttg aaagtacaga tttgtttaaa tatgaaccaa   1020
cttcgaatag tctttccatt ttttcttata aaaagtcttt ctgatgtgga tactagttag   1080
agtatcctat caactcatcg atccaaagaa catactttca atcgtaagtc gtccattcta   1140
cttcgatcta aaatgatgct aggtttgctt caccttcacc cttcacaaag acaagtgcag   1200
gtgtgcttcg ctctatcaca tgattttgat tatgtcttca agaacttcac agcggtttta   1260
aaaaaacaag aaagaaaaga gtgagagtgt tttatgtca gaaacatatg cccaagctta    1320
tgaaacttgt tgatccttgta gcgattgaat aacaaatgga agtatctca tacaatttct   1380 ctatttttca cttttatcga agaactttgt ctcactaact cgtaatctaa aatacaaact   1440
cttcgactct aatatattaa ctccaaactt cattttcac atctatggaa cagataaagg    1500
tctaattttt taaaaatatg atgggaatta agtatagta aagagattag cttcatcaat   1560
gggcttggat tggagtccaa agggttagcc caaacccaaa acatagtaaa tccaagccct   1620
```

```
ggaacaatga atagcacgga aagtttgtgc tgccggagga gcgtattgga aatgaagggt    1680
ttaggatagt tatggagcag aaaacgacac cgcatcatta aggacggatt tgggatttta    1740
agaatatatt agggacagaa taggaatttg aaaagtagcc ctagccactc aatttggtaa    1800
cagtagcaca aaaattggag gataccaagg gtaagcgaca tggggtaata cacagaattg    1860
tggctatggc agaattggat agaactccca tttgaggctc tcttttctct taccatttct    1920
acaagataac actactcttc ttcactctcc aaaacccat cttcttcttc ttctcttagg     1980
ttcctctctc ccttcctcca                                                2000

<210> SEQ ID NO 40
<211> LENGTH: 2000
<212> TYPE: DNA
<213> ORGANISM: Cucumis melo

<400> SEQUENCE: 40
aattggaacc tgctgatatg aaatgcataa gagaactgaa cctatcagta tcatgcgaaa      60
cctgcagcat agacatacta ccgtgatgtt tcaattttc aagcaaacaa aatatccaaa      120
aacacacaaa atagaggaaa ataaggcgaa attacaaacc tctctaggat tttcaagatc      180
ttccatattc ctctcagatc cgggtgtaaa gacaaccagt tcgaagttcc aaagctgttg      240
caatactact tgtctaaacg tcatagcaag tatattttg gacgaggtac ttgaatggaa       300
atcttgagcg agagactttc tgagcttcgt ggccttttcc ttgacttctc tggcaggtaa      360
aaactgttaa cacagtcaac ttaggaatga caaatacaat cggatagcta aattttatct      420
aacgacaata ttccagagag gggagagaga cacattgttt tataacaaga ctcccaattt      480
catgagatga caacatcgca cgacagtcaa acaaaattct aagagaacat caaataatac      540
tagaaacgga catattagtg aaggagctct taaaggtagc cttgaaccag agatgggaac      600
gccatcaaat caatctcatt catcaatcat ggagttaatt gttccgatgg tggaattcaa      660
aatcggtcat agattttat tttaagaata aaaattaaaa tggaggctcc tgaagctaac       720
atgccaggtg caaagtttg ggagaacgcg ttcacgtcaa cattcgaatt cagtctcata       780
aatggaaatt gtagcaatga cgaaaaatat tcatagttgt tagtcacgga aatcggttcc      840
ataatacacc accgtcgaat gcgagctaaa acgagcacca aattacgcag tcaggttaaa     900
aaataactaa ccagccgggt cgagacagtg ctgtgttcat cagaaattcc cggaaataca      960
gtctccacaa ccattgcagg catcccagaa tcaaggtgct cagtggcggt ttcaccgcca     1020
tcagccgcag ccgcagtaac agactgccgg aaatcgacgc ctccgaccag agaaagccga    1080
gacaagtcat tctcgtacgt ccggacacag ggaagaatct tctcatcgga ctccagcaca    1140
gcttgaagaa cctcttcctc ggtcgtcgga attggcctcc cagcagagca agagaaggta    1200
gaaaagcaat gccttgagtt tttcagaaca attttgggag tataaattaa gggtatagca    1260
aacagttggc gagctggtat agcctgtata ggagaataat ggataaaaga caaactcaac    1320
gccattggag aaatggccat aaacctctga gcgagtgcta gggttttcgt tttatagtgc    1380
tactagctgt gcgtcgccgg agaagcgatg tctcgtgccc acatcttttt ccctccattt    1440
cttttcgggg ttatttctct atataccctc ccaaaatatt acaattaaaa cagttccatt    1500
ttgttttaaa aaaataataa aaatttattt ctcaataatt tttttgaaa attgaccgtc     1560 aatttcgtac aatctacttt taagaaatg attacttcat ggatggtttc taaagggaat     1620
ccaaaattta aaagtttaat taatttagat tatgtttat ataacattga ttaaatgaaa     1680
```

| | |
|---|---|
| tatgaaataa ggtgtaagtt gatattagcc ctaatatcaa agatgagggt aaaagtaaaa | 1740 |
| taatagtgaa aagatatcca actgattctt gggtaccggt tcgggtaggg tttgggggaa | 1800 |
| tccggttggc gttttttgag cacagagaga tgtaaacggg acgggaagaa ataaaggcca | 1860 |
| acacaactat aaattctcct ctcggcggaa aggcggagca gcgtccaact tcgcctttca | 1920 |
| caaaatttac taagaggggg cttccattct acgtcgattc tgctcctctt ctacttttc | 1980 |
| ccttctgctt tttgtcgacg | 2000 |

<210> SEQ ID NO 41
<211> LENGTH: 2000
<212> TYPE: DNA
<213> ORGANISM: Cucumis melo

<400> SEQUENCE: 41

| | |
|---|---|
| ggtctcagac ccataggaat agatcattta ttgccttatg aattagttta tgagtacata | 60 |
| ataattgtca accgtataca aatcaacatg aaagaatata atgttgtaca tagtcattcc | 120 |
| aagtttacta atattatatt ttaggagtgt tctacaccga acctgtcaca tgtacactgg | 180 |
| gtatgctacc cctgaattca atatcataaa gcaactttaa ttgtcaagca ttctcttgac | 240 |
| catttgtgac ccatttgctc ctactttttc aatcaataac tatcacaaaa agctagatac | 300 |
| cacatgtgat aaactcactg aaatcaggta tatggttacc tgtgcttggt cagcactcaa | 360 |
| tcagattcga aggcctagtc tttgtatttc cccccctctg cacactacaa atagtcctcc | 420 |
| acgtaaagac ccataacaaa acgcaaacca agtacagaaa atctagccga aatccagacc | 480 |
| actcaaacat aacaaatctt ctggtaagtt tgaataaaat ataaaactaa cctaatttaa | 540 |
| tcaaataata caataaaatg gaagcaacta acataacata tctaaatatg atcacgtagt | 600 |
| aggaaaaaaa aaaacattcc aaaactatta acaatcattc ttaatggtat gggtcaatcc | 660 |
| ccattattta ggactataac aagaattcct catacctaat gccacatcct atgtccaacc | 720 |
| ctcgagatta cctcgtgagt aatcaatctt attcatcctt atttcaaatt atgtgaaatt | 780 |
| tctcatcagg ttgatcatat tgactttcaa tacaacttat gattaatctt tcccttgata | 840 |
| taatttcgta tgaaaaggaa gttgacatta tgtgattttc tcataaggta aaccaagtaa | 900 |
| acttgacatg acgtcttaac aagtcttggt ttctaagtgt aatttactgc agaaaaaatc | 960 |
| ctaaattcta tgacttttcc tatgagattg accaaatcaa ctttacgaga atcttggga | 1020 |
| agccatacct acaaagtctt cccccaagaa attacaattt ctagtaaaga ttgttgaaat | 1080 |
| ttaccctcca attttccgt gaaatttgac aaacttgtaa gaatatcaaa tttgggttgg | 1140 |
| atattgacat tccaaaataa gtagttttaa aaaggattta tccaacaata atagaagaaa | 1200 |
| aaagatagga aataacatac ccacgtaaat ggaatgtaaa tatttatata ttaggtgtct | 1260 |
| tgaacgaccg tcaaacgaaa ataaattgtt catccgaagt tgaaactctt taagtgtaca | 1320 |
| tttatctttt cgtaagaata aaatgtaaaa ttaacgtgtg aaaggttggg ttaaataagt | 1380 |
| tatgtagaga taatattgaa gatgatagaa taatcacgat cgatgaatta gtatagtccc | 1440 |
| agagcggatt taaacctctc tcactttcat gctttctata tatatcaaaa taatttcaag | 1500 |
| tagttggttt agtcgtaaaa aagtcaacca atctctttta gataaaccct gagttattaa | 1560 |
| aaaattagat caaagataat cgttgaaatt gaaattttaa gagtataatt ataacaaatt | 1620 |
| ggaaagttct aaagtagttt ttgcaatatt ctccatcaaa atagagtaga aaaatatttt | 1680 |
| agtaattttc ttatccttaat tttagttttg taatagttat taggatggtc ctaagttctc | 1740 |
| aatccgctttt tagtccataa aaagaaagaa gagagagaaa aaaagtcccc gatccgcgac | 1800 |

| | |
|---|---|
| acataccaat ccaaccaatt atgcacaatc catgtgatat cgaacggtca caagaataaa | 1860 |
| tgctttctac acacggatca ccatccaacg gcttttcctt ccatctcatc ctctatataa | 1920 |
| tctaccaact ctgtcatctt cgacacactt caattatctc agctttatt tcatcggatt | 1980 |
| ttccatcaaa caaggcaaca | 2000 |

<210> SEQ ID NO 42
<211> LENGTH: 2000
<212> TYPE: DNA
<213> ORGANISM: Cucumis melo

<400> SEQUENCE: 42

| | |
|---|---|
| actccattat ttggtttgat taaagcttcc atctgattaa taaataataa taattataaa | 60 |
| ataaaaaaaa gcgagagttc cattaagtaa tattatctac cgaaagagag caactatcac | 120 |
| ctcaaacttc aaaagataa aatagagacg aaacttgacc aagtcaaaca caaaccacaa | 180 |
| acaaccgatc tgacagaaag tttgccagaa tcttcaatgt acacgcgaag ataaacaaat | 240 |
| aattaaatct cgttcgtctg dataacataa cacagcaaat gaattttttt aatacatatt | 300 |
| ttaaaaaaga aatttaaaat tggtagattt tataaatcat ttccaaaggg ttttttcttgt | 360 |
| tttaaaatgt ttttttgttt aaaataggca gttcatcacc acttgagaag atccaaactg | 420 |
| ggcggcaccg gttctgcgac gcttgagggc cgtctccgac tcttcgccgt aggaggccga | 480 |
| tttacgcaaa gaataaccgg acaatgttgg acagttttga cgagaagtta aaccgagtaa | 540 |
| gggcttatgc ttcttctcaa tgcgctcgtc gtcgtcgtcg gcgacggcgg cagcggtgat | 600 |
| ggggacttgc tctgttgcgg ggtgaacatt gggattccga caagaaggtg ggttcttagg | 660 |
| gttggaggga aagtggaaag cgttatgggg ttcttgatgc tgttcctgca acttttgctg | 720 |
| tttgaggaag cgcttttgga gatctaaaag agaagggcga cccttttttct tcttcttctt | 780 |
| catggtggat ttagaaacct cgcccattgt tcttcttccc tttctcgcag gaacgaagcg | 840 |
| cagggaggtt aattgatttc agttttcacg gcggagggtg caggatttct aggcacgtgc | 900 |
| gaatcgcatg accctatcac gtgcgaatca gtgacggtat aacgtgcatg caaaggaata | 960 |
| gaaacacaaa ccgctcttac aattataaaa ctctaaacta aactacgaac gcatctcata | 1020 |
| atgggcccac tccatcatcc tatgggcctt tgaatttta tgtatactat ttttttttt | 1080 |
| tttttttttt tctttaatca caatcaattt ttctggtatt ttttaaata ttcaacaaac | 1140 |
| tttttgtttt aatgttgtgt atatctaatt aattagttt tattggatgt catttttct | 1200 |
| attttgaaa aaactcttaa aaaaaatata acaaaaaaa gaatgaaaa agaatatcaa | 1260 |
| acaaagagag gagagagcaa ccatacctaa aaagtttgaa agtaaaattg aaaaaaagaa | 1320 |
| tatacattga gggcagtgtt gaaaatgaaa ttaatgaaaa aggaaagggt acgtaacaat | 1380 |
| aaattacatt ttcttgcagg cttaaacgaa ggcccatata tgaaaaggga agcttcgatt | 1440 |
| tgggttcagt tatgcgggcc tgggttggt attgggctta atttataaa gaaggcccaa | 1500 |
| atgttggaaa gacgggcttt gagagagggt gttcggcttt tgcccgaggg gggtggggga | 1560 |
| gtggcaccgc caagcgaaga caacgaatat taggagagaa aacacaaaga ggcggagaga | 1620 |
| tggaagagaa tgaggtggac caatgagata agagtgcgca gattattgag gtggcaataa | 1680 |
| atttagaatc ccgcctaaat cccagctttc atttcatgcg caattgaatt tcaatttgcc | 1740 |
| attccctcc atagggactt aattatcccc tttttttttac tctcataact ccctctcttc | 1800 |
| ccaccacgtt cgcttcttcc tccccctcc tcttcaaacc ctaaacctaa cctaacctaa | 1860 |

```
cctccttccc caacttcttc cgtcggtacg tttcatccat ctcctcccac tttttcatctt    1920 tttttccttc taatttcatc tcttttcttt gtttttcctt ccaattgttg ctgatcccat    1980
actatactgc aggattcgaa                                                 2000
```

<210> SEQ ID NO 43
<211> LENGTH: 1115
<212> TYPE: DNA
<213> ORGANISM: Cucumis melo
<220> FEATURE:
<221> NAME/KEY: misc_feature
<222> LOCATION: (1)..(1115)
<223> OTHER INFORMATION: n=g, a, t or c.
<220> FEATURE:
<221> NAME/KEY: unsure
<222> LOCATION: (1)..(1115)
<223> OTHER INFORMATION: unsure at all n locations
<400> SEQUENCE: 43

```
aaagaaatca aagcgaaaaa acgaggagga aaagaagaaa aacgannnnn nnnnnnnnnn      60
acataaataa agaatagaaa aataaggaag atgaggaaag aaatcgcaga aaagaaaaag     120
agaaaagaat aaagacaaaa ttgcagggaa agatggagaa gatgaaataa taggaagaag     180
acgaatcgcg agaagaaaat aaagatgaga gggcaaacct gaaatattta aaaaattgct     240
aactttatgg gttttgttac acgggccgta aatagttttg ttacatttat gtaaatttac     300
aatcaattaa ttatacaatt aatcaaattt ccacaaatac aataattgga tattttccca     360
aaatatctaa taagtttcaa tttctaccca tcaaatattt caaccattat taacaccaaa     420
aaattcaaag attaaactta agataattac aaanaaatta ccttaaattt ggggcattac     480
acatttacat tgaactatac aattgtttac cataatcaaa cgatcgtttt ttttatgatc     540
gacatgataa tttcctatga tcaacacgat tttttatcat atcaacacct tcatttaaat     600
ttgaagtttt tttcccatcg ttaaaagaa gtacacgatc ttttagaaga agattacttg      660
cgcgggctga ttaatcgtct gttgactgtg acattttta tatttttcat catgagcctg      720
tatgtctttt ttgtttttat aattgtttta catcgtgtaa atagtttgcc gattagttat     780
atttgttaga aaacacttt tcaaatgtcg aaaatttgat tttgatttat taaaactta      840 gtaaaggata gtgtttatta cgtatagaat cccaaatttt cacaataatt tttcaaaagt     900
aatccaaaag aaaaaagcaa caataataaa aggctcaaag cgacgtcgtt tagggcaaca     960
gctggggaga agaggacgat ctgaaaaatc atttcttgag cgaagggaaa aggagctcta    1020
ctaaagcagt cgaaaaaaga aaactcaaac ctcgctgcga ctctcgacat tgattctgtt    1080
ttcaattcat tttgccaaag ttaatcgatc cgaac                               1115
```

<210> SEQ ID NO 44
<211> LENGTH: 2000
<212> TYPE: DNA
<213> ORGANISM: Cucumis melo
<400> SEQUENCE: 44

```
tatagtttgt aacaatctac tctatgttct ttcaattttg atacatttga atcttaaact      60
ttattgagtt acacaatata gtccttgtat tttaaaattt ataatgactc tatttatatt    120
aatattatag aaattttgt taaggtttaa taaaaatttt tctgtataaa taaatcgaac      180
acgaagtcta tatttagact gcaatatagt aaaacctgac atctaagttt ggtgaatttt     240
gttttgcttt aaaaactaaa ctattacaat tttaaaaata ttttaattta gttaatgcac     300
attaacttta cggagtaaat ttttacaaga ttgaatatac atagattaaa tagttataaa    360
```

```
accaaagatt agagtaaaaa catttaaata gaaagaacta agattttttt aaaacgaaaa      420
tgatactaga tacatatata tgtatctata ttataattac tcattttaac atatagtttt      480
gaaagaacaa agattagttg catgtgttga ttgtttttaa gaaggaaata attttgaat       540 ggaaaatttt caaagttttt aaatttgaca ataaactcat atttaaagtg tactacaaat     600 tttaacttt ggttaaactc cttgtttagt tcaatcatgt aataaattct cattccaaga     660
atcgttttag aaaattttat tgtgcattta ataaatata gaacatatat ggcatataaa      720
aattgattac ttttttcttt ttttgggacg aaaaacacat tagatataat cttttttgaa     780
agtttatgaa ctttaaaaat gggttatttt atacggtggt caactttatt ttattgaaat     840
tattgagttt ataaagattg ttatatcatt ttcttcttct ctttcactag aatacaatca     900
aacctatcaa actctctatg acttatttag aattctttt gttatatttt tgaaattaat     960
aaatgaaaag cttagagtct aaattataac aattaaaatt gaaaattttg caataatttt    1020
atttttagca aaatgacgtt tggttttttgg ggattgggaa tggatcgata ctatcccgat    1080
tccggacaaa gaaaccgacc cgagattcga attttttcca ttcccaaaca gagcacttaa    1140
aatttaagca acgttataac ggcgtcaccg aactaaacgg aaaaatatga agaaaattag   1200
aaaaagaaaa acggaacagt caaacgttac ttcacgtcaa tggcaatatt cattttttt   1260 tttgtttaaa taattgaatt taattaattt ggtttataaa aatagagtcc tcatatatcg    1320
cgaatgcgca tttgatcgtg aaggacagct tctcccttgt gttcaagaga gagagatcta    1380
tcattcttat ttggggccga tctctctatt ctcctctctt ctattccgta agttttctc    1440 attcattctc ctctctcatt tctctccgag atctgtttac aatccttttg attttcattt    1500
ttcctgcttc gatctgtgct cctggtgatt ccctttcct gttttatctt ttgttgatct    1560
tggaattgat tgttcttttg tgggttttca ttgatttgta ttttctgatc tgggtttctg    1620
ttttctcgcc ttgatgtttt gtatttggat ctgatctgac gtaccttttt tttttttttt   1680
tatttgaatt gcttttccaa tgtttatacc tggatttta ttgatgcatg ggtttaaccg    1740
attggttgga tgcgttttct ttgtgctgga tctaggtgtc cttgtttttta atttgaattg    1800 tgggtaaaaa tggcattatt gtaatgtgtt tggagtttga ttttgaatct tggctagttg    1860 attttttgaat tacaaagatc ggatcctctt cttttttggg ttgtcttaag attttttggct  1920 ggtttaagta tttgatgtcg ttgtattta agggtaact gatgccggct tgttgtgttt    1980
gtattcagtt tacttgaaaa                                                 2000
```

<210> SEQ ID NO 45
<211> LENGTH: 2000
<212> TYPE: DNA
<213> ORGANISM: Cucumis melo
<220> FEATURE:
<221> NAME/KEY: misc_feature
<222> LOCATION: (1)..(1115)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 45

```
attatctaaa cattaactgc aactaataca gattacagta aatttgaatt atgatgttat       60
ctagagtcat ttgtcttcaa tgatattgac tcagattcaa actttatgaa aatgttaccc     120
tggaaaatat tctaccgcaa aatttcaatc caaagttaaa ggttgaataa tttagaagtt     180
```

```
ttctgcgact tccacccact tattatttag aagacctgaa atcaaaatga tagaagatga      240
atataaatat attttttttgc tttaaaattt ataaatcaaa catttgacct agtaattgat      300
aatacataat attatgtgac tcgtaagtaa aaaagaaatt gaaataatat atatatacgg      360
agatcgcaaa aaataaaaat gaaagtaata taaagtaaac gcaaagtaag aaagcaagca      420
ttttcaagta agattgaaac ccccgtccct gggggctcca agataacacg ggtgcccaat      480
tacccggtac acgacttttg ttgaacaaca ttgataatt  agcccaaatg aaaatatttg      540
tcgacatatc tttcttataa tatgtaaatt agataccaac acaaacactt gtaacaatat      600
cctaactaac ttggttttaa atatatatat atatattatt ttttttttcta tttatttatt      660 tnnnnnnnnn nnnnnnnnnn nnnnnnnnta gataccaata tttagtggcg ggtccataaa      720
ttttatatag ggttattata taataaacac taaaaattta gatattatta ttttcaaagt      780
taggccacaa gtaaaagtgg ggatataatt attatactat aaccatattt tggtaaaatt      840
aagtattaaa tactttaa aattaatatt aaaatataaa atcgataat  gtgtgggata      900 aatttatgga tgtaaatatc aatgttttaa tgttcaaata aataaatagt aaatagaaac      960
aaaacaagaa gtcagtcttt actactaatc gggactaaaa tttgaatttg atttaaaatt     1020
taaaacttaa ataggactaa aaatgttagg acaaaatagt aacaaacacg aaatttaggc     1080
aaagaaatat aattttattt atttattatc atttttttta tatatataat tgaaaattga     1140
ttactaaaaa aaacaaagaa cggtaaaacc ctagattaaa atcaaaatag aaannnnnaa     1200
cccgaaagga gaattttgat ttccagagct aaacataaca cgatccaaac ccataaatcc     1260
cgcatcgagt ggaaccgata tcttctcccc ttcgaagttc caactctccg tttccgtctt     1320
tcttttcgat tctccttcaa accctctttt cttcgtcttc ttcaaatctc tacatttcaa     1380
aatcttcgct aatctcttct tcccctccc ttccgatctg accgtgaccc cattcgaagc     1440
ttcttctttc accaagcttt ctctccgcta tcaactttaa ctttcgtcct gtattcctta     1500
gccttccctt gcttttgcag tctccgccac cgaacaattc ctatcccgag ataatcccac     1560
ttttgggtcg tgtttctcac ttattcaaat cgctggttct ttgattttgg gcttatttca     1620
ctctgcatct gctgcgactt ggaggttata acatctctct ctcggtcttg ttaggtatga     1680
aggatttgag atattttcta atctatctga actgggtttt cttcgcttc cgtttatgag     1740 atgtaatttg ttgttctggg aagttttcag atcctttcta atgggcttct ttaatttaat     1800
ttaaagcttc tttgtttgta cgagatgtca agtcttaatt tctagcaata tcagtatctg     1860
ggttggtggt atttaggatg atcaagtctt ttgttattta atggatgaga acaattattg     1920
tcattgttat tattattttt tggaaaaaaa atcaatgggt tttcactggt tttgttgatc     1980
tttttagata attgaagttc                                                 2000

<210> SEQ ID NO 46
<211> LENGTH: 2000
<212> TYPE: DNA
<213> ORGANISM: Cucumis melo

<400> SEQUENCE: 46
cttctcgatc gcagcaattc aacttcataa acaagtccaa gaacgaagag tttgattccc       60
ctaatttaac ttaattttct ggtgaaaatg gaccatactt ttaattacat attattttgg      120
ttattgcctt ttaaatggtc tattttaatc tctaattttt tttattaaac aatgatggtg      180
aatcttttct aaaagaaaga aaaaacttct ttacaaacta tccaactcta ataacaacac      240
taattataaa ctagtctact acctttatta taacagcaat taaaagaaaa aatcgtattc      300
```

```
actgacaaaa attcgttctt ttgaatgctt atcgaatgtt ttaatttttt taaaaaaata    360
tataaatatt tgtaagggaa ggatcagaat taaaactctc tccectcaat gaaattgaat    420 tatttgtttt tcttgttttt cttttttaa aataaaccta tggatttagt tggtcggtcg    480
aattaaaatc gtgaggtcgc acacgcggtg tcttgtggat tcaaaattat gattatttcc    540 atcaccectt ggcttttcg ctccattcgg ccatgcctta caaatttcgc tccactccca    600
ttcttctctt cctctcctct ttcaactgca ttgaggccga tcctttaggt aaatggttct    660
ctcccatttc atctctaatt cctctgtttc ttttattt acttgttctt tttccagccg    720
gatcctccat ttctgtggtg aaactgaatt gttcttatcg atttcttgtt tgaattctgt    780
ttttctctgt ttgtgtctgt gtgtgttttt aatttgtttt ggcatgttga agtttaaaga    840
taccaaaagt tgcgcttcac tactttccag tttcgatggt agctgctagt tgtaacgctt    900
acgttcttgg ttttttagtt aaaattttt tgcttcttgt tgtttactgt ttagcaaaaa    960
gcatggggaa tactaccaaa gtcccgaact taatagatag atgatcatgt gctaagaagt    1020
gcgatacttt ccgtagctga tacgtgacac agtgtctgac atttgtttga cacatattag    1080
aaacttgtta gtataacata tgtgttaaac aggcatagaa cacctgttgt actaaaaaaa    1140
atatttgtat gataataata ataactttga agtgtaaaat atccagct aagttttttc    1200 aagtatacaa gtgcattaac tcatttcctc ttgattttct tttggtataa aaattatata    1260
tattttgaaa accgtatact ttaataaatg tatccttgtg cattatgtcc tagatttta    1320 gaatatggtg tgttgttgtg tctatatcgt gtcgtatcaa tatctcgtat tcgtatctgt    1380
gtttgttaga tcatatgtat aagcgaggac agctatttct gatgttacaa gaccttcttc    1440
aaattttaca ggaaatcatt caatttgaaa attcaagatt acaaatgcaa tctaaaccaa    1500
acttcaagaa caaaaagtgt tatttgttaa tatccttgcg acctcaccca agtatctat    1560 tacaaacttc agaaaaaact tcataataag ggttgggttg aaaaaaaaca tgaagaagtc    1620
ccaccccaac ctaactctaa aaagcataaa aaattcaacc caacccaaac cttacaattt    1680
gggttgggta gtccgtgttg ttcgggttgt cgggttattt gaactcctag ttttagctaa    1740
gtgtaaactt atttaaggat gttgaaggtt agcattgatc tttctctctc aaatttggtc    1800
aagaggaatt attttttgag tcattcatat agttccattt tgcttttgag catttgaatt    1860
gtttgttaac tacttctttg attaatatat tcgaaagtga aatttccttg gtttacttta    1920
ttgatcagtg tcccatttta ccagttattt cagttctcct aataaccttc attggacttg    1980
agttcggtta acacaaaaca                                                 2000
```

<210> SEQ ID NO 47
<211> LENGTH: 2000
<212> TYPE: DNA
<213> ORGANISM: Cucumis melo

<400> SEQUENCE: 47

```
aatgtatcgt gggcatttat tatgacaata gtgtaaaaat gttgttaaca tatctgtgta    60
ttgtcgatga tgtagatcta ctacgccaat agttatagtt tccatcggta tatctatgaa   120
atgtcaacgc cttaaaatag ttgcatgggc atagacttgt tttttagaa aaatatgttt    180 tatatttgta ttttttttcac taacatcctt ttggttttgt atctaaacac aactcaaaat   240
atatcaaata ctgaaattca tttcctaaaa aagttacaat tgtttcaaat ataagtcacc   300
tgaatgaagt tcttaaaaca caaagaattg ttccttacaa aattaacata agcaaaatag   360
```

```
taagatcgtc caaaataaca acattacat aaactttaga ccaacttcta atttgtttgc      420
caggaagtga tctccattga aagtttgtct taaaaaacaa ataaaaagaa aataatagaa      480
acatattcaa taaactagta cattttgcac cttacatata tatacaaaaa ctttacctac      540
tttaatttct tgaaaatcta aattttgaat taagaacttt tcttacaacg ccaaaacaat      600
aataacttat aaatcttagt gatggaataa taagttataa ttcattggtt gattgtatca      660
ttaaccattt ctttcttttg gtgtgagaaa cttatccaac taaaaatatt cacaatagta      720
gggcgggttt gtcgtggctt tgtctgaatt tctacaacat gtgtaaatat tttcaactgt      780
tttatcctct aagacaattt tcctaaaaac aatcatgttg ttcacacgag atttccaagg      840
aaatttaatt caaggagttg aacttgtatt tatgttgatt tgatgcctat gcttaatttt      900
aagatttgag aaagcacgtt atatttgtaa agttggagta ttggaagaaa agtttgtatt      960
ttcaaaagaa cctcaatatt cgagatcgac ggttggcttc aaaagttagg aagtctttga     1020
ctcataggag aatcctatct agactttatg caatataaag agagttctgt tttatggact     1080
tagttggata ataattaat ttgattcaac ggtcataatg aaaacatgtg acatcattat     1140
aattaaccaa tttatatctt taatacacat atcaactttt aaatagttct aaattcaatt     1200
atttgtattt atcatcatta attaaataaa taatgtgaca atttgtgatt gatccaaaaa     1260
tttcatattc aatctatact atattagtta agcttaaaat tttactaaat gcttaaagtt     1320
ttggattatc gagcttccta ccaaacaaaa gcctctattg cacatttaaa atatagaata     1380
gtaggtttat ataatatgaa agattgactc ttaagaccat actctatgac ctaatgaaat     1440
cgacatttat gtaattgata attaataatt aataaaaaaa gtgtgacaaa aaagtggaca     1500
taataaaaga aaggaaattg tgaagcatta gcatccgaat ttcgaagaaa acaaagggcg     1560
ccctcagatc aaagaggaca tactataaag tctccacgct atttcaagaa ttggcgtgat     1620
tctcaagcga catttccgta attcaccaca aaaattaaaa acaaaaaaga actcacagat     1680
tctgatttga cttttgaaac cccaaccccc atcatctccc aatttaattt tccctcgata     1740
tttatccaaa ttcagaaaca taatcttgac aattttatgc tccattcttc caatctcagc     1800
cgtacgtttc attcaaactc caattctccc ccactgcgcc ttccactacc tttttccttt     1860
ctattaaagt gtcctcacaa actcacctcc tctctctgtt tctgtctgcg gtaggatcgc     1920
cgactccgga tttacatttc aggggtcgaa gatttgttct ggggtttctt taatttcttt     1980
atatatatac acacacaatc                                                2000

<210> SEQ ID NO 48
<211> LENGTH: 2000
<212> TYPE: DNA
<213> ORGANISM: Cucumis melo

<400> SEQUENCE: 48
gccaaggaaa atgaattgtc taagaagaag aaagaaaaga aagaacattt tttgcaaggc       60
tacaaatcaa aacttaaatt atccacgtga cacaacaagt tcagagagga aagaaccctc      120
taaaactccc atataccttg gcaataacca tgacaatagc aataaataaa caagtccatg      180
acataaaata aatattgttt tcattaaatc tcaataattc atatgtagtc cgctccgatt      240
atgccacagt catatatcaa gttcagtatt ttaacaattc aagtagacat acataaagct      300
actatggaaa acataaacaa gaatggaaga aggagggtta aggaaacctt tatccctgat      360
ggagtttcag taaaactgag cttgtaggta ttagtacgaa agctgtgaaa tgaacaacct      420
tggccaggta attgaggcac cccaagattt cctttatcaa cactatcaaa gaaagtaaag      480
```

```
aaagttatca cttcaaaacc caactcccaa aagcagctca tcattttcca gtaagttaat    540
actttgaaag atcaaaatca aatctacaat caaattagac ttcttaatag ttattgccac    600
gaaccatgca tttgtcacgt tattaagact atggtttgca ataatctcct atctggttgg    660
atcactactt atactaggca cagcataaac taaagtagtt tcccagagaa ggaagaaaca    720
tgaacctggt tgggtccatc ttggcagtaa aggatttaag ggagaagagc aaaccaaaca    780
taagtttatg gtcttgctgg ggattcaatg tccggagagg ccgattccac tccctgtaga    840
acaagcaaac tccattccta ttgaaaatat acatcatatg cacattgttt ccagtcgctg    900
tcggtaccgg aggcgaggga ctaatttctg acccaccaaa gaactgcatg gtttctggaa    960
taaactaaac taaatcaaat caattgtcat ataaaatgat ctacgaatct aagattctaa   1020
caaacccaac atttcactca actctacaat cagtaaccta gcaaagcaac taataattca   1080
atcattccta ataattcatt gaggttaaaa ataaaatagc gaattgtcaa caggtaaaat   1140
ctaacccgac ccaaatcagg aatcactaaa gcaagaagct gtatgactcg atcaaaaata   1200
acccagatgc atttcccttt ggcctctcta cagaaccact caatatagtt agaaacaaat   1260
ctagtgtaaa attgggagtc ctattcatac ataattccaa ggaaaatgga ttttacttat   1320
gcatcgtata agagactgtg agcaggggaa aatggagaga taatcaccaa tgagctggat   1380
ggtgacagat tcaagaagaa gcatcaaaat caaacaacgg agagcagaaa gatacctcaa   1440
agagcagaga ctgcaaagta aaggaagcga tcaattcaac gacgaagctc ttgattcgtc   1500
aggcaatgat tgccggcgac aacaacgtca gcagatcgga gccttacggc accggagacc   1560
cctccgacaa ggacagagtg aacgaacgtc gtttgtgaac ggtgtaagca atcgatctc   1620 tcggagtcca actccaaagt actgtttcga tatgcattaa tacatttgat ttttgttata   1680
tcaaaaataa atattatatt aaaatttata aacattaaca aaaaaaatt aatttcacat   1740 aatttaaagg accatttggt aatatataca aaattgcaaa atcaaattg ggcctatttt    1800 gttgttattg gaggcccaag atgggtggtg ataaatatgg gcctccaaaa gaataagcaa   1860
aaaaccctaa tttcctctct tcctctcttt cccaatacta taaatcttca ccatttcct    1920 gattagggtt tttgttcgtt cttggccgtc cccttcatcg ttcccagaga gagggagaga   1980
gtaagttgca atagtaaaac                                               2000
```

<210> SEQ ID NO 49
<211> LENGTH: 2000
<212> TYPE: DNA
<213> ORGANISM: Cucumis melo

<400> SEQUENCE: 49

```
aattagcaaa ttgtatgtaa caacgtcatg aagaggcatt tcatcgaaca atttaatagc     60
agagtcaaga tggcccagtt ttataagttt attgatttct cgattcttaa ggtaaatgag    120
atcgcgagca tggaaatgca gacccaaacg agaatatggg tgtggtaaat ggaccggtga    180
tgttgtggct acaaattcgg atttacagc agtaatagtt ctgacgaagg aagcgaattt     240
agtgaccttt cgcatcacag tttaagctta tcagagacct gaacaagggc tctagctcta    300
caacttagaa aggtttgata tggtccgtga tcggagggga ccgaataaca ggcgcttaaa    360
ttgttgttca taagaagag gattgtcgtt gatgtatttt aaccaagaga tgattagtta    420
tccacatcca cagagagaac agaagacggc tttctaaatc tacaccgata aaataaccc     480 taccactttg tttctttaga aaagggtcac attctttaaa aacattagcg tcgaggatta    540
```

| | |
|---|---|
| ataggggtata ttgactaatg ctctgtttgg atttcgagaa ataccaatt acaattgatt | 600 |
| tcaaattaat tatgttttgt tgttgcacga aagataaaaa gaatttaaaa ttcaaaagga | 660 |
| tctcaaatct tattttaac ttaaaaactt ttatgaccca aacggtttat gtatgattta | 720 |
| aaagtagaat acctctgtga attcttaatt ttttttcc tccaattacc acataaatat | 780 |
| gaaattttaa atacatttat tttaaatttt atatccgaaa caaaataata atttaaaact | 840 |
| atttctcata tatgaagtgt gattcgatct aaattataaa ataataaaaa tttacatcta | 900 |
| gttttgatta ttttttttcg ttagatacta aattgttaag aaaataacat ttttaatcca | 960 |
| aagttttgaa gaatatatga cttttaaaat ggtatttatc tttttagtgt ctgatttta | 1020 |
| aaaaatggat ttcaaaagtt catcaaatag cattgtattt ttattttaaa taattttgac | 1080 |
| atttaaaatt agagtaatgg tttataaaag acacttgatc tctaaaacta ttttcttaga | 1140 |
| tataaatacg tatgattatt tttaaaaatc aatcaaaata ggtaaattgt aaaaaaaaaa | 1200 |
| aaaaatcaca tgaatagtag ttgtaattat gctctcaaac tttcggttat gaaaaataaa | 1260 |
| cattttaact tttagacgtg tcaaagttga gtcaagttgg accttcaaag ttatgtagtt | 1320 |
| atataaattg taatatatgt ataagcttgt ggattcaatt ttatcattta tgggtccaat | 1380 |
| ctctacaatt atcgtaagtc tatgggtcaa ttgtaacaca tgtggagttt aagagctcaa | 1440 |
| ttttggacgt ggatgtgttt tgcaaccaac tccacacctt aaaaggtgt tttttttaa | 1500 |
| tttatcaaaa aacaagaatt tagaatcttt aagtttatct ttaaaaatca acggacattt | 1560 |
| tgaaaaccaa ttgaaactac tgttataaac ctaacaacta aaagtatatt ttttaagacc | 1620 |
| gaaagcataa atccataaaa aaaaatcca gaactgaaaa tgtaactttt atagttgaaa | 1680 |
| atttagctaa attatacata ttaaaattca aggaccatat aaaattaaag tacctgatta | 1740 |
| aataataacg aattaatgtt tggtattttt aacctacatt agaaaaaaaa aacaaaagaa | 1800 |
| aaacggcata ctatttgtca agcgtccgat gggaagaaaa tccaacggtg agtgttagta | 1860 |
| ttgaaatacg cagttctcgt gaatgagcct ggcttagatt tgggaacaag agccaacccc | 1920 |
| tttcgaccga gaagccgtcg tcttcaccat attcgcctca accattcgat agccacgttt | 1980 |
| gaagaagaat taggattgcc | 2000 |

<210> SEQ ID NO 50
<211> LENGTH: 2000
<212> TYPE: DNA
<213> ORGANISM: Cucumis melo

<400> SEQUENCE: 50

| | |
|---|---|
| agccaatggt tcaattaaca gctctagttc tagcatggct accgctggta acctttctat | 60 |
| gactagagac gtcttggagg tggagggtag ggcacgagga ttgaaaggtg agggtttggt | 120 |
| gaaaactcaa gcctttcaaa ttcaagaaag catgcttgac ctagtagcat ctggtgatct | 180 |
| tggggaattt gcaatggata ctcataccct tagtcggcat tcgtctcttg gttctgctgg | 240 |
| tatatatttt tttctcttgt tttctagtga tatttctttt tatcaatttc cattatgaag | 300 |
| atggaatctt atgttctatt ttttcatttg gaatgtaggc tttcacaatg aaaaaattgc | 360 |
| taatacgttt ccagaagagg ttgctaaaga cccgtaagtt cttatttctt aacaatttcc | 420 |
| tcagtttaac aagttttatt tactaacata tccttagttg tataaatatg aatctattat | 480 |
| attaactatt tcatttatct atcttttaac agggtgacca ttcacaacaa agataatact | 540 |
| tcattgaaac gccctcctgt ctcacgcact tcggcatccc aggatggatt gtctgtcctg | 600 |
| attcctgatc cggttgttag aggaaagaac tcagatggta ataataagt gatccattct | 660 |

```
gttatcttct ttattcatttt tcaattttgt attttgtata tatttatata atatttttaga      720 aagataaaag atccatcctg aaactttgtt tcaggtggaa gaccggaccc aactagtatc        780
ttggtgaacc aagaaaacat ggcagccatg aagaaagaga tgcgtttccg gcgctcttct        840
tcttgtagtg acagcgacgt gtcagagact tcttttattg atatgctgaa gaagacagct        900
ccacaagaat cccatttgac aacggcggga gttccagagc catctgatgg aatgcaggga        960
gggaaaggtg ggaaaaagaa agggaagaag gggagacaga tagatcccgc actactcgga      1020
ttcaaagtca ccagcaaccg aattatgatg ggtgaaatcc aacgcttaga cgattgatcc      1080
attaggcaag atatagaaca gaaattgatt ttttttttttt tttttccaat catttttgta      1140
gattgtgcag ttatttgttt tcgtgtttgt ttaaccctct tgtaagttgt tgtatatagg      1200
tttcttagag ttgtcagctg cgttgaaaca tgtggccggt atatgtattc caattctttt      1260
cttttttccc gcagttgtaa atgatcaaat ttgagttggt caaattacca aacctttgta      1320
caggaacttc gaagagagtt gaaattttat tcttttttctt ttttgttctt ttatagagtt      1380
cgagattatt tgtatgaata taatcaaaag caaagcatgt aaaaataaaa tgatttgaaa      1440
gggaggtttt ctatcccatt caatgtgacg aatccaacac ttaaagtaaa tttgaaaact      1500
gtctaattta tatgtatgga atgtaatgct cttcaagaaa ttatcttatc ttctaatatt      1560
taatgggatt cacataaaata tgaaatttca acgttttttct tttccttttt gttgtgagat      1620
taaggatact agataataac cgacctcaac cttttaggcc aagaggtctg gagtctttat      1680
acttgaaaaa agtttacaca tattctaaaa gattaaaagg ttaattgttt ggtaaaacat      1740
taatgatgac gatacttaag gtttcattaa aaaaatattt ggaacaattt gtttataatt      1800
taataaaatt gtaactttga acattttgaa ttacattttg ttttttccatt tttacggtcc      1860 tcgaactcat cgatactcac aatggagaaa aatatcacaa tgccgaaaat acccttcttg      1920
ttcccttctt atacaaaagc aacactattg gccttatcaa cggagcagca gctactctcc      1980
tttagcacaa atctccatcc                                                  2000

<210> SEQ ID NO 51
<211> LENGTH: 2000
<212> TYPE: DNA
<213> ORGANISM: Cucumis melo

<400> SEQUENCE: 51
tggtgtaccc acttggtttt ttctcttttt ttcttttagc ttttgctcc taaatttctt         60 gccttagttt tcaaaagctt gttttttattt ttgaaattta accaagtgaa tagaaaaaaa       120
aaagagaaaa caaagctttt taaaagcttg tttttattt tgaaatttaa ctaagtgaat        180
aggaaaaaaa gaaaaaagct tataaaattt gacgaaattt gctgtatttt gtacatttta       240 ctattttct atttaaaaa atgtgtctga acgaaaaact tatattatga gatttaattt          300
tcaaaataaa attataccaa acagacttta gaattgtcaa tcaaatttga caatgattag       360 gtgcatttt taaagttatc ctaaagtttt tttttttttc gtagtcttgc ccttgctttt       420
atcgttaaca aataaaattt tccttatata tatatacaca tttaactact caaggtctgt      480
attttttcca cctgatttat ttaatatttt ttttttttgc agaaaatcta tttgtattt        540 agggaaaaca aatgagtgaa gagatcatca agcaacggtt gcgatgttgc agcggaaaaa       600
tctttggttt gtcattcttt gtgatggggg tttatagggt agtatggtta ttgtattttta     660 ggatgttgat ttttatttta atgagccaag agagagatgt ggattctaaa attgatgatt      720
```

```
gatattattg atgtgatata aatatataat tttgtgcgaa aattgctatt ttattttctg      780
tatgctcatt cagatcacac aataatattt gatgtagctt tacttattga caaaatatag      840
gttttaatct tgtgctcata caaacaacag ctatgggtga attattttc tgattttatt       900 tggcaaagat gatgtcagca ttgtgtaaat ttaatgtgaa ttacacttct gatttcttcc      960
caatgtgccc tctcaaatat tggcaccaag ccatttaatt gtaaatacgg aaaggtcata     1020
aatttccatg caagatttat ttcatgttta aaatgattgt gtgaaacaaa atgaaaaaca     1080
agaaattctt acctccaacc tcaaagtagt cgatatgtca aggttcaata tcaattttaa     1140
atatccatga atagctttga tatctttat aaatgcttgt aatatatata tactaatagc      1200
aatgtctata agttagtttt gagagtaata cttgttatag ataacaatgt tactctattt     1260
accactctac tattgaaagc ttctttttct tccatttatg aattaataac ggtcaagatc     1320
caattgcatg agttactttt aattaattac aatctaaaat gttaatataa gtctaaaatt     1380
gtccaatata tgtgattttt ttttctctc tcaaaccttc ccttcttttc attgaacttg      1440
tggttcaaat ttgatggagg acactggaa acagcacaat tcaaagagcc aaagattgag      1500
taattttttg atttcagagt tttcatctct tcttcattct acacctttca cttctcatcc     1560
acaactatcc aatcaaccat tgccacgtgg catcaaaaat atccaaaact gaatgagatc     1620
caccacaaag ttcctctcat cactgtttgt catcaactca tcaagaactt catcatcaat     1680
cagaaatcca acatttcaac ttctcttagg aaatgacatt tttaccagtc tccaatgtca     1740
aaaactcaca caaatcccct ctttccaatc taaattttac aaagataaca ggggtaattg     1800
aagaaactta gcagtaagtt aacatattat agctttcatc aacccaagtt tttttggttc     1860
ctttctaaac tgtagtttgt tttcttgatc cattctaaat attttcctctg catgaaaaga    1920 agaaaggaaa agtgaaggcg aaacctgttt tatgcttcag aaaaccaatt cagagtaacc     1980
aaagatctga acttcagacc                                                 2000
```

<210> SEQ ID NO 52
<211> LENGTH: 2000
<212> TYPE: DNA
<213> ORGANISM: Cucumis melo

<400> SEQUENCE: 52

```
cgctcaaatt actaacatcc ttctctttct tgttcccatt cgactagaga gacactatct       60
tatccacctc agttggctgg gtgaaatcat tgaaactaac ggttgattgt ccagattgtt      120
aaactaccct atgttttatc atcttggtta catttatagg attgtcagaa taataattcc      180
ttttgaaatc atattctaat tggcacagga ctaaataat gcctttctta agctgtaata      240
attagaatct aaacagtgaa gttagtaact gattgatgac atttccacga ttttcattta     300
tatcctgtgc agctattctg acatcacaaa acatttcttg attttcattt ttacttgtca    360
tccatcagtc aggacgatat cggcgcgctt gttgacgacc ttgtcctaaa tacaaagagg     420
cttatccgag ctacttcaag ggagattgac aagtggaaaa gatgaaatta ctcatttgtt     480
attacattgt acaagtgatc tattaggaag aaccacaatc aaaactgaag aaaaaagaaa     540
cgtgctggct gtctacgtgg cttttagagg tagaatttat gtacaattgt ttagaaagat    600
gtatttaatt gctctaaatc tcatatgcat tggattttga gcaatcttaa aatgccgaat    660
acttaatgta ttatcgtagg ggtccctaga tggcagattt atcatgtcca ttctccagaa     720
agaaagaaaa aaacccttttt tattatactt gttcattta agcttttttct ggttgattat    780 aatgtcagta atttaaaaaa aaaaaaaaat tactgtgtat tggcatcggt tatatgttat    840
```

```
atacaacccct agttaaaagg taaagttttg ttcattcggt cattagtcat tcctatacga        900
acgtcacatt gtgctttata atttcaatag gttaaaagta ttcaatatag ttttttaagt        960
tacctagtag aggtgatcat tggttgatcg gaatcggttt tttgacaaaa ccgccactga       1020
accgatcata gtcggtttag taaatgttca aatcgacctt gacatcgatg agtaaagatc       1080
ggtcggtcgg tttttgtcgg atgggccggt ttaacacttg gaaatactat tttgaaattt       1140
ttcgaaatta atccctcttg ttttcctacc gaccgatttt gggtttggtc ggtcagttcg       1200
attttttcgg cctatcttac tcactcttat tacctaggga ttgaatttca ttttatcctt       1260
agttttaggg ttcttttttt atactttga aatatttatg tcgatgtcta gagtttaaaa        1320
ataacacttg aaattataat ataatttttt ataattgtta gctataattt tacgtccaaa       1380
tatcaactca ctcgcaactt gtttaatcaa ccaataatat gtgtctggaa tagtaagtat       1440
ataacttgtg gaaatgact ttaaaagact tttttaaagt atttatttaa tgccaaaata        1500
tctatattta tgtttataca ttaacataca tatccaaagt tacatattag atttgttaaa       1560
taattcaaaa tgagctaaag aaaaaaagaa gttccatata ccaaaataaa atataaaaag       1620
ttgaagacta aaatagagat tttgaaacaa ggtaagttag atttacaaat tgcaatatgg       1680
gagaccaaac caccacataa caaaaatccc aatgtccaaa tggcgcaatt ttgtttagga       1740
tagctcacgt tatccaaatc actcaatcgg agagaccaaac ttaaaggcca catctgccac      1800
gtcaccatac tccaccaatc acaacacagc attggatttc tcagcttatg agaccaatca      1860
caaacctgaa tccgacgtgg catgtccaca tccaccagta ccaaccatat agcttctacg      1920
ttctccacat ctaatcttca ccatttacac aatattcttc attcttcttt cctcccttca     1980
atccttcatc ctctccgccc                                                  2000

<210> SEQ ID NO 53
<211> LENGTH: 2000
<212> TYPE: DNA
<213> ORGANISM: Cucumis melo

<400> SEQUENCE: 53
aattctaaca actccggaac caaataattt agcatggatt gaaatataaa tcttcttgac         60
ttgcaaaaaa atcattgtaa tggtcttatg ttggttatag ttagggtatc gaaacgccat        120
acaggaatat gggattaaag ttaacttttg ttcatcaatt tcagcttatg aacttctaaa        180
atatcaattt tacctttgaa cttatatgtt attacccctt tcgattgtgg tatgttaatt        240
aatatctgaa tctcagtcct tatgaaactt ttttatactg tcacaaacat atgaagtttt        300
attgtaagtt cttagaaatc atctaaaaag agtagtttgt tggactattt attttatttt        360
ttcttattaa gttgttttca cgccatttca gtaaaataac tatagtgaat agagaatcaa        420
acttctaatc ttaagttaag gtagtagggt atatgctaat tcaataagat aatccgtgat        480
gcttgacatc tgacttaatt gttataagtt ttaaattttt tattgtaata tttaaaatac        540
tagtttttgg tttctaataa agaaataatt gaacaattac aaatatttat acaaaattaa        600
actagaatat atgatcattt tccttcgtgt tagaaaaagg gaaatatatg tgtgtattta        660
tacatattag atattgtttt actatattcc attttcctca cgggaaatgg aggattgagt        720
gggagataaa cattgtcccc aagagaattg ggaatggaaa tgcaaatgac atggccctcc       780
acaaaattgt tcgcctaaaa atgggctttc tcacttctca ctccgcaaga aaatatcgt       840 ttccccttcga attattcggg cggcaagatc tcaaaaccac atgttttct ttcttttattt      900
```

```
ttcaagccta cattatttat aaaaatataa cttaagcaga gaattatgta aattcaagtc     960 cattttcgc ttcacttagc taaatcatta acaaatctgt aattttgttc ataaattagc    1020
tcaccaatta tgttttagcc cactaaggcc cattagacat ttttattaga aaaacatgaa    1080
ccgttggatc aagatgtgtg ttttcttttc tttttctttt tattttttt gggttttggt     1140 ggggttttgg tggatcatgg tggatcaatt cgtagcttta gcaacctatt attatatgga    1200 gggaagggc gtattaatct gttagcgccg tccgggagtt tagctttctt ccccgagcct     1260
cggtcttatc ccctaactcc aaaaccctag cccaaggta atccactcct tccccctccg     1320
ctcttcatct ttttctattc atcatcttta atctgttctc cctttggtt cttagattct     1380 tcttttgttg gattctttta atctttactc atggttggcc ttgtaagttt agacgacgtt    1440
tttatacatt ggttaatcct gcttctctat ctattcgcac gctagggttt tcctattgtt    1500
ttctattctg ctctacttct gcaaggttgt gttcttcttc gttcaggtcc cttttttaa     1560 ccgaaattaa attaatgcaa attcgtttgt gcttctaatt aggaagcctt ttggaacatc    1620
tcgacatttt gattgctgca tttcatttcg ggtatatttc tatgattgaa ggatgtgggt    1680
ctgttcactg catggtcatt acttatgcag ctatgcttat cgagtccatt atgtttgtgc    1740
aatctgtttc cggattcata attttttagt aattgatcag tagatgaaaa aagatattgt    1800
aatattcctt gagtgttgca ccagtcttgg tgggtatctg ctcctgctct ttgcttgtgg    1860
attttacttt tattatatct gtattattcg aaatgttctg ttcttgttat aacttatacc    1920
cgaagatgtg ttcctccccg cgtctagcgt tgtgggttac ttatgatgga catggttttg    1980
attctgtttg gtttgtgcag                                                 2000
```

<210> SEQ ID NO 54
<211> LENGTH: 1547
<212> TYPE: DNA
<213> ORGANISM: Cucumis melo
<220> FEATURE:
<221> NAME/KEY: misc_feature
<222> LOCATION: (1)..(1547)
<223> OTHER INFORMATION: n=g, a, t or c.
<220> FEATURE:
<221> NAME/KEY: unsure
<222> LOCATION: (1)..(1547)
<223> OTHER INFORMATION: unsure at all n locations

<400> SEQUENCE: 54

```
ataatgtgtt gatgttgatg atcatgcatg gtatattaat ctcatgatta aagacgttaa      60
gattaatatt cattccatgt ttatgatggg tgttcttagg gttgtaccca tatgggtgtc     120
cctcgggatc accaccttt ttatgactgt atggttctac gagaccacca gtctgtcatg     180
atatgtttat gaatggtacg acggggtcac ttacagccca attgcttaag tgttccttcg     240
ggttcactga agacctattt ttcctaggtt ttcctttgac ttcagcaaaa atcagttttg     300
tcctaggtgt tcctcgagtt cactgaagac tagttttgtc ctaagtgttc ctttaggttt     360
atcgaagatc agatgtgttc ctacagaatc attagattgc aagtgttcgg gaacacatcg     420
gtttaggggt acttctttac atgaacccta atggaaaatt aacagacatc tagcggaatt     480
agtagttggt cccttactga gtatatattt atactcactc ttttatgtt taatatttca     540 ggcaaaggtt aaggtagagg aaagttgacg agtgatagaa aaggatctgt gacatgtcat    600
atggggactc agtttcgttt ctgcttctat gtatcagtgt ttcagtattt tgttnntaa     660 tgaaaattta gtcttcctct attcaagaaa gtgtctcttg ttattgttta ttttagtaa     720 tgatttcaac ttagtataaa tagttggatc attacaaata atatattggt gatatacttt    780
```

-continued

```
gtaatgatac attgagttat attattcata tgtttaatat acaaaactgc aatattaaaa      840
aatgaaaatc acgtaataag tatatcaaca aaataataca tatattacaa gcacgtcaca      900
acactaatat acaaaactaa tataaagtaa gatcaaagca aaccaacgt aaaaataaa        960 acaaaatcat ttgaaattaa atttaactca aaatacacat cgaagaaagt ggagaaaaat    1020
cacaatagag ttaaattact ttgattaata accattatat ttcatattga aaataatatg    1080
tcattagtat tttaaaatca agattaagat aggaagaatg aattgctctt ttcgtataaa    1140
aagggatgat tggggcctta cgaaggaga aaaatacata tgttatcgaa aaacaaatt     1200 attttcttg taagagagaa tgattatatc cttaaaaaaa tgaaagaaag aaacaatcat    1260
ggcattaaaa aggaaaataa ataaattatt aaagggcagt tcgataataa taacaaattc    1320
aacgagagta ttaaaagaaa atgagaattt gcaaaattta acaaatgtg tatattaagt     1380 acagccaatg caattttcaa attttaattt atttggttta cccaaaattc aatttctaaa    1440
ttgagaggag gatatagtaa attcacacgc attatcccct tcgagtttca tcatctcacc    1500
cattcttgca tacagtgcag ttacaattcc ttcattctgg atagaca                  1547
```

<210> SEQ ID NO 55
<211> LENGTH: 2000
<212> TYPE: DNA
<213> ORGANISM: Cucumis melo

<400> SEQUENCE: 55

```
aaacacttat catgttatgt atcccacatc gaaaagataa aagagacttc atgatctta      60 catgatatat gagttactcc ttcgactacc attggttttg gagatggatt caacccaata    120
atatgaatct gacccaacaa tggtcaactc aaagagacac catcttgaga tacatgttgt    180
gtacccatat tagatgaatg actataccctc gcaatattta taacatacat gaattacttc    240
tcttactgta atttggtttt gacgtggagc ccatgattat ctaattaacc ataactggta    300
tatgatatat tagtaggtaa cccgaagagg ttctaagata aacacagaat tcaatagaat    360
cagagccttt ccaatgatat ggctttagat gggaatgatt tgaagtataa tcattctacc    420
acacccttta tatttgtctg tcaccagaaa tctcatcttt tcttgaggta ttattcactc    480
gaaaagaggg aggcattttt gggttaccca tctaatgcac gatgaactaa gggaggtcaa    540
gttctgggaa tacagctagg caaccttcac agtggataca ttcgaacaaa tgataaatgt    600
gaaaatgaat catttcatga gtgtgactaa cccaatcatt cctccttcta tatctttgaa    660
tcccacagtg agtcagagta aaagttccag caacaagtcc tacaacccaa attctttagc    720
tatttcttcc accagaacaa aaccaagcaa aaaatcagcc acaaacacag ctcaacaatc    780
tataaaggcc aaaatactaa gacagtcacc attaccacat tgaaagccgt atttccaac     840 agactttgcc tgcaaaatag atcacaaaga cacgatttca cattggacag acgccacagc    900
tccacaatct caatttcaat caaataaaag taaatcaaag ctaaatagca agtgtatggt    960
accacgaaag cagcatggct gacgccactg aggcctgtaa gagagaaaac aaaataagtg   1020
tagaagataa agtgaaatag aaaaatcaat cgataagata gattttcaga ttaccatttt   1080
tacgggaatt gtacggaccc aaaacacaaac cccatagagc gccggcctga agatgaacag   1140
gggcaggaaa ttcagaggaa gaaattaaag aaaatgaatc atagtttgag aaattattcg   1200
taaagtttac cgttccgacg cgaatgctgg attcgacggc gagggaagaa caaggaacga    1260
cgccgttgag ttcgtcttcc atcttccaat tctcaatttc cttcggaggt ccgtatgctg   1320
```

| | |
|---|---|
| agagctctgt gtctaccaag ttccaaccat actacgtcgt tttggatttt tattttttatt | 1380 |
| ttctttcctc tcttttgcca aaaagaaaa aatagtatt ccaacctaaa acctcaaaat | 1440 |
| aacatatttg ttgtacaaat tataattagt aaacatttgt cattgtgagc ttggtatgta | 1500 |
| atattaacac gaactttatc gctaataatt tagacgttaa tgataatttt gagcattgcc | 1560 |
| ttcttatatt gttattgtgt ttataatagg attgcttaca atgtaaccta gtatgttgtt | 1620 |
| gagctcgtta actttttgt ttttcttgaa tattcaaagt taaaaaattg tacaagtttt | 1680 |
| tggtgacgtt ttcttactac attatcggga tgaagatcaa atatagctta gattagagaa | 1740 |
| gataatcatg ttgattttatc gttaaacttt gactacaaaa tccgtttaat ttttttttgg | 1800 |
| atgaattagt tatacaattt aaacttaaaa ggggtgaatg aagaaagagg atagttttac | 1860 |
| aaattcgaag tgaaatgagt tatttctgct taaagaaaac aaatctcctt cgtgctttaa | 1920 |
| aacacaaact caaaacccta aattcagcgc cgattcttca atacatctct gcaggaagtt | 1980 |
| agggcaaagc agaagcaaaa | 2000 |

<210> SEQ ID NO 56
<211> LENGTH: 2000
<212> TYPE: DNA
<213> ORGANISM: Cucumis melo

<400> SEQUENCE: 56

| | |
|---|---|
| acttccaaaa atcagcctca tgggatattt aaagaaaacg taaattaaaa ttagcatcat | 60 |
| ttcatattga acaaactaca aaaattaact ctaaagatg atggtaacta caactaaacc | 120 |
| ttcaattttt cattgtaaaa atcgaactct taaacttgtt caaatattaa aatttgaccc | 180 |
| tcaaacttaa aagagctaaa aaaagacctt caaatagtaa aagtagaact ctcaagctta | 240 |
| tagaattatt acggttatga ttatagccat agatgattca atcgattttc ctccaagatg | 300 |
| atggagtata attcttcaaa tctagctgct tagatgttat cacgataatg aaatcatatg | 360 |
| ggaactcaac aaaagaaag cacttaatgt tgaaagacat tattctttgg gtgttgagtt | 420 |
| gggcgaactt gatttttatt attaatccgc aaaggacctt ttgagtaagt tgtggcaatc | 480 |
| tttattggag tgctaagatt tgttattcga aatttcttgt tttgatattt ttccaactaa | 540 |
| aactaatttt tttaagaaat gcaccttcaa ctgatttcat gcgtgtcctt ttgcaagact | 600 |
| cgcatgggac ataacacatc atcttatatg gcaaggccta tgtgtcagtg gagatttgac | 660 |
| gtcaatttct ttccactgag agtcgtcctc tttgtgatgg cagaactttg gagagtcatc | 720 |
| aaaattggtt ctttgaaaat gtttcttatt ttgatttttt tttttgaaag aaatgagagg | 780 |
| aataagatat ttttacgagg actctactag tgggtcaatt tgcccgcata tggatatgca | 840 |
| taagagtcct tttggagaga aagggtatga tggaaagaca ttgcaaaggc ccgtccacta | 900 |
| actttctatt atacaattag gtggaagcca cccatagcaa tgtcttggtt gaacactgat | 960 |
| attacttgaa accatgcatt taagatgtga aatctcgact agatgcttta ggaatttgga | 1020 |
| ttgtgtctgt tttgttgaat tcaagttcat tcctaaatac catgaagtta agatccttga | 1080 |
| agcaatgaag accatttatt tagatcctta attcaaatct ctttactaaa gatgattgtt | 1140 |
| tataaatgat caatttgttg aatgatgttc tacttgatat ctctaaagca tctcttttcg | 1200 |
| gtgagaagcc cacaacttga atagtattcc ataaatcatc tatttttagt ttctatcatg | 1260 |
| ttctttaaca tcaaaacatt ttagcgcact ctcttataac taagacttag aaaaacacga | 1320 |
| atcttccttt cttacgatat atatcctaaa tggttttcta tatttgtgcc ttacaatata | 1380 |
| atcaattctt tttctatttg atattgtcat aaaataatac tgataacata gtttttatgt | 1440 |

```
tttattaaca cctaacaaga aatatggaag acgttaatat atcttcaatg tcgatattga    1500
atcattttat ttatgaatat atccacgcgt caaaaaatat tttaatcatt aacttctagg    1560
actaaattca aacattcttg gaaccataga caaaagaaca aaatttgcaa cctcaacaaa    1620
caaaatttta tctttacatt tgcggctaca attcacaaat tcccaaacca tgatagaaag    1680
gccccaatct cccacgtgat aaacacacat atggcacgtg accaaatcaa aatcatccac    1740
atgatgaaaa cttaatggac agctcggatc ccaacaccca ataaaaagca gccatgaagc    1800
tgacgtggca gatttccccg aaaaccttt  aaataataaa caataaaaaa atatatacat    1860
aaccgttggc aacgtttttc cctccacaca ttttcccatt gccttatctt tctttccctc    1920
caaacagcga gggaagaaga atccaatcat cttcttccaa taatttctaa aacgaaattc    1980
tgctcgattt tccctctcca                                                2000

<210> SEQ ID NO 57
<211> LENGTH: 2000
<212> TYPE: DNA
<213> ORGANISM: Cucumis melo

<400> SEQUENCE: 57
tgggtaacat tatgagtttt attataattt aaatgaagat caaactttaa gttgtagggt      60
caccatagga ataaaatata atcaataagt tagggcccct tagtcccacc tcgtaaagga     120
gttctgtcat acatatacat tatgatatta attctatctc catgagtcat acatgtgatt     180
ttagtacttg taattttcat tcttttttcct attataattc attcaagtac tgtcaatatg    240
gttaggtatt gaaattaatt atagactcag atatcatctt cattaatgga aatggaatgt     300
tatattctac ctctcatttt tacacgttga tgataaatta aagaaaaaaa aattattatt     360
tatattgttt taattgtgag atattagttc aaaatgtaat taataaaatg atacgtgtct     420
tataataaaa ttaaacaagt ataattaaat ataaacaac  atacacactc tttaactaaa     480
agacacaact cacctaatgc tcgacttaaa atcactttgt gtcgtaactt aaccatcaaa     540
gcatgttagg gtaaacacaa taagatgat  ttttgagtta tgcatgtcat ataatgtcac     600
ttccaatttg acttatcttg cttgcttgat tcatgtatat aaacaaaaac atgaaaagta     660
gtgtaaggat accaattacc tactgatttt ttttaaaagt agtttgtcta agacgtgtta     720
aattactaac ttagtcacat ttgagttttta gttctaactt attaaacata agtaggtat     780 ctcccttact catgtgtgtt tcgataatgt caaattccaa tgtttgatta accaaattgg     840
gtaatttaac ataaatattc ataatataat atttttttatg gaataccgac atctaaaaag    900
aaatcaaaat gaatattatt aggaggtgag tttttaagag agaggaaaat aataaaatat     960
ggcatcaaca agaacaataa taataagaat agaaatccga caaggaaga  agtggatgcg    1020 tgttagtact attgacattg gcatatgaac ggttgggttg ggcctcaaat aatttgcatt    1080
tctaacttcc aaacacctaa ttccttttt  tttatccata cttgcaaata tatatttata    1140
tatattcaac aagtagttta atttatttga tataccactt taagttttaa attgatggta    1200
gtgtataaat aaataattta ggattaagca tgtctatgaa cctttttgaaa tttgatggag    1260 tatatataaa acagaatact catgggttca ttataaaaat ctaatagtaa atgtattttt    1320
tatttcattt aaacattttc aaactttttaa aaattaaaat tatcttaaaa aacacgtgtg    1380
gtttcgaacc atatggttaa aaatattgag gttctctatt ttgcaaaaaa tttggaaacc    1440
ttcatggaag ttgatataaa ttgttgtaat tagttagtat tttttctttta tttgtggctt    1500
```

| | |
|---|---|
| aatcatgcta tgattgatca ttttatcatc atttctataa tgtaaaacaa tatatttgat | 1560 |
| gtgtattgta aatttttatg caagagtaga aaattaataa aaaaaaaaga gagaaaaata | 1620 |
| attataaagt aatataaagc tattaacatt ttaagaaaaa taatagtgaa aatgaaagtt | 1680 |
| tcggacaata attcaataaa gaaatttgta gatttcgatt aaaatttcca aaattaagat | 1740 |
| tttcattaac acgtgtgcct cgcaaccgtc tcctacgtta tcccgtaagt agcccaatct | 1800 |
| atcccattct tacacaagcc gtcggcccaa attgattgta ggccatcggc ccactcaaca | 1860 |
| cccacaaacc ctagcccctt gctcctcctc ctcctcttttt cacggctgct cactccctct | 1920 |
| cttttttacac cttctccttc tccttctccg tccctcttcc cttttctgct actatcttca | 1980 |
| gcacttgctg agcttcaacc | 2000 |

<210> SEQ ID NO 58
<211> LENGTH: 1591
<212> TYPE: DNA
<213> ORGANISM: Cucumis melo
<220> FEATURE:
<221> NAME/KEY: misc_feature
<222> LOCATION: (1)..(1591)
<223> OTHER INFORMATION: n=g, a, t or c.
<220> FEATURE:
<221> NAME/KEY: unsure
<222> LOCATION: (1)..(1591)
<223> OTHER INFORMATION: unsure at all n locations

<400> SEQUENCE: 58

| | |
|---|---|
| aatgttgatt taccettgct ttgtttgaat ttcgtcctcg tggacttgac ctttggtctg | 60 |
| cttcgtatag gactatttac ggctgccctc atagtccaag tccttgtccg ccttaccceta | 120 |
| tactctctat ctctagacaa tgtgaagcgg gcccttctat aatattgggc cttgaagttt | 180 |
| tgggctttgg atctgccgaa ttgtgttggg ttttctctcccc aatttatttc atttctttat | 240 |
| tcaaataatt ataaatatgg aattttattt tatttaaaat ataaaagtta aaattgaacg | 300 |
| aatccaaaaa taatggaatc aaatcgacgt tttaacatat ttttcaatta tgttttaca | 360 |
| ttcattttcg tcctacaaaa atattcccac ctttatttcc tcgatatcgg aggtcacttt | 420 |
| gtatgtttca ttcgggtgat gtgatataga tcgagttcct atgcttgatt gactatggaa | 480 |
| atatatttta agaagatgtt ataaaagtaa aataaatgtt ttgattgtgg atataattat | 540 |
| atttaaaca agatgaggaa taattagatc cgaaccaata atcttgagtc aagagtgtac | 600 |
| attgaaagtc gtatattaaa taatggttga gtttataata atattgatag attgcagtta | 660 |
| accatatttt ctcaagttgt tgaccaaagt acttatttta taaacagttt agggaatgtt | 720 |
| tatgaagttt tgccaagtgt tttgaaccta tatgagtatt gacttaattg gtatataagt | 780 |
| gcattaacaa tcaagaggta tttaatttga atcgtcctac ccctatcatg ccaacaaaac | 840 |
| aattatatgt ttgtcatatt ttattgaaag tgttttcagc gcaatttagt ttgatttgcg | 900 |
| tacaaaacat gtctacacgt atcgagttag tagtaatggt tgctagttaa gactgtgaac | 960 |
| taaaacttta aatttacatt aaaaanaaaa acattatggt cgtttggtcc tcatatgtga | 1020 |
| ttgatagata ttgattaatg agtatttgtg gttgttgcca acaataaaga tgtagacaag | 1080 |
| tgaactatgt tggttgtcaa atcttgtttg tatttgttat gtgtggtttt caccaccaat | 1140 |
| gttgtagagt gtcagatcca gaatagcttg atcattttc atatatatct acagactcaa | 1200 |
| ttagtagata aaaactataa gactttgact tatttctctt aaaatgtctc ctcgttctgt | 1260 |
| acaatcctca acaacgtttg gtgacttttaa aacatcacaa gaatctaaga agaatgatga | 1320 |
| attagatgca atgcaaagat ttggaccttta attttgttac tttaaacttt atatccgaac | 1380 |

| attggaagag gcaagcaaaa agcgcgcttt agaatcgcgg tttctttggg ccgagtgggt | 1440 |
| tgctcataac agcggaggtt tgcttttctg ccaagaaaac ccctcaaaga aaagggctt | 1500 |
| aataagcagc tgctccattt ctaagtgggt ttagccttta gcacggaagc gccaattcga | 1560 |
| ttcaactctg atacactgca aaaattccgc c | 1591 |

<210> SEQ ID NO 59
<211> LENGTH: 2000
<212> TYPE: DNA
<213> ORGANISM: Cucumis melo

<400> SEQUENCE: 59

| aaagaatgga gcaagctgat attgctaagc aaaagcttct gcatgattgt gaagttcttc | 60 |
| accaccgcct tcaagattct actgtcgact ttttcattga gcaggaaaat aaactaattt | 120 |
| tggaaactgc ttcgacagct gacgacgcaa tagatctgtt ggcaacatct gataatcaca | 180 |
| ttaaccttct tttagcagag gtacttgcgt ttgtttccat tgaaatgcat ttgcatattg | 240 |
| aacttcttca tcctgaatgg cacaagtttt tgtccataca acaggcaaa gcttctggct | 300 |
| catgatgcta acaacagcga tgacactgct ggatcagccc gtccaaatgg aactgataaa | 360 |
| ggggcagctg accaagtatt aagtaacata ctagcaaata tgcttgtcga aatgcccga | 420 |
| ttaaggatgc agatgaacgc cgtcatccgc tgtgttctaa atgcaaatgg acaagtgag | 480 |
| aaagatgaag atgaatctct caaggaagaa ctgttctaag caagtttta gaggaagaga | 540 |
| ttcctgaatg cacatataca atgacccttat actgtcgtgg caagaaatgg gagagctgta | 600 |
| gattttgaat aaatgcaaca gatgttgccc attaatttgc aagtcctgac aaatttggtt | 660 |
| gtcggaggtg tagaaatgat gtatcaatta aatatttaac aaagtgcctt ttggcttggc | 720 |
| taatcatggg catttgaaga cttttgcactt ggtaagagct caaacaaaat ctgggtggct | 780 |
| aaatttagtg ttgattaaat ggaatttcac tgatattcat gatctgtctc ttcttccttc | 840 |
| attgatatat tatcttctca gtaaactcct gggcctgatg cagaattgct tttaaccatc | 900 |
| tgcatacaga gaagaagtaa aaactagctc acgtggataa agggaaattt ctactgacat | 960 |
| gttggcatta gaagaaaatt tgaaagagt tctattacca taacatcatc tacttccgtg | 1020 |
| tattattgaa actattattt ctcttacccg gagatattaa attaataaat ttctatttac | 1080 |
| attttgaaga tgctcgtgat tattgataaa aatgatgaat cattatttg attacgttac | 1140 |
| aaaaaagtca agagagtaa caaagctatc aacaaaatat tagtaatata tacaaaaaaa | 1200 |
| gtgtaaattt aatattaaca ctgagaaata tacacttaag ctaatgggtt aaaatattta | 1260 |
| tccattgaat taaatatggt ttttctgtat ttgtgatatt ccataaaata tgaagctgtt | 1320 |
| atactgtcaa attcatattc tgcctataca atcaattca gtcactcaa ttttgcaaaa | 1380 |
| ccatatcata ttgagttcaa ataaaatttc atatctatat acataacgaa aatgttatgt | 1440 |
| ttttgctttt aatgttttgg gtatctttct aagctacaag aaaatgtaaa aatgataata | 1500 |
| agaaatagat tatattaaaa ttattttaca aatcaaattg cggggatagc tcagttggga | 1560 |
| gagcgtcaga ctgaagatct gaaggtcgcg tgttcgatcc acgctcaccg caaattttt | 1620 |
| tcttcttttt tttcccttgt gtatcatttt aaatgggctg ttcttacttt gaactgcgga | 1680 |
| agcccatgaa agctaggccc aatttagaaa ccgaccatct caagggtcgg ttcgtcattt | 1740 |
| atcaagatcc gataacccga ttcgctccat tttagtctct gctctttcat ctcccctcacc | 1800 |
| cattctcgct tccactgagc gggcaaggga gcttaacccc tcaaagccct agaaaccgcc | 1860 |

| attggagaag ctccactagc ttcttcttct atcagcgaac gtatttccgt cttgtataga | 1920 |
| cctttcatct ctggaaccga tcggaagttt ggagtttctt ggtctcagtt tgtagattag | 1980 |
| ttttatcttg gcgtctcaat | 2000 |

<210> SEQ ID NO 60
<211> LENGTH: 2000
<212> TYPE: DNA
<213> ORGANISM: Cucumis melo

<400> SEQUENCE: 60

| gtgcatttaa ataatctag ttgcatgttc taggttcgat ttattatttg gggatttagt | 60 |
| tgtgtctgta tgattgaaaa aattaatgtt gatcttgtaa cacaattgtt tttccctcga | 120 |
| tgatttgaga ttatttcaac aatttagatc caatgtttaa aaagccacct tggcatcttg | 180 |
| ccttcctcat tcgcaacctg cctccagttg aagcctcgag gctcaaagcc cagtgcccta | 240 |
| ggacttcttt attaatttta cttaaaaata agtttgtat ccctaaatgc ataaaatacc | 300 |
| cttgtgttta aggcttttctg tttcttcgcg tttcacgtca ggtcagacca tgctcagcta | 360 |
| ttttttccacc attcttcttc ttctctccca aagtctatca agtatttat ttccacacat | 420 |
| atattcacct acgccaattt cttttttaaaa tttatagat atatacagtg cacctcacga | 480 |
| aaacaaagtt tgcacttctt cagttttttg tttcgcctca cacttaagct acaaaaggtt | 540 |
| attacgtttt agtaacccac tactcagctt taaaaacact atttgtatca tatgacgtcg | 600 |
| cccttatgga ataatttcac ttgattatcg ggttgtttca taaacaatct tactctgttg | 660 |
| taccttttgac aggcctggag agcatgcaac tcctctcttg cttgagtttg agtaacaata | 720 |
| aaatcggaaa ttttactgca ttggagcctc tgagactgat aaaattctta aaagttttgg | 780 |
| atatatcgta caacgagata ggttcgcatt cgatcgacac aaccagatat ctcttctcat | 840 |
| ctccactgtc gcattccgaa gaaattgatt tgagcagtga tgaaatggca acaaatttta | 900 |
| ctgatatggc aagttactgg gaagcatatt ttctattcaa agatataagc ttgatgcaat | 960 |
| tggatataga aggaaacaca atatctagtg aaagtttcaa agcatttctg gtaaagattc | 1020 |
| ttcccaaact ccactggctt gatgggaaac gggtacaata gatatggctt aatttatcta | 1080 |
| catccaatcc tctgtccatt gtggttgttc atcccctgaa tgtaaaaagg tacgctacga | 1140 |
| actagcattg atcctaaatt gaagacattg gttttgattt cttcccaatg caaggttaag | 1200 |
| aactaaggat ttgatattgc atccaataag cataggttat ttaagatttt ggtgatagtg | 1260 |
| aaaattaggt gacatgtctc gaaagcttaa agggatacat gaggtatgga gatggagatg | 1320 |
| gatgtggtta caacatggaa atgaatacgg tgcccagttt tttggactgc tctaaatcaa | 1380 |
| attttatcat atacattatg atactgtgtg ccaattgtat ttaaaaaggt actgaacttt | 1440 |
| acatttttgt tgtcccaaat tttgaaggat tgtagttta ataattctta taataactat | 1500 |
| caatgttaat taaaaacttc agtatattta caattttttct aaaaatgttt gctatacgtt | 1560 |
| tagttattat cttgatcaat tgccccaaga gaaaaattac cctggactat ttcccaaaaa | 1620 |
| catcttctag tcgtccatca gctatagttt caaatctgtg tgggcccagt cggcccagtt | 1680 |
| cattgggcct gagaatagag atcatgaacc ggacggccca aaccttttc aggcccagc | 1740 |
| caagcctggc ctacaaactt ctaacctaaa accttatccg ttgaagcaat ccaataaaac | 1800 |
| aaagccacgt aagcacccag gatctaaaaa tgtatccaaa tccaccaatc tgaggccaca | 1860 |

| | | |
|---|---|---|
| aatttagcct ctgtggctga atggatgtcg aattacaaga atctctcgat ttcttcctct | 1920 | |
| taaatccatt taccctcaa acaaataaac acaaataaa gaaaggaga agaaacaatt | 1980 | |
| gtcgtaatta gcagcaagaa | 2000 | |

<210> SEQ ID NO 61
<211> LENGTH: 2000
<212> TYPE: DNA
<213> ORGANISM: Cucumis melo

<400> SEQUENCE: 61

| | |
|---|---|
| acctagaact tctaaacgat aatctcggaa aaaaaattgg aacaaatcat aataatgaca | 60 |
| attaagaagc aagaaccgtt gacaaaagca agatttagag ggagtaaatt tgcatggttt | 120 |
| ggtgatgatt atttagttga atttagccta ctcttaggaa gtatccaata atcatacgca | 180 |
| aatttcacgt agcatatgaa gcaagtgcat cataataccg cataacctgc ggggttttgt | 240 |
| catctcgatt aaacacaatg tgaacatgat gatgtctatg tgtttccagc ttttgttcta | 300 |
| atgatgatag acgatagtgt ggtatagttc atatccttga tttaattgtt ccatgtata | 360 |
| ctatcgaatt tttaatatat aattaatgta tgaaatcaaa tatcaaataa tgattgtgat | 420 |
| ttaatggaat aagatcatgt ctaaaattgg taatagtaat aacgaagaag gaagagaata | 480 |
| ataaactacg atttcttgtg aatctcctag ataaattagg ataaaaacta cgagtaagaa | 540 |
| tagaataatt atactatata aataggagt tacaattttt gtttcttaaa ataccaagct | 600 |
| ctgttacaag aaaaactttt aggtattata tcttcaacat tttgttaatt tgttagagat | 660 |
| tttaggatag tttgtcaact atgggtcttc taagaaactt ggtcatcaag caaatctaat | 720 |
| gactcgaatt gtccttgatc gatgtgaaag atccaatgac ttcgaattat ctttatgcaa | 780 |
| tgtgtaagat ctaattgtca taaattgatc tcatgtgcaa agtgtaagat ccaatgatcc | 840 |
| aaaattgtct ccaacaactt cttgaacaat aagataactc tttgaagaat cttgaatatt | 900 |
| aattttgaca tagatagatt gatcttgaat attaggaaat aaggaaattt tcttatgtac | 960 |
| atgcctgaac tccttcaaca tagcattttg aatcatatct cttctctagt aacttgtata | 1020 |
| gttgcaatat attttgcttc tgttgttgat atatcaacac tgattgaagt tttgaaaccc | 1080 |
| aacatatagc tctagtggca agagttaaga catatatgtg gtgaatttac ttctatcaag | 1140 |
| atcacaatct aagcagatat actttgaaaa taaagttaga ttatccatta tacaatgtaa | 1200 |
| tatttacgga ccatttaact cgcttagaaa ttagagttat tttgcaaact ttattgacaa | 1260 |
| atatcttcaa aaatttcata caccgtatag acactatcat aagatgttaa agaaaaaaaa | 1320 |
| aaggtgaatt ttccatacaa ttaaaaaaaa tcttaaacta taaaggtggt ttcgatacct | 1380 |
| ttaaactttg aaaagtttca ttttaattct cgcacttatt gttttaaaac aaacttagta | 1440 |
| aaatttcgt ataaatttag aaagaaattt tatatttaca ggtggggaaa attctaaaca | 1500 |
| catagatgaa gataaataaa aacacgatca actataaact ataccttata tttaccttcat | 1560 |
| ccttaacacc atgcactcaa atattcatta attctctata ttttttttcta tcttagcctc | 1620 |
| aaaatttact ttcatcctaa acttcgagcc ctcaaatttg cgttatttca ttcacgatat | 1680 |
| tccttttta cgttctttca tttatggtat tcttcttac gttcttctat ttacgatatt | 1740 |
| cttcttgctt ttatagtgtt ttagatttgt tcataaacaa cgtataaatt gaaaacttta | 1800 |
| taaatttagg gcattaaggt ataattgaaa ttaaaaccat atttatagtc attaaccaca | 1860 |
| gtattattta tcctttatt attaaaaaaa aaatctactt ttagttttaa atttaggcat | 1920 |

-continued

| | |
|---|---|
| tttacgcaaa gctaattacg acataaaaca ccaaaaggag accccgttcg atcttcacat | 1980 |
| cttctcggcc agaaacgacc | 2000 |

<210> SEQ ID NO 62
<211> LENGTH: 2000
<212> TYPE: DNA
<213> ORGANISM: Cucumis melo

<400> SEQUENCE: 62

| | |
|---|---|
| gcaatggcgg aaataacgta gcagagggca caaacaacga agaggagctt cgttcttcgg | 60 |
| tgcgccatct gggaaagtga gaaatggtgg acgaaacaca aacggggaa tcggattgga | 120 |
| tctctcagaa aagaaatggt tggattcgat cacagatcaa tgaagcacat tactcggttt | 180 |
| ttcaagaaga ttacaagaac ttgcttcttg aaacctctct tcttctgttt gaaattttg | 240 |
| ggcgtagaat tgaggaccgg agcagtcgcc tgaatttggt cgtcgaatcg attccacgga | 300 |
| aacaaaaata tgaagaaacc aaatgaatga cttagcccac tcactacgct tggcgacgtg | 360 |
| ttcttcttac gaacggacca atcaaatgcg agcctgatga atatgggcca atcatatta | 420 |
| gccacgtaag actttacttt tgcccctgac ctatgggaag aaaattgtgg tcttttctta | 480 |
| tgtcaataga agaaaaataa aattatatga aagtcttaaa aggaaaaaaa caaaccatgt | 540 |
| taatattact gtttaaaacc ataacacaaa atcaattatt gtttatgttt tgagactccc | 600 |
| ttatggtgtt tgctagatag tgtggatttt gtttttgaaa attgttttg aattttgtta | 660 |
| ttcttaagtt tttttatccg aaaatttcat tctagaaaac aaaattatat aaaaccattt | 720 |
| taaaacataa tatatcgtgt tatagttttt taatgtaacg ggattacacg gcctattatc | 780 |
| aattatataa taagatagat taaataaaca aaaatgattt atatggcttt tttaaaaata | 840 |
| aaatttaatc tctaccgctt ataactataa ttaagtcatt ttggtttaat aaaatcatat | 900 |
| tatatagtct cactcgtatg tattatttac aaaagatgtc gacttttat caaattatag | 960 |
| actaaactat aattttcttc gaggctaaaa ttataattta accaaatta taaatgtaaa | 1020 |
| atgtatttat aaataaacga ataatagctt gtcgtcaact atatttagt ggataagtaa | 1080 |
| gattagttt atgatttata aatatatagt ataaacaca tttaaacatg ttttgttcat | 1140 |
| tgcgtttggt tgatatttaa acctagtaac gaaaaagtat taggtattac attaaattag | 1200 |
| catccaccta caatgttaaa tttttaagtc agttaataat ttaagagact ctcttcaaca | 1260 |
| ttgacttcat gcaacataaa atggtagaaa ttttcacacc attgtttatc gacattacta | 1320 |
| cgtaggagaa tggcaaaact ttcttatatg tatgtgtgct tttagatgtg tcttacatc | 1380 |
| ccttatcaaa acgaaaacct aattctaacc aaatcaaacc aacccggggtt gttgggttat | 1440 |
| tcttacaagc catttgttgg attaaaaaac caaaatagag gatgttcggt tcaagcattt | 1500 |
| taaagttttg ggctatttag ttcgaccact ggtttgttca aagtcgggtc ggaccaaacc | 1560 |
| gtgagcgatg taaacaacaa aggtctaaat tgggccggga tcagatgggc tgaagatcca | 1620 |
| cgattctggt ttccaaccca aggcccaatg aattacaaca aaaagcgta ctcaggaaat | 1680 |
| ccgaatctgg atctcaacgt actctaacct ctcacagttc gccacgtcaa gaaaacacgt | 1740 |
| caatacttta ggcgaaaatc aagtgaagaa ttccccacaa taaggaatcg tatatccacg | 1800 |
| aaactatcca atcagcttac gccatcggaa gattcggaac aaagcaacag ttcaatggta | 1860 |
| tatcataggg tgagaataag tcggttccgc agactagtat ttcttagtca aactttacct | 1920 |
| gcttcaatcg gccgccgatt tcccgatatt tacaacattt agttccgatt tttccctcga | 1980 |
| agctctgaag tatcgtaaaa | 2000 |

<210> SEQ ID NO 63
<211> LENGTH: 2000
<212> TYPE: DNA
<213> ORGANISM: Cucumis melo

<400> SEQUENCE: 63

| | | | | | | |
|---|---|---|---|---|---|---|
| gatcaacctt | gaaatttttcc | cacatactgt | gttgtaaagt | tgtccccaat | ttcattcaca | 60 |
| aattacctac | ttgaggaatc | ggcagtaaga | agagatcata | atgtattttt | gctactacac | 120 |
| tcgcaagtct | aatcagagga | tttgattaca | atatcttgct | gctgtaatag | attcgttcat | 180 |
| aaattaatcc | agattgaaaa | gtcaagcttt | acttcatttt | catcgacaat | gtagaaattt | 240 |
| tgtttataac | tttgtactat | tgaatctatt | gctcctcgat | ttgccccctt | ggtacgatat | 300 |
| caagccatta | ttttccaac | tcttactcgc | aacttcaacg | catgaacttg | accagcttca | 360 |
| acctataatc | ttatgcatgt | ttttaatgat | aaagctgaa | atagattgtg | aaacgtacct | 420 |
| tattctcact | accgctgcca | aagccaacca | agcttccacg | ggtacccata | aggtccacaa | 480 |
| tcatggcact | cttggatgac | atgtattggt | tcctactgtc | tcttccgggt | tctcttatta | 540 |
| atggccccga | aagcaacctc | tcccggcatt | ctcgaaattc | ggctcactaa | tattctttag | 600 |
| ctactaaaac | acatgtcctc | aaatttctca | tttaaatgtg | atctgagaaa | gtcattcgac | 660 |
| ccattttagt | ttaaataagc | atcaagtcaa | aaaccattta | acgtgggctt | aaaaatttac | 720 |
| agcagcgcag | cgtacactaa | agtttatgaa | cgatgaaagt | gggtggcaga | agaaagcaag | 780 |
| aagtccgaga | gacatgccaa | aaagagtaaa | agtcatttgt | tggggccttg | acagcaaggt | 840 |
| tccatatgca | tcggtccatt | gcagcatggc | ggctcaaaat | taaattttca | cccttgcttt | 900 |
| tgcttctcta | acctacccctt | ctacgcatcg | tgtctatctt | ccttcacact | cattttgtgg | 960 |
| taagctttaa | cgcaacattt | tcttaatgta | atttaagctt | ggcccaccaa | tccctttgaa | 1020 |
| aagtttcctc | tagatggtgc | gtgtcaattt | caaattaaca | atttgaactt | atagttctaa | 1080 |
| cccccatatt | gtctgccctt | tttctcttct | tcttcttctt | cttctagttt | tgttctggtt | 1140 |
| taatcttttt | cggttttctc | tgtgcagggt | agtagctttt | aagcttagtg | attttctctt | 1200 |
| gttaacaact | ctaagcagtg | aattgttaga | gacctattat | ttcatataaa | tactagatga | 1260 |
| cttcgactca | ttgattaggc | tggaagctgt | caaaattaaa | gagtttgaca | aatacccact | 1320 |
| aatttggtaa | ccaagagcca | gcaggaacat | ttgtatttat | tgagacaagt | gaaagtttgt | 1380 |
| tattttcttt | actcaaaatc | tctctttaat | tttatagata | tagacattac | ttggataaga | 1440 |
| aagggagttc | accggccgga | ggttttcctt | caaatttaac | agtgactgag | gtctctttca | 1500 |
| gctttgtttt | tttggtgtta | ttactgtttg | ctcaatcctt | tgaacgagtg | gtgtaacttg | 1560 |
| ttaaatgccc | acaaattcat | gggacgcaat | cctttaggag | aaaggttggc | cactagttat | 1620 |
| tggtggttac | cgtggctctt | agcaacttag | catcagaatt | tgtcttgaac | ttctagtcgt | 1680 |
| tgaaaattct | cttcatacaa | agctaagtct | gcttatttgt | aggatccata | aacatgagat | 1740 |
| gataagggtg | atgggcctaa | gaatgcttga | tggaaacatg | gtcattggac | ttgcttatta | 1800 |
| attgaaaaaa | ccagccccgt | ctctggttag | aaccctcatt | aggattgtat | tgtttcaatt | 1860 |
| ctttcagctt | gttctggatt | ttaaaggctc | caatggtttg | agatgatagt | catggaggtg | 1920 |
| ggaaggaatg | gacaatacag | ttttgaagaa | ctgggttatc | tcaaatggga | aggtgaaatg | 1980 |
| tttatgtcag | tatttgcttg | | | | | 2000 |

<210> SEQ ID NO 64

<211> LENGTH: 2000
<212> TYPE: DNA
<213> ORGANISM: Cucumis melo

<400> SEQUENCE: 64

| | | | | | |
|---|---|---|---|---|---|
| atcttcaccg | ttaaatcgcc | gtggttgtta | gcggcggcga | ggagagagag | tgctctttct | 60 |
| ctgagaactc | ctgccatagt | agacctaaag | gaagaaagtg | gtagtgaaac | aaggaatggt | 120 |
| gaggagggtg | agaattgagg | aagtggttag | ggctttgaag | gaacggggaa | ttttatttcc | 180 |
| gggaagggaa | acaacagggg | agaacacagc | cggagcggtg | tggttgtgag | aaaatttaag | 240 |
| caagcagatg | agacgacggc | ctggcgccga | ggacaggcat | atgaatatca | cgtggctatg | 300 |
| gctatgggaa | attgaacgta | ggcccttttct | cattcttata | ccaatcttca | tttttctatt | 360 |
| ttctagggtt | tcttttcttt | cttttttctt | tttccttttt | cacatttttta | tatgtcattg | 420 |
| aatttcgaag | tttggagtta | atatgttgga | gtcgtgtatc | tatttagctt | catgggttat | 480 |
| aacattattt | tggatgatgt | atgatattta | atctcaattt | aagaaggaaa | cgagtaacca | 540 |
| aaaaatctta | taatgaggtt | tgtccatctt | ttatgtatta | ttctccactt | atcacatttg | 600 |
| tttgaaataa | ataaataaat | aaatgttgtg | tcacctcaaa | cacaaccata | tggttcaaat | 660 |
| tgaaatttaa | cacttgatgg | tccctatgtt | ccatacgacc | taacaaggtc | atcttttgat | 720 |
| tgtgaggttc | atccaacata | aagttgttat | aaactaagaa | tatttcacttt | atgagtgttt | 780 |
| atgtgcacgt | tgttggtata | ggccataatt | ttcaatcatt | taaaacttttt | attaaccatg | 840 |
| atttcacatt | atcttgatct | ctcccattcg | aatatgattt | tggttcatct | atattcccct | 900 |
| tataaactca | acgttacgtg | cctaccagtt | ttcgcttggc | tcatcccccaa | cccatatctt | 960 |
| actgtggaat | gttttttctc | tgataccatt | tgtattgttt | cacaccttcg | aatcatattt | 1020 |
| tagaatgttg | atacagtacc | taatgcatgt | gatattcccc | tccatttgtt | gtgacatggc | 1080 |
| agcatttgtt | cttacttgtg | tttgaattgt | tttctaagag | aaaaaaatga | tatctccaca | 1140 |
| aaccaacgca | catcattttta | gcatatcatg | tgtctcattc | acgtggttct | taaaaaaaaa | 1200 |
| tcaggacatt | atccaataag | acgtggtcaa | gggatgaacc | aaatgaaaat | taaaagggca | 1260 |
| tgtaatggcc | gagttcatga | atgcgtcata | aatgaatcaa | tatcacacta | aaataagacc | 1320 |
| gatcacaagg | gtgtgaaagc | atagttaaca | ataatataaa | aaaaactaaa | agctcatatc | 1380 |
| tatgccaaca | acatacacat | tattttcgat | tgcttaatcg | tatgaacttt | aaagttaaac | 1440 |
| gtgtttatttt | taaagttaaa | cgtgcttatc | ttaaaacaat | cttatgttgg | acgacctcca | 1500 |
| caatttttttc | cattacgcat | gtgagaaaca | cattgaaagg | actcgaatta | gcatgtagag | 1560 |
| aatggtgtag | cccccattct | ataaaagcaa | ctcaagatct | gaacatgcat | tgaaatttca | 1620 |
| ctcttcattc | ctgacacata | cataaagaga | agcaagtacg | agaatcatcc | tctactttttt | 1680 |
| attcacaagt | tttaagtcaa | atttcaactt | gatttgtatg | tttcaaaacg | acacacctac | 1740 |
| tcatttaatc | ttgagcgtta | cttcaattgt | ttttatgttt | caaatgttta | aaaaagaaaa | 1800 |
| aaaaaaaaag | ttcaatagtt | ttgtaaattg | caaaaaaaga | gaattacgag | tatgccctg | 1860 |
| tacatttaga | agaagcgtaa | ggtccatatg | ggaatcagaa | caatcaatcg | acggccacat | 1920 |
| ctcacgagac | ataaacaggg | ggagttggag | gaatcgacgg | agatcggaat | ctggtttagg | 1980 |
| gttttagcaa | aagaagaaca | | | | | 2000 |

<210> SEQ ID NO 65
<211> LENGTH: 2000
<212> TYPE: DNA
<213> ORGANISM: Cucumis melo

<400> SEQUENCE: 65

```
aactcagtga atacgataag aaatttaatt gaagttaaca aactcaaact taaatatttt      60
ttaacacgga caatttaaaa ccaaattcat agtctccttg tatagtgttt agagtgtgtc     120
gcttcattaa acctttctat cgtggaacaa atctcttcta atattttgtc aaaaacctat     180
catcacccaa aatatcatga taattatttg atgaggatca aggcttagag aggaacaagg     240
gaacttttca caagggtgga gagatttagc tattaggttt aactcgttgc ttctaatggt     300
ggatgaataa cgacaaattt taaacaatga acgttatcac gttgaaacta tctacttctc     360
tcaacctact actttatcat aaggtttgaa aagttctatc gaaattttta aatacataaa     420
acataaaaag gaaaattttc attggagaat tttccatata tgtttaccca caaaactaag     480
gctaattaaa aagctaacct taagactaag gctaaaatgg tatcttatgc tacattttc      540
agttgctatg ttttgaagca aaagctaatt atttgctaat aatgagatag gcatgtgggt     600
gagtgatgag cttagcctgg cctgcctttg tgtttcttct tattctctta aatatcattg     660
ttcaatcaaa atagttttgt taaatttagc ccatcctcac ttcaacctct tatatttgga     720
ttggccttct ttgttttttg ggcttttgat atttgatgta atggacttca atcatttata     780
gaagccttac cctacagaaa caaacaaaca aaagaggaa aaaaaaatg gtgagttggt     840
taataacaac tttctaactc aaccaatata tggtgtgtgt atatatatat atatatcgaa     900
tacaaaatat gaatatgata tgaccacata aaattgttga aagggttgaa aattagtgaa     960
ttggactttt aaattttgta gtgtagtggt ttacctatga tgctcgtaat gttatttaat    1020
tttaaatgtg tttttttttt ttacaaaaaa aagtctcgcg gtgcaagttc aataagttga    1080
tttaaaaaca aatccatcaa aataatgttc gcttgatatg atcgagtata gagccgaatg    1140
tgtatcaaac ataaattcaa actttaatag agtgaaaaat aaatgctacg caaacaaagt    1200
ttttgtatta gcttcttaaa tgtacatata tacttttccg attcaaacac ctccaaaata    1260
aaactcaaaa gttaaaattt agactcagaa aatgagagaa aagaaaact aaaaacgaat    1320
tctaaagata agcattttca aatataggaa aatgaacaat aaatatttac aaaatagaag    1380
aattgtaaaa aacgacaaat tgacataata cttacaaaac ataacaaaat ttcagattct    1440
atcaatgaca tacactgata tatctttatt agtcatagaa agtctatcat ttataaaatc    1500
caaattttg ttatatattg taaatattta aatttgtttt accatatttta aaaatttag     1560
atttatcacc aacaaataac catagatttc aaattttgct ataaatattt ttaaccgttt    1620
atttaccata attttctat tataaaaaca aaaaaaacaa aaaacagata aaagcgaaga    1680
aaaagtaaga gagcagaaat attttttgat ttaggtttca tttggtaaaa aattgttatt    1740
aaaaaataca aactaatggg aaacaataat aataatttaa ttttttaaa atctaaaaag    1800
aaaatagttg acaacaataa tttaataatt taatacacaa gccagtgtta ttaatctctt    1860
ttttctaac aacgcctttc acgagacatc ctctcaatcc tcgacatcca gtggaaaaac    1920
agtatccctc aaccctcagc tttccccaac cgccctccgt cgttcttctg atcgtcgcca    1980
ccctactccg tcatcggaaa                                                2000
```

<210> SEQ ID NO 66
<211> LENGTH: 2000
<212> TYPE: DNA
<213> ORGANISM: Cucumis melo

<400> SEQUENCE: 66

```
catatattta ttatgttcca cttgataacc attttgtttt tgaaaattaa gtttaaagac        60
gacactaatt ccatcttcaa ctttcttctt ttgttatcaa cattcgacca atagtccaga       120
aaaccaatta agttgttgaa aactaaaaaa aaaaaaaatt cttataaagt tgttttttt       180
ttaaatttgg ttaaaaattt taatcattat acttaaaaaa tatatacacg aatcatagta       240
gaaaattgaa aacaaataaa cttaattcca aatctacttt aaaggctcac tatctgtcaa       300
gaggctttgg tatagttgtc tgtactgatt aagtgtgaga gttctttaa tatttgtagc       360
tgaccaataa attcttttcct ttctttctaa ttttgcttta actccctatc ctattcatac     420
acaataaata tacaccatat tctaattgac aatattgttt ggatttgttt gttttcttta      480
cggtaggcaa gaagttgcct agttgttgtc tgacctcaaa acctttgtt gataagagca       540
aacaaagtct agttttccaa aaaaaaaatc accaactcaa ccaaatcttg agccttttac      600
taatttccat cccaaactaa tatctaatca gtgcttacat gtttgagcct tcaactcaat      660
ttaacatcaa aacatcttgc aaccacacct tgacatgagt atgaaaacaa tataggagag      720
aactttagta ttacattgag ttccattatc attgtacatt ctcaaccaac gaaaccaacc     780
caaaacaaaa tagttttttg taacatatga gattaggtat cgtcctagtt aatgattta       840
caaagttata tgagtattca tttgttgata tagtttgacc ggatcggaca gttggctaca     900
atggtatatt tctataaact aaggtataca atttttcatg tatgttgttt gatattgttt     960
tattattggc acatgtcttt tgtgtccaat agtaataaca aggttgtttc ttatctaaat    1020
aaaataaact cttgccagat aattgaagtt agactttaa tcaaacgta atattaaatg     1080
gggatgagaa ataattgatt attaggtaaa cctaacaata aaatctttaa attgtgttag    1140
aatcatttag ttagtcgagt tctacactaa aaaaaattaa aaacactaaa atcatttata    1200
aataaaatat tcaatatctt caaaatgtac taaaacattg aagctcataa aactaatcat    1260
ttttcttttg attaaatttc tctctcatat taccaagaaa cctaagataa cattaccaac    1320
gattcatacc aaaaaaattt attatcattg aacatatctc aaactagtgt attcaataat    1380
ggttagagta gtagttatat taaggtgcca tgagtttgat attttctttt tttgcctaaa    1440
ttaggttaag ccgtagctag cttgaacaat gctaaagatc ttcttaagag tttcgtagtt    1500
taacgtttat atgataaatt ttattacatc cgaacttgat atttaatttt tgtggctctt    1560
atctgtgttt agttttcctt attctctttt aacttgtagt aatcaaatga aagccatttg    1620
caaatgagga caaatgcatc tgcaagatat atattagcca atctcttgat atttttatgc    1680
tctatgagac aatatattct gccatttgcc catcaaatgg ccataatttc tcaagatttt    1740
tccatttcga gtttgtttca atcttctact ccttttgttt ttcctttgtt caatttttg     1800
gacctttgat gaaatatctt cataactcct atgacgtggg caccatccat tggttgtcat    1860
ttgataagaa atatgtgtca atggcacaat tcccattcca tttatatatt atatagttcc    1920
taaagccata tccccatgat ttatatcctt cttcaagctc acaattgaac tttaacatta    1980
cttcttccct acacaaagat                                                 2000
```

<210> SEQ ID NO 67
<211> LENGTH: 2000
<212> TYPE: DNA
<213> ORGANISM: Cucumis melo

<400> SEQUENCE: 67

```
aaataatttg tggatttat catattatgt accttagact ttgtaaggtt tataacacaa      60
gatgtggaga aatcccatga tgaacatgga cgttattata tcctttgaaa ctaaaaacaa    120
aggaaaaaaa gacaaatggc tgagtataag aaaaagagaa gaaacaacca aaaagctaaa    180
atgtcatgct ctcatatgta acatatttga attgggattg atttcaagat gtattttaaa    240
ataatttaac acacgataaa ataattctaa caaactcaaa attactctta aacatttact    300
tgatatcttc gacataatga cttttgtttt aatacaactc aaaacataat taaggttggt    360
tttaaatgac aacaaacgaa aaactcgatt ctaatttcaa tactagtctt tgaaagccct    420
aaggagcgtg gttttgaatt gtatagcaag gtttcgaaaa ttttaatcat caaacaatag    480
gtatatttac ctgttcctca agtacagtta attcatagct acttgtcgtg cttcctacga    540
caacattgta agacttgcca cacactaatt gaagccgttg ttgaaggtag ttttccatgt    600
atagcttgaa tcgacggatg accaagagg ttgaagaagg tttgaaaaat aggggaaggg    660
atatacaaag tttgagagtg agagagggag agaaatagaa atagaagaga ctgaaaaatg    720
taaagaaag gatgaaaaaa tgtggggtaa acgcaaattg gattttata gtagtatttt    780
gaaaatgcta tagaaaggct atgtatagta gtgcttccaa agttctatat gaatgagaca    840
aatcaaaata tatttttttt gattaattaa ccccaaaaag actcataaaa aaatcttata    900
aatcccacta agatattgca tgttatatgt agtaaaattt atcgttcaaa taaaccttaa    960
acataattca aacgaagaaa gtaaaaattt gaatttctta tcttacatca ttcaaccaaa   1020
caatttccat ataagagatt aaacttctaa ctttaagaga gagatatcca gcatatgcaa   1080
cctaaaccaa cagtgacttt gctatatatt tgcacaaaat gtgggggaca agttgtaat   1140
ttcggaatat caatgattaa agaaaaggta aaatttaaaa ttcggaagct tgacgtggca   1200
acacggaatg gtgatgatat tccaactcc tcgcgacttt tagaagttgg cctcaccaac   1260
cgcatatccg cccctttgcc acgtgtcaga ctacaacaac ttccaacaat ttcctttaag   1320
aacaccaaat tatatcaata aatatttaac ttaaattaag aatatatttg ttacaatttt   1380
cctactgagt tagatagata gacagacttg tcaattaact aataagtcca aagtcaattt   1440
actcaacata gatacaattc taatttgagt gtgaaataca tattcaaatc aaaattatta   1500
ttaagaggaa aaactgattt gctttctcaa tttaaaatat aatattttga aaagaaaca   1560
cacatgtatt atggttttca atatatttac tttcttagtc acctaatctc aaactaattt   1620
ttgaagaaat taaatatata tattatcatt tttattttct tggttatgat attggtatag   1680
aatcaacaaa actacaagtg tcctctcctc tgctatcgat ggggattaga ctctaaactt   1740
gtttagcgat tagtaattat atattagaaa aagtttatgt taatgtggac ccgacaatct   1800
caccaatagg ctcttcactt caccaacccc cgacccattc cctctaataa ttcgacacgg   1860
ctcatccccg gttcgaaccg ggccgacgtc ttcctattta acacacctcc atttcctctt   1920
ccctccgcaa cacaaacaga gacctcaccg gaaaatcaag ttaaagcaaa accaaagaga   1980
agcttcatca ctctccggaa                                              2000
```

<210> SEQ ID NO 68
<211> LENGTH: 2000
<212> TYPE: DNA
<213> ORGANISM: Cucumis melo

<400> SEQUENCE: 68

```
taatagttgc aggtcttgtt taaaatacta atctaggtgt gtaaaacata gaaagtttaa      60
tgtggaattt cttatgagaa cgattaaggc tggtgaatct cgcttggtta aatttgaagt     120
agtttcactt cgatggagac tagacgttta ggcattcgta atttcagaga caacataacg     180
aggctacgtt gggaaaatag ttatgtcatt ttatcataac tgcatacttt gtggtaagga     240
tcatactgat tagtaagtac ggtttccact ctatagtgtt tgagtcaact tctgtgcccc     300
tttactaatc tcacgagaga atccgcctgg tcctgtaaca tttgggtgtc aaagaaactt     360
gtaggaaaga ttccgaccac catggattga atcataagtc aagggccatt agtaaaaacc     420
tctaacttgc tcttgcttta aattttcctc tattctcctt attcgttaag cattgggtgt     480
gggtgctata ctaactttg tgggttgtta atggcctttg tttctgtaga tagtaaggac      540
ttctactgta aacttgcttt ttgtttgcac tttctcactc tttcattttg ttaaaaaata     600
taagacaaca taacagagcg acagagagaa agagagacta accatagcaa ctggagctcc     660
ttgtgaaatt tatccaattc ctcagaagta gacaatatag gcttctttac agcaactttt     720
ctaccatcca accttccttc atacacagta ctctcggccc ctgcatcacc attcgataaa     780
aatccaatat gtcaacagaa cctctcaggc aattgaaccg aataaaatta gtgcagcgtt     840
gagtgcttac ctcgggcaat tggagagagc agcgtgaatg cggaaggttg aagatgaaga     900
ggaatcgaat tgctggagca gcagccctga tgcaggtgtt cggatccata attcccaaat     960
ccatatccgt tttcgtgaag aaatgttgag gaaaaattca ttatgcgttc agtttatacc    1020
attggagagt gggaaagttc gtattgtttt gctaatttcg tcgattctca ggtcttggag    1080
taaaaacgtt gtaccgcca cttcccattg ggccattgtc caatattgtt tgggttgggc     1140
gggtggatga cccaaatttt ggggaagata tgagatttgt ccaactctgt tatcaaatat    1200
gaccaaatga acaaaatatt gactttttt tttctatatt tttttgaatg aagtataagt     1260
agttgtttta ttttgtttat tttaactcaa aattaccaaa tttggatttc acaaacataa    1320
aatagatttt atactttta taattcaatc gaaagttgat cgtatatgaa aagaacaatg     1380
aataaagaaa gaaatgtaaa atttatatca acttaattaa aacctcgcaa tacaaaaatc    1440
gagtgaaata gagggtggag gatgagagga agaggagaa gacatccata ccctccatgg     1500
acatgggtag atgtatgggt tgggttgggt tgggttgaat tgggtcaacc catccactcg    1560
gttcatatag acagcattcg ttttataatt tatccaaaat aaaatataat taaaagaaga    1620
aaataaaaga aaaacgaaat ctccaattcg cgtaggaaat taaaaaggaa gagttaattc    1680
aattcgattc tctcccatct tcatcataat tttgcgaaag gatcgtaagt tgtatacttc    1740
tctccttgct gcttttcgaa tcgggataag aatattttct ttttgtcttc cccattccta    1800
ctcttcaaaa ttctctgcat tttctaccca tcacttttac ttcaaccatt tttgttgttg    1860
ggagttccat atttttgattt cctctacaac gcctaaactc ttcttcttct tcttcttctt    1920
cttcttcttg gagtgatttt tcagttcaat tttggggatt tcatctattt ctttgatctg    1980
cagcgttgct ggaagttgcg                                                 2000
```

<210> SEQ ID NO 69
<211> LENGTH: 2000
<212> TYPE: DNA
<213> ORGANISM: Cucumis melo

<400> SEQUENCE: 69

```
agtttattct gttgtagcaa ttcaaagcag tgtgatccag atgagtacat atttggtagt      60
agactcaatt atcattttat ggttgaaaac cacatcctct tctgtcattg ttcatattat     120
tacgaggaaa aaagccacgt cctctttcaa aatttcttcc acaaactctt tcttaaaagg     180
aggaattaga gtttgaaaga ctaattagat cgagaattat tcatattcag attggtacct     240
aattgagtag caaccatcgc agtaggttga agagaaaggt cctcttgttt acgatgtttt     300
gcaagagcaa attcttcaaa tttcaagaga gtatgaagtt cttcaaagat tactgattgt     360
gaacgagtgc gcatagagat gtgaaaatat tgtattcatc tagaaatcaa atgagagtat     420
agatcaacaa atcttcatcg tttactattg aaacacacat ttgcaagttt atctttgatt     480
tttttgcccc tcctcatgta tgaattaata gattcatcaa cttctttgaa atcgattgaa     540
gattagtttt gagattaaca atatttgatc gtaaatttga gtagtgattt tcaagtgcga     600
cccagacttc ctttgatgaa gtacaaccaa caattagggt ttttacagac atagtagcac     660
tgatcaaggt cataaaagct tgatctttag caatttaatc tttatatata aaagattcaa     720
cattgtcgtc gattgatttt gtattgtaga tgaactagtg gtcgaagaaa tcaaaatcga     780
ttttgaaatc aaaatcgatt ttgctagagc tgtacttatg tcatcaacaa atccatataa     840
atccatatag cttgtgtgct ctcaaaatag tggagaattg gaatttctaa gaaacataat     900
ttgttgattc gagtctgata aatatgaggt acatatattt gtgaggaaga tcaaaaaatt     960
gatttctttt gttcaagaag actcagcgga agccattgat ggagagaaca aaaatcggag    1020
gggatggtta atcatgggtc tttgatctgc tctaatacca tgtgatcttt accaagttgt    1080
gaaaaaataa tctctcattt tctcattaat ttacaataat agaatatggg tatctattac    1140
aacccaattt acagaggaaa tactagctga ttacaacaga atcagtgcca aatcaattat    1200
taaaactaat actcaacact aattaccaaa gaattagtgg ttttttttacc acgaatttat    1260
ggggtaaaaa aagtgaactt ttaccaaatt agtaaaataa aaaagaaag aaaaaaaaac    1320
gtaatattca aatggatggt gaggcatgaa gaagagtagc ctaaagtaca tgaagagcta    1380
aaagacttat tatcttccat tggtcccatt gaagaccaca aagaaaatat cagtcctttt    1440
tctctttaga gacacaaacc caagtagaaa agaatctttc acaagaatta ggaatttaat    1500
gcaattttc ttttttaaaaa aaatctccaa ttttctatct cattatccac cctttccact    1560
ctaaacttca ctacaatttg atgaaatctg tttccaccaa tcagattgca ccaaattcca    1620
tcaaaaacgc cccatcagat aattatggat gtcttcttct tcctctcttc tttcgtggct    1680
gaaattgaag ctcaactcaa aaatacattt cattttcaaa attccctgat gacccaattc    1740
gccacgtgtc cctccactc accactaccc acacaaaaca actgcttctc ttcctcttcc    1800
tcttcttctc cattaaattc ccagacccat ccctctgcaa cttcgaatgc aacagaaaga    1860
aaacggacca aaaatcccctt gaggaatttc tcattttga agcataattc aaagattaaa    1920
cccgtattaa ccctcttcat cttaccagag gtttgattta ttgatcgaat tgttttattg    1980
gttttttttc aaggtcacca                                                2000
```

<210> SEQ ID NO 70
<211> LENGTH: 2000
<212> TYPE: DNA
<213> ORGANISM: Cucumis melo

<400> SEQUENCE: 70

```
gcatcttatg gatgtagtca caacatattt atatggattt tctgataatg atatttatat    60
gaaagtccca aaaggattta agatacctaa aacatataaa tcaaattccc ataaactatg   120
ttcaataaag ttacagagat cattgtatgg attgaaaaaa tcatgacgaa tgtgatacaa   180
tcgcctgagt gaatatttag ttaaaaaaat aatatcaata taattcaata tgtccatgcg   240
tttttataaa gaaatcaccg tcaggatttg ctattataac tgtatatgtt gatgatttaa   300
atataattga aattttgaag agttttcaaa ggcaatagaa tattaagaaa gaatttgaga   360
tgaaagatct cagaaaaata aaattttgtc ttgattttca aatcgagcat ctagtaaaag   420
ggatatttgt tcatcaatta acttatacag agaaaatttt aaaaagattt tatatagata   480
aaacacattc attgaacatt ctaatgcaag ttcattcatt aaatgtgaag aaagatattt   540
ttcgacgtcg agatgataat gaagaactcc ttagtccaga agtaccatac cttaatacaa   600
tggtgcact tattttgtca ataatcaaga ccagatattg cattttctat aaatttatta    660
gctagattca gttctccaac aaaacaacat tggaatgaag ttaaacatat acttcgttat   720
tttcgaggaa caattaatat aagattattt tattcaaata aatcaaattt taacctagtt   780
agttttgcat attcttgatt tttatctgat ccacataaat ctagatctca aacaggttat   840
ctattcacat gtggaggaac tgctatatct taacgatcag tgaaacaaat taccataaca   900
gtcaactctt caaaccgtgc tgaaattctt acaattcttg aggcattcat gaggctagcg   960
gagaatgaat atggttaagg tcgatgactc aacacattcg aaaattatgt ggtttgtctt  1020
ctagtaaact ccttccaaca acattatacg aagacaacac aacttgtata gctcaaataa  1080
aatgaggtta tattaaaagt gatagaacaa aacacatctc accgaagttt ttctatactc  1140
atgatcttga agaaaatggt gacatcacag tacaaaaaat ttgttcaaaa gataatttgg  1200
tagatttatt tacaaaatta ttacctactg caacctttga aaaattggtg cacaacattg  1260
gaacgcgacg acttagatat ctcaagtaat gttacatctt acttgccaag ttaactatac  1320
atagtgacat ttggtggagt tgtaagaaac actaatattg gagaaaaatc gaagaaatt   1380
ggaaaatatg gagaattgaa ttttttttag attttcctta ttttctaatt ttaggtttcc  1440
gtattctgat tatgcctcat tttcacaaca ttaataactt taataagatg atttcttggg  1500
ttaagggaaa aaatcatttt tttagagttg cacgtacaaa aatattatca taacatatcg  1560
attataataa accaattcac cgtcaaccta acctaggtag agtttgagtt aaatgttaaa  1620
agaatatcca cccctcaaca ttgtaatccc aactaataaa tcagcaacct aaagtttttt  1680
ttaaaaaact aaaaagaaga gcaatatatt ttttttacta ttatttttt aaagagtgga   1740
tttatttatt aaattaaaaa atgaaaagaa gaaaatttgt tagtttgggt aatccgaaaa  1800
cccgattatt tgggcccgag aaaccgacgt tttgtttatt gttcctcacg gcaataagta  1860
atggcgtgaa tcgaccgcgt gcgcttcaag ctatctagac attttatat cctccgatta   1920
gaaaccctaa ttcagattct ccgtattacc cacactggaa catctttgaa acgcgaaaag  1980
gtgacccgaa gaaacttgaa                                               2000
```

<210> SEQ ID NO 71
<211> LENGTH: 2000
<212> TYPE: DNA
<213> ORGANISM: Cucumis melo

<400> SEQUENCE: 71

```
taataaagtc gatgatatga attaattaga cggatgggtt atactatagt tattttattg      60
tcttttatag agaatttaac attggtagcg gggaaaatcc gatagatatt ggtgaagagg     120
aattcgttgg tggatgtaaa ggaaagttag tttcgccttg gcacaacgaa gggtttgaat     180
ggaaaatcat gataagttcg actgcctgtt caactaaacg aaagatacca agtcaaacct     240
tagttttctt taaggattta tgatcttagt agtgtatcta tttaaagatt caaaggtatc     300
aatagactat ttatttcaat cgttgtgttg aaatctagga gtatatttaa cgattaactt     360
aaaagatttt gctatcttgt tttgtgtttt tcattttttt gggaaaacct agtgtctttt     420
tattttattt gatacaataa gtattataaa aatgactaga atgactatat acttgatcat     480
tattttgaca tatttgcaat atattaaaaa tgactactta ttttaattac cttcatggtc     540
tttttttaat ttatgaaggg gtgggctcgt gtggcagatg aggcctgtca taattagcct     600
taccttaaat aattgggccg gttctttggg aaatatcggc ccaacctaac ttttcatggg     660
ctcaaatgat gctttatcta atacccatac tttccattac ctttgtatat tgaattagaa     720
tgatagaaaa acatactaca cagttgagtt aggatataaa taaatgcatt gaactatgta     780
ttacatagtt gagaaaaatg agaatgaagt tttgtctttt gaatatatat tctgtgaaag     840
ttagatgtat atagaaatga tgatacttcg gcgtttgttg aagattgagt gggggtgtcaa    900
cctaatcata gttggtttaa gaaaagttttt aattataaga taaccgttttt aagtgactta   960
tgccatattt tgattgcagg ttcacaatga aatgttttaa tttggtgatt agactttgac    1020
aatgtggtaa tttatgttaa gtgagttgtt gtctcgttta ccttgatcat ttgtctctac    1080
tcatttctca ttttgtttca tcccttgtta tatggcatcc attgttgttg tatttgtcat    1140
tgttcacatt cgatgcttaa ctaggtaaga acaacatttt cattttagaa ttggaacgat    1200
agaaattcat aagttttatt tttgaggcac ttggttcatt ttaatcatag aacattagtc    1260
cacaatcgtt tggaataaat ttacactcta tctagatatg gaactcttga caacctctac    1320
caaggaagga tgaaaagcaa aaaaagagta gaaaaacgaa agtagacact ataacaagcc    1380
aattagccca ttgacaaata ttaccacgtt attaaagttc attttaatca tcgtgtcaat    1440
tatcaacctt ataggtcaaa taccatttat aattattttc aaattcaatt aatgaaacaa    1500
gactcaaaaa accaaacaaa tatccaaacc caatatttga gtttagaata taataatttc    1560
atagttagac ttggagacag atttgtacgt atatgttaaa ttaaaaattt aatcaaagta    1620
taaataaatg atttggagtg gcaagaaaat attggccaaa atttcataag aaaaaggaag    1680
aaaataaaaa ggtgtattgg ctaacaaaaa cccaattcca tggggaggag aaaatttgag    1740
tcctcaaaaa aggatttcag ataggaacc aaccaatcaa aacgaaggac gtctccacgt    1800
gtcgctacaa gaggccatct ttccaaaatg agatcgcgga taaacaagcc tttctgagc    1860
atagaaaaat ggcgaatttt aacaaaaaga aaatctcag taaagtcatc agctacagct     1920
gctcttgac ggccacttga ttcactattt ccctctcttt ccggcgctga ttctagtgtg     1980
gttgaacttt ctgcaaagaa                                                2000
```

<210> SEQ ID NO 72
<211> LENGTH: 2000
<212> TYPE: DNA
<213> ORGANISM: Cucumis melo

<400> SEQUENCE: 72

```
attacttgaa cttaatccac atttatgtct ttatataaag ttcgaatact cataatatag      60
ccaagaaacc ttgtttattg gattttgagt tttatcataa gcaaatctct tatccaataa     120
caaattatta aacaacactt caacaataac tttattcaac aatatattag tttaacattc     180
acaaatcacg agtattagaa cataaaacgc aacaaagaat ggactaaggt actatattct     240
aacttaggtt gtttaggatt tccatatgtc aatgctttg tgattttga actagatttt      300
cttgttagat taattcaatt ctatttttaa atggcttaat atcttatttt cggatgcttg     360
gggattgcta gactaccgct tgttgaagc aataagttaa atttgtttgt tacaggtatt      420
gatcaatcta acatagaatt gaatttgtat gaatatttag ttagacgctt gaaaactaat     480
tattctacca atgagccgta gatcttaatg caattgttat taatttgaac tttgtatgct     540
tctcatcgat taaatttata tcaagtagtt aattaggaca aatctattgg cttttcatt      600
taattttgtt aagtaaaagc aacttagaat tttgaaaatg atgaacccat gatccaatac     660
attgaaagag aattttgttt aactcaaact aggattcttc tcacattgat ttcgtataat     720
ttaactttt caatttatat caatcccccc agggtgaaaa aaatttgttt gaagaattca      780
tgtgctttct aaatctgatc tagacttgcc actaaaatta acttttgata tgtaatttgg     840
ttaaatattt gattcggatt tcgacgacaa acaattgatc aatgtggtat taaattctga     900
tctccatgta agaaatttac acattttcat aagttcaatg ttgacacaaa gagagtaaga     960
gcatttttaaa aaaaagata ctttttaatct tttctaaaaa aacaccaaaa tgccattatg     1020
taaatgtaac ctaataata aacatttaaa cttagaattc atgcaattag ctttgtatg      1080
ggacattgaa ttgattatta aaatcagtag ttatagaccg tgagttataa tggtttgtat     1140
tagaagcata aattatttta attttgatcg taatagcatg tatttgagat ataaattaat     1200
ttagtttggg tggcaaatag taaacagtaa agcaaaatat aaaaaaatga atttaaaata     1260
gtaagatttg taacaaatga ttaatactat aacaaacgtg gttttaaaat aacgttgatc     1320
gtagctaatt gaacattatt tattgtaaaa ttgagtgttt ttaatatttg gagcctcaaa     1380
cttcgggtgg atcaccacaa tataatcata ttcaaattta aaatttttatt tttttatta    1440
attataaata ttgattgtta atagatgctc attatgggcc atctgtcact ccctccgtgc     1500
atatcctacc tgaaacatca tatatcttaa acaatgtcca ttgccatgtg tcactatttt     1560
tacatcccat ccacttgaca aatatgttga agatgcctac tttttaggg atcatgtaat      1620
ctatctcatg cttgtcaaat tgttcgataa tagtgttaca aaaaatttag taattattat     1680
tattatattt cttcgatatt tatgcttcat atgccattgt gctctccatt tttaccatac     1740
ttaaaaaaat ttcttattat aaattttttc aaaaaaaaat ttactatata gtcatcatct     1800
ttattaaaat taaaattgag aacctgatat ttttgatatt ataatttaa atttgaatt      1860
aatccacttt aaaattatta ataatttatt cgaatttggg ccttaaggaa gagatacgga     1920
aacaaaccct agatcccatc tatatataaa tcgccacaaa accctacctt tctctcagtt     1980
tctcgtttta gccggcaaaa                                                2000
```

<210> SEQ ID NO 73
<211> LENGTH: 2000
<212> TYPE: DNA
<213> ORGANISM: Cucumis melo

<400> SEQUENCE: 73

```
tgaaaaacta aattaaattg tccttacatg tgtataaaag aaaccttcgg acatttgatc      60
tgagaactat gttaaataat aagatccaaa aaactgaacc ccaacatctt cgaaatcgat     120
ttgatttcaa ttcttaagat aagctacatt caagttacct agatgatcta agaaactaat    180
gattggacaa agttagaaac tcccaataaa ccaatgatct tcaaagcact ctacgatcaa    240
gacagattaa ttttagttt gaatgctttg aacactcgtg cattctatca caagaacaaa    300
aattatacgt tttagaattt tcaaatatca ttcatcccaa tttttatttt aaacgtgaaa    360
attacaactc tatttatact aattaaaata ttaattaaca tgttacaata tttaattta    420
tgtcatttca actaatgtaa taaataaaaa caaataagac aacgtaaata cacaatttca    480
taaacattta atttcacgac ttttaagttt tctaaataaa ttttcaactt tttcatttga    540
tttaattatg atttctcgga tcatatctat atatatatat atatatgaag ctgagtttta    600
gaaattgtaa attcaaattt ctttaaatgg tacaaattca attagtaaga ggaaaaacag    660
ctaattaaat aatgtgtgat gccccactcc ctaaaacagt gggtttggat cgattaatca    720
actaaaactg accacaaaac aatattcttc tacaaccccca ttgatttttt taatcattaa    780
gtgccgattc aaagaaacaa taaacaaaag aagttgaaaa gattgagact tttaaattaa    840
atctgcaaga ttctctccaa actcatgttg tattcaagtg tttaaagctt aaaatatcag    900
taattatgtg ttatttaacg gtgaaaccaa tcaaatcaag caagattctt caatattcaa    960
ttccaaatcc tcaagtttcc atgaaaaactt cataacgcct ttatccctcg aaagccaaaa   1020
ttcaatttcc tccattcatc ttgcagccct atctactttc caaaagccaa caaatacccct  1080
tttaagcagt agccttttgt ttggttgtag taggatcttt gtttctcttc cattttaaca   1140
caagccacag gagaatctct atctctatcc tgcaaccttc atccccacat tgttcttcct   1200
ccattatcgg aaaaacccag tacagggttt gctttccggc cactatccgg ttgttctttg   1260
taagttttt gggttttcat tatctgggtt tgtggctgct tgtggattca gggtaatgtg    1320
gccatgtttt atagtccaca gcctttttt cttcttttga catgggatta tttctgattc    1380
tatttgtcta ttgttacttt gtgctttttc tggtttgttc ttgtggtcat catttcttat   1440
gcttggaagt tcgaacatga atcaattcaa caactaagtt gagagtgttc gactctctca   1500
tctcattgac cctgatggta tatcttggct tggaagttag aacatgaatc aattgaacag   1560
cttacttgag actcgagagt gttcaactct ttcatctcat tgaccctgat gatatatctt   1620
ggctttggag ttatgaacta tgagagcttg gaggatgaac taaaagaag ggactatttt    1680
ttgagatgga tatttagttt tagtaattta gcttttttt tttagtacat agtacattaa    1740
ctttgttcgc gaggaaatag tggtcttgtt gacgagcatt tcttaaacaa tgtagttttt   1800
gtctcatctc tttaaaagtt tatggagggg caaacaagtg agatcaatag ttatagtatt   1860
tcaatctata actttggaac agctgatttt taacttttcc tttgtctttt ttttattata   1920
gaacacatta gagtgcgtta gattcttcag ttctgagatt ttgatctttg agtgctctct   1980
tttagcagta gaggcaaaca                                                2000
```

<210> SEQ ID NO 74
<211> LENGTH: 2000
<212> TYPE: DNA
<213> ORGANISM: Cucumis melo

<400> SEQUENCE: 74

```
actttcagta gattttatct cataaaagag tcataaagat aattagtaat gaataaagct      60
ttgtttgaag aaatgtttca ttgcaactga tatttgtcat tgatgtacaa atggctttgt     120
aactctccac ttttttctaat ctaaccattt acatacaaaa tatctacgat acactaaaat    180
gaataaagaa attttttttg tcaaaaactg tggggagaat tgctccttgt tctcaaatca    240
ttcatgaact ttgcaattta gaagtaacat caatgaaggc ttcttccttg cagggaattc    300
tcaaacctcc agttgggtgg ctgaatccaa actcttcttc agccttgttg agcaagtcta    360
tgaatgaagg ctgactcaag tacgatattg gaacgaaaaa ccgctttctg tcggtttctc    420
ccacgtacac tggaatgtgg cctttgggaa caatggactg acatcttgct gagacagact    480
gcatcttgag aacttgcttg gcagcggaaa gaagaaccga aggcaaacga attcccatgg    540
ctaaattgga ttgaatcttt ttggaagtgg taaacttcaa tgcttgaatg agaatatgtg    600
aaagatttga agttggagat tagttgtttg tttagagtct atatatagaa tgagaaaaga    660
gaaggtattg tgacatatga atagaagatg ggaaaccaag aaagttgggt tcatcaatgg    720
ctcacatggg ttgctccatt ggttaaggta cattcatttt ctcattggca ccaatttctg    780
gtaagatggc cccatatgtc ataatacgtg aagtcatatt gatctaaaca aaatgggaca    840
caaaaattgt aactatttca attagcatta aaatcatgtc aagaaaacta cattaaatat    900
agatatatta gttaatgatg taataatagt ttcatgtgag atcaaactac gatttttttt    960
tataaataat gttactttta aaaaaatgtc aaaaatatgg tagaagaaaa gctattacaa   1020
aaagttaagt catctactcg gttcataatg cgttatcgtg gatcgggtac acgacaaggc   1080
aatgaagaca tagacccagt ctatgacttc gatgtaaaat gtgggttttt cctaattact   1140
cgtaaaaaaa tattttgaa aacttttctt tttaacaaac ttaaattttg gttaattata   1200
tatataaata ccatctttac tttcttatta tccaaaacaa tttaccatat ataattatat   1260
ttattcaata aataataata taaaatattt agataaacaa aatcaattat ttcaatctta   1320
tatattttaa atatacacta agctaattta aatttacatt ctgaaaattt taattatatt   1380
tctatctaat ttaagatttt aattatattt ctatttaatt taaaatttta atggaaaatt   1440
aaattgtaaa taagaataag agtacaaact tactattttt atttcatttt taatttataa   1500
acttcatctc ttttttcata tattttaag aaatccaacc ttatatttcg aaatttattt   1560
aaaaaaatta taaatttttt taaactatat ataaataaaa attgtaattt ttgaaataat   1620
ttattaattc ttcaacaaa cttataataa taacaataat aataataata atgagggtac   1680
tcgattctca aaaaaaccga accgatcaaa caacgttaga tcaccaacac agaagtaggg   1740
ttttcatcg gcacataaaa accctcactt cttcttcata aaaccctca cttcttcttg   1800
acctaattcg cgccgttgat ctccggttcg atcggtttct acgctgtaat ctcaagctat   1860
ctcctacctt atccttccct ctcttttttct tcttcttctt cgtatatgca tatcttcaaa   1920
tttgctgctt tttttgtctg attattcatc tgggtttgtt tgcaacagga aggaggaaga   1980
atttcaaatc aagaagaaaa                                                2000
```

<210> SEQ ID NO 75
<211> LENGTH: 2000
<212> TYPE: DNA
<213> ORGANISM: Cucumis melo

<400> SEQUENCE: 75

```
tttattaatc tgaatcattc tgtttcttct gagagtttta ttccttttaa gattctaatt      60
ttattttgga tagttgaatt ttggtgtgct ctctttgccc cttctttatt atacattcct     120
ttatcttaaa aaagccaaaa agttaaaaaa caaaaactaa tcaaaattgt aacatttaca     180
atttatgag catgacattt aaaatatcga ttttgaagtt aagacgttgt attctcacca      240
tcggttttta tctcttccca ttccattaga gtgataggct ttatctttca tcactgtcaa     300
aattcatcca acgtccaaga tctcttctgc aaagagttac ccacaattct ctcagactca     360
ttggcccacc ggataccgag tggatggata gaacctccaa gattgcgaga gcaaaagctc     420
agccaaaact tgcacaaact cacccatggc ttccctctct tgtactacct ccattaatct     480
caccccaaga tccttcaatt ctcgccccca ttcaaattag cttcccattt tcttggtctt     540
cagtccaacc ttcgatggct ctcacccctc tccattggac cctccaatgg gtctagagca     600
acttgctggt tcaatttaag gcaaaatgcc gagggtgcag gcatttatgg cagccagtcc     660
cgagatgatt tcaacagaga tgatgttgag caggttcttt tactaatttc tctcttcttt     720
ctttgtattt tgttttgtga ctttgattgt tgaagagtgg tgtcttttgt ttaattgctg     780
gtttgggctg attcttatgg gtttggagtt gaaattgttc ttaccctctg gctgttctgt     840
tttcttttaa gtattgtgaa ttttcaatgg ctcctttagt gaagatagat gaagaaattt     900
aaattagtaa ttttcgtac cgatgactct cttccagtgg tgttaatgtc aaactaacct      960
tttctttacg tcataaagca cttaatcggt tggaactcag tagacgtctc actcatgttt    1020
gtagccctaa cctaatgcca tggcaatcga aatttatatc gtatccctat tgcgattatt    1080
aaacatcacc ataggtgaga cattcctaac gtgatatact gagttctaga tggttaagtg    1140
ctctgacatt tcacattaac gcctcatccg cactggttag tcgaaagaag aaggtgtttc    1200
tgttatgaga ttgtgagaaa ggacctcctt aaacattata accaacctca taacttgtgc    1260
atttgtgtat caaactctgc tttcacataa agaaactaaa acaaggtatc acattgccgt    1320
tatgaaaagt gcatagaact tcctgcttcc ctcaaacaaa acttgcaaat attactgatt    1380
ggccttagcc tttaggtaag ggaagaatca aaagtattcc ttcatccttc tgctttaaaa    1440
atgtgctaaa tgacgttgtc catagtttaa aaactcgacc aaatcgcatt tgtcttacag    1500
tctctcaacc cttttttaagc actctcagag tcaatccaaa tagattccta gttcctaata    1560
tgtaacaaga agagtgatac tatgaaaacc cacaaaaaac ccacaaacat gtgacttgag    1620
ttaagatgac tcccaatccc actgtatcaa gcttttcaaa tagaggaatc acgatgagat    1680
gaacaataat atcccaacgt gctgctatcc caaattagat acagaagtct acttgtggtg    1740
ttcttaatcc aataattcat tatgaaattc ttatataatt tcttaatgag tatcttagaa    1800
ttaatgttac aacttatctc ttattctata tgatagaatc ttaacataag tattcatatt    1860
aagagcaaga ttatgttgat acttctcgaa tcataccaaa aacttggaac catgacatta    1920
acttcattcg tggaaacaag ttttgaagga aaaagaagga ttgacaaatg aacgttatgg    1980
ttgtgcagta ttttaactac                                               2000
```

<210> SEQ ID NO 76
<211> LENGTH: 2000
<212> TYPE: DNA
<213> ORGANISM: Cucumis melo

<400> SEQUENCE: 76

```
atctaaaact gcatttttta ctacatacag attcaccttt aggtgctggg gcttcccta         60
tttcatttta tcaatgaaat gtttcttatc tagaaataaa agaactaca tacagattca        120
caccactgca gaaggtcaa ataaaacatt catcataatt caaggtaagt aagcataatt        180
ttgtgaaact tatgtgatgc acttaatata tgaacgattg ccccttgttc tctcaaagtc        240
agatcttctt tttcctaaca attgaagaaa gtggaaataa gttaattacc acggccacgc        300
aataatctcc tgatggcctc caatgaaccc cccaaacata atgctgtagg gaatgtcttc        360
ttgcaatcct tcaagacgca caatgtgaga catgcaaaat attaaaaagt gacatcttca        420
aatatagcaa agaaatcaa aatatttaca aaaaatatag caaagtttca tattttatca        480
attatacaca ctgatcgaca tattttgtaa atattttcaa tagttttgac atctacaata        540
attagttgag attttgtagt caacaggatc cagatttgtg tgttgaaagt gaaacccat         600
gataagataa aatcccggtt aaatatttca ttttcattct taagttttg aaaaaggaat         660
agcttggtaa gctacattcc gcatggtaaa caagcataca acttttgttt caagaaacca        720
acaagtacta caaacaaaag agtaattgat ttaatccaag ttaacaatga caaattggta        780
atatttatag gatattagtg agataataca atcaagttcc aaaagatgtt atatttacaa        840
ctatgagcat tcatcttgtt actaccacca agaaaaagta gcggttttcc aatctctgtc        900
aagtatccat ttgagttatg atttcatatt caagactgtc acaaaattt cattaaaagg         960
tgcaagtgca acatttcctt aagaaaagga taactgagag atcaatgact ggaattcaca       1020
agttaaaatg aacacaactt cagaacatca caagctaata cctccaaacg gtccaataag       1080
ttttctgcaa cactgtcaac aagcgaatcc tttgggcgca tcaaccaagc agctcggtcc       1140
cgctgttacc aagaaacagc aatttcagca agaacaaaat atagaaatcc tccaagaaaa       1200
ataaacaaac aaataagttc gaaggcacca catatcagaa agcttatgga ggagtacatg       1260
tagtacaaac gctcttgcca tttagttta cttgttaaaa gtgatttgct cagaataaac       1320
ataaccaaag cagaatccga acatatgaac caatgaatta ataaacccca tcacagaaag       1380
acaagtaata ctcccagaat tgtactctat acagacgacc actacaattt agccacacaa       1440
tatcaccatg ttctctccaa atatatttaa aaaaaaaaaa aaaaaccctc ctattgttgc       1500
ggttaacaca aatagatcaa aaagaagaaa gaaaaaacta aaaggagaca aaggtgttaa       1560
atttggttta cctgtttacg cttaagatca cgatcaaaaa ccttaacctt tgagctgtgc       1620
attccatcac cgattcttcc gtcataatta tcatcaccag tagagaaaga acaacaagga       1680
attgaatttg gaaaatctcg ccatcttgca cttctcaaca ctgagaacga tcttatgatc       1740
gtagacggcg acagccctct catttcacag tcaccgattg aacctcgccg gagagacgga       1800
gggaaatttt gtaaattttt aatgggcctg gccgtaaag tcgtgtccaa acactcctta       1860
aacggaccaa aaccggcgta gaaatgaaac tatccagata agggacgtgc tatacattta       1920
tccaaacgag gtctcttatc gtatcttgta caagttcgtt gcttttcacg gctgtctcta       1980
gaattttggg ttgggcgaaa                                                    2000
```

<210> SEQ ID NO 77
<211> LENGTH: 2000
<212> TYPE: DNA
<213> ORGANISM: Cucumis melo
<220> FEATURE:
<221> NAME/KEY: misc_feature
<222> LOCATION: (1)..(2000)

<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 77

```
aaacctactc tgtaaatgaa ggtttacatc tcttaaggca gtaccatttc tgccattact    60
tctaccattc ccacgaaacc acctcttttc tctttcattc tccccgtcag gtatgcattt   120
ctcatctcta agtccgccca ctgttttccg actgattttt cgattttaa ttagtgagtc    180
ggttttattg tttcttattc taagctttct tttactcttt atattttag atatttaatt    240
tcggatccat tcttcccatc atgcccaatc caaagactgt cgaaagtttt gattgttggt   300
aatgggacat taggtctggg gtttctgttt ttcttatcct ataaattggt tatccttcgt   360
ttcctctatt ttgactttat tccgtagtta ggttagaaga agaaactact gaataatgtt   420
tactatacaa acacctcaaa atagccaagc ctgtcgaaac acatttagct gataagctag   480
ggatgaagag atcaagagat ggttagctca gctgtattgc atctcatggg ggacgggtga   540
aacgaaccag agaagtaata tacacgtttt ttttttaaaa aaaaaaccga ataatttacc   600
tgttcttgct acaattacac cgataagttt tcaacttgag caattacacc gtctaatttg   660
cattgctgaa gaaattggtc tgttccatta ccactgttga ttaaaaagtt ctacttgtca   720
gcacagcatg tccatgtgcc cagatagttc ttgatctttg gaaaaagtgc tatgtttgca   780
tgcttcggta agatgtgagg ttaaaatgag gaggacataa tgttggcata gggaggtcaa   840
aatgtgttaa ttgagagaaa aaatgtggtg gatattggag aggagacatg gaagtagaga   900
gaaagagatg aggagggagg ggtgaaggta aagggaaata gacatacaga aataaagaac   960
tgtgcgagta atgtgttgcg ataagtgaaa gagagaaagc aagagaaaca gtggtagaaa  1020
attgaagtat agagagagat gtagagaggg aaaatatgga gaactacaag ataaaatatc  1080
tttattcttt ctctatctaa gtatttatct ctttagaagt tatctctctt tgtttctgag  1140
tttaccccta gtattttctt ttttctttct caagcccttc ctctctaaca caatttctct  1200
ctctctcttc tccctctctc tctgtatctg gctgtggcac tttttttgac ctcttccttt  1260
ctgtctttat ctcctttgaa gacatttga ttttcctaca cccctcaatt ggtcttctac   1320
tcaaactcat ctacttgtta ttatattaaa tgcatgaaat cctaatattt taggaagctg   1380
gagactcatt gtgcgtgcat ctgcttgctt gtagaaagtt ttaaattgaa aggcaagccg   1440
aaggggccta attattcagg ccaggacaat gatgttggtt ttagtttttt gttttgaaa    1500
nnnnnnnnnn nnnnnnnnnn nnnnnnnnnn nnnnnnnnnn nnnntttga aactaatttt   1560
tttcttagtt ttcaagactt ggcttggcat ttaaaaacat tggtagaaaa tggataacaa   1620
aaccaagaaa cttacatgtg gaagtagtat ttataaagct tacttatgtg tggaagtagt   1680
gtttagaagc ttaattttta aaagtctata accatatggt catcagtaga gtctcatgca   1740
acttatgttg tgacagtggt gtaattgttc taattaaaaa ttttcgggta caaatgtaaa   1800
aaacattatc gaacagtggt ggtttgtgaa atatgcatta acttttgaa aatttgatgt    1860
gtcatcatat tcattccatg ccgtgccttg tttccctccc agctccttat ccatgctaat   1920
tagattcaga ccattatccc tttggaacag ctatgcttaa ctctgttctt ttctccctct   1980
gtacaacagt atatcaaaaa                                              2000
```

<210> SEQ ID NO 78
<211> LENGTH: 2000

<212> TYPE: DNA
<213> ORGANISM: Cucumis melo

<400> SEQUENCE: 78

| | | | | | |
|---|---|---|---|---|---|
| tagcttgtta | attcttgtgt | tgaagacgtg | tttcaacaaa | tctgatgggg | tattcatctt | 60 |
| aagtgtccac | tgaagaatgg | gggttctgtg | gcagatctgt | atgttatgta | gtgaaaacaa | 120 |
| atctgtaaag | tttttttta | cttcgaattt | aacgttgctt | aagcttctgt | gtacagtttt | 180 |
| atcactgcct | cgaggttatg | attattattg | gattaaatta | caatttagtt | tacgtttacc | 240 |
| ttggaactgt | gtatttcttt | tgattgctca | acttttctcg | gggattttc | aagaattgta | 300 |
| tttttaaaat | tttaatttat | ttggaacatt | aagaagttgg | ttatttacag | atgagatata | 360 |
| acactgtgat | tggggtggaa | aataaacaca | gcttcaaaca | cggagtgaga | tatagttaat | 420 |
| tacattacat | agtactagag | attatataaa | tcactccact | cacatgagtt | ttcatcttaa | 480 |
| aagattggaa | tttacatctt | aacagatgca | atcttttaat | gtagagttct | taacgtgttc | 540 |
| tcttacggtt | gtatctttc | gttttcatta | ttctttggtc | aaatcaaaat | tagacttat | 600 |
| agttttaat | gaaatattgg | acacactacg | attcatcaaa | gtaacccatg | atcttataaa | 660 |
| gttgtgaaat | gtatgtatat | tgtctttgat | caaactttac | gtttaattat | atcttgaatt | 720 |
| tataattttg | tatttaagag | atgaatgaat | tttagaaaat | tctaaagttc | ctaggccaaa | 780 |
| gttgttatag | aagggtaaag | aatgctttaa | atcatttatt | ccataatcat | tagttttata | 840 |
| atttttattc | ttcgtaacta | ttttaaca | aaaaaaaaa | aagttatgca | tctcttaaat | 900 |
| actatctttt | aaaagggaaa | ttttcataaa | taaataaaaa | aagacgatag | tatacacata | 960 |
| aaaaaactc | aaatgattta | tagagagttt | gatgaatttt | gctggattta | taaatagttt | 1020 |
| agaaaaataa | gtattaacct | aaaatttgc | ctatatctca | atggccttct | atgtctatgt | 1080 |
| tatttcttaa | ctaaaatcga | aaggatatag | gcttatggat | tggcttaagc | taaaaaatgt | 1140 |
| cggtccaaat | agttgagatg | tcaaaccta | aaagtactac | gattatgtga | ttttcacatg | 1200 |
| acatagtgtt | ctatggtcaa | attttatagc | gtacttattc | caatccatca | cttttatag | 1260 |
| aactaaaatt | catagttcct | attttaatat | atatatatat | attaaaaaca | cacattaaat | 1320 |
| gatgatttta | tctcttctag | gttgattgaa | aattactaac | taaaaaacac | ggtgcctcaa | 1380 |
| acctccaacg | taaatacgat | ttctaagaac | tgtgttttt | gtaaacgcca | agtgactgat | 1440 |
| taaatctctc | cattctctgt | ttacttctat | ttggggttat | ttatgctaaa | ggatattatt | 1500 |
| cattcaatag | aataaatgtg | agatagtcga | gttatattca | tagatgttac | aatgaggtga | 1560 |
| ttcattcctt | tgtcaaacaa | tgctttctcg | actcgtattt | tactgtattg | gatcgaaatc | 1620 |
| cttcttactc | gcatggtttg | ccttcgttga | ttagttttgg | tatgaattga | tgctttgttt | 1680 |
| aaggggaaa | atgaaaatgg | ttcaattgga | ggacaattgt | ccaaatttcg | ggacattatg | 1740 |
| ggttaaacac | aaagaagaag | tccaacagtg | taattttgtt | aaagattgcg | ttacatttcc | 1800 |
| gaaatataaa | tgagggtatt | ttggggaaag | gaaatcaata | taggccttgg | ccgggtgaga | 1860 |
| tgcgaaaaag | tctcaaaact | gagtgagaag | cgtttgagct | gggctcgcag | ctattgaaaa | 1920 |
| agagagaaca | aacccttcg | tcgctcttat | tttcttcctt | tgatctgaaa | tttcctgttc | 1980 |
| cgatctcgct | ttaggacgca | | | | | 2000 |

<210> SEQ ID NO 79
<211> LENGTH: 2000
<212> TYPE: DNA
<213> ORGANISM: Cucumis melo

<400> SEQUENCE: 79

```
aattcattcg ggattgttat gaggtaataa aaaatatctg agtgcgaaca tgataattgg      60
taaagtgaaa aaatgttcag ctattctgtt ctagatacag ggatggaagt gggaacaatg     120
ccaccttgct tattgacaat aaaatgagga gtggcaatat tttgtttctg aataaatatt     180
cactagcata acatattagt gatgattcaa actaaagtgc actaggtcac tagtttcttg     240
attcatcgtg tttggtagta atggtaggta ttgtatctta tagtattgga caaagcttta     300
ccgaccataa attgtggata atgtgcagag aagaattggc agttgaacgt tcctggatat     360
tcaagtgatg agtggaagaa tcacaacaaa aatgtaagaa aattatatta ccctctctaa     420
aacatcattc tattctcctc cctaaaaaat cattctgttt caatttaact ttcaaaattt     480
tgttttagtt taaccatatt gagttttttt tcttttttaa ttatcgtagt tatcatcaag     540
tgatgtccac aagaaacgtt tggacatggt aagttggact tatctcttca agtgtttgct     600
ccatttcttc ttttatcatt tgtctcaaat tttctcttct ggggtttcat cagatacgcc     660
tattgaagga agcctcctgt gtcgaaacaa atgtaaacag ccctaaagag atggtacgac     720
aaggggttgg aatgtcaatt ggtcccaaca ctctaacaag gccttcaccg agttcagaac     780
aactattatc acaaacgtct ggttcacagt tgctgcagca atgatgagg ttttagtgta     840
ttaactacgt ttgaaactaa tgcttggtag agatcccaac tacttggtga ataaccaacc     900
ccagtgtcag ttcagggata caacaaataa aatgagattt agaggatgcc atatcagagg     960
gaacctggac tggacatctg tgtggagtgg agtgtgatga ttttagtga tacgtctttc    1020
ggaatcaatt tttttaggct gtataatatg aagttgcatt atctggaaca cgggcgtaat    1080
gttaattgta caaatatttt ggcaggtcat attagtatag gccttaagta ttgttgttgt    1140
ctaccatgaa ggcatttttc caatttatga ttgataatct ttacttacaa tctcgagtca    1200
tatgaagttt gttgatcagg atcatagcac aattattaca aaaatgaaat agaagatatg    1260
attttcacc cccccccac cccccccccc ccccccctc ccattcccat ccccccttt    1320
aaactgttac attcaaactt gttaactgtt gattttccag atgagagaaa gggcctactt    1380
gtcttgtaca gaaaattcat ccatgacgat aaatgcagat gacctgaacc aaacgtgaca    1440
gtaggggttt cttctatgcc acaaagctcc aagccattca tggtgcgcat gtggtacaga    1500
gaggcttgat ggagcctctt caccttggtc cttagctatc taaaaattgg cttcttatgc    1560
tgatatatct cttcccatgt gcatttggtc cactccactt tcttcgtcga atatccttgg    1620
gttaatcctg aatggtaagc acaacattct tgctaattaa tccctctttt tatcctactt    1680
gccaactgta caagatgagc agaagaagaa ttgcccaatc atgaggtcat taactgcaaa    1740
aaagagaatt tatttctttc tttgagaatc tgatcttctt gagagttcat tgacagccac    1800
atgcatcaca aaatgaaatg ctgtgtggcc ctcattcatt cattcatcaa tcttcctatc    1860
ctgccatttg agtgaatgtt actccaactt gcaggaagct aaattagtac ttttttatat    1920
aaacccctatg aaactcatca agaaaccaca ccatcccaaa aaggaaacga gtgaacaact    1980
agacaactca ccccgaaaaa                                                 2000
```

<210> SEQ ID NO 80
<211> LENGTH: 2000
<212> TYPE: DNA
<213> ORGANISM: Cucumis melo

<400> SEQUENCE: 80

```
cagcgatctt cgtagaaact aattcaatgc tagctcatta tttgactttt ctcaggcaag    60
gctccgcgag gaagagaaaa ggtccaattt caggaaccaa gggcatggac aggttccggt   120
cagaagaagc ttttacgta aacccttgc cagattgttt atgtcaagga gaattaccaa    180
atggaagtac gacttccatt ttcagatagt tcagtagaac atcaaagata aaatgctctt   240
agagagctca atgtatatgc aggcgaccac tcaacgtgtc accagctttg tacatccaat   300
aagccagcta cgatggaacg acggagtgtt tataacctga gttttggtag ttggcggagg   360
cggtgatggt ggtatagaag gaaggtcgag ggatggcaaa ccctttacgc caagtagtgg   420
aagggagtag ttggagatga acacattttg agaagtttcc aagatcactc catttggggg   480
agagggatg ttggttattt agcacaattg ttttcatgtt ttagtaattt tatccaataa   540
tgagcgaggc attgaagcaa ttaaatttat ttttaatgat tttttcaccc ttccataggc   600
ttttcttttt ttctttttcct tttagtttgc aaactttagc tcctttttatc ggctgtcgaa   660
ctcattttg aagttattga atgaaacaca gtttgggctg tgtcagatgg gtggtgaaat   720
tttatacatt ataattacta cataaaatga aatcatattg taattttcta tctatgccac   780
aatttttttt tattgcatca tgaggattaa attgtacgag tccaaatttg tacagtcatg   840
tttttaaagc tttcgagcat tgttactaat gcatggaaag gatcgattat caagtatcct   900
cccaacttca tgaaagttat tatttgtctt ctaaatttgt tttagaaaat gtttaattaa   960
ttatttgaga agaaagttta actaaatcct attggtttcc tctaaggttg tcatacttat  1020
ccaataacaa ttacgtttaa aatcaaaatt attctaatgg tataagacta atgttttaaa  1080
agcataaaat tgatgaggaa ggattggaag taatactatt tattttgaag gtaaacattc  1140
ttgaatgtct gtcctaaaat cactaatgtt ttccttagttt gagactttga gtcgttgaac  1200
ctctccatct ttataaaata taatacgagt ccttcacaat aacttaaaat atatactaaa  1260
tcctaattaa tgaaaaataa ataaataaaa ggtacaaaat cattaaagcc taaaaatcta  1320
ttactccttt aaaacttttc aagggtccct acaaccaatg agaaactacc acgtcattt   1380
cacaatccgt tcagtgttta gaaaagtcaa atcgcaccgt ccatttatcc actcgtacca  1440
agtacggtag gaatctatct accgtccgat taagcacaaa gaagcacagt aaatgtcaat  1500
cgtgtccatc cgccgccata ccgcacatcc ttcgtccgac cggaaggccc tatataaagt  1560
cctttggttt tccgaatttc tacttcattc gcttttgaaa gatttcccaa tctcttcgtc  1620
ggccaaaatt ctctctcgct tctcaaccct tcttcggctt tttcatccag gtttgtttct  1680
cttctctttt ttcttccttt gttgttcttg gaatatgttt aatttcattt gttttccat   1740
tcaatttcat gctagatttt acgattaggt tgattttctg ttcgtagatt gtaattgatg  1800
gttagggtta gcttttctc ccattccttc tggaatctgt ttcttgacct tcgaacttcg   1860
ttgataaatc tttagaaaca tttacataac caaacaataa ttgaacaact cgtgttgtta  1920
tgcctatata atagcggtta ggaaactgga aacgcccta taattgaaat cgccttagaa  1980
atttgttttg attcatacag                                               2000
```

<210> SEQ ID NO 81
<211> LENGTH: 2000
<212> TYPE: DNA
<213> ORGANISM: Cucumis melo

<400> SEQUENCE: 81

```
tgtaatgact aaacatacta tagcctattt ggaccgggtc gaaaatccaa attaaccaat      60
ctcccctcag cctcacacca aggataaatc atgtcaacct tctccatttg acatgctagc     120
tggacaaaga gaaatactaa ctcaaattcc atataaatat atctttacga ctccttatca     180
ggtaatttag actcaacaat tagtaataaa tttagtataa tgaatgatag tttccataga     240
tcaattatat catttattga tttgctagat ctagagtgaa cttattgact aaatataccaa    300
atataaaata tatcaatgaa cttacccacc aaacataaaa atgtaatatt tatatctaca     360
tgaattttac aataaaaagt gtatcatata aaatacttat atacataaac cctattatat    420
atatatatat ataaaaggaa ggtaagatgg aaaaaattgg aagagaataa tttgacctaa     480
aaaaatcgaa agagaaaaga gtatttaata tataaataaa aagaaaaaga gagaaagaaa     540
aaaatcttgt tcgtcgactc ctcaaaaacc ccagcgtgta gcggttgtga gagaaggaga     600
gctcgtttcc atcacgataa aaccttatct ttctccattc ttctatcttc tcttccggag     660
ctctctccat ttctcagccg ctccccacaa tttcctctaa acacacacat acacgactat     720
ttttccattc aaattccttc acttcgtttt ccattttcct tttctttacc ccacccactc     780
acccacctct cgtcgatgga ctccatggac ttgcccaac aaccgtcgca acagaattca     840
gtctcctcag gttcttcttc cacttcctcc tcctctttta cgtcttctac cgttgattcc     900
catgtcgata ctccctctct cgatgaacct gagatggggg ttgctgaaat taaaactagt     960
gtagttgccg atgggggtgg tagtgatggt gctggttccg aaactgaagg gttttttgagt   1020
ggggaggagg aatttgagtc tgcttcagat agaccaattg tgggttatcc agaggaagag    1080
tccatcggga agtccgccca agggctgat actggtactt cttttgtggg ttattctcaa     1140
ctttctgctc cggttagtgt taggccaatt gcgaaggttt ctgttgatag tgacgttgag    1200
gaggaggatg aggaggagga ggaggaggag gatgaccttc aggtggatga gaacttgagg    1260
ggaaaggagg aaattgagga taaagtgggt ggagaagatg tttttgttga gagtaagaag    1320
gggaggaag ttgaggttcc agtggaaaag gaggagacta ttgttgtatc tgatggaaac     1380
aagaatttgg atgatgtggt gaatgatgat gatgatgcca gtcaagtgca ggaaagaaca    1440
attgagttgt cggggaactc aaaagagggc aatgtgcctg aaagcttagt agctgaagat    1500
gttggctctg tgcccgagga atctgttgat ggtgggaagc aggtgtcaga aggggatgaa    1560
ttgaatgatg tgacagttaa acagtcacaa aatgaggctt cagatggaaa aaagaagcag    1620
agttggataa agaaactctg gcgtctggga agcaggctgg taaagggatt gacttgagtg    1680
agaaggtggt tgctgaggat gtagagcaat tgaaagaaca ggaaacacct ggttcttctt    1740
ctgacgagaa agctgttttg ggagaccaag caagctctaa gcttgtgaaa ctagcagatg    1800
aaaaacaaga agaggagacc tctgcggctg agaagcaggt agatgtggag gtcaaattga    1860
atgacacggt ggctgctgct gaagatggag agcagttaaa aaatttagaa actgattctc    1920
ctgttgacga caaaattgtt ctagctgatg acgaaaactc taaggtttta gaaccagcag    1980
atggaggaca agaagcagaa                                                2000
```

<210> SEQ ID NO 82
<211> LENGTH: 1072
<212> TYPE: DNA
<213> ORGANISM: Cucumis melo

<400> SEQUENCE: 82

```
tttaatatgg tatcagagca aatggtccag agaggtcttg tgttcaagcc cctgcattta        60
cgtttccttc ccaattaaaa ttgtttccac ttgttgggct tttcaaatat ttcaagccca       120
caagtgaggg ggagtgttag tgtatataat taaatttgcc ttcttcaacc actagctgaa       180
gtttgtgggt gaattggtgg tttaatagta actatatcat gcaattagct tttttgagtt       240
caacaatatc tgtggtggag atttgaaatc gagattatga tgccttaacc atgtgaacta       300
tgcttaggtt gacaactata tcatgcaact atcgaaaaca tcatctctaa tttataggtc       360
tttttttaaca tagttgaagt ttcaatattc tatatgaaca cagctggcta tttaaattac       420
catattgaaa agcagcactt gaaatgcttc taaaaattaa tgccaattag aagtgtttat       480
gattctaatt ggttaacatt actgaacaca gattagttat agttattgaa agaataaaaa       540
ttgtaaaatg ccgaactaat accaaatgga tgggtagtct gcaaatttta ccaaatggta       600
ctacagctgg tgatgaactt agaaggggta aaggtatagt gtaactgtct aagttaatgc       660
cataaaggta tagtgtaact gtctaagtta atgccattag cagatcaagt ccgttgtatt       720
atgtactgaa cacatttttt aatcgtatag ttctaaatcc tataatctgt cgaccaagtt       780
ttaggtttgt taggctgaaa gttcatgcaa atctaggtgc ttttttgtac taattgtttg       840
agattcagaa attgtatctc aatgttctcc atgattatgt gcgtgtattt gcaaacagct       900
ctttggtttt ttcttcttct tctgacaagg atagtcaaat caattacagg acataatttc       960
aagatttaag gagagaaagc aagggaaaga ttcacgggag tggactgagt ttccaagcag      1020
agttgcagtg caattaaatg atactcatcc aacccttgca attcctgaac tg              1072
```

<210> SEQ ID NO 83
<211> LENGTH: 1730
<212> TYPE: DNA
<213> ORGANISM: Cucumis melo

<400> SEQUENCE: 83

```
gttcaactcc acaagtcaaa ttttttggaa atctcgtgt gaacacttgt gaaacacttt         60
atttttatat taaaagaaac aagaagattt aagatgagaa tcccgtattt gtttggttga       120
aggacaatga aattggtaaa tatatcccat cgaaaaataa tcaaatctag acacaaaaat       180
ttaaagttaa aacttactta ataatcagct ggagcatagt ttaatttgaa tgaaaataaa       240
aatcctaaac tagagaagtt tcttatggta ttgaaaggcc agtttagaaa gcccaatagc       300
gtgggttttt cttggaccca tgtgtatgtc tcactcatga aattaaatta attggcctcc       360
acattcacct ctctcctccc aattcccata actcaatttt agacctctta aatgaaacat       420
atcatatttt cataaacttc tttttttacgt tacttatgag attaaaagac tttaaataaa       480
gtgtcaattt atattatagt agatgagatg gagtgtgtgt ctttgtgccc tccttgggc       540
ccaaggacta agtaaggatg aaagggcaaa gaaatacaaa atagaagaga gtagaaagaa       600
aatgaaatgg aatatatagt aagggttatc gtttatggtt attatgaggg aagggctgaa       660
attgataatg aacctatcct tatcttccct tcttcacctc tcattttgct tgaaattaca       720
aatgactttt ttttcaatta ttttgtgtgt acatccaaat gtggtatgca catatgggcc       780
tcccattaac ttgtgatcca aattaattct tttgcaacct aagttgaaat taaacacttt       840
tacctctctt ttttttccta acaattttac tttcattgtt agatggttga ttatcttgac       900
atgtaacaaa aagttctctc atgtcaagat agaaaaatcg aatatttgat tttgagattg       960
```

| | |
|---|---|
| ataatattat aatatcagtt gagctatact cattttaact atcagtaaag cttcattaac | 1020 |
| atattttta tttagtaaac taagattaat ataaatagaa tcttactttc attatatact | 1080 |
| ttgacgagac ttaaaaccta tttagcgcat gatttttaaa agttggtagg attttaaccc | 1140 |
| ttgaaaaatt ggtcattcgg gaatcaaaac attagtttcc ctttgagcat ttatttttaa | 1200 |
| agcacttcaa aagctaaatt agtagcatta aaaaaaaaag tcaaatagta tatatatata | 1260 |
| ccaaaactttt gttttttcaaa actatatttt aaaccaacat tctttttttt ttattattta | 1320 |
| ttactaatta agtgcagatt atagtggttc tcttttgtag ttggatcaaa tatttcattc | 1380 |
| tttttttgaca ataacaaaag ttaaaatact cattaaatgc taaaaacttc catactaaca | 1440 |
| ttattgaacc attaaatata tgagcaacga agtataggt aagaatttat attgttgttg | 1500 |
| tttagtttgg aaatagaaaa tggaccaatg ggtgagcttg gtttaagtta gggttcttgt | 1560 |
| ggttggatga taatgaaata aaatggccaa aattttaatg gagaagaaga tcccttttaag | 1620 |
| ttcaaccact aatggagtct tttaggatca attcacaacc cctttctcct tctgccacgt | 1680 |
| gtcatctcag ctaatctcaa ctgtgtggtt gttgagaaat tttgaaactc | 1730 |

<210> SEQ ID NO 84
<211> LENGTH: 2000
<212> TYPE: DNA
<213> ORGANISM: Cucumis melo

<400> SEQUENCE: 84

| | |
|---|---|
| aactagacta gcgagtgcac aaccaaatta caaaatcctt aacagagaca accatctatc | 60 |
| tcctttaaag caacaataac atcaaccgaa ttagaatcca caatcagtaa agacgatgcc | 120 |
| gacaccaatg accaaaaccg atcaaatata gcttattacg gaccattact tcaacagtta | 180 |
| catcaacaaa aaaaaaaaat taaacattgc taataaaatc tgaaaatgag gaaaagagaa | 240 |
| ttaaaagttt tgaagataga aagaataaat ctgaaatgtt ctaatttgat atataagaaa | 300 |
| tatgaggtaa tatgacgaaa gcattttgat agttttcacc aactcccttt gtgaaaggat | 360 |
| acatccaacc aattttacaa tttctgttca aattttgtcc acctacccctt ctcttctgcc | 420 |
| ccccaaggct gctttctttc ttttattatt tgctaaatta ccaaaaacta ttttcgaatt | 480 |
| aaaccatcta tttcaattat atacgtcatt cgaattttaa cttaattaac attagtatat | 540 |
| gtttcggatc aaggatagtg gtataaatca tcctaatttc aatttgtatt tagaaaagtt | 600 |
| caattatact taaaacttct aaaaatttta tattttaaat ttggatataa attaaattta | 660 |
| agattatgg aaggtaaata attagagcaa aacaaacttc aaactatatg gaaaatagaa | 720 |
| aaggaatatt ttagccaaac aaaaacactt attatattta ttttgttttt tgttttttt | 780 |
| aatttaacaa tttttttttt tattggttga atgtgttct ccactggtga gtctccaact | 840 |
| ttgacctgca aagggtctat atagcgagtt tcacgagcac ctaaccaata tctgtgtaat | 900 |
| aattcccatt tttctttcat acccacttca tttgatcatc tttttcacaa ccccggatct | 960 |
| ctaattcttg ggaatttgcc tctttctcga tccatttcca ccgtaattga aaatatttca | 1020 |
| ggtttgattt cttctgggtt ttcattcaac tgtctaactt cattatgccc tttatgtgtt | 1080 |
| tgttgaaagc ccccccaccca ccatcgttca atgcggtttc tttaccttt gttcggtttc | 1140 |
| aacgatgatt tagaagttat agatggatgc taattgtttc gttgttggtt tgatccactg | 1200 |
| atctgccttt gattggcata aaaggagatt ctagatcttg ttttgatgtt gtgatttatg | 1260 |
| gatattattg ttatagtcgt ggaagttttt cttgtcgttc tgcggtatat ggttgtttta | 1320 |
| tttttttgagt ggtaaattga gcagattgtg aacttttggg ttttatggtg aaagcatgaa | 1380 |

```
ttagtaaatg tagagctgct gaaacaaaat ggaggtttgc tagacctctt tgtgaattct    1440
taatggtcag cctccatctt aagaggctaa gtccaaaaat ttaaggcagt cttttgttat    1500
tgttacaaag gacaagaaat aacagaggag ttattttaat tgaatcaagt tggaagaag     1560 tactacttca tgcttctttc aaaagcaggt caaagtgctt taaagtcttc ttatttattt    1620 atttttcct gaatcaattt aaactaatga tagaaagaag tgtttttaa tgggttatta     1680 taagtaacat caattttaa ccattccaaa agtacatca aattcatcat agtgtgagtt      1740
tacgaatttt ggaagttgta attttaagtt aatacttctt ttaaggaaat gtacactttg    1800
catgttgtgt tcataagggg tatttctttg acaaacgcag caaccacccc ttaatgaaaa    1860
ctacaccacg gtggttggtt ttttcttgtt atttttttac ttggaattta caataagttg    1920
ttatattcgg atatatggca aagcagatat ctgttttat ccgaaacctc ataaatcttg     1980
aatgtgcagc aggtaaaaac                                                2000

<210> SEQ ID NO 85
<211> LENGTH: 1020
<212> TYPE: DNA
<213> ORGANISM: Cucumis melo

<400> SEQUENCE: 85
tcattgatga agaaggaaac tttaagccaa ttcgacaact tatccattca acaactttcc     60
accttcagac attcagattc aactataata taacataaat tgatagtcaa gtctttttg    120 agacaaccat aaatcatctt agcttcgaga actgtcactt ccttaaattg gtgaatatat    180
cacattccat ccattcaaaa ctttgttttc gaacttttac tgtagttatg aatcaataaa    240
ttgggagaga tattgtttaa aaagagagag catatttgtt tctattattt actctctcct    300
aagagagggt taattagtct ataaatgatc tattcttctc gtccattgaa attttgttat    360
cctaaattta tgaatacttc tacccaaaat aaagactttt tttttgaaa agtgtcaaaa     420 aaacataaag aaattgacaa acattcatt tttagtggat tttacggac gtaaatagtt      480 tgttttgttt cttttaataa tacaattttt ttactttaaa aaatattttt gttataaaac    540
caccgtattt ttattcaatt ttaataaata ataaatgaa agaatataaa aaagaggaag     600
gaaaaagaag ccaacgaacc aacggttgcc acgtatcaaa ggtctaaagt gcgcaaaacg    660
aggccttcgg aaaccaaaat gcgtggcttc aattggagca agtaaacatg gaaaccacgt    720
ccattgtaac gcttcctgat ctcttcttta caaccgttgg attcgagtac ttttttctcaa   780 cgattaacga ctgagtggac ctccacttgc ttctgttcca cgcgcgtggg attgacgtgt    840
ggtccacgca actcttctcg ataggatcat tcgagaacat cctttactta aaccgcctct    900
ctctgcctca atttctcgtc acttccttct ccttctttac cctttccact gcggctgatt    960
cttcttcgcc ttttattctc tcgtacgccg ccatattctt cacttctttt tccggcgaca   1020

<210> SEQ ID NO 86
<211> LENGTH: 2000
<212> TYPE: DNA
<213> ORGANISM: Cucumis melo

<400> SEQUENCE: 86
aaatcatctt ctcccatttg catgtgttaa cgcctaatgt agtacattta ccatgattcc     60
tagaataaga ccgattttac caacgagaag ttgcttcaa cttgctacaa tatacataac     120
atttctttgg tacgttattg atgagaagag gtataaagca tttcacagta ttctctcagc    180
```

```
aactcattag tttaaaaaaa aattaaagga atatttgaat atcggggat gaattaagta    240
tagcctcaca atttgccagc tccttctcct tagcggctgc caacctccga agctttgcag    300
cctgtgcaaa tgtagacggt ctacaagaac ataaaagcaa atgaatacga tccccatgac    360
agccataaca gttgcaaaca atcatataga atgaatgatt tgagcctttt tttttttgtaa   420
gatgatttga gccgaattaa cagtgtctaa tgctgaatcg agctggaaaa tactacttac    480
tgagataagg tgctagcctc cctcagaagt tgctttattg atttgcgcaa ctccaattcc    540
acctggctgt tggaacctcc ctgaaaagta cacgcatgat ggaaacatga ttgtttcaaa    600
acaaacaagt tgacaagatt gaacggataa caattataac atagcaaatt cccagacatt    660
aaaactgaaa atgtcaatag atctccacat taaatgcatc acgtccctaa actaatcaaa    720
tcaaatgtct tcaatccaat atcgtaaact taacgaagca cagttaggca tattgcattc    780
tcaagtctgt caacgaaata ctgaaacgcg ctacagccca aacctcaaaa ttttcaacta    840
taaataacaa gctttgaatt gaaaacaaaa cggaatgata gaaaatacaa acacgaaaaa    900
attccgacgg gaaaagaaa atcaaacgaa aaggcgaacc ttcttcaggt gctccagcca    960
tctagcgaga aactgaaaac cgataacgat aaagaaaata aatggagcgg caatggagct   1020
tccatgctct acgattcctt ccgcttccat ttccatttcc agaggacttt tctgccacaa   1080
cggtgaatta atcaaacaaa gaaactccgt tcatcgtcgc aattcgacgg aggttattct   1140
ggaagaagtt gagatcgtaa tgggctacg aatatcatca aagggcttc aataaaaggt    1200
ctctcaaaac ccaaggccca aaaaaacgaa aagcccagcc caattagtgg agaatcaaaa   1260
cgctgcgttg tagatacaaa tatcttagga aagggaacca agttacgaaa ataccccctga   1320
gtagtgagat caatgattac ctcaacgacg cgttaatcgt tttatcacgt ttattgtgat   1380
aagttccgca ctaaggaagg gacgagttgt aggaagggag gggtaaactg gtgatttcgc   1440
attcaaacaa cgggctttaa ctcacgtgtc cggatctgtt gagagggaac aattcacagc   1500
gaggaaattg caaataacac acaaaggaaa cacaaaagag cggaaagcaa atgtgaagag   1560
acgaagagta gccaatgaga aaaaggacg aggatcgatg acatggcaaa agattttga    1620
aatcccgcct aaacccggag tttcaattga tatcgcgatt tatctctccc tctctttaac   1680
gaaaccgact cccttcatat ccctctctct cgctccctct tcacttcaaa gggcttttcc   1740
ttctttccac ataaacacac gcactcgaag ccaatctcaa aaccgcatca cacgaaccaa   1800
actaagccta acccaatttt ttctcctcat atttcactct cacactcttt ccttatcttc   1860
ttcttccccc aaaccctaga gttttacagg taaactccca atctctccgc cgctccctcg   1920
ctcgattctc cttcgtttct ccgccttttt tcttataatc attacctgtt ttctccttcc   1980
ctctatctgc aggattcatc                                                2000
```

<210> SEQ ID NO 87
<211> LENGTH: 2000
<212> TYPE: DNA
<213> ORGANISM: Cucumis melo

<400> SEQUENCE: 87

```
gtgtagagtg agtgacggtg gccgacagtt cgtaacattt agttgttagt gagagacggt     60
gagacgtttg gtaacaaact tgttttttag ttcaatcatt gctttgtttt ctctttcttt    120
tccttaatgt ctaatgtttt catcttcctt tctttatttc ttacccaatt tccgaatcaa    180
attttaattt ctaaaaaagt atttaaaaaa aaaaaaaaaa ttagtcgctt tattcgagaa    240
tttcataatc aacctaattt tcaaaattaa tcatcaatct ggaaactttt ttattttttt    300
```

```
tctcctttgg attatcctgt atgaaagtca acatactttg cactccttga gaatattttt      360
agtggtgttt ttttttttctc ttaataaata aaaaagttta catctataat aatcaagatt      420
ccttggcagg tgtcactgtc aaaataattc ctatttgttg aagttgaaaa taatttaact      480
ataaacttta tttgaacgtc aaaaaaagaa aaaaaaaaga tatatgaatt cacccattcc      540
ataatttaac tatataactt tatttgaatg ttgaaaaaga aaaaaatgaa gacaaagcaa      600
attcacctgt tgccattacg acaaaatttc aaatgcgttt tattttgttt ttatgtccac      660
aagattctct atttgtattc tgcgaaatta aagtcacggg cttcgcacgt gtgtgattaa      720
tagtatttgt aaaagggcat gtagtcgaac aggatgggaa ttaaaggaga ttatgaatgg      780
gttgggtcgg gaaggcccat ttctataatg aattgatggg ccgtcaagga catttgtcta      840
cataaagggc atggaccatg aagttaagcc cacttcctaa acgagttcct tagtgtgtct      900
acattcatat ttaaatcatc tttaattcag aattttcacc atcatcaaat aatgtcttat      960
aaacctccca ttttatagtt taattatgga ttctaataaa aaatctctaa cttcaaagtg     1020
gataattttt ttttttttt aagttgaacc atgttcattc atttaattac atggaataaa     1080
aataacgtaa tttaggttaa aagttgagag gataagatga agttgaaaaa ttacaacaag     1140
ttaagaaggg aatatgaaga agaagaattc aaaattgaga acataataaa ggaattaggt     1200
ccaaagctgt aaagactagg agaaacgagt agagaaggga aggactcgtt tttcaaagaa     1260
aagaaaagtg tggaaaagga aaaaggttca ttaggggtgg tgaggaaatg gatggatatg     1320
gaatgatgat gatgagaaag aacagcacgg gaagtttccg agtagttgcc ttttgcatat     1380
accaacaagt tatctaataa aatgttttga ttaattacat taatttattc aattgattta     1440
tcggaaattt ccatactctt cacgtgatat gcacgtggtc ttcccatgtt ctaatatttt     1500 ttgttttttga aaatttgaat tcctactctg ttttgttatt ctgctcattt aactactcaa     1560
atattttagt ttgtagatat aactttgtaa attttttatta taacattttg taaatatttt     1620
aaattgtgcc catagattat gagtagataa atttacgaat taaaaaaagt ttaattctca     1680
cttcaattta atttttttt attattatcc aaatctattt gtcgcagtgg ggaaaacggg     1740
gacgtacggc cgattggagt ccaattagtg gatgtgaaac gtggacggta gagatgcaat     1800
atgaagctgg acatcaactt tgcgaaggaa ttgttccttc tttccctctg acgcttgtcc     1860
cgttattgct cgttttaaag caattcgagc tccgcgttgt ctcttccctc acgttttcct     1920
ttcaatccca ctgctcctcc tttcaccaat aaaacaaaaa cgcctcaaag aagaagaagc     1980
aacgaccaga aacctcaaaa                                                 2000
```

<210> SEQ ID NO 88
<211> LENGTH: 2000
<212> TYPE: DNA
<213> ORGANISM: Cucumis melo

<400> SEQUENCE: 88

```
gttcgagcat gtgaatgtct tctgttgttt gatgttagaa ggaaagagat gggttaggga       60
gttcctgttg atgtctagta ggttcttttt tttttctctt gtgcaatgta acatagtaac      120
ttcgctgcaa agcagctctt atccttagaa tacgaaaatc ttctgttttt tgttatgttt      180
ctaactttat cccttcttga ttttaacttt tgagttaaat tccatctctc tgactttgct      240
ttgtggtatt ctgtttctgt tgtatgataa ttccttatgga actccatatgc tctctctcat      300 tgccttcttt ttcggctgtt acttaattac tttcttcact tgaaatttat agcttctctc      360
```

```
acaaatttga gctcattcaa gtatcaaaat tacacccatc tcataccata tttctatctc    420
tgaaggagga ttttcccct tttaaggagg gtagattgac aaagctgata gggtgagaca    480
atttaataac tcaggtcaga tgaattatac attgaagaac tctcatccag ggccagtgct    540
ttgtttataa caagatgatt aatgtgttgc tatcaaaact ttgctggttc actaaaaaaa    600
actcttggtc cttgaaagta ggcttttact agttttagct ttaatgcaca tctgtatgtc    660
aaccacgaac tccatttttc ttacttgatg catgtgcaac tttagcagct ttctaagttc    720
atatcaaagc aaatgtacct ttattcctat tgtaattcct tttctgcttt cctcttttat    780
gaattgtcaa aaatatggac aggaaagtaa gctgagcacc aacaggttgt accccttttt    840
catgtcttga aaatgaacta ccaggacaca aatcagatga tgattgttgg gagaaggaat    900
gtaagattat tcgttctgtt tgatataaga atgtaagtt cacatgtctt acaacttttt    960
gaaatttgtg tgtcgcttat gtgcagattc ctgtatgtca ttagtggcat ttgtaagcta   1020
caattgttga atttttgtat tattatctta aaaggaaatg acaaaaggta taatcaaatc   1080
aagctgaacc taaaagaagg tacaggtttt tagtattatg catgaagaag gttttcatg    1140 tctcttctgc catttggatt ttgtctgtga caagggacta agacactaca catgatgctg   1200
gaaactgcaa gagtgttttt accctaataa gattaaaacg tgaaaagcaa ttagattttc   1260
gtgcatatct atctttttgt gcattccacc aaactgttcg atcataactt gtcaagatct   1320
tgctttttcc tttttttat aaatatttta atatccttct aatgtgaatg gtgaaaagag   1380
atgcacaaag ataagtgata ctatagatgt atctaagtat tacccttata cctttgccac   1440
gtaagattag atacgagaag agaaaaaaat ctatgagtta gtaatagggc aacaataaac   1500
cacagaaaaa ccaattaata cctttcctca ttgtctaata atatctaaaa gaaacttctt   1560
ttcatgttaa tgaaccaaac tatgttgtgc tatagcatga gcacattatt tctacccttt   1620
agacaagtga tgagaatgga caatatttcg actgagttca ccagaatgta accaacggtt   1680
ttgcatttgt aatatgaatt tgaaagtttg agattcctta tacgaggacc ttttttcatg   1740
tatctaacaa cacgagaacc accaaaatga gaagggagtt ggtccaagcc aaaagaattt   1800
tgacctccat gaaaatccag atagtggggc atccttatcc aaacaatcag aacctgaagt   1860
ccgacgtagc cttatccaca tttcaacttc aaaaacactc cctctaagat cctttcgaac   1920
caccaaaatc taagaaaatt tctcttcctc atcctcctcc gacacaaaat ctagcttcaa   1980
tttcattcct ctgtaaaaac                                              2000

<210> SEQ ID NO 89
<211> LENGTH: 2000
<212> TYPE: DNA
<213> ORGANISM: Cucumis melo

<400> SEQUENCE: 89
attcgtcttc gcattatcag taaatttatc attttaagag tttgttcttt tttaaaaaaa     60
attaatcatt tcgataaagt tggagaattc aaaaatttct ccaaataatt tataaaaact    120
ttcggttata tatcgaaaaa attaacatgg tattaaaacg atcataactc aattaacata    180
aacactccct ctcaacttta ataccaaatt tctttattaa cgcaaaattt aaaatttgtt    240
tttaaaattt tcacataaca aatagaaat acttttcttt atggcaaaaa tacaataatc    300
aaaattgatt gatggtgaca ggacaccaca caatattttt aaattttgaa tatcgaaact    360
atataataag atatttatga gattcccatc ctaaagattc ctagagattt ccttgtgtac    420
aatattacac aagtatcttg gaagtccaaa gtcctgagaa aaaagctatg tataaagtaa    480
```

```
tgtgtttgtc gtaggaaatt tacttcattc gtgtcattag cttttttattg aaaaaaaaaa    540
ttaggtatat cttagtgaat ctcacttaat cgttgtcgat agttattctt ttaatatcat    600
tatatactaa aatataacaa tattgaaaag ctaaaactgt atataaaaaa aatgttacct    660
ctaaactttt atcgtttatt taaaagataa atatattctt tcaaaactta caatcaacat    720
cctacgacta tcattatagg tacaaatctt tcatgtttta cacaaaaatt agattttttaa   780
atggtgtaat gatgatatat aacgaaattt tgaatgatta ctatttgagg ttaccattgt    840
aattggtcgt gttgtttgaa atttaatttt attagaaaat ttgtcaaaag tagcaaaaat    900
gaataaacta tttaaacttt aggataaaat caagtgttat gagttttttgt ctagtttata   960
tattttttatt tttattgaaa accctttttcc tatctttttca ttacttcaaa atagtttttaa 1020
aatgtctatt aaggctaaag ttagtataaa taaaatttcg gaattttttt ttcgaaaaaa   1080
attgataaat tatttatatt ttatattaaa gtcaaaattt attacgcgta gatgtttatc   1140
aaattttctt tctttttgtt gataattttc caaaatttgg ataatttttt aaaatagtaa   1200
aattattaaa aaatgaaaac aaactattta taccttaagc aagaaatact aaaaaggcaa   1260
aaattcattt acttcatgaa gcgtaaaaat taaatatttt accactttttt gttatttttt   1320
accatctcta tcaattattt gtaaaaagaa aactacaaaa ttagatgttt tttctttttt    1380
aaggtttaat caatattaaa atttcttaaa ttggcagaca agttggtgtt ggtaattacg   1440
aataaatccc gaattgacta aaaataaatt cttctccaag taaaatagac acgtggatga   1500
agaaataagt gaatcaaagg catccacagt tcaataaatg gaaaaaacta ctttctgctg   1560
actcattcat aagttttttcat aaaatttcat aagaaaggcc aaagggctta tgaaagtgaa  1620
tgtcatagca gtaaatgaag cacagcgcca ttgaaagaca actcaaattg catgcaaacc   1680
cacataatta ttcaacaaac ccacatcaaa tttcccataa agatcaattc tttagggggt   1740
tcaattaccc aaaagtgagg tagttgaaaa ccattaaaca acaagaaatc aacaattttg   1800
taatttgttt gtacagaagt aagagataaa atcatcgtta accattcctt tatttcgtaa   1860
tacaacccat caaccatctc tctctctctc tctctctctc tctcggcctt tatctttctc   1920
ttcctcaatt aatttaagta ctacccaagt gagctaaaag caagttcagt ggacagtgtt   1980
gtaagaacca ctacagaaaa                                                2000
```

<210> SEQ ID NO 90
<211> LENGTH: 2000
<212> TYPE: DNA
<213> ORGANISM: Cucumis melo

<400> SEQUENCE: 90

```
aatcatcagg tctccttcca atgaaaccga cgacaacgac agtgtcggaa aagcgaggaa    60
gggatggcga aggcgaggaa ggagaaaacg aagtagaggg ttccggtaaa gcagaatgag   120
gagggagagg agttggggaa ggtgaagagg aagaggaagt gggagttgat aatggtggcg   180
gccggataag tactcggaca gaggaggaat tgggtacgtc catggatgag agaaaatttt   240
gagcttttcag atgcaactga aaactgcttc actgctttca cttccgatga ccgccgaggg   300
gaaacttatt ttttccttgc cctttttgcc tcctcaatat tttcctttta ccatttcctt    360
tccaaattta ttttttctatg ttttgatttt atgttttgtt atattttttga tttactttta   420
cgttatttttt aaatattttt gatttaattt tgttatattt gaaaacaaga tattcattat    480
atactgtaaa tcttacttta ttattgttta aatgtcgttt tggtaattca aaattaagtt   540
```

```
gaataaacac aatattttaa atattatttt agtaaaataa ttttaggtt ggagaatggc      600
aaaagaaaca aaggattgaa agactgaacc catatttgag gatagaagtc aaagccaatg      660
tcaataagtg aaactcactt ggaccaaaat accaatttta gttttatatt tttaattgtt      720
caatcttagt ttccatactt tcaatgcata ttaaacttat agttcattat tcttttttcaa     780
taaatcttaa cattttacta caaattttta aaatgtttca catactttat ttttttacat      840
gaaaatgatt gttattgttt aatccatttc aataaaatta aaatttgaaa agctaaaaat     900
tcaagaatta tcgatagaca attacaattt tgtcccatta aaattatcaa attgaagtgg      960
ctacacaatg gaatggtaaa tcctttattc ttgtattggt gtgatttgga ttgagatatg    1020
aaacattata atctaaagga acatgtttaa accgaacatc acgtattttg tctttcaaaa    1080
tttcgtaagt ttgtaggttg tttttttttt gtcattttat atagttacaa ttatttaagt    1140
cagatcggat aaattttgtt atacaccaat aggaaactaa aaattccaca aggagtatga    1200
atgacctcct acgggagcat taatgaaaat gaccaagggt taaaaatgg taagaaaaat    1260
gttcttcact aatgacaatt cctcgtgaaa gtactaacat gttcttaaaa tgcttgcaag    1320
catatatgtc accaagaatt ctcattcatt cctctggctt cttctctca tttctcatca     1380
acattaatat gacacacttt ttccttcttc tttttgtatg tgtttataat cttactcatt    1440
ccttattctc attgtcactc aacgattcca acaagcaata tgggaacaaa cgaaggaaga    1500
agagaaaaat acactaagaa gaagagatga acaaagttgc attagaacaa ggcgtagaat    1560
atcaaagaat tcaaaataaa aaggaaaaaa agattactag acgagagaga acgagacttg    1620
aaaagaatta gaataatttc ggtaatttta cattggacga cgaaagcaaa tgacaaaaac    1680
aatttttttt tcaaaaacat agctcaaatt tcatttagat ctttcatccc aaatggcata    1740
atttctctaa tttcacatac accacaaata taatgatgac tgattaaacg aagtaaatta    1800
caataggact aaatatataa ttaaacttct taaattgagt ttgagataaa acctttgaag    1860
ccacgaggggg tcgggtcggg ggcgaaagag acatgccata taagcagttg gttgctgtaa    1920
agtggcacac gcatatctac tggaagcctc catttccaat ctcccattat cccattatca    1980
tcggcagttc cccatagcta                                               2000

<210> SEQ ID NO 91
<211> LENGTH: 2000
<212> TYPE: DNA
<213> ORGANISM: Cucumis melo

<400> SEQUENCE: 91
ctttcctgac ccaataagag atcaaatcac tgtctcctgt agcctttccc ttgccgctct      60
attattgaca tttgggccta ccttcccccc cccccttct cccgattcat cacccttggg     120
ccttggccca ttaaaacatt acccagctcc ttactacttt ttaataacta tcacgtctat     180
tccttcgcaa gtgggtggaa gcgaatattt ataccaatta tcttttggtt gatcatgtag     240
ccaaaatttg gctcaccaaa ctcgtacaaa gacatttact tgttttccac tgtagatttt     300
aattttggaa gaagagatca gttgccaata gattgaatta atgcatttat gtacactttc     360
atacttaact tttggcaaag agttgaaagc aaggttttaa agaataaaat gaacttactt     420
tttttacaaa tctcatgatt tacgctagct caaacttagg atttctttcg tttgaaaaat     480
tggaccaaat atatatacaa tagattgaat aggagtcttt taaaatactg gcctcaaaga     540
aatagacaag ttagctaggt cgggataatt gcctcactca ttcttcacct cagagatgcc     600
tctcctccta ggcatgtttt ctaccctcat aatttaattc actcattttt gcttccttat     660
```

```
tgattagtaa aagtaccgat ttgccttctt ttctatgttg acaagttccc actagaaaac    720
aaattagatt atgagtttat aggaaagaat taaacacaaa tacataagtc aaattgtgaa    780
gtatcaagat aggctgttag gacagaaagt tcaaatttgg aaaacaaata tatatgttat    840
tgagttgtca tcttcttaga taatgataaa atgtgaactt ttgacacata taataaatag    900
catgttcttg ataaatagtt ttccattaaa acaataagct attattggat gatagaaact    960
cccctgggac tacaagaaaa agctaaaata gaatcagcat taaaacttcc tttaatagga   1020
tcgttatccc aaataacaac tccatctcaa aacacttcta agaagtagt taagaataa    1080
caatgtatat tagttatgga tgttgatgat agagaacttg gattttagct aaatttagaa   1140
tcttaaaaag ggaaggaaga aaaaggaac aaaataaaaa gataacagta tgattactcc    1200
aacttgtgat gaacagtacc actcatggta tgtcaaacat atacatagaa tgagaacaat   1260
ttagatcaat taatttactc atttatcctt cttgctacag attgttgaga aaatagaaaa   1320
acaaattaaa gtaggaaaaa aaagaataaa tggggaatta tggaaccaaa atatcaagaa   1380
aaaggagggg caataaatta agaggaata gtgtaggcct tctcacagtg gaagtattag    1440
cgtttaagtc agtaccttac ctttatttgt tttcatacta agttctttct ctttcatgtt   1500
aataaatttt caatcgatcc atctattcaa aatggtgtgt tttattagga agaaaggtaa   1560
tttcatacaa gaaggctaaa aaatagttga cagctgtggg atttgaaccc acgccctttc   1620
ggaccagagc ctaaatctgg cgccttagac cactcggcca aactgtcgga attgtgagtt   1680
gaataactaa gatgatcgga aatgtgacga aataaattgg gctaaagaaa agaaaagccc   1740
aaacaatgaa gaacaattcg gcccacttaa tttcacgcgc atggcacgtg taaagaaatc   1800
ccaatctgtt ctactaggtg gtggtggtgg cgaggcgaag caaagcaaag caagatcagc   1860
cttatcaaat tgtgtggtga agaatgaaga ttgtataatg tagatagaaa aagatccccc   1920
cattcccatt cccattccct tttctgaatc cgccattgtt atctctctca gacctccata   1980
acctccattt ctacccagcc                                                2000

<210> SEQ ID NO 92
<211> LENGTH: 2000
<212> TYPE: DNA
<213> ORGANISM: Cucumis melo

<400> SEQUENCE: 92
cttctaaaca tcctcaatgt tcgattttga tcaaggtcgt ttgcttctaa acatcctcaa     60
tgttcgattt tgatcaagag gtcgtttctc tatagtaaac atctgttaca ccttccattt    120
ctgttattca attttttccaa ttttattgag cagtttattt atttccgtaa ctactttgca    180
tcggaggcga tcatcagttt ttaaggtaca aaactagatt atatataatt atgaagcaca    240
gcaaagtata aaattttgaa gatgaaattg attggaccdt gtgaacagaa ctctaaagag    300
aaaatgcatc agatagtctg gatcgttaga atttgaaatt taaatttcta tcttccacta    360
aagatatctc tgttttgcaa actaatgttc ctcattctaa acagagaatg ccagtggtat    420
tttgttcgtt ttttgcgaat atgattaaat tacccatttt atttgcatat tttatttatt    480
ctcatatcag ctccaaaaga atatgatccc ttttcctcg ataagaaaaa atatttaata    540
ctttcaactt catgcattgt gagactgccc atttgttttg tttaaagtag caccaacttc    600
tcaattgtat aagtttgtga tttttttctct atctaaattg acttgaatta ttttagata   660
taattaaatt aattgctttt aagagcaagt taaattaagg tttcgtaagg atatggatta   720
```

```
aatttaatta agaattggct tcttgctcta aatacaaatt agagtgagat tgaaataggg    780
aggaaaaaga gagtatggtt acaaaggata tgaaagatca aatttcaaac ctttgccaac    840
tgaggctttt cagaactctt aaaccatcac agttttttct ttgcccaaat gaaatcaaac    900
attaagaaac agtgataacg aaaacgaatt atccctatgc caaccgtgac agatgatagg    960
caagaaaccc acgattagtc tctcatccgg attgttccaa caaatgaaaa agcgttttct   1020
gagactacac aaacaacaaa cacagagtta gatagttcaa gcaaatgatt ctagcagatt   1080
agaggataag gtttcttatt aaatgtttga atacattcta accaaaaacc aaaaacccta   1140
tttgcaaatc agcttatgta aaccaaaaac atatttacta agaattcaga atttcgctgc   1200
ttgaaatttg aaggatacca tataaaacaa taatagattc ccccaatcgt gttcagtagc   1260
tcaatatagg caccgtgcaa aaggttgttt gttgtaagat taatgaacaa acacccgtgt   1320 ctgatttttaa tgccaattca aactctaatt caaaaaccct acaaagacct aattgcagat   1380
aatgggatta gaaattttaa aaaatgtcga ccgggcattg tatcttaaaa ctattaagtt   1440
tcaaggatct tcctccggta acaaaatatc ggctccatgc ggcagacgga tcgccattaa   1500
aacggcgcct gctgctgact cgatgataga gccaattcag aataaccaac ccatttcatc   1560 gaaatttta aagagagaga aaataaacga ttcaagatat caaacgcatt tcgcttctat   1620
tgaaggagaa gacaatgaaa atcaaaacaa atcggaaatt aaagttaaag aagaaggaga   1680
taatctcagg acggacggaa gataattcta aaggtgcgat tcggttgaaa tttatagagg   1740
atttgtgaag gaaccctaaa ttctgattgt gaatttatc ggaaagaccg gagaggaagc    1800
ccattgtgtg aggcccaaag taactgatct gggcctttttt tagtttcagc ccaaacggaa   1860
gcgacacgtc gtttctatgt agagccaaga gcgtgccacg tcaacagacg acgtcggtta   1920
gtaggaataa taccgatttg tggatttaag aattgttcat ttcggtttgt atcggaagtt   1980
ctgaatcttg atccgtggca                                                2000
```

<210> SEQ ID NO 93
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 93

```
aagtagaaat tcagcgaaaa atgcagatgg tttcatagac aataaaaagc aggaacaagc     60
gcagagaatg gttaatcctc cagaaaatgt gataaaaggc gccaccaaga ccagtaatcc    120
ctttaccaat cacagaatac tcaacaagaa aagcgattcc agcaaaaacg aagatgaaac    180
tctcacttac aagaagaggg tcgacatttt cccgcaaaac gatgagaatg gcgagtgccc    240
agaagaagaa aatggccagt gattgctggg agaatgcgaa tctgtaagtg gggtttccgg    300
aaaaagcgag aaaaaggaaa atttcagaga aggcgacgat ggggaggagg aggatgaggg    360
aatataaatc gaatttttc catttcggtt ctgataaata ccaggttttt gatcggtaaa     420
gagatgggtt gttgaggtaa atggaggaag aacagaggag gcgacgaagg ccaatgggga    480
tgaggaaaag ggaggcggag agatgcgttg ctagtgatgc cattgaaagg cttttgaat    540 ttgttgaagc attcagattc ttctctgtct atggttccgt agattgttct ccaattcttc    600
```

```
cattgggaag acggagttcg gtggctgaac gttgaccta acaagtttga tcacgttgat      660
ccgttcaatg ttaaacagct cgatgatttt cgtctaaaaa agaagtgatt ttttttttaa      720 ccttttatt attgaacaaa aaaagatct gtttatacca tagtttacgt tcttccacat       780
gagaagtttt ataatagttt atagaatcta tccaaattgt gttttattgg gtttcgattt      840
tatagaaatg tcatatcaaa aaaaaattta aaatgataa aaatcattat aattatttta      900
tgaaattttt actgtgactt aattagatta taaaccgacc attctttaat cattatttg      960 gatgtctatc gtatgtgtat ttatagatgt caaacatgag agcatagatt taaaaaacaa     1020
atagcttaaa caaacaacaa taacttttta tctttcagaa aagnnnnnnn nnnnnnnnnn     1080
nnnnnnnnnn nnnaagaaa agaaaagaaa agaagtcttg aaaaaagtat taaatttcac     1140
aataaatttt ttaaaataaa atacattaaa tggggatgag gaagaaacaa ctaagagtcc     1200
aagaagagaa ataaaaaatg agaggtggtg ttttttttgg tatgttaatc aaattatggt     1260
ctccacatac aagaaatgaa gccacgttaa tgacccaaca acactaacac atcaattctt     1320
aaaattcaat tccttctttt cttcccttcc aaaattatgg gtcctccaac ttacaaatta     1380
acaattgact ttagctaact atgttttta aatataaaaa acgaatacaa gtcagtttaa     1440
taggacttga agattgtata aaccaatatt agacaatcaa acaatcaat tttaggttca      1500 ttcccaacga tacatcaatt tggattagat taattttca ttatggtttg atagagtgga     1560
tttagtttta gtggaatgca gggagggaaa agtaatttga agaaaagga atgaggttgg     1620 tcaattccga agcctaggta tccaaataca agaatccata tcaaatttat gaacacctag     1680
aaaataatag taatttaat aataaaatgg agaaatgggg tccggtcgtc ctcttcctcg      1740
cggcggagat gaagccaccg cgataagaga aagagaccct tttcaataca attcaacaat     1800
cacatgaatt attccaattc acatctctgc ttttgaaact aaactaaacg ccaaaaaccc     1860
ttctgtggct cataagtttc ctctctcaaa tctccgattt ccctcaccca catcccacat     1920
ttcgcatcca aataaaaaag ggacacggac aacaagaagg agttttttaat tcagtagtgc     1980 ctctggaaga agctgtttca                                                 2000
```

<210> SEQ ID NO 94
<211> LENGTH: 2000
<212> TYPE: DNA
<213> ORGANISM: Cucumis melo

<400> SEQUENCE: 94

```
ttagtgaaag ttcaagatgt aattcactct ctttaacaag gttgtttctt tgcttcacta       60
cgcatcaatt caaatattta gatattgatg tttaagctta atctcctatc ttagctcaga      120
acaaaattgt caaatctca ttcttatttg tctacctggt aactttgctg ctatagttat       180
ttgtgggaga ttgtagcaaa tgactgtaga tcgaaccat ttcagcatca atttcgaccc      240
actcttctcg tcaacaactt gatcggcagc ttcgacattc ttcaagcgcc agcttctatt      300
ggatctttag ctcaaccaca tcttcgtctt tgaattgcat gtgagctgtt gggctccttt      360
cttttgtgct tatcagttgg gagattatta ctataaatac aaagcctcac gggtatttta      420
agacacaaca aaaaattaaa agtctctcct ctgaatcacc acttccattt tctataaatt      480
ttgttctgag caacttttgt ttgtttctat ttcttattct gaagagtgca tgtttgagta     540
tggggagtaa tgttaacctt gaggaacaat tggcaacacg attggcacct cggtcaatca     600
tagttgcttt taggacagtg gttcgtcaca acacaacaat ttattttaag ttcaacattc     660
```

| | |
|---|---|
| tcattctttt cttctacagt attcaaagtt atagtgttta tttctcttat tgttcccttta | 720 |
| gttaacaatc taccctttaa ctaaagtaac aacttaaaag taaaatggat tattctactt | 780 |
| tttcttaatt gttactttta aaggtttaag aactgaattg ttactccgat gaaagtctaa | 840 |
| agaccaatag tggtttctat ccttaaaaaa ctattcaatg aaatttatgc taaaaaaata | 900 |
| atcactaatt catcgtgagc ttccaaacca cttgaaatta gctcaatgag attgtaactt | 960 |
| ggtcgggatc tcatcaaagg gatggtcttg gctagattct taaagatcat tttagaaagt | 1020 |
| agatcatgaa aggttgcaaa gatgctagaa acaactgggt tgtcgacgtt ttggaagcta | 1080 |
| aagcggtgat gattgacgta atagatatca ctaaacattg gcacaatcat acttggaaat | 1140 |
| agcttctata gatatattcc attttgtaag gtcttaaaga caagaacaaa gctacctata | 1200 |
| agcttgtatc ttagtttcct cttgcgatct tcttgtcgag agatgacttt ccggttttgg | 1260 |
| gttgtgtctt tgtttgtttt tctttataaa aaagtcaaaa caaataaat ttggattaat | 1320 |
| tatcctcgta ctgaaatcaa ttggtttgga actaagtaac aataggatac atgcggcgca | 1380 |
| ccggatcatg ccattctccc tctttaaata tcaaagcaga tccctaaacc ctaacaaaga | 1440 |
| tccaaatatc aaacctcccc tcttactaca cgctccggca cctccaaaac tccatctcga | 1500 |
| ggtttgtcac ttttatgttc ttgttttttct ttatttagaa tatgatgatg attagaccga | 1560 |
| tggctatttt ctttaaatgc ctttactcct ctgactagag tggtctgtac tctgaatcag | 1620 |
| agggttcatt tcgaatcttc gaacgttgta tttcgcttca aaagctagac ttttcccaat | 1680 |
| ttacttgaac ttattgtaat tttagtgcta gcccattgat cttggtctcc aatgccactc | 1740 |
| tctgttccga ataactgccg attattgagg ggttttttttt ggacttcatg atttcgagtt | 1800 |
| gttgtaaaat gattggggat tcatttaaat atgaaatata tccatcgttt atctcaaaag | 1860 |
| tatatatctt aagataaacc atgaacaaga agtttccgat ctaattccca tgggttgtct | 1920 |
| aacgagttat tctcaacaga ttacgaactg ataactagac gtttgaattt tggcacagag | 1980 |
| agaaatcgca tcactttgaa | 2000 |

<210> SEQ ID NO 95
<211> LENGTH: 2000
<212> TYPE: DNA
<213> ORGANISM: Cucumis melo

<400> SEQUENCE: 95

| | |
|---|---|
| taaatgggaa attggaaact aacttgaaac gaccacaaac catggggact taaaaaagtg | 60 |
| ataatctaac aaaggcttta cactcctttt tcataataaa gaacaaaaag aaagctcaag | 120 |
| agcaatcaag tttatcataa ctaattaaag tcaaacacta catttctcaa aagaatgata | 180 |
| taaaatgacc aaacatctag ctgctttaca gtgtaatgaa cacccaccat taaaggaacc | 240 |
| aaggcaactg aataaattgg taacttaatt gccctccaaa tcagagtccc cataccaaca | 300 |
| tcctcttccc cattctcttg gggcatcgaa tcaacctcca tcgctttaca ttccgataac | 360 |
| aaacctctaa aacggacatt tctgcacaac cccaattgcg ttctacgact cccgcaggca | 420 |
| aatttatgag catcagtcga caaactcgat gaatttaaac gacccagatg aaagctgtga | 480 |
| tagtagaaga gtcaagaaga taaatggggc taaacgataa ggttttgaaa gaagatgtag | 540 |
| ttgccattgt gaagtggtac ttgccttgga gtaatggtgg tgaaggagag gtggtcgttg | 600 |
| agtttgttct ttagggcgcc gagttgggtg ggtatgcaga ctatggaggc cattggcatc | 660 |
| acatagctga agatgaaact gcagagtgaa gctgcttgtt gaagcagagg atggattaat | 720 |
| taaagtggga cgattttagt tgtgtcttat cttcttcaac tttatgtttc ctcttggttt | 780 |

```
gacacggttt taccattatc gctaccattt taagtaacaa tagtagtgat gaatgggtaa    840
aatataaatc ttattccatt gttagaacct tcgacaagtt ttccattatg tgtggctgtg    900
tttgacccac caactcgagt agagttgaat ttgtttggtc tactatattt acaaactaat    960
attaaataac aaaactctat taatttcatc ggtgttcact gttgaaatat atacatttag   1020
tatgaatctt tatctatttc tctcttaccc ttcctctaac atttctagtg cctccatcat   1080
caattgtcat caacgacgaa atgtgacgat aactatagtc aacgagtatt tccaccttac   1140
tttgacaata ttcattgcca caatatgctc ttgacgacct ctagcactcc acgtatgata   1200
aagactacat tgatgacca attaaggaaa tcgtatttga caccacattc caatggctat   1260
ctctagtgat caatttcgac tatcacttgt ggttatcgac tttcaaccat ttctaacgac   1320
taacttgacg accatcttaa tcaatcatat actagaaaaa caaaaaaaaa aataactcat   1380
caaatggaaa cattttaaa tgcaattttg aaactaccac ttctctgtat ttaatagtaa   1440
tttgacatta acaaaaacac ttttaagtac ataaaaaacc aaacaaactt gtatataaaa   1500
cacttttgaa aaaacggat gtaaccaaac acacaagtat ttttcttta gattatgttt     1560 taaaagatag aaataaaaat attaaagaaa agcaccttt ttacaaacat gtaaatccaa    1620
atcaaacatg ctattttta atactaaaag aaatagaaaa aacatgttaa acatatccat    1680
tagcaaaata aagtgaaatt ccaagaatta gaaagatggt ttgaaaattg attttataaa   1740
gcgaagaaaa acctttttcc ccaaaagaat aatattctta ttttggaaaa aacagaaaac   1800
aaaaaatgtg acaaaaagtt acattcctgc ggatttgacc ctctggtggc tgcattcgaa   1860
tctttgattt cgaataactg aagtaaacat taaccaaagt ccgtcgaaat cttccttttt   1920
ttcatttggg attccctcaa tcttcatcac caccatcacc atcctccact ttcactctgt   1980
ttccctccaa acatcaaaaa                                                2000

<210> SEQ ID NO 96
<211> LENGTH: 1373
<212> TYPE: DNA
<213> ORGANISM: Cucumis melo

<400> SEQUENCE: 96
tttaaatgtt actttgatat gatctatgtt tagatttgaa gtattttct catcattaaa     60 aagaactaca cgatcgtatt catttagaag aagaattgta cgtacgcgtg tagccgatta   120
atcacgtgtt gagtgaaaca tttttatat ttttgctaat agacctatat attgttttca    180
tttttaaaat tgatatgtaa atattttggt ttgttatata tatatatttt ttttggaaaa   240
aaaactcctt tatttatttg tcgttaagta ttaatttctt ttttagtac ttttattacc    300 attgtggcct tgttttgctc ctcaatttag atatttatta tttgtggttt atttatttct   360 tttgtttcg ggacaagtga tgtttgggat attaaagtaa aggaaaaaa agagagatat    420 tttgattgtc aaaatgtcag aaatatctaa acccggagct tctgccacgt aggcatcact   480
ttcattacct tttataaaaa gtacgaattg aaccttcatg acactgctcc cctgctccct   540
tatataaaac ccaatcctct tccatgctca gtattatctt cactctttgc tcgaaccgcg   600
tgtttaacag ataagattca actcacaagc attcatcgct aggttcttcc aaacaaaaac   660
cctacatctt ttccatttcg cctccttaat tctctcatat ttctgtatct taatccattc   720
taaaactaca ttttaatgca ctgccttgtg ttctgtattc cactatctgt tatcgtttta   780
ttgcgttttc tttgatcaga tcgctttgtt gttgcatgaa ctgctgagtt cgtttgatga   840
```

| | |
|---|---|
| ttttgtttgc gcttcagttt tcatcgtttg ccgtccagat tgtttgattg gcgagagtga | 900 |
| agtgaaaatt ctgtatgata ttggagcgtt tcgtgtaaaa tctgtcttgt ttttctatta | 960 |
| tctgtatttt agtgatttgt ttttcgttga cgattttgta tgacgtaaag atattgtcca | 1020 |
| ttttaaagga ttttcttcca ctggttacta gagatcttag attgagcttt cattcggctg | 1080 |
| tattttgatg atgcttttg tgtttttttt tcctttcttt ctttagcttt tgcggactca | 1140 |
| tggagtcttt ttctgaacga catcttaaga tgtttaagat gcttatttgc ttttttctat | 1200 |
| ttttggtatg acggggtcga gtctgatttt gaacgacatg ttaatattta tgatattttt | 1260 |
| gaagctagtt gtgcttgatt ctgaaaattg cttttgatac acgagaaact tttttgtttt | 1320 |
| cttcaatggt aggattttga ccattattat tattatttt taaaagatca aat | 1373 |

<210> SEQ ID NO 97
<211> LENGTH: 2000
<212> TYPE: DNA
<213> ORGANISM: Cucumis melo

<400> SEQUENCE: 97

| | |
|---|---|
| ccgaattcgc tattgggctg cataaacttta tcacttgctg ggagactgca atttgtttgt | 60 |
| ttagtgctat gtagttttca agtttactag gctagtatgt ttgtattgcc tgagagtgtg | 120 |
| catcatgagg tggataaaat tcttaggtct tattttgga ggggtaagga ggatggtaga | 180 |
| gggggtgtta aggtggcatg agcggaggtg tgtcttcctt ttgaggaggg caggcttgcc | 240 |
| atccatgatg ggccttcttg gaaatattgc tatgtctatg aagattcttt ggtcgctatt | 300 |
| ggcgaattct ggttctcttt ggtggcttag gtggaggctt acattcttaa ggggaggtcg | 360 |
| ttatggacga ttgatagtga ggttggttga tattgtgtct tcgggctatc ttgtgtaagt | 420 |
| gggatagttt gaaagcactt gttcctatgg aggtggggga tgggagaagg tgtagagttt | 480 |
| ggcttgatac gtagttgcat ggcggtccta tccttgatta ggttggggag agggtgcttt | 540 |
| atgacgcgac gagtcggagt gaggcttgac tttctaattt tcttggtcat gatgaggagt | 600 |
| ggaggtggcc acgagtttct ttggagttgg ttaacttatg ggatacggtt cagactgttt | 660 |
| gttcgtgtct tagtgttagt gataggtgag tatgaattcc tgacagtcat ggtggttttt | 720 |
| cgaccgcgaa tgtgtgggat actctctgtc ctcgaagtag tcaggttcct tggactggtt | 780 |
| tattgtgggg taggggggaa ttgttttcca aaacatttct ttttgagttt gacttgccat | 840 |
| caaagatagg ttgttctttt tgtagttctt tcttttggtg ctttttgttt ctatggatcc | 900 |
| tgtgagggtt ttctgctctc gtgccttaaa ctcaggctgt gaggtcctcc ttgttatggt | 960 |
| ataataatat taccttttca aacaaaaaaa aaacaaattg attcagaatg atttttttt | 1020 |
| cttttctttg tatttattct atgtttcctt attcaggcta ctagatttga atatgttatt | 1080 |
| tgttacttcc ttttctaaca aaattagtta taattaattt tatttggttt ctttaaaaag | 1140 |
| tgtgggttg aagcttcttg cagaatatag gatcacaaat gcctaataca cttctttcta | 1200 |
| cttctttgtt ttgcagcagg gtatgaaaaa acaaattaat atgtattttt tatacttctt | 1260 |
| tctcgtatgc attattcttc ttttgtttct gttggctttg cattgtagcc gttttcttgt | 1320 |
| tcttgtctca ttttttctct acctttgtt tcttctctaa attcctttta tgttcatttt | 1380 |
| tcataatgcg gattttttca aaaagaaaaa ttatagttgt tagttgtgtt tgatgagaaa | 1440 |
| caagaaaaga gagtgaaaag agaaaagagg tagaagagaa aagaaaagaa gaatctgagt | 1500 |
| agaggaaaaa aattgaacaa aaaagttgga attgtgttgg atgaagtgag agcaagaact | 1560 |
| aaatttttgtt tgagcgtcaa gccccccaccc cacacgtttc taagaacaag atggtaattt | 1620 |

-continued

```
taaatacaac taatataagc aaaatacaat ttctcgagga aataggaaac ttcattccag    1680
gcttcaaagg aaaaaagaaa aaaaaagaaa aagaaagtaa aacgattaga acgtgaattg    1740
cacgtcacta gacaaaacca tcttttggta gagaaaaaca cgtgattaca aaaaacaaac    1800
gaaacccaaa taaatatata tagaaaaaaa ataaataaaa gaaatagaaa aatctaaaaa    1860
aattgggtta gcgggcaaac aagaaaccct tgtttcgatc ccccaaaacc cccccaccct    1920
ttctcccatc ttctttcttc ttcttccctt cccatttttt gaagaaccaa ccagcacctc    1980
tgaccaacat ttgcttaccc                                                2000

<210> SEQ ID NO 98
<211> LENGTH: 2000
<212> TYPE: DNA
<213> ORGANISM: Cucumis melo

<400> SEQUENCE: 98
tagtttggtt cataggttat agtttccaaa tttgttaggc tatcattaat caaacacaat      60
acttctcttg taggatggct gcccccctata gtacttttt aacttaggag aaggatataa     120
taattatatt cctttagaa aatataataa taattgtgta gtgctttgat ataccttaaa      180
ttagctactc acgttttag gaggaagctt ccgttgcttt tcatggtgtt atgatctttt      240 ttatttata aaggactgaa cttaaaatt tctctttcat ctattttgga ttggattcca       300 tctatttat acgggaagtg aactctaaga tttctcttca cctattgtga atcggactcc      360
gtcatgtagg tcaagactac gacagataag aatagacttc cacgaaagaa agtggtcaat    420
cgagatggct atatttggct ctttcagctc aatttcttct ttttccttg catgttcttc     480 cgttggtaca tttcttgcac ttttttttgtt ctcacatgac taatgtattc caagtttatc    540
attggcattg tgcctctttt aggcttgtaa actctcgatc caaaattatc taggacatat    600
gtttcctagt gaagaaatac tagtatattc cttatgtcaa tatgtcaaaa ttttcaattt     660
cttaaccttt gagtaaatca atattatatt tttatggagg ttatttataa ttggaaaaaa    720
gttacaccca tctcaaccct aattaacacc aaatgaaatt gtaccatgcg gcacaatatt    780
tttttgtgag tttttttgcaa agagaaacaa agtagcagac aaagaacaaa cattccccca   840
aaaacagcag agaataccta agagagaatg ctctctcgta aaaaataata cccaagaatc    900
ttcccaaaaa gagggagtaa aagagtccaa aacaaacgaa ccgaagattg acaagaaggg    960
cactctcgcc ctccactgcg ccgctaaatt gtaagaagca tattttcttg agttaacata   1020
ggaataggtg taactcaaga gaaatgtaat tcgtagaatt gaactttgta tattaattta   1080
tatggtgttg tagatacaat ctttagtatt tactcatttg gtgcttttctc tcaaatacaa   1140 tttaaactta gaacttttg atcttcgatt ttcaggaagt tggagttgca aatcaattcg    1200
agtttcaatc tctggaattt aataaaagtt tgatcttcca agttttcaat ctttcagaag    1260
acgatgatct tgatatggat aaaaaattgc acatcatgag agcttttga agtttaaatc     1320 ttcaattctc tagagcttaa attcttcctt aaaccaaaga tcaccaaatg aatgacaaat   1380
gtctctattt atcgaaaaat ttcatagact tttagatggg cttaggcaca ttacttgttg    1440
ggcttggact tgggcttatt tgcttggcgg gctcatgctc gagcccatta tttctttggc    1500 ctattttca tgaggggctt gaacttggtt gtatacgaaa aaacttgact acctaaatct    1560
aatcaaatta taatcatcac aatttgtacg tgttacgatt taattggcca aaaattcttg    1620
ttcaacactt gtctctaatc attttcctat ataatttaac taaatatttt aactttaagt   1680
```

```
aacttaaaag atatagttta attcgaatca aaatacaaat acaatttcgt ctatctattc    1740
ccatcataaa tgttgattga gattcatatt ataaacttct ttcaggaaaa gaaagaggaa    1800
aattcaccta aaccacgttt tcctattttg gtaagaatcc ccaaaccata aatcattcca    1860
aaattatttt ttttagaaaa aagaaattca catggcgtaa aatttcagcc ccgtgagata    1920
ttttcgaacc cccagataca atctacaccg tgaaaacaaa atcggacggt ggagattgct    1980
ataatgtccg tttagaggca                                                2000
```

<210> SEQ ID NO 99
<211> LENGTH: 2000
<212> TYPE: DNA
<213> ORGANISM: Cucumis melo

<400> SEQUENCE: 99

```
acactttgaa agtccatttg agagattagg gtaaatttga gtgaggatgg cgtgatgaca     60
acgataaaag tgaaaaatgt cagatccaag agagactcaa aagtgaatga cgtgaagaca    120
atcggaatcg aaattgaaaa atcagatttt aaattatctt aaaccacata ttaattaaat    180
ttcgattcca gtttcaattt ggtttgctgt gataaaacta aattcttaat tgtacctaat    240
tttctattaa ataaataggt aaaaaaagta tagtaaaaat attggcgtcg cccggactcg    300
aaccggagac cttcagtgtg ttagactgac gtgataacca actacaccac gacaccgttt    360
tgttacatga gtaaaatgtt tcctattgtg ctaatattat tattactact actacttctt    420
cttcttcttc gagaaaaacc aatttctatg ggtttaaatt tccaaattga tgttgagtgt    480
atcaataata tagcactcac atgctactta acaaaaatca attctttctt tttagttaaa    540
accttttctt ttatatttag tgaaaggatt aagctatgtt ctacgttaaa ttgttataaa    600
caaaatttga ttgttactta tcgagattaa tttatttaag tggatatgtt ggaatatgtt    660
actaaaatga taattgatag tgatacgtcg agtttatgct aaacacattt tgatatggtt    720
ttctttttca atataataat ttgacattaa ttacattttt ttttcatata ctctcaagaa    780
tgtttatttt tattatgtac ttttaaaaat taagattttt tatggtttta tccataaatt    840
tgtttcattt tttaatcgaa attttagtat tagactttag ttgttaaaga tcctaaaata    900
tagtcattat atttattaa agagtctccg tcacgtgtat aaattaaaat agtcttaacc    960
gttaaaagta tagtgaacaa aatttctaac aagaattgga tcggagtaga agggtgattg   1020
attcaacatg atccttgtgc cattattgtt gttactcaag ggacgttcat caatagataa   1080
cttgaaatca aaatggcata aactattgct cagttgaaag gttgtttgtt gattgaagag   1140
ttaggtttgg atatttgggt ggaagccaat ggccttgtcg tggttaataa ggtgctttca   1200
tttaattttg cactctctcc tcatgggggtt tattacacta aagtggttca tttaattgag   1260
agcatattgg acgaaaataa acaattaaga ctaaggacga aagtaatatt taaacattat   1320
tttaagaaaa agtcatttta attcctaagt tctttttttag tataattttc atttgtttgc   1380
tatattttaa aaggttacgc ttttatcaat aattctttag tttagttttc atttgaccta   1440
taaattttaa aatatcacct ttttccttt atatttgggg tttaattttc cttccttgca    1500
ttttcatatt ttcactaat accttaaaac aactaaggct tactcctagt ctttgaaggt   1560
taaacgttga gtttcaacta attgatttaa tcatctaaaa ttttgagatt tttttaaaag   1620
caatgattag gtgcagtctt ctgcttccca tttattatc acgtaaaaaa attataaaaa   1680
aatcattttt taaaattgtt acctgacaat ttttgagtg caactcgaac tgcctatcgt   1740
tgtaacccga ctgtacctaa atattttcaa tatttttaaaa cctttgatta aatgataaac   1800
```

```
aaattaaaac taagggggaa attacatttt ccttaattta aaaacaattt tgttgataag    1860
atggggcctg gcccatgagg ttttgggctg ggccttttcg aatcgtctat ttataatgag    1920
caaacgagtc tgagcttcga agaaatcccc ttttttttcac ttgcgaaaga gacgaacaaa   1980 cgcaaaaacag tcgaaggaag                                               2000

<210> SEQ ID NO 100
<211> LENGTH: 2000
<212> TYPE: DNA
<213> ORGANISM: Cucumis melo

<400> SEQUENCE: 100
tgttggcaat gatttctttc agaaactttt gccaccttaa tgcttgcgta gtttcaaact      60
aaatgctgat tgctgtcagt aactgattaa attttgattt aagtatagta gctgccttat     120
tgtgttaaca agtttctcca tcattttttg cattgacttg atgatttgac ttcttttggg     180
tcatatcttt gattctttcc atgtttgaaa gttctaattt agatgttggt ttgtatagcc     240
attgagaagt ttaattggca aaacatttta tagcgacctt gacatagaag aagatgatat     300
cttcgtttct gatggtgcaa aatgtgacat aacacgactt caggtatgat ttgttttagt     360
ttggaacatc tttcatccat gtaatatttt tattttcctc attttttttg aactttaatg     420
ttggttacta accttagtta aatatgtaag atagcctggt aatcgtatct ttcatcttgt     480
tactatttaa cttctcttcc caattttggc agcttgtttt tggatccaac gtgtcgatgg     540
cagtgcagga cccatcatac ccggtgattt tctcttctca ttaatgaaaa ctttcgatga     600
ttaattggta cactaataat attttgcctg tccacctata tatcagacat ttacttaaat     660
gatcatttga aaaatatcaa gctcttgggc aatcattttg tgtgtctcat ctttactgtt     720
gtgcttgaat gagtgaccac gatggataga cttttgaga aagatccctt tgttaatggg     780
tcttttttgt tgtattcttt gtcggaaagc ggaggaaacc cagatcatct tatttaggag     840
tcttagtttg tgaggtctat gtggaatttt ctttcaaaag ttttgatgtt gtacttgctt     900
gctagaggga tgttcatttg atgattagag agtttctcct ctagttgcct ttcaaagaga     960
aatgacaact attgtgggtt ggcctagtac taaaatagga gacatagtct caataactaa    1020
ctaagaagtc atgggttcta tccatggtgg ccacctacct aggaattaat tttctatgag    1080
tttctttgac atccaaatgt agtagggtta gacgggttgt cccgtgagat tagtttaggt    1140
gagtgtaagt tggtttggac actcatggat ataataaaag agaaatgttg ttttctattt    1200
tgtggtttgt gggtgtgtca tgtgtgctttt gttgtggaat ctttaaggaa agaggaacca    1260 caaacccctat tgaggtttgg ttcttggtga agagtgtgag gtttcatgtt ctgggcttcg    1320
gtttcaaaga ctatttgtaa ttattcactc tcacttagtt gcaaacactt tcttttgagg    1380
gtttccgtgg gcttggtttt ctgtatgctg ttgtgttttt ttcactttttt ccctcaatgg    1440 atgcaattct ttattcaaaa gaaatctttt actcttgaat ttgcatatgc acccttttgat   1500 aactttggt aggttagtca cttcagatca aaccacaaat aataatatat tttgttttcg    1560
caaaacttag aaaatatatt tttgatatca gtctgttggt ccattctccc acttattggt    1620
ttatgttttt ttggtagtta tgaagtaaca tccaaaggcc tgtattgttt aggctgtaga    1680 acttttataca aacctctgct aagtcaattc ctaatcaaga atttgtggaa ctgtaggctt    1740
atgtggactc gagtgtcatc ttggggcaga ctggacagta ccagaaggat gttgagaaat    1800
atggcaatat tgaatacatg aggtgtacac cagaaaatgg attttttccc gatctatcta    1860
```

```
aggttcctcg aacagatatc atattttct gttcaccaaa caatcctact ggctcatctg    1920
caactaggga acagttgacc caacttgtgc agtttgacta aaagaatgga tcaattatag    1980
tctatgattc agcatatgca                                                2000

<210> SEQ ID NO 101
<211> LENGTH: 1078
<212> TYPE: DNA
<213> ORGANISM: Cucumis melo
<220> FEATURE:
<221> NAME/KEY: unsure
<222> LOCATION: (1)..(1078)
<223> OTHER INFORMATION: unsure at all n locations

<400> SEQUENCE: 101
ataatattaa tttcatttaa aaataacttg aattttttcc tcctatattt atcatgcatt      60
tttacaaatc cacgttcgaa aatcccatta atcataggag ttaaattgtc atcacttgat     120
ttgaatattt attttttttt aaaattaata aataaataat gtcacgaaaa tgataaaaat     180
gcaaagtatc gaatttaaaa attaaacaga acaaaattta aaaattaaat gataaaaata     240
aatataaaat ataggtggat gttaaagata ataatttaaa tctttatcta tcatcaaatg     300
acgatcctcc aatggaaaaa gaaaaaaaaa actttattct ttacctcaaa ctcctcgcta     360
aaaagtaaca atggtaagat aaaactttat tttaaattat tcttccactt gcaagcaaag     420
taaatagtta tttgattctt acacaaaaga gaattttac ttttttacttt tcattagtta     480 tatataactt tataatacat ttccctctca tggaatttaa aactaccatt tgagcaaaat     540
attttaaact aaagaaaaat atgaaactta aaactatgtg acagggatga taatgacgtt     600
tactccaaat tttcatttta aattaacgta cgttatttta taagtatatg tcaaaatttt     660
aaggatctat tttattagac aattcaaatt atatgttgtg ctttcatatt ttgttaaatt     720
caataaatat gcctttggtt gattatacta ttttttctaat taactctgga gacatttcaa     780
aagatttttt atttatttat ttaagaaaat atattaaat ggtcaataga tatgtattat     840
gcacatgata taaaaannnn nnnnnnngta ataatattat tacataatta aattctttca     900
tcttcctaac agagagagag gatcgtcctc tcagcgacgc tgatcccaac tgttccagta     960
ccaaatctct gtgtcccaat ccaacagatc cttcttttaa gctaaaccca ccattttttt    1020 tttttttctga aacccatttc ttatctctcg ccggaccttc agattttacc tcaaaacc     1078

<210> SEQ ID NO 102
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 102
cactatctat catagataaa taagtgatag atctaaacga tcatttacca aagtctcaaa      60
gatcatgtac caatatctaa acgagtttgg tacaagattg tataccaaaa tcatttgatt     120
tgatacaaga tcgtgtacca aaattgttta gatttgatac aatatcatgt acaagatagt     180
gtatcaatat ttaaacaatt aatcgtctat cctagataaa caaagataaa ccactaggaa     240
atcgcacgaa gagaaataga ggaagtgaag aaaaaaatta ctcatataaa ttgatgaaaa     300
```

```
atgttatcct tctctaatat ggttttaatt tttgcactag gaaatcacac attaatgatt      360
ataatacaaa gtcctacaaa gagatctgaa ttgattcatt tgtgaaactt tacaatttta      420
atcgatacaa ttattaactt aagagtgtaa ttgatttaag ctacaaggtt taagcaaaaa      480
actaaaacat aaacagaagt caaacttttc ttaattttg agtttagtga gctacttatt      540
tattgggtag ctttagaaaa gtcaaacttg aattgtcatt tttaagtatg atcaaactta      600
atttaaccca aacttctgtt gtaggtgaat tagcagctag tttgtatata ttgactgatt      660
tacaaattct tattttaatt aattttaacc atccattaaa atggagagtt atagttattc      720
aaggatttta actactctca aaatcatcaa gatcacttgc atatttagta taagttcaag      780
gacttaagtc cttattgata ttttcatcat catctggaaa actaatcaaa taatcatgtt      840
gatgcaactt agatgattaa gattaaagct aagacttttg aaatgataaa gaatataaat      900
aaaaaaggaa gttttttaaa aatataacaa ataggtaaaa tatttacatt atataaaaca      960
attctagaaa cgaaaaaaac ccacggtctc acaatgaaaa atacaaaaaa tacccctagtc     1020 aatagcaatt aatcagccag cttgcgcgaa gaatattctt ttaaacgact gtgtactaca     1080
atttcaacga ataatccagt attgtttagg tcatgacacg atcatgtagt tctatttaa     1140 cgatgggaaa aaaggttttg aatttaaatg atcgtattga tcatgaaaaa caactatgtt     1200
gattacgata agcgatcatg tagtccaatg taaatgaatt tcaagtctaa cgatcatgtt     1260
gaccatgcta acgattgtg ttagctatgg taagcaattg tgtagatcat gtcaacacga     1320
tcgtttagat cattttaaac gatgtgaaaa agactnnnnn nnnnnnnnnn nnnnnnnnnn     1380
nnnnnccatg ataaacgatt gtgttgacaa tggtaaaaga ttgtgttgac gatgataaac     1440
gattgtgttg ataatggtaa agatcgtgtt gacgatggta aacgatcggc taaatcatgt     1500
caaaatgata tttagacgat gtagatatt ttgaatatga gaaagatgaa gtgactttaa     1560
agatgaagta gcttttaggt caaaagcaaa taaaaacata taaaaacata cgaggaaaag     1620
ttaacatatt tttagtctat tcagactcat ccaaatttta attgtgtcat caaatctcaa     1680
tccacagctc tcaccttgat taaatacata acatatctaa gatcttataa ttaagttcat     1740
gaacgtatct aacttttaa ttcattgatc tgccttgctt agttcaagtt acatacctc     1800 ttgcttaaaa aaaaaagtta catccctct tgcttaaaaa aaaaagtta tatccctct      1860 ttgacaaata tcaaggaga aaaagacaaa aactgacatt ggcttccat catccagaga     1920 aaagaaagaa aagccgcgcg ggttgtttat ccacttgttt cccttattat cctcatcgat     1980
tccaagtttt gaactcaaca                                                2000

<210> SEQ ID NO 103
<211> LENGTH: 2000
<212> TYPE: DNA
<213> ORGANISM: Cucumis melo

<400> SEQUENCE: 103 ttcctatttta aattaactgg ttttcttaga aaataacaga attcctgtgt ggaatcccgg       60
ctctaatcca aatttcatag ggatgaaaaa tgaaatgggg agtagacatg gagatggga      120 gtggcattcc tgacctcacc ccgtccccgt ggacatcttt ggtgacagaa tcatcccatc      180
caaatcaatc tgtgggcaaa tttcaacact cacaacaagt tgaaagactt tgttttgtaa      240
tgtatttcga gttcaactca catgtggttg tatagtctac catttcaaac ccactccaaa      300
taagaaaaaa atataaaaaa acatatttta gaaccccaca acatttttt tatttgaaac      360
```

-continued

```
aaacaaatat ctccacgtgt ttctgtttga tctcaaattg tacaaaaggg agacaaacaa      420
gagcaactta atcgtgtggt cgaaagttca taaaaaacgt tgtttttcat tactattatt      480
acatcaacca atgcgatctc aatcttgtga agatttttct tccatgtgtg agtcatttct      540
tctcgatctt aattatcttc tcacaatcca tttattatag cataatctaa gttaatttag      600
attcaaaact atacaataat aataattaag aaaattacaa atttaaatag caaaagaacc      660
atttgttctt tatagtttct acactaactt tgaaaaggt taaggttatt ggaaatcttt        720
ttctggggca ttttctcca attctacaat agacaatttt ttttaattaa ttaattaatt        780
aaatttaaag tttaccttgg agtagtcaat aattaatttt tatgcacatt tgtcttttat      840
atgattgaat gtaacaaaca ataacttatt cttcttcttt tattctattg ttttgatgca      900
aacccacaat atttaatgag ctcatagtta tgtgtttgct ttactaatta attattttct      960
tttcataaaa taaaaaaact tgtacaatat aaactctatt atcattgaat ttttagtact     1020
taatttaaac gtactaaaat aaaatacatc attctgactg acgatccatg taaataaaat     1080
ctaaaaataa aagaaaaatg tcagaaatag caaattgaca aaatatttac aagccatagc     1140
aaaatttcat attctaccga taacaaacat tgatagaca ttgatattct tctgtcagtg      1200
gtattggtag acagtgatag aagtctatca atttctatca tcgatagaat tcaaaatttt     1260
gttatagatc gtaaatattt taatttattt gttactttta aaaatgtctc aatataaaaa     1320
ttattaaata aacattaatt ttttattttt caattttaat atctaagctc ataaatatta     1380 actttacccca ttatttattt ggtttcttac cgcttaaatg ttgcaaaaat attttaaatt    1440
ttatttttga aatttggtta aattcgtttt tacttaaaaa tttccgtgat aaaaatattc     1500
gaatttttta ggtttttata agatttaaaa gtaaactaca taaatgaaat cgttattttc     1560
taattctcaa tttaacttt ttatactttt taattaccaa atggaaacat gaaatttaa       1620 atatatttat tttaaatctt actcgttaca acaaaacaa taaatttaaa attattttc       1680 cgagttttaa attacaagat ttaaaattaa tttttcaaca agaccaaaag aattgtaagt     1740
ttcgaataaa aaggtttctt tttgggctat aaagtccaat ttcctataaa agaatttgat     1800
caattggagc ccaaagtcag atccattaac ttttgggccc aaatagaaca atgaaaagaa     1860
agcccaaaag ctgacccacc aattaacctt attattaggg ttttgctctc tcttttaaca     1920
tccgaaaatc aggactctct tgccgctttt ctcttcgccg tcgccttctt cgagcttcaa     1980
gtctcccatc ctcttcagcc                                                 2000
```

<210> SEQ ID NO 104
<211> LENGTH: 1974
<212> TYPE: DNA
<213> ORGANISM: Cucumis melo

<400> SEQUENCE: 104

```
tttgctattt tcgtttcatg tgggaaaaat agtatagtat gtttacgtct taaattattc       60
caaattccta gctaggaatt aaaactttaa tatatccaaa acgttcttta tttattataa      120
agatctgcaa tagcacaatg ccaatttctc ttctttgaaa tccaggttca atcccggtt       180 gcggaatat gttttgctat tttcgtttca tgtggaaaaa atagtatagt atgtttacgt       240
cttaaattat tacaaattcc tagctaggaa ttaaaacttt aatatatcca aacgttcct      300 tgttttattac aaagatctac actagcacaa cggtaggtag tttctcttct ttgaaatcca     360
aaatctttgc tattttcatt tcattttcaa attgaatgca tagctttaga ttgtagtaaa      420
cattgtatat atatgtttag gttgtgctaa ctttaaatgt acaaaattca aatgtaata      480
```

```
gaattagatg tacatgataa agagttgcaa tatttagatt aaaatataag aatttaaatg    540
taagacttgc atatatcaaa aaaagatttc tttataaaca atatttttt atacaatttg    600 aaggcaactt attgttactc atgggcttga tccaaacttt tgttgtcttc actaaaattc    660
ctctaaatag ttcaacataa agttgttcat gagaaaactc attaagatat attccaacat    720
tatgaattgt ttgtccttgt attttgttaa ttgtcattgc aaagtataaa tgaatggaga    780
tttgttttct tttgaacttg aatagatatc cattatcatt tggtgggttt aatggtattc    840
atggaagaaa aatttatttt tctgcataat cacccattat tatttcagca tgtataatat    900
ttttgctaaa taattgacat actaatcttg tctcgttaca caatccatta gatgaatcca    960 aattttcaa taacaacgtt ggtaaaaaaa atcaagacag ccttttatat agtaaaaaaa    1020
atgttacaac aacttttcaa cgttcaagtc tttaaatttg tattgttgat tagaattaat    1080
aagatatttg atttgcaaca aatttctaaa atgtaaataa aaaccatttt gcattcaaac    1140
tctttacatc caatactttta attccttcgc atcctatact ttaattccac tcacttaaat    1200
ataattaatt aaaaatatag tggataaatg aaaaccaatt tgcatttaat ttttatatat    1260
gcatacttta attccactaa acttcgttag aattaattca aaaagttgtg ggagagaatg    1320
tgcattttat catattacaa gaaaaataaa attaaaaaag aatttaccat aaagtcatta    1380
aacaaaattc aaaggttgaa tggagagaat aaaatttctg cacgctttga tatatacaag    1440
atatttaaaa ttaaaaaaat agttttaaag agaatgtttc taaattatta ttctaacttt    1500
aaatataatt actcataatt atacttattt tttttttaaat ttagaaacta aaatgataca    1560
ttctcgaaaa ctataatcaa acgagttaat gttataaact ttgaaaacta ttttttgttt    1620
ttaaactctg catagcaaat agcatataga ggttttttaa aaaataataa taattaaaaa    1680
aacattaaag gcaaaatcta ttattccttg atttgtgtat agggtgtaaa tattttgtta    1740
ctgtgttatt tttaaccatt tgcgcactga tacggactaa aagtaaaaa cataattttc    1800 tcgaattgtt attagaaaac tggggaagaa aaaggaaatc aaatcgcgcg aggtgggatt    1860
tgacccggga acctaagact agctcggtgt ggtgttgaaa tccacgcgtt gttcaccgat    1920
tttcttcata caaacgcac ccaggctacg gcagtcttcg aagctctctc aatc          1974
```

<210> SEQ ID NO 105
<211> LENGTH: 2000
<212> TYPE: DNA
<213> ORGANISM: Cucumis melo

<400> SEQUENCE: 105

```
gtcgtcgagc agagctctgg cagttaccct acaacccgga gcacgataac tgcagtgatc     60
cctatcctca gcatcagtta aatgggccga ttcaaaactt tatgggcct cagcccactt     120 ccacttacaa ctattacaaa catggatacg atagtcacga tcaggcccat catcttaatt    180
actccacaca ttccaatatc ttcggccgcc aaactgcctc cgtttttagc gacgaaaatg    240
tccataattg ctctattatg taataaggct aaacactaat catctatccc tttaaatctt    300 gaattttgt aataaaacca atctatactt tttgccatag tttatttcta gaaaagttta    360
gaatacattg aagatttgag aaacttgtct acaaggcatc aacaaaacta cgtgaaaatg    420
acaaattgga aacaaataaa aatatcttat gtttgagtat atggaatgaa gggattgatg    480
taataaaact taacgtcaag tgttaatatt acgctatagt tattttcttg ttgtagtaat    540
tttctcttag ttaattttttt tattattgaa ataagtgata aattttctaa taagaacgta    600
```

```
aagatttaaa cctctaatta agttaaaaaa aaaaacttga attattgttt gagttatgag      660
gtaacgtaaa agacaactta aattttaaag tcaaaccgaa aggaaaagag ttaaataccc      720
acaaatggat caaagaagtt aataacacac acgcacgttg ggaagcttaa aaattagcaa      780
caaacaagca atcattggtg tgggacagta ttgaaattcc acaaaactac aagggtatat      840
tggaaaatcc aatttattta tttattttt aataggaatt aaatttactg taaaaaaatg       900
taagaccgtc gattgacaat tggtggactg tgaaacgtgg caaaagttaa ttggcgaaaa      960
ggagaggaaa gattttctct tttcattata atgaaaaaaa ttaatgatag tacacgtggc     1020
aaaaaagtat tggagagaaa tttccgggaa ttatctctaa tacgcggcta atttggatgt     1080
caattttgca aagaccagaa tcttttttgaa cagcgaagaa gaacaaatat atagacatac    1140
aataataaat aaaaataaaa atatattaag cataagagaa aaagaagatt tgaaggttat     1200
attgaagtga tattgttggt ttctccattt ctgtgggtct gactctgcct ctctcttttc     1260
gagccagaac caccaaaacg aaaaaaccca cacactgtat agcaaaccct aattctttgg     1320
tctcagatcg cccatggctt ccactaaaga acgcgacaac ttcgtttaca tcgctaagct     1380
cgccgagcag gccgagcggt ttattgtatt ggttttccta ccttcctttc cacttttttt     1440
ttttgggttt gcttctcatt tctatttat gcttttctta atttgtgttt tacttttcac      1500
tctctctttg ctcagatcgt atttcttctg gttgtttaat tttgtgttta tgttttttga     1560
cttcggattt aagccacgat cgcttgcctt tttgtgtact attttcagaa gtgttgttat     1620
gtttatccgt ttacacgatc tgtttgaaat ttatggaaat ttagtttgct tataattttg     1680
ctacatttct attgtttagc ttctcgagca gttttttttt tttttggccg atccattgat     1740
ttatactgtt tttctgtctg atctgtttta tttaatggag aatactcttt ttttgcgaag     1800
cttggtagct catttttcac tcatacttac acagactact tggtcattgt ttttatctgt     1860
aagcacaaag caaattcaag tttctgcctg ttctttcttt gcttgtcaaa cgacaaaact     1920
atgtttgtag ttgcttttgg atgatagatg gtgattctga ttttaattta cgttttcctg     1980
ctgttttttt tttaaaagaa                                                 2000

<210> SEQ ID NO 106
<211> LENGTH: 1643
<212> TYPE: DNA
<213> ORGANISM: Cucumis melo

<400> SEQUENCE: 106
tccattggcc ctctcaaacc tttatgtgca tatcactaat atggttgaat atgtatatct       60
tctttctcga atagatgatt cttggtggtt tcaataatca tttagcaaat ccagaaattg      120
ggacctcaag ttcggttgcc gtggaaatag ctaaattaac tctgaaatcc tcaaactgaa      180
atgtgagaat aatcacgatg aatctgaacc gtcaacggcg gaacatagca acagtaatca      240
gaattaccaa atttcaattg ggggaattcc tttgtatgat ccttccttgg gcctaacagg      300
gattcttgat ttgaacctct cttcttcgta aaaattacac aaaatattta gctgctagag      360
ctagacaaaa caagatttag attggaaaaa caacaatgca gctcccaaat tgcaatccta      420
attccactat ttctttttc ttttctttt tttaatcctt aggattcaat tcatcattca        480
tcaattttat tgttactgct cattgatgac caatgttttg gattttgtgt gtcaaatatt      540
ttagtttata tatggtgaaa agataaaatg aatagtttca aatttgtgt tttatgaatt       600
cctcactacc tctttctttc actaatacgt atgaaatgtg tatggttgtt tataaataag      660
atggatggat gttttgattt tgatttgaat gttaatgtta cttaaattat agattttaac      720
```

```
catttgaatg aaatatggag agaacagttt ttatatgtaa aaacaaatta atgtgagaaa      780
gaaataaata gcaatgcctt tcttcactaa taaatgtatt tatatttttt attaacaaaa      840
taaaatttat attaattatt agtgtatgag gtgtgttctt gtacaaagga aagtattgca      900
aaattacaaa aatggaaagt tgaaattact gcactcattt gctaaaatca aattagttaa      960
ttatagaacg aaaaataaat aaataagttg tatttgatga tcctagataa ataacttttg     1020
aagaataaag atcaactatt taaaaaaaat atgtgtatca caaaaagaa tagagaaaaa      1080 aatcacaaaa atcacatccc aaattataat aattcatatt ataataattt ataccaaa       1140 cataaactat aataatcacg tattattata actcatagac tataataact cactccacgt     1200
cccgtagtta ttaaataaaa gaaagtaacg gtaacattaa cattataact tcgccctcat     1260
ttatggcaag gaaaaattgg ggggattggc aagtattata tttgtttatg gaaaactttt     1320
gtgaaggtgg aaaatagaga gagccaaatt aacaaaaata ataacaaaat caagggtgt     1380 agaattcatc cagtttgaga gcggaagatt agatgggtga agaaaggatt attctagaac     1440
cctagcccac gtgtcataat ccaaccctca ccttttcttc aaaaacccctt tcttcttct     1500 ccctccccta tatctccttc ttcgaccacc aaactctttt ctctcaattt cccagcatct     1560
tcttcatttt tcattcttaa ttcaacccat ttcttctctc ttttcgtttc tattttcatc     1620
gtttctctat aatttctccc tta                                            1643
```

<210> SEQ ID NO 107
<211> LENGTH: 2000
<212> TYPE: DNA
<213> ORGANISM: Cucumis melo

<400> SEQUENCE: 107

```
ggatgggcaa tcgtgcgaca cttgttctac tcgattaaca aattagccgt gtaaaatcca       60
aaaattgtgg acaatttacg gtatgatgta gcccctcttc acgttcttaa gaaattttt       120 ataaaatgag aaagggaaag gaaatcattg aaaagatcat aaaagaaagc attgaagact      180
gttaattgca aagaaagctt agcttaaaaa gagtgcaaca aggcttagtt ggggatttaa      240
ctactatgtc tcccttattg tacattttga atattttat ccttggcaga cttgcatatg       300
aaaatgtcga aacgtcacac actaggtcga caacataaaa atgaaagcaa tagagcaata      360
gattaaacta agtagaaaac ataaagacaa ggtgatttga aggtatttgg atatgtggcc      420
ataggcaaat aacgcgctgg acaagcatgt tcatgacata tgacactttg cacgcatgct      480
caatgtggat atatcagcat ggcgcacgtg cctcactcgg acacataaac atggtatgcg      540
cggcatcatg tgcgcacgcc ttacacgacc aacgagctag gtgtagtcca agcacacacg      600
cgatgggcaa acgtgcctat ggctgcccct ggcgcagaca gtctcgaaag atgcatgtcc      660
atcctaggcc catctagaca cgtccaaaag ttccaatgac ggtccaaaag gatacaatac      720
ctttagaagt gtcatggtag gtctagaatg ttctagagtc atttgtaaat tgttaaactg      780
ccttatatct tctagatata caggtcctcg gccgaccttc aaagcaccta ggtcggttag      840
gaaagctata aatagatgta aggtggctta tttgtaatca ccctaaaatc ttggcataac      900
ctagccaagt aagacaacct tgcctcatca tttgtacaca aggtaccttt acaaatggta      960 atacctggc aaaggactac actcatttgt atacaacttg tacacaagca atcttggaac      1020
gcaaagtact cttccaagaa gtgtcaagct aagctccatc attctcacaa aatgatctct     1080
cttgcctttc aactatctta aatcttctac tgccatattc tttctcatag tgcttagtgc     1140
```

```
actaacctct caaaggctta cttggctacg tgggcgttaa tattagtcaa gtgttgtacg    1200
tttggttagt tgaaaaatct aaccacgtga caatagacaa acatcaattt tattttattt    1260
tagagtctca ccaagttctt aaataaaatg tttattgtaa gacaaacaaa aatgaaaata    1320
tgttattata gtgatataga atttttcacta ttagtacaag atataaaagc gaaaggaaga    1380
atgaatgaac actcaacatt tagaaagtgt tttgagtaaa gaagtaaata gtgagaaata    1440
acgagtacaa atgtgtggaa agttataaac ttctaagatc tacagaacaa aagattgata    1500
agatataaaa ttgatgttag gataggagct acaaactcct ttgaccaaat atcgagcagg    1560
attcacaagt catactctct tactctacca aattcattag aagtacataa tgggcatgca    1620
tgtgaacgaa ttaaaaaatt ggtattttta tttttatatt ttaaaaaaat tggatgaatt    1680
ggcaatggcc atgaatgaac cagttgttaa agtttagagg acaaaaccca aaagagagaa    1740
gtgtacctca taaaaaacaa atccaccaat tgagaatcac ataaattata ggaagacgtg    1800
tcactctatc ggccgatcct caaactcttc caccaaatcc acatgcacaa tctccttctc    1860
ttcccttcca ccatacactc aaaatcccac tgatcttctt cttcataaaa acccatataa    1920
tcataaatta atttcctcaa gttttttcttt tccaattaaa caaacaactc tgcaaaagag    1980
gcctttcttc caccatttcc                                                2000

<210> SEQ ID NO 108
<211> LENGTH: 2000
<212> TYPE: DNA
<213> ORGANISM: Cucumis melo

<400> SEQUENCE: 108
agacgaagaa gaagacaggg tgtgatcatt taagaatatg cgttttaact ctgcccttt     60 tagggctttt ttcttttatt tatttgcctt ttttctcgct cctagggttt ttccctccat    120
tgaattagaa ggatgactgg gccacagact tatgatgggc ttcacggtca ttatttgaaa    180
gtgtgatatt ctaaaaaaaa taaaaactca tttgaattaa aatagggttt ccctccatgg    240
gagtatgaaa gacttttaat tgaattgggg ttttttaaacc ctaaattgaa ctaaatatat    300
ttttatgatt tttacaaaaa ttaatactac aaaacaaatt atgattaata aaatttgttg    360 atattttca aaaacaatt atataataaa acaaactaaa tattcaattt ggtatttta     420 accatgctat aggaaaagat tcatatgggc atcaaaatga agcaagaaca tggcaaagca    480
agttgggtga agataagtat tgtcctaaat cgaaggacga ggcaataaac tcgatatctc    540
gaagagtctc caggtcaaca tcacaacgcc tgcacaaacc aaatattatt atatatatag    600
ccatcgttta ctataagact atgtatttac gaaaaattct atattgtttt cgacgattac    660
atttatatta tataggaata aaatacaaac ttttcgaaaa gtcatatatc ccaccatata    720
aagatcaaac gtggtagatt gaaaacatta tacagtatat tctctatttt tttctcataa    780
aacttattac gctttgtcaa gttataaaga ttaatggttt tggtatattg tgctaacttc    840
gtccatttgt tgtgaaatta cattttcact acttttttcc acattgcacc attttttcata    900 tgttttatttt ccattatctc gtagaatatg agcaaagaaa aagattaaag atgaaatttt    960
tcaacgtgtg agagaaacat cattaaaggt tacttaataa ggaattagaa aaagagcat    1020 gaacctagaa caacaagata caaaatatca aagacaaaag agttcgatgg agagctagaa    1080
agataaatca agattttgta aaagaaaagt gctcggtggg gaactagaaa aatgttatag    1140
aagctagaaa gataagccga taatttgtaa actataagag gccgtttaga ggaagagttg    1200
ggttgtgaaa tgttagtgtt atgataaaac tattgttatg tttggggaaa gagtttaaaa    1260
```

```
aggtacttt   atgataaaat  atgtctggga  taagagttga  aaaacgtagt  tttatgggag   1320
agttgaagat  atagggttat  gaagagttaa  aaaaggtata  agaaaaggag  agagagagag   1380 ggaataggg   ttatgatcat  agtcttaaaa  cagaattatc  ataacccaat  ccaagtgata   1440
acccttggac  caaacgacct  aaaatatcaa  agagaaaact  gtttggtgag  gaactataaa   1500
aatgttatag  aagctaaaaa  tacgaactag  aaagataagc  ggagccaatt  ataagggttg   1560
gttaagtgta  gggtttattt  atttgagggg  aatgataatt  taagatataa  attaatagaa   1620
tggcaagttt  tgtaagaaaa  attaataaca  actcgataaa  cttttgtttg  tgttggtaga   1680
gaaaacatgg  gccacaaaca  tgagcccaaa  tgtggagaag  cccagctgat  aatttaattt   1740
taaaaataat  aaagattaga  ttattttgt   tcgcccaaaa  ttcggcgcgg  ctaggaggtt   1800
gcttataaat  ggaaataaat  ggaaagggtg  ttaggtctcg  aacaagtgtg  cgacggtatt   1860
ttaaaggtcg  gccacgttga  ggcggccctt  tcactcctt   tttcctcgct  cgtattcaat   1920
ctagggtttt  aggtttccaa  cttctcttcc  tcccttccc   cttccccttc  cccttccttc   1980
tctactcatc  actattctca                                                   2000

<210> SEQ ID NO 109
<211> LENGTH: 2000
<212> TYPE: DNA
<213> ORGANISM: Cucumis melo

<400> SEQUENCE: 109
atgggtagtt  ttcaaattaa  tccgaccttt  gaagtacttt  ggttttaaa   ataattttt     60 atcatctgaa  atcactccat  agacttatgt  taccgtaaat  cattattctt  tacaaatgat   120 ttgatttac   ttaaagtat   attatttcaa  acacgttata  ggtattatga  agttttaccg   180
tcaacaatta  tagttagtaa  gccaactatt  tataaaaatt  taaaaggaa   tatttgaagc   240 atggtgcatg  atgtatgttc  ttctctctct  taagttgact  atcaaaactt  aatcatgctc   300
agaataacat  acctcacata  gcatgtgcaa  tttaatctaa  gcaattcaaa  attcattaac   360 ataattcat   acacactaca  aagtcatacc  acctatgtca  cccaagaact  actattattg   420
taacaagtca  aataagaagt  ccctatccta  tccatcctaa  gatggagtaa  ttttttcttt   480
ccttaaattt  ttggaaagaa  gaatattgaa  attcaggaca  ttaaatcaaa  gctgttcgga   540
gataaatgaa  ccattcttca  agtaaaattc  atatttgtca  tcatgcaaac  aaatattgaa   600
aacatgatat  caagaaaaag  aacaaattat  ttaaaaacat  cataccgcac  atcaaactta   660
aataaacctt  ttgtgcatat  caaacttaaa  ataacttttc  tcaacaaatt  aaagcgacat   720
aaaattgata  attttgttt   tttttttaaa  tatatattca  agaaaatcga  caaatccaaa   780
tgacaagttg  ttcacctgta  tattaaaaaa  aacaataatg  aaaatttgaa  aggagagatg   840
agaaaaaaaa  aatcaatcca  tcaatccaac  ttgaattttt  gggtcgacag  catatcccta   900
attataatag  gaagcacccct  actttttta   caaaagtatc  gaaattatta  gtcgaaaatc   960
ttaattagag  tccaaattgg  atgcagcaag  gatagtttta  aatccaatta  atagcatgcc  1020
taatgctatt  acaaatatat  tttggattat  acataaatag  aaaaaaaaaa  gtgaacttcc  1080
agactcaaat  agatttact   ctattgttat  aaaaactata  cattaaaatt  agatgtagag  1140
aatgagagct  caaaaccaag  aaaagtaaat  gataaaaggg  aacaggagg   tgaaaagaaa  1200 aggtgatacc  gcggatttga  tgtggctctc  ggttttttgcc  tcccaagcaa  tccccattgc  1260
ccatctcctc  tacaccaacc  cacttttctc  cctttctttc  tttctttctt  tctaaaactt  1320
```

```
ttgttttcca atttttgacct ctcttcttgg gcccacttac taacaaatca aaaccaattt    1380
tcattttttt ttcttttctc tattcccttc cacaaataag aaaaaacttt atataaatca    1440
atacaagaat gacatttatt ataatagtat atactataag gtgggaggga tggcaattgc    1500
caattgtata agtaactatt aatagacagt aaaactttga aatagaaggt atttagatgt    1560
ctgagggtaa acttataaca ttttatgaaa tctaaaaact aaaattaaaa ttattgggac    1620
aatataaact ttagacataa gaagaaaaca tatttttgtt aataatttaa caaagaacac    1680
aacaagaatg gtagagtgtt gattaagagt gagcataata gacaaaaaaa aatatagtca    1740
atcagccaaa atagacggtg gttggtcgga gatgaagaga gtttcaatct aatcagttgg    1800
taaaaaattc aaacatcgtc acattcttta aaacttttaa aggtttaaat ctgctaagat    1860
ttatcgaaca atgacctatt tgtactactt tatgattgac atcaatttaa atatttaccg    1920
gtgaatttag taacgattag ggcgagagcg gttttaaaaa caggagtgga gtagtggaca    1980 aggaggggc ggaccaaccg                                                 2000
```

<210> SEQ ID NO 110
<211> LENGTH: 2000
<212> TYPE: DNA
<213> ORGANISM: Cucumis melo

<400> SEQUENCE: 110

```
ataatactat aaaacaaata aattttaatt aagttgtttt tactttcata ttatactaac      60
aagaacagtt tgttaagttt tatatgtatt tataaaagat atatgagtta ttggttaatc     120
tataatatca atgtcgaatc tctaacaaat attttagtgt ctagacctta tgtaaaaatc     180
agaagtgacg ctcaatattt ggaaacagga atcattggga tacgtggaaa tcaatctttc     240
tgacattgtt acaaacaaaa gaataaacga aaagtatcac cttatagact caaagaatgg     300
aaggattcag attgagttgc aatggaggac ttcatcctga agtacctata tattttttctt    360 cttggttagt ttttcagtct tctcttctat ggatcaagtg gggaatacag caagagacaa     420
gaaagacatt ttcctataca aattcatttt attattcttt cattgtctct ataaataaag     480
aggcatttaa atccttttcc taatttaggt ttggtatcaa tattttgttt gtaacagagt     540
aatagaacca aaatatttca ttatgttact tgaaatgttg attttttttgt gcccattctc     600 ttctgagtcg acaagtgaga gtagatatga aagtagctta catttatatt ttaagagttt     660
ggaatctctt accttaaata ttttctaaaa gaatatcgtt gtgggaatat gattttttcta    720 ttttataaat ttgacactat cgatcaattt aaacacgacg tataattttta gttttatttt    780 tagaaaaata agctttttag tttaagtttt tttttacgta attactattg aatccctaaa     840
gttttaaaat gctatagctt tactcttata ctttgagttt agtttgtata tatggtcgat     900
aaattttaag attatgtacc gtaattctaa gttaaaacat tgctcacctc ttgtcctcaa     960
agttaatgta aatgaaatta taatactcat acataataga acttttttttt attcttaatt   1020 atgcaaaaag aatagtgaag gttaatttag ttataatcag ttctagaaaa ttaacacaaa    1080
cattctaaaa gtagtttgaa attgagataa aatgaaagtc aaattcaaaa caacgaaata    1140
aagttataaa tatgaaactt tgaaaaatat agataaaatt agaactacgc atgaaaactc    1200
taagacaaat agacaattct cgagatagaa gtttgaaatc gaaatctggg gaaggaaaaa    1260
tctttacatt tccattttat tcctatatct actaataagt tttgtattaa aaaagaacat    1320
caaatagagt aaataactgc acactaaaca acactcaccc aaccacccca tatctcaatg    1380
agaaatctta atgtgaacta caaagctagg gacagaaaaa tgattcatta gattccagaa    1440
```

```
caataataat tatgattaca ttttggattc attagattcc aaaataataa taattatgat    1500
tacatttggt gtttgaccta tttatttatt tattttatat aaatattttg tcgaagagat    1560
agaaaaaagg atgcatttaa attaaaaaag aaaaattata ttgataaaga agaagatggc    1620
gggctgacaa gagaagaccg ggaggctgat gtggcaatgg gaattccaat tttccaatca    1680
aaaactaaaa acaaaaaaga aaaaaaaaaa gcaaataat tttggttcac tgaaaatttt     1740
catataaata catgtggcgg ttgatggccc aaaggatgag ctttgaaggt cgcattatca    1800
aaagtttggg gaagcagatt tttgctaact tcgaggtact ctcctctcct ctcctctcct    1860
cactttcctt tctctctata ctaactataa tttccattcc tcctccatca ataatttctt    1920
catcctcttc cttagctaat ctctctcttc tctaccagtc aaacgccctc ccttttggtg    1980
ctctctagcc tcctcctccc                                                2000
```

<210> SEQ ID NO 111
<211> LENGTH: 2000
<212> TYPE: DNA
<213> ORGANISM: Cucumis melo

<400> SEQUENCE: 111

```
ttctctctct cttttaatct acaacgtatc caattatatg gagaaagttg aggttgttgg      60
atttaattca ttttttcaca ttttttaggg ttaaaatcta aaaacacatt tcgattttgc     120
gactgttcaa ggcgtatatg tttctttaaa tattatagtt gaaattacga tcaaattctt     180
acgctggtta agaaagagaa aatcgtagga gagaaattgt gagcatataa gtgaaaataa     240
cctcctagag ttttttggat ttttgagcga aacaaaagta aggttgtaac gatttatgtc     300
taaaatgaac aatgtcatat cattgtggga atatgtgtga atgataaatt atcacaactt     360
ccaacaatga gtatcacaat acatatcatt gatgggtttt gagaaaatga gggttgactt     420
ggacatgaca acttgataga cttataactg tgtggtgtac ttataagaaa tcggaagttg     480
gtttaaaagg agaatcattt gcgtcgacaa gatgattatt attgcaaaag atgcaaccaa     540
ggtatgtcga tacataggct agataaaaag aagatcaagt aatgatataa ctatgtctct     600
gttgatatgt tttaagtgaa ataaaaaac aaaactatta atcctatacc taaaatgaac      660
catatcgtac tatattagaa aagaataatg tacctcttga tagaaactta tagtaaaagt     720
gattaataaa atatcactag agagatacgt aaatacttcg ttatcataat ttatttttact   780 tataaatgaa ctataacaaa aagtatttat atccacaaaa tcaacgttaa gaatattagg     840
gcgtcgaaga agacgccaaa ctattttaat ataggttacg tttggtatct catctacata     900
acaatctttt gctttcaaat acactcaata aagtaaatgg aatgattttt tgttttctaa     960
ttttgtcatt aaaaacagtg ttttacattg tacttgaatt tgtgacatat aatgatatat    1020
ttctttttac aatacccaaa atcaacagta aaaaaacaaa tacttacttc ttttcattca    1080 aattttcat atgcttttga ccgttattag cctttagtag tttatcgtaa atagattgtg     1140 atattttat caagaagttt tatttttaa aataaatttc cttttcata accacaaaaa       1200 gcacccttgc aaaatcaata tttcattttg gaccgggttg acattaggtg ctttaaggat    1260
cggcccaatc tagattcaat aatctcagta aggcccactg taaaccaca aaaggcatg      1320 gcccaccgag cccactatgc caatagttgg gcctttcttt cgcaaatgca cgcagctaat    1380
taaggcttca ttacttaata atcagtaatt aattttgctc caaaacgggt caaagagcga    1440
cccgacccgc gaatatgtat ctgggccgtt gattatttta gtagtaatct caaccgttca    1500
```

```
gtcggtcctt ttatatgtct gtcctccctc gtaatcaatt cttagggttt tctagggttt      1560
ttagttcttc tctacgcttg gttggaagtg cccttcctct cattcttcct gctttactac      1620
aggttttcaa tcttcaacaa tttaaatctc aacatttaat ttgttttgca cattgattca      1680
agtgtgtttt ttttctttcg tttgggcttt tgttgattga aattactcaa gaaattgcag      1740
ccacaaggat agtctaaaaa tgcatttgat ttagtgtagg tgctgctctc ttttttgtga      1800
ttgttcttag cttacttgga gctgtatgtt aatgctagag ttcattgagt atcaatgctc      1860
aattacagat agttttgttt tgtaatttcc acatatattt tcgtatttgt gaaattaagc      1920
tcgtttgttt tcattgtttg ttggcaattt atgttttatg ttatgccaac gattcatgat      1980
ttgtagcttg actcgaaagg                                                   2000

<210> SEQ ID NO 112
<211> LENGTH: 1027
<212> TYPE: DNA
<213> ORGANISM: Cucumis melo

<400> SEQUENCE: 112
ggggggggtt gtcttcctca aactctgtta tcgaaattag gtttacattt agtatctggt        60
tgacgttttg attgtattcc tgggcctgaa atatgataaa taaatatgac cattgaagtt       120
ggtgtttatt ctgggtttct atcattaaga gggtgtgaac ttacgaggga accaagaaag       180
ggatggaaat aggaatattt agaatagtag gaagctcaaa tgaattattt cgttcgataa       240
ggcggagtga atataaataa tatgcaagga gatgcggaga atattaccca ccttatgaga       300
gagagccaca atcagaaaaa cagtaacaaa tataacaaat caaacaacac catttgcaag       360
cgaattcaaa cgttttttcgg gtatgttgtt ccattaccac attcaaacat gaattgaaac       420
ctgagctctt gggcacttta atttttatttt caacacatta cgtttaaatt gccgagtggt       480
caatatcatg tattgcttag tactaggtgg atacaaacct tacatataag gtcaaagtat       540
tgtgggcatg atataaatgc tctagcatat tggtctcata gagtttttta tacttttaca       600
tatccattaa tgagataagt taatgtttca acattaaatt tttagttaat atgaattcta       660
gatgcatttg ttatacaaat ggtctgatgt atttgaggtt ctgaatgtca ataggattg        720 tagtttattc acgttgaata ttgtaaagag ttaggacgtt tttttaagat tagatgatgg       780
gtgccatatg ctaccccata cgccaacaat tataatgaaa attatatttt gtcatttggt       840
atttaacaat ttttttttaaa aaataagcta ataacgcata gaattcctga gatttaaaca       900
actttctgta atttcttttc tatgtactaa ttgttataga acctgtgatg tgcttgtcca       960
tcatgcagat tacaacgact ttgaacataa cttcaaaatt gttgataatg gtagccgagt      1020
ttttgcc                                                                1027

<210> SEQ ID NO 113
<211> LENGTH: 2000
<212> TYPE: DNA
<213> ORGANISM: Cucumis melo

<400> SEQUENCE: 113
agccaaagtt taatatgatt caatcttgca caaatgcagg ttacccaaat ggttaaggtt        60
aagacaggca acaccactct agcagttggt gatggtgcaa acgatgttgg aatgatccaa       120
gaagcggata tcgggatcgg tattagtggt gtagaaggga tgcaggtaaa tttaaaacag       180
atcccagctg gagtgataaa atatagcttt cattcatctc aatttgtttt tatacttctt       240
atctttctga atttcaggcg gtcatgtcaa gtgatattgc aatcgcacag ttccgatact       300
```

```
tggagcggct gctccttgtg catggacatt ggtgttacag aaggatctct tccatggtac      360
attatgatct ataaatatta ctttatatta gcttcttagt gagaatcatc cagattaatg      420
tgcaactata cagtctcaac atcattttca gcttgaaaat ctttgaaata tgtcgaactc      480
atcgcatttt atatatggca gatatgctat ttcttctaca agaacattgt ttttgggttc      540
actctattct tctttgagat gtatgcatca ttctccggcc aaactgtata caacgactgg      600
ttcctttctt tgtataacgt cttttttact tctctccctg tgattgcttt gggagtgttt      660
gaccaagacg tctcatcccg gtactgtctt aaggtaagtt caacttttcct ttatttcatt     720 ggtgcaatct tttgccttcc ttaagtacaa tatcaaatgg ctcattgccc tcaacatttt      780
tggattttca gttctcactt ttataccaag aaggtgtcca aaatgtgtta tttagttggg      840
ttcgaatttt cggatgggtg ttcaatgggc tactcagttc tgtcatcata ttcttctttt      900
gtgttggggc aatggaccat caagctttcc gcaacagcgg agaggtcgtc gggctggaaa      960
ttcttggtgc caccatgtac acttgtgttg tttgggttgt aaactgccaa atggcattgt     1020
ccatcagtta cttcacctat attcaacatc tcttcatctg gggcagcatc attctttggt     1080
atttattcct catggcatat ggagctataa acccagccat atccaccaca gcatttcagg     1140
tattcattga ggcctgcgcc ccggcaccat cattttggat cctcacacta ttggctcttg     1200
gagcttccct tcttccatac ttcgtctttt catcgatcca aatgcgattc ttcccaatgt     1260
atcatcaaat gattcaatgg ataaaagctg acggacaatc gaacgatcca gaatactgtc     1320
aggtagtgag acagaggtca ttacgtcaca caaccgtcgg ttacacagct cggttcgaag     1380
catcaaagca ttttgaagaa ttctcagaaa tcaagagtca ctaggtttga tgattagatc     1440
gtagaaagat tcaaaacatt ttttctacgt aaagtttctt ctcagtgtat atatatatat     1500
acatttatat atttatacaa catgtgtaca taagattctt gtgtagtttt gatctccttg     1560
tagcttaagt gaccattccc aattcaaatg gtcaaaaatt ttcttccttt catgaaattt     1620
ttaggaaata agccaattgt agtattcaat cgtatatttc aaatagtcat tgagaagttc     1680
taactctact atagttctca attataagta tgatggtttt gtcttattca tcttgtagta     1740
gaaacaaaag aataaattta cgaaggatga agcattgtta ttttaattat aatttgggaa     1800
atttggagcc acgaaatgaa atccaatttt gtgccaagta gatgtgcaac aatgggcaaa     1860
gaatcacttt ttcttttttca taattttccc ttccaacact caccactaat tcatcacctc     1920
aatcctcttc ttcttcttct tcttcttctt cttcttcttc actcgccttt gggttgaggt     1980
tggctctgtt acagtcatcc                                                 2000
```

<210> SEQ ID NO 114  
<211> LENGTH: 2000  
<212> TYPE: DNA  
<213> ORGANISM: Cucumis melo

<400> SEQUENCE: 114

```
aaaagagtca tagtgaaaaa agctgagatc ataatagttt caccctaaac acaacttata       60
ataacacata ctatcataat atacacacca aacacagact ctatagtctt cactctaaac      120
gcagattaca ataGtctgca ccccaaacgt agactattat aatcttctga ctattataat      180
actcttttca cttatcgccc caaacgtccc ctaagagaac aaagataggt tataaaagag      240
agatgagggt ttatattatg caacaagtat aaggttctag aacgatgtag tcttcaaagt      300
aacgaaagca ataggctaca cgagaaaaat atttttaaaa tatagtgctt tccctaaact      360
```

| | |
|---|---:|
| agatttcaat gacaaattat tataaaaaat agaatcatta atccaacatg gcttgcatgt | 420 |
| cacaccttgg ccaaaactga agacggatgt catactcgac ttcaatatat tttttttaatt | 480 |
| aattttcatg tgacaacaca taaatattta aaatttagat tgggttggat ttttttttcaa | 540 |
| gtgggtccca aaatactctt caaacccaaa ccaacccaac ttgtttaccc atctaataat | 600 |
| aacccaccag gttcaagaag acgaaccgaa ccgaaccgat ccggtctaac tttgtttcat | 660 |
| acttaagtcg aacttagcgg tacttttggt tcggtctcg gtttccccaa acagagccac | 720 |
| tcaaaattag atttagggtt ccgttcgcaa ttttcagcgc attttattt gaatcggtcg | 780 |
| tttgttgaac acgttctctc tcagctggtt tagggttcat cgttctctct tctcgcgcta | 840 |
| tatctttctc tctctcaggt tcgtttcttt ctcttaggcc attttatcag aaagatcctc | 900 |
| ttcgtttctc cgattttctt tccgtgttcg ccctcggttt ctcagcagac gtaggaagtt | 960 |
| tggtttccgt ttagtgaatc tgtttggggt attacgaatg atattttgta ctgggctttc | 1020 |
| cgcatagtct ttttctttct aggaatatat gcatctgaga atttatttgt ttggcttttc | 1080 |
| tttataaagt atgaggacat atacatctcg attgctaatc cttgattata atctttttttt | 1140 |
| ttctatgttg tttgaatctg ttttttttttt tttaatttct aggttttttg aatctaaaaa | 1200 |
| tgtatttctt ggatgaattg catactgttg aattagaagt ttattgatta gattgttgat | 1260 |
| atttgcccta agttccatgg ataggtttgc gtctttcacc ttttcgtttg cttttctttt | 1320 |
| tggctgacga catcttacat agcctctgct ctaaaaggtg ccatgatttt tttttcctggc | 1380 |
| tttatctgag tttgcgcaat ttagatttga agtgatgatt tgtctaaata taaatatcta | 1440 |
| tcggccatac tatttttttgt tattttgagt ttttcaagga tgactgctag agaatgaaaa | 1500 |
| atcttgaaaa cattgtgttt tgaagttcaa ggatcttgta gttttgttct tttctagact | 1560 |
| atctcatttg atatagccct ttaaatttaa tcaaaatttg ttaatattca aatcctcgga | 1620 |
| cattttaatt atttatctaa atagttgttt aggcattact caggttgccc actatttttaa | 1680 |
| gcttagaagc ctactctggt tgacctaaag tttgcatgct atttgcctta tttcgcacga | 1740 |
| ctctaaactg ttatagacat cttttttcag ccttcaggta aatgaacaca aaaaggagtg | 1800 |
| aaagtctgac ttctgtgtga tggtcttta atcaattata gggattaaga tggttttttt | 1860 |
| attcattgta taaatattaa attagaatga tgacaaccaa taatattaaa actgacaatg | 1920 |
| gaaggttcct tatattattt ggagtgtaca ttacaacagc ctgattcttg gcttggcagg | 1980 |
| ttcctgatca ccttgtaaac | 2000 |

<210> SEQ ID NO 115
<211> LENGTH: 2000
<212> TYPE: DNA
<213> ORGANISM: Cucumis melo

<400> SEQUENCE: 115

| | |
|---|---:|
| aatgtaaata gttataaaac ttaagataaa attggtaatt gtttaataca aatacaaatt | 60 |
| gttaaatgaa atgacacacc ttgagcaatt ttcttttcta atcttctctt atagattaat | 120 |
| tttatttaat catgaaggtt agaatttctt tagcattatt tatttattta tttattagaa | 180 |
| aaagatagtt tgtgtatatt ttatatcata aagtttcaga agaaaccata aaattaatgg | 240 |
| agaataataa aaggtgggga tctctaacat ttttgccata aacaaatcac taagttaaga | 300 |
| atatgacact aaacttcttc taatttaata ttatatacaa agattttaaa attataaagt | 360 |
| aagagccttg aattgtagct aatttaagaa tatgctctaa gttttttaaa atcacttttg | 420 |
| ccctacggtt attatttatt tttttgttga aatatgttta atccaaatca atttcaatcg | 480 |

-continued

```
aacatagtca aggatatgac tgcggattcg tatattagtt gattttgaaa cgattaaatg      540
tttgaaatat tgtagtttag gaacaattac aattataaca atcagattca aaattttagt      600
atatacagta acatttaaaa gaataataaa tatatcaaaa tctatcgaca atagacttct      660
cttcatagat aaattatcag ggtctgactt ctctcataga taaattatca gggtctatta      720
gcaatagact aaatccttga tggtttatca ttggtagacc aaaagagttt attagtgtga      780
tagactttac tacataattt gcaatttgtt taaaatgttg ttatacattt ggttgctatc      840
cttaacatta caatccataa catttgtcgt gtctttaact tgaattgatt gttatctgtg      900
ataaaaagag atgatcactt tttgtcatga gatttgaaca attgatgtta aaagtggtaa      960
ttaatgtacc attcactaac caatgtcaat atttattttg tttaataaaa agaaaaagga     1020
gattgtgaca ttagttttat actcttttct aaacataggt ttggtttgtg ttagatttgg     1080
cctacactta gctcaaatcc actctttata aaattcccct acttattaca agttatattt     1140
tcactccaat cataatcttt taaaggataa tatttgtatt agaagatacg acacatgtag     1200
aagataattc tttttttaacc aaaacaacat acaatttcga ggatatgaca aattacctttt     1260 tctattttta actatttgat cttcaagtcc catctaaaca tcaaatgaaa gttgattagg     1320
ttaaagaatt ggacaattag agaaggaatg gagaatcaaa cctctaactt ttaaggaatt     1380
aggtcattca cattttcatt gagctaagct cacattaaca agatcaatat tacttgtatg     1440
tagttaattc agatgtgaat cctttgaggtt tcaaaagtga cactttagtt cgaggtttaa     1500
aaaatattta tatatataca catgttacaa cccaaattta aggtatatat ataaatatat     1560
ataatttaat tatcttgaat tataattacc ttaaattact taaagtaaag attggtttat     1620
ttatgattaa gttatgatga atgttaagta atttgaaaat ttgaagttta gaggattgtt     1680
aattcacttc attgtgggcc tcattaattg gcccattaaa tctccatatg ggcctgtcta     1740
gggcttcatt tccccaagct tccaactgta atggcggcca cagttctctc ctccatctcc     1800
tctcttctta cctacttatt atgttaatat ctacgttttc cagattcatt ttcttttat     1860 ttgtattatt ctaaatctcc agaactgctt agctgctctg gttttttgggg attttagggg     1920 gctcgatctg gtgggtttac ggttaaattt tgcagctttt cgaggtcctt ttcggcttcc     1980
attttgtcgg aagttacaaa                                                 2000
```

<210> SEQ ID NO 116
<211> LENGTH: 2000
<212> TYPE: DNA
<213> ORGANISM: Cucumis melo

<400> SEQUENCE: 116

```
acacttgtaa tgttgagcag ggtaacttat ggtaaatttg acatgagctg gcgcacaaag       60
gcctagcatg ctcggagctg tttttccatg gagtcaatgc ttgatcgcat tattggctat      120
attctaaatg aaactaaaat tattgatggg ttccatctgt ttggatacca acttatataca      180 caggtgtttt tctatttatg agtgtaaagt ttgatttgct tcatcatcgt atattcaacg      240
tagagtttct tagttaatcc aatccatatg cctcaactat catgctcttt tccctgtaat      300
tgaatgtttt ttttggtgtc cacatggtca tggaggtttt gttctgcact agcttcacga      360
tgctactaaa catgatgatg aagcttgagt ttatttattt cttagtactt tgtgatgaaa      420
aaaaagtaga agaaaacggt agaaaattgg aatggatacg gtacaatgga tgggttgtgc      480
taagtcacgt ctcgtggata caactacaat tagttatttt gttttgtaga tttcatatta      540
```

```
gcatttccttt ctgaatagtt gaaatcacca tagaatgtgt actgatgttt tgtgatttta      600
gtgcttcggt ataatttgaa cgctttacaa gtaaaattt  cctcaggtaa acgagtcttc       660
cgaagtactt gttcataaaa tgttcttgtg tgggagagtt gattggagag gatcatggtc       720
aaattcttct tggtgtgttt tatataaggt tttaatgatt ctttgaaatt gtaatgtttc       780
cttagttttt ttaagtgata ctggtgggtt ttccttggaa taaatattaa gggctgaaac       840
ttaggaatta tatggatttg agggaggttt gtggattctc aaatcaaatc aaaccaaaac       900
cagataattt taaattctag aattttgaag ttactatttg tgtttagaaa taaaaagaaa       960
gaatatcgct tctttgtcct tccaatattc tttagaacca aaagagaacc aaaattatat      1020
ataaaagagt cgataaaatc aaatatatat ctataatata gtttattatt attttttcatt     1080 tgctatcaat aagaattttg aaatgtaata tttgctccaa attatattaa aaacagctgt      1140
tgaaatttca acaaaatgag aatttgtact ctggattttg ttattagttt ttttttcaat      1200
atcttaaact atttcttaaa tattctcatt gcgagtcctt ccatttacat agaactaaaa      1260
atggattgag tttggttaga gaataatccc aatcttactc atattttag  gttgattaga      1320 ttggtaattt gattagcggt taagttattg ggttgtattg tttcataaat tcgatagatt      1380
acatcgatgg caatgtagtg tggaacataa aaaataatga aataccagcg gaacacaatg      1440
gagactgaaa aggatagacg atcgaagatg atgaaatgag aagctgacaa caatgagggg      1500
cgtgagttga gaagccgaga caagaggggag agagtgagtc ggaaagagat gtggggcgtt      1560
acaagttgtg ttgaacaaag tgaggtcaaa tttaaattta ctatttgcta aattaataat      1620
aaaataaaat ataaatataa acatataaat atatatgaa  ttgggttggg ttgatacaaa      1680
atttctaacc ctaactcgat aaagcaaaat gcaacccaaa ttttaaatta accagatcgg      1740
gttattctta tcctaacctt aggacagtga ttacttaatc tgtacgcagg ggcaattttg      1800
accttgatta aactctccca ttttgttttc ttttttcggc aattttccct ccctctctag      1860
tctcttctgt tctcagttca gctctctagg gttttgtcga acagccattt ctaagtgtac      1920
atctcctctc aatttccctc gctttattcc attttttcac gtactatcgg cggatccttt      1980
gagctccaac tctctcatcc                                                   2000

<210> SEQ ID NO 117
<211> LENGTH: 1025
<212> TYPE: DNA
<213> ORGANISM: Cucumis melo

<400> SEQUENCE: 117 ttttcttac  ttcattatcg aacaataatt tgatttccaa gcgacccttt caaattcaaa       60
caaacccatt tctcctctca gccagagcaa gtgattgaac tgctgcgctg cgcgtgacct      120
gttatcttct ccgttttct  taccgccgcc cgcccctcac ggcggagtag tttcaccgcc      180
gacccatttc gccggccgcc ggcggtgttt cgattcctct tgttttgtcc cttttcgtct      240
taccagtttt ctctctgtct acattgtgtg ctcgttaaca gccagctgta tagccactgc      300 ttttttttatt gactcttgaa acagagagat aggggagatt ctgtatagtc ccactgtttc      360
tgctcaactt tttcggttta atgtctgttt ctatattcga ttcttcgttt tatgttcgtg       420
attcgatatt gcttttgctt ggaatcgttt agaggcaagt gattgtctct gcttttgcta       480
tgtagttact ctgtttttt  tccctttctc tctctctctc tctcccccc  tcttctcaa       540 aagggggttg gttttttat  cgtcggagga tgttgggttg atcttttgat agggtctgtt      600
gactaattta gctggtgttc ttggtctgct gaatccgaac ttctcttagt tttagagttt      660
```

| | | | | |
|---|---|---|---|---|
| tcgatgttgt | tggtttacac | tgattcttct | tcgtttgttt | gggattattt | ttgacaggac | 720 |
| tatagtgttt | aactgctagc | tgccatggaa | catgcagaat | ctgcggtgag | tttttagaat | 780 |
| aaacttgttc | ggttggtgag | aaaagcatgg | gaaagaggag | ggggaggttt | ttctttatgt | 840 |
| caaatatttt | ctcaaactca | ggttttagaa | taaaaaagcc | tttgtttctt | aaccaaatag | 900 |
| tttatttgat | aatcagctgt | tttgttttag | ctccctcatc | tcattttcgg | aaatcttagt | 960 |
| tatcagttta | atcaactctg | tgttctatga | tgctcatttg | tacttaggca | aaggttataa | 1020 |
| agaac | | | | | 1025 |

<210> SEQ ID NO 118
<211> LENGTH: 2000
<212> TYPE: DNA
<213> ORGANISM: Cucumis melo

<400> SEQUENCE: 118

| | | | | | |
|---|---|---|---|---|---|
| tgcattttat | cagagatgaa | attgaaaaag | gaagaataaa | cacgtactgt | aaaatcaaaa | 60 |
| cataagaaac | ccagctgact | tagcttgtta | attaaccaaa | caaagtttga | gcattgtcta | 120 |
| aattaaagtt | gttcaacttg | actgttgtag | ggttattaat | ttttcttgaa | aagaaaacgc | 180 |
| agcatataat | attaaaggag | tattttgtct | cgaggggggaa | gattattggt | taaaagtata | 240 |
| tatggtgtga | cataattaaa | tactttgtaa | ctaaaaaata | aaacataatg | ggaagttatc | 300 |
| tctaccaatt | ttttttgttaa | agggctgaat | atataacctc | caacattact | tagttactga | 360 |
| tatatcagtt | tctctagccg | tcaacagtac | tacatagttg | ctgatcataa | atagaagaaa | 420 |
| caagttagaa | attttgtgaa | gagaaaggcg | agattatgtg | atttttgctt | tgtataattt | 480 |
| tgaaacccct | tgatataagg | aagttccttg | ttgctgcatg | ccttcttaga | gatcagcagt | 540 |
| tactgtatgt | ctatatataa | ttctctctct | caatattttt | ttctgttctt | gagcttgatt | 600 |
| gtttactgct | tcagaaatct | tcttttacaac | tactactgta | tttggaagtt | ttagttccat | 660 |
| atatatttct | atttttttttaa | tgatttcaaa | tcttgttgtt | tcaaacagta | ctctcctaat | 720 |
| tacaaataca | ataaaattat | atctagcatt | acaattttac | aaagtccttt | tcttgtgaaa | 780 |
| aataaattac | gtgagacttt | gtaaatggta | ttttgaatgt | attaaggtac | tatatgcacc | 840 |
| ttagaattgc | tttgctttag | ctctaaccat | gggttcaaat | gtaaagttaa | aaataaaaca | 900 |
| atcaactatt | taaggtttta | cttaaaaatg | taattatttg | tcaaaataag | cataataatt | 960 |
| gagtagtaat | ttacatatat | tgcctccaca | tttgagatca | aaactagaga | tgttcatttt | 1020 |
| cttagatata | ttattaagct | aagaatgaga | gaatgggtga | ggggaaaagt | gaacggaggc | 1080 |
| aggaagacca | aatcacccat | tcctgaaaat | ggaaggatta | aaattgcaat | tttccttgca | 1140 |
| atttaatacc | aacatgattt | tgtatatata | tatttgaaga | ggggttttaa | aaaaatataa | 1200 |
| caaactgtta | aaatatttac | actatataca | acaatcgtta | agataaaaaa | actcataggt | 1260 |
| ccacaatgaa | aaatataaca | aatgtcatag | tcaaacgcg | attaatcagc | cacactcacg | 1320 |
| ttcgagtaat | cttcttctga | atgattgtgt | attacagtca | aaatacacaa | tcgtagagtt | 1380 |
| cttttctaat | gatgttgaaa | aatacttcaa | atttagggtt | tagggtttag | ggtttaatga | 1440 |
| tcgtgttaac | cgtgaaaaat | aatcgtgtta | atcaatggaa | aacgatcgtg | ttgattatga | 1500 |
| taagtgatcg | tgtagtccaa | tgtaaacgat | cgtgtttgac | tatgttaaat | gatcactatg | 1560 |
| gtaagtgatc | gtttaaatca | tataaacacg | acgatcatgt | agttcttttt | aaaagatgga | 1620 |
| aaaagaattc | aaatgcaaac | gttcgtgtta | acaatgacaa | atcattgttt | agatcatgtc | 1680 |

| | |
|---|---|
| aaaattaata tttaaacgat ctattgatat tcttaaatag gaggaagatg aagtagttct | 1740 |
| aaagaatact gtcgaaaaca ataaagatag aatatgatat ttaaattaaa aaataaatga | 1800 |
| tatcggaaga gaagatgaat aaatcagaga aacagatata aaggggaag tgactgatcc | 1860 |
| tccaaatcta aaagataaaa atattttaca tgactctgta aactttggtt tcttttgcta | 1920 |
| ggcagtaaat atttgagggt tttggtattg tatttgtggc ggaatggagt aagtgggcct | 1980 |
| ggcattgggc cgtatacgta | 2000 |

<210> SEQ ID NO 119
<211> LENGTH: 2000
<212> TYPE: DNA
<213> ORGANISM: Cucumis melo

<400> SEQUENCE: 119

| | |
|---|---|
| tcattccaga aaaggtaatc tttgattttg agaagttaat ttgaatttta ttttaaggga | 60 |
| attcaggcag caagattaat catctggctt cctggaaaaa ggtcaagttt tctcaatcag | 120 |
| aagggggct aggtttgggc agtttaaaaa ataaaaaaa taaggccctc tttctttact | 180 |
| aaataaatgg tgttggaggt ttttgaaaga agactccaca ttgtgggta agttatcaaa | 240 |
| agtatccatg gcttcaaaaa aatttaattg gcagactcta aacaaactag aaaatagcct | 300 |
| tagaagttcg tggatcatgg gaaagttgag ttggcaactt tcaaaacaga gaacgaaagg | 360 |
| agagtaactt tctggacaga ttcgtggatt agtgatctcc ctcttaaata tccatttcca | 420 |
| aatatattca gattagctca acaacccaat gattcaatta ctgcgcactg ggattatgtc | 480 |
| actaattctt ggtcattagt attttgaaga ttgctaaaag atgaagaaat tcaagatttc | 540 |
| caaaggcttt taacactcaa atcctagaaa gtaatagact tggatgatag aagagtttgg | 600 |
| tcattaaaaa cctcaggcca tttttcagtt aagtcccttt cgaagcacct ctctccttct | 660 |
| tcacctttgg aaaagatta ctttaaagca ccttggaaaa ccaggagtcc aagaagaata | 720 |
| aatgttctgg tttggattat agcagtgggt tctctaaact gttatgagac tatataaagg | 780 |
| aagcttccta atatgtgttt actaccttta gtgtgctcca tttgcttgaa aaacagtgag | 840 |
| ctcctaatac acttattcat tttttgtccc ttctcatcta cttgttggtt tagcatattt | 900 |
| tctatgctca acaacttgg gtctttgatg gttcattaaa caccaacgtt gttcctaatt | 960 |
| ttttagggg tccttattta tatatatata tataaaaaaa acttttctaa tttgggttaa | 1020 |
| tttgataaaa gcactcctag ctgagatttg gtttgaatgt aaccaatgca tcttccatga | 1080 |
| taaaagagag agagagagat tgggttgaca ttgtagacaa ttctaaaaga aacgtggtag | 1140 |
| cttggtgttc ttcaaatgca gaattcaaat gcaggatatc tacttattgg actaccttca | 1200 |
| tatgaagaga ttcaatgcag tttcccccga ctactagttt agaatttgtg tttttgtagt | 1260 |
| tttaatgggc tgtaatatgt atttctacct ttaagttttt acttttcagt cttgcttctg | 1320 |
| tctaccatag gtagtattgt tatttgggt atttacttt gtcttttcat gaccttagtc | 1380 |
| ttgttcttgt attttggata taatgagggt gctatcgggg tatcaaccta gttgagatgt | 1440 |
| tcgagtgcac ctactgatcc ccttatttgt aggcttctct attattctca atgtataact | 1500 |
| ctcttgtact ttgagtttat caataataaa gaagcttgtc tcattctaaa aaacaaaaa | 1560 |
| ggaaaaggaa gataattgct cctaatcgtt gaaattacta ctaattactc ttaattactc | 1620 |
| caaatgatcg tataacatac atttataatt tttaactttc ttttccttttt taaataccaa | 1680 |
| cattaaattt taaatacatc cattaaatttg aaattagttt tcaaattcca aatcgaaaga | 1740 |
| tttaaagtcc tttgaatcca aagggagaat gagcccatcc aagcaagttt ttgtgtcgta | 1800 |

```
gttgcatatt ttaagtcgtt tcatattagc ctcgagtttg gcttaatgac ttggtggtgt    1860
ctagtgcagg cttgtggcga ctggcgagcg tggttctaaa gataaggttt gcattcgctc    1920
cttctccctc cctttcacta cttcatatcc atttcctttc tcgatttctc gtcttccctt    1980
ctgaattccc cattccagcc                                                2000

<210> SEQ ID NO 120
<211> LENGTH: 2000
<212> TYPE: DNA
<213> ORGANISM: Cucumis melo

<400> SEQUENCE: 120
atttatttgt ttagagataa gacgcacatg agaatatgag atggattcca ctccactcac      60
actccaattt ctaccatatcc tattactgtt tactattatc attccacccc tcgaccctc     120 attcttcttc tcaccttact tttttatgat ttactactac ttcattttgg atcacaatct    180
gatcaatgct gggtgggctg ccctcggcct gtcaccaggc ccagcccact tccaaattaa    240
acctcttggc ccaccgccca ttgtccccat cccattccat ttaatattcc caaccttccc    300
tttttctttc ccaatgcgat gcttctccaa tataccttc ctgccctcca tgtttccttt     360
ttactgcttt cttatattta aacacacct tctacagtct tttggctggg aatgctgcgt      420
atgtgaatga gattcaagat ttcgttgatg ttatttgagt ctctatattc ataagttttg    480
ttcttagttt tctctagacc aactgcaaga gttagcgttc catatgctca taagtttcag    540
atttctgctg tgtggtttga agacagtcat cgatccatgg gtgaattcgg cttttattat   600
ttattattat tattatttat tgttgtctta cttttctatt tgaatcttcc tatcttttta    660
ctcattgttg gactctaata attcttgcta aacacaatct ccattttat tggacatttt    720 aaatcccatc tcaactcata attttagtta ccttccacca tcaccatatc caaatccgaa    780
ataaactcaa ataaaatcct tcacgtgcat gtgctctcca tatattttt ctacatggta     840 aaaataaaat gaaaacaatc taaatttaat aaaataacat atatggcaga ctttttatga    900
tgtagagact gggtgttgta caagaacagt gcagccaaga aaaaaaaat acttccaatg     960 aatcgtacat tttaaggatt atgaaactaa ctagttccaa ccattttttc acgaccacgt   1020
gcttgttaaa cacgcaagta gaatcaaaat gtgggcttct tcgctttata taactgtgaa    1080
tcattctcca aaagggaag gggatctcat tccctaattc aataagaaa aagaaaaatg      1140 ctagcgaact tcatccatct cattccttt acctatttca tgagatgccc attgtatata    1200 agtattttt tttttttat ttcattttac ttagttact cctcacctct aaaaaaaatt      1260
aggagagttt gctaaatcca ttctcaaact tagctttatt tttttaattt tatttaacct    1320
cgtcgtggat gttaacctca aatgtcagtt ctttttattc tatttattga tgttataatt    1380
tactttagga ttccaatttt ataaaaataa gaatacaaat aaagataaag agtgtgaaag    1440
ccagaaagaa aaaaggaaa tcgtaatatg ggtaaaattg gtacaaattg ggtcccgtta     1500
aatattaact caaaaaatgc gagaaaatgg tagaaaagga aataggggt aagagcaaag     1560 tagtggaagg agagcattga acatattctc tagttttttgc acttggatct aaacacgagg   1620
aattataggt ttattcattt actaattaca taaataggat tggattttaa aatttgaccg    1680
agtgattatg catatttgat agagttagaa aatagtggtg gggcaggtac aagttacaag    1740
taatgtataa gagatatgat gagcatatta ggaaactata gatttaaatt cgtccgtaaa    1800
taaataatta gaaatataat attcgagtgg aagggtatta gggttaggcg aaaccaattg    1860
```

```
cagttgcacc tataaaaccc cttttacgcc tccacccgct tcaacagcgg tctcggcgtc    1920
tacaactaca cactcacac tacacactac acactacaca gttgcagacc agaagcataa    1980
cgtaacgccg gtccacaaaa                                                2000

<210> SEQ ID NO 121
<211> LENGTH: 2000
<212> TYPE: DNA
<213> ORGANISM: Cucumis melo

<400> SEQUENCE: 121
tgaagagccg gaaaagcatg gcaaggtcaa ggcatttcag caagaatacg aggatgaatt      60
ctgggtttgt aagtccggtt cttcttcgga gttgtggttc gaatttcaaa cggccatgag    120
gagccctaca gcttaggaag cttcaggtct gagactctga ctccgacaga aattgctgat    180
ttttgtgtgt gttttgaata accattgtat gagtatgatt ggttgtatag gtttgaaatg    240
agggaaagtg atccatctcc ttgttgtctt tgcaggaaag gctcatattc gaccaagaac    300
gctttgtcat tgcttttcgat aatcatgaa tccacaatgg tttggcatat tagcaaacaa    360
atcttcttta ggcattgcag acagaaaatt ggagagtaag ttattataat taaggattct    420
aaatgagtaa gaataataag atcaggcaaa gattggaaga actaaagcgt ttagtatttt    480
gtgtggtaca gaagaattgt aattagatac gtagtctaga gaagcagatg gtgagatttg    540
tgaaagacaa atgttagtgg agagtgaaga gtgtttctca caaccgaca tagaaggatt    600 ctcagaaaat gagaaagatt tttattgcgc aaaatagctc ccatatcatc atatgccgtt    660
gccattccct ctggggttgc atgtaatgag taatggaaag ctgtagacag gctaacttca    720
ccctttgtct tgggtatagg gtgcattttt ggtcactcca ttttaagttt tctaataata    780
aaaggatgaa gaaagatat tgaaaaacag ctcaggtttt aaagttgtca cacttgagaa    840
taatgcattt aacagttaga atttttgcatc aacgtctttc aaatagaaaa gtaaaggaga    900
gtctagtttg agctggatag ctaaactggt ttaatcatat cttctatcaa gtggttagag    960
ttttagacct cccaacttta tatgtcgttg ccctaacaat gttgatggat gtttagtcct   1020
aagctctaac attgtccccg tatcatattt cataatagaa tgtactgagt aatggaaaac   1080
tagagaggta ggaagttgga cgaactttga atctatattg attttactat agtctttctt   1140
ccaagtctta atgagagctt tagctaaagt ttttcaaaaa ctcaaaagaa gtttttgttt   1200
tccaattctt cgatccatag attgtcaaga tggctataat atccttgaag ttaatagcct   1260
tcaaagtttc atagctttta tcctatgatc tttagaaatt caagagttat attctttaga   1320
actacagaac tttgatcttc gattcttcac ctcttccaga acctttatag tagagtttct   1380
tgaccttaca tgggcttggg attgggcctg gctacttatg gcttagaga ttgaccttgg    1440 gtttaagcac attcgtttta cttggcccaa ttttcttaaa cttctgcaaa atcctaatta   1500 actaacaccct caacaaaagt ccagtattaa atggggcata taaacaaaag ttaaacaaaa   1560
ttgtcgtaca gaatcctaat ttgctaacct cagcaaattt tatgccattc gtccttgtgt   1620
atctaattag tgttaatttg aggaaatata ataatataga cgtaggacgg atattggtat   1680
ttggtgcaac atcctccgaa ccaattcctg gaaagtaatt ggggcaacaa gataatgtta   1740
tcgtcagttt caagtgcaaa acttgccacg tggaacagcg gcaacatgat atctcaaata   1800
tggacctctc acccggtcaa gcttccacca ccaccaccac ctccgtattc taaaataaag   1860
```

| | |
|---|---|
| tcaggaacaa gaacagacac accttaacaa aaccaatatt cttcatctct atctctctct | 1920 |
| catttcagca tagaagagag ctgagtaaaa ggaaaaaact tcaatcaaat ttgacagaga | 1980 |
| agagcccaag agaaaaccaa | 2000 |

<210> SEQ ID NO 122
<211> LENGTH: 2000
<212> TYPE: DNA
<213> ORGANISM: Cucumis melo

<400> SEQUENCE: 122

| | |
|---|---|
| agatgaacca gaaagatgga aaatctactt ggggttcagc agtgagtttg gaaaagagag | 60 |
| aactatttga agaaagagca gaaccatct tgctaatact taaacaccgc ttccctggaa | 120 |
| ttccacaatc ttcactagac atcagcaaaa ttcagttcaa ccgggtaaaa gaacgctcct | 180 |
| tccttgtcta taatctcatc taaaattatc aacaatccaa acacaattta tacaaactaa | 240 |
| aatgaaagct tctcaacttt aggctacaaa aacagatgct tattataatt ctgcccaaca | 300 |
| atatcttctc ctaaataaga tgatatatgt tttttgccca tataatcaaa taggaaataa | 360 |
| caatcctgtg cccatttctt tggagtgtga gatcataaaa cactgtctaa acaacatgt | 420 |
| ccaaacatat cgtaaatacc tagtttcata gtgtgatgaa ccaccacaaa caaacttact | 480 |
| ctttggtgaa ctgcaggacg tggggcacgc cgttttagag agctactcca gaatactgga | 540 |
| aagcttagcc ttcacagtga tgtcacgaat tgaagacgta ctccacgccg ataggttaac | 600 |
| tcagaaccca tcacaaatag caacaaggag gaaaccgacg agcgaacccc caatggagaa | 660 |
| atcagaagag ttgaacaaca acggcccaga aacgccagct tcaatgacgc tgttggattt | 720 |
| catggggtgg ggacaggatc aaaacgagtt ggagatgaag aaggaatggt ttgggaattc | 780 |
| agatgattta aacgcggatt cagatctgaa acaagggaat aagccaggga atatagtgac | 840 |
| gaacaagagg gtttcatacc tggagaattt gagcgctgtg agaagtccaa cggcgcgcca | 900 |
| ttgaagaaga agaatagata gagagatgat ttggaggcaa aattccatga tttcagttat | 960 |
| atacattcct tttgtgtaaa taggaagaag aagaaggaga atgagatcaa ccccattttt | 1020 |
| ttctctcttc ttttttttaat ttggattttg gaatcacaac tctttgtgtt tgtgtaaaac | 1080 |
| caaaattgtt ctatgtatca tttgtatcaa ttaatgtagt catttttagat tcatacattc | 1140 |
| aaaaatatca actccatttt ccaactacta tcttcctcca tctcacctct aatcataatt | 1200 |
| caaagcggat acaaattcat gttagaatga aagattcgag tatagcctat tccattgatc | 1260 |
| aaatgcatgt atctatacta ttgacactt tcaactcaag tcatgcttga acaattgttt | 1320 |
| tttataaatg ttaattacaa gagtgtacac aaatcgagtt gggaaaaaat atgaaccaac | 1380 |
| ccaaaccaaa aactttgagt tggaccgaat ttgaataaat aattcaattt tcattatttt | 1440 |
| tatatagttt ttcaaccaaa ttttttatct ttttttttctc aaatttcaag tttacaataa | 1500 |
| tgtccattca aaagtttaaa ttttcatatt tcgaacattg aagttggaag gtccaaacga | 1560 |
| aagaactaaa tgattatgac acatgtctag ggtttatata tattgttgag ttgagtaatc | 1620 |
| caagttttg aaacaccact agttatttat gttaaataat taactgagta ctcgactttc | 1680 |
| ttagttcgag aatattttt agaaaaaaga agagaggat tgtttagaaa taatagcaag | 1740 |
| ttagggtgtt ggtgagtgag aaatattttg ggatcttctt gtaatagtta ttaagaagat | 1800 |
| ttttcaaaga atttgagagt taagaaaata ataataataa ataagtaaac atttaatagt | 1860 |
| aaacgacatg tcgttttata cagcatcgta tttacttacc atgtgctcat tcacacacga | 1920 |

```
ttcctcctcc tcctcctccc gttcatctct tcttatcttc gtcttcttca tttcggataa    1980
cacaaaaatc cctaaaaaaa                                                2000

<210> SEQ ID NO 123
<211> LENGTH: 2000
<212> TYPE: DNA
<213> ORGANISM: Cucumis melo

<400> SEQUENCE: 123
tcattttcgt ttggttaaag aatatatcat cgtttctttt ataaaatgtt tttgtagaat      60
taatcttcga gtacttctca taaaaacatt ttttttaatt acatagagtc agtaataatt     120
agaactatct caaaccaaag tactataaca tttcaaacca taacactgta tttttttagaa   180 aagttattgt aaaggataga attacaaaaa tattatagca tatgaaacat tattgttata    240
ttttataaat attccatata caatataatt gattctagat gtctctaaaa atagggaagc    300
atatgtgtta ataactaaat ttaaaaatta aaaaattact cgattactgt ttatttattt    360
atgtgttgag gctatacata ctatatttta gtaattattt taaaattaaa aacaaaatca    420
catggctaat agaaacgata gatatctagt agtaaaattt tgttatattt ataataagtt    480
gtcttatttt acttaatgta actacaaata tctcactgtt attttccttt ttttttcagc    540
ttattggttt atatgtttag aaaatttggt aaaatatttg tgtagctgcg gttatcatgt    600
atcaacttaa ctatgtaatc tatgaaaaaa tagtcattct ttaaaaaaaa aatgaaaagt    660
taaaaaagaa aaaaggata aatttataac aatattcttt aattgaattt tatcatttga    720
ttcaaagata ttcttatact tttaaaagct gcaatgttat ttatgaaatt gttttaaaat    780
tacatttata atgaaaaaat ctttaaaaat gtagaaaaat caaggcttag aattgtattg    840
tcatttccat caaggagagg atgtaatttt ttctttatca cttttatttga atcctcaaat    900 tttcgataag tatatatttt gacatttgag aatattttttg tttactttaa atttaaagtt    960
atttttaaaa caaatgaaac aaaatattca taacgtggat caaatcacca taatttagaa   1020
agcgttcttt tgaaacatga ccccaaaact ttagaagata aattacaatt tgaactattt   1080
tgaaaatggt agcaaggaga caggtaaaaa aagaccacat aaatcacttt aggctttaaa   1140
gaaacaatgt taattggaga aagattcatt ggcatataat tttgaaatat gattgtattt   1200
tatatttcaa atcatattcc atgaatttat ctatctttgc ttgtagtcta aatcatgcaa   1260
actttgaaaa taacaatgtt attgtatcaa aatttaaaag tttaaaacat ataattgatt   1320
aaataaagaa aaatatttag aaatgttgta tgccaatagg tattatgtaa taaattataa   1380
atgatataat attaaaaaca ataattcata ccattttttta aacataaaaa catgcttagt   1440
agattagtta taaacagttt caagtaatat ttaaaagaga gtcataagta gttttataat   1500
ttataaaata caatatcaaa cgtacttaaa actaattgct tttaacttca aatctaaatt   1560
aagaataaga aaagggagag tgggaaagag caaaatgaga gaaaatgtcg aaaatacgcc   1620
caacggttcg gaccggtcca tttttgtccc gcgcaatggt aaaaatagat taggttacga   1680
caatcaccat gatgatgagg atgatgatga tcatagcaat tcaagaagca tagggcccca   1740
cttttggccc tcttattttc tcttctctta cttactttaa agaatctaac tgtcctccat   1800
taccccgccg atcaatgctc tattttctc tctcttttt cttttcttta ttaaacaata   1860
ataacaaaaa ccatcaaatt ttcaaaattt tgaattatat tcccttaaca caaaacactc   1920
tcctcttttc ctttctctta taaatacaag tggagctcca cacacttgtc attttgtacc   1980
cttcttcccc aacctcccaa                                                2000
```

<210> SEQ ID NO 124
<211> LENGTH: 2000
<212> TYPE: DNA
<213> ORGANISM: Cucumis melo

<400> SEQUENCE: 124

| | | | | | |
|---|---|---|---|---|---|
| gggcttccat | tggcctcctt | cccgtcgccg | tagtgagaga | aaaagaaag | aaagggaga | 60 |
| ggcagaagaa | tttgagagat | ggatcgagga | gaggttttgg | aatgaatggg | aaatttgaag | 120 |
| gaagaggttt | aaacataaaa | gtgaggcacg | tgcgagaatg | caaatattta | cggggctaaa | 180 |
| aatgggagag | ccaacggatt | caccccagta | aaaaggtaaa | ttcaaacacg | tttatgcctt | 240 |
| tttacctttt | tctttctttt | tttaacacct | atagatgtaa | gatatttcat | attcttaact | 300 |
| ttctctttct | cttttctttt | ttgttttact | atttcccttt | cgttggctaa | taataaaaat | 360 |
| tgatggatac | agtatatttg | gtatgtcatc | ataaatttag | agaaggtatt | aagattttgt | 420 |
| gacataaaaa | cccaatttct | tttaatgaga | ttcttagaaa | ttttattgaa | gagaattata | 480 |
| aactttacgt | aaattaggta | aagtctttcc | ctccttctcg | atagaagttg | ataataaaca | 540 |
| tagcataacct | agataaaagt | ttgggaacat | ttttgttgtt | tggagggttg | aaaaaaatta | 600 |
| agaaatttca | atttggttag | gatttgatgt | cttgattttt | tgaaatataa | actttcaatt | 660 |
| ccaaatggtc | ggacttggaa | cctaacaaat | cgtgttttca | attttaccct | gatattttag | 720 |
| atgtgtgaga | ctccattaag | tattctcttc | gctctcttct | tactatttct | ctgttttgct | 780 |
| atcgaacgat | attttttta | aaagatttat | tttttaattg | gtggaatgtt | tgtatgagag | 840 |
| tatataagtt | aaggtaaaca | ataataatt | ggttatttag | caatcttcct | agtcaataag | 900 |
| caaaacagac | ctaacatgca | tcaaagaaac | aaaatcaaaa | ccttaaaata | tcatggttgg | 960 |
| gcgttgattt | ttttttttctt | ttaatgtttg | aaaatgtggg | ctttgggtgc | cgcagtcgta | 1020 |
| tggttgtagg | gatttctttt | aagaaaatta | ttttatattg | tattcgtttt | gatctgaaga | 1080 |
| tatcaattat | acaataattg | gaatataagg | agtaatttaa | ctttgttcgt | gattgttttc | 1140 |
| tactttattc | gatgtgtatt | ttggaattaa | atatgatttc | aaatgatttt | gtttatttct | 1200 |
| ttttattgat | tttgttttga | ttttactttg | tatcaatttt | gaatatcaat | gtagtgatgt | 1260 |
| gcttgtatta | aatgtattgg | ttgataaatt | tactatgcaa | attttttttc | aaaatttatg | 1320 |
| caattcattg | tagtattatt | aactatatca | acacatcagt | aaagtgaatc | attatcaagt | 1380 |
| atatcaatta | agttacaaag | tgtatatatc | aataatgtat | caagtttatc | agtagcactt | 1440 |
| taagcatata | aagtgtattt | aatcaattaa | ctgtaccagt | gaatcttact | agatgtatttt | 1500 |
| gcagtacatc | cgacgtatca | aacatatcat | gtgtatcata | tgtttaaatt | tgttgagtat | 1560 |
| attagtgaaa | cataacaagt | ttattagtag | tgcatcaagt | atatcaaatt | tatcagttaa | 1620 |
| acatttaagt | ctactaagaa | aaatgagtg | caataaaaat | tattttcgg | atatataaaa | 1680 |
| aaatattgag | tgtatcgaag | agttccatgg | tgcatcaaat | atataaagat | aaaaaaatat | 1740 |
| caagaaatat | taaatgtata | tccatatatc | aagaaacaaa | cctaacatgt | atttcgtgat | 1800 |
| ccaacaaccg | gactggaaga | caaatttcgg | cccgggactt | tcatagtcca | aataaaggcc | 1860 |
| cattaaactt | aacctgggcc | caaattaatt | tgtaaatttt | aagtataaaa | agaagagaaa | 1920 |
| ccctagggtt | tccttcattc | accaggcctt | cctatcccct | tcccttcccc | cctcccat | 1980 |
| tcccatttt | gccggccgcc | | | | | 2000 |

<210> SEQ ID NO 125

<211> LENGTH: 2000
<212> TYPE: DNA
<213> ORGANISM: Cucumis melo

<400> SEQUENCE: 125

| | | | | | |
|---|---|---|---|---|---:|
| ggacttatgg | ggaatggggtt | caagtgatgg | taactagcta | cttcagattt | aatatcctaa | 60 |
| attgccttgg | caacccaatt | caaatgtatt | aggattagat | aggtgttttg | tgaggatagt | 120 |
| taataaggtg | cttgcaagtt | ggtgtcgaca | ttcccaaatg | tgaagggaaa | aaaacccccaa | 180 |
| tctttggtct | caactggact | ttggttcatt | gcagttgaaa | ataaattatt | ttagttcaaa | 240 |
| ccaataaaac | acatttttta | aaatctttgg | atatttgttt | cttaaagttc | ctgaaacagc | 300 |
| ccaccaagtc | catagcaatt | aggaaggcat | aagttagagc | tagtatgctt | ggcatggttg | 360 |
| ggggtgggtt | accttgttat | gtaaattcat | agaaatattc | atatcttgtg | ctaaaagtca | 420 |
| aatgaaaga | gggtgattgc | tgtgatgctg | tctaatacaa | agtgctagaa | gccatatgga | 480 |
| gaaagggtat | ttctacagtg | tctaataagt | taattacata | ataaatttct | aggttatgag | 540 |
| aatccaatcc | gcatgaattt | aaggactgca | cacttgctcc | atttgcaaca | tgtgtaccac | 600 |
| tttagaatca | tatttcacct | gagttcatta | ttcaactaga | ttaatgtatc | tcttttggtg | 660 |
| ttacatgttt | ttaagaacat | aattatttta | gtttactgtc | ggagagaagc | aagtactggt | 720 |
| tatgcatggt | tctagtgagc | ctaatagagt | aaggctatgg | tttgggcatt | tggaagtttt | 780 |
| agtggattag | aattttgaag | gcaaagctaa | ggatcataca | cgcccttctt | cccttttgac | 840 |
| cagttggaga | tctatcatgt | aactctattg | tcttgggctt | cggccttatt | ttataaattt | 900 |
| catatatcaa | tgaaatttat | ttcctataaa | aaaagaaaa | aagaaaaaaa | gctaaggatt | 960 |
| ttaatatcat | tgttagtttc | tttaattttt | tctttggga | agtgtgcatg | tagagctcct | 1020 |
| ttgaaagaga | aaaagcaaag | aactcttgaa | tgtaaaatct | ctatgtttga | gttttatagt | 1080 |
| agcgtaccac | attcacttca | tggtgatgta | gttatagttt | tcctatggaa | tatggctatt | 1140 |
| aattttgcg | aggctcttat | tttatagttc | ttttggggtg | ttctttcctg | tacccccctcc | 1200 |
| ccttttgtg | agaaggggag | gtttctgtgg | ctagctgggt | tggtttagat | ttgtggacct | 1260 |
| ttttgtgag | aggaaccata | gaaccttttg | atgaggacct | cgagcactat | ttgatcattt | 1320 |
| ataagtttcc | ataggctttt | gtaattacct | ttttggtctt | attttaattg | gagtcccctt | 1380 |
| cctccccttt | tgttggcttt | tttgttgtat | ggttgggcat | tctttcgtta | gggaagtttg | 1440 |
| ataattcaca | taataaacat | acaataaaca | accatcaata | caatcaacaa | gcaggattag | 1500 |
| tgtaatactg | taaatgtctt | ttattttctt | tactccttttt | ttcttttgag | gtctatgata | 1560 |
| attgatatcc | aacagtgtat | tggccaaaat | gatttatcat | ggtcagtacc | ttaggggttt | 1620 |
| gacttccaat | ccaggattta | aggtttgaga | ccagatattc | tgtgcctcaa | ggccctcaac | 1680 |
| aaccttctca | tggcttttc | ctgtatacat | attattatat | aaagttataa | ccaataaaag | 1740 |
| ggacaggtca | aatcctctta | atatatgcga | aaatcaacct | aatgtctact | gtataccttc | 1800 |
| tcaatcgcca | ccttcctcct | gctgtcatcc | aaggtagggc | cttattgtat | cagctagctc | 1860 |
| cctttactta | tttatttatt | ttttgaagtg | cgcagtttgt | ttgttacct | tgttataggaa | 1920 |
| aattcaatct | attctcattt | tattggtgca | ttcgtctcag | aaattcttgt | acggtttcag | 1980 |
| gttatcatct | acccttgtag | | | | | 2000 |

<210> SEQ ID NO 126
<211> LENGTH: 1397
<212> TYPE: DNA
<213> ORGANISM: Cucumis melo

<400> SEQUENCE: 126

```
tatatatatt aactttttaaa attttgaaaa cgtcatagat aaattatata caaaataaaa      60
agtttgatta tttacgaaag ttaaaaagtt tatccgaaag ttgactcaac gataaaaaca     120
ctaaatatca cttttagaga tgatgatatt atacataaac atacgaactt acgcgtcaaa     180
cttttatact aacacaagat caaaacaact tgttgagta gtgagaattt tatctgctga      240
tatggttgaa acttgggaag caagcagagg aagttccatt cattaccaaa atccattttg     300
tattcatcaa aatatgaagt ttagcgactt gataaagtca agtcaagtgg tcctatcgat     360
ttgttaatgt caatgtttgg ttttgaattt gatacctatt agacaatgat atataatttt     420
aagtatggtt tacactgtga tgctttatat atttttaaat gtaaaatatt agaacttgta     480
atttcaataa atttttaaaaa tgattttgtg ttatttcctt ttttaaattg aaatatcaat    540
gtatcaatat tgcgtcatag agtattgcaa cacaaccta tgttaaattg tttattgctt      600
attgctctaa ttcaactcct tcatcaaatg tgcacagaat ttaaacaaga aaagagtag     660
gtgcttttt actaaaatat actaaaagct ttttataccaa atcttatga caaaatcatt      720
ccaacaaaat gactatttaa atataagatc gaatccctaa tttaaaaaaa aaaaatcaaa     780
gatgttaatt tctattatta aactcacttt agcgtagcta acaaaaaaag gaaaaatgag     840
aggctacaaa gcttgagccc tctgcctccc tttattgcat tgtttgaaat tagatcaata     900
ctttgtatt ttttcaaaat gaaaaatcgt acatagaatt aattctatgg acaaaaaatc     960
agagaaggaa ataatctaga ataaaattcg attttttaacc caaaaaaaaa aaaaaaactc    1020
gattctgatt tttgtaagca atcacccaaa ttaccataaa taaatggtat tcaattactc    1080
aattatggat attttagaaa tgataaattt ttattcataa actctttct ttctctttca     1140
aaaagaaaaa aattagcata aacttcaatg acatttattt attcttcttc gtttggagtc    1200
aaaagtttaa attgagcatc agtccagccc aaaagcccac gaagaagccc aagaatcttc    1260
agcttttcg ttcaaacgtc ccttttttggt ttataaaatt aaagaaaata aaaactaaat    1320
ttatttgtta tttaacaaaa cattttttggt taagacattc tctttgatta ttttttcttcc   1380
attcttcgtc gtcaatc                                                    1397
```

<210> SEQ ID NO 127
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, c or t.
<220> FEATURE:
<221> NAME/KEY: unsure
<222> LOCATION: (1)..(2000)
<223> OTHER INFORMATION: unsure at all n locations

<400> SEQUENCE: 127

```
tttatattta tgaaaatgaa gtctctaaac aattttttcta ctcccaaatt tgttgatttt     60
tctgcctatt ctttatcggt gctttaaaaa atgaaaccaa atttcaaaac taaaaaaacc    120
aagcttttaa aaaaatgtta ggttattttt gaaattcaac taaatgttga actcttttac    180
ttattaaata ggcaaattat tgaaataaat ttagagcaag taagcttaat ttttaaaact    240
aatatactta ccaaatcgag gactaaaata ttcaaatact ctttaaaatt aagattaaca    300
ttaatcactt tgttatgttt aaaaagttgc agtgtcactt gaaccttttt aaattaatat    360
```

```
aatgaaaatg aatccaactc aatatatata atatctatat tattaatctc gatgtcagat    420
gtttgatacg cacatatctc aaaaattata cctcaactaa catcggtgca cgatgtatta    480
tttcgtgagg ataaaaatcg ttttagtat aaattgatgg aaagattatt tgaattactg    540
aaaaatgcac cggtacatta tttgaaactt ccccttcatt taaagaggct aatattagaa    600
aaagacacgc tgaggctatt tttacaatta atgtgggctg ttgacttggc ccagcccaaa    660
acataaaccc taaagtagca caaacaaacg cctctttctt cttgaaaccg catattaagc    720
gttttatcac ttctcaccac ctctcattcc tcctcttccg cacgttgttt cgctcctcaa    780
cgggagtgcc ttcccttttgc tctccctcca ggttcttctt ccttctcatc tcatttccaa    840
gtaatttcat tccgtttctt ttctcttaat cgtatcttgt tcagactctt tcgcgttttt    900
ttttagttgc gccttaccag atctgtgttt tcactcgttt ctattcgata catgcttcca    960
agatccattt cttaatcgca tgtattcggt tgattggatg attgtctttt tgtaagtttt   1020
gattactttt ttggaatgga tcggttgaac caacggggtt taagtcgatg gaagtaggtt   1080
atgttaaaga tttgcttctt ttttttatg aagatgtgtg tgttcttttt ctttgctaga   1140
tgatgttatt atttgattgt tttaacagtc gtgttttgtt tttctgcagt ttatagtcct   1200
cggtcttttg aagacttgtc aagatggtta gtacacctct tgtcatcgtg attttgattg   1260
agtgatgtgt taagtgcttc tttaggttac agctaacgcg attttttata ttcaattgtg   1320
cctgtgcagg tgaagtttac agcagaagag ctccgtcgga ttatggacta taagcataac   1380
attcgtaata tgtctgttat tgctcacgtc gatcatggta agctacttag tttaagttta   1440
tttatgccga gcgtctattt aagaagatta acatcttagc tttcatttat tgtttatttg   1500
gtaagcatcg tttctttttc tccgaggaac tgtacatgtc agttcacatg acaataaaac   1560
gatcttcctt ggacattagt ttttgaagtt caattgacg ccaaattttg ttggttaaaa   1620
gatgcttgtg gagcatatgg acctaatgga atcagtactt tttgatggat ggacttgtct   1680
tttgttcttt tattttcaaa agaaattgca tgtgcaatta catcatcttt gatcgaaaga   1740
ttgggtaatt gggtaattgg ggtaaagaca tgttgtaaaa actaatgtta attatcaatt   1800
accattatat accttattta gtgcttattt atatccttttt tccccatttc agggaagtcc   1860
actctcacag attctcttgt ggctgctgcc ggtatcattg cacaagaagt tgcnnngatg   1920
tacgaatgac agatactcgt caagatgagg cagagcgtgg tatcaccatt aaatctactg   1980
gaatctccct ctactatgag                                               2000

<210> SEQ ID NO 128
<211> LENGTH: 1657
<212> TYPE: DNA
<213> ORGANISM: Cucumis melo

<400> SEQUENCE: 128
ggcaaaatgg agagaaaaaa gtttctccct attgccacat ttatatatag tatatagata     60
tatactatag acatgatgga gaatcataag ataaggtaag gctgaggaag attttgacga    120
tatagaatgg aaaattttga agatataaaa tggaagattt tgaaaatata gaataagatc    180
atcaaatgat agcaaaaaaa tccaaatgag tcagatgaaa cactacgcca aatttttcatc   240 actccaaaat tgttgcaaag gagattgatt aatagggtat tatacacaat catattttc    300 gtagcatgat aattggttaa taattagaca taatggcaat caattagtta actaatacaa    360
cattttaggt agcaatatta aaattggaga tccggaaaaa aactaaaaac tcagaaaaat    420
cttgggcaaa atgagcacgg tttatcaaat ttttaggctt ttttggtaca attttgtcta    480
```

```
ggatgaaacg agatccataa ttttctttga gaagataaaa aaaattaaga tttggtgtaa        540
gatttgggaa gatttgaata attttttttaa aagaaaaaat aagatttgga aaatggtaga      600
ataacggtct aatgtctccc aagatgcacc gggaaagcaa aaaacaacca aaacaataaa       660
taaattggaa aattttaata ttttaggaaa atctcgatgt caatttcgtc taagattgga       720
tcgagaaaaa cagttttacg agtttttaaa aaatgtgtta tatttaaaaa taaaatcaaa       780
attgtgctac ttttgtcaat ttcccaagat aaaaatgtat gcttccacgt aaaaagtaac       840
attactaccc ttctttcatt taatctctat atttggaaat gtcgcactag ttcttggtag       900
ctaatatttg gatactaatt atcttatatg acaaaatatt taatgtactt ttttttttaca      960
acaaatattg aatgaactta aataatcttt tcactgcaat gaaaaaagat aaattagagc      1020
atcccaaaaa gatgaaaagt tcgaaagtct gctaactaca ttgaaaaaca aagcatttaa      1080
ttcttcaaac ttgatagttc aattaaattt ctaccaacta actcaagtaa atctattatt     1140
agtgtttgag tgaggctatg aactctaaga ctaagcctat aagtttggtt aaatttaatt   1200
ataccagccc ttttgtaagt aatttgattt gaaggtaag  acgtaatacc gattacccaa     1260
cccaaaatta ctgtgaatga gttaaaaaat aaaattagtt gaattttaaa taaaaagcat      1320
accaataaga cgatgacaca tgtacaaaat cttagaagga gaagcttcat ttgaggacaa      1380
aaaagagtgt gtggagtgag aagaaagaat agtcacgaat attgctgact gtgcaacaaa     1440
tgtacatttg gcaccaatca aaacctataa aaccttatcc aaaaatcaat aatctcatcc     1500
cttcttcgct gttcttcccc aatccaaacc ccaaccattc tcctccacac acacacacac    1560
tcacatacac aaatccttcc aacattattc tatacccact tcccaattct cattgcattt     1620
cacaatcatt gttctaactc acttacaacc tccatca                              1657
```

<210> SEQ ID NO 129
<211> LENGTH: 2000
<212> TYPE: DNA
<213> ORGANISM: Cucumis melo

<400> SEQUENCE: 129

```
atgaacgaag gagaatatcg gataatgaag aggagatcca tgaatcacag agaatgaatg         60
aaggagaccc acgtgaatta aatagaacga aggagaatga agagaaagga tgaatacttc       120
ttttcttttaa ttttaaccta atcgggtgaa tcaaactcaa atcgaaactg gtttagttcg      180
attatgtttg gtaccattgt cttttaaacc gatcaaacct gaaccaaacg aatcggtacg       240
gtttttttgca cccctaattt atatcatgtg aaaggtttta agttaagggt cagctagtgt       300
cgtttagagg gaatgatatt ggttgacttc atgtcgtctc ttggatcaag agtaggagat       360
tcgggagggg tgtgacgaaa tcaaccccga gattgtccta cagatggcat gtaaaatgca     420
tcatatctcg ggactccttc tacaaactcg agaaaaatgt ctcttgagat tcttcttcta      480
cacagcccca aattgatgaa atgactgaga ttctttgaaa gacaccacat gcattaactg      540
aaactaatgt tgtacatcta aaaaactaca tcacgccacc aactaaaaag ttttccattt       600
gcctgatttc aaactaaaaa caaaagactt aaacgataaa ctaaaaacta aaccacaaac      660
aatgaaatcg ttaaaagtgc accttgagag atttaagaga gtaaatgagt tcacatagtt      720
ttttgaagga aaaatcacta aaacaagttg gattgtagga gcgaaattgt tcactcctta      780
accgaaatta gcaaaatgtt tggagtttag cgttttttaga gaatatgtaa cgttatgaat      840
aataagggta ttttggtaat ttgatatatc cctttatttt caattttta ataaaaaaca      900
```

```
cacatcttgg tgacacactc gactgaaaag gaccaagata tttccttgaa agattttttt    960
ttttaaattg ggaaagaatc ttggggtcga tctcgatcga gattgatcga gaaaaataga   1020
attacgagtt ttctaaaact gtgcttttga aatatcacac caaaaaagcg ttatttctca   1080
aaatttccca agtttatatg tgggggttat tgcgagttag cttttgatgg gtttgctttt   1140
gggtgtttgt ataggtttt gaaatgtacc tttaatgtcg attttgaag aaaggtacct   1200
ttattgttta aaattgacat tgtaccttca tatttgattt cagtttaaaa ttgatattaa   1260
ttatccgcat tttaaaaacc aacatcaaac atccatgttc atttctttc aaatttaagc   1320
ttgaggatga cttcgtgaaa cttttgagc aaacacgttt atcggttgtt caaagtaaat   1380
caccttcaca aatttaagct tgaggacgac tttgtgaaat tcggcaagc aaaaatcaga   1440
caaatctctt caatctttt tgagcaaaca cactttatct ctgctgaaat gagcacaagg   1500
tttagggttt tgagaatatc tagcatttag gctttcaatg gtattttggt catttgagaa   1560
taccattat tttgaaattt taaaacaaaa acctaccatc ttggtgacga tcatttaggc   1620
cgagatgtat tgaaaaatta tgttaaaatg agtttttcaa atttgattag aacctcgtgt   1680
tgaggtcgac cgaaattgac cgagaaaaat aaatttacga attttttttc aaaatgtgct   1740
acttttaaaa tataaaacta aatgggttac ttctcaaaag ctaaccgaaa ctattagtta   1800
tattgcggaa atatcaattt cgcccaattt tagtcatcca gagcctgact catcgaattt   1860
aggagattct agacgttgca ttcaggagat ttttatccgt tgtcgccgac tctctttact   1920
gatctacatt gtacttcatt gctgaactca acgagtcaac tcaatcgttt ctagatttgg   1980
aagaatctgc ttcagcgacg                                               2000

<210> SEQ ID NO 130
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 130
aaaaggcgaa aaaaagtta gcttcccgag aaggagaaga cgaggaagag tttgacttcc    60
cggggagata aagtttgtgt ctcgagggaa tctctaatct ggagttgacc gtcgacttat   120
gtgtcgagcc tggatttagt tgcatggtgc gacaaagcga taaggcggca tatgtaaagt   180
agtaattcaa aactagcggt taagaaaata atcagccaaa aaatttagta caaatacggg   240
tggaggccct aagtgaagtg ctgctattca gaggttttgg caaagagtg caaagagttg   300
agttgtgcag agaaagtact aggtgaggag aggcgtttgg aaaagaaaag gatcaaacat   360
ttgcatgagt gatattctta aactaaacac tcttgtgtga gtgacttgcc taagctaaac   420
actcttgcat gagtaacttt cttaaactaa acgttttgta atgttttctt aatggattct   480
tttcgagtct gagttatgct taacacgttt tgtttctctc gtgttattgt tgttgttgtt   540
tgaaaagaga aaactattgt tttctatgtg ctgattgtga tgaatgtgtg cgaaccatta   600
gccttaatcc tatcaagtga atagtgatta tgtggtgtgt gcacataatg taaatgacat   660
tgtgtggatg gccagtgcaa caagaaatga atcagaaagc ttcccaaata ctgtgaatgg   720
agtgaacatc acactagctc aatggcaaga tattggcgat agtgaatcac aataggcttg   780
```

```
acaaggggaa ggattcatgt tcttggttga aaggaataag agaggctaat gtgagatttc      840
tgtgatttgc aaaatgaggc gttggaagac acgtttgaga aatgaaaacg aattagtgct      900
tgacttgtat tcctaaaaaa gttgtccaat atcttcaatc actaaatatt tgatgtgcct      960
aagttttcct tccttagttg ttgaggcgtt gaggccgagt aaggaaagat aagataatta     1020
tgacgttgaa aagctggtca agttatccat ctttggatgg tttaaagtta ttacatgtag     1080 ggaggggttgc attccaattt tgtgtgtgag atgagtctta ttttcgagat gggttgctag     1140
gcgatcaagg agaagtataa gaaatgagtt cttatactct tgaacaactt gacacgaaga     1200
ataacatcct agtggatgaa ggaaggtgat ggaacttaaa gtttaggttt tattttnnnn     1260
nnnnnnnnnn nnnnnaaatg taattgtaaa gtattagatc aagtaataaa acagagttgt     1320
gttttctatt tttgctgtgt tgggttgtgt atctttattg tgcttatggc ctagttgcta     1380
aagagttaag gttattacct aaatgtttta cggtgtgttg agttgtaaag atctcctgag     1440
ttaaagttgg aattttgtat tggagattgt tttgagaagt ttagcttact aattgtttaa     1500
ctcattaggt gtctaagcga cacgcctcct tttggtcgca tgaagtggct agcagggtgg     1560
ggcggaccgg ggtggggtgt gataataaac ctaaaaaatc acccagataa gcctaaatta     1620
tacgttgaag ttaaacttac aatttgatta gaagaagaag gaatatctga tttggacatg     1680
aattaattac aaatacggcg ccaatcatac aaagcacatg taagatcaac gcattctaca     1740
ctcaatctca gccgttgatt gctttcaatc cttcaaaaag aaaaaagaa gggcagttcg      1800 ggcagagtca tacctacccg ttgactataa aagcaactac aaatcgaaaa cctccatttc     1860
tccgttacca ttacagagaa aatcaaagaa atttggcgtt gagagattgg gagagaggtt     1920 tctcttttcta gggttgcttc ttcttcttca tcctccattg ttgcaaattt cacttccttc     1980
tcctcttgtt ctcatctccc                                                  2000

<210> SEQ ID NO 131
<211> LENGTH: 2000
<212> TYPE: DNA
<213> ORGANISM: Cucumis melo

<400> SEQUENCE: 131
atagagtaac caatatgccc ttttcagcag ccaaagtttt ctatgggcag acttaatcaa       60
ttaaggttcc tattgaggcc ccactcttag tgaaaagcct agacccttct ttccaacatg      120
tctcaattgg tcacctccat caaaagcttc tatcatttaa tctaaaagca tactcttttt      180 tccttttttaa atttcattttt gatggtctat atttgaaaat aataatcact acaacgacga     240
cacgttgttt tcaaactatt attttgtatg aattaataat ttttttaata gtatagttgt      300
tttacttatg gaatctatac gtttaatcga ttcggtcaca tctatttact ttgatgtttt      360
tgttatttta tttagacgtg gttgtaaaga gtttaaagca atggagaaga aattgatgct      420
ttccaaagca atcaaatttt atatataccct tcaaatgaga ctaacattag acaatacata     480
aactataata aacatttgga agtacatag atcaaaatga accaaagtcg aaaaagtaca     540
attatcaaat tagtttttaa accttggata aacttcagca ttcaaacttt gtatttcttt     600 ttttttttcga tcgatatata tagtgataga agatttttt tttctgttta ttattttga     660 cgatacgttg agtagaagaa tcgaacatca aaccctttaaa tcaataatat atattttacg     720
actcaatatc tagccatcaa tattttaaaa tagcaattat tattcactaa attatgttag     780
agattggatg tcatacaaca attgttaaag attatttgtc tagtttgttc aattaatcaa     840
```

```
gagagcatta agcattaaag tcaattattg tgataagatg cttttgcact atgtaactaa      900
aaatagttgg atacaccatt taaggcccta catgcaaacc atgataggcc cacaaaaaaa      960
aatctctttt tggaaacaat ggtcaaataa tttctttcaa ataataataa taattacaac     1020
aaataaatac ataaaccaaa ttactaaact aatgtatcaa gttctagaga aaacaaaatt     1080
atgccctttc aagttgcaac atcccctact ataattttc ttcaaatttt ccatttaata      1140
taatccaatt ctaaacatgg aaaagaaatg taacaatatt tacattattt caatctttcc     1200
tatattcatc gactaatttt aataagacgt gaaatcaaca ttttctaaa ctcgttgatg      1260 tcataaaaaa taaacttaaa ttatgtacaa gatcgtctat taaattatgt ataacacgtg     1320
tggtgtatga gtaatagaaa ctttaaactc ttgatcaagg acatgtacct ataaataaat     1380
agatttcttt aagtcttgac tattaaccaa cttgtattca gtaaggttaa agtgatctat     1440
tatcatacta aatacacaag tttatttcga gtatgaatgc aaagaatcaa agatatatgg     1500
tttaaacaaa atctattata ccaataaaaa aggttaacca tatgcaataa aaactaaaaa     1560
gtctattgct caaatctctt tcgagaccat attaaaaatg ttagtttaat tgacgtatgt     1620
atttattgga tttatctaat aacattttaa gagattgttg caaatatagc tattagattc     1680
aaaataatta agtatatagc aaagtctgtc aaattctatc gatgatagga ctatgttaaa     1740
attgttgttc gatcgttggt aaactataaa aatctacgac aataaactac tattcaaaaa     1800
ttttttacta cccaaatttt aaatccatct catggatcga gtcaagccca cttctaaatt     1860
gggccacgaa tattgattgt gaagctcaat aatcccatac gtatggctga aaacgcatta     1920
cgaacgaacg cccttcaact atccaaatcc gaacccaccc aaattccggt taggcttctt     1980
ctccgagatc gacgaccgcg                                                 2000
```

<210> SEQ ID NO 132
<211> LENGTH: 2000
<212> TYPE: DNA
<213> ORGANISM: Cucumis melo

<400> SEQUENCE: 132

```
tgcagctgca caaagattc caaatgatat aacataatag tttatgaaaa tttaatgcat       60
ttaatttccc cttccacaga agacactata tttttcaact acccaacaat accaataatt      120
atcattatta ttatacctct aattagtaat tagtcacaac ataaacagct attctcatta     180
atacatataa tcaacaactt cataaattct taaatttgta tgtgtacttg atgggtgtag     240
atttaagaag tccaagagtt tgacacccct tgttaaaatg atatacaaat tcctgcaaat     300
taaatttacc attggtatga ttgttgttgg agtggtcaca acactaattt actaattagc     360
ttcgtattta acatagttgg ccatgcgagg aggtagcttt tgaacttcca ataacctggc     420
ttggaaggac gtcgataaac agaataacaa ctatgctaaa ttttgaataa tatactttat     480
atatattata taaagacgac aaagttgagg agcatccgtc ccctacattt gttggtgctc     540
atatcatcct attgcatatg ccttttacca atgaaaccct atctccttaa ttatttctac     600
tccacactca taattatcat tcatttattt tcatgcatga ctttctttta ccaaatttag     660
tttccaatta aactccatta actaccaaca atcaactcca ataacgtaac tcacattcat     720
tctaaccaat tgtttggatt gactcgagaa aaaaaatgt ttttctaac tcatttttac       780 ttatacattt aaaaattctt ttggaagtga tcgtcaaaca ttttgatatt tttttccttt     840
taaaatgact tattttttaa aaaacttaaa tattcaaaaa ggtttccaa atgaatgtaa     900 ttaattactc aacatagatc tccattaatc attattatat gtaacaatag taattcaaag    960
```

```
taaaaaaaaa attatgtgga gtgcaaagat gaaaattttg acctatttta catgatttga    1020
actatatgtt tatgcgtacc tatgatttaa ctcttatata cacatatttt tgtctcaatt    1080
taatttaatt ttacgatttt cttgaataat tttattctct aaccactttt gaaaaacatt    1140
ttttaaactt tagaaaagaa tatctttacc aaacttaatt caatatatga aaatagctaa    1200
ataaaattta aaaaacagat aaccaccctt tgataactgt agctgatatt attaattaat    1260
tgtcatattt atatttgcaa tatgaaaaag gagatgtcat gagttttttt tttttaatc     1320 aatctaatgc aattttctta aatttaatta atgtgaaggt gagagagaga ggcaatttca    1380
aattttaggt aagtattatg aataaggtta cttaacatta ttttaattta attttacatt    1440
atgttttatt tgaattttt taaagactct cattttcca ttttggaact tttggaaaag      1500
aaaattttac ttcaatctct tatgcaagca agttaaaact acatttgtct tttcatggga    1560
tttttaagga gatgtgtggg gaaatacaat aagccttttt ttatttgcaa tttgctaaat    1620
gtgtattctt ccaattggct aattattaaa gtgaaattta gattgaaaaa agagataaaa    1680
ttgaattgaa gttgtataga tgggttagga atatgaaaat tgtttgagat atagtgagta    1740
ttggttttat ccaatgccat gtcataggg tggaatccaa atgaaccaat gagaatcact     1800
caaaagaaaa cagatataat gcactatcca aacctaaaac taaaagccac acattgctca    1860
tccattcact cccattctca aaaccacaca aaaataaata tcaaatcaat ctctttccct    1920
tttccatata taccactttc ccctctcttc gcctctttga ttattaccca ccaaatattc    1980
ccatatatct tacaacaacc                                                2000

<210> SEQ ID NO 133
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 133
aagcttgttt gaccctattt ttaatgtctt aacacaggat tatgaacaaa agaagaaact      60
agtgaatcac agaggaactc acgcaaagac taggtgagaa gatcatatca aaatgagaga    120
ataagttcgc tagaagataa aagtggtagt tgaagttgat gtgacttgac caagaggcag    180
cttctggtgt tgatatattc agaagactag atttcctgcc taaatctacc tatataaaga    240
actccatctc cattaagaaa atgaggcctg aatggaccac ccaagtggtc gactgtgtga    300
agagccaaat gtttgtgaac tgcccatgag tgcctgaaag gcccgatcct agagagtggt    360
gggaaggagc agccttttcca ccatctgtaa agtcttctt catcttctcc agttagttta    420
agagtgaaag tttgaggttg agtgaagaag attccattcc tatcttttc taactggtaa     480 tgtcatttct attctttcca ttttgtata tttctttgta atgtatttnn ncatattgta     540
cagtggccta agacctatat tctttaatac atttcatgtt tatatctttt caatctatca    600
cgtttgttat tattcatctg tccttgtgct attggtagct taagatttat gataagttct    660
tgataagaag gttagcttat atttcttatg tgtgttagt gtgagctatt ttcatcacct      720
ggctagtgta tattgcaaac tacctgagag ggtaagtagc aaagatatgg cttaggcgca    780
```

```
caaggaggag tttggagaca aaatccacat tggcaagata acttccatca tttgtgtctc    840
aaaaggagaa caagtgtggg tattaagcat tgagatgttg tgacccttaa acgagaagct    900
atataagtct tagtgaaggt cgtttggatc tcgagaggtg agcaagtgtg gtgtttaaag    960
acaccgagag gtgctcgtct taatcataag ctcgttaact aagttatatt gcattaggga   1020
tattttattg cttaatttct tggtaatgca cgaacttttt ttcacccatt cttttatgcc   1080
agctagttca caattccatc tcgcatccat tttaatcccc ctttacagat tctccggtgt   1140
agataagtag atatagttta aacttacatg ctttcacact atatatttta ttcttttata   1200
ctacctaaat gcctagtgaa gcctagaact aagctttgat atcgattccc tgcattcgac   1260
tctaaatcgc ccatataaac ctattgtttc gcttacactt gggcaagcaa taggaaaact   1320
tgtactcaac gaggacttat gagttacatg atgacgagat acatagagag catctaatat   1380
gcattgacca tgatcattga ctcttcatgt agatttaaat acctttcagc ttaattagat   1440
agaagatata taataaagcc attccattag tttaaaagaa ttaagttaga ggtagttgaa   1500
atgctttata agtgggggtt aattctattt tagctgtaat gctgagctga tctcaagcca   1560
aggttgcctt gagatatccc cgagtttaaa aacagaagct aaaatggaaa ctaaaaacta   1620
agacatataa acttttttagt tacttttagg gaaatatctt agctataaat taagaatat    1680
gaccaacatg gaagttcctc catcacttttt ccaccaactc attttattgg gggttagtca   1740
ttttaaggcc aattagttta aattaaagtt caatctcagt gatgcactag gccgagagag    1800
accgagataa atcattcaaa tattttttta aatttgggaa gaatcttgag gtcgagattg   1860
atcctgagaa aaacaaaatt acgagttttt taaaactgtg aaatataaaa caaaaagtg    1920
ctagttttgt caattcccat ttatcttgct cattgttgat acaagatcat taaaagttta    1980
tggataaatg ttggttgaga                                                2000

<210> SEQ ID NO 134
<211> LENGTH: 1696
<212> TYPE: DNA
<213> ORGANISM: Cucumis melo

<400> SEQUENCE: 134
tatatatata tataaaaaga ggaatacaat taagacatcc cattgttaat aagggggtgga    60
ataaattggg aaattaccat tcgagaaatc attgacgaga gcaaatatgt caaagtagaa   120
aattagtcat ctcaaaagaa tgtaatcgtt acaaaaatta aaagtacgta aatttaatca   180
tcgttacaaa aattaaaaga atataaatta caccgttaca caataatacc aacaatccat   240
ttataatatg ttgttttttat ttcaacttttg aataaaattt gaactctttg ataaaatttg   300
tttaaaataa atttaaaacc atttcaaaag ctattttttat attatccaaa tacatatatt    360
cttttcttt  tccaaaatga cttgtttcta aattcgaaca tccaaaaatt aaaacataac    420
atttttagta tattaagaat tataaattaa gagataaaat attcaatact attataataa    480
aatcggtgtt ttcagtaatt gtatttgtac aagtaaataa aattaatagt aaaatttta    540
atatataaac aagttttaaa agaaacttaa agatatataaaa aataaattga ataaaattc    600
aaacccatca acaaataaag aaaataaaga tggtttttatt gaaatgaatg aactaaaatt    660
tgaaggaggc aaaagtaagt acaccaaaaa tagaatacta aaatggtaga ggacaataat    720
tgcatatgtt tggtagattt ttcattaact atcataccaa ttaacaataa tgaaataaac    780
tttctcgttg atattgatta caatcgtaat agggcaaccc actgtttaac ttgtcaaagt    840
tttcttaact ttattatttt tgactttatt tgtttgttttt attgattaga ttgatagatt    900
```

-continued

```
atatatttta atcatatttat ttatagtaca acaactacga ggtaagtgat tgaagcttta      960
gtctctaaga acaaaggttc gacctaattt tttagtctgt tttttatttga catattttgt     1020
ccattgatag aattactatc acttaagtta aatgtattat tattgcaaac cactaattct     1080
acgtaaaatc tctaagtagc aagtgttatg tcaataaaat agcaattttt tttttaccaa     1140
ttacacacat catggtgata attattatca tgcacgggta aattttttaat tataaaattt   1200
caactttcaa aattataccaa atactaaatt tattacaaaa gttatttttag gtaaattata   1260
aaaacttgat aacaattaca agtacattct aaaactttca ataataaaga ttgaatcatc     1320
caattcatcc aaatgttaaa tttataatcc gatttcaaga agaaaattaa aaactcaatt     1380
tttatgaaaa tgtaactaca accacaacca tattaaacaa aaactcacaa tttgtccata     1440
tttttttaagt taaaaatata ggtttaggat tcaatatttt ataaaataaa ataaaatgaa    1500
actatttgaa aacatagttt aaaaaagaag aagaagaagt gttaaataaa gtcccatttt    1560
ttaaaaaaat atcaagaccg atattaatat tatatatata tagaaaatgta cacaaagtta   1620
aaaaaaagta tcctataaat atctaagttt ctccccgtct agccttcgcc aaccttatct     1680
caaaaactcg gaagcc                                                    1696
```

<210> SEQ ID NO 135
<211> LENGTH: 2000
<212> TYPE: DNA
<213> ORGANISM: Cucumis melo

<400> SEQUENCE: 135

```
tttacatatt tatgaacatt ttcctatttt tgtaaatatc ttgattcaag attttttgttc     60
gatatattta aaaataaact tattttaaat tcatacttct ttctccttct atatgattat    120
ataagtattg tagttactat agattaaact cataacctcc tagttagata ttgagattat    180
tactttctttt tattatcggg ccagtacaga aacgcttttta tgacgattac attcgtcatt    240
cgtcacttat ttgtgcatta aagttggcat tgtaatgttt gtttttacat gattctctat    300
tccatagatt tccttttatcc ttttttccttgc atttgagtgg ccctttccta agatgtattc   360
ttcggacttt caaataaata aagattagaa gcatttttct cttcaatatt gacttcatcc    420
ttaatcctta agccttaagc ggaggctaaa aaggctttat ttgcctcgaa tcccaactaa    480
ttctccctct catgcccatt tcaatctctt gcctaattgt taattaatgg gtcaaatttc    540
gtattgaatt tcaatttttgg atcaatccta cgattatctc aattagggggt caaaattaat   600
ggttgatgta ggagcaagtg gaagacacaa ttttggtgta gcaattggag cttcatcatc    660
aacaacatga gatttaatcc cgtggttgca gttaaatggt gtagaagaag tagtcaacac    720
aacccaaggt gaagaagagg gagacaagag aagtggttga ggttgtggct ctatttgcct    780
atggcagcct tcacctcttc tctctcgctc cctctccgtt tcaatcccctt atccccttcc    840
tctccccgcc attttcttct tctcttcttc ttccctccac caatttccacc tcccgattct    900
ctgccctaac catctcttcc tcctccttgc actccgcctc cgacaatttc gatcatgcca    960
aaagctcccc ttttttcatct aaggtctgat tcatttctgt tgtttgttta actcaatttg   1020
tcttagttat attcaatcgg gatttttgctt gcttgtggaa ttaatttttcg tttattaagt   1080
ggaagatatg ggtatgcttg gtgacactgt atttactgtt aaatttcaaa caatcctacc    1140
aaatttttggt ttaaattgag tatttttagt tccttcttgg taaattggat ttgcgaatga   1200
ttaacttaac tatgttggca cttcgttgta agaccgttaa ctatttagct tccttacggg    1260
```

| | |
|---|---|
| taatgatgtt tagaaggggg gtgcttggtc cactaagtgg agttaagtct atggtaaaca | 1320 |
| tgttggcatt agtaagtttt tggtaaacat gttggcatta gtaagttttt ggtaaacacg | 1380 |
| ttggcattag taagttttig gtaaacatgt tggcattagt aagttttgt ttgtgatgta | 1440 |
| gagttgtaag attgagttct ttaataattt gagttgtaag attgaattct tcgataactg | 1500 |
| tgaaaagtat attaagaaag taagatagag ttacttgata aatttgaata gtggagatag | 1560 |
| gggcaagatt gagttccttg ataaaagtat aataaagtaa atgtgcaact cttgcctata | 1620 |
| tacagcttag caggaactct tacttttgtg tgtcatgtat tcttattggt tcgttcttat | 1680 |
| tgcatttagt agatagtgga tcccagtgaa ctttttiaat cgctagaatg gcgccttaaa | 1740 |
| aagttagttg gagcttctac ttgttggttg gtatggtgcg gttgcaagta ttttcctit | 1800 |
| ctatgattat gttttagat ctaaatttta agcactcga tgaatgctga tgcttgatat | 1860 |
| gttttctgtg ttaaattctt ttgttgatga atattatttc cattttcag aaatcagttc | 1920 |
| tttcatcttt gatacaagag atagagccgt tagatgtaag cttaattcaa aaagatgttc | 1980 |
| cacctactac tgtggatgct | 2000 |

<210> SEQ ID NO 136
<211> LENGTH: 2000
<212> TYPE: DNA
<213> ORGANISM: Cucumis melo

<400> SEQUENCE: 136

| | |
|---|---|
| ttcttgatta gcttggtgtg ctgttgtata tcatatttgg tgcgagcata acttacccit | 60 |
| ggctaccttg catctaccct aagtgggtta gtcagattgt atgatttgag gtatttcgtt | 120 |
| tctttgttgc tctaagtggc tttgagcttc tactgaggga acctaggacg tctcttcit | 180 |
| ttgggatctt ttttctcgag tagttggatg cctagttggt ttttttgttc ctttactcaa | 240 |
| gtcctttgtt tgtcatttga tcgtgtcaaa gtccaaatgc tttctattgc aattcagtat | 300 |
| cttaaaaaac tgttctttgt tgatttatgt aaatgacata ctgtatgtat aaaaggacag | 360 |
| aatgctacca tttcttgaag tttctggcac ttaccctgat aatcgttacg gtaattatta | 420 |
| tgtgcagatt gacggcaata acgcagctag cacatcatgg tatgatattt gtacctcttg | 480 |
| ggtacacatt tgggagtaag atgatggaaa tgaatgaggt gaaaggtggc tctccttatg | 540 |
| gtgctggaac ctttgcagcc gatggaactc gacacccgac tgagtggag cttgaacagg | 600 |
| ctttttacca aggtaagtat gttgctgagt taaccaagaa actcaaaaac taatgccatg | 660 |
| tttgaaatgt tgtgggtat ttgaaaacgt gttattacac tagcacactt ttactgtact | 720 |
| tccttccaac atctattatt cagcttctca catcatggct atataaataa aggttaatgg | 780 |
| aagttactaa aaatgatgta aatctatcac attgttaata ctcctgtaat tatattgatt | 840 |
| gatgaacaat tcgatcacca tcttttgtta tttaaaatta aacttgtaat atgtattcga | 900 |
| acgtttttag cttattgca tgcttattat ttcactgtit taaaactatc tttgacttc | 960 |
| aaatcaaatt ctgaaaaaca aaattaagtt ttcacataca ttatgtcatg aatataaaat | 1020 |
| tttagatatt ttagttcatt ttactatatt taaaaatgtt ttattattat taattttgta | 1080 |
| aaacaaccat gatcgtttat taattgaatt gtcacaatta agccattatt ttttttta | 1140 |
| ctttccttit tcccatcaat ttctttattt tctaaaaatt attggcctcc cagactcit | 1200 |
| gttatttgca aataatgagt ctaatcataa tagaatttca ttgataaaac caatcatagc | 1260 |
| gagtcttaaa accaatcata gcgagtcgta attataaata ttattgaatt gctcttggtc | 1320 |
| cagtttagct agaattatga atttgatcaa attttctgtt atcattaccg tataacaata | 1380 |

```
aatgataaaa ttcaaaaaaa aaaagaaag aaaattgata tgttaacgac aatggtaatg        1440
ataaccataa ttgtaatggt aaccgtaact acaatacata atttttgaat ccaatgagat        1500
gaatcactta cttagttgat ttgcgtacca aattatagaa caccaatcat ttttgtaatt        1560
aggattgatt tactagcgtt agattagaga aaagcttggc ttatttctaa ttcctcctcc        1620
ctcttccact cattttgtcc ttaactaaaa catagtgata gttccctttt tcttttagag        1680
aaaagaaaag aaaagaaaag aaaagagtg ttaattggta atacataata acatatcaca        1740
tacataaata aatcatgccg agttcgcctt agaaacgacg ccgtttaaag taagtcaaca        1800
agtcaacact gacagctaat ttccgcaata aatacgtaaa aatgaaaaga aaattaaaaa        1860
acgatataat ataaatagaa gcaagaggct cccatcacaa gatcccattc gcaaccacat        1920
tccggccttg aggcttcaaa aaatcgaagg aaaacactct ctgtatctct cccctctacc        1980
caccgattcc gtcgcggccg                                                    2000

<210> SEQ ID NO 137
<211> LENGTH: 1575
<212> TYPE: DNA
<213> ORGANISM: Cucumis melo

<400> SEQUENCE: 137
atatatatat atataattta actaaataaa caaatgaaag aaaaaagtga gttcccattc          60
ggaaaatgca gatggatcca tttcttcaaa tattaaaaaa taaaaaataa aataaaataa         120
cttaaatatg caaatagaaa gaattttaat ttctggatta tccatatggg acaattttta         180
aaactcattt attttatttt ttttatttat ttgattttga tatatctatg gggaaatttt         240
tcgtaataat tttcgaaaaa atattgcaat atatcatttg atcagatcgg tattattaaa         300
tctctatcac atttggtctt aaattatcca aagattcctt taagataatt tagataacca         360
tctacagatc actactataa tcaacaaaag gaacaactta aattatttaa acaaattcat         420
taatattaga ctttgtgctt cattagaaaa tgatcttatc acaaccacaa ccatagtggt         480
ggtttaaaat tttatttaa actcttatta gtattatttt aattcatact taatcaaact         540
aattacttta aaaacatat atatataaat aagttaaatc attcccctt atctaaataa         600 cataaaaaaa aattgtttac tctacaagaa gtttgtatat atatatgctc ggtactattt         660
agcatcttta taataaaatt tctaaatcaa tttttttat ctctttatta aatgtatagt         720
catcaaaaaa tttaacgaga taatgtgtca aagatttatt ttattaacgt tcataaatat         780
caaattatac ttagcttata attgaaaaca tgttcgataa atataagtaa ataaaatttt         840 attttttta aatattacaa aataaactaa ataagttata aatatgacaa taaacattat         900 atatttatt atatttataa atacttaata atttagtcgt ttaaaataat tttcttaatt         960
ttcaaaacat gtttcatatg ttaataataa ataaatggaa aaccttccaa aagaagaaaa        1020
aaagatatct taaaatttaa aaattgagat tttgaggatc aataattaat aaaagaagga        1080
ttaataaggg tgaaattaaa tcccaaaaag aaaattgaaa atgaagaaaa gaaaagtgaa        1140
gaaataattg aacgtgggaa gtggattcga tgtctccaga gaacaagcga aaggagacga        1200
aatccacata atttgcacgt tacgtgtccc tatcaaccgt agacacgtgt caacatctca        1260
acaccctacg ccgaattgct tcgctggatc tggacggtca tcggataaca gcggcaacca        1320
attaatattt ccccttatat ttcacagcct ggccatgtcc accaatcacg ttcaactatt        1380
aattcatttt tcatttcctt tttctttttt tttttaattc ccctcaatta ttaccgacaa        1440
```

| | | |
|---|---|---|
| cctgttgtag ccggttaacc ctaccctcca acgttccatt ataaggccta gaaaatggac | 1500 | |
| gtgaaaatgg agtactacaa actacaatta attttaaaga attttaattt taaagttctc | 1560 | |
| taattactat tagcc | 1575 | |

<210> SEQ ID NO 138
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 138

| | |
|---|---|
| ccgtcgggaa cctctgctct gacataatta atattcatgt atttcctgat acccatgcaa | 60 |
| gtcgtcggga aatatgttac caattttcga cgccagacga gaatcgttag gaacaagtgt | 120 |
| caccatgccc aacttcttgt atggggcatc aggataagtt aaatttcttt tttagttgtg | 180 |
| aactattccc gacgccataa acctagatgt cggaaatgtc ttcttgtttt tcgacggctt | 240 |
| cgtgaatctt cgaaaaaacg taagattaaa ataatgtttt cgacgagttc cgacctgtgc | 300 |
| aaaacgacat cgggaatagg tatttattcc aacgttctag cttctgacat ctagaaccct | 360 |
| tcaatttctt gtagtgccag tgcaaagatt gacactctta aacgatggga cttgtcaaat | 420 |
| agatgttgcg cagatatcca taggttatct aaggttttgt tttgttacct aagttatcat | 480 |
| caaacttctt catgaattct cttagctatt tctaagtacc taagttctcc tctatccact | 540 |
| aggattgtct ctcttaaagt caagggtggc tgttggtagg atgtagactt tgtcggcatt | 600 |
| ggtctaccaa tttaatctct tatatcccta aagacctaga ctccatggtc tccacctatt | 660 |
| tccataaatg tacccataac atcattaaat gaaattatta ctcaagtaca aaaaaattgt | 720 |
| ttaattttat tgataaaaac catatgtgaa aaaatagatg acatttttaa aagcttgtaa | 780 |
| acagtgtgtg aaataagtat cctaagtgaa ggctattaat ttaacttaaa cacaataatt | 840 |
| attattgttt taatgatgaa ataattaac ttatataacc aattttcatc aacacataca | 900 |
| tacctttgt ataaacattt atttgaacac aaatgagaga caaatagaca tttttatttg | 960 |
| gtaattttct cagcattatt aattatcatt ttcagatatc ttaattgaaa ttctgaata | 1020 |
| attttttatt tttcggattt tcacattata atattttgaa ttagttagtt gaaaaccaaa | 1080 |
| gccagcatca gtgaaaactc attaatacat gtaaaatact aaaattgttt ttttaaactt | 1140 |
| ctcaaagaaa aaaagtctta atttttattt tcttaacttg acataaaaat cattggtgtt | 1200 |
| gttttaata aagtaaatgt taaagtagac tcagttaaaa acgaaaaaaa aagttaaagt | 1260 |
| ggactcaaca cttggagtaa acatttttt taaaaaaaat taatcctaaa attatgatta | 1320 |
| taattttat ttggcttaaa tatttcaaaa tgtgttacac atggtttagt ttcaatttag | 1380 |
| ttgttacaaa atttattatt gtatttgaat ttttgataga ctaattaaaa tttgaaaatc | 1440 |
| aatttattta tacagttgtt tttctttaa tgatgtaaat agaggtctaa tgattttaac | 1500 |
| ttgtaagggt taattttct tatgatctaa tgtaattcaa tgagcattaa ttttagaaga | 1560 |
| aaatgtgtac ttattttgtg taaaaataaa ttataataac aattttttca ttttggtata | 1620 |
| acgtatgatt aagttccatg aaaaaacaaa ataaaaaaga ataaaatatt tttccattta | 1680 |
| aagaaaaaca ataataaaaa tggagggatt caataggaat ttcggagggc ccacttccca | 1740 |

| | |
|---|---|
| attccaactc cccactcact cactcactca cnnnnnnnnn nnnnnnnnnn nnnnnnnnnn | 1800 |
| nnnnnnnnnn nnttttttttt attattatat tagaaattaa taattattgt ttatttcgct | 1860 |
| gtcaaataaa aataaaattg tggggcaggt gcagctcacg tgcctcctca cattgacacc | 1920 |
| acatttaaac actttcattt tcaaaggctg ctgctttata ttcttcacaa aaacttcctc | 1980 |
| ttcccttttct cacactacta | 2000 |

<210> SEQ ID NO 139
<211> LENGTH: 1006
<212> TYPE: DNA
<213> ORGANISM: Cucumis melo

<400> SEQUENCE: 139

| | |
|---|---|
| ataataataa taaatacata aaataaaaaa ataataatag taatgaaaat caatagaata | 60 |
| attttaaaat cgggaaggaa gtcgtgtaca atccttgcac gttggagagt caaatggcct | 120 |
| aagtggtgat gtggaagtcg tgtaccgggt acacgatttt cctacaagtc aataataata | 180 |
| atatggttat ttttttttcta gtttagggtt catgacaaaa gattgttcag tcgactggat | 240 |
| gtagacaaat ctaaaaaata aattaaaatc taatatgaaa actagttttta atttccaaat | 300 |
| tattaagggt tgaattcgac caataaataa taataatacg gttattttga aatttaggaa | 360 |
| attgaataaa gttgttaaaa tcttcaagca aattgttaag ccccgagata ttaagaagag | 420 |
| gtaataatag aggattctat atttataaca tgttaaaatt aattgcaaac tcataaatgc | 480 |
| atcacacaga ttaacaacat aggagggact tccgataaaa gtgcaaatat tgaaataatt | 540 |
| acagttcgcg aacatgagta ttttaatatt ttataaaata gtatgcacgt gtatttttgc | 600 |
| caaaagaaaa aaagaataga ttttgccatt tttcaaagtg actctcggtt atatctttta | 660 |
| tggcgattgt attttatagc gtatgttgtt tgtagttaac ccatttctca ttggcaaatt | 720 |
| caatcgtggg ccacaacgtt tgggcatagc ttcaatttgg attaactcaa ttatgtctga | 780 |
| atgggttgga ctagttcgga ctcttcggct gggccagaat cagattcggg ccgcaatctg | 840 |
| ttcatttcac acctatatcc aaacaccccc aaaatcgata cccatcaaac cctaactctc | 900 |
| aataacccccc atatataaat tccttctttta gggttttttca tcctcataca ctctcaaacc | 960 |
| tccggtcatt ctcatttttcc ctgccgcttc ttcaataacc ctaatc | 1006 |

<210> SEQ ID NO 140
<211> LENGTH: 2000
<212> TYPE: DNA
<213> ORGANISM: Cucumis melo

<400> SEQUENCE: 140

| | |
|---|---|
| aaggagtaga ctctcaagtc cactattcta acttcttacc cgaaagagcc aaaacttttc | 60 |
| attcaaattc aactagaaag ttattattga tctatcaatt tgattttaat ctacaggcgt | 120 |
| gcgttgcaat ttgggaaggg attgagtttg taactggagt acgggcaacc tcattgaatt | 180 |
| ctcttcgatc aacgtgggga tgaagttctt tcaccagttg gagtctggaa aaacttttgc | 240 |
| tagactaacc tattgctact gccttttggt gaaatctttg tgctctaata ttaaaaagac | 300 |
| tccaactttg aatcgttaat tataaactag tgttatttgc ttgtaaatct tacttatagt | 360 |
| ttgaaatgag tgcttggcga aagtgttgtt caaatcggta cgtgtaagtt taaagattct | 420 |
| tatttcagct ttgaatcaga tcagagtctt ttaaacttaa tcaaccgaca ccaccacacc | 480 |
| ccactcttgt tcttctccac gtgggagttc ccaaattggt tgatttgtta tctctttgaa | 540 |

```
tcatctcaaa tcaagaaatt tcagaacagg tttggggaaa tttgataaac tacactctct    600
tgctcgaact ttgcaaggtt tttactgttt gttatatgat tcaatattcc catttcttct    660
aattggatga actgttgaaa attggaaatg ctcagctgcc aagtttttt  ccgaaatagg    720
tataaattca aagattcaat cagtgtgggt ttacccaaaa aaccaatggg gtaagtccat    780
tttggactca tgtggagggc acatgtttag gcaaagcctt atctctttgc cagtgggctc    840
acaatcaata cggacaagac aagaaatgct tcctaacacc gtcattgtca gcgaccatgt    900
gagctttcag caaattggat ccttcaagta actcacgtga aagatattta gtgattgact    960
taattactct cccccttcctg tttatctaaa ttaggcgaat agatccaaag tgggtatttt   1020
tggagatcat ttatctgttt cctgttcttg tttatcgttt ataattattg attgttttc    1080
tggctcaagt aaaacgagga ctttgacatt tcaatacccc cttttttgtt ttctggtagg   1140
tagcgctaag tgggtttctg atatcgtact gaaaaagtta tagttttgct agaacactcg   1200
atagattta  gcttttgtat tgattttttt gttgatattt cctggtttca gtgaatgaat   1260
gatattcttt tatgacggtt gttgtgaaga ctcataagtt tgtctcagat cttcagttat   1320
actcttgaag cttcttcgtt catacttcaa cagttcttgt acattttacc ccctctgttc   1380
ctctttccat cggcttgtga atctgtgatt gtaaattgtg ctgatgattg tttttaagct   1440
gttgagatgg cgttgggtt  gtgtcctaat ttgagactgg tcaacttgat catttggggt   1500
agtgatggcc ttcttttcta tatcattctg tgaagagtac tttctaaccg attttgttaa   1560
aaacacatgt cggattgctt gcttgttttg tggtgtttct gatttgtgat atgatttgat   1620
taatctctga tcgagttgtt atgaatttga ttgacagcaa ttgggggacc atggaatcat   1680
tgtggttcct ctcatagatt ttgatttctg aggtgttgag aaggctttaa ccttttttgtc  1740
actgaaatgg atggtggaag ctctgaatcc ccagatatgg gttgtaacaa gaccatagta   1800
tggtttcgta ggacctcagg attgaggaca accctgctttt agctgctgct gctaggaatg   1860
gttttgtata tcctgtgtac atatggtgtc ctaaagaaga gggacaattc tatcctggtc   1920
gggtatcgag gtggtggttg aagcaatccc ttgcccattt gaaacagtct cttaaatcac   1980
ttggtgctga cctagtgctg                                               2000

<210> SEQ ID NO 141
<211> LENGTH: 1556
<212> TYPE: DNA
<213> ORGANISM: Cucumis melo

<400> SEQUENCE: 141
ttttagtcat tatacttcaa catctcgttg gttttaggtt tttggaaagc aaacctacaa     60
aacacactct ttcattcatt ggttttaagt tttgttgaca acttttttagg agtgctttga    120
ctaagatttc aaagtcttgt acttaaaatg atgcatacta tcgtaaaatt agtataagag    180
actagatttt taaaaagaa  gaagatcggt ggaagtatgt tctaatttct aagttttttca   240
acacttacaa atttattgaa aaacagctgt cggtacatgc acacatacta tttatggatc    300
tacaattcca agcatagaag agtttagtat atatccaaat tcttattttt aagggggaaa    360
aatgaacgaa agaatgcatt gtattctcgc ttttgtcgtg ataacgtatg atttttcaagc   420
tctttcgtcg aaaaacatca acaaacaaac aagctaagtg taatctaaat aatcttcaac    480
atccttggaa atttattgaa aaataaagat ggctagcaat gcatactttt tatggatcta    540
tatcccattt caaccgtaga agattcaaag tattcgaatt cttaaaaaaa caaaacaaac    600
tgccttgtta agataaaatg gaattagaat gaaattttca aaattgaagt ggggccttgt    660
```

```
aaaagaataa actttgtttg aaaattaatt tccatcgttg gttggtagat gtgtccttaa      720
ttgaaaaagt ggaagaaatg aaggatgaat atgaaagttc tgaaaagaat atggacggaa      780
ttggaaaaaa caaaaaacct aatttcataa attaaccaga atctaaacat tgggggatga      840
agggagcgga ggccattcat gtaattggcc gtacagattc atggtttaac aaaagccaca      900
acgactccca ttcttccacc acagaaattt cctctcctcc taaattcact tatctctttc      960
tatataattg cttcgttccc caactttcta tcttcgtgca gccccattca atccccatt     1020 ttacccactt cgtcttctcc tttctccttc gtcttccagt tccgttttcc ccatctgggt     1080
tctcctgatt tctcttttaaa atcaactacc catgttcgac tttgaggaac tggtgcgttg     1140
gaattgagct ttcgaaggag atttattgtt tttatcacaa cccatctgct cgaggtaagg     1200
ggtaaaaccc gggttcgtca ggctgtagac atcacggcta tacacgtagt ttcccggtcg     1260
ttctttcatg tccgggctgt acgacggaag ggttgtataa ctccgacaaa cccttcgccg     1320
cacggcggac gtggtgcttt gccttccgaa ggtggtagtc cttctgatct tcttttctc     1380 gccggcggtg gattctcttg cttcttctct tcttcgtatt agctttgcaa cgagtccgtt     1440
tgtgttttag ctctaccggt ttaggatttg acatcagcaa gtttctgttt tgcgtttctt     1500
tgttttgggt ggggagattt tggtgttggg tttggtttga attagaagca gacgat        1556

<210> SEQ ID NO 142
<211> LENGTH: 2000
<212> TYPE: DNA
<213> ORGANISM: Cucumis melo

<400> SEQUENCE: 142
gagtacctaa tctaaactaa ttaactcgct caccctctta tttactgccc catactaatg       60
atcctaatag attgtttggt tgggttgata aattctcttt aaaattatca agttttccaa      120
tttttgccac ctaagttgtt ttcttacaaa aaataaaaaa taaaaaaagg caatgttatt      180
tctcgtatgc attaattgat tgattttctc aactaacccct tcaatttgac tttatatgta      240
ataatagtgt aaaatatata cgcacatacc tacatatgac caacaataaa aacgataaca      300
ttaaattcag acagaaataa aaattacgat tatgatttta ataaatataa atgcacataa      360
ataaaattta cagttcatag aaaaatccga tgtaatgaag tttaaatcgt tagttatttt      420
atttcgtaaa ataccaattt atgatttgca tgacaaaattt ttaaaatata acttatgaaa      480
ttaaaagttg gttttgagaa acattcaag actttattac aaccaaacaa aaattttatt      540
gagttttgtt tcattaaaaa aattattaaa ttacaaatat ttggacttac gtaatttgtt      600
ttctttcttt ttagggtaga aaaatatgat agattaaaag gattcgaaat caaactttat      660
atcaatttcc ttttaaataa ttatttcttt ccaaatttag ttttttatatg atagcctaag      720 tctccatcat aagaaacaac gttaattata ataaaaaatg gatgtagatt caccaatatt      780
ttccaactat attattactt tcacgtttac attaaaatta aatccacaca ataatataat      840
agttttcttt gtttgattca agtttctct tggttaaaat taaattcga atgataata      900 aataaactcg tgattaataa actttaattt aaatttcaaa cttaggtgtc taataaattc      960
ctatattttg tatcacaact tttcaattat gtgcaataaa ttttctaatg atttattatt     1020
ttttttaaga atgtaaagtt gattatattc atattaaaca taagattgaa aagagagagt     1080
tgattatata ccgagtagcc gacagtcatt ggaagcatta acccattatc atctccggcg     1140
agcaaaagca aggatctaca aacaaacatg acaattaata tgaaactcat caatccacgt     1200
```

| | |
|---|---|
| atccaaacat tccatatgtt agacatggaa gagcaataat tacaaagctc tctcatcgtc | 1260 |
| tccgatcact ccatttatcg tacaaatccg tctttcttca ccttaatcat tttccccgaa | 1320 |
| attcatccca ctgtttcgca acaaaatcca agtttggaaa gatgagtttg tttttagtga | 1380 |
| tcaaggaaag gacaaagaat gtagcattgg caatgacggg caaacaagag aggtgtggct | 1440 |
| aaacttatac atgcttttgt ttggtgaaag gttaaagcga agaacgccaa agacagagga | 1500 |
| aaccgtataa aatatgagta aatgtcaatg ctaatgaatg ggcagaggtg aagcggtcgt | 1560 |
| ctatggctgg agaagggcag atgtgaaaca atatgaggta gacgaaggtg gagacaaaac | 1620 |
| aatttagtaa agtcaaaaca attcatccat atcctaatcc aattatattt ctttaaaaag | 1680 |
| tttaagtatc aaaattggac tgcttgatca tctatcaagt tattttttgaa ctttattta | 1740 |
| aaaagtttaa gattattaat aaaaatgtaa tgtttaaagt ggttagtgct ttggaagcca | 1800 |
| ttacgtccta tggattatgt ggtgtgttgg gctactctct atttggacat gttttgacgt | 1860 |
| accgtgcgaa gtcctgactc tatttgtaaa acgtcacccg gcaaaaccc aacttaaaaa | 1920 |
| acagaacttt atttcattta atttgcgggg tttatccgga aagaattgtg agagctctct | 1980 |
| tgtgtttggt ttgcttatct | 2000 |

<210> SEQ ID NO 143
<211> LENGTH: 2000
<212> TYPE: DNA
<213> ORGANISM: Cucumis melo

<400> SEQUENCE: 143

| | |
|---|---|
| gtaatgcaat attagcaatt attttggagc aatacaaaca actaggtttg gatcaaatat | 60 |
| cacgaaatac aggagcaata acattaacaa caaataaatg cacgaagttt ttttttttga | 120 |
| acaaacactt aactctctcc aaaccaaaac gagctaagtt agacctaaaa aaacaaagta | 180 |
| tcggaataca atatagctta aacaaaaatc atgtttagat tattggttag gttcatctaa | 240 |
| actagtggtt agccattttt caaaagaaaa atatgatttg tccttgctaa ttttccaaat | 300 |
| ctatatttta aaagtatcac tctcgtcata attttccata gctcaattaa tactaatctc | 360 |
| acggtagctt ttaattgttc ttgacaagta atggattaac ttaaaacatt tatataactt | 420 |
| tgtaggtatt attttataga aaaattagtt tatacgtgaa aacttcttaa atatctaact | 480 |
| acaatcaaat acctagatta cataatgtat ttttcataat attatacat tatatttgaa | 540 |
| aaaggactct catttctttt attggtatct acgcagaaat taagattttc gagttgcgac | 600 |
| atctcaatca acgaaccagc taagaagacc ggcaaattcc aaacgtatcc ttcgggaagc | 660 |
| actgagtgtt tccacgtcaa taacaaaata ttgacccaat aaatttcagc cacgtagaaa | 720 |
| caaagcaatg aaagccgtcg gattctccac atcggctacc gtatgccgtt aagatcatca | 780 |
| agtagacttc taattcccat gtcttccgtg ggggccagaa atggaaaatt gaaatcgctt | 840 |
| tatccacgtc aagctaacaa aaaacaacca ataataattc gccacgtttt ctcattagaa | 900 |
| aagtgcaccg ttggatcatc cacgttggca acatagatcg atccgatgga cttatataaa | 960 |
| tttgggtagc tcgtcgagaa atcagatcag tgatcgaagc tactggaagt ttttgctaag | 1020 |
| aaccatgagg aagtggacga tcgcttctgc tcttctcctt ctttgcattc tctctctcgt | 1080 |
| tcccgatgaa ggtgtgattt cgtttcttcc ttcagcagtt tgatttattt gttggaatgt | 1140 |
| aaactgaatg cattgcatta tcttaatcac gagggctgat gctttaattt tgggggttc | 1200 |
| gaggagaaat ttggatgaga ttcgagcttc gtttgaactg cgaaggtttg atggtgatat | 1260 |
| ttctattgtg tttgaatttt caggtcctag atttcatgcc aaggccgacg gtgatgccga | 1320 |

```
cgaggttgta gatccaccaa aggttgagga aaaaatcggc gccgttccac atggtctttc      1380
cactgattct gatgttgtta agaggttcgt gaatgtctaa tctcgttgat acacgcttca      1440
agtatagatt tgtccacttc gggaaaaaaa attatcgaac cttcttttga atgttgattc      1500
agagagtcgg agtcaatctc gaagagatct cttcgcagta gcggggagaa atttgagttc      1560
caagctgagg tgtctcggct catggatatt atcatcaatt ccttatatag taacaaagac      1620
attttcctaa gagaattgat ctccaacgct tctgatgtaa gttcactctg cctcttctca      1680
cttcattaga tctagtaatc tcattgttag atttgtgtta gttaataatg gcgtctctgc      1740
atttcaggcg ttggataaga ttaggttcct ttccctaacc gacaaagaga tattgggtga      1800
gggagacaac tcgaagctgg agattcaagt gagttcgacc ttcatactga catattgttt      1860
tcttattacc tcgctgaaaa aagctgctcg ttctggttga tgaaccttgc atacttttat      1920
tgttgtccat aaatcaaata tcgcagatta agttggacaa agcaaacaaa atcctttcaa      1980
ttcgcgacag aggtattggt                                                 2000
```

<210> SEQ ID NO 144
<211> LENGTH: 1337
<212> TYPE: DNA
<213> ORGANISM: Cucumis melo

<400> SEQUENCE: 144

```
ttttttttaa ttttcttttt gcagattgtg gggctgatcg tccacgatat gattccactt        60
tggctacgag gggtgtcggg caccttgtcc gtaagggcac tggtgggaga tcgtctgtta       120
ggtaacctag ccctagcttt tcgtgtttg gattcttcta tttaattgtt ggcttgatgt       180
tgtagatgta atgctgggtt tgagtgcttt gaaatgttga gggaaattta agaaatttaa       240
tgggatgaag atgaacagtg gtacttcaag cctcaaattg aattaaaatt attttaaaca       300
tcctaaattg gtatgactaa gtattgctaa acatgatagt catataaaag cgcaaaagaa       360
aagaaaaatc accoctctac taggattggt ttattctatg gattttttgcc ttcagtgttc       420 ttgaagtcac aataataaaa gtagtaatag ttgcagtcac aactcaaacc tttatatgtt       480
ttttaagatt gtggtaaata ttgttttgat cattagacaa gacatagaga ttttaagtct       540
ctgggccttt tcacgaagcc ataagcctct tatggttcag caaaggcata ctcaaggcta       600
gaagttaaaa aagccttgcc ttgagatgta attctgaata cctttttaaa acatttggta       660
cttcaaattt ataagtttat tagtggaaaa tataatcttt cagtctcttt tttagctgaa       720
atacttatac cttttttccc cattgtcatt gatttcttaa ttcatatgca gaggaaagga       780
ctaattagat atactttgtt ttattgagta atctaaaaga tgtggcacta cccactatga       840
acattttgac gtcattccag cttttatggg atattgaagc aggcaatttt aatctgagct       900
ggtttctctg tcgctgtcag ataatccttg tttgtgctta tgtgttctct ttcaagcatg       960
cacattagga ttctcaggca gatcagatca ttgatattta attcaatttg tggatttagt      1020
ttgtagtgaa tacactaaat tctgtctctg gtttctctga tcttactgtt ttattacaaa      1080
attgttttgc agtgggattg ttgctactgt cttcggagct actggattcc ttggccgata      1140
tgttgtacag caactaggta ataggtgaac ataaatggta ctagcattcg actttctttt      1200
tgcttagata tgtaatttat tacgtttctc tataccttct actactagtg ggttttggca      1260
gctttggctc tattccttgat tttatatca attttatgct aagcatgatt ttggaaatga      1320
attgtgtttc agctaaa                                                    1337
```

<210> SEQ ID NO 145
<211> LENGTH: 2000
<212> TYPE: DNA
<213> ORGANISM: Cucumis melo

<400> SEQUENCE: 145

```
atatgtgacg attaattacc taaaaattaa ttatttacat agggttagtc aagttgtccc      60
gtgagactag ttgaggtgag cataagttga tccgaaagct cacaaaaata taaaatacgt     120
caatctccat gctttcataa aaataacaat ttgattctca tgactactca ttcacttatc     180
gtaaactctt ttaaagaata ttaagagcgt attagtgtag tgggctagtt tgttacaaaa     240
gttggcgaca aatagatgaa attagagtta tctcgagatt cgacgagggt taaaaagagc     300
atttgcttta ccctgtattt tcatcgtagt tcatatttat ttatattcaa attctatcaa     360
gttaaggcca cgtatattcc aagaaaacat aatccattaa tggtaatatg aaaaatgagt     420
tttaatttga tcatgttgtc ggcattatgt aatcacaaag atatctaaag ctcaatgtta     480
aatctaatta atggaggccg ataatccaat tatatttgaa aattaagtgg aacctacggt     540
gagatatttg tactatcaca attacaatta ctcttacttg ttcggaaaag aaattttgta     600
aacatgtcaa aattatcgtt actattccaa atattgtcac tgacctgaac attgtcaaaa     660
agaaataaat aaataaaata atattagata atgtaaaata aaccacctaa actttaatct     720
attatggtcg caaatgcttt gataacacat aaaccgattg atccgtcaat gaaattttac     780
cataatcttt attatggatc gataaatatg acttaatttt cttttaaaaa agtgtttttt     840
aatttaaaaa aaaaaaagga aaggaaaggg ggaggggcaa aggttctaga gtgttccaaa     900
taggacaatg gaggagggtc tccaatggag ggaggagcca aatccaacgg ccaacaattg     960
ctggaagctt caggagccta catgattctt gggttcgttt ttctctcctc ttcctatcca    1020
tccttttgaa atttgctata agaaaccta cttctcttct ccttacaaaa aatccatttt    1080
acactctctg taataccccc agttttgcct cactcgcagc gctcatttct caccctctta    1140
tccaaatcaa tccttctccc tctaaaccct aaaaccccctt tgcacctccg ccgttttctt    1200
gtaagattcc ccctctcttt tcattctgtt ggactttctt atccttttac tttactgggt    1260
catgcttaca tttctatttg ggttttgttt ttgcttgccg attcagtctt ctgtattgtg    1320
ttttgagctt tctgactgtt ttggcttcct gggtttcaat tgttggtgta gacttatcga    1380
ttgattcgtt tgttttgtgt cctttcattt ctgggttttg atttctttaa catttcttc     1440
atgggttttg gatttggggt cttcttcttg tgtgcatctc tgtagcttgc tgattcattt    1500
gtatctcgtg tttatctatt tgtttgagtt cctgacatgt gggttttgt tgttgtctga     1560
gaattatgtg tcaaatgtca attgtcaatt cctatgttct tgaatttgtt tatgtcattt    1620
cctttctggg ttttctctgt tcaatcttgc tacatgggtt ttgggttttc ttacccttgt    1680
tgtgtgtagt tttagctgat ttttgtttat gcttactgat tcggttctgt attctcgatg    1740
atttgcttac ctggtttttt atgtcgtttg agaattgtgt gtcaattcct tgttgttga     1800
ttttgtttgt catttctggt ttgacattcc atccaatcct ctctgctcta agtctacttg    1860
gttttcaatt catgaatttc catcagacgc attgtcggcc cctgctcta tttgtttaca    1920
attctggttg tgaagttgtt tcagtttgaa ctaattgatg gtctggtgat tacgttctgt    1980
atcagtttgg aagagggtaa                                                2000
```

<210> SEQ ID NO 146
<211> LENGTH: 1212

<212> TYPE: DNA
<213> ORGANISM: Cucumis melo

<400> SEQUENCE: 146

```
atatatatat atataatgga ataggctatt tgatttagat gaaagctatt acgtcctggg    60
gtttacatca taatctctat tataatgtta atcgagaaac tttataaagg ttaactcatt   120
atctctcttg tcttcagttt attattgttg tttttatatc ggtggaattc cacctttcac   180
caactctcaa gctgtggtgt gaatctatgg gattaatcta gggcgaataa gggagctgag   240
tattttctat tgtggaatt aaatctatag tacacaaaac atttgctcaa ctactaagga   300
tatgaaaacc cttggctctg ccaacatggc ttatagaaag tatctgaaaa cgttcaccac   360
tttgcaattt caacaataag tgtaaattct tttcctattg ttgttattta gtcgatttga   420
tcgttgtaca atatttgctg taacatgttt gattttggc cattttagtg ttcacaagaa   480
gatattgttt gttataagaa tctacctgat cctttcaat tgttattcaa tatattgcct   540
actccgttga cagcaggtcc atgcagagga acaagttcta aagttcaaac tcgatgctga   600
tattcttcag gtactacttt tctgttttca caagtttgtt gtttcaatag ttctaagaca   660
gtgacactca tcccttatc tccgtaaccc aattcattaa cgatgacttt tgatcggttt   720
gaagaaaaaa tttataacac tttctcatct cgttcccttt ggattttcag ttttttaaaat   780
tgcatctata tgtattcttt tgttatcaaa ttttacttga taatgacttt taaattgtac   840
taactcattt agatgtgaat attaataatt ttaaacttca tttctgacgt ctaatactaa   900
taaaataata ataacaatta tccttcttaa ttaaatatgg tttacctacc ggtctattgt   960
tctgaactgg atatattcaa tttgtttat ctgaataatc ttttgaggtt gagttatcaa  1020
gagcctgttt aacttaccta aagcatttct aacctgaact atgccccata tgaatacttc  1080
attttcttta ttctattgta aaacattgtt gttattataa tttgaaacgc ctgtaatagt  1140
ttttacgatg tcttgcagga gtctatcgtt cggcatgtaa acgaacaccc acaggctggc  1200
tggaaagcta cc                                                    1212
```

<210> SEQ ID NO 147
<211> LENGTH: 2000
<212> TYPE: DNA
<213> ORGANISM: Cucumis melo
<220> FEATURE:
<221> NAME/KEY: misc_feature
<222> LOCATION: (1)..(2000)
<223> OTHER INFORMATION: n=g, a, t or c.
<220> FEATURE:
<221> NAME/KEY: unsure
<222> LOCATION: (1)..(2000)
<223> OTHER INFORMATION: unsure at all n locations

<400> SEQUENCE: 147

```
acatagtatt aataaattag ggaatgactt agttatttaa tttaagcggt agtaaatatt    60
attaactttt gttcgttgtg ttattttact ttcaaaacgt tcatcttgat ctttatcctt   120
tctaatatt attattttta gttaatatca aaaaactaaa tttaatttat acgttaagtt   180
acaacttcat ttatttcaat ctaaaacttt tagaattaca ctttattcac taaaaaatta   240
ctcgtaaatg caaccattcc aaaaaggttt caatattata taaaatatca taattttttcg   300
aacattctta aaataaatta aacaaaatag tagttttcat atacataaaa ttcgaataaa   360
tcctcataca aaaattttaa atttgaatca tcacattgtt ttattttaga taatcaatca   420
aataatttag gaaaagagaa gaaagaaaag taaaaggaag ttgaaggtat tttatttagt   480
```

```
gatagaatta taaaatagg tattttagaa ataaaaacac aaatatataa aaatacagaa      540
attgatgcat ttaatggaac actatttgac aatcaataag aaagaaaaaa aagaannnnn      600
nnnaaaaaaa gaaaaagag aaaaggtttg gtattgggtt tgtgggattt tattaataaa      660
tgaaataaaa aaaaagaaa gaaaaattta attgattaat ttggtgggag aatattacaa      720
tgaaacccca ctttgtgaac aaatacattg catttgggtt gtaatcaagt gtacatgcat      780
ctacccaaac ctttcttgaa ctcaccataa atccttcttt tagaccgctt cgacttccca      840 attttcttc acttttttc cccttctct ctcttcctcc gtttcccccc ccttttttt      900 tccctatctc atagggtttc catccacctt cttcttcttc cgttctctca tgcattgtca      960
ttcacaatct cattctgaat tcctcttgat cttcttcatc ttcatttcct ccttattttt     1020
tgctctcttt cgagggtttt tcggttcatt tccgtccaga ttccaccacc tcccgtggtt     1080
ttttcaccca tactcatgtc gaagctcttc gccttttccg gtaagtttat ggattttac     1140 tgattttttt ttttttgttg tttgccttt ctttggattt gacttagatt gggtagctgg     1200
tagggttaag cgtcgtgttt tgtatgggtg tttggattgt tatttggatc gtaggggaag     1260
atttggaatt attggtttta gtttttgggg gtttcttgat tcgccaggtg gcggatcatg     1320
gcttggtatg aattgtgagg gaatatggat ttgggtttct ttctattagg attgttttat     1380
tgtgttgatt gattggctat tttattgtct tgaacagtcc atgccagatg taagtttctt     1440
gaaaagagat atcgtagttt gaagatggg ttaccttta agtgatgtgt atgtgttgtt     1500
gatctgtcgt tcccgtacag atttagattt gaggtttaga ataagagagc acatcaatag     1560
taaatattaa agggtcaaat atagttttgc agagattgct tcttgttttt ctctgttgat     1620 aaatttcga tcttttgatc tagaagttga ggggtatttt ggtctgagga tttatttgtg     1680
atgttggatg atgtatctaa cttgtagttc ttgttgttga aatttcaggt agtgaagatt     1740
tttgcactgg agggtcaata tacccaaatc ccaaggactc cagtttattc ttgtcccttc     1800
ctcaccacgt tgatgtctat tttcctcctc gaaagaggtc tcgcatcact gctccatttg     1860
tgtttggtgg agaagaagtt gaatcaaaag caaatgtttc tatcgagatt cttccggatg     1920
agtgcctgtt tgagattttc agacggttgt ctggtggcaa agaaaggagt gcctgcgcaa     1980
ccgtttctaa acgatggcta                                                 2000
```

<210> SEQ ID NO 148
<211> LENGTH: 1254
<212> TYPE: DNA
<213> ORGANISM: Cucumis melo
<220> FEATURE:
<221> NAME/KEY: misc_feature
<222> LOCATION: (1)..(1254)
<223> OTHER INFORMATION: n=g, a, t or c.
<220> FEATURE:
<221> NAME/KEY: unsure
<222> LOCATION: (1)..(1254)
<223> OTHER INFORMATION: unsure at all n locations

<400> SEQUENCE: 148

```
tcataaatat atatataaaa aaacaaatat tataacctac cttttgcaaa tgataaaatt       60
gtaaagtctc gtgccgataa tgtgttataa aataaaagaa caagaaaact aaataagaac      120
aatgcaacaa nnnnnnnnn nnnaatagag aagagaggaa gaaggggaaa caattaaaaa      180
ctcaattgta gtgtgactta cacaaatgca acacatatat ctatttatag gacatatcat      240
ggtatatgtt atattatgaa attcaatgaa atgaatgtta caataaagaa ttgaatgaga      300
gttgtatgaa aattgtaacc ttcataaatt atggatatct actcttataa tatatcatta      360
```

```
tatttataat gtatactata tgtttgtatt ttaataagaa aattatccca ttggatttgc      420
gatcttagat ctaacctact aaacaaatat tccaacgaag aggaacgaga tgagaacgcc      480
gttctaacct acgcaatatc aatcgtttct tcgctgctac tttacgcctc aagttcctac      540
ccttcaagtt tcatcttcaa cgatcaaccc aacgattaac ccactgcacc accttatctc      600
ttgttggtgt catctaatcc atcttcttcc tgcatcttct gcaaatgctc tcaggttctt      660
tcctctctct tgtgcacaaa ctgatcaccc atgttgttcg ccggaaaatg attcagattc      720
ttcgtatctt gcctgcattg tctttgacta taatatgatt gaaattcact tgttgattgg      780
ttttcaattg ttaattaccg ttggttttgc tgtttagtga tagtatatta tgaggttttt      840
gttcgttttc gggttttgg atgtgatttc atcctataga atgaagagta tgcaacgtat      900
gctgtcacct tgcgggggaa atggtacacg tggacccgaa atggagctag gttttgatac      960
gtgcagtttg agttttggtt ttgggaggat ttggcattcg ttatatgaat tttgtaatta     1020
actatgccgt ttgattgtta tttataacgg tgcattgctt tttgaggttt agaatttgga     1080
cttaacgcct cttctattc atggttattg gttttatttc ttcctttttg ttgactgaga      1140
ttggtcgtag aactcgttgc ctgtctatgt tttaatgttg gcctgatttt gaatttctaa     1200
tccatgacta agtatttctt tattgtcttg atatagttga ttgaatcatc aatc           1254

<210> SEQ ID NO 149
<211> LENGTH: 2000
<212> TYPE: DNA
<213> ORGANISM: Cucumis melo

<400> SEQUENCE: 149
cattttaaat tgacctttca tgaaaaatcg tatgtttttg gtgtgatttt gagtataata       60
aaaatgattt taaccatttg aaaatcactt taaattacac ctaatgggtg actgaggttt      120
tagctttcgt ctttgtttag ctctaaattt gcatggcaag ttttccattc caatgattga      180
tgtggcttgt aatagttgaa atatatatat atatatatga ggtatcaaaa tccccagcct      240
tgtgttaggt tgaatatgga gggagtgggg agttattttt cctgctctta ccccgttcct      300
aattcccacc ttgtttacta tgtgttattg ttattgccat atttactatg tacataatat      360
ttcgattaga aattttattg tttaaccatt agacaatttt atatgtctaa accataggtt      420
tgaacaaacc atttagatta tatatatgtt gacaattaga ttgatagggc aattattttg      480
tttatcctaa aaatggtaaa taatgttctt aaacttggtt ctttgtgaaa taccttcaac      540
tttcaaagtt tttaataata ttcttacgct tataaaaaga aaaaaggat aagttgaaaa       600 aagaatactt ctatgataag ttttagatgg aaactattta cttttcatt taaaaaatac       660 ttttcaaatt tatgaagttc caaagtatg acttaaagaa atagttatac ccttattgat       720
aatatacgac aaaaacaacg caatatttcg ttacaaaaat aaatctagct gcattactat      780
cttactttaa agatactctt atcgtctatc taaactacct tactctagaa ttaataatta      840
agttcctttt actttataaa tataacttat tcctactatt agtatatatt tatattggta      900
tctaatagct aattttgaat tttgttccaa aaaaaaaata tcgctgagtt ttgttttgaa      960
gtcttttttt tttttttaaat atatattttc gattaaagct agatgttgca gttgatatgt     1020
agatttaaaa gaaatgtgtg agatcgttta aactatata gaagattaag catttattac       1080
ttcaaaatat atcgttaaaa ttattcacat aaccaattt tactcatcaa atattatgtc      1140
agagaaaaga aaaacgaaaa agaaaaccta cttcaacgga caaagaagtc cttagttcaa     1200
```

| | |
|---|---|
| atcttcaaac ctttatttgt attaaaaaat ggcatataaa ttttttcaat ttttacgcat | 1260 |
| tacctgttgc gtgaaaaaca ttgatttaat agaaaagaac tgtcctttca gttttgtttt | 1320 |
| tttaaaacca atttcgaaat tcaagaatag aaacaaaact ttaagtctag aggatcacta | 1380 |
| aaatctatca taaggctaga aatacatctt gtaatctgca gtaggcattt gccgggatga | 1440 |
| caatttctg gtgcttggat taagaaaaaa gaaaaaaga aaaagaaaa aaaaatggtg | 1500 |
| aggacttaga ggccataatg agtttggcat tgggcccaca gtaggatgag taaattataa | 1560 |
| ttgggagaaa atgagcatag ggtgtggagg ggaaaaggag aaggctaaaa cactatcaca | 1620 |
| aatcacacag tagaagatac acagaagaag taaccacagc cattcattga gtgagaggct | 1680 |
| atccataatc tcatcctctt acccttctca tcattcattc aaagccattc aactcaacat | 1740 |
| cccactctta gttaaccaac aaaatatata tacatccttc tcaatttccc ttctctctac | 1800 |
| tgctttaatc ttttgcttct tcttcttctt cttcttcttc ttctgctttc tcaataccct | 1860 |
| caaccatggc tacggctact ctatcagtag ccaaaccatc tattcaggtt cctccattac | 1920 |
| taaacaccat cctctttccc ttccactctt ctttaatttt ttgtatctga taaacattac | 1980 |
| tgcattttct tgcatagcag | 2000 |

<210> SEQ ID NO 150
<211> LENGTH: 1680
<212> TYPE: DNA
<213> ORGANISM: Cucumis melo

<400> SEQUENCE: 150

| | |
|---|---|
| tttttatgaa gggagttgtt attttccttt gggatttgga gggatatgat atatatcctt | 60 |
| tttttgcaat ttgatgacag aattctgctt ttagagactt ttcaaactgt ttcgtaatga | 120 |
| atttgatggg ttgggggtgg cttagttcaa tactttgtgg gttgaaaatt ttgatttgca | 180 |
| ataaatgaaa gccaaaaatg tggggaagct ttcagttcaa gtaagttaag ggaaaactgc | 240 |
| agaatatctg gcttgaaata agagatgtct tcgaaggtta atagttttac attgactttt | 300 |
| ttaaaaaaaa gattatatta taagtacaaa tatgggtgga tgtgaactta tattattcaa | 360 |
| agagactaat ataagttttg ggcgcttaat atttatatt ttcatttagc agtcaaagat | 420 |
| gtataagaaa actttggtaa tgcattttat actagtttat ttatgtagga tgtaggatct | 480 |
| atcgaataat acaacatatt tttaaatgat gtgtacaatt gtgaaaaaaa aggaacata | 540 |
| cagtattgta gaaactaaaa tattttctaa gatatatcga gatgtaaaaa aaatgaatgg | 600 |
| atgtcaattc cagcataact taattgttga actaaaaaca aaaagaagaa ataagggggg | 660 |
| caatggtttg atcctcatgc cccacatgaa agtcaaagtt atgtaaaggt tccgtgtagg | 720 |
| atatccttcc tcctaataag gggagatagg attttatgag ggtgccaaca gctcagaatt | 780 |
| ccaaattccc aaaataccct cttgcttgaa aatttcaaac tcttctgttt ttgccttgtg | 840 |
| taccattcac tattccgatg cgtacagttc attaaccaca caagttctcc ttttgcaggc | 900 |
| aggtttagct aaacttattg gacttgctgg agagaccaat gttcaggtaa gatcttattt | 960 |
| gttataatga actcacaaac taatttagat tagccaaaga attctgtttc tgaagaaaga | 1020 |
| gaggatgaaa atcatctcat accaaatttc tttcttttt tggaattatg tcttcacatt | 1080 |
| tattcatttt ccttgtcaac agggtgaaga gcaaagaaa ctggatgtgc tctcaaatga | 1140 |
| agtctttatc aaagctttgg tcagcagtgg cagaactgta agctgctatc taatcataca | 1200 |
| aatgacacga caaaaatatc tggtgactta ctctaatagt tgacaaattg gtggcagtgt | 1260 |
| attcttgttt ctgaagaaga tgaagagcca acatatgtcg agccatctcg gcgtggaagg | 1320 |

```
tttgttttcc attcttgatg attttttgtct aatgcttaca attatcatca gtatcaactc    1380
ctcttacttt gttttaattt taatgttatt tcttcttatt ttccaatgac aaaggtattc    1440
tgtggtgttc gatccactgg atggttcctc caacattgat tgtggtgttt ccattggaac    1500
ggtaacatcc ctatgctacc ttctgaatga gatttcaaat attttggta taatttcttt    1560 ccaataagct gagtgtatga ttgtttgaat atctactttt tcatgtagat ttttggaatt    1620
tatcacttga acgacagcca cgaacctaac ctagaagacg tcttgcaacc tggaaagaat    1680
```

<210> SEQ ID NO 151
<211> LENGTH: 1524
<212> TYPE: DNA
<213> ORGANISM: Cucumis melo

<400> SEQUENCE: 151

```
tatatatata tatataggta atgagtaaag aaatgaaaaa gaatgagttg aagaatcaca      60
cccttaccat tctatttgaa actcgtgagt cttgtagact tttacatgtc ttctccttca     120
cttaatatca ttctggattt tgattatatg tatctttatt tctaaacagc ttggacagat     180
ttattattgt tagaatacct tgaatatgtt ttctggtgct tagaacgatc atacatgggt     240
ttttctaggg ttagaggagt gcgctataca taaactttct agttctagag gcattgctgt     300
aatcttaagt ttaacagttt ctctttaata acaaaaactg ctcttcccct acggtttaag     360
ttttctcctt atcttaacag ttataattat gaaaaatgat ggaaccaaaa caaagttctg     420
ttaaaatttg actaattgat tgaatgaact tttgtttcca agattcttaa tttgtaaagt     480
aataatgttc ttacaaatca ttatttgat gtctgagtta taaccttaa gcttggtggt      540 tcatattcca ttcaggtgaa gaagattgtg agtgaaagct gttcccaaga ggttttagaa     600
gtggcgttaa actccatctc atccctaatt accatcctct cctccatgtc atcgtctacc     660
aaactccatt cttcactttg atggtataag aaagtgaatt agatttggga ttgagcttca     720
aaacatgtat gatgatgtga atatttactc gtgtaaataa tataacatgt tgtattcttg     780 cttgttctc tttgctcatc ttcgttttgt taagagcaaa gaaaagctta cgagcatgaa     840
catgtgcaaa tttatgaagg tcaatgggct tcgtaatttt ttttccccat tgatttaacg     900
atttatggaa gatggatata gtaaatttag gttaagctgt acaaaaccag agaattttca     960
ttatagtaaa tactttacaa ttttcaatta gctacaataa acaccgtttc aaaatctccc    1020
tcatttgcta ccatatttac tattcgatat ttatcatttt ttttattcct gttgtaatgt    1080
ctactatttt tcttttaaac tattacacca caaacacata ctattataat tcaaattaaa    1140
ataatcacta gtataactca actataataa ctcagatgat ttcattccat gaaagtggta    1200
attataaata tttaatatct tatatgataa ggataactat ctatttggtg aaaccaaatc    1260
acaatgatgc agtggtaagt gctttggact ttgaatctct tttttatagt atttcattct    1320
tttttcaacg aagcagcatc atgggccttg aatggaggcc agctagaacg agcccattac    1380
atttgacaga gcatctcttc ggcccatgag cccaaacact attcatcttg ttaaaccacg    1440
aacaaatcga gactgccgag agtgtaagag aattgagtaa ttttttttcga gacacaggga    1500 gtttagagag taagtcggag aaca                                           1524
```

<210> SEQ ID NO 152
<211> LENGTH: 1851
<212> TYPE: DNA
<213> ORGANISM: Cucumis melo

<400> SEQUENCE: 152

```
ttgggtcgtt acaatatcac tgtttaaact taagtttatt tttatttatt ttttattt         60
ttaatctttt tcccttcttc ctttcatctt ccattcattt atacaaaaat aaataatgag      120
aaaattactt ttcacttttg agtttaatta tttttaagtt ctaaaatcta cattttaatc     180
tttaaattta aaaaaaaaag gatttacaag attcttgagt aatttattat tattattatt    240
ttgaacgtaa atataacctt ttacaaaatc taaatgagtg tttgggacaa tgagttgatt    300
attataagta ttgaattata ataatttttt gtggggtata gactatttta atttgaagaa    360
taataggtac gtgtttgaaa tataaattat gttagttggg aaagaaaata gtaaatatcg    420
tagaaaaaaa taaataaat gaacaataag aatataaaat atggtaataa attgggactt    480
tgaaataatg gtaataatta attaattaat tgaaagctac aaaacaatgt tcacttcatt    540
gctatagttc taaacagact aacaatctca atcaatgacc taatgggtca ggccattata    600
ttgggctcaa atagattttg gcaaaacgaa tcgaaagccc aatggggcct atattatgta    660
gggccgaaat gaatttcaac gaaaggaacc caaagcccaa taggcccaaa ttgagactta    720
caaaggcgca tgttagcatg aagagagaat tgaaagctta acagcgcca tcacaaaaca     780
tttgcatttt cgtgttgaaa tcgcatttgg gccgtaaacc aatgaaacac aaaacaaaca    840
aatcctggaa tagcctcaac ggttctggaa gaagaagaat cttctggaac ctccaatccc    900
acaataaaaa tcaaaccta aactcttaca ttcagctctt tgcttaccttt atcccaacaa     960
accttcacca acgctctacc ggaactaaaa cccctccgac ctcccacttc cgacttacga    1020
cctctgttgc ctgaacatgg cgtctgccaa tgctctttct tccgcttcta ttctatgttc    1080
ttctcacaag gtacttcact tataaccccc tcatttcttc cttgtatttt tcacaattcc    1140
tctttggaaa tgatgatatc tagattgtag tagttgggat tgtatgttag gtagagatttt  1200
tgtggagtta gctgagagcg gctgagaata ctaatatatc gtttccagta gcttacgttg   1260
cgtttttcta atgttgcaga gcttgagaaa ggtgaatcaa acgcagaaca acagagtaaa   1320
ttacagacag gctggtagta gattgttgt gagagccact gcaaggaga tagcattcga    1380
ccagagttct agaactgcac ttcagtctgg gattgataag cttgctaatg cagttggttt   1440
gactcttgga cctaggggta actttctgtt tatatttatt tatgaattgg ttagtattgg   1500
atgttgttct aatattgaaa tccctacagg atatattcat cacatttata gattcgtgtt  1560
atggttatgt tgagaaattt gggttcttca cataattctc aatcttgttg tgatattttg   1620
tatttgaagg gaggaatgtg gtgttggatg agtttggtag tcccaaagtg gttaatgatg   1680
gtgtgacaat tgctcgggca attgagttac ctgatcccat ggaaaatgct ggtgcagctt   1740
taattagaga ggttggtttt ttatactttg ttatgaagca aaattttctc atctatcgat   1800
tattgaagtc ttattagttc ttacattgcg ttgacaagta ttctatatgt c           1851
```

<210> SEQ ID NO 153
<211> LENGTH: 2000
<212> TYPE: DNA
<213> ORGANISM: Cucumis melo

<400> SEQUENCE: 153

```
actaattaat agtaatttgt atgggatata tgtatatgtg tgtataacag gaactacaga      60
gatagagatt cactttctag aaataaagtt gactgccatt ggagtttatt tggagccttc    120
agttgtggag catttgcaac aatggaaggg aaaagctgct aaggacttag tggaagatga    180
tgacttcttt caggctattg tttctggtat ctccctagtt atcctatttt taactatact    240
```

```
atctcatcac attcctaaat gtgaattact tgacgatctg ttcaaacata tatatttcat      300
tgtttgatcg taatgtttca tatttatgat gtttcatata ctacctcgtc acacgtgcaa      360
aggatttaga tccgttcaaa catatttcat tattggatcg taatgtttca tatctatgat      420
gtttcttata ctatcgcatc acacatgaga tccattcaaa catatctcat tgttagaaag      480
attatacatt atttcaattc aaatagctct aaccaatgac aaaattagat tcgtcccgtt      540
tagcttattc tatatatata gatagataga tagatagata gtatggatat gcttgtgata      600
agtgtttttt tcttcttttt tttttctttt tttgttttt ttcttttttt gtcactttct        660
aaattatcta tctcacagtt agctagttgg cggggtgatg acttttggtg tgtcagtcta      720
gtgagaagtt tgggggttat ttttattttc gaaagcttcc taattgaatg acttgtaaag      780
gttaatgttt atgttttgt acatgttttt catgaactat tggttttaca agagttacaa        840
ttctatttat ttgtgtaaga aagatcatat cacattttta ccctggtgt gttcgtttta        900 tgttcttgat ttgcttttg tttttcaata atttacgggg aaagagagaa taaaattttc        960
tttctccgat ctccgcattc aatttttttt tttttgaaag gtgcattcaa ttttttttgtg     1020 cttattaaat attcacttac atcttttgtt ttgtttattt ttttattttc atctttctta     1080
tatgaaaata aaatatttt tagtacaaca atagaacctc ttgttaccat tgaaatgaat       1140
tacaggaaat taaaacttt acttttatt tgagagaatt aaaagagtag ttttaaata         1200 taacaaaacg actttcgcaa tagatccaga tgatcattta ttaacaattt tctaattaaa     1260
attgttacta aattttaaca attattaaaa aatattaatt gaaaaacacg tgtatatata     1320
taggaacatt ttcaattata gccaaaagtt ataattattt actctataaa attctttaga     1380
gtctatttaa ccttttgtt aaattttgtt aatagtttta ctttgccatt cataaaaatt      1440
tctcatatta tatacagtga gaattttata agtctcaaaa gtcaaagatt tgattaaaaa     1500
aaaaagaaat gaaagcatat ctaaatatat tatttatact ttgaaaatta cttccgaagc     1560
aaaatgtaaa accgttataa gtgaacttag aatccaaaaa catatattaa attaagttta     1620
aattatataa caacaccttt ggattttgtc attttctaaa ataccttta tcatttcaat      1680 aattgtaaaa tgagtcctaa attttcacaa atgtttcaaa aatatttgga ggagacaatt     1740
ccttgagaat ttcaaagata tattaaagag gacgtattga cccaaatctt ttgttctatg     1800
tcactatgat caccctttta tatcacaatt tatttccatc tacaattcta aagaatttat     1860
aatttaaaag tagtttcaaa atgtttctaa attttcgagg gtaatatttt aacttttgga     1920
agtacggaaa gttaatcaaa tctttgtctc aaaatctcaa ctaataactg gaattgggaa     1980
agctaaagtc tagaccttaa                                                  2000
```

<210> SEQ ID NO 154
<211> LENGTH: 1288
<212> TYPE: DNA
<213> ORGANISM: Cucumis melo
<220> FEATURE:
<221> NAME/KEY: misc_feature
<222> LOCATION: (1)..(1288)
<223> OTHER INFORMATION: n=g, a, t or c.
<220> FEATURE:
<221> NAME/KEY: unsure
<222> LOCATION: (1)..(1288)
<223> OTHER INFORMATION: unsure at all n locations

<400> SEQUENCE: 154

```
cgagaagtac ccggcgttgg tcaccggatt tttcttcttc atgtggtggg tttaattgtt      60
ggtcacgtgt tttgcacggc gaaggccggg tggtaattat tacgttgcgg caagtttgag     120
cttggttgtg tgaaattacc gtgttgtcct ttctgttttg taggtacttt ttgaacgtga     180
ttttcaatat cctcaataag aagatatata attacttccc ctatccatag tatgtatttc     240
caatttacat tttcatccct gtattttcct tcttcttctt cttnnnnttt ttttttttaat     300
attgttatta atatttgttt acgttccagt tttgtgtcgg tgatccattt agttgttggg     360
gttgtgtact gtttgataag ctgggcagtg ggtcttccta agcgagcagt aagtcaactc     420
tttctatagc ccaatatgcc aattttgtct ttttctttca ttaaaattgt tattttttaac     480
tttttcatac ccaatttagt tttttagtc tgtttattag tcttgttttc ttcaaattta     540
gtagtattgg tagtctaatt ggtagggctg ttttgaaagt aattacctaa tataatgagt     600
atttagattg agacagtact atagtctaaa cgatgtcatt gcagttttga ttgaaatttt     660
ttctccttta tttatttcga aaatgacaat ataacttctg taatctttgt aaccatgttt     720
atttgaagct acgttgtaaa ggggaaaaag aaaaggaaag tgtaaaatgg tcaaataaat     780
tatattttta agtgaataga ttatataatg tgcggtaaaa tatagcactc acaagtaaat     840
gcaacttagt aatctaaaga ttgaactatc aattcatgaa ttttttttata attagcatgg     900
ttttctatag ttttgggag tctgttttc aatgaaaata ttgccagtat ggtaatcttg     960
tatgacaatg tattttctaa agtatggata taattaaatt ttctttaatt tatcggctta    1020
aacttttcgt tgtactaaaa atctaggata ggacgtttaa tatttgaacc tttgtaatgc    1080
catttaatca ccgattaata tagatctaac tattgaaact tcttcaaaag ttttaatcca    1140
acggatggct aagagtgtta aaatattgat acaattaaat ttatcgtagc ttaagctttg    1200
acagtgtcaa aagctaattc agttatttc tctgcccttg gtataagggt aactctgttc    1260
tctctatttc acacaagtga ttgctaac                                      1288
```

<210> SEQ ID NO 155
<211> LENGTH: 2000
<212> TYPE: DNA
<213> ORGANISM: Cucumis melo

<400> SEQUENCE: 155

```
ttatgtttta ttaactccat agtttttacta acccccatttc acgggaaagt acaataaaac      60
atttgtgtta aaaaggagtt gtttgtatag atcgaataaa cattttgtac taattccaat     120
catattacca aatgttttaa gagcatgcgt tcttgtgtgc ttgaatagg gtgatcatca     180
attgagtggc gtcagattta aatttaaagt ggcaccaatc atcgacttgt tggtttagat     240
cgatcggtag ttgttgtttg tgggacaatc atagttatca ttttctcct tctatatgaa     300
taatagtcaa ctagatagaa ttgacatttc ttagtattaa aaaaacgacc actgacctgt     360
ctatatcact aaaactgcttg acctaagtga gtttggttgg acttgattgc ttcgttgtgg     420
tctaattcac ttaaccctac ttgaaagtaa aggtagaata taacatgatt ctttccaaat     480
tggcaagttg tgacttgatt tatgcatgca cgaagattct tccactctcc acctaactag     540
tactcgatca cattggaaaa tggatctgtc ccgtgaagga tcgcaatatt acatgccttc     600
ctacttttt ctttctcttcc accaaagaaa aagaaaacgg gacacacaat aactatacat     660
tatcaataat aattaaacga atcatcccac caaatgtaaa ccatgaatat tgaaatcatc     720
```

```
atgttttaag aatcatttta ataattatgt tatttcattg ttttatatag aacacaccgt    780
tcatgaaatc aaacaaagag agagaaatta taattttgta acaaattacc aacattcttt    840
ttctttctat ttttcataaa tgagcatatg tttgtgtata tatacatact gttatttgat    900
ctccacattg ttgaacaaaa aagttggtgt tcttgaaaat agctatcacc gaaaatacgt    960
catatactgg gttgttatgt accaaggccc agaagaaagc ccaaaatcac cggcccatga   1020
gcagtgaaca ataattggg ctaaaagccc aatatacgtg atgatgggcc aacccagaga   1080
agtttatagt tatgttatta tagaattcca gatcagggag tatcgaaaca aaagcctcca   1140
ttgtcctcgt tctcttctcc ttgtgctctc tctctctctc tcttgctctt ttctcttttct  1200
cttcctctcc gacgacaggt tcctgaagct cgaccagcca agggcattga tctaggtgag   1260
tccgcttttca cttttccact ttcctctgcc gttttttcttg tcatttccaa ttctccattc   1320
tttgttctgg atttcacttc tttacttcgt cgttgattag aagataatag tgagatcgaa   1380
ttctatgtct cgcataccctt cagtttcaag gaacaagaca atgattcaac cgcgccgtcc   1440
acgttatgga tagagggttt tgattctcac ctttatagct gcataacacc gttcttaggg   1500
ttcggaccctt tgaatctgcg atatttctca cactgttttg gacgttttta ccgttttcct   1560
atggttcttt agccttacct tatccttgcct tcagatcttc gattgcggat ctgattcgtt   1620
catttctact tgttacttttt tcttggaagt cgaggattat aaatcaacaa caaagcattc   1680
aaaatctcta gtgcaattag tgttttccat ctagttattg gagatcgttt gtagctttga   1740
ttttgtccac tttcttattt tgaacgtctg gaagacgttt tatacatgtt ctttgggtaa   1800
agttgcgttt gggcactgtt cttcacctct gggttttcgt tcttatgcta tgtttcatga   1860
tttcttttga tatctttgtt attgtttccc catcatcgag tatctgattc ttattcggaa   1920
gccgtcttct tgaagctgcg aaccggtttt ctttttctcc ctcatcaagt ctttaatttt   1980
acaggaaagc gctgaataag                                               2000

<210> SEQ ID NO 156
<211> LENGTH: 2011
<212> TYPE: DNA
<213> ORGANISM: Cucumis melo

<400> SEQUENCE: 156
ttgttagagg agttagcttt tcagggagtc ggttacaact tacaagacag acaaccatac     60
tgtacaatca atcactactg cctcaaagtc gaaaccattt aataccagtt gagcctcatt    120
gtgactgcat aattttgacc cctaccacga ggtaatttca gttcaaatca attgtatctc    180
tcttctggat atcagtcaag aatctcatgt tctcaagtta tagtacattg ataattactg    240
tgcatttttta ttaatttatg agttaaaatc ctgctgatta attcaactaa aggaataaaa    300
tagttattgg catttggatg agaatagaat gtgaatccca tcattcatcg ctagattgga    360
ccgtaattat aagtgagagg gagaaacttc tgttgctatt cccttttat ttcttaattc     420
atttataaat tgttttttagg cctttttatat atatatattt ctaccatttt tacatttaaa    480
attcttttaa ctttattatg tatggactca aactaacaag ctttatttga taaaattgtt    540
caaactatta tattagtttt atatttgtaa accataaaac aaatccataa aattccacct    600
gcatcactca ctcatgttgt tgaatggtac gaaataaaca atacatgtga aagatgaaaa    660
taagaattgt tctcttatta aatctaaaat ctagattttc tttttagtac atttaacact    720
tcaatgaaag gtctaaaaca ttattgaatg acgtcacgaa ctattacaaa agattattcc    780
gattatctc aaaagggggtc tatttcacta attttggtgt cccacatctg taaagagaat    840
```

```
tttcgtgata tgtgtagata tttaaatata attgaattcg atgaaagcaa agcaagaatc        900
gatatccgta gttattttga tatagatcgg tgataaataa aagacaatat gcataaagtt        960
tgtgggtaca gagtcggcta gttgcaatga ggggtatggc cccaagactt ttccccaacc       1020
ccaacggtca attaatcacc ccaatggggc atcgaatctt ccccaccatt ttcctttttct      1080 tcgccgactc ttctacccat ctcttttgcc gactctttct cacaggtttg attaaatccc       1140
attcatattc agatacacta tttcaaaata ctcgcaaatt aatttgtttt tttaaatatt       1200
ggtataataa taaaattaat tataaattgt gacctaaaaa gtactttgtg aagaggggga       1260
tatagtctgt ctaatatatt attgattaaa tatataatag aaccataaat gcaaaccact       1320
agaattgtta ataaaaatca acgctctttt aagtctttcc atagaaagaa aggcaaagac       1380
gcgcaacgtc tagaattttc tttataacgg aagctaactc tgttataacg gccgtccaca       1440
taatatggta gatttaaaat gacgtcagca tgtcgcttct aaatttgggt ccaaaggggg       1500
gattcattta tagggaaggg aaacggcaaa tgcaagcata gtgagtaaat acgtggcggc       1560
aaagtaatgg ataattctgc ctctgccgtg acgacattgc ccttccattt cactataaat       1620
acacctcctc tatccctcga tttcttcgca attgaatttc tcttctcatc tctgtcgtag       1680
caaaccaaat cgatttcttc aaaggtattt cttcctttcc tttttttttt tttttttttt       1740
tttttaaatc atgttgttca aactttgaga gatgaaatga ttaggggctt tcaaagtggt       1800
tttcgtttga tatgtttctt agatcgatag ggtttagaat cgagcatcct tgtaggtatc       1860
ctgaggtttg gtggttggat ctgcttaatt tttatgtggt tgcatggaaa attgggatt t      1920 ttttttttcta attacgtgat tctggaaata ttgatctgtg gttcagatgg aattgaatct      1980
gatctttctg ttttgttctg tataggtggg c                                     2011
```

<210> SEQ ID NO 157
<211> LENGTH: 1698
<212> TYPE: DNA
<213> ORGANISM: Cucumis melo

<400> SEQUENCE: 157

```
ttgttagagg agttagcttt tcagggagtc ggttacaact tacaagacag acaaccatac         60
tgtacaatca atcactactg cctcaaagtc gaaaccattt aataccagtt gagcctcatt        120
gtgactgcat aattttgacc cctaccacga ggtaatttca gttcaaatca attgtatctc        180
tcttctggat atcagtcaag aatctcatgt tctcaagtta tagtacattg ataattactg        240
tgcattttta ttaatttatg agttaaaatc ctgctgatta attcaactaa aggaataaaa        300
tagttattgg catttggatg agaatagaat gtgaatccca tcattcatcg ctagattgga        360
ccgtaattat aagtgagagg gagaaacttc tgttgctatt ccctttttat ttcttaattc        420
atttataaat tgttttttagg cctttatat atatatattt ctaccatttt tacatttaaa       480
attcttttaa cttattatg tatggactca aactaacaag cttattatga taaaattgtt        540
caaactatta tattagtttt atatttgtaa accataaaac aaatccataa aattccacct       600
gcatcactca ctcatgttgt tgaatggtac gaaataaaca atacatgtga agatgaaaa        660 taagaattgt tctcttatta aatctaaaat ctagattttc tttttagtac atttaacact       720
tcaatgaaag gtctaaaaca ttattgaatg acgtcacgaa ctattacaaa agattattcc       780
gatttatctc aaaagggggtc tatttcacta atttttggtgt cccacatctg taagagaat       840 tttcgtgata tgtgtagata tttaaatata attgaattcg atgaaagcaa agcaagaatc       900
```

| | |
|---|---|
| gatatccgta gttattttga tatagatcgg tgataaataa aagacaatat gcataaagtt | 960 |
| tgtgggtaca gagtcggcta gttgcaatga ggggtatggc cccaagactt ttccccaacc | 1020 |
| ccaacggtca attaatcacc ccaatggggc atcgaatctt ccccaccatt ttccttttct | 1080 |
| tcgccgactc ttctacccat ctcttttgcc gactcttttct cacaggtttg attaaatccc | 1140 |
| attcatattc agatacacta tttcaaaata ctcgcaaatt aatttgtttt tttaaatatt | 1200 |
| ggtataataa taaaattaat tataaattgt gacctaaaaa gtactttgtg aagaggggga | 1260 |
| tatagtctgt ctaatatatt attgattaaa tatataatag aaccataaat gcaaaccact | 1320 |
| agaattgtta ataaaaatca acgctctttt aagtctttcc atagaaagaa aggcaaagac | 1380 |
| gcgcaacgtc tagaatttc tttataacgg aagctaactc tgttataacg gccgtccaca | 1440 |
| taatatggta gatttaaaat gacgtcagca tgtcgcttct aaatttgggt ccaaggggg | 1500 |
| gattcattta tagggaaggg aaacggcaaa tgcaagcata gtgagtaaat acgtggcggc | 1560 |
| aaagtaatgg ataattctgc ctctgccgtg acgacattgc ccttccattt cactataaat | 1620 |
| acacctcctc tatccctcga tttcttcgca attgaatttc tcttctcatc tctgtcgtag | 1680 |
| caaaccaaat cgatttct | 1698 |

<210> SEQ ID NO 158
<211> LENGTH: 313
<212> TYPE: DNA
<213> ORGANISM: Cucumis melo

<400> SEQUENCE: 158

| | |
|---|---|
| tcaaaggtat ttcttccttt cctttttttt tttttttttt ttttttaaa tcatgttgtt | 60 |
| caaactttga gagatgaaat gattaggggc tttcaaagtg gttttcgttt gatatgtttc | 120 |
| ttagatcgat agggtttaga atcgagcatc cttgtaggta tcctgaggtt tggtggttgg | 180 |
| atctgcttaa ttttatgtg gttgcatgga aaattgggat ttttttttc taattacgtg | 240 |
| attctggaaa tattgatctg tggttcagat ggaattgaat ctgatctttc tgttttgttc | 300 |
| tgtataggtg ggc | 313 |

<210> SEQ ID NO 159
<211> LENGTH: 2010
<212> TYPE: DNA
<213> ORGANISM: Cucumis melo

<400> SEQUENCE: 159

| | |
|---|---|
| tagaaaaaaa ttgaagatct tcttaatgct aataataaaa gcatatataa aaaggcttca | 60 |
| tattacacaa gcatcttaaa accaaaccga acttgatttg aaattatccc actaattctg | 120 |
| tagatttcac caaagtcctt aacctttata ctaacatctg catttgactc tttcatttga | 180 |
| cctccaacat attctttctc attttccttc cattcaccac aaaaaccaac aaatacaaaa | 240 |
| aaccacaaat acatagaaaa ttaataaaaa aatcaaaatt tcgagatgaa atcattataa | 300 |
| actcatccga taactttgag atttgaaacc ttacactata taaagaaact catccgataa | 360 |
| ctttgaattc gcatcgaaat tacgtaagtg aagacgaaaa tgtaaatgat tagatgcgaa | 420 |
| taacaaaaaa aacataattt ctaaacgtaa aacactatat tcaccttatt atacttgatt | 480 |
| attttggaaa agtatgaaat ttgagtgtgg gagaggagcc aaagaattgg aaacttgtta | 540 |
| ttaggagtcg ttatgaaaca ttttcaacaa gccaatattc tttcacatac tataatgata | 600 |
| tacatagaaa taatacaata atatttttga aattgaggca ttttttgtcgt aatttatcta | 660 |
| aaaatgtcag ggtagattca tcatgtatac aaatctctcg ctatcaaaac tatataaaaa | 720 |

```
tcttgtgaat gatttcaatc gaaatggacc gagaaaaaac atcgtaacca cctctaaaat    780
cgataaattt gtttcaattt caaatcccta aaactaaagg tgctactttg tacaatttcc    840
cctgattagg gtgctaaagt taaaccctaa ataaaggtgt gtacgtttcc ggaagtttct    900
agaatcccca gcgaagttct ccaaatcgtg gcttgcagac caaggacccc cattaaaatt    960
cgtttcttcc tctaaacctc ctcccttaat tttggcattt tggtattttg gctcctataa   1020
attcaccccc tccttatccc taatcctttg tcttccaaat tttccttcaa agcctgcttt   1080
tcccatttcg tcgtgctttt tcttcatcta aaggtatatt tcagttctag ttttctttct   1140
ctgttgatct cttggatttg agggacgttt gaagttggct ttgtttaatt ctttgttatt   1200
caatctcttt ttttgttaga gttgttgttt aatcgtttcc cttgttgttt ttctcccttc   1260
tagttcgatt ttagaacgct ttttgtgggt tgattttaat ttctccgttt tcttacatct   1320
ttcacaaaga aacgattgaa atcgtgtttg tttttttttcc cacggcatac gttattagat   1380
cttgtagata atgatctcaa tctattgttt agttttttgca aataagaagt tggttttta   1440
tctccaactt ttatatattc gattcgatga gatgttctac accgttagga tggaaccaag   1500
aagtgaggta agggtgtttg attgaaaaat tgaactgaga agttaaagtt ccttcctaac   1560
ttttttaatgg attgtataat tcgttcaatt ccttgtcgtt ccattttttat ttctgtttcg   1620
tttttcgtgt tgctgcgtat cgcttcccctt gttgttttcc tccctattg attttgcgtt   1680
tcttggagtt tctctgtttt ctctcttcat ttttctacaa aaatcaattc tatttttatt   1740
cgttttcaat tcccgagctc cttggaatgt tatccttttc tcctgtgtaa ataagaaccc   1800
gtattcaatc ccagttcata gtttggcttt cccaaataag agcaaaaaga ttgtactgag   1860
aagttgaaga tttcaaaatt ttgtacatga tttcttctaa tttatcaatt tgattggact   1920
ttttgtatat agatttggtt cttgagctat ttatgttatg acgttttcat attgaggcca   1980
tgcgttgaat tggtttctta acaggtgggc                                    2010

<210> SEQ ID NO 160
<211> LENGTH: 1107
<212> TYPE: DNA
<213> ORGANISM: Cucumis melo

<400> SEQUENCE: 160
tagaaaaaaa ttgaagatct tcttaatgct aataataaaa gcatatataa aaaggcttca     60
tattacacaa gcatcttaaa accaaaccga acttgatttg aaattatccc actaattctg    120
tagatttcac caaagtcctt aaccttata ctaacatctg catttgactc tttcatttga    180
cctccaacat attctttctc attttccttc cattcaccac aaaaaccaac aaatacaaaa    240
aaccacaaat acatagaaaa ttaataaaaa aatcaaaatt tcgagatgaa atcattataa    300
actcatccga taactttgag atttgaaacc ttacactata taagaaact catccgataa    360
ctttgaattc gcatcgaaat tacgtaagtg aagacgaaaa tgtaaatgat tagatgcgaa    420
taacaaaaaa aacataattt ctaaacgtaa aacactatat tcaccttatt atacttgatt    480
attttggaaa agtatgaaat ttgagtgtgg gagaggagcc aaagaattgg aaacttgtta    540
ttaggagtcg ttatgaaaca ttttcaacaa gccaatattc tttcacatac tataatgata    600
tacatagaaa taatacaata atattttga aattgaggca ttttttgtcgt aatttatcta    660
aaaatgtcag ggtagattca tcatgtatac aaatctctcg ctatcaaaac tatataaaaa    720
tcttgtgaat gatttcaatc gaaatggacc gagaaaaaac atcgtaacca cctctaaaat    780
```

| | |
|---|---|
| cgataaattt gtttcaattt caaatcccta aaactaaagg tgctactttg tacaatttcc | 840 |
| cctgattagg gtgctaaagt taaaccctaa ataaaggtgt gtacgtttcc ggaagtttct | 900 |
| agaatcccca gcgaagttct ccaaatcgtg gcttgcagac caaggacccc cattaaaatt | 960 |
| cgtttcttcc tctaaacctc ctcccttaat tttggcattt tggtattttg gctcctataa | 1020 |
| attcaccccc tccttatccc taatcctttg tcttccaaat tttccttcaa agcctgcttt | 1080 |
| tcccatttcg tcgtgctttt tcttcat | 1107 |

<210> SEQ ID NO 161
<211> LENGTH: 903
<212> TYPE: DNA
<213> ORGANISM: Cucumis melo

<400> SEQUENCE: 161

| | |
|---|---|
| ctaaaggtat atttcagttc tagttttctt tctctgttga tctcttggat ttgagggacg | 60 |
| tttgaagttg gctttgttta attctttgtt attcaatctc ttttttttgtt agagttgttg | 120 |
| tttaatcgtt tcccttgttg tttttctccc ttctagttcg attttagaac gcttttttgtg | 180 |
| ggttgatttt aatttctccg ttttcttaca tctttcacaa agaaacgatt gaaatcgtgt | 240 |
| ttgtttttt tcccacggca tacgttatta gatcttgtag ataatgatct caatctattg | 300 |
| tttagttttt gcaaataaga agttggtttt ttatctccaa cttttatata ttcgattcga | 360 |
| tgagatgttc tacaccgtta ggatggaacc aagaagtgag gtaagggtgt ttgattgaaa | 420 |
| aattgaactg agaagttaaa gttccttcct aactttttaa tggattgtat aattcgttca | 480 |
| attccttgtc gttccatttt tatttctgtt tcgttttcg tgttgctgcg tatcgcttcc | 540 |
| cttgttgttt tcctccccta ttgattttgc gtttcttgga gtttctctgt tttctctctt | 600 |
| cattttttcta caaaaatcaa ttctattttt attcgttttc aattcccgag ctccttggaa | 660 |
| tgttatcctt ttctcctgtg taaataagaa cccgtattca atcccagttc atagtttggc | 720 |
| tttcccaaat aagagcaaaa agattgtact gagaagttga agatttcaaa attttgtaca | 780 |
| tgatttcttc taatttatca atttgattgg acttttttgta tatagatttg gttcttgagc | 840 |
| tatttatgtt atgacgtttt catattgagg ccatgcgttg aattggtttc ttaacaggtg | 900 |
| ggc | 903 |

<210> SEQ ID NO 162
<211> LENGTH: 1235
<212> TYPE: DNA
<213> ORGANISM: Cucumis melo

<400> SEQUENCE: 162

| | |
|---|---|
| aaatttttaat aattaaaatg aacaatttttt caagagtaat agagtttgag agatgtcaga | 60 |
| gaagtttgag gaagaagata acaagtggga gaagagaata agtttgttgt gtgaaagaga | 120 |
| aggggaaatt tcattcaagg gtatattgaa ctttttactc aaattttgta agtctatttt | 180 |
| ttccgatcaa tcctaaaatc acacacaccc ttaaaaaatg gattatattt ggcaattttc | 240 |
| catgataaac tcattttttaa tttagagtta ttttttcaac gagatattaa cagttttagt | 300 |
| tcatatacta attgtaagaa tagtttctttt taagttgaat agaattttttg aaacttttaa | 360 |
| tagttcaaaa ggtattttttg aaacaaaata agaatgtttt tgaactttttt ataaaagaa | 420 |
| ttgagatttt tttgaaattt ttgataaaga gaaagaaaa gaagaaagaa aaagagaaaa | 480 |
| caagtttgta gaactccgtg ggaaaatcgt cgagggccct gtgaaggaat ttgaaatta | 540 |
| taatgagggt attttcgtca acaagggaat ttagacatcg tatataagca tcctcaaacc | 600 |

| | | | | |
|---|---|---|---|---|
| ctataattaa | gcccttcaat | ccaattgcca | ttctccatct | ctcgccgcaa gggtttaaga | 660 |
| gcagcttctc | tcctcaggtt | ggggtttccc | cctatcttct | tcattcttcc tcttctcgat | 720 |
| ttctttcttc | tatttgctcg | atagtctctt | atttcttgag | cttttgctgt ttttctcctg | 780 |
| tacatcctaa | catgaattat | aacttggttt | tgattttgtc | ttttacttct gtattaaaca | 840 |
| acttttctta | ccctttattt | cttctcttct | tcttcgtgtc | cctgccctt tgttttatg | 900 |
| ctaattttat | gttctgtttt | atcaatctat | cgaggcgtga | cctgtcgttc ttccaatagc | 960 |
| gtagatctgc | acttaatcta | ttctagctga | ttggattggt | cgttttcgt tttttaatt | 1020 |
| tattttctct | gttctagttc | cgataaattt | ttttatatat | aattaacaag ttctccagcc | 1080 |
| aaaagggtta | atattgcgtt | ggatatttta | attttacgt | tatttagatg tgtgaatcta | 1140 |
| ataaaattag | ggttattcat | aaatttcagt | aatgatattt | tggttatctg ttcttgctgt | 1200 |
| tcctgtttcg | cagttctttt | acctaatatt | caagc | | 1235 |

```
<210> SEQ ID NO 163
<211> LENGTH: 617
<212> TYPE: DNA
<213> ORGANISM: Cucumis melo

<400> SEQUENCE: 163
```

| | | | | |
|---|---|---|---|---|
| aaattttaat | aattaaaatg | aacaattttt | caagagtaat | agagtttgag agatgtcaga | 60 |
| gaagtttgag | gaagaagata | acaagtggga | gaagagaata | agtttgttgt gtgaaagaga | 120 |
| aggggaaatt | tcattcaagg | gtatattgaa | cttttactc | aaattttgta agtctatttt | 180 |
| ttccgatcaa | tcctaaaatc | acacacaccc | ttaaaaatg | gattatattt ggcaattttc | 240 |
| catgataaac | tcattttaa | tttagagtta | tttttcaac | gagatattaa cagttttagt | 300 |
| tcatatacta | attgtaagaa | tagtttcttt | taagttgaat | agaattttg aaacttttaa | 360 |
| tagttcaaaa | ggtattttg | aaacaaaata | agaatgtttt | tgaactttt ataaaaagaa | 420 |
| ttgagatttt | tttgaaattt | ttgataaaga | gaaagaaaa | gaagaaagaa aaaagaaaaa | 480 |
| caagtttgta | gaactccgtg | ggaaaatcgt | cgagggccct | gtgaaggaat tttgaaatta | 540 |
| taatgagggt | attttcgtca | acaagggaat | ttagacatcg | tatataagca tcctcaaacc | 600 |
| ctataattaa | gcccttc | | | | 617 |

```
<210> SEQ ID NO 164
<211> LENGTH: 54
<212> TYPE: DNA
<213> ORGANISM: Cucumis melo

<400> SEQUENCE: 164
```

| | | | | |
|---|---|---|---|---|
| aatccaattg | ccattctcca | tctctcgccg | caagggttta | agagcagctt ctct | 54 |

```
<210> SEQ ID NO 165
<211> LENGTH: 545
<212> TYPE: DNA
<213> ORGANISM: Cucumis melo

<400> SEQUENCE: 165
```

| | | | | |
|---|---|---|---|---|
| cctcaggttg | ggtttcccc | ctatcttctt | cattcttcct | cttctcgatt tctttcttct | 60 |
| atttgctcga | tagtctctta | tttcttgagc | ttttgctgtt | tttctcctgt acatcctaac | 120 |
| atgaattata | acttggtttt | gattttgtct | ttacttctg | tattaaacaa cttttcttac | 180 |
| ccttttattc | ttctcttctt | cttcgtgtcc | ctgccctttt | gttttatgc taattttatg | 240 |

-continued

| | |
|---|---|
| tttctgttta tcaatctatc gaggcgtgac ctgtcgttct tccaatagcg tagatctgca | 300 |
| cttaatctat tctagctgat tggattggtc gttttttcgtt tttttaattt attttctctg | 360 |
| ttctagttcc gataaatttt tttatatata attaacaagt tctccagcca aagggttaa | 420 |
| tattgcgttg gatattttaa tttttacgtt atttagatgt gtgaatctaa taaaattagg | 480 |
| gttattcata aatttcagta atgatatttt ggttatctgt tcttgctgtt cctgtttcgc | 540 |
| agttc | 545 |

<210> SEQ ID NO 166
<211> LENGTH: 19
<212> TYPE: DNA
<213> ORGANISM: Cucumis melo

<400> SEQUENCE: 166

| | |
|---|---|
| ttttacctaa tattcaagc | 19 |

<210> SEQ ID NO 167
<211> LENGTH: 2003
<212> TYPE: DNA
<213> ORGANISM: Cucumis melo

<400> SEQUENCE: 167

| | |
|---|---|
| cagtgtgctg gaattcgccc ttatccaagg agattaatgt cgagagatta ttatcgaggt | 60 |
| ttgaatttat tttgtccaat catatgattc caagagctga ccatcaattc aacgaaacat | 120 |
| gaaccggaac ctcataccta ttgtaatggt tcacagcatc ctaatacaga acatgaaccg | 180 |
| aaacctctta cccattgtaa tggttcacag catctttata cgtattatag gtagtaccat | 240 |
| tgaagatgca tttaaatgct gtccatgctc tgttctctaa aaagttggac ttggacttgg | 300 |
| acgtcagctg aaagtatgaa atgcactgta gccaacgaag ctatgttttc aggcttcaac | 360 |
| atggttttag gaaagtggag gctctttggt tgaagggttg aatgaatgct ttctaattc | 420 |
| cagcatgatc ttcaaatttc gacacaaaaa gcttaagtat tttgttccgt tattctttta | 480 |
| atccttgtat tgttatatat tcttttctct gaactgaatg tacgatgatt gcaggggtcg | 540 |
| agagcaagtc cgatataatg aaacacgtaa ggacgtgatt gaatgaaaaa ctatgagcag | 600 |
| agatacaaag tctaacttac gggatgaacg atgagaggtt tgaccaagag ctgtgacgcc | 660 |
| tgtatatttc aacaaaagtt gatgactaac atcacatgtc agagtaatca agaaatgca | 720 |
| gccgcacata tatatatcta tatatatatc gagttttttt tttttttttt tttttttttt | 780 |
| ttttttatc taatatattt taatctattt tcctctgccc cctccccct cctcttcccc | 840 |
| caccttcctt ctgcacatag tagccaagga ttgatcggtt tcttttgatt cggggggaaa | 900 |
| atgttgtaca atttttgctt ccatagaagc ttgaaagttt tgcagattat gttgtaaaat | 960 |
| taccttgtg tactcacact agttcttctc gtggaaactt atattacaat ggttgagttt | 1020 |
| taagggcat attcacactg gtaactacca ttttctaatt tatgaatgcc gagtttctct | 1080 |
| ccatgaaaga cctttcaaat gcccttttcct ccgcggtgcg tttgttgttg taaatgtgca | 1140 |
| gtgtcgttgg atacacgatt gtgtgaaagg gaaaagggaa tacgattaac tcttaaattc | 1200 |
| aaccccctatc tccatcagta tcaatcacat ttcagcaact agctcttgaa taacattgag | 1260 |
| attcttgttt aatccacgta ctactactac tattactact atttgacagt tgatatctca | 1320 |
| aataacatcc atatttatca aattggtatt ttaaggactt ttaattcctt cgtacatatt | 1380 |
| tcattataat ttaactactc tgccatcat tgaaaatttc acaaagaaga cattttaaat | 1440 |
| tgaattgagt tgaattaagt tgatataatg gttgaacgtt ggatttaatt tataatttag | 1500 |

```
tggtgtatgg gtccattgta ataattctta aaaaaatat catattctga attctaaaga    1560
accatctaag accaaaacta aggggtcacc aatgagtatg gtaaagtcaa caaagtttgt   1620
ctacttttct tatccttatc atcaagagtg caatatgata tcaaagataa attgtacgtg   1680
ggcgtcatcc attgggtaag accaagaagc aaaatatcat agagaagttg ttttagtagc   1740
cataggaagg aaggaagcaa ataataata tagatttgaa attgtggatg ataaactgcc    1800
aaatgggaat tcaaaataaa ctaaataaat aaaataaaaa gagaaatctt gggagtttcc   1860
attttagcca atgaggaaac agatagagat ctcatcaaga taaggaccct attctcttct   1920
tcatctataa aacaaaaaca aatcaaaccc tcatttcact cattcaaaac aaaaagtact   1980
ccaaagtcaa actaacaaat acg                                          2003

<210> SEQ ID NO 168
<211> LENGTH: 2004
<212> TYPE: DNA
<213> ORGANISM: Cucumis melo

<400> SEQUENCE: 168
tggatcgacc atgacattca aaaccttta agatatggat cttataaaat aaatgtaaag     60
ggtaaacaat tcttccttgc ttaacccaag ctatatattt tatgcactaa tttaggtatt    120
agtatatatt cagctgaaca ccacctacca atgctagtac tttaatcagt caattctaac    180
ttcgataata tatctcaacc aaattagtga aaaagagtcg taaatgaaaa actatgtacc    240
aagatattct atttgttttt tttatgttta aatatctcaa agataatacc taaaacgttt    300
tctcctcgta caaagattcc tcatttactt tttattgtcg taaactctaa tacaataaac    360
taaaacaagt acaatacac tagctttaga aatctacttt ttattgaaac caaaaccaat     420
aattcaacat ttcattttca ccgacaaacc tttgtaaaca attgaagtaa ttttttgttgg   480 tactatgaat agtaacatca agtcttcaag tgcatcatat caaccaagac atgttcttaa    540
aagcgacact aaaagattta aaaccaaaag catttatgaa atccgaactt aatcaaatcc    600
taaatatttt tcacttaaaa aaaaaaaat aggaagaaaa attgacataa atgggatatt     660
ttcgttttca aactggcaag ccagcatgca ccacgttgtt gacgtgtcct tccacgtcgg    720 aaaaaaaat attaccacag taaaagaga ataaaatgaa agtcgttgac tctcccttag      780
tcggaggaag cgcgtgaagc tgaagccgga ttagaaatcg gcaataaccc cgacacgtca    840
tcgaaatgct agtatcaaat attgtccgtt ggatcttcct tcaccaactc tatttgaacg    900
gccacgatct tccaggtcca acggttcgga agaatctttt cgaaattcca tggctagtcc    960
ctacactcct ccctattggc tccctagggc atcccgaccg gttattccgg ttgccgggaa   1020
ggtggctgga cgctataaat acccgctttg ttcatctcgt agtccttgta ccgttgagct   1080
tcgccttcta atagagctct ggttcggttg gcgtattagc tcgaattctt tctctcttcc   1140
agatctacgc tgccgatttc atcaggtttg cgagctctgt tccaccattt ttcttttcct   1200
gaagctttga gcatgcttgt gattcttcat ttcctcattt ctttgatggt ttatgaaaga   1260
atttagggga attttctctt tttgtattct agtggtactg gtagatttgt ttgaagtttg   1320
tttctcttct tctgagaagt gaattcttcc agatctgaca gttgcttttg attttttctt   1380
tgggaattag tgaatgatac ttcgatactg ttttttgctc tctgagattc tggatctcgg   1440
gccttggggt tttctattgt cttttggtag ctatgtttcg tttgtcagct tgtatttgtc   1500
attgttgaat ggttcgatcc ggtttgtaaa taaaataaat tttgtaggcg cacttgtttt   1560
```

```
ccacggtttt cgtgttacgg tttcatgatt ccctagatct ctggttagaa ctaagttttt      1620
tgtcggtaat tggatttggt aagggactgt tactgtggtt gaattgtaga tccagtcatc      1680
ttctacatga gtgtagggtt ccttagggca gatcttgtgt tttataattt taattttgtt      1740
gtttccctga ttttgaacct gtttggttgt tcagattcgt cgagtcattt ccattcatta      1800
aaagtttcta taattttatt tgaatcttct gaatctgtgc ttgtattacc cagatttcta      1860
taaacctatc ttgatttcaa gtgtgctatg tggtaactgt tgatattttc aagcttaagc      1920
aatactgatg tgactaaaac ttaactaatg aactgaatgt tttttgtaca cgaactaata      1980
tggtgttttg ttatgtttca gagg                                            2004
```

<210> SEQ ID NO 169
<211> LENGTH: 1067
<212> TYPE: DNA
<213> ORGANISM: Cucumis melo

<400> SEQUENCE: 169

```
tggatcgacc atgacattca aaacccttta agatatggat cttataaaat aaatgtaaag       60
ggtaaacaat tcttccttgc ttaacccaag ctatatattt tatgcactaa tttaggtatt      120
agagtatatt cagctgaaca ccacctacca atgctagtac tttaatcagt caattctaac      180
ttcgataata tatctcaacc aaattagtga aaagagtcg taaatgaaaa actatgtacc       240
aagatattct atttgttttt tttatgttta aatatctcaa agataatacc taaaacgttt      300
tctcctcgta caaagattcc tcatttactt tttattgtcg taaactctaa tacaataaac      360
taaaacaagt acaaatacac tagctttaga aatctacttt ttattgaaac caaaaccaat      420
aattcaacat ttcattttca ccgacaaacc tttgtaaaca attgaagtaa ttttgttgg       480 tactatgaat agtaacatca agtcttcaag tgcatcatat caaccaagac atgttcttaa      540
aagcgacact aaaagattta aaaccaaaag catttatgaa atccgaactt aatcaaatcc      600
taaatatttt tcacttaaaa aaaaaaaaat aggaagaaaa attgacataa atgggatatt      660
ttcgttttca aactggcaag ccagcatgca ccacgttgtt gacgtgtcct tccacgtcgg      720
aaaaaaaaat attccacag taaaagaga ataaatgaa agtcgttgac tctcccttag        780
tcggaggaag cgcgtgaagc tgaagccgga ttagaaatcg gcaataaccc cgacacgtca      840
tcgaaatgct agtatcaaat attgtccgtt ggatcttcct tcaccaactc tatttgaacg      900
gccacgatct tccaggtcca acggttcgga agaatctttt cgaaattcca tggctagtcc      960
ctacactcct ccctattggc tccctagggc atcccgaccg gttattccgg ttgccgggaa     1020
ggtggctgga cgctataaat acccgctttg ttcatctcgt agtcctt                   1067
```

<210> SEQ ID NO 170
<211> LENGTH: 92
<212> TYPE: DNA
<213> ORGANISM: Cucumis melo

<400> SEQUENCE: 170

```
gtaccgttga gcttcgcctt ctaatagagc tctggttcgg ttggcgtatt agctcgaatt       60
ctttctctct tccagatcta cgctgccgat tt                                    92
```

<210> SEQ ID NO 171
<211> LENGTH: 845
<212> TYPE: DNA
<213> ORGANISM: Cucumis melo

<400> SEQUENCE: 171

```
catcaggttt gcgagctctg ttccaccatt tttcttttcc tgaagctttg agcatgcttg      60
tgattcttca tttcctcatt tctttgatgg tttatgaaag aatttagggg aattttctct     120
ttttgtattc tagtggtact ggtagatttg tttgaagttt gtttctcttc ttctgagaag     180
tgaattcttc cagatctgac agttgctttt gattttttct ttgggaatta gtgaatgata     240
cttcgatact gttttttgct ctctgagatt ctggatctcg ggccttgggg ttttctattg     300
tcttttggta gctatgtttc gtttgtcagc ttgtatttgt cattgttgaa tggttcgatc     360
cggtttgtaa ataaaataaa ttttgtaggc gcacttgttt tccacggttt tcgtgttacg     420
gtttcatgat tccctagatc tctggttaga actaagtttt ttgtcggtaa ttggatttgg     480
taagggactg ttactgtggt tgaattgtag atccagtcat cttctacatg agtgtagggt     540
tccttagggc agatcttgtg ttttataatt ttaattttgt tgtttccctg attttgaacc     600
tgtttggttg ttcagattcg tcgagtcatt tccattcatt aaaagtttct ataattttat     660
ttgaatcttc tgaatctgtg cttgtattac ccagatttct ataaacctat cttgatttca     720
agtgtgctat gtggtaactg ttgatatttt caagcttaag caatactgat gtgactaaaa     780
cttaactaat gaactgaatg ttttttgtac acgaactaat atggtgtttt gttatgtttc     840
agagg                                                                 845
```

<210> SEQ ID NO 172
<211> LENGTH: 2018
<212> TYPE: DNA
<213> ORGANISM: Cucumis melo

<400> SEQUENCE: 172

```
actattggag acgacgaagg aaaactctaa tgtgagctta gaattgaaga tggtgaacaa      60
ttgggagtct tttttaaaaa tctttcgtcg gtatattgaa atttccttttt acactcaaat    120
aaccccccctt ttcacgcgtt caacgtcttc aaaccttcct ttttcaatta ttttttcgtt    180
tacattaatg acatttaggt aataagataa attagtggat tcttttgtga aaaatgttag    240
cccatttaag acttttatga aatatattag aaaaaaatca tatagcaatt tatattattc    300
tagttaaaag cccataatag aaactaaccc aacctaaagt aacgtaaaca ttcaataaga    360
gagacaaatt ttaaaataat ttctaattaa aaaaaaaatt gtcaagaccg tccgggtcgg    420
atccaaaata taacccgaac cggccggttt agcatctata taaatacacc tttagggttt    480
ttattctctc aagacttcac cgcatttcca cttctctgag gccacggtca gccattggag    540
cagctcaata atcctttgac tccctactac ggtaagtcga ccttactgct ttcggcttct    600
agttttttca atcctgtcat tagtcctttg gagttcttct gtacatttat gacgttttcg    660
gctcgtgttt tgtttcgcct gtatgtagtg ggttttttcga gttttgtttt tactttttttt   720
tatacttgca ggaattagtt gaaatctatg tacttcatgc cttggataat actcttgatc    780
tgttgtgtta ttcaaaaatg aattgttttta agatggtatt tgagaatggt catgtgagtt    840
ttgcctactt ggttattaaa atgaattgtt ttaggatggt atttgagaat ggtcttctgg    900
gtatttggtt ggaacctttg tgctctgcta tgaattaggg tgttctcccc gttttttttt    960
tttttttttct tttggttatt aatatatctt ttatgactac ttattcatat atgatatctt   1020
ttactcgtaa attttgactc atttgaaagt tttatcctta gtcctttctc attcaggctg   1080
taaaggtatg ttgttagggt taaaatagcc tatgcaggaa agttctgtat tgttctaat   1140
```

| | |
|---|---|
| tattgcattt gtgtgcattt gtatctagtt tatttcttgc tgagagtatg cttcatttt | 1200 |
| tagtacacat cacttgtgcc actttattat agttgcacat ttttgtttat ggagaggatg | 1260 |
| aatagcattt agggatgtca atttttatt gagaaaaccc tctctcctac ttaagcttgg | 1320 |
| ggaattttg ttctaaatgt ggtaaacata atacttcttc ttattttaat ttgaatggaa | 1380 |
| ggggaagacg aatactaata ttttcaacga accttcacaa cttttttttc ttatttagga | 1440 |
| agccatgttt ttcaaaattg tactgtgtga tccacatatt tatcgattat tagtgaatcg | 1500 |
| aataataatt agagttttat tggtataatt ttgaagttca gacttattac atttgtggaa | 1560 |
| agtttggtta caattttcaa ttttattgga atcctaagaa ctttgtgtta acatatattg | 1620 |
| agttttcttc tctttttttt tactcattaa gttctctatt aggaatgttt ggttcaatgt | 1680 |
| cacatagtcg atagctaaga ccagtgaccc acaaagctat gattgaacga aaacaagcc | 1740 |
| tttcacatct tggtaggaat ttgttatttc tcaatagatt tacagagctg tttcatgtga | 1800 |
| tcacaatttt tttctatttt tctgaagttc tctattagga atgggctatc tggttagttg | 1860 |
| cttttgagag aacatgtgga ttggtgttgc tcggtttcct tgcctttgta atttttgtcct | 1920 |
| tggaaaaagc aaaatgatta ggtatcctga tatgcataac atgtttaagc caactagttc | 1980 |
| tcactttttt agtgcaaata attgatcttc aggaatcg | 2018 |

<210> SEQ ID NO 173
<211> LENGTH: 565
<212> TYPE: DNA
<213> ORGANISM: Cucumis melo

<400> SEQUENCE: 173

| | |
|---|---|
| actattggag acgacgaagg aaaactctaa tgtgagctta gaattgaaga tggtgaacaa | 60 |
| ttgggagtct ttttttaaaaa tcttttcgtcg gtatattgaa atttccttt acactcaaat | 120 |
| aaccccctt ttcacgcgtt caacgtcttc aaaccttcct ttttcaatta ttttttcgtt | 180 |
| tacattaatg acatttaggt aataagataa attagtggat tcttttgtga aaatgttag | 240 |
| cccatttaag acttttatga aatatattag aaaaaaatca tatagcaatt tatattattc | 300 |
| tagttaaaag cccataatag aaactaaccc aacctaaagt aacgtaaaca ttcaataaga | 360 |
| gagacaaatt ttaaaataat ttctaattaa aaaaaaaatt gtcaagaccg tccgggtcgg | 420 |
| atccaaaata taacccgaac cggccggttt agcatctata taaatacacc tttagggttt | 480 |
| ttattctctc aagacttcac cgcatttcca cttctctgag gccacggtca gccattggag | 540 |
| cagctcaata atcctttgac tccct | 565 |

<210> SEQ ID NO 174
<211> LENGTH: 1453
<212> TYPE: DNA
<213> ORGANISM: Cucumis melo

<400> SEQUENCE: 174

| | |
|---|---|
| actacggtaa gtcgacctta ctgctttcgg cttctagttt tttcaatcct gtcattagtc | 60 |
| ctttggagtt cttctgtaca tttatgacgt tttcggctcg tgttttgttt cgcctgtatg | 120 |
| tagtgggttt ttcgagtttt gttttttactt tttttttatac ttgcaggaat tagttgaaat | 180 |
| ctatgtactt catgccttgg ataatactct tgatctgttg tgttattcaa aaatgaattg | 240 |
| ttttaagatg gtatttgaga atggtcatgt gagttttgcc tacttggtta ttaaaatgaa | 300 |
| ttgttttagg atggtatttg agaatggtct tctgggtatt tggttggaac ctttgtgctc | 360 |
| tgctatgaat tagggtgttc tccccgtttt tttttttttt tttcttttgg ttattaatat | 420 |

```
atcttttatg actacttatt catatatgat atcttttact cgtaaatttt gactcatttg        480 aaagtttat ccttagtcct ttctcattca gggtgtaaag gtatgttgtt agggttaaaa         540
tagcctatgc aggaaagttc tgtatttgtt ctaattattg catttgtgtg catttgtatc        600
tagtttattt cttgctgaga gtatgcttca ttttttagta cacatcactt gtgccacttt        660
attatagttg cacatttttg tttatggaga ggatgaatag catttaggga tgtcaatttt        720
ttattgagaa aaccctctct cctacttaag cttggggaat ttttgttcta aatgtggtaa       780
acataatact tcttcttatt ttaatttgaa tggaagggga agacgaatac taatattttc       840
aacgaacctt cacaactttt ttttcttatt taggaagcca tgtttttcaa aattgtactg       900
tgtgatccac atatttatcg attattagtg aatcgaataa taattagagt tttattggta       960
taattttgaa gttcagactt attacatttg tggaaagttt ggttacaatt ttcaatttta      1020
ttggaatcct aagaactttg tgttaacata tattgagttt tcttctcttt ttttttactc      1080
attaagttct ctattaggaa tgtttggttc aatgtcacat agtcgatagc taagaccagt      1140
gacccacaaa gctatgattg aacgaaaaac aagccttca catcttggta ggaatttgtt       1200
atttctcaat agatttacag agctgtttca tgtgatcaca attttttttct attttctga      1260 agttctctat taggaatggg ctatctggtt agttgctttt gagagaacat gtggattggt      1320
gttgctcggt ttccttgcct ttgtaatttt gtccttggaa aaagcaaaat gattaggtat      1380
cctgatatgc ataacatgtt taagccaact agttctcact tttttagtgc aaataattga      1440
tcttcaggaa tcg                                                         1453
```

<210> SEQ ID NO 175
<211> LENGTH: 1999
<212> TYPE: DNA
<213> ORGANISM: Cucumis melo

<400> SEQUENCE: 175

```
ggtctcagac ccataggaat agatcattta ttgccttatg aattagttta tgagtacata         60
ataattgtca accgtataca atcaacatg aaagaatata atgttgtaca tagtcattcc        120
aagtttacta atattatatt ttaggagtgt tctacaccga acctgtcaca tgtacactgg       180
gtatgctacc cctgaattca atatcataaa gcaactttaa ttgtcaagca ttctcttgac       240
catttgtgac ccatttgctc ctactttttc aatcaataac tatcacaaaa gctagatac        300 cacatgtgat aaactcactg aaatcaggta tatggttacc tgtgcttggt cagcactcaa       360
tcagattcga aggcctagtc tttgtatttc cccccctctg cacactacaa atagtcctcc       420
acgtaaagac ccataacaaa acgcaaacca agtacagaaa atctagccga aatccagacc       480
actcaaacat aacaaatctt ctggtaagtt tgaataaaat ataaaactaa cctatttaat       540
caaataatac aataaaatgg aagcaactaa cataacatat ctaaatatga tcacgtagta       600
ggaaaaaaaa aaacattcca aaactattaa caatcattct taatggtatg ggtcaatccc       660
cattatttag gactataaca agaattcctc atacctaatg ccacatccta tgtccaaccc       720
tcgagattac ctcgtgagta atcaatctta ttcatcctta tttcaaatta tgtgaaattt       780
ctcatcaggt tgatcatatt gactttcaat acaacttatg attaatcttt cccttgatat       840
aatttcgtat gaaaaggaag ttgacattat gtgatttct cataaggtaa accaagtaaa        900
cttgacatga cgtcttaaca agtccttggtt tctaagtgta attactgca gaaaaaatcc       960 taaattctat gacttttcct atgagattga ccaaatcaac tttacgagaa atcttgggaa      1020
```

| | |
|---|---|
| gccatacccta caaagtcttc ccccaagaaa ttacaatttc tagtaaagat tgttgaaatt | 1080 |
| taccctccaa tttttccgtg aaaatttgac aaacttgtaa gaatatcaaa tttgggttgg | 1140 |
| atattgacat tccaaaataa gtagttttaa aaaggattta tccaacaata atagaagaaa | 1200 |
| aaagatagga aataacatac ccacgtaaat ggaatgtaaa tatttatata ttaggtgtct | 1260 |
| tgaacgaccg tcaaacgaaa ataaattgtt catccgaagt tgaaactctt taagtgtaca | 1320 |
| tttatcttttt cgtaagaata aaatgtaaaa ttaacgtgtg aaaggttggg ttaaataagt | 1380 |
| tatgtagaga taatattgaa gatgatagaa taatcacgat cgatgaatta gtatagtccc | 1440 |
| agagcggatt taaacctctc tcactttcat gctttctata tatatcaaaa taatttcaag | 1500 |
| tagttggttt agtcgtaaaa aagtcaacca atctcttttta gataaacctt gagttattaa | 1560 |
| aaaattagat caaagataat cgttgaaatt gaaattttaa gagtataatt ataacaaatt | 1620 |
| ggaaagttct aaagtagttt ttgcaatatt ctccatcaaa atagagtaga aaaatatttt | 1680 |
| agtaattttc ttatcttaat tttagttttg taatagttat taggatggtc ctaagttctc | 1740 |
| aatccgcttt tagtccataa aaagaaagaa gagagagaaa aaaagtcccc gatccgcgac | 1800 |
| acataccaat ccaaccaatt atgcacaatc catgtgatat cgaacggtca caagaataaa | 1860 |
| tgctttctac acacggatca ccatccaacg gctttccttc catctcatcc tctatataat | 1920 |
| ctaccaactc tgtcatcttc gacacacttc aattatctca gctttttattt catcggattt | 1980 |
| tccatcaaac aaggcaaca | 1999 |

<210> SEQ ID NO 176
<211> LENGTH: 2004
<212> TYPE: DNA
<213> ORGANISM: Cucumis melo

<400> SEQUENCE: 176

| | |
|---|---|
| tatagtttgt aacaatctac tctatgttct ttcaattttg atacatttga atcttaaact | 60 |
| ttattgagtt acacaatata gtccttgtat ttttaaaatt tataatgact ctatttatat | 120 |
| taatattata gaatttttg ttaaggttta ataaaaattt ttctgtataa ataaatcgaa | 180 |
| cacgaagtct atatttagac tgcaatatag taaaacctga catctaagtt tggtgaattt | 240 |
| tgttttgctt taaaaactaa actattacaa ttttaaaaat atttttaattt agttaatgca | 300 |
| cattaacttt acggagtaaa ttttttacaag attgaatata catagattaa atagttataa | 360 |
| aaccaaagat tagagtaaaa aacatttaaa tagaaagaac taagattttt ttaaaacgaa | 420 |
| aatgatacta gatacatata tatgtatcta tattataatt actcattta acatatagtt | 480 |
| ttgaaagaac aaagattagt tgcatgtgtt gattgttttt aagaaggaaa taatttttga | 540 |
| atggaaaatt ttcaaaagtt ttaaatttga caataaactc atatttaaag tgtactacaa | 600 |
| atttaacctt ttggttaaac tccttgttta gttcaatcat gtaataaatt ctcattccaa | 660 |
| gaatcgtttt agaaaatttt attgtgcatt taataaaata tagaacatat atggcatata | 720 |
| aaaattgatt acttttttct tttttggga cgaaaaacac attagatata atctttttg | 780 |
| aaagtttatg aactttaaaa atgggttatt ttatacggtg gtcaacttta ttttattgaa | 840 |
| attattgagt ttataaagat tgttatatca tttttcttct ctctttcact agaatacaat | 900 |
| caaacctatc aaactctcta tgacttattt agaattcttt ttgttatatt tttgaaatta | 960 |
| ataaatgaaa agcttagagt ctaaattata acaattaaaa ttgaaaattt tgcaataatt | 1020 |
| ttatttttag caaaatgacg tttggttttt ggggattggg aatggatcga tactatcccg | 1080 |
| attccggaca aagaaaccga cccgagattc gaatttttc cattcccaaa cagagcactt | 1140 |

```
aaaatttaag caacgttata acggcgtcac cgaactaaac ggaaaaatat gaagaaaatt    1200
agaaaaagaa aaacggaaca gtcaaacgtt acttcacgtc aatggcaata ttcattttt     1260 tttttgttta aataattgaa tttaattaat ttggtttata aaatagagt cctcatatat     1320 cgcgaatgcg catttgatcg tgaaggacag cttctcccct tgtgttcaaga gagagagatc   1380 tatcattctt atttggggcc gatctctcta ttctcctctc ttctattccg taagttttc    1440 tcattcattc tcctctctca tttctctccg agatctgttt acaatccttt tgattttcat   1500
ttttcctgct tcgatctgtg ctcctggtga ttcccttttc ctgttttatc ttttgttgat   1560 cttgaattg attgttcttt tgtgggtttt cattgatttg tattttctga tctgggtttc    1620
tgttttctcg ccttgatgtt ttgtatttgg atctgatctg acgaccctt tttttttttt    1680 tttttatttg aattgctttt ccaatgttta tacctggatt tttattgatg catgggttta   1740
accgattggt tggatgcgtt ttctttgtgc tggatctagg tgtccttgtt tttaatttga   1800
attgtgggta aaaatggcat tattgtaatg tgtttggagt ttgattttga atcttggcta   1860
gttgattttt gaattacaaa gatcggatcc tcttcttttt tgggttgtct taagattttt   1920
ggctggttta agtatttgat gtcgttgtat tttaagggg aactgatgcc ggcttgttgt    1980
gtttgtattc agtttacttg aaaa                                          2004
```

<210> SEQ ID NO 177
<211> LENGTH: 2005
<212> TYPE: DNA
<213> ORGANISM: Cucumis melo

<400> SEQUENCE: 177

```
aattagcaaa ttgtatgtaa caacgtcatg aagaggcatt tcatcgaaca atttaatagc     60
agagtcaaga tggcccagtt ttataagttt attgatttct cgattcttaa ggtaaatgag    120
atcgcgagca tggaaatgca gacccaaacg agaatatggg tgtggtaaat ggaccggtga    180
tgttgtggct acaaattcgg attttacagc agtaatagtt ctgacgaagg aagcgaattt    240
agtgaccttt cgcatcacag tttaagctta tcagagacct gaacaagggc tctagctcta    300
caacttagaa aggtttgata tggtccgtga tcgggaggga ccgaataaca ggcgcttaaa    360
ttgttgttca taagaagag gattgtcgtt gatgtatttt aaccaagaga tgattagtta    420
tccacatcca cagagagaac agaagacggc tttctaaatc tacaccgata aaaataaccc    480
taccactttg tttctttaga aaagggtcac attctttaaa aacattagcg tcgaggatta    540
atagggtata ttgactaatg ctctgttgg atttcgagaa ataccaattt acaattgatt    600
tcaaattaat tatgttttgt tgttgcacga agataaaaa gaatttaaaa ttcaaaagga    660
tctcaaatct tatttttaac ttaaaaactt ttatgaccca aacggtttat gtatgattta    720
aaagtagaat acctctgtga attcttaatt tttttttctt tccaattacc acataaatat    780 gaaatttaa atacatttat tttaaatttt atatccgaaa caaataata atttaaaact    840 atttctcata tatgaagtgt gattcgatct aaattataaa ataataaaaa tttacatcta   900
gttttgatta tttttttttc gttagatact aaattgttaa gaaataaca tttttaatcc    960 aaagttttga agaatatatg acttttaaaa tggtatttat cttttagtg tctgattttt    1020 aaaaaatgga tttcaaaagt tcatcaaata gcattgtatt tttatttaa ataatttga    1080 catttaaaat tagagtaatg gtttataaaa gacacttgat ctctaaaact attttcttag   1140
atataaatac gtatgattat ttttaaaaat caatcaaaat aggtaaattg taaaaaaaaa   1200
```

```
aaaaaaatca taaaacatga tagtagttgt aattatgctc tcaaactttc ggttatgaaa    1260
aataaacatt ttaacttttta gacgtgtcaa agttgagtca agttggacct tcaaagttat    1320
gtagttatat aaattgtaat atatgtataa gcttgtggat tcaattttat catttatggg    1380
tccaatctct acaattatcg taagtctatg ggtcaattgt aacacatgtg gagtttaaga    1440
gctcaatttt ggacgtggat gtgttttgca accaactcca caccttaaaa aggtgttttt    1500
tttaattta tcaaaaaaca agaatttaga atctttaagt ttatctttaa aaatcaacgg    1560
acattttgaa aaccaattga aactactgtt ataaacctaa caactaaaag tatattttt    1620
aagaccgaaa gcataaatcc ataaaaaaaa aatccagaac tgaaaatgta acttttatag    1680
ttgaaaattt agctaaatta tacatattaa aattcaagga ccatataaaa ttaaagtacc    1740
tgattaaata ataacgaatt aatgtttggt atttttaacc tacattagaa aaaaaaaaca    1800
aaagaaaaac ggcatactat ttgtcaagcg tccgatggga agaaaatcca acggtgagtg    1860
ttagtattga aatacgcagt tctcgtgaat gagcctggct tagatttggg aacaagagcc    1920
aaccccttc gaccgagaag ccgtcgtctt caccatattc gcctcaacca ttcgatagcc    1980
acgtttgaag aagaatagga ttgcc    2005
```

<210> SEQ ID NO 178
<211> LENGTH: 1978
<212> TYPE: DNA
<213> ORGANISM: Cucumis melo

<400> SEQUENCE: 178

```
aattctaaca actccggaac aaataattta gcatggattg aaatataaat cttcttgact      60
tgcaaaaaaa tcattgtaat ggtcttatgt tggttatagt tagggtatcg aaacgccata     120
caggaatatg ggattaaagt taacttttgt tcatcaattt cagcttatga acttctaaaa     180
tatcaatttt cctttgaac ttatatgtta ttacccttt cgattgtggt atgttaatta      240
atatctgaat ctcagtcctt atgaaacttt tttatactgt cacaaacata tgaagtttta     300
ttgtaagttc ttagaaatca tctaaaaga gtagtttgtt ggactattta ttttatttt      360
tcttattaag ttgttttcac gccatttcag taaaataact atagtgaata gagaatcaaa     420
cttctaatct taagttaagg tagtagggta tatgctaatt caataagata atccgtgatg     480
cttgacatct gacttaattg ttataagttt taaattttt attgtaatat ttaaaatact     540
agttttggt ttctaataaa gaaataattg aacaattaca aatatttata caaaattaaa     600
ctagaatata tgatcatttt ccttcgtgtt agaaaaaggg aaatatatgt gtgtatttat     660
acatattaga tattgtttta ctatattcca ttttcctcac gggaaatgga ggattgagtg     720
ggagataaac attgtcccca agagaattgg gaatggaaat gcaaatgaca tggccctcca     780
caaaattgtt cgcctaaaaa tgggctttct cacttctcac tccgcaagaa aaatatcgtt     840
tcccttcgaa ttcgggcaag atctcaaaac cacatgtttt tctttcttta tttttcaagc     900
ctacattatt tataaaaata taacttaagc agagaattat gtaaattcaa gtccattttt     960
cgcttcactt agctaaatca ttaacaaatc tgtaattttg ttcataaatt agctcaccaa    1020
ttatgtttta gcccactaag gcccattaga catttttatt agaaaaacat gaaccgttgg    1080
atcaagatgt gtgttttctt ttctttttct ttttattttt tttgggtttt ggtggatcaa    1140
ttcgtagctt tagcaaccta ttattatatg gagggaaagg gcgtattaat ctgttagcgc    1200
cgtccgggag tttagctttc ttccccgagc ctcggtctta tccctaact ccaaaaccct    1260
agcccaaagg taatccactc cttccccctc cgctcttcat ctttttctat tcatcatctt    1320
```

```
taatctgttc tcccttttgg ttcttagatt cttcttttgt tggattcttt taatctttac    1380
tcatggttgg ccttgtaagt ttagacgacg tttttataca ttggttaatc ctgcttctct    1440
atctattcgc acgctagggt tttcctattg ttttctattc tgctctactt ctgcaaggtt    1500
gtgttcttct tcgttcaggt ccctttttttt aaccgaaatt aaattaatgc aaattcgttt    1560
gtgcttctaa ttaggaagcc ttttggaaca tctcgacatt tgattgctg catttcattt    1620 cgggtatatt tctatgattg aaggatgtgg gtctgttcac tgcatggtca ttacttatgc    1680
agctatgctt atcgagtcca ttatgtttgt gcaatctgtt tccggattca taatttttta    1740
gtaattgatc agtagatgaa aaagatatt gtaatattcc ttgagtgttg caccagtctt    1800
ggtgggtatc tgctcctgct ctttgcttgt ggattttact tttattatat ctgtattatt    1860
cgaaatgttc tgttcttgtt ataacttata cccgaagatg tgttcctccc cgcgtctagc    1920
gttgtgggtt acttatgatg gacatggttt tgattctgtt tggtttgtgc agggtacc     1978
```

<210> SEQ ID NO 179
<211> LENGTH: 1263
<212> TYPE: DNA
<213> ORGANISM: Cucumis melo

<400> SEQUENCE: 179

```
aattctaaca actccggaac aaataattta gcatggattg aaatataaat cttcttgact      60
tgcaaaaaaa tcattgtaat ggtcttatgt tggttatagt tagggtatcg aaacgccata     120
caggaatatg ggattaaagt taacttttgt tcatcaattt cagcttatga acttctaaaa     180
tatcaatttt accttgaac ttatatgtta ttacccctt cgattgtggt atgttaatta     240
atatctgaat ctcagtcctt atgaaacttt tttatactgt cacaaacata tgaagtttta     300
ttgtaagttc ttagaaatca tctaaaaaga gtagtttgtt ggactattta ttttattttt     360
tcttattaag ttgttttcac gccatttcag taaaataact atagtgaata gagaatcaaa     420
cttctaatct taagttaagg tagtagggta tatgctaatt caataagata tccgtgatg     480 cttgacatct gacttaattg ttataagttt taaattttt attgtaatat ttaaaatact     540 agttttggt ttctaataaa gaataattg aacaattaca aatatttata caaaattaaa     600
ctagaatata tgatcatttt ccttcgtgtt agaaaaggg aaatatatgt gtgtatttat     660
acatattaga tattgtttta ctatattcca ttttcctcac gggaaatgga ggattgagtg     720
ggagataaac attgtcccca agagaattgg gaatggaaat gcaaatgaca tggccctcca     780
caaaattgtt cgcctaaaaa tgggctttct cacttctcac tccgcaagaa aaatatcgtt     840
tcccttcgaa ttcgggcaag atctcaaaac cacatgtttt tctttcttta tttttcaagc     900
ctacattatt tataaaaata taacttaagc agagaattat gtaaattcaa gtccattttt     960
cgcttcactt agctaaatca ttaacaaatc tgtaattttg ttcataaatt agctcaccaa    1020
ttatgtttta gcccactaag gcccattaga cattttatt agaaaaacat gaaccgttgg    1080
atcaagatgt gtgttttctt ttcttttct ttttattttt tttgggtttt ggtggatcaa    1140
ttcgtagctt tagcaaccta ttattatatg gagggaaagg gcgtattaat ctgttagcgc    1200
cgtccgggag tttagctttc ttccccgagc ctcggtctta tccctaact ccaaaaccct    1260 agc                                                                1263
```

<210> SEQ ID NO 180
<211> LENGTH: 715
<212> TYPE: DNA

<213> ORGANISM: Cucumis melo

<400> SEQUENCE: 180

```
ccaaaggtaa tccactcctt cccctccgc tcttcatctt tttctattca tcatctttaa    60
tctgttctcc cttttggttc ttagattctt cttttgttgg attcttttaa tctttactca   120
tggttggcct tgtaagttta gacgacgttt ttatacattg gttaatcctg cttctctatc   180
tattcgcacg ctagggtttt cctattgttt tctattctgc tctacttctg caaggttgtg   240
ttcttcttcg ttcaggtccc ttttttaac cgaaattaaa ttaatgcaaa ttcgtttgtg    300
cttctaatta ggaagccttt tggaacatct cgacattttg attgctgcat tcatttcgg    360
gtatatttct atgattgaag gatgtgggtc tgttcactgc atggtcatta cttatgcagc   420
tatgcttatc gagtccatta tgtttgtgca atctgtttcc ggattcataa ttttttagta   480
attgatcagt agatgaaaaa agatattgta atattccttg agtgttgcac cagtcttggt   540
gggtatctgc tcctgctctt tgcttgtgga ttttactttt attatatctg tattattcga   600
aatgttctgt tcttgttata acttataccc gaagatgtgt tcctccccgc gtctagcgtt   660
gtgggttact tatgatggac atggttttga ttctgtttgg tttgtgcagg gtacc       715
```

<210> SEQ ID NO 181
<211> LENGTH: 2000
<212> TYPE: DNA
<213> ORGANISM: Cucumis melo

<400> SEQUENCE: 181

```
aaataatttg tggattttat catattatgt accttagact ttgtaaggtt tataacacaa    60
gatgtggaga atcccatga tgaacattgg acgttattat atcctttgaa actaaaaaca   120
aaggaaaaaa gacaaatggc tgagtataag aaaagagaa gaaacaacca aaaagctaaa    180
atgtcatgct ctcatatgta acatatttga attgggattg atttcaagat gtattttaaa   240
ataatttaac acacgataaa ataattctaa caaactcaaa attactctta aacatttact   300
tgatatcttc gacataatga cttttgtttt aatacaactc aaaacataat taaggttggt   360
tttaaatgac aacaaacgaa aaactcgatt ctaatttcaa tactagtctt tgaaagcct   420
aaggagcgtg gttttgaatt gtatagcaag gtttcgaaaa ttttaatcat caaacaatag   480
gtatatttac ctgttcctca agtacagtta attcatagct acttgtcgtg cttcctacga   540
caacattgta agacttgcca cacactaatt gaagccgttg ttgaaggtag ttttccatgt   600
atagcttgaa tcgacggatg accaaagagg ttgaagaagg tttgaaaaat aggggaaggg   660
atatacaaag tttgagagtg agagagggag agaaatagaa atagaagaga ctgaaaaatg   720
taaaagaaag gatgaaaaaa tgtgggtaa acgcaaattg gatttttata gtagtatttt    780
gaaaatgcta tagaaaggct atgtatagta gtgcttccaa agttctatat gaatgagaca   840
aatcaaaata tatttttttt gattaattaa ccccaaaaag actcataaaa aaatcttata   900
aatcccacta agatattgca tgttatatgt agtaaaattt atcgttcaaa taaaccttaa   960
acataattca aacgaagaaa gtaaaaattt gaatttctta tcttacatca ttcaaccaaa  1020
caatttccat ataagagatt aaacttctaa ctttaagaga gagatatcca gcatatgcaa  1080
cctaaaccaa cagtgacttt gctatatatt tgcacaaaat gtgggggaca aagttgtaat  1140
ttcggaatat caatgattaa agaaaaggta aaatttaaaa ttcggaagct tgacgtggca  1200
acacggaatg gtgatgatat ttccaactcc tcgcgacttt tagaagttgg cctcaccaac  1260
cgcatatccg cccctttgcc acgtgtcaga ctacaacaac ttccaacaat ttcctttaag  1320
```

```
aacaccaaat tatatcaata aatatttaac ttaaattaag aatatatttg ttacaatttt    1380
cctactgagt tagatagata gacagacttg tcaattaact aataagtcca aagtcaattt    1440
actcaacata gatacaattc taatttgagt gtgaaataca tattcaaatc aaaattatta    1500
ttaagaggaa aaactgattt gctttctcaa tttaaaatat aatattttga aaagaaaca     1560 cacatgtatt atggttttca atatatttac tttcttagtc acctaatctc aaactaattt    1620
ttgaagaaat taaatatata tattatcatt tttattttct tggttatgat attggtatag    1680
aatcaacaaa actacaagtg tcctctcctc tgctatcgat ggggattaga ctctaaactt    1740
gtttagcgat tagtaattat atattagaaa aagtttatgt taatgtggac ccgacaatct    1800
caccaatagg ctcttcactt caccaacccc cgacccattc cctctaataa ttcgacacgg    1860
ctcatccccg gttcgaaccg ggccgacgtc ttcctattta acacacctcc atttcctctt    1920
ccctccgcaa cacaaacaga gacctcaccg gaaaatcaag ttaaagcaaa accaaagaga    1980
agcttcatca ctctccggaa                                                2000

<210> SEQ ID NO 182
<211> LENGTH: 2000
<212> TYPE: DNA
<213> ORGANISM: Cucumis melo

<400> SEQUENCE: 182
gcatcttatg gatgtagtca caacatattt atatggattt tctgataatg atatttatat      60
gaaagtccca aaaggattta agatacctaa aacatataaa tcaaattccc ataaactatg     120
ttcaataaag ttacagagat cattgtatgg attgaaaaaa tcatgacgaa tgtgatacaa     180
tcgcctgagt gaatatttgt taaaaaaata atatcaatat aattcaatat gtccatgcgt     240
ttttataaag aaatcaccgt caggatttgc tattataact gtatatgttg atgatttaaa     300
tataattgaa atttttgaaga gttttcaaag gcaatagaat attaagaaag aatttgagat    360
gaaagatctc agaaaaataa aatttttgtct tgattttcaa atcgagcatc tagtaaaagg    420
gatatttgtt catcaattaa cttatacaga gaaaatttta aaaagatttt atatagataa     480
aacacattca ttgaacattc taatgcaagt tcattcatta aatgtgaaga agatatttt      540 tcgacgtcga gatgataatg aagaactcct tagtccagaa gtaccatacc ttaatacaat     600
tggtgcactt attttgtcaa taatcaagac cagatattgc attttctata aatttattag     660
ctagattcag ttctccaaca aaacaacatt ggaatgaagt taaacatata cttcgttatt     720
ttcgaggaac aattaatata agattatttt attcaaataa atcaaatttt aacctagtta    780
gttttgcata ttcttgattt ttatctgatc cacataaatc tagatctcaa acaggttatc    840
tattcacatg tggaggaact gctatatctt aacgatcagt gaaacaaatt accataacag    900
tcaactcttc aaaccgtgct gaaattctta caattcttga ggcattcatg aggctagcgg    960
agaatgaata tggttaaggt cgatgactca acacattcga aaattatgtg gtttgtcttc   1020
tagtaaactc cttccaacaa cattatacga agacaacaca acttgtatag ctcaaataaa   1080
atgaggttat attaaaagtg atagaacaaa acacatctca ccgaagtttt tctatactca   1140
tgatcttgaa gaaaatggtg acatcacagt acaaaaaatt tgttcaaaag ataatttggt   1200 agatttatttt acaaaattat tacctactgc aacctttgaa aaattggtgc acaacattgg   1260
aacgcgacga cttagatatc tcaagtaatg ttacatctta cttgccaagt taactataca   1320
tagtgacatt tggtggagtt gtaagaaaca ctaatattgg agaaaaatcg aaagaaattg   1380
```

-continued

| | |
|---|---|
| gaaaatatgg agaattgaat ttttttttaga ttttttcttat tttctaatttt taggtttccg | 1440 |
| tattctgatt atgcctcatt ttcacaacat taataacttt aataagatga tttcttgggt | 1500 |
| taagggaaaa aaatcatttt tttagagttg cacgtacaaa aatattatca taacatatcg | 1560 |
| attataataa accaattcac cgtcaaccta acctaggtag agtttgagtt aaatgttaaa | 1620 |
| agaatatcca cccctcaaca ttgtaatccc aactaataaa tcagcaacct aaagtttttt | 1680 |
| ttaaaaaact aaaagaaga gcaatatatt ttttttacta ttatttttttt aaagagtgga | 1740 |
| tttatttatt aaattaaaaa atgaaaagaa gaaaatttgt tagtttgggt aatccgaaaa | 1800 |
| cccgattatt tgggcccgag aaaccgacgt tttgtttatt gttcctcacg gcaataagta | 1860 |
| atggcgtgaa tcgaccgcgt gcgcttcaag ctatctagac atttttatat cctccgatta | 1920 |
| gaaaccctaa ttcagattct ccgtattacc caccctggaa catctttgaa acgcgaaaag | 1980 |
| gtgacccgaa gaaacttgaa | 2000 |

<210> SEQ ID NO 183
<211> LENGTH: 1989
<212> TYPE: DNA
<213> ORGANISM: Cucumis melo

<400> SEQUENCE: 183

| | |
|---|---|
| attacttgaa cttaatccac atttatgtct ttatataaag ttcgaatact cataatatag | 60 |
| ccaagaaacc ttgtttattg gattttgagt tttatcataa gcaaatctct tatccaataa | 120 |
| caaattatta aacaacactt caacaataac tttattcaac aatatattag tttaacattc | 180 |
| acaaatcacg agtattagaa cataaaacgc aacaaagaat ggactaaggt actatattct | 240 |
| aacttaggtt gtttaggatt tccatatgtc aatgcttttg tgattttttga actagatttt | 300 |
| cttgttagat taattcaatt ctattttttaa atggcttaat atcttatttt cggatgcttg | 360 |
| gggattgcta gactaccgct ttgttgaagc aataagttaa atttgtttgt tacaggtatt | 420 |
| gatcaatcta acatagaatt gaatttgtat gaatatttag ttagacgctt gaaaactaat | 480 |
| tattctacca atgagccgta gatcttaatg caattgttat taatttgaac tttgtatgct | 540 |
| tctcatcgat taaatttata tcaagtagtt aattaggaca aatctattgg ctttttcatt | 600 |
| taattttgtt aagtaaaagc aacttagaat tttgaaaatg atgaacccat gatccaatac | 660 |
| attgaaagag aattttgttt aactcaaact aggattcttc tcacattgat ttcgtataat | 720 |
| ttaactttttt caatttatat caatccccccc agggtgaaaa aaatttgttt gaagaattca | 780 |
| tgtgcttttct aaatctgatc tagacttgcc actaaaatta acttttgata tgtaatttgg | 840 |
| ttaaatatttt gattcggatt tcgacgacaa acaattgatc aatgtggtat taaattctga | 900 |
| tctccatgta agaaatttac acattttcat aagttcaatg ttgacacaaa gagagtaaga | 960 |
| gcattttaaa aaaaagata cttttaatct tttctaaaaa aacaccaaaa tgccattatg | 1020 |
| taaatgtaac ctaaataata aacatttaaa cttagaattc atgcaattag ctttgtatg | 1080 |
| ggacattgaa ttgattatta aaatcagtag ttatagaccg tgagttataa tggtttgtat | 1140 |
| tagaagcata aattatttta attttgatcg taatagcatg tatttgagat ataaattaat | 1200 |
| ttagtttggg tggcaaatag taaacagtaa agcaaaatat aaaaaaatga atttaaaata | 1260 |
| gtaagatttg taacaaatga ttaatactat aacaaacgtg gttttaaaat aacgttgatc | 1320 |
| gtagctaatt gaacattatt tattgtaaaa ttgagtgttt ttaatatttg gagcctcaaa | 1380 |
| cttcgggtgg atcaccacaa tataatcata ttcaaattta aaattttatt tttattataa | 1440 |
| atattgttaa tagatgctca ttatgggcca tctgtcactc cctccgtgca tatcctacct | 1500 |

```
gaaacatcat atatcttaaa caatgtccat tgccatgtgt cactattttt acatcccatc   1560
cacttgacaa atatgttgaa gatgcctact tttttaggga tcatgtaatc tatctcatgc   1620
ttgtcaaatt gttcgataat agtgttacaa aaaatttagt aattattatt attatatttc   1680
ttcgatattt atgcttcata tgccattgtg ctctccattt ttaccatact taaaaaaatt   1740
tcttattata aattttttca aaaaaaaatt tactatatag tcatcatctt tattaaaatt   1800
aaaattgaga acctgatatt tttgatatta ataatttaaa atttgaatta atccactttg   1860
aaattattaa taatttattc gaatttgggc cttaaggaag agatacggaa acaaacccta   1920
gatcccatct atatataaat cgccacaaaa ccctaccttt ctctcagttt ctcgttttag   1980
ccggcaaaa                                                           1989

<210> SEQ ID NO 184
<211> LENGTH: 1463
<212> TYPE: DNA
<213> ORGANISM: Cucumis melo

<400> SEQUENCE: 184
ttttcttctt gatttgaaat tcttcctcct tcctgttgca aacaaaccca gatgaataat     60
cagacaaaaa aagcagcaaa tttgaagata tgcatatacg aagaagaaga agaaaaagag    120
agggaaggat aagtaggag atagcttgag attacagcgt agaaaccgat cgaaccggag     180
atcaacggcg cgaattaggt caagaagaag tgagggtttt tatgaagaag aagtgagggt    240
ttttatgtgc cgatgaaaaa ccctacttct gtgttggtga tctaacgttg tttgatcggt    300
tcggtttttt tgagaatcga gtaccctcat tattattatt attattgtta ttattataag    360
tttgttgtaa gaattaataa attatttcaa aaattacaat ttttatttat atatagttta    420
aaaaatttta taatttttt aaataaattt cgaaatataa ggttggattt cttaaaaata    480
tatgaaaaaa gagatgaagt ttataaatta aaaatgaaat aaaaatagta agtttgtact    540
cttattctta tttacaattt aattttccat taaaattta aattaaatag aaatataatt    600
aaaatcttaa attagataga aatataatta aaattttcag aatgtaaatt taaattagct    660
tagtgtatat ttaaaatata taagattgaa ataattgatt ttgtttatct aaatatttta    720
tattattatt tattgaataa atataattat atatggtaaa ttgttttgga taataagaaa    780
gtaaagatgg tatttatata tataattaac caaaatttaa gtttgttaaa aagaaaagtt    840
ttcaaaaata ttttttacg agtaattagg aaaaacccac attttacatc gaagtcatag    900
actgggtcta tgtcttcatt gccttgtcgt gtacccgatc cacgataacg cattatgaac    960
cgagtagatg acttaacttt ttgtaatagc ttttcttcta ccatattttt gacattttt    1020 taaaagtaac attatttata aaaaaaaat cgtagtttga tctcacatga aactattatt    1080
acatcattaa ctaatatatc tatatttaat gtagtttct tgacatgatt ttaatgctaa    1140
ttgaaatagt tacaattttt gtgtcccatt tgtttagat caatatgact tcacgtatta    1200
tgacatatgg ggccatctta ccagaaattg gtgccaatga gaaaatgaat gtaccttaac    1260
caatggagca acccatgtga gccattgatg aacccaactt tcttggtttc ccatcttcta    1320
ttcatatgtc acaatacctt ctcttttctc attctatata tagactctaa acaaacaact    1380
aatctccaac ttcaaatctt tcacatattc tcattcaagc attgaagttt accacttcca    1440
aaaagattca atccaattta gcc                                           1463

<210> SEQ ID NO 185
```

<211> LENGTH: 2006
<212> TYPE: DNA
<213> ORGANISM: Cucumis melo

<400> SEQUENCE: 185

```
cagcgatctt cgtagaaact aattcaatgc tagctcatta tttgactttt ctcaggcaag    60
gctccgcgag gaagagaaaa ggtccaattt caggaaccaa gggcatggac aggttccggt   120
cagaagaagc tttttacgta aacccttgc cagattgttt atgtcaagga gaattaccaa    180
atggaagtac gacttccatt ttcagatagt tcagtagaac atcaaagata aatgctctt    240
agagagctca atgtatatgc aggcgaccac tcaacgtgtc accagctttg tacatccaat   300
aagccagcta cgatggaacg acggagtgtt tataacctga gttttggtag ttggcggagg   360
cggtgatggt ggtatagaag gaaggtcgag ggatggcaaa ccctttacgc caagtagtgg   420
aagggagtag ttggagatga acacattttg agaagtttcc aagatcactc catttggggg   480
agagggatg ttggttattt agcacaattg ttttcatgtt ttagtaattt tatccaataa    540
tgagcgaggc attgaagcaa ttaaatttat ttttaatgat ttttcaccc ttccataggc    600
ttttctcttt ttcttttcct tttagtttgc aaacttagc tccttttatc ggctgtcgaa    660
ctcattttg aagttattga atgaaacaca gtttgggctg tgtcagatgg gtggtgaaat    720
tttatacatt ataattacta cataaaatga aatcatattg taattttcta tctatgccac   780
aattttttt tattgcatca tgaggattaa attgtacgag tccaaatttg tacagtcatg    840
tttttaaagc tttcgagcat tgttactaat gcatggaaag gatcgattat caagtatcct    900
cccaacttca tgaaagttat tatttgtctt ctaaatttgt tttagaaaat gtttaattaa    960
ttatttgaga agaaagttta actaaatcct attggtttcc tctaaggttg tcatacttat   1020
ccaataacaa ttacgtttaa aatcaaaatt attctaatgg tataagacta atgttttaaa   1080
agcataaaat tgatgaggaa ggattggaag taatactatt tattttgaag gtaaacattc   1140
ttgaatgtct gtcctaaaat cactaatgtt ttcttagttt gagactttga gtcgttgaac   1200
ctctccatct ttataaaata taatacgagt ccttcacaat aacttaaaat atatactaaa   1260
tcctaattaa tgaaaaataa ataaataaaa ggtacaaaat cattaaagcc taaaaatcta   1320
ttactccttt aaaactttc aagggtccct acaaccaatg agaaactacc acgtcatttt    1380
cacaatccgt tcagtgttta gaaaagtcaa atcgcaccgt ccatttatcc actcgtacca   1440
agtacggtag gaatctatct accgtccgat taagcacaaa gaagcacagt aaatgtcaat   1500
cgtgtccatc cgccgccata ccgcacatcc ttcgtccgac cggaaggccc tatataaagt   1560
cctttggttt tccgaatttc tacttcattc gcttttgaaa gatttcccaa tctcttcgtc   1620
ggccaaaatt ctctctcgct tctcaaccct tcttcggctt tttcatccag gtttgtttct   1680
cttctctttt tcttccttt gttgttcttg gaatatgttt aatttcattt gttttccat    1740
tcaatttcat gctagatttt acgattaggt tgattttctg ttcgtagatt gtaattgatg   1800
gttagggtta gcttttctc ccattccttc tggaatctgt ttcttgacct tcgaacttcg   1860
ttgataaatc tttagaaaca tttacataac caaacaataa ttgaacaact cgtgttgtta   1920
tgcctatata atagcggtta ggaaactgga aacgccctta taattgaaat cgccttagaa   1980
atttgttttg attcatacag ggtacc                                       2006
```

<210> SEQ ID NO 186
<211> LENGTH: 1664
<212> TYPE: DNA
<213> ORGANISM: Cucumis melo

<400> SEQUENCE: 186

```
cagcgatctt cgtagaaact aattcaatgc tagctcatta tttgactttt ctcaggcaag      60
gctccgcgag gaagagaaaa ggtccaattt caggaaccaa gggcatggac aggttccggt     120
cagaagaagc tttttacgta aacccttgc cagattgttt atgtcaagga gaattaccaa     180
atggaagtac gacttccatt ttcagatagt tcagtagaac atcaaagata aaatgctctt     240
agagagctca atgtatatgc aggcgaccac tcaacgtgtc accagctttg tacatccaat     300
aagccagcta cgatggaacg acggagtgtt tataacctga gttttggtag ttggcggagg     360
cggtgatggt ggtatagaag gaaggtcgag ggatggcaaa ccctttacgc caagtagtgg     420
aagggagtag ttggagatga acacattttg agaagtttcc aagatcactc catttggggg     480
agaggggatg ttggttattt agcacaattg ttttcatgtt ttagtaattt tatccaataa     540
tgagcgaggc attgaagcaa ttaaatttat ttttaatgat tttttcaccc ttccataggc     600
ttttcttt ttcttttcct tttagtttgc aaactttagc tccttttatc ggctgtcgaa     660
ctcattttg aagttattga atgaaacaca gtttgggctg tgtcagatgg gtggtgaaat     720
tttatacatt ataattacta cataaaatga aatcatattg taattttcta tctatgccac     780
aattttttt tattgcatca tgaggattaa attgtacgag tccaaatttg tacagtcatg     840
tttttaaagc tttcgagcat tgttactaat gcatggaaag gatcgattat caagtatcct     900
cccaacttca tgaaagttat tatttgtctt ctaaatttgt tttagaaaat gtttaattaa     960
ttatttgaga agaaagttta actaaatcct attggtttcc tctaaggttg tcatacttat    1020
ccaataacaa ttacgtttaa aatcaaaatt attctaatgg tataagacta atgttttaaa    1080
agcataaaat tgatgaggaa ggattggaag taatactatt tattttgaag gtaaacattc    1140
ttgaatgtct gtcctaaaat cactaatgtt ttcttagttt gagactttga gtcgttgaac    1200
ctctccatct ttataaaata taatacgagt ccttcacaat aacttaaaat atatactaaa    1260
tcctaattaa tgaaaataa ataataaaa ggtacaaaat cattaaagcc taaaaatcta    1320
ttactccttt aaaactttc aagggtccct acaaccaatg agaaactacc acgtcatttt    1380
cacaatccgt tcagtgttta gaaaagtcaa atcgcaccgt ccattatcc actcgtacca    1440
agtacggtag gaatctatct accgtccgat taagcacaaa gaagcacagt aaatgtcaat    1500
cgtgtccatc cgccgccata ccgcacatcc ttcgtccgac cggaaggccc tatataaagt    1560
cctttggttt tccgaatttc tacttcattc gcttttgaaa gatttcccaa tctcttcgtc    1620
ggccaaaatt ctctctcgct tctcaaccct tcttcggctt tttc                    1664
```

<210> SEQ ID NO 187
<211> LENGTH: 342
<212> TYPE: DNA
<213> ORGANISM: Cucumis melo

<400> SEQUENCE: 187

```
atccaggttt gtttctcttc tctttttct tcctttgttg ttcttggaat atgtttaatt      60
tcatttgttt ttccattcaa tttcatgcta gattttacga ttaggttgat tttctgttcg     120
tagattgtaa ttgatggtta gggttagctt tttctcccat tccttctgga atctgtttct     180
tgaccttcga acttcgttga taaatcttta gaaacattta cataaccaaa caataattga     240
acaactcgtg ttgttatgcc tatataatag cggttaggaa actggaaacg cccttataat     300
tgaaatcgcc ttagaaattt gttttgattc atacagggta cc                       342
```

<210> SEQ ID NO 188
<211> LENGTH: 2003
<212> TYPE: DNA
<213> ORGANISM: Cucumis melo

<400> SEQUENCE: 188

```
aactagacta gcgagtgcac aaccaaatta caaaatcctt aacagagaca accatctatc      60
tcctttaaag caacaataac atcaaccgaa ttagaatcca caatcagtaa agacgatgcc     120
gacaccaatg accaaaaccg atcaaatata gcttattacg gaccattact tcaacagtta     180
catcaacaaa aaaaaaaaaa ttaaacattg ctaataaaat ctgaaaatga ggaaaaagag     240
attaaaagtt ttgaagatag aaagaataaa tctgaaatgt tctaatttga tatataagaa     300
atatgaggta atatgacgaa agcattttga tagttttcac caactcccttt tgtgaaagga     360
tacatccaac caattttaca atttctgttc aaattttgtc cacctaccct tctcttctgc     420
cccccaaggc tgctttcttt cttttattat ttgctaaatt accaaaaact attttcgaat     480
taaaccatct atttcaatta tatacgtcat tcgaattttta acttaattaa cattagtata     540
tgtttcggat caaggatagt ggtataaatc atcctaattt caatttgtat ttagaaaagt     600
tcaattatac ttaaaacttc taaaaatttt atattttaaa tttggatata aattaaatttt     660
aagatttatg gaaggtaaat aattagagca aacaaactt caaactatat ggaaaataga     720
aaaggaatat tttagcccaaa caaaaacact tattattta tttttgttttt ttgttttttt     780
tttaatttaa caatttttttt ttttattggt tgaatgtgtt tctccactgg tgagtctcca     840
actttgacct gcaaagggtc tatatagcga gtttcacgag cacctaacca atatctgtgt     900
aataattccc attttctctt catacccact tcatttgatc atctttttca caaccccgga     960
tctctaattc ttgggaattt gcctctttct cgatccattt ccaccgtaat tgaaaaatat    1020
tcaggtttga tttcttctgg gttttcattc aactgtctaa cttcattatg cccttatgt    1080
gtttgttgaa agccccccac ccaccatcgt tcaatgcggt ttctttacct tttgttcggt    1140
ttcaacgatg atttagaagt tatagatgga tgctaattgt ttcgttgttg gtttgatcca    1200
ctgatctgcc tttgattggc ataaaaggag attctagatc ttgttttgat gttgtgattt    1260
atggatatta ttgttatagt cgtggaagtt tttcttgtcg ttctgcggta tatggttgtt    1320
ttattttttg agtggtaaat tgagcagatt gtgaactttt gggttttatg gtgaaagcat    1380
gaattagtaa atgtagagct gctgaaacaa aatggaggtt tgctagacct ctttgtgaat    1440
tcttaatggt cagcctccat cttaagaggc taagtccaaa aatttaaggc agtcttttgt    1500
tattgttaca aaggacaaga aataacagag gagttatttt aattgaatca agttggaaag    1560
aagtactact tcatgcttct ttcaaaagca ggtcaaagtg ctttaaagtc ttcttattta    1620
tttatttttt cctgaatcaa tttaaactaa tgatagaaag aagtgttttt taatgggtta    1680
ttataagtaa catcaatttt taaccattcc aaaagttaca tcaaattcat catagtgtga    1740
gtttacgaat tttggaagtt gtaattttaa gttaatactt ctttaagga aatgtacact    1800
ttgcatgttg tgttcataag gggtatttct ttgacaaacg cagcaaccac cccttaatga    1860
aaactacacc acggtggttg gttttttctt gttattttt tacttggaat ttacaataag    1920
ttgttatatt cggatatatg gcaaagcaga tatctgtttt tatccgaaac ctcataaatc    1980
ttgaatgtgc agcaggtaaa aac                                            2003
```

<210> SEQ ID NO 189
<211> LENGTH: 1024

```
<212> TYPE: DNA
<213> ORGANISM: Cucumis melo

<400> SEQUENCE: 189
tcattgatga agaaggaaac tttaagccaa ttcgacaact tatccattca acaactttcc      60
accttcagac attcagattc aactataata taacataaat tgatagtcaa gtcttttttg     120
agacaaccat aaatcatctt agcttcgaga actgtcactt ccttaaattg gtgaatatat     180
cacattccat ccattcaaaa ctttgtttcg aactttactg tagttatgaa tcaataaatt     240
gggagagata ttgttaaaaa gagagagcat atttgtttct attatttact ctctcctaag     300
agagggttaa ttagtctata aatgatctat tcttctcgtc cattgaaatt tgttatcct      360 aaatttatga atacttctac ccaaaataaa gactttttt ttttttgaaa agtgtcaaaa     420
aaacataaag aaattgacaa acattcatt tttagtggat tttttacgga cgtaaatagt     480
ttgtttttgt ttcttttaat aatacaattt tttttactt taaaaaatat ttttgttata     540
aaaccaccgt attttattc aattttaata aataaataaa tgaaagaata taaaaaagag     600
gaaggaaaaa gaagccaacg aaccaacggt tgccacgtat caaaggtcta aagtgcgcaa     660
aacgaggcct tcggaaacca aaatgcgtgg cttcaattgg agcaagtaaa catggaaacc     720
acgtccattg taacgcttcc tgatctcttc tttacaaccg ttggattcga gtacttttc      780 tcaacgatta acgactgagt ggacctccac ttgcttctgt tccacgcgcg tgggattgac     840
gtgtggtcca cgcaactctt ctcgatagga tcattcgaga acatccttta cttaaaccgc     900
ctctctctgc ctcaatttct cgtcacttcc ttctccttct ttaccctttc cactgcggct     960
gattcttctt cgccttttat tctctcgtac gccgccatat tcttcacttc tttttccggc    1020
gaca                                                                 1024

<210> SEQ ID NO 190
<211> LENGTH: 2001
<212> TYPE: DNA
<213> ORGANISM: Cucumis melo

<400> SEQUENCE: 190
attcgtcttc gcattatcag taaatttatc attttaagag tttgttcttt tttaaaaaaa      60
attaatcatt tcgataaagt tggagaattc aaaaatttct ccaaataatt tataaaaact     120
ttcggttata tatcgaaaaa attaacatgg tattaaaacg atcataactc aattaacata     180
aacactccct ctcaacttta ataccaaatt tctttattaa cgcaaaattt aaaatttgtt     240
tttaaaattt tcacataaca taatagaaat acttttcttt atggcaaaaa tacaataatc     300
aaaattgatt gatggtgaca ggacaccaca caatattttt aaattttgaa tatacgaact     360
atataataag atatttatga gattcccatc ctaaagattc ctagagattt ccttgtgtac     420
aatattacac aagtatcttg gaagtccaaa gtcctgagaa aaaagctatg tataaagtaa     480
tagtgtttgt cgtaggaaat ttacttcatt cgtgtcatta gcttttttatt gaaaaaaaaa     540 attaggtata tcttagtgaa tctcacttaa tcgttgtcga tagttattct tttaatatca     600
ttatatacta aaatataaca atattgaaaa gctaaaactg tatataaaaa aaatgttacc     660
tctaaacttt tatcgtttat ttaaaagata aatatattc ttcaaaactt acaatcaaca     720
tcctacgact atcattatag gtacaaatct tttcatgttt acacaaaaat tagatttta      780 aatggtgtaa tgatgatata taacgaaatt ttgaatgatt actatttgag gttaccattg     840
taattggtcg tgttgtttga aatttaattt tattagaaaa tttgtcaaaa gtagcaaaaa     900
```

| | | |
|---|---|---|
| tgaataaact atttaaactt taggataaaa tcaagtgtta tgagttttg tctagtttat | 960 |
| atatttttat ttttattgaa aacccttttc ctatcttttc attacttcaa aatagtttta | 1020 |
| aaatgtctat taaggctaaa gttagtataa ataaaatttc ggaaatttt tttcgaaaaa | 1080 |
| aattgataaa ttatttatat tttatattaa agtcaaaatt tattacgcgt agatgtttat | 1140 |
| caaattttct ttcttttgt tgataatttt ccaaaatttg gataatttt taaaatagta | 1200 |
| aaattattat aaaaatgaaa acaaactatt tataccttaa gcaagaaata ctaaaaaggc | 1260 |
| aaaaattcat ttacttcatg aagcgtaaaa attaaatatt ttaccacttt tgttatttt | 1320 |
| ttaccatctc tatcaattat ttgtaaaaag aaaactacaa aattagatgt ttttctttt | 1380 |
| ttaaggttta atcaatatta aaatttctta aattggcaga caagttggtg ttggtaatta | 1440 |
| cgaataaatc ccgaattgac taaaaataaa ttcttctcca agtaaaatag acacgtggat | 1500 |
| gaagaaataa gtgaatcaaa ggcatccaca gttcaataaa tggaaaaac tactttctgc | 1560 |
| tgactcattc ataagttttc ataaaatttc ataagaaagg ccaaagggct tatgaaagtg | 1620 |
| aatgtcatag cagtaaatga agcacagcgc cattgaaaga caactcaaat tgcatgcaaa | 1680 |
| cccacataat tattcaacaa acccacatca aatttcccat aaagatcaat tctttagggg | 1740 |
| gttcaattac ccaaaagtga ggtagttgaa aaccattaaa caacaagaaa tcaacaattt | 1800 |
| tgtaatttgt ttgtacagaa gtaagagata aaatcatcgt taaccattcc tttatttcgt | 1860 |
| aatacaaccc atcaaccatc tctctctctc tctctctctc tctctcggcc tttatctttc | 1920 |
| tcttcctcaa ttatttaagt actacccaag tgagctaaaa gcaagttcag tggacagtgt | 1980 |
| tgtaagaacc actacagaaa a | 2001 |

<210> SEQ ID NO 191
<211> LENGTH: 4175
<212> TYPE: DNA
<213> ORGANISM: Cucumis melo

<400> SEQUENCE: 191

| | | |
|---|---|---|
| tagtttggtt cataggttat agtttccaaa tttgttaggc tatcattaat caaacacaat | 60 |
| acttctcttg taggatggct gcccctata gtactttttt aacttaggag aaggatataa | 120 |
| taattatatt ccttttagaa aatataataa taattgtgta gtgctttgat ataccttaaa | 180 |
| ttagctactc acgttttag gaggaagctt ccgttgcttt tcatggtgtt atgatctttt | 240 |
| ttattttata aaggactgaa ctttaaaatt tctctttcat ctattttgga ttggattcca | 300 |
| tctattttat acgggaagtg aactctaaga tttctcttca cctattgtga atcggactcc | 360 |
| gtcatgtagg tcaagactac gacagataag aatagacttc cacgaaagaa agtggtcaat | 420 |
| cgagatggct atatttggct ctttcagctc aatttcttct tttttccttg catgttcttc | 480 |
| cgttggtaca tttcttgcac ttttttttgtt ctcacatgac taatgtattc caagtttatc | 540 |
| attggcattg tgcctctttt aggcttgtaa actctcgatc caaaattatc taggacatat | 600 |
| gtttcctagt gaagaaatac tagtatattc cttgtcaa tatgtcaaaa ttttcaattt | 660 |
| cttaaccttt gagtaaatca atattatatt tttatggagg ttatttataa ttggaaaaaa | 720 |
| gttacaccca tctcaaccct aattaacacc aaatgaaatt gtaccatgcg gcacaatatt | 780 |
| ttttttgtgag tttttttgcaa agagaaacaa agtagcagac aaagaacaaa cattccccca | 840 |
| aaaacagcag agaatacta agagagaatg ctctctcgta aaaataata cccaagaatc | 900 |
| ttcccaaaaa gagggagtaa aagagtccaa aacaaacgaa ccgaagattg acaagaaggg | 960 |
| cactctcgcc ctccactgcg ccgctaaatt gtaagaagca tattttcttg agttaacata | 1020 |

```
ggaataggtg taactcaaga gaaatgtaat tcgtagaatt gaactttgta tattaattta    1080
tatggtgttg tagatacaat ctttagtatt tactcatttg gtgctttctc tcaaatacaa    1140
tttaaattta gaacttttg atcttcgatt ttcaggaagt tggagttgca atcaattcg      1200 agtttcaatc tctggaattt aataaaagtt tgatcttcca agttttcaat ctttcagaag    1260
acgatgatct tgatatggat aaaaaattgc acatcatgag agcttttga agtttaaatc     1320 ttcaattctc tagagcttaa attcttcctt aaaccaaaga tcaccaaatg aatgacaaat    1380
gtctctattt atcgaaaaat ttcatagact tttagatggg cttaggcaca ttacttgttg    1440
ggcttggact tgggcttatt tgcttggcgg gctcatgctc gagcccatta tttctttggc    1500
ctatttttca tgaggggctt gaacttggtt gtatacgaaa aaacttgact acctaaatct    1560
aatcaaatta taatcatcac aattttgacg tgttacgatt taattggcca aaaattcttg    1620
ttcaacactt gtctctaatc attttcctat ataatttaac taaaatattt aactttaagt    1680
aacttaaaag atatagttta attcgaatca aaatacaaat acaatttcgt ctatctattc    1740
ccatcataaa tgttgattga gattcatatt ataaacttct ttcaggaaaa gaaagaggaa    1800
aattcaccta aaccacgttt tcctattttg gtaagaatcc ccaaaccata aatcattcca    1860
aaattatttt ttttagatta gaaagaaaa aagaaaaaaa gaaattcaca tggcgtaaaa     1920
tttcagcccc gtgagatatt ttcgaacccc cagatacaat ctacaccgtg aaaacaaaat   1980
cggacggtgg ttgctataat gtccgtttag aggcaatggc agggatgaaa ttgccaacgc    2040
aagataagga acgaataaga gaaggacacg taagtacaag tttaggatgg gcgggcccac    2100
agccacaagt gccgttcgtg cttatataca agtcgctcat attcctagaa gtgtctccaa    2160
ataaaggaaa gaaaagttca ctcatagaga gaaagagaaa aataaagctt cgttgccggc    2220
gatctgaagg cggcggccat ttctctcggg agagagaaag agagagattg atagagcgga    2280
gagttcgagg ctctctcaaa cttcggtcct cttcttctct ttcaggtatc gttcttctct    2340
atcccttcgt attctgtttc ctctttctc tttcttcgcc atcatgctct ttctcttgtt     2400
ttgtactcac tcaatgtgat tgactttatg ttgtttttct gttttatttt tccattaatg    2460
ctcgttgtaa tgtgtagatc tatgataaga tttgaattat tgctcattaa tgtgttgcat    2520
gcttttgatt tcattttaaa aacagagatt actttctcta tattgattaa atcgttggat    2580
tttaggttct tacagagttt gtaaacagtg atgttaagga ttgctgagat ttatgactga    2640
tgagagttag tgtttgtctt ttagcttgtc gttttcctct ttgaaatcac atggattcga    2700
tctggatatc tgggtttggc tcgtctgaaa tggctacact atagcatatt tgagtttgtg    2760
atgttgaaga tttgttaatt tcttggaaaa tcgggagttc gttttgtttt tcctcttttt    2820
acaggtttta ttgattggtt tattgatcgg cgatatctcg ttttcaactt ccgaaatgct    2880 attttcata agaagaaatt gtggatgtct tttctactc gattagagat ccttgaaact      2940
atgccaaaaa aaattggttc tttcaccaaa ttgttttttg tcgttgtga tattaatgca     3000 ttttcttatt cttaattaag ttcaagtatt cttttattat ttttaatga tggttgttgt     3060 aatggttttt tccctttta caaaagcttt ttccatgtga ttcaaggtg tacttggggt      3120 ttcccggtct ttgttcccaa gtcaattagg atgggcgcca attcgatttt agcttctgta    3180
tcattggtgt atattctgtt ctggggagga aaaaaaaaa gaaaaaaatc ttccgtccta     3240
cagtgtgctg agtaacaatt tgaccagcct tttctgccga aaacttttg aaattatttt     3300 ttaattgtga tttggtgaac ttaaattgtt ttaataaata aggtggattg aatcttaaca    3360
```

| | |
|---|---|
| gaaacatcaa ataaaatcga gttttaaaaa aaaaacatat ttttagtgaa tgtttatttt | 3420 |
| atttaaaaga tctccatcag tcctgatgtt tcctagaaaa cttatacatc ataggtcttg | 3480 |
| attaacaaat ttggaggaag tcaataggtt attcttttt tcttttcca ttctagtttg | 3540 |
| aaacaatttt cttttctttt ttaacttaga aaataatggg tagctagaaa tatggaaatc | 3600 |
| aatgtatttt gggcttctcc ttgaaactgg agcagcggtc aatttctctt tcgtttgtat | 3660 |
| agatgtgata gaaatagaat gtttccttcg cttacggcat cagagagttg gaattggtct | 3720 |
| ttctcaacct caatatcaat taaatcaagt ttcgtcataa acaggttttt ttttcttcg | 3780 |
| tttcaaatgt ttggtagggt caaataattt gtaaaatacc tagccgtcca atatgataca | 3840 |
| aactggagga tttcacttgc tcttttaaat tacaaaaaat attttatcat tgatgttgcc | 3900 |
| tgtctgtgtt tatcttttct ctttccgcct caagtaggcg tctaattgtc ttggcaagtt | 3960 |
| ggttttttgt acttccgccc cttgtccttt ggcccttttg attaagtttt tcatttaatt | 4020 |
| ttctggtcgg cgtacgttga attattaggt ttgcatttaa tgtggtacct ggtgctttga | 4080 |
| ctcttatttg ataaggtatt ttgaagtcta aaacgttaaa ccctttgttt gatgtttatt | 4140 |
| tttttatcgt tccaggacaa tatcctttgg aaaaa | 4175 |

<210> SEQ ID NO 192
<211> LENGTH: 1999
<212> TYPE: DNA
<213> ORGANISM: Cucumis melo

<400> SEQUENCE: 192

| | |
|---|---|
| aaaagagtca tagtgaaaaa agctgagatc ataatagttt caccctaaac acaacttata | 60 |
| ataacacata ctatcataat atacacacca aacacagact ctatagtctt cactctaaac | 120 |
| gcagattaca atagtctgca ccccaaacgt agactattat aatcttctga ctattataat | 180 |
| actcttttca cttatcgccc caaacgtccc ctaagagaac aaagataggt tataaaagag | 240 |
| agatgagggt ttatattatg caacaagtat aaggttctag aacgatgtag tcttcaaagt | 300 |
| aacgaaagca ataggctaca cgagaaaaat attttaaaa tatagtgctt tccctaaact | 360 |
| agatttcaat gacaaattat tataaaaaat agaatcatta atccaacatg gcttgcatgt | 420 |
| cacaccttgg ccaaaactga agacggatgt catactcgac ttcaatatat ttttttaatt | 480 |
| aattttcatg tgacaacaca taaatattta aaatttagat tgggttggat ttttttttcaa | 540 |
| gtgggtccca aaatactctt caaacccaaa ccaacccaac ttgtttaccc atctaataat | 600 |
| aacccaccag gttcaagaag acgaaccgaa ccgaaccgat ccggtctaac tttgtttcat | 660 |
| acttaagtcg aacttagcgg tacttttggt tcggttctcg gtttccccaa acagagccac | 720 |
| tcaaaattag atttagggtt ccgttcgcaa ttttcagcgc atttttattt gaatcggtcg | 780 |
| tttgttgaac acgttctctc tcagctggtt tagggttcat cgttctctct tctcgcgcta | 840 |
| tatcttttctc tctctcaggt tcgtttcttt ctcttaggcc attttatcag aagatcctct | 900 |
| tcgttctccg attttctttc cgtgttcgcc ctcggtttct cagcagacgt aggaagtttg | 960 |
| gtttccgttt agtgaatctg tttggggtat tacgaatgat attttgtact gggctttccg | 1020 |
| catagtcttt ttcttctag gaatatatgc atctgagaat ttatttgttt ggcttttctt | 1080 |
| tataaagtat gaggacatat acatctcgat tgctaatcct tgattataat cttttttttt | 1140 |
| tctatgttgt ttgaatctgt ttttttttt ttaatttcaa taggtttttt gaatctaaaa | 1200 |
| atgtatttct tggatgaatt gcatactgtt gaattagaag tttattgatt agattgttga | 1260 |
| tatttgccct aagttccatg gataggtttg cgtctttcac cttttcgttt gcttttttctt | 1320 |

```
ttggctgacg acatcttaca tagcctctgc tctaaaaggt gccatgattt tttttcctgg    1380 cttatctga gtttgcgcaa tttagatttg aagtgatgat ttgtctaaat ataaatatct    1440
atcggccata ctattttttg ttattttgag tttttcagga tgactgctag agaatgaaaa    1500
atcttgaaac attgtgtttt gaagttcaag gatcttgtag ttttgttctt ttctagacta    1560
tctcatttga tatagccctt taaatttaat caaaatttgt taatattcaa atcctcggac    1620
attttaatta tttatctaaa tagttgttta ggcattactc aggttgccca ctattttaag    1680
cttagaagcc tactctggtt gacctaaagt ttgcatgcta tttgccttat ttcgcacgac    1740
tctaaactgt tatagacatc ttttttcagc cttcaggtaa atgaacacaa aaaggagtga    1800
aagtctgact tctgtgtgat ggtcttttaa tcaattatag ggattaagat ggttttttta    1860
ttcattgtat aaatattaaa ttagaatgat dacaaccaat aatattaaaa ctgacaatgg    1920
aaggttcctt atattatttg gagtgtacat tacaacagcc tgattcttgg cttggcaggt    1980
tcctgatcac cttgtaaac                                                 1999
```

<210> SEQ ID NO 193
<211> LENGTH: 2000
<212> TYPE: DNA
<213> ORGANISM: Cucumis melo

<400> SEQUENCE: 193

```
atttatttgt ttagagataa gacgcacatg agaatatgag atggattcca ctccactcac      60
actccaattt ctacctatcc tattactgtt tactattatc attccacccc tcgaccctc     120 attcttcttc tcaccttact tttttatgat ttactactac ttcatttgg atcacaatct    180 gatcaatgct gggtgggctg ccctcggcct gtcaccaggc ccagcccact tccaaattaa    240
acctcttggc ccaccgccca ttgtccccat cccattccat ttaatattcc caaccttccc    300 ttttctttc ccaatgcgat gcttctccaa tatacctttc ctgccctcca tgtttccttt    360
ttactgcttt cttatattta taacacacct tctacagtct tttggctggg aatgctgcgt    420
atgtgaatga gattcaagat ttcgttgatg ttatttgagt ctctatattc ataagttttg    480
ttcttagttt tctctagacc aactgcaaga gttagcgttc catatgctca taagtttcag    540
atttctgctg tgtggtttga agacagtcat cgatccatgg gtgaattcgg cttttttatta    600 ttattattat tattatttat tgttgtctta cttttctatt tgaatcttcc tatctttttt    660
actcattgtt ggactctaat aattcttgct aaacacaatc tccattttta ttggacattt    720
taaatcccat ctcaactcat aatttttagtt accttccacc atcaccatat ccaaatccga    780
aataaactca aataaaatcc ttcacgtgca tgtgctctcc atatattttt tctacatggt    840
aaaaataaaa tgaaacaat ctaaatttaa taaaataaca tatatggcag acttttattg    900
atgtagagac tgggtgttgt acaagaacag tgcagccaag aaaaaaaaaa tacttccaat    960
gaatcgtaca ttttaaggat tatgaaacta actagttcca accatttttt cacgaccacg   1020
tgcttgttaa acacgcaagt agaatcaaaa tgtgggcttc ttcgctttat ataactgtga   1080
atcattctcc aaaagggaa ggggatctca ttccctaatt caataaagaa aaagaaaaat   1140
gctagcgaac ttcatccatc tcattccttt tacctatttc atgagatgcc cattgtatat   1200
aagtattttt tttttatt cattttactt agtttactcc tcacctctaa aaaaattag    1260 gagagtttgc taaatccatt ctcaaactta gctttatttt ttaattttt atttaacctc   1320 gtcgtggatg ttaacctcaa atgtcagttc ttttattct atttattgat gttataattt   1380
```

| | |
|---|---|
| actttaggat tccaatttta taaaaataag aatacaaata aagataaaga gtgtgaaagc | 1440 |
| cagaaagaaa aaaaaggaaa tcgtaatatg ggtaaaattg gtacaaattg ggtcccgtta | 1500 |
| aatattaact caaaaaatgc gagaaaatgg tagaaaagga aatagggggt aagagcaaag | 1560 |
| tagtggaagg agagcattga acatattctc tagtttttgc acttggatct aaacacgagg | 1620 |
| aattataggt ttattcattt actaattaca taaataggat tggatttaa aatttgaccg | 1680 |
| agtgattatg catatttgat agagttagaa aatagtggtg gggcaggtac aagttacaag | 1740 |
| taatgtataa agatatgat gagcatatta ggaaactata gatttaaatt cgtccgtaaa | 1800 |
| taaataatta gaaatataat attcgagtgg aagggtatta gggttaggcg aaaccaattg | 1860 |
| cagttgcacc tataaaaccc cttttacgcc tccacccgct tcaacagcgg tctcggcgtc | 1920 |
| tacaactaca cactcacac tacacactac acactacaca gttgcagacc agaagcataa | 1980 |
| cgtaacgccg gtccacaaaa | 2000 |

<210> SEQ ID NO 194
<211> LENGTH: 2000
<212> TYPE: DNA
<213> ORGANISM: Cucumis melo

<400> SEQUENCE: 194

| | |
|---|---|
| tgaagagccg gaaaagcatg gcaaggtcaa ggcatttcag caagaatacg aggatgaatt | 60 |
| ctgggtttgt aagtccggtt cttcttcgga gttgtggttc gaatttcaaa cggccatgag | 120 |
| gagccctaca gcttaggaag cttcaggtct gagactctga ctccgacaga aattgctgat | 180 |
| ttttgtgtgt gttttgaata accattgtat gagtatgatt ggttgtatag gtttgaaatg | 240 |
| agggaaagtg atccatctcc ttgttgtctt tgcaggaaag gctcatattc gaccaagaac | 300 |
| gctttgtcat tgctttcgat aatcatgaaa tccacaatgg tttggcatat tagcaaacaa | 360 |
| atcttcttta ggcattgcag acagaaaatt ggagagtaag ttattataat taaggattct | 420 |
| aaatgagtaa gaataataag atcaggcaaa gattggaaga actaaagcgt ttagtatttt | 480 |
| gtgtggtaca gaagaattgt aattagatac gtagtctaga gaagcagatg gtgagatttg | 540 |
| tgaaagacaa atgttagtgg agagtgaaga gtgtttctca acaaccgaca tagaaggatt | 600 |
| ctcagaaaat gagaaagatt tttattgcgc aaaatagctc ccatatcatc atatgccgtt | 660 |
| gccattccct ctggggttgc atgtaatgag taatggaaag ctgtagacag gctaacttca | 720 |
| cccttttgtct tgggtatagg gtgcatttt ggtcactcca ttttaagttt tctaataata | 780 |
| aaaggatgaa gaaagatat tgaaaaacag ctcaggtttt aaagttgtca cacttgagaa | 840 |
| taatgcattt aacagttaga attttgcatc aacgtctttc aaatagaaaa gtaaaggaga | 900 |
| gtctagtttg agctggatag ctaaactggt ttaatcatat cttctatcaa gtggttagag | 960 |
| ttttagacct cccaacttta tatgtcgttg ccctaacaat gttgatggat gtttagtcct | 1020 |
| aagctctaac attgtccccg tatcatattt cataatagaa tgtactgagt aatggaaaac | 1080 |
| tagagaggta ggaagttgga cgaactttga atctatattg attttactat agtctttctt | 1140 |
| ccaagtctta atgagagctt tagctaaagt ttttcaaaaa ctcaaaagaa gtttttgttt | 1200 |
| tccaattctt cgatccatag attgtcaaga tggctataat atccttgaag ttaatagcct | 1260 |
| tcaaagtttc atagcttta tcctatgatc tttagaaatt caagagttat attctttaga | 1320 |
| actacagaac tttgatcttc gattcttcac ctcttccaga acctttatag tagagtttct | 1380 |
| tgaccttaca tgggcttggg attgggcctg gctacttatg ggcttagaga ttgaccttgg | 1440 |
| gtttaagcac attcgtttta cttggcccaa ttttcttaaa cttctgcaaa atcctaatta | 1500 |

| | |
|---|---|
| actaacacct caacaaaagt ccagtattaa atggggcata taaacaaaag ttaaacaaaa | 1560 |
| ttgtcgtaca gaatcctaat ttgctaacct cagcaaattt tatgccattc gtccttgtgt | 1620 |
| atctaattag tgttaatttg aggaaatata ataatataga cgtaggacgg atattggtat | 1680 |
| ttggtgcaac atcctccgaa ccaattcctg gaaagtaatt ggggcaacaa gataatgtta | 1740 |
| tcgtcagttt caagtgcaaa acttgccacg tggaacagcg gcaacatgat atctcaaata | 1800 |
| tggacctctc acccggtcaa gcttccacca ccaccaccac ctccgtattc taaaataaag | 1860 |
| tcaggaacaa gaacagacac accttaacaa aaccaatatt cttcatctct atctctctct | 1920 |
| catttcagca tagaagagag ctgagtaaaa ggaaaaaact tcaatcaaat ttgacagaga | 1980 |
| agagcccaag agaaaaccaa | 2000 |

<210> SEQ ID NO 195
<211> LENGTH: 1400
<212> TYPE: DNA
<213> ORGANISM: Cucumis melo

<400> SEQUENCE: 195

| | |
|---|---|
| tatatatatt aacttttaaa attttgaaaa cgtcatagat aaattatata caaaataaaa | 60 |
| agtttgatta tttacgaaag ttaaaaagtt tatccgaaag ttgactcaac gataaaaaca | 120 |
| ctaaatatca cttttagaga tgatgatatt atacataaac atacgaactt acgcgtcaaa | 180 |
| cttttatact aacacaagat caaaacaact tgttgagta gtgagaattt tatctgctga | 240 |
| tatggttgaa acttgggaag caagcagagg aagttccatt cattaccaaa atccattttg | 300 |
| tattcatcaa aatatgaagt ttagcgactt gataaagtca agtcaagtgg tcctatcgat | 360 |
| ttgttaatgt caatgtttgg ttttgaattt gataccctatt agacaatgat atataatttt | 420 |
| aagtatggtt tacactgtga tgcttatat atttttaaat gtaaatatt agaacttgta | 480 |
| atttcaataa attttaaaaa tgattttgtg ttatttcctt ttttaaattg aaatatcaat | 540 |
| gtatcaatat tgcgtcatag agtattgcaa cacaacctta tgttaaattg tttattgctt | 600 |
| attgctctaa ttcaactcct tcatcaaatg tgcacagaat ttaaacaaga aaaagagtag | 660 |
| gtgctttttt actaaaatat actaaaagct ttttataccca aatcttatga caaaatcatt | 720 |
| ccaacaaaat gactatttaa atataagatc gaatccctaa tttaaaaaaa aaaaaaaatc | 780 |
| aaagatgtta atttctatta ttaaactcac tttagcgtag ctaacaaaaa aaggaaaatg | 840 |
| agaggctaca aagcttgagc cctctgcctc cctttattgc attgtttgaa attagatcaa | 900 |
| tactttgtat ttttttcaaa atgaaaaatc gtacatagaa ttaattctat ggacaaaaaa | 960 |
| tcagagaagg aaataatcta gaataaaatt cgattttaa cccaaaaaaa aaaaaaaaaa | 1020 |
| ctcgattctg atttttgtaa gcaatcaccc aaattaccat aaataaatgg tattcaatta | 1080 |
| ctcaattatg gatatttag aaatgataaa tttttattca taaactcttt tctttctctt | 1140 |
| tcaaaaagaa aaaattagc ataaacttca atgacattta tttattcttc ttcgtttgga | 1200 |
| gtcaaaagtt taaattgagc atcagtccag cccaaaagcc cacgaagaag cccaagaatc | 1260 |
| ttcagctttt tcgttcaaac gtcccttttt ggtttataaa attaaagaaa ataaaaacta | 1320 |
| aatttatttg ttatttaaca aaacattttt ggttaagaca ttctctttga ttattttct | 1380 |
| tccattcttc gtcgtcaatc | 1400 |

<210> SEQ ID NO 196
<211> LENGTH: 2019
<212> TYPE: DNA

<213> ORGANISM: Cucumis melo

<400> SEQUENCE: 196

```
tttatattta tgaaaatgaa gtctctaaac aattttttcta ctcccaaatt tgttgatttt        60
tctgcctatt ctttatcggt gctttaaaaa atgaaaccaa atttcaaaac taaaaaaacc       120
aagcttttaa aaaaatgtta ggttatttttt gaaattcaac taaatgttga actcttttac      180
ttattaaata ggcaaattat tgaaataaat ttagagcaag taagcttaat ttttaaaact       240
aatatactta ccaaatcgag gactaaaata ttcaaatact ctttaaaatt aagattaaca       300
ttaatcactt tgttatgttt aaaaagttgc agtgtcactt gaaccttttt aaattaatat       360
aatgaaaatg aatccaactc aatatatata atatctatat tattaatctc gatgtcagat       420
gtttgatacg cacatatctc aaaaattata cctcaactaa catcggtgca cgatgtatta       480
tttcgtgagg ataaaaatcg tttttagtat aaattgatgg aaagattatt tgaattactg       540
aaaaatgcac cggtacatta tttgaaactt ccccttcatt taaagaggct aatattagaa       600
aaagacacgc tgaggctatt tttacaatta atgtgggctg ttgacttggc ccagcccaaa       660
acataaaccc taaagtagca caaacaaacg cctctttctt cttgaaaccg catattaagc       720
gttttatcac ttctcaccac ctctcattcc tcctcttccg cacgttgttt cgctcctcaa       780
cgggagtgcc ttcccttgc tctccctcca ggttcttctt ccttctcatc tcatttccaa        840
gtaatttcat tccgtttctt ttctcttaat cgtatcttgt tcagactctt tcgcgttttt       900
ttttagttgc gccttaccag atctgtgttt tcactcgttt ctattcgata catgcttcca       960
agatccattt cttaatcgca tgtattcggt tgattggatg attgtctttt tgtaagtttt      1020
gattactttt ttggaatgga tcggttgaac caacggggtt taagtcgatg gaagtaggtt      1080
atgttaaaga tttgcttctt ttttatgaag atgtgtgtgt tcttttttct ttgctagatg      1140
atgttattat ttgattgttt taacagtcgt gttttgtttt tctgcagttt atagtcctcg      1200
gtcttttgaa gacttgtcaa gatggttagt acacctcttg tcatcgtgat tttgattgag      1260
tgatgtgtta agtgcttctt taggttacag ctaacgcgat tttttatatt caattgtgcc      1320
tgtgcaggtg aagtttacag cagaagagct ccgtcggatt atggactata agcataacat      1380
tcgtaatatg tctgttattg ctcacgtcga tcatggtaag ctacttagtt taagtttatt      1440
tatgccgagc gtctatttaa gaagattaac atcttagctt tcatttattg tttatttggt      1500
aagcatcgtt tcttttttctc cgaggaactg tacatgtcag ttcacatgac aataaaacga      1560
tcttccttgg acattagttt ttgaagttca attagacgcc aaattttgtt ggttaaaaga      1620
tgcttgtgga gcatatggac ctaatggaat cagtactttt tgatggatgg acttgtcttt      1680
tgttctttta ttttcaaaag aaattgcatg tgcaattaca tcatctttga tcgaaagatt      1740
gggtaattgg gtaattgggg taaagacatg ttgtaaaaac taatgttaat tatcaattac      1800
cattatatac cttatttagt gcttatttat atccttttttc cccatttcag ggaagtccac      1860
tctcacagat tctcttgtgg ctgctgccgg tatcattgca caagaagttg ctggtgatgt      1920
acgaatgaca gatactcgtc aagatgaggc agagcgtggt atcaccatta aatctactgg      1980
aatctccctc tactatgagc agaagagctc cgtcggatt                             2019
```

<210> SEQ ID NO 197
<211> LENGTH: 1999
<212> TYPE: DNA
<213> ORGANISM: Cucumis melo

<400> SEQUENCE: 197

```
aaaaggcgaa aaaaaagtta gcttcccgag aaggagaaga cgaggaagag tttgacttcc      60
cggggagata aagtttgtgt ctcgagggaa tctctaatct ggagttgacc gtcgacttat     120
gtgtcgagcc tggatttagt tgcatggtgc gacaaagcga taaggcggca tatgtaaagt     180
agtaattcaa aactagcggt taaagaaata atcagccaaa aaatttagta caaatacggg     240
tggaggccct aagtgaagtg ctgctattca gaggttttgg caaaagagtg caaagagttg     300
agttgtgcag agaaagtact aggtgaggag aggcgtttgg aaaagaaaag gatcaaacat     360
ttgcatgagt gatattctta aactaaacac tcttgtgtga gtgacttgcc taagctaaac     420
actcttgcat gagtaacttt cttaaactaa acgttttgta atgttttctt aatggattct     480
tttcgagtct gagttatgct taacacgttt tgtttctctc gtgttattgt tgttgttgtt     540
tgaaaagaga aaactattgt tttctatgtg ctgattgtga tgaatgtgtg cgaaccatta     600
gccttaatcc tatcaagtga atagtgatta tgtggtgtgt gcacataatg taaatgacat     660
tgtgtggatg gccagtgcaa caagaaatga atcagaaagc ttcccaaata ctgtgaatgg     720
agtgaacatc acactagctc aatggcaaga tattggcgat agtgaatcac aataggcttg     780
acaaggggaa ggattcatgt tcttggttga aaggaataag agaggctaat gtgagatttc     840
tgtgatttgc aaaatgaggc gttggaagac acgtttgaga aatgaaaacg aattagtgct     900
tgacttgtat tcctaaaaaa gttgtccaat atcttcaatc actaaatatt tgatgtgcct     960
aagttttcct tccttagttg ttgaggcgtt gaggccgagt aaggaaagat aagataatta    1020
tgacgttgaa aagctggtca agttatccat ctttggatgg tttaaagtta ttacatgtag    1080
ggagggttgc attccaattt tgtgtgtgag atgagtctta ttttcgagat gggttgctag    1140
gcgatcaagg agaagtataa gaaatgagtt cttatactct tgaacaactt gacacgaaga    1200
ataacatcct agtggatgaa ggaaggtgat ggaacttaaa gtttaggttt tattttggc     1260
cttgtgataa aaaaaatgta attgtaaagt attagatcaa gtaataaaaa cagagttgtg    1320
ttttctattt ttgctgtgtt gggttgtgta tctttattgt gcttatggcc tagttgctaa    1380
agagttaagg ttattaccta aatgttttac ggtgtgttga gttgtaaaga tctcctgagt    1440
taaagttgga attttgtatt ggagattgtt ttgagaagtt tagcttacta attgtttaac    1500
tcattaggtg tctaagcgac acgcctcctt ttggtcgcat gaagtggcta gcagggtggg    1560
gcggaccggg gtggggtgtg ataataaacc taaaaaatca cccagataag cctaaattat    1620
acgttgaagt taaacttaca atttgattag aagaagaagg aatatctgat ttggacatga    1680
attaattaca aatacggcgc caatcataca aagcacatgt aagatcaacg cattctacac    1740
tcaatctcag ccgttgattg ctttcaatcc ttcaaaaaga aaaaagaag ggcagttcgg     1800
gcagagtcat acctacccgt tgactataaa agcaactaca aatcgaaaac ctccatttct    1860
ccgttaccat tacagagaaa atcaaagaaa tttggcgttg agagattggg agagaggttt    1920
ctctttctag ggttgcttct tcttcttcat cctccattgt tgcaaatttc acttccttct    1980
cctcttgttc tcatctccc                                                  1999
```

<210> SEQ ID NO 198
<211> LENGTH: 1578
<212> TYPE: DNA
<213> ORGANISM: Cucumis melo

<400> SEQUENCE: 198

```
atatatatat ataatattta actaaataaa caaatgaaag aaaaaagtga gttcccattc    60
ggaaaatgca gatggatcca tttcttcaaa tattaaaaaa taaaaaaata aaataaaata   120
acttaaatat gcaaatagaa agaattttaa tttctggatt atccatatgg gacaatttt    180
aaaactcatt tattttattt ttttattta tttgattttg atatatctat ggggaaattt    240
ttcgtaataa ttttcgaaaa aatattgcaa tatatcattt gatcagatcg gtattattaa   300
atctctatca catttggtct taaattatcc aaagattcct ttaagataat ttagataacc   360
atctacagat cactactata atcaacaaaa ggaacaactt aaattattta aacaaattca   420
ttaatattag actttgtgct tcattagaaa atgatcttat cacaaccaca accatagtgg   480
tggtttaaaa ttttatttta aactcttatt agtattattt taattcatac ttaatcaaac   540
taattacttt aaaaaacata tatataaa taagttaaat cattcccct tatatctaaa     600
taacataaaa aaaaattgtt tactctacaa gaagtttgta tatatatg ctcggtacta    660
tttagcatct ttataataaa atttctaaat caatttttta tatctcttta ttaaatgtat   720
agtcatcaaa aaatttaacg agataatgtg tcaaagattt atttattaa cgttcataaa   780
tatcaaatta tacttagctt ataattgaaa acatgttcga taaatataag taaataaaat   840
tttatttttt ttaaatatta caaaataaac taaataagtt ataaatatga caataaacat   900
tatatatttt attatattta taaatactta ataatttagt cgtttaaaat aattttctta   960
attttcaaaa catgtttcat atgttaataa taaataaatg gaaaaccttc caaaagaaga  1020
aaaaagata tcttaaaatt taaaaattga gattttgagg atcaataatt aataaaagaa  1080
ggattaataa gggtgaaatt aaatcccaaa aagaaaattg aaaatgaaga aaagaaaagt  1140
gaagaaataa ttgaacgtgg gaagtggatt cgatgtctcc agagaacaag cgaaaggaga  1200
cgaaatccac ataatttgca cgttacgtgt ccctatcaac cgtagacacg tgtcaacatc  1260
tcaacaccct acgccgaatt gcttcgctgg atctggacgg tcatcggata acagcggcaa  1320
ccaattaata tttcccctta tatttcacag cctggccatg tccaccaatc acgttcaact  1380
attaattcat ttttcatttc ctttttcttt ttttttttaa ttcccctcaa ttattaccga  1440
caacctgttg tagccggtta accctaccct ccaacgttcc attataaggc ctagaaaatg  1500
gacgtgaaaa tggagtacta caaactacaa ttaattttaa agaatttaa ttttaaagtt   1560
ctctaattac tattagcc                                              1578
```

<210> SEQ ID NO 199
<211> LENGTH: 1023
<212> TYPE: DNA
<213> ORGANISM: Cucumis melo

<400> SEQUENCE: 199

```
ataataataa taaatacata atagtaataa taataaaaaa aataaaaaaa taataatagt    60
aatgaaaatc aatagaataa ttttaaaatc gggaaggaag tcgtgtacaa tccttgcacg   120
ttggagagtc aaatggccta agtggtgatg tggaagtcgt gtaccgggta cacgattttc   180
ctacaagtca ataataataa tatggttatt tttctagttt agggttcatg acaaaagatt   240
gttcagtcga ctggatgtag acaaatctaa aaaataaatt aaaatctaat atgaaaacta   300
gtttaatttt ccaaattatt aagggttgaa ttcgaccaat aaataataat aatacggtta   360
ttttgaaatt taggaaattg aataaagttg ttaaaatctt caagcaaatt gttaagcccc   420
```

| | |
|---|---|
| gagatattaa gaagaggtaa taatagagga ttctatattt ataacatgtt aaaattaatt | 480 |
| gcaaactcat aaatgcatca cacagattaa aacatagga gggacttccg ataaaagtgc | 540 |
| aaatattgaa ataattacag ttcgcgaaca tgagtatttt aatattttat aaaatagtat | 600 |
| gcacgtgtat ttttgccaaa agaaaaaaag aatagatttt gccattttc aaagtgactc | 660 |
| tcggttatat cttttatggc gattgtattt tatagcgtat gttgtttgta gttaacccat | 720 |
| ttctcattgg caaattcaat cgtgggccac aacgtttggg catagcttca atttggatta | 780 |
| actcaattat gtctgaatgg gttggactag ttcggactct tcggctgggc cagaatcaga | 840 |
| ttcgggccgc aatctgttca tttcacacct atatccaaac accccaaaa tcgatacccca | 900 |
| tcaaacccta actctcaata accccccatat ataaattcct tctttagggt ttttcatcc | 960 |
| tcatacactc tcaaacctcc ggtcattctc attttccctg ccgcttcttc aataacccta | 1020 |
| atc | 1023 |

<210> SEQ ID NO 200
<211> LENGTH: 1654
<212> TYPE: DNA
<213> ORGANISM: Arabidopsis thaliana

<400> SEQUENCE: 200

| | |
|---|---|
| tgatgattct tgttgttgta gttcttttta aaagtcccac ctgagcctct atagactctg | 60 |
| attctctttt aagttactat tttcaccgct ctctaataag gctcgtgatt ttttgggagc | 120 |
| catactgtat actcgccggc cctctcacga tgttgttcaa ttcacagact aaatttgatt | 180 |
| tatctatttc gccaaaacat aacttcatta aaaaatgttc tccaaataac taaacgaatt | 240 |
| aaataaaaga aacctttcat gtaaagttaa aggtatgaga ctttaagggc agttgctgaa | 300 |
| cattcgtaac acatgggaga acaatagaga agttgaaaaa gaaacgtagc atatagaaaa | 360 |
| attatctttg taaccaagtt gatttagaaa aatatcacta tttgtgaaaa atactagatc | 420 |
| agtttattat tactttttttt ttttgtata ttcacaaata tcatattcat atagaagaaa | 480 |
| ataaacaaag ttgtaaaaat ctggcattta aaataaaatt gaacacttca atttatttcc | 540 |
| tttcataata ataattttgg cataagatat ttgcaaattg atctggttcg gtatggtcga | 600 |
| caaaataatt ttccacgcta cccttccagc cgtccattca ctatttgccc tcaacgttac | 660 |
| caaataacgg tccagattcc tagggcaaga tctaacggtt agcaagtaaa gtcgtaccat | 720 |
| cagaaagaat aacaattctt tcacaaagta aacataacca acggttaaca agttcttagg | 780 |
| gttaaatcag taagatccaa cggatattaa attgcaaggc ccaaatagtt tttttgcagc | 840 |
| agataataac tcgtccccac tggcgagtga cgaccgagac tctgtgaccc tattttcga | 900 |
| gacgataaaa gggcaaacaa tcgctctttt caaagctcgc ctcttcacca cagagaaaac | 960 |
| ttcgtctctc ttctctgctt cgccctctca tttcctgtga gataaaggcg gagtctctct | 1020 |
| ccagttattt tgctcatcca tcgattctta ggtatgactc gtttctctca gatctgtgat | 1080 |
| tctttataat ctcgtcgttc ttcaaatcat tgttatattc gtttcttcga tctgtgtttt | 1140 |
| ttagatctgt aaggtaaatg agacgtttcg atctgtagat ctgattgtta tattgataga | 1200 |
| ttatgttatc tgctttgctt aaagtccgat cggaatgttt tgtgctcatt gtcgaatatc | 1260 |
| tgatgtatcg gtttcataga tctgcttctt tttgtgcgtt tcgttgatct gataatcttc | 1320 |
| tagtgatcaa aatcgtttgg atctgttgac tttagtttaa aatgtatccg atctgatgtc | 1380 |
| gaggcttcat tattggaagt tgttattgtt gtaatcctga tttaagttgc tgttcttaaa | 1440 |
| tttatatgat ctttgcgtta taatatgaca tggtagatct tggttcatgg ttcactgttt | 1500 |

| | | |
|---|---|---|
| tccaataaac ttggtttgtt tggttggata gcgttctgtg atacgaccat gtcttgtgtt | 1560 | |
| ggataagaat tctctgaatt tccttggctg gtttgtagta tgttattcac gtctggtttc | 1620 | |
| tcatcaatga ttatgtgatt ttgcagagtt cacc | 1654 | |

<210> SEQ ID NO 201
<211> LENGTH: 712
<212> TYPE: DNA
<213> ORGANISM: Artificial sequence
<220> FEATURE:
<221> NAME/KEY: misc_feature
<222> LOCATION: (1)..(712)
<223> OTHER INFORMATION: Chimeric transcriptional regulatory expression element.

<400> SEQUENCE: 201

| | |
|---|---|
| ggtccgatgt gagacttttc aacaaagggt aatatccgga aacctcctcg gattccattg | 60 |
| cccagctatc tgtcactttta ttgtgaagat agtggaaaag aaggtggct cctacaaatg | 120 |
| ccatcattgc gataaaggaa aggccatcgt tgaagatgcc tctgccgaca gtggtcccaa | 180 |
| agatggaccc ccaccacga ggagcatcgt ggaaaagaa gacgttccaa ccacgtcttc | 240 |
| aaagcaagtg gattgatgtg atggtccgat tgagactttt caacaaaggg taatatccgg | 300 |
| aaacctcctc ggattccatt gcccagctat ctgtcacttt attgtgaaga tagtggaaaa | 360 |
| ggaaggtggc tcctacaaat gccatcattg cgataaagga aaggccatcg ttgaagatgc | 420 |
| ctctgccgac agtggtccca agatggaccc ccacccacg aggagcatcg tggaaaaga | 480 |
| agacgttcca accacgtctt caaagcaagt ggattgatgt gatatctcca ctgacgtaag | 540 |
| ggatgacgca caatcccact atccttcgca agacccttcc tctatataag gaagttcatt | 600 |
| tcatttggag aggacactct agacagaaaa atttgctaca ttgtttcaca aacttcaaat | 660 |
| attattcatt tatttgtcag ctttcaaact ctttgtttct tgtttgttga tt | 712 |

<210> SEQ ID NO 202
<211> LENGTH: 938
<212> TYPE: DNA
<213> ORGANISM: Arabidopsis thaliana

<400> SEQUENCE: 202

| | |
|---|---|
| caaaagccga gccgataaat cctaagccga gcctaacttt agccgtaacc atcagtcacg | 60 |
| gctcccgggc taattcattt gaaccgaatc ataatcaacg gtttagatca aactcaaaac | 120 |
| aatctaacgg caacatagac gcgtcggtga gctaaaaaga gtgtgaaagc caggtcacca | 180 |
| tagcattgtc tctcccagat ttttttatttg ggaaataata gaagaaatag aaaaaaataa | 240 |
| aagagtgaga aaaatcgtag agctatatat tcgcacatgt actcgtttcg ctttccttag | 300 |
| tgttagctgc tgccgctgtt gtttctcctc catttctcta tctttctctc tcgctgcttc | 360 |
| tcgaatcttc tgtatcatct tcttcttctt caaggtgagt ctctagatcc gttcgcttga | 420 |
| ttttgctgct cgttagtcgt tattgttgat tctctatgcc gatttcgcta gatctgttta | 480 |
| gcatgcgttg tggttttatg agaaaatctt tgttttgggg gttgcttgtt atgtgattcg | 540 |
| atccgtgctt gttggatcga tctgagctaa ttcttaaggt ttatgtgtta gatctatgga | 600 |
| gtttgaggat tcttctcgct tctgtcgatc tctcgctgtt attttttgttt ttttcagtga | 660 |
| agtgaagttg tttagttcga aatgacttcg tgtatgctcg attgatctgg ttttaatctt | 720 |
| cgatctgtta ggtgttgatg tttacaagtg aattctagtg ttttctcgtt gagatctgtg | 780 |
| aagtttgaac ctagttttct caataatcaa catatgaagc gatgtttgag tttcaataaa | 840 |

```
cgctgctaat cttcgaaact aagttgtgat ctgattcatg tttacttcat gagcttatcc      900
aattcatttc ggtttcattt tactttttt ttagtgaa                              938

<210> SEQ ID NO 203
<211> LENGTH: 633
<212> TYPE: DNA
<213> ORGANISM: Pisum sativum

<400> SEQUENCE: 203
agctttcgtt cgtatcatcg gtttcgacaa cgttcgtcaa gttcaatgca tcagtttcat      60
tgcgcacaca ccagaatcct actgagtttg agtattatgg cattgggaaa actgttttc     120 ttgtaccatt tgttgtgctt gtaatttact gtgttttta ttcggttttc gctatcgaac     180
tgtgaaatgg aaatggatgg agaagagtta atgaatgata tggtcctttt gttcattctc     240
aaattaatat tatttgtttt ttctcttatt tgttgtgtgt tgaatttgaa attataagag     300
atatgcaaac attttgtttt gagtaaaaat gtgtcaaatc gtggcctcta atgaccgaag     360
ttaatatgag gagtaaaaca cttgtagttg taccattatg cttattcact aggcaacaaa     420
tatattttca gacctagaaa agctgcaaat gttactgaat acaagtatgt cctcttgtgt     480
tttagacatt tatgaacttt cctttatgta attttccaga atccttgtca gattctaatc     540
attgctttat aattatagtt atactcatgg atttgtagtt gagtatgaaa atatttttta     600
atgcatttta tgacttgcca attgattgac aac                                  633

<210> SEQ ID NO 204
<211> LENGTH: 315
<212> TYPE: DNA
<213> ORGANISM: Gossypium barbadense

<400> SEQUENCE: 204
tgatcacctg tcgtacagta tttctacatt tgatgtgtga tttgtgaaga acatcaaaca      60
aaacaagcac tggctttaat atgatgataa gtattatggt aattaattaa ttggcaaaaa     120
caacaatgaa gctaaaattt tatttattga gccttgcggt taatttcttg tgatgatctt     180 ttttttatt ttctaattat atatagtttc ctttgctttg aaatgctaaa ggtttgagag     240
agttatgctc ttttttcctt cctctttctt ttttaacttt atcatacaaa ttttgaataa     300
aaatgtgagt acatt                                                      315

<210> SEQ ID NO 205
<211> LENGTH: 315
<212> TYPE: DNA
<213> ORGANISM: Gossypium barbadense

<400> SEQUENCE: 205
accatatgac actggtgcat gtgccatcat catgcagtaa tttcatggta tatcttaatt      60
atatggttaa taaaaaaaag atggtgagtg aataatgtgc gtgcattcct ccatgcacca     120
atggtgaatc tctttgcata catagagatt ctgaatgatt atagtttatg ttgtagtgaa     180
attaattttg aatgttgttt ttaaatttta atgtcacttg gcttgattta tgttttaacg     240
aagcttatgt tatgtatttt actttaatga tattgcatgt attgttaatt taacattgct     300
tgatcagtat actct                                                      315

<210> SEQ ID NO 206
<211> LENGTH: 2001
<212> TYPE: DNA
```

<213> ORGANISM: Artificial sequence
<220> FEATURE:
<221> NAME/KEY: misc_feature
<222> LOCATION: (1)..(2001)
<223> OTHER INFORMATION: Codon redesigned coding sequence.

<400> SEQUENCE: 206

```
atggtccgtc ctgtagaaac cccaacccgt gaaatcaaaa aactcgacgg cctgtgggca      60
ttcagtctgg atcgcgaaaa ctgtggaatt gatcagcgtt ggtgggaaag cgcgttacaa     120
gaaagccggg caattgctgt gccaggcagt tttaacgatc agttcgccga tgcagatatt     180
cgtaattatg cgggcaacgt ctggtatcag cgcgaagtct ttataccgaa aggttgggca     240
ggccagcgta tcgtgctgcg tttcgatgcg gtcactcatt acggcaaagt gtgggtcaat     300
aatcaggaag tgatggagca tcagggcggc tatacgccat tgaagccga tgtcacgccg      360
tatgttattg ccgggaaaag tgtacgtaag tttctgcttc tacctttgat atatatataa     420
taattatcat taattagtag taatataata tttcaaatat tttttcaaa ataaaagaat      480
gtagtatata gcaattgctt ttctgtagtt tataagtgtg tatattttaa tttataactt     540
ttctaatata tgaccaaaat tgttgatgt gcaggtatca ccgtttgtgt gaacaacgaa      600
ctgaactggc agactatccc gccgggaatg tgattaccg acgaaaacgg caagaaaaag      660
cagtcttact ccatgatttt ctttaactat gccggaatcc atcgcagcgt aatgctctac     720
accacgccga cacctgggt ggacgatatc accgtggtga cgcatgtcgc gcaagactgt      780
aaccacgcgt ctgttgactg gcaggtggtg gccaatggtg atgtcagcgt tgaactgcgt     840
gatgcggatc aacaggtggt tgcaactgga caaggcacta gcgggacttt gcaagtggtg     900
aatccgcacc tctggcaacc gggtgaaggt tatctctatg aactgtgcgt cacagccaaa     960
agccagacag agtgtgatat ctacccgctt cgcgtcggca tccggtcagt ggcagtgaag    1020
ggcgaacagt tcctgattaa ccacaaaccg ttctacttta ctggctttgg tcgtcatgaa    1080
gatgcggact tgcgtggcaa aggattcgat aacgtgctga tggtgcacga ccacgcatta    1140
atggactgga ttggggccaa ctcctaccgt acctcgcatt acccttacgc tgaagagatg    1200
ctcgactggg cagatgaaca tggcatcgtg gtgattgatg aaactgctgc tgtcggcttt    1260
aacctctctt taggcattgg tttcgaagcg ggcaacaagc cgaaagaact gtacagcgaa    1320
gaggcagtca acggggaaac tcagcaagcg cacttacagg cgattaaaga gctgatagcg    1380
cgtgacaaaa accacccaag cgtggtgatg tggagtattg ccaacgaacc ggatacccgt    1440
ccgcaaggtg cacgggaata tttcgcgcca ctggcggaag caacgcgtaa actcgacccg    1500
acgcgtccga tcacctgcgt caatgtaatg ttctgcgacg ctcacaccga taccatcagc    1560
gatctctttg atgtgctgtg cctgaaccgt tattacggat ggtatgtcca agcggcgat    1620
ttggaaacgg cagagaaggt actggaaaaa gaacttctgg cctggcagga gaaactgcat    1680
cagccgatta tcatcaccga atacggcgtg atacgttag ccgggctgca ctcaatgtac    1740
accgacatgt ggagtgaaga gtatcagtgt gcatggctgg atatgtatca ccgcgtcttt    1800
gatcgcgtca gcgccgtcgt cggtgaacag gtatggaatt cgccgattt gcgacctcg     1860
caaggcatat gcgcgttgg cggtaacaag aaagggatct cactcgcga ccgcaaaccg      1920
aagtcggcgg cttttctgct gcaaaaacgc tggactggca tgaacttcgg tgaaaaaccg    1980
cagcagggag gcaaacaatg a                                              2001
```

<210> SEQ ID NO 207
<211> LENGTH: 1653

```
<212> TYPE: DNA
<213> ORGANISM: Artificial sequence
<220> FEATURE:
<221> NAME/KEY: misc_feature
<222> LOCATION: (1)..(1653)
<223> OTHER INFORMATION: Codon redesinged coding sequence.

<400> SEQUENCE: 207
atggaagacg ccaaaaacat aaagaaaggc ccggcgccat tctatcctct agaggatgga      60
accgctggag agcaactgca taaggctatg aagagatacg ccctggttcc tggaacaatt     120
gcttttacag atgcacatat cgaggtaaca atcacgtacg cggaatactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgaacatt     360
tcgcagccta ccgtagtgtt tgtttccaaa aaggggttgc aaaaaatttt gaacgtgcaa     420
aaaaaattac caataatcca gaaaattatt atcatggatt ctaaaacgga ttaccaggga     480
tttcagtcga tgtacacgtt cgtcacatct catctacctc ccggttttaa tgaatacgat     540
tttgtaccag agtcctttga tcgtgacaaa acaattgcac tgataatgaa ttcctctgga     600
tctactgggt tacctaaggg tgtggcccct ccgcatagaa ctgcctgcgt cagattctcg     660
catgccagag atcctatttt tggcaatcaa atcattccgg atactgcgat tttaagtgtt     720
gttccattcc atcacggttt tggaatgttt actacactcg gatatttgat atgtggattt     780
cgagtcgtct taatgtatag atttgaagaa gagctgtttt tacgatccct tcaggattac     840
aaaattcaaa gtgcgttgct agtaccaacc ctattttcat tcttcgccaa aagcactctg     900
attgacaaat acgatttatc taatttacac gaaattgctt ctgggggcgc acctctttcg     960
aaagaagtcg gggaagcggt tgcaaaacgc ttccatcttc cagggatacg acaaggatat    1020
gggctcactg agactacatc agctattctg attacacccg aggggatga taaaccgggc    1080
gcggtcggta aagttgttcc attttttgaa gcgaaggttg tggatctgga taccgggaaa    1140
acgctgggcg ttaatcagag aggcgaatta tgtgtcagag gacctatgat tatgtccggt    1200
tatgtaaaca atccggaagc gaccaacgcc ttgattgaca aggatggatg gctacattct    1260
ggagacatag cttactggga cgaagacgaa cacttcttca tagttgaccg cttgaagtct    1320
ttaattaaat acaaaggata tcaggtggcc cccgctgaat tggaatcgat attgttacaa    1380
caccccaaca tcttcgacgc gggcgtggca ggtcttcccg acgatgacgc cggtgaactt    1440
cccgccgccg ttgttgtttt ggagcacgga aagacgatga cggaaaaaga gatcgtggat    1500
tacgtcgcca gtcaagtaac aaccgcgaaa aagttgcgcg gaggagttgt gtttgtggac    1560
gaagtaccga aaggtcttac cggaaaactc gacgcaagaa aaatcagaga gatcctcata    1620
aaggccaaga agggcggaaa gtccaaattg taa                                 1653
```

<210> SEQ ID NO 208
<211> LENGTH: 936
<212> TYPE: DNA
<213> ORGANISM: Artificial sequence
<220> FEATURE:
<221> NAME/KEY: misc_feature
<222> LOCATION: (1)..(936)
<223> OTHER INFORMATION: Codon redesigned coding sequence.

<400> SEQUENCE: 208

```
atggcttcca aggtgtacga ccccgagcaa cgcaaacgca tgatcactgg gcctcagtgg      60
tgggctcgct gcaagcaaat gaacgtgctg gactccttca tcaactacta tgattccgag     120
aagcacgccg agaacgccgt gatttttctg catggtaacg ctgcctccag ctacctgtgg     180
aggcacgtcg tgcctcacat cgagcccgtg gctagatgca tcatccctga tctgatcgga     240
atgggtaagt ccggcaagag cgggaatggc tcatatcgcc tcctggatca ctacaagtac     300
ctcaccgctt ggttcgagct gctgaacctt ccaaagaaaa tcatctttgt gggccacgac     360
tgggggggctt gtctggcctt tcactactcc tacgagcacc aagacaagat caaggccatc     420
gtccatgctg agagtgtcgt ggacgtgatc gagtcctggg acgagtggcc tgacatcgag     480
gaggatatcg ccctgatcaa gagcgaagag gcgagaaaa tggtgcttga aataacttc       540
ttcgtcgaga ccatgctccc aagcaagatc atgcggaaac tggagcctga ggagttcgct     600
gcctacctgg agccattcaa ggagaagggc gaggttagac ggcctaccct ctcctggcct     660
cgcgagatcc ctctcgttaa gggaggcaag cccgacgtcg tccagattgt ccgcaactac     720
aacgcctacc ttcgggccag cgacgatctg cctaagatgt tcatcgagtc cgaccctggg     780
ttctttttcca acgctattgt cgagggagct aagaagttcc ctaacaccga gttcgtgaag     840
gtgaagggcc tccacttcag ccaggaggac gctccagatg aaatgggtaa gtacatcaag     900
agcttcgtgg agcgcgtgct gaagaacgag cagtaa                               936
```

<210> SEQ ID NO 209
<211> LENGTH: 253
<212> TYPE: DNA
<213> ORGANISM: Agrobacterium tumefaciens

<400> SEQUENCE: 209

```
gatcgttcaa acatttggca ataaagtttc ttaagattga atcctgttgc cggtcttgcg      60
atgattatca tataatttct gttgaattac gttaagcatg taataattaa catgtaatgc     120
atgacgttat ttatgagatg gttttttatg attagagtcc cgcaattata catttaatac     180
gcgatagaaa acaaaatata gcgcgcaaac taggataaat tatcgcgcgc ggtgtcatct     240
atgttactag atc                                                        253
```

<210> SEQ ID NO 210
<211> LENGTH: 622
<212> TYPE: DNA
<213> ORGANISM: Cauliflower mosaic virus

<400> SEQUENCE: 210

```
ggtccgattg agacttttca acaaagggta atatccggaa acctcctcgg attccattgc      60
ccagctatct gtcactttat tgtgaagata gtggaaaagg aaggtggctc ctacaaatgc     120
catcattgcg ataaaggaaa ggccatcgtt gaagatgcct ctgccgacag tggtcccaaa     180
gatggacccc cacccacgag gagcatcgtg gaaaaagaag acgttccaac cacgtcttca     240
aagcaagtgg attgatgtga tggtccgatt gagacttttc aacaaagggt aatatccgga     300
aacctcctcg gattccattg cccagctatc tgtcacttta ttgtgaagat agtggaaaag     360
gaaggtggct cctacaaatg ccatcattgc gataaaggaa aggccatcgt tgaagatgcc     420
tctgccgaca gtggtcccaa agatggaccc ccacccacga ggagcatcgt ggaaaaagaa     480
gacgttccaa ccacgtcttc aaagcaagtg gattgatgtg atatctccac tgacgtaagg     540
```

```
gatgacgcac aatcccacta tctagacgca agacccttcc tctatataag gaagttcatt      600
tcatttggag aggacacgct ga                                              622
```

<210> SEQ ID NO 211
<211> LENGTH: 1446
<212> TYPE: DNA
<213> ORGANISM: Cucumis melo

<400> SEQUENCE: 211

```
tcccttcagc cacttaacac ttaaaaatct taggaaactc catgggctcc tctttctcca       60
atgaaatttt gacatctgtg ttgttgatag ctcctatatc ctttgagaat ttgatataca      120
cctgtcattt gctgatttgt ggataactgt tagccttttg atattgatac gttcctttt      180 ttatgaattt ttgtaaatcc attcaatttt aatgctgtcg taaatgaaaa gcccttcat       240 taatgttgtt tatatacata ttttaaaatt aattcaataa caagtttagt tctgttagct      300
tctaggtttg tatctatttt atctattaaa ggtatgtttg ggcttcaggt tggaatggag      360
tagaattgaa tgggttgggg agtaaatttt ccattcaaca agttcaattt caaaatggct      420
aataagtttt gaactcaatt ttattttcaa taaattcctt aattttttgt tccttgtttg      480
taaactattg acttattcga tatattttaa aattgaggta tttaaaaaa ataatacaat       540 attaaaatta tttataaaat ataacaaaat ttatgtatag tttatttgaa aattttacta      600
tagtttcatt tttatattat tcctaaccat ttccatttaa aattatttca attatttctt      660
ttattaatat aattgaaatt tcatggattt attagacaca tgatttgaaa ttttatgggt      720
ttattaagta ttttctaaca caaaatcgct tccgcatcgt tttcaattca ttcagtaata      780
gaagtaattt tttaaaagaa ccaaatttgc caaattttga gttccataag gactctgaaa      840
actcattatg tctattactc ttcactaatt gtagagactt aaattcaaga taagagacac      900
taattgatga taattgccca aaaataaaa ataaaaatgt tcttcccca tcctcaacct        960 ccatgaattc acagagccca agattaatt attgggcccc aattcctact catatatacc      1020
ttacagtccc tcaaagaaat cttaggaagt aatcaatttc tgtttattca agatgtagcc     1080
tcccaaaaga aaatacatc acatcaaatt caaacaaaaa tatctacagc tagcaaaacc     1140
tcaaaccgtt aaaatttcaa gccacataaa tgaaattttc atctgaaaaa aggacaatct     1200
atctagacgt tagatttcag ccctaatatg aatctgaagc atttggtgga cgagaaagag     1260
ccatgtagga atgcatcaaa caaggaaaaa atctttgaac tccaatggga ttgaagatac     1320
agataccaat ggataagaat ctgttctctt tgcccactat ttaaactcac caaacccacc     1380
agtatcttcc tcaccacaaa atacattcca ccgttgatca caagccttat tccaccacct     1440
ccaaca                                                                1446
```

<210> SEQ ID NO 212
<211> LENGTH: 2018
<212> TYPE: DNA
<213> ORGANISM: Cucumis melo

<400> SEQUENCE: 212

```
actattggag acgacgaagg aaaactctaa tgtgagctta gaattgaaga tggtgaacaa       60 tgggagtct ttttttaaaaa tctttcgtcg gtatattgaa atttcctttt acactcaaat      120 aaccccccctt ttcacgcgtt caacgtcttc aaaccttcct ttttcaatta ttttttcgtt     180
tacattaatg acatttaggt aataagataa attagtggat tcttttgtga aaaatgttag      240
cccatttaag acttttatga aatatattag aaaaaaatca tatagcaatt tatattattc      300
```

-continued

```
tagttaaaag cccataatag aaactaaccc aacctaaagt aacgtaaaca ttcaataaga    360
gagacaaatt ttaaaataat ttctaattaa aaaaaaaatt gtcaagaccg tccgggtcgg    420
atccaaaata taacccgaac cggccggttt agcatctata taaatacacc tttagggttt    480
ttattctctc aagacttcac cgcatttcca cttctctgag gccacggtca gccattggag    540
cagctcaata atcctttgac tccctactac ggtaagtcga ccttactgct ttcggcttct    600
agttttttca atcctgtcat tagtcctttg gagttcttct gtacatttat gacgttttcg    660
gctcgtgttt tgtttcgcct gtatgtagtg ggttttcga gttttgtttt tactttttt     720 tatacttgca ggaattagtt gaaatctatg tacttcatgc cttggataat actcttgatc    780
tgttgtgtta ttcaaaatga attgttttaa gatggtattt gagaatggtc atgtgagttt    840
tgcctacttg gttattaaaa tgaattgttt taggatggta tttgagaatg gtcttctggg    900
tatttggttg gaacctttgt gctctgctat gaattagggt gttctccccg ttttttttt    960 ttttttcctt ttggttatta atatatcttt tatgactact tattcatata tgatatcttt   1020
tactcgtaaa ttttgactca tttgaaagtt ttatccttag tcctttctca ttcagggtgt   1080
aaaggtatgt tgttagggtt aaaatagcct atgcaggaaa gttctgtatt tgttctaatt   1140
attgcatttg tgtgcatttg tatctagttt atttcttgct gagagtatgc ttcattttt    1200 agtacacatc acttgtgcca ctttattata gttgcacatt tttgtttatg gagaggatga   1260
atagcattta gggatgtcaa tttttattg agaaaaccct ctctcctact taagcttggg    1320 gaattttgt tctaaatgtg gtaaacataa tacttcttct tattttaatt tgaatggaag    1380
gggaagacga atactaatat tttcaacgaa ccttcacaac tttttttttc ttatttagga   1440
agccatgttt ttcaaaattg tactgtgtga tccacatatt tatcgattat tagtgaatcg   1500
aataataatt agagttttat tggtataatt ttgaagttca gacttattac atttgtggaa   1560
agtttggtta caattttcaa ttttattgga atcctaagaa ctttgtgtta acatatattg   1620
agttttcttc tcttttttt tactcattaa gttctctatt aggaatgttt ggttcaatgt    1680
cacatagtcg atagctaaga ccagtgaccc acaaagctat gattgaacga aaaacaagcc   1740
tttcacatct tggtaggaat ttgttatttc tcaatagatt tacagagctg tttcatgtga   1800
tcacaatttt tttctatttt tctgaagttc tctattagga atgggctatc tggttagttg   1860
cttttgagag aacatgtgga ttggtgttgc tcggtttcct tgcctttgta attttgtcct   1920
tggaaaaagc aaaatgatta ggtatcctga tatgcataac atgtttaagc caactagttc   1980
tcactttttt agtgcaaata attgatcttc aggaatcg                            2018
```

PLANT REGULATORY ELEMENTS AND USES THEREOF

REFERENCE TO RELATED APPLICATIONS

This application is a divisional of U.S. application Ser. No. 16/549,573, filed Aug. 23, 2019, which is a divisional of U.S. application Ser. No. 15/802,843, filed Nov. 3, 2017 (now U.S. Pat. No. 10,550,401), which is a divisional of U.S. application Ser. No. 14/117,342, filed Oct. 23, 2014 (now U.S. Pat. No. 9,845,477) which is a 371 National Stage application of International Application No. PCT/US12/037561, filed May 11, 2012, which claims the benefit of U.S. Provisional Application No. 61/485,876, filed May 13, 2011, each of which is herein incorporated by reference in its entirety.

INCORPORATION OF SEQUENCE LISTING

The sequence listing that is contained in the file named "MONS304US.txt", which is 463 kilobytes (as measured in Microsoft Windows®) and was created on Nov. 12, 2013, is filed herewith by electronic submission and is incorporated by reference herein.

FIELD OF THE INVENTION

The invention relates to the field of plant molecular biology and plant genetic engineering, and DNA molecules useful for modulating gene expression in plants.

BACKGROUND

Regulatory elements are genetic elements that regulate gene activity by modulating the transcription of an operably linked transcribable polynucleotide molecule. Such elements include promoters, leaders, introns, and 3' untranslated regions and are useful in the field of plant molecular biology and plant genetic engineering.

SUMMARY OF THE INVENTION

The present invention provides novel gene regulatory elements such as promoters, leaders and introns derived from *Cucumis melo*, a plant species commonly referred to as muskmelon, for use in plants. The present invention also provides DNA constructs, transgenic plant cells, plants, and seeds comprising the regulatory elements. The sequences may be provided operably linked to a transcribable polynucleotide molecule which may be heterologous with respect to a regulatory sequence provided herein. The present invention also provides methods of making and using the regulatory elements, the DNA constructs comprising the regulatory elements, and the transgenic plant cells, plants, and seeds comprising the regulatory elements operably linked to a transcribable polynucleotide molecule.

Thus, in one aspect, the present invention provides a DNA molecule, such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. In specific embodiments, a transcriptional regulatory expression element group, or promoter, or leader, or intron is at least 90 percent, at least 95 percent, at least 98 percent, or at least 99 percent identical to any of SEQ ID NOs: 1-199, 211 and 212. In particular embodiments, the heterologous transcribable polynucleotide molecule comprises a gene of agronomic interest, a gene capable of providing herbicide resistance in plants, or a gene capable of providing plant pest resistance in plants.

The invention also provides a transgenic plant cell containing a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. Further, the transcriptional regulatory expression element group, or promoter, or leader, or intron regulates the expression of a gene. The transgenic plant cell can be a monocotyledonous or dicotyledonous plant cell.

Further provided by the invention is a transgenic plant, or part of the transgenic plant containing a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. In specific embodiments, the transgenic plant may be a progeny plant of any generation that contains the transcriptional regulatory expression element group, or promoter, or leader, or intron.

Still further provided is a transgenic seed containing a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule.

In yet another aspect, the invention provides a method of producing a commodity product from the transgenic plant, transgenic plant part or transgenic seed which contains a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule. In one embodiment, the commodity product is protein concentrate, protein isolate, grain, starch, seeds, meal, flour, biomass, or seed oil.

In another aspect, the invention provides a commodity product comprising a DNA molecule such as a transcriptional regulatory expression element group, or promoter, or leader, or intron, comprising a polynucleotide sequence selected from the group consisting of: a) a sequence with at least 85 percent sequence identity to any of SEQ ID NOs: 1-199, 211 and 212; b) a sequence comprising any of SEQ ID NOs: 1-199, 211 and 212; and c) a fragment of any of SEQ ID NOs: 1-199, 211 and 212 exhibiting gene-regulatory activity, wherein said DNA molecule is operably linked to a heterologous transcribable polynucleotide molecule.

In still yet another aspect, the invention provides a method of expressing a transcribable polynucleotide molecule in a transgenic plant using a DNA molecule such as a transcriptional regulatory expression element group, or promoter, or leader, or intron which has a DNA sequence which is at least 85 percent identical to that of any of SEQ ID NOs: 1-199, 211 and 212, or contains any of SEQ ID NOs: 1-199, 211 and 212, or consists of a fragment of any of SEQ ID NOs: 1-199, 211 and 212; and cultivating the transgenic plant.

BRIEF DESCRIPTION OF THE SEQUENCES

SEQ ID NOs: 1, 5, 7, 9, 11, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 159, 162, 167, 168, 172, 175, 176, 177, 178, 181, 182, 183, 184, 185, 188, 189, 190, 191, 192, 193, 194, 195, 196, 197, 198, 199, 211 and 212 are *Cucumis* transcriptional regulatory expression element groups or EXP sequences which are comprised of either a promoter element, operably linked to a leader element; or a promoter element, operably linked to a leader element and an intron element, or a promoter element, operably linked to a leader element, operably linked to an intron element, operably linked to a leader element.

SEQ ID NOs: 2, 6, 8, 10, 12, 163 and 169 are promoter elements.

SEQ ID NOs: 3, 164, 166 and 170 are leader sequences.

SEQ ID NOs: 4, 165 and 171 are intron sequences.

SEQ ID NOs: 157, 160, 173, 179 and 186 are sequences wherein a promoter is operably linked to a leader element.

SEQ ID NOs: 158, 161, 174, 180 and 187 are sequences wherein an intron is operably linked to a leader element.

BRIEF DESCRIPTION OF THE DRAWINGS

FIGS. 1a-1f depict alignment of promoter variant segments corresponding to promoter elements isolated from the *Cucumis melo*. In particular, FIGS. 1a-1f show alignment of the 2068 bp promoter sequence P-CUCme.Ubq1-1:1:15 (SEQ ID NO: 2), found in the transcriptional regulatory expression element group EXP-CUCme.Ubq1:1:1 (SEQ ID NO: 1), vs. promoter sequences derived via 5' deletions of the promoter, P-CUCme.Ubq1-1:1:15. Deletion, for instance of the 5' end of P-CUCme.Ubq1-1:1:15, produced the promoters, P-CUCme.Ubq1-1:1:16 (SEQ ID NO: 6) a 1459 bp promoter which is found within EXP-CUCme.Ubq1:1:2 (SEQ ID NO: 5); P-CUCme.Ubq1-1:1:17 (SEQ ID NO: 8), a 964 bp sequence comprised within EXP-CUCme.Ubq1:1:3 (SEQ ID NO: 7); P-CUCme.Ubq1-1:1:18 (SEQ ID NO: 10), a 479 bp sequence comprised within EXP-CUCme.Ubq1:1:4 (SEQ ID NO: 9); and P-CUCme.Ubq1-1:1:19 (SEQ ID NO: 12), a 173 bp sequence comprised within EXP-CUCme.Ubq1:1:5 (SEQ ID NO: 11).

DETAILED DESCRIPTION OF THE INVENTION

The invention disclosed herein provides polynucleotide molecules obtained from *Cucumis melo* having beneficial gene regulatory activity. The design, construction, and use of these polynucleotide molecules are described. The nucleotide sequences of these polynucleotide molecules are provided among SEQ ID NOs: 1-199, 211 and 212. These polynucleotide molecules are, for instance, capable of affecting the expression of an operably linked transcribable polynucleotide molecule in plant tissues, and therefore selectively regulating gene expression, or activity of an encoded gene product, in transgenic plants. The present invention also provides methods of modifying, producing, and using the same. The invention also provides compositions, transformed host cells, transgenic plants, and seeds containing the promoters and/or other disclosed nucleotide sequences, and methods for preparing and using the same.

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e. a polymer of deoxyribonucleotide bases or a polynucleotide molecule, read from the 5' (upstream) end to the 3' (downstream) end. As used herein, the term "DNA sequence" refers to the nucleotide sequence of a DNA molecule.

As used herein, the term "isolated DNA molecule" refers to a DNA molecule at least partially separated from other molecules normally associated with it in its native or natural state. In one embodiment, the term "isolated" refers to a DNA molecule that is at least partially separated from some of the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated when integrated into the chromosome of a host cell or present in a nucleic acid solution with other DNA molecules, in that they are not in their native state.

Any number of methods are known in the to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or fragment thereof, can also be obtained by other techniques such as by directly synthesizing the fragment by chemical means, as is commonly practiced by using an automated oligonucleotide synthesizer.

As used herein, the term "sequence identity" refers to the extent to which two optimally aligned polynucleotide sequences or two optimally aligned polypeptide sequences are identical. An optimal sequence alignment is created by manually aligning two sequences, e.g. a reference sequence and another sequence, to maximize the number of nucleotide matches in the sequence alignment with appropriate internal nucleotide insertions, deletions, or gaps. As used herein, the term "reference sequence" refers to a sequence provided as the polynucleotide sequences of SEQ ID NOs: 1-199, 211 and 212.

As used herein, the term "percent sequence identity" or "percent identity" or "% identity" is the identity fraction times 100. The "identity fraction" for a sequence optimally aligned with a reference sequence is the number of nucleotide matches in the optimal alignment, divided by the total number of nucleotides in the reference sequence, e.g. the total number of nucleotides in the full length of the entire reference sequence. Thus, one embodiment of the invention is a DNA molecule comprising a sequence that when optimally aligned to a reference sequence, provided herein as SEQ ID NOs: 1-199, 211 and 212, has at least about 85 percent identity at least about 90 percent identity at least about 95 percent identity, at least about 96 percent identity, at least about 97 percent identity, at least about 98 percent identity, or at least about 99 percent identity to the reference sequence. In particular embodiments such sequences may be defined as having gene-regulatory activity or encoding a peptide that functions to localize an operably linked polypeptide within a cell.

Regulatory Elements

A regulatory element is a DNA molecule having gene regulatory activity, i.e. one that has the ability to affect the transcription and/or translation of an operably linked transcribable polynucleotide molecule. The term "gene regulatory activity" thus refers to the ability to affect the expression pattern of an operably linked transcribable polynucleotide molecule by affecting the transcription and/or translation of that operably linked transcribable polynucleotide molecule. As used herein, a transcriptional regulatory expression element group (EXP) may be comprised of expression elements, such as enhancers, promoters, leaders and introns, operably linked. Thus a transcriptional regulatory expression element group may be comprised, for instance, of a promoter operably linked 5' to a leader sequence, which is in turn operably linked 5' to an intron sequence. The intron sequence may be comprised of a sequence beginning at the point of the first intron/exon splice junction of the native sequence and further may be comprised of a small leader fragment comprising the second intron/exon splice junction so as to provide for proper intron/exon processing to facilitate transcription and proper processing of the resulting transcript. Leaders and introns may positively affect transcription of an operably linked transcribable polynucleotide molecule as well as translation of the resulting transcribed RNA. The pre-processed RNA molecule comprises leaders and introns, which may affect the post-transcriptional processing of the transcribed RNA and/or the export of the transcribed RNA molecule from the cell nucleus into the cytoplasm. Following post-transcriptional processing of the transcribed RNA molecule, the leader sequence may be retained as part of the final messenger RNA and may positively affect the translation of the messenger RNA molecule.

Regulatory elements such as promoters, leaders, introns, and transcription termination regions are DNA molecules that have gene regulatory activity and play an integral part in the overall expression of genes in living cells. The term "regulatory element" refers to a DNA molecule having gene regulatory activity, i.e. one that has the ability to affect the transcription and/or translation of an operably linked transcribable polynucleotide molecule. Isolated regulatory elements, such as promoters and leaders that function in plants are therefore useful for modifying plant phenotypes through the methods of genetic engineering.

Regulatory elements may be characterized by their expression pattern effects (qualitatively and/or quantitatively), e.g. positive or negative effects and/or constitutive or other effects such as by their temporal, spatial, developmental, tissue, environmental, physiological, pathological, cell cycle, and/or chemically responsive expression pattern, and any combination thereof, as well as by quantitative or qualitative indications. A promoter is useful as a regulatory element for modulating the expression of an operably linked transcribable polynucleotide molecule.

As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a dsRNA, a tRNA, an rRNA, a miRNA, and the like.

As used herein, the term "protein expression" is any pattern of translation of a transcribed RNA molecule into a protein molecule. Protein expression may be characterized by its temporal, spatial, developmental, or morphological qualities as well as by quantitative or qualitative indications.

As used herein, the term "promoter" refers generally to a DNA molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, that is a promoter produced through the fusion of two or more heterologous DNA molecules. Promoters useful in practicing the present invention include any of SEQ ID NOs: 2, 6, 8, 10, 12, 163 and 169, or the promoter elements comprised within any of SEQ ID NOs: 13 through 199, 211 and 212, or fragments or variants thereof. In specific embodiments of the invention, such molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent sequence for recognition and binding of the RNA polymerase II complex for initiation of transcription.

In one embodiment, fragments of a promoter molecule are provided. Promoter fragments provide promoter activity, as described above, and may be useful alone or in combination with other promoters and promoter fragments, such as in constructing chimeric promoters. In specific embodiments, fragments of a promoter are provided comprising at least about 50, 95, 150, 250, 500, 750, or at least about 1000 contiguous nucleotides, or longer, of a polynucleotide molecule having promoter activity disclosed herein.

Compositions derived from any of the promoters presented as SEQ ID NOs: 2, 6, 8, 10, 12, 163 and 169, or the promoter elements comprised within SEQ ID NOs: 13 through 199, 211 and 212, such as internal or 5' deletions, for example, can be produced to improve or alter expression, including by removing elements that have either positive or negative effects on expression; duplicating elements that have positive or negative effects on expression; and/or duplicating or removing elements that have tissue or cell specific effects on expression. Compositions derived from any of the promoters presented as SEQ ID NOs: 2, 6, 8, 10, 12, 163 and 169, or the promoter elements comprised within SEQ ID NOs: 13 through 199, 211 and 212 comprised of 3' deletions in which the TATA box element or equivalent sequence thereof and downstream sequence is removed can be used, for example, to make enhancer elements. Further deletions can be made to remove any elements that have positive or negative; tissue specific; cell specific; or timing specific (such as, but not limited to, circadian rhythms) effects on expression. Any of the promoters presented as SEQ ID NOs: 2, 6, 8, 10, 12, 163 and 169, or the promoter elements comprised within SEQ ID NOs: 13 through 199, 211 and 212, and fragments or enhancers derived there from can be used to make chimeric transcriptional regulatory element compositions comprised of any of the promoters presented as SEQ ID NOs: 2, 6, 8, 10, 12, 163 and 169, or the promoter elements comprised within SEQ ID NOs: 13 through 199, 211 and 212, and the fragments or enhancers derived therefrom operably linked to other enhancers and promoters. The efficacy of the modifications, duplications or deletions described herein on the desired expression aspects of a particular transgene may be tested empirically in stable and transient plant assays, such as those described in the working examples herein, so as to validate the results, which may vary depending upon the changes made and the goal of the change in the starting molecule.

As used herein, the term "leader" refers to a DNA molecule isolated from the untranslated 5' region (5' UTR) of a genomic copy of a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable polynucleotide molecule. Leader molecules may be used with a heterologous promoter or with their native promoter. Promoter molecules of the present invention may thus be operably linked to their native leader or may be operably linked to a heterologous leader. Leaders useful in practicing the present invention include SEQ ID NOs: 3, 164, 166 and 170, or the leader element comprised within SEQ ID NOs: 13 through 199, 211 and 212, or fragments or variants thereof. In specific embodiments, such sequences may be provided defined as being capable of acting as a leader in a host cell, including, for example, a transgenic plant cell. In one embodiment such sequences are decoded as comprising leader activity.

The leader sequences (5' UTR) presented as SEQ ID NOs: 3, 164, 166 and 170, or the leader element comprised within any of SEQ ID NOs: 13 through 199, 211 and 212 may be comprised of regulatory elements or may adopt secondary structures that can have an effect on transcription or translation of a transgene. The leader sequences presented as SEQ ID NOs: 3, 164, 166 and 170, or the leader element comprised within SEQ ID NOs: 13 through 199, 211 and 212 can be used in accordance with the invention to make chimeric regulatory elements that affect transcription or translation of a transgene. In addition, the leader sequences presented as SEQ ID NOs: 3, 164, 166 and 170, or the leader element comprised within any of SEQ ID NOs: 13 through 199, 211 and 212 can be used to make chimeric leader sequences that affect transcription or translation of a transgene.

The introduction of a foreign gene into a new plant host does not always result in a high expression of the incoming gene. Furthermore, if dealing with complex traits, it is sometimes necessary to modulate several genes with spatially or temporarily different expression pattern. Introns can principally provide such modulation. However, multiple use of the same intron in one transgenic plant has shown to exhibit disadvantages. In those cases it is necessary to have a collection of basic control elements for the construction of appropriate recombinant DNA elements. As the available collection of introns known in the art with expression enhancing properties is limited, alternatives are needed.

Compositions derived from any of the introns presented as SEQ ID NOs: 4, 165 and 171 or the intron element comprised within SEQ ID NOs: 13 through 199, 211 and 212 can be comprised of internal deletions or duplications of cis regulatory elements; and/or alterations of the 5' and 3' sequences comprising the intron/exon splice junctions can be used to improve expression or specificity of expression when operably linked to a promoter+leader or chimeric promoter+leader and coding sequence. Alterations of the 5' and 3' regions comprising the intron/exon splice junction can also be made to reduce the potential for introduction of false start and stop codons being produced in the resulting transcript after processing and splicing of the messenger RNA. The introns can be tested empirically as described in the working examples to determine the intron's effect on expression of a transgene.

In accordance with the invention a promoter or promoter fragment may be analyzed for the presence of known promoter elements, i.e. DNA sequence characteristics, such as a TATA-box and other known transcription factor binding site motifs. Identification of such known promoter elements may be used by one of skill in the art to design variants having a similar expression pattern to the original promoter.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide sequence. Unlike promoters, enhancer elements do not usually include a transcription start site (TSS) or TATA box or equivalent sequence. A promoter may naturally comprise one or more enhancer elements that affect the transcription of an operably linked polynucleotide sequence. An isolated enhancer element may also be fused to a promoter to produce a chimeric promoter.cis-element, which confers an aspect of the overall modulation of gene expression. A promoter or promoter fragment may comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e. deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed by the present invention.

In plants, the inclusion of some introns in gene constructs leads to increased mRNA and protein accumulation relative to constructs lacking the intron. This effect has been termed "intron mediated enhancement" (IME) of gene expression (Mascarenhas et al., (1990) *Plant Mol. Biol.* 15:913-920). Introns known to stimulate expression in plants have been identified in maize genes (e.g. tubA1, Adh1, Sh1, Ubi1 (Jeon et al. (2000) *Plant Physiol.* 123:1005-1014; Callis et al. (1987) *Genes Dev.* 1:1183-1200; Vasil et al. (1989) *Plant Physiol.* 91:1575-1579; Christiansen et al. (1992) *Plant Mol. Biol.* 18:675-689) and in rice genes (e.g. salt, tpi: McElroy et al., *Plant Cell* 2:163-171 (1990); Xu et al., *Plant Physiol.* 106:459-467 (1994)). Similarly, introns from dicotyledonous plant genes like those from petunia (e.g. rbcS), potato (e.g. st-ls1) and from *Arabidopsis thaliana* (e.g. ubq3 and pat1) have been found to elevate gene expression rates (Dean et al. (1989) *Plant Cell* 1:201-208; Leon et al. (1991) *Plant Physiol.* 95:968-972; Norris et al. (1993) *Plant Mol Biol* 21:895-906; Rose and Last (1997) *Plant J.*11:455-464). It has been shown that deletions or mutations within the splice sites of an intron reduce gene expression, indicating that splicing might be needed for IME (Mascarenhas et al. (1990) *Plant Mol Biol.* 15:913-920; Clancy and Hannah (2002) *Plant Physiol.* 130:918-929). However, that splicing per se is not required for a certain IME in dicotyledonous plants has been shown by point mutations within the splice sites of the pat1 gene from *A. thaliana* (Rose and Beliakoff (2000) *Plant Physiol.* 122:535-542).

Enhancement of gene expression by introns is not a general phenomenon because some intron insertions into recombinant expression cassettes fail to enhance expression (e.g. introns from dicot genes (rbcS gene from pea, phaseolin gene from bean and the stls-1 gene from *Solanum tuberosum*) and introns from maize genes (adh1 gene the ninth intron, hsp81 gene the first intron)) (Chee et al. (1986) *Gene* 41:47-57; Kuhlemeier et al. (1988) *Mol Gen Genet* 212:405-411; Mascarenhas et al. (1990) *Plant Mol. Biol.* 15:913-920; Sinibaldi and Mettler (1992) In W E Cohn, K Moldave, eds, *Progress in Nucleic Acid Research and Molecular Biology*, Vol 42. Academic Press, New York, pp 229-257; Vancanneyt et al. 1990 *Mol. Gen. Genet.* 220:245-250). Therefore, not each intron can be employed in order to manipulate the gene expression level of non-endogenous genes or endogenous genes in transgenic plants. What characteristics or specific sequence features must be present in an intron sequence in order to enhance the expression rate of a given gene is not known in the prior art and therefore from the prior art it is not possible to predict whether a given plant intron, when used heterologously, will cause IME.

As used herein, the term "chimeric" refers to a single DNA molecule produced by fusing a first DNA molecule to a second DNA molecule, where neither first nor second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments; an example would be the fusion of a promoter to an enhancer element. Thus, the design, construction, and use of chimeric promoters according to the methods disclosed herein for modulating the expression of operably linked transcribable polynucleotide molecules are encompassed by the present invention.

As used herein, the term "variant" refers to a second DNA molecule that is in composition similar, but not identical to, a first DNA molecule and yet the second DNA molecule still maintains the general functionality, i.e. same or similar expression pattern, of the first DNA molecule. A variant may be a shorter or truncated version of the first DNA molecule and/or an altered version of the sequence of the first DNA molecule, such as one with different restriction enzyme sites and/or internal deletions, substitutions, and/or insertions. A "variant" can also encompass a regulatory element having a nucleotide sequence comprising a substitution, deletion and/ or insertion of one or more nucleotides of a reference sequence, wherein the derivative regulatory element has more or less or equivalent transcriptional or translational activity than the corresponding parent regulatory molecule. The regulatory element "variants" may also encompass variants arising from mutations that naturally occur in bacterial and plant cell transformation. In the present invention, a polynucleotide sequence provided as SEQ ID NOs: 1-199, 211 and 212 may be used to create variants similar in composition, but not identical to, the polynucleotide sequence of the original regulatory element, while still maintaining the general functionality of, i.e. same or similar expression pattern, the original regulatory element. Production of such variants of the present invention is well within the ordinary skill of the art in light of the disclosure and is encompassed within the scope of the present invention. "Varients" of chimeric regulatory element comprise the same constituent elements as a reference chimeric regulatory element sequence but the constituent elements comprising the chimeric regulatory element may be operatively linked by various methods known in the art such as, restriction enzyme digestion and ligation, ligation independent cloning, modular assembly of PCR products during amplification, or direct chemical synthesis of the chimeric regulatory element as well as other methods known in the art. The resulting "variant" chimeric regulatory element is comprised of the same, or variants of the same, constituent elements as the reference sequence but differ in the sequence or sequences that are used to operably link the constituent elements. In the present invention, the polynucleotide sequences provided as SEQ ID NOs: 1-199, 211 and 212 each provide a reference sequence wherein the constituent elements of the reference sequence may be joined by methods known in the art and may consist of substitutions, deletions and/or insertions of one or more nucleotides or mutations that naturally occur in bacterial and plant cell transformation.

Constructs

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. As used herein, the term "vector" means any recombinant polynucleotide construct that may be used for the purpose of transformation, i.e. the introduction of heterologous DNA into a host cell. The term includes an expression cassette isolated from any of the aforementioned molecules.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. A leader, for example, is operably linked to coding sequence when it is capable of serving as a leader for the polypeptide encoded by the coding sequence.

The constructs of the present invention may be provided, in one embodiment, as double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *A. tumefaciens* cells, permit the integration of the T-DNA into the genome of a plant cell (see, for example, U.S. Pat. No. 6,603,061). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404; however, other strains known in the art of plant transformation can function in the present invention.

Methods are available for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells can be found in, for example, *Molecular Cloning: A Laboratory Manual*, 3 rd edition Volumes 1, 2, and 3 (2000) J. F. Sambrook, D. W. Russell, and N. Irwin, Cold Spring Harbor Laboratory Press. Methods for making recombinant vectors particularly suited to plant transformation include, without limitation, those described in U.S. Pat. Nos. 4,971,908; 4,940,835; 4,769,061; and 4,757,011 in their entirety. These types of vectors have also been reviewed in the scientific literature (see, for example, Rodriguez, et al., *Vectors: A Survey of Molecular Cloning Vectors' and Their Uses*, Butterworths, Boston, (1988) and Glick, et al., *Methods in Plant Molecular Biology and Biotechnology*, CRC Press, Boca Raton, FL. (1993)). Typical vectors useful for expression of nucleic acids in higher plants are well known in the art and include vectors derived from the tumor-inducing (Ti) plasmid of *Agrobacterium tumefaciens* (Rogers, et al., *Methods in Enzymology* 153: 253-277 (1987)). Other recombinant vectors useful for plant transformation, including the pCaMVCN transfer control vector, have also been described in the scientific literature (see, for example, Fromm, et al., *Proc. Natl. Acad. Sci. USA* 82: 5824-5828 (1985)).

Various regulatory elements may be included in a construct including any of those provided herein. Any such regulatory elements may be provided in combination with other regulatory elements. Such combinations can be designed or modified to produce desirable regulatory features. In one embodiment, constructs of the present invention comprise at least one regulatory element operably linked to a transcribable polynucleotide molecule operably linked to a 3' transcription termination molecule.

Constructs of the present invention may include any promoter or leader provided herein or known in the art. For example, a promoter of the present invention may be operably linked to a heterologous non-translated 5' leader such as one derived from a heat shock protein gene (see, for example, U.S. Pat. Nos. 5,659,122 and 5,362,865). Alternatively, a leader of the present invention may be operably linked to a heterologous promoter such as the Cauliflower Mosaic Virus 35S transcript promoter (see, U.S. Pat. No. 5,352,605). The expression properties imparted by such operable linkages of heterologous elements is not necessarily additive of the elucidated properties of each promoter and leader, but rather is determined through empirical analysis of expression driven by the operably linked heterologous promoter and leader.

As used herein, the term "intron" refers to a DNA molecule that may be isolated or identified from the genomic copy of a gene and may be defined generally as a region spliced out during mRNA processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable polynucleotide molecule. A DNA construct may comprise an intron, and the intron may or may not be heterologous with respect to the transcribable polynucleotide molecule sequence. Examples of introns in the art include the rice actin intron (U.S. Pat. No. 5,641,876) and the corn HSP70 intron (U.S. Pat. No. 5,859,347). Introns useful in practicing the present invention include SEQ ID NOs: 4, 165 and 171 or the intron element comprised within any of SEQ ID NOs: 13 through 199, 211 and 212.

As used herein, the term "3' transcription termination molecule" or "3' UTR" refers to a DNA molecule that is used during transcription to produce the 3' untranslated region (3' UTR) of an mRNA molecule. The 3' untranslated region of an mRNA molecule may be generated by specific cleavage and 3' polyadenylation, a.k.a. polyA tail. A 3' UTR may be operably linked to and located downstream of a transcribable polynucleotide molecule and may include polynucleotides that provide a polyadenylation signal and other regulatory signals capable of affecting transcription, mRNA processing, or gene expression. PolyA tails are thought to function in mRNA stability and in initiation of translation. Examples of 3' transcription termination molecules are the nopaline synthase 3' region (see, Fraley, el al., *Proc. Natl. Acad. Sci. USA*, 80: 4803-4807 (1983)); wheat hsp17 3' region; pea rubisco small subunit 3' region; cotton E6 3' region (U.S. Pat. No. 6,096,950); 3' regions disclosed in WO0011200A2; and the coixin 3' UTR (U.S. Pat. No. 6,635,806).

3' UTRs typically find beneficial use for the recombinant expression of specific genes. In animal systems, a machinery of 3' UTRs has been well defined (e.g. Zhao et al., *Microbiol Mol Biol Rev* 63:405-445 (1999); Proudfoot, *Nature* 322: 562-565 (1986); Kim et al., *Biotechnology Progress* 19:1620-1622 (2003); Yonaha and Proudfoot, *EMBO J.* 19:3770-3777 (2000); Cramer et al., *FEBS Letters* 498:179-182 (2001); Kuerstem and Goodwin, *Nature Reviews Genetics* 4:626-637 (2003)). Effective termination of RNA transcription is required to prevent unwanted transcription of trait—unrelated (downstream) sequences, which may interfere with trait performance. Arrangement of multiple gene expression cassettes in local proximity to one another (e.g. within one T-DNA) may cause suppression of gene expression of one or more genes in said construct in comparison to independent insertions (Padidam and Cao, *BioTechniques* 31:328-334 (2001). This may interfere with achieving adequate levels of expression, for instance in cases were strong gene expression from all cassettes is desired.

In plants, clearly defined polyadenylation signal sequences are not known. Hasegawa et al., *Plant J.* 33:1063-1072, (2003)) were not able to identify conserved polyadenylation signal sequences in both in vitro and in vivo systems in *Nicotiana sylvestris* and to determine the actual length of the primary (non-polyadenylated) transcript. A weak 3' UTR has the potential to generate read-through, which may affect the expression of the genes located in the neighboring expression cassettes (Padidam and Cao, *BioTechniques* 31:328-334 (2001)). Appropriate control of transcription termination can prevent read-through into sequences (e.g. other expression cassettes) localized downstream and can further allow efficient recycling of RNA polymerase, to improve gene expression. Efficient termination of transcription (release of RNA Polymerase II from the DNA) is pre-requisite for re-initiation of transcription and thereby directly affects the overall transcript level. Subsequent to transcription termination, the mature mRNA is released from the site of synthesis and template to the cytoplasm. Eukaryotic mRNAs are accumulated as poly(A) forms in vivo, so that it is difficult to detect transcriptional termination sites by conventional methods. However, prediction of functional and efficient 3' UTRs by bioinformatics methods is difficult in that there are no conserved sequences which would allow easy prediction of an effective 3' UTR.

From a practical standpoint, it is typically beneficial that a 3' UTR used in a transgene cassette possesses the following characteristics. The 3' UTR should be able to efficiently and effectively terminate transcription of the transgene and prevent read-through of the transcript into any neighboring DNA sequence which can be comprised of another transgene cassette as in the case of multiple cassettes residing in one T-DNA, or the neighboring chromosomal DNA into which the T-DNA has inserted. The 3' UTR should not cause a reduction in the transcriptional activity imparted by the promoter, leader and introns that are used to drive expression of the transgene. In plant biotechnology, the 3' UTR is often used for priming of amplification reactions of reverse transcribed RNA extracted from the transformed plant and used to (1) assess the transcriptional activity or expression of the transgene cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette.

3' UTRs useful in providing expression of a transgene in plants may be identified based upon the expression of expressed sequence tags (ESTs) in cDNA libraries made from messenger RNA isolated from seed, flower and other tissues derived from Foxtail millet (*Setaria italica* (L.) Beauv). Libraries of cDNA are made from tissues isolated from selected plant species using flower tissue, seed, leaf and root. The resulting cDNAs are sequenced using various sequencing methods. The resulting ESTs are assembled into clusters using bioinformatics software such as cic_ref_assemble_complete version 2.01.37139 (CLC bio USA, Cambridge, Massachusetts 02142). Transcript abundance of each cluster is determined by counting the number of cDNA reads for each cluster. The identified 3' UTRs may be comprised of sequence derived from cDNA sequence as well as sequence derived from genomic DNA. The cDNA sequence is used to design primers, which are then used with GenomeWalker™ (Clontech Laboratories, Inc, Mountain View, CA) libraries constructed following the manufacturer's protocol to clone the 3' region of the corresponding genomic DNA sequence to provide a longer termination sequence. Analysis of relative transcript abundance either by direct counts or normalized counts of observed sequence reads for each tissue library can be used to infer properties about patters of expression. For example, some 3' UTRs may be found in transcripts seen in higher abundance in root tissue as opposed to leaf. This is suggestive that the transcript is highly expressed in root and that the properties of root expression may be attributable to the transcriptional regulation of the promoter, the lead, the introns or the 3' UTR. Empirical testing of 3' UTRs identified by the properties of expression within specific organs, tissues or cell types can result in the identification of 3' UTRs that enhance expression in those specific organs, tissues or cell types.

Constructs and vectors may also include a transit peptide coding sequence that expresses a linked peptide that is useful for targeting of a protein product, particularly to a chloroplast, leucoplast, or other plastid organelle; mitochondria; peroxisome; vacuole; or an extracellular location. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (See, Klee et al., *Mol. Gen. Genet.* 210:437-442 (1987)) or the *Petunia hybrida* EPSPS CTP (CTP4) (See, della-Cioppa et al., *Proc. Natl. Acad. Sci. USA* 83:6873-6877 (1986)) has been show to target heterologous EPSPS protein sequences to chloroplasts in transgenic plants (See, U.S. Pat. Nos. 5,627,061; 5,633,435; and 5,312,910 and EP 0218571; EP 189707; EP 508909; and EP 924299).

Transcribable Polynucleotide Molecules

As used herein, the term "transcribable polynucleotide molecule" refers to any DNA molecule capable of being transcribed into a RNA molecule, including, but not limited to, those having protein coding sequences and those producing RNA molecules having sequences useful for gene suppression. A "transgene" refers to a transcribable polynucleotide molecule heterologous to a host cell at least with respect to its location in the genome and/or a transcribable polynucleotide molecule artificially incorporated into a host cell's genome in the current or any prior generation of the cell.

A promoter of the present invention may be operably linked to a transcribable polynucleotide molecule that is heterologous with respect to the promoter molecule. As used herein, the term "heterologous" refers to the combination of two or more polynucleotide molecules when such a combination is not normally found in nature. For example, the two molecules may be derived from different species and/or the two molecules may be derived from different genes, e.g. different genes from the same species or the same genes from different species. A promoter is thus heterologous with respect to an operably linked transcribable polynucleotide molecule if such a combination is not normally found in nature, i.e. that transcribable polynucleotide molecule is not naturally occurring operably linked in combination with that promoter molecule.

The transcribable polynucleotide molecule may generally be any DNA molecule for which expression of a RNA transcript is desired. Such expression of an RNA transcript may result in translation of the resulting mRNA molecule and thus protein expression. Alternatively, for example, a transcribable polynucleotide molecule may be designed to ultimately cause decreased expression of a specific gene or protein. In one embodiment, this may be accomplished by using a transcribable polynucleotide molecule that is oriented in the antisense direction. Briefly, as the antisense transcribable polynucleotide molecule is transcribed, the RNA product hybridizes to and sequesters a complimentary RNA molecule inside the cell. This duplex RNA molecule cannot be translated into a protein by the cell's translational machinery and is degraded in the cell. Any gene may be negatively regulated in this manner.

Thus, one embodiment of the invention is a regulatory element of the present invention, such as those provided as SEQ ID NOs: 1-199, 211 and 212, operably linked to a transcribable polynucleotide molecule so as to modulate transcription of the transcribable polynucleotide molecule at a desired level or in a desired pattern when the construct is integrated in the genome of a plant cell. In one embodiment, the transcribable polynucleotide molecule comprises a protein-coding region of a gene, and the promoter affects the transcription of an RNA molecule that is translated and expressed as a protein product. In another embodiment, the transcribable polynucleotide molecule comprises an antisense region of a gene, and the promoter affects the transcription of an antisense RNA molecule, double stranded RNA or other similar inhibitory RNA molecule in order to inhibit expression of a specific RNA molecule of interest in a target host cell.

Genes of Agronomic Interest

Transcribable polynucleotide molecules may be genes of agronomic interest. As used herein, the term "gene of agronomic interest" refers to a transcribable polynucleotide molecule that when expressed in a particular plant tissue, cell, or cell type confers a desirable characteristic, such as associated with plant morphology, physiology, growth, development, yield, product, nutritional profile, disease or pest resistance, and/or environmental or chemical tolerance. Genes of agronomic interest include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent such as an antisense or RNAi molecule targeting a particular gene for suppression. The product of a gene of agronomic interest may act within the plant in order to cause an effect upon the plant physiology or metabolism or may be act as a pesticidal agent in the diet of a pest that feeds on the plant.

In one embodiment of the invention, a promoter of the present invention is incorporated into a construct such that the promoter is operably linked to a transcribable polynucleotide molecule that is a gene of agronomic interest. The expression of the gene of agronomic interest is desirable in order to confer an agronomically beneficial trait. A beneficial agronomic trait may be, for example, but is not limited to, herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production. Examples of genes of agronomic interest include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. USRE38,446; 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658; 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304, 730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; and 6,380, 462), high oil production (U.S. Pat. Nos. 6,495,739; 5,608, 149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380, 466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. USRE37,543; 6,228,623; and U.S. Pat. Nos. 5,958,745, and 6,946,588), environmental stress resistance (U.S. Pat. No. 6,072,103), pharmaceutical peptides and secretable peptides (U.S. Pat. Nos. 6,812,379; 6,774, 283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristic or phenotype by encoding a RNA molecule that causes the targeted modulation of gene expression of an endogenous gene, for example via antisense (see e.g. U.S. Pat. No. 5,107,065); inhibitory RNA ("RNAi", including modulation of gene expression via miRNA-, siRNA-, trans-acting siRNA-, and phased sRNA-mediated mechanisms, e.g. as described in published applications US 2006/0200878 and US 2008/0066206, and in U.S. patent application Ser. No. 11/974,469); or cosuppression-mediated mechanisms. The RNA could also be a catalytic RNA molecule (e.g. a ribozyme or a riboswitch; see e.g. US 2006/0200878) engineered to cleave a desired endogenous mRNA product. Thus, any transcribable polynucleotide molecule that encodes a transcribed RNA molecule that affects an agronomically important phenotype or morphology change of interest may be useful for the practice of the present invention. Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. Nos. 5,107,065 and 5,759,829, and posttranscriptional gene suppression using a construct with a sense-oriented transcribable polynucleotide molecule to regulate gene expression in plants is disclosed in U.S. Pat. Nos. 5,283,184 and 5,231,020. Expression of a transcribable polynucleotide in a plant cell can also be used to suppress plant pests feeding on the plant cell, for example, compositions isolated from coleopteran pests (U.S. Patent Publication No. US20070124836) and compositions isolated from nematode pests (U.S. Patent Publication No. US20070250947). Plant pests include, but are not limited to arthropod pests, nematode pests, and fungal or microbial pests. Exemplary transcribable polynucleotide molecules for incorporation into constructs of the present invention include, for example, DNA molecules or genes from a species other than the target species or genes that originate with or are present in the same species, but are incorporated into recipient cells by genetic engineering methods rather than classical reproduction or breeding techniques. The type of polynucleotide molecule can include, but is not limited to, a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding ß-glucuronidase (GUS described in U.S. Pat. No. 5,599,670), green fluorescent protein and variants thereof (GFP described in U.S. Pat. Nos. 5,491,084 and 6,146,826), proteins that confer antibiotic resistance, or proteins that confer herbicide tolerance. Useful antibiotic resistance markers include those encoding proteins conferring resistance to kanamycin (nptII), hygromycin B (aph IV), streptomycin or spectinomycin (aad, spec/strep) and gentamycin (aac3 and aacC4). Herbicides for which transgenic plant tolerance has been demonstrated and the method of the present invention can be applied, include, but are not limited to: amino-methyl-phosphonic acid, glyphosate, glufosinate, sulfonylureas, imidazolinones, bromoxynil, delapon, dicamba, cyclohezanedione, protoporphyrinogen oxidase inhibitors, and isoxasflutole herbicides. Transcribable polynucleotide molecules encoding proteins involved in herbicide tolerance include, but are not limited to, a transcribable polynucleotide molecule encoding 5-enolpyruvylshikimate-3-phosphate synthase (EPSPS for glyphosate tolerance described in U.S. Pat. Nos. 5,627,061; 5,633,435; 6,040,497; and 5,094,945); a transcribable polynucleotide molecule encoding a glyphosate oxidoreductase and a glyphosate-N-acetyl transferase (GOX described in U.S. Pat. No. 5,463,175; GAT described in U.S. Patent publication No. 20030083480, and dicamba monooxygenase U.S. Patent publication No. 20030135879); a transcribable polynucleotide molecule encoding bromoxynil nitrilase (Bxn for Bromoxynil tolerance described in U.S. Pat. No. 4,810,648); a transcribable polynucleotide molecule encoding phytoene desaturase (crtI) described in Misawa, et al., *Plant Journal* 4:833-840 (1993) and Misawa, et al., *Plant Journal* 6:481-489 (1994) for norflurazon tolerance; a transcribable polynucleotide molecule encoding acetohydroxyacid synthase (AHAS, aka ALS) described in Sathasiivan, et al., *Nucl. Acids Res.* 18:2188-2193 (1990) for tolerance to sulfonylurea herbicides; and the bar gene described in DeBlock, et al., *EMBO Journal* 6:2513-2519 (1987) for glufosinate and bialaphos tolerance. The promoter molecules of the present invention can express linked transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, aryloxyalkanoate dioxygenases, acetyl CoA carboxylase, glyphosate oxidoreductase, and glyphosate-N-acetyl transferase.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g. by ELISA), small active enzymes which are detectable in extracellular solution (e.g. alpha-amylase, beta-lactamase, phosphinothricin transferase), or proteins which are inserted or trapped in the cell wall (such as proteins which include a leader sequence such as that found in the expression unit of extension or tobacco pathogenesis related proteins also known as tobacco PR-S). Other possible selectable marker genes will be apparent to those of skill in the art and are encompassed by the present invention.

Cell Transformation

The invention is also directed to a method of producing transformed cells and plants which comprise a promoter operably linked to a transcribable polynucleotide molecule.

The term "transformation" refers to the introduction of nucleic acid into a recipient host. As used herein, the term "host" refers to bacteria, fungi, or plant, including any cells, tissue, organs, or progeny of the bacteria, fungi, or plant. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism or progeny produced from a breeding program employing such a transgenic organism as a parent in a cross and exhibiting an altered phenotype resulting from the presence of a foreign polynucleotide molecule. The term "transgenic" refers to a bacteria, fungi, or plant containing one or more heterologous polynucleic acid molecules.

There are many methods for introducing polynucleic acid molecules into plant cells. The method generally comprises the steps of selecting a suitable host cell, transforming the host cell with a recombinant vector, and obtaining the transformed host cell. Suitable methods include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.* 42: 205 (1991)).

Any transformation methods may be utilized to transform a host cell with one or more promoters and/or constructs of the present invention. Host cells may be any cell or organism such as a plant cell, algae cell, algae, fungal cell, fungi, bacterial cell, or insect cell. Preferred hosts and transformed cells include cells from: plants, *Aspergillus*, yeasts, insects, bacteria and algae.

Regenerated transgenic plants can be self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books, see, for example, Allard, *Principles of Plant Breeding*, John Wiley & Sons, NY, U. of CA, Davis, CA, 50-98 (1960); Simmonds, *Principles of crop improvement*, Longman, Inc., NY, 369-399 (1979); Sneep and Hendriksen, Plant breeding perspectives, Wageningen (ed), Center for Agricultural Publishing and Documentation (1979); Fehr, *Soybeans: Improvement, Production and Uses,* 2nd Edition, Monograph, 16:249 (1987); Fehr, *Principles of variety development, Theory and Technique*, (Vol. 1) and *Crop* Species *Soybean* (Vol 2), Iowa State Univ., Macmillan Pub. Co., NY, 360-376 (1987). Conversely, pollen from non-transgenic plants may be used to pollinate the regenerated transgenic plants.

The transformed plants may be analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The expression of a transcribable polynucleotide molecule can be measured using TaqMan® (Applied Biosystems, Foster City, CA) reagents and methods as described by the manufacturer and PCR cycle times determined using the TaqMan® Testing Matrix. Alternatively, the Invader® (Third Wave Technologies, Madison, WI) reagents and methods as described by the manufacturer can be used transgene expression.

The seeds of the plants of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include leaves, stems, roots, tubers, seeds, endosperm, ovule, and pollen. The invention also includes and provides transformed plant cells which comprise a nucleic acid molecule of the present invention.

The transgenic plant may pass along the transgenic polynucleotide molecule to its progeny. Progeny includes any regenerable plant part or seed comprising the transgene derived from an ancestor plant. The transgenic plant is preferably homozygous for the transformed polynucleotide molecule and transmits that sequence to all offspring as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immunoprecipitation, and ELISA.

Having now generally described the invention, the same will be more readily understood through reference to the following examples which are provided by way of illustration, and are not intended to be limiting of the present invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1: Identification and Cloning of Regulatory Elements

Novel transcriptional regulatory elements, or transcriptional regulatory expression element group (EXP) sequences were identified and isolated from genomic DNA of the dicot species *Cucumis melo* WSH-39-1070AN.

Transcriptional regulatory elements were selected based upon proprietary and public microarray data derived from transcriptional profiling experiments conducted in soybean (*Glycine max*) and *Arabidopsis* as well as homology based searches using known dicot sequences as query against proprietary *Cucumis melo* sequences.

Using the identified sequences, a bioinformatic analysis was conducted to identify regulatory elements within the amplified DNA, followed by identification of the transcriptional start site (TSS) and any bi-directionality, introns, or upstream coding sequence present in the sequence. Using the results of this analysis, regulatory elements were defined within the DNA sequences and primers designed to amplify the regulatory elements. The corresponding DNA molecule for each regulatory element was amplified using standard polymerase chain reaction conditions with primers containing unique restriction enzyme sites and genomic DNA isolated from *Cucumis melo*. The resulting DNA fragments were ligated into base plant expression vectors using standard restriction enzyme digestion of compatible restriction sites and DNA ligation methods.

Analysis of the regulatory element TSS and intron/exon splice junctions can be performed using transformed plant protoplasts. Briefly, the protoplasts are transformed with the plant expression vectors comprising the cloned DNA fragments operably linked to a heterologous transcribable polynucleotide molecule and the 5' RACE System for Rapid Amplification of cDNA Ends, Version 2.0 (Invitrogen, Carlsbad, California 92008) is used to confirm the regulatory element TSS and intron/exon splice junctions by analyzing the sequence of the mRNA transcripts produced thereby.

Sequences encoding ubiquitin 1 transcriptional regulatory expression element groups (EXP) were analyzed as described above and each transcriptional regulatory expression element groups ("EXP's") was also broken down into the corresponding promoters, leaders and introns comprising each transcriptional regulatory expression element group. Sequences of the identified ubiquitin 1 transcriptional regulatory expression element groups ("EXP's") are provided herein as SEQ ID NOs: 1, 5, 7, 9 and 11 and is listed in Table 1 below. The corresponding ubiquitin 1 promoters are provided herein as SEQ ID NOs: 2, 6, 8, 10 and 12. The ubiquitin 1 leader and intron are herein provided as SEQ ID NOs: 3 and 4, respectively.

Sequences encoding other *Cucumis* transcriptional regulatory expression element groups or EXP sequences which are comprised of either a promoter element, operably linked to a leader element; or a promoter element, operably linked to a leader element and an intron element, or a promoter element, operably linked to a leader element, operably linked to an intron element, operably linked to a leader element are provided as SEQ ID NOs: 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 159, 162, 167, 168, 172, 175, 176, 177, 178, 181, 182, 183, 184, 185, 188, 189, 190, 191, 192, 193, 194, 195, 196, 197, 198, 199, 211 and 212 and are also listed in Table 1 below. Additional promoter elements are provided as SEQ ID NOs: 163 and 169. Additional leader elements are provided as SEQ ID NOs: 164, 166 and 170. Additional intron elements are provided as SEQ ID NOs: 165 and 171. Elements wherein a promoter is operably linked to a leader element are provided as SEQ ID NOs: 157, 160, 173, 179 and 186. Elements wherein an intron is operably linked to a leader element are provided as SEQ ID NOs: 158, 161, 174, 180 and 187. With respect to the subset of sequences provided as SEQ ID NOs: 13 through 199, 211 and 212, these sequences were selected and cloned based upon the results of experiments such as transcript profiling or expression driven by promoters from homologous genes of a different species suggesting desirable patterns of expression such as constitutive expression, root expression, above ground expression or seed expression. The actual activity imparted by the *Cucumis* sequences is determined empirically and is not necessarily the same as that of a regulatory element derived from a homologous gene from a species other than *Cucumis melo* when used in a transformed plant host cell and whole transgenic plant.

TABLE 1

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| EXP-CUCme.Ubq1:1:1 | 1 | Ubiquitin 1 | EXP | 2611 | Promoter; Leader; Intron | 1-2068; 2069-2150; 2151-2608 |
| P-CUCme.Ubq1-1:1:15 | 2 | Ubiquitin 1 | P | 2068 | Promoter | |
| L-CUCme.Ubq1-1:1:1 | 3 | Ubiquitin 1 | L | 82 | Leader | |
| I-CUCme.Ubq1-1:1:1 | 4 | Ubiquitin 1 | I | 461 | Intron | |
| EXP-CUCme.Ubq1:1:2 | 5 | Ubiquitin 1 | EXP | 2002 | Promoter; Leader; Intron | 1-1459; 1460-1541; 1542-1999 |
| P-CUCme.Ubq1-1:1:16 | 6 | Ubiquitin 1 | P | 1459 | Promoter | |
| EXP-CUCme.Ubq1:1:3 | 7 | Ubiquitin 1 | EXP | 1507 | Promoter; Leader; Intron | 1-964; 965-1046; 1047-1504 |
| P-CUCme.Ubq1-1:1:17 | 8 | Ubiquitin 1 | P | 964 | Promoter | |
| EXP-CUCme.Ubq1:1:4 | 9 | Ubiquitin 1 | EXP | 1022 | Promoter; Leader; Intron | 1-479; 480-561; 562-1019 |
| P-CUCme.Ubq1-1:1:18 | 10 | Ubiquitin 1 | P | 479 | Promoter | |
| EXP-CUCme.Ubq1:1:5 | 11 | Ubiquitin 1 | EXP | 716 | Promoter; Leader; Intron | 1-173; 174-255; 256-713 |
| P-CUCme.Ubq1-1:1:19 | 12 | Ubiquitin 1 | P | 173 | Promoter | |
| P-CUCme.1-1:1:1 | 13 | Phosphatase 2A | EXP | 2000 | Promoter; Leader; Intron; Leader | Reverse compliment; see SEQ ID NO: 155 |
| P-CUCme.2-1:1:1 | 14 | Actin 1 | EXP | 2000 | Promoter; Leader; Intron; Leader | 1-964; 965-1028; 1029-1991; 1992-2003 |
| P-CUCme.3-1:1:3 | 15 | Actin 2 | EXP | 1990 | Promoter; Leader; Intron; Leader | 1-1243; 1244-1319; 1320-1982; 1983-1990 |
| P-CUCme.4-1:1:2 | 16 | Ubiquitin 2 | EXP | 2005 | Promoter; Leader; Intron; Leader | 1-1646; 1647-1704; 1705-2005; 2006-2008 |
| P-CUCme.5-1:1:2 | 17 | Ubiquitin 3 | EXP | 2004 | Promoter; Leader; Intron | 1-748; 749-819; 820-2004 |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| P-CUCme.6-1:1:1 | 18 | Tubulin beta chain | EXP | 1935 | Promoter; Leader; Intron; Leader | 1-1436; 1437-1482; 1483-1919; 1920-1935 |
| P-CUCme.8-1:1:2 | 19 | Tubulin beta chain | EXP | 1606 | Promoter; Leader | 1-1527; 1528-1606 |
| P-CUCme.9-1:1:2 | 20 | Tubulin beta chain | EXP | 1487 | Promoter; Leader | 1-1384; 1385-1487 |
| P-CUCme.10-1:1:1 | 21 | Tubulin beta chain | EXP | 1448 | Promoter; Leader | 1-1363; 1364-1448 |
| P-CUCme.11-1:1:2 | 22 | Elongation Factor 1 alpha | EXP | 1235 | Promoter; Leader; Intron | 1-617; 618-677; 678-1213; 1214-1235 |
| P-CUCme.15-1:1:2 | 23 | Elongation Factor 1 alpha | EXP | 2003 | Promoter; Leader; Intron; Leader | 1-1330; 1331-1435; 1430-1975; 1976-2002 |
| P-CUCme.16a-1:1:2 | 24 | Ubiquitin 7 | EXP | 2015 | Promoter; Leader | |
| P-CUCme.16b-1:1:1 | 25 | Ubiquitin 6 | EXP | 2006 | Promoter; Leader | |
| P-CUCme.17-1:1:2 | 26 | ubiquitin-40S ribosomal protein S27a | EXP | 2017 | Promoter; Leader | 1-1969; 1970-2017 |
| P-CUCme.18-1:1:2 | 27 | ubiquitin-40S ribosomal protein S27a | EXP | 1353 | Promoter; Leader | 1-1308; 1309-1353 |
| P-CUCme.19-1:1:2 | 28 | Chloropyll a/b binding protein | EXP | 2005 | Promoter; Leader | 1-1960; 1961-2005 |
| P-CUCme.20-1:1:2 | 29 | Chloropyll a/b binding protein | EXP | 1445 | Promoter; Leader | 1-1390; 1391-1445 |
| P-CUCme.21-1:1:1 | 30 | Chloropyll a/b binding protein | EXP | 1282 | Promoter; Leader | 1-1233; 1234-1282 |
| P-CUCme.22-1:1:3 | 31 | Elongation Factor 4 alpha | EXP | 2002 | | |
| P-CUCme.24-1:1:2 | 32 | S-Adenosylmethionine Synthetase | EXP | 2003 | Promoter; Leader; Intron; Leader | 1-1067; 1068-1165; 1166-2001; 2002-2003 |
| P-CUCme.26-1:1:2 | 33 | Stress responsive protein | EXP | 1372 | Promoter; Leader; Intron; Leader | 1-577; 578-654; 655-1366; 1367-1372 |
| P-CUCme.28-1:1:2 | 34 | Ribosomal protein S5a | EXP | 1122 | | |
| P-CUCme.29-1:1:2 | 35 | Ribosomal protein S5a | EXP | 2017 | Promoter; Leader; Intron; Leader | 1-490; 491-571; 572-2012; 2013-2017 |
| CumMe_WSM_SF143981.G5150 | 36 | LHCB6 (LIGHT HARVESTING COMPLEX PSII SUBUNIT 6) | EXP | 2000 | | |
| CumMe_WSM_SF144839.G5080 | 37 | EIF2 GAMMA translation initiation factor | EXP | 1760 | | |
| CumMe_WSM_SF146040.G5050 | 38 | EIF2 translation initiation factor | EXP | 1767 | | |
| CumMe_WSM_SF16408.G5350 | 39 | elongation factor Tu | EXP | 2000 | | |
| CumMe_WSM_SF16429.G5670 | 40 | unknown protein | EXP | 2000 | | |
| CumMe_WSM_SF16444.G5140 | 41 | histone H4 | EXP | 2000 | Promoter; Leader | 1-1947; 1948-2000 |
| CumMe_WSM_SF16530.G6000 | 42 | HMGB2 (HIGH MOBILITY GROUP B 2) transcription factor | EXP | 2000 | | |
| CumMe_WSM_SF16553.G5090 | 43 | PBG1; threonine-type endopeptidase | EXP | 1115 | | |
| CumMe_WSM_SF16563.G5560 | 44 | ATARFB1A (ADP-ribosylation factor B1A) | EXP | 2000 | Promoter; Leader; Intron; Leader | 1-1329; 1330-1427; 1428-1988; 1989-2000 |
| CumMe_WSM_SF16675.G5720 | 45 | chromatin protein family | EXP | 2000 | | |
| CumMe_WSM_SF16920.G5650 | 46 | CSD1 (COPPER/ZINC SUPEROXIDE DISMUTASE 1) | EXP | 2000 | | |
| CumMe_WSM_SF16953.G5180 | 47 | SCE1 (SUMO CONJUGATION ENZYME 1); SUMO ligase | EXP | 2000 | | |
| CumMe_WSM_SF17051.G5470 | 48 | 60S ribosomal protein L9 (RPL90D) | EXP | 2000 | | |
| CumMe_WSM_SF17111.G5790 | 49 | ubiquinol-cytochrome C reductase complex ubiquinone-binding protein | EXP | 2000 | Promoter; Leader | 1-1895; 1896-2000 |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF17142.G5920 | 50 | peptidyl-prolyl cis-trans isomerase, chloroplast | EXP | 2000 | | |
| CumMe_WSM_SF17190.G6200 | 51 | PRK (PHOSPHORIBULOKINASE) | EXP | 2000 | | |
| CumMe_WSM_SF17250.G5910 | 52 | LHCB5 (LIGHT HARVESTING COMPLEX OF PHOTOSYSTEM II 5) | EXP | 2000 | | |
| CumMe_WSM_SF17252.G7330 | 53 | nascent polypeptide-associated complex (NAC) domain-containing protein | EXP | 2000 | Promoter; Leader; Intron | 1-1195; 1196-1297; 1298-2000 |
| CumMe_WSM_SF17253.G5150 | 54 | RPS9 (RIBOSOMAL PROTEIN S9) | EXP | 1547 | | |
| CumMe_WSM_SF17322.G5110 | 55 | 60S ribosomal protein L22 (RPL22A) | EXP | 2000 | | |
| CumMe_WSM_SF17349.G5770 | 56 | PGRL1B (PGR5-Like B) | EXP | 2000 | | |
| CumMe_WSM_SF17357.G5630 | 57 | 40S ribosomal protein S10 (RPS10B) | EXP | 2000 | | |
| CumMe_WSM_SF17494.G5140 | 58 | MEE34 (maternal effect embryo arrest 34) | EXP | 1591 | | |
| CumMe_WSM_SF17524.G6410 | 59 | SUS2 (ABNORMAL SUSPENSOR 2) | EXP | 2000 | | |
| CumMe_WSM_SF17672.G5610 | 60 | PSAK (photosystem I subunit K) | EXP | 2000 | | |
| CumMe_WSM_SF17773.G6620 | 61 | aconitase C-terminal domain-containing protein | EXP | 2000 | | |
| CumMe_WSM_SF17866.G6050 | 62 | ATPDIL5-1 (PDI-like 5-1) | EXP | 2000 | | |
| CumMe_WSM_SF18004.G6600 | 63 | hydroxyproline-rich glycoprotein family protein | EXP | 2000 | | |
| CumMe_WSM_SF18045.G6670 | 64 | | EXP | 2000 | | |
| CumMe_WSM_SF18053.G5410 | 65 | endomembrane protein 70 | EXP | 2000 | | |
| CumMe_WSM_SF18287.G5380 | 66 | CP12-1 | EXP | 2000 | | |
| CumMe_WSM_SF18488.G5340 | 67 | caffeoyl-CoA 3-O-methyltransferase | EXP | 2000 | Promoter; Leader | 1-1923; 1924-2000 |
| CumMe_WSM_SF18504.G5090 | 68 | vacuolar ATP synthase subunit H family protein | EXP | 2000 | | |
| CumMe_WSM_SF18530.G5750 | 69 | GUN5 (GENOMES UNCOUPLED 5); magnesium chelatase | EXP | 2000 | | |
| CumMe_WSM_SF18536.G6480 | 70 | MBF1A (MULTIPROTEIN BRIDGING FACTOR 1A) transcription coactivator | EXP | 2000 | | |
| CumMe_WSM_SF18575.G6410 | 71 | unknown protein | EXP | 2000 | | |
| CumMe_WSM_SF18634.G5190 | 72 | 60S ribosomal protein L23 (RPL23A) | EXP | 2000 | Promoter; Leader | 1-1971; 1972-2000 |
| CumMe_WSM_SF18645.G5380 | 73 | GS2 (GLUTAMINE SYNTHETASE 2) | EXP | 2000 | | |
| CumMe_WSM_SF18716.G5860 | 74 | 40S ribosomal protein S12 (RPS12A); reverse compliment: Auxin-induced protein x10A-like | EXP | 2000 | Promoter; Leader | Reverse compliment; see SEQ ID NO: 184 |
| CumMe_WSM_SF18801.G5040 | 75 | | EXP | 2000 | | |
| CumMe_WSM_SF18806.G6220 | 76 | unknown protein | EXP | 2000 | | |
| CumMe_WSM_SF18850.G5630 | 77 | PAC1; threonine-type endopeptidase | EXP | 2000 | | |
| CumMe_WSM_SF18863.G7550 | 78 | ATP synthase gamma chain, mitochondrial (ATPC) | EXP | 2000 | | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF18986.G6110 | 79 | GER1 (GERMIN-LIKE PROTEIN 1); oxalate oxidase | EXP | 2000 | | |
| CumMe_WSM_SF19064.G5690 | 80 | histone H3.2 | EXP | 2000 | Promoter; Leader; Intron | 1-1581; 1582-1670; 1671-2000 |
| CumMe_WSM_SF19323.G5120 | 81 | chloroplast outer envelope GTP-binding protein, putative | EXP | 2000 | | |
| CumMe_WSM_SF19452.G5090 | 82 | glucan phosphorylase, putative | EXP | 1072 | | |
| CumMe_WSM_SF19631.G5170 | 83 | RuBisCO activase, putative | EXP | 1730 | | |
| CumMe_WSM_SF19647.G5760 | 84 | 6-phosphogluconate dehydrogenase family protein | EXP | 2000 | Promoter; Leader; Intron; Leader | 1-936; 937-1021; 1022-1992; 1993-2000 |
| CumMe_WSM_SF19839.G5090 | 85 | ATPDX1.1 (pyridoxine biosynthesis 1.1) | EXP | 1020 | Promoter; Leader | 1-928; 929-1020 |
| CumMe_WSM_SF19850.G5130 | 86 | HMGB2 (HIGH MOBILITY GROUP B 2) transcription factor | EXP | 2000 | | |
| CumMe_WSM_SF19902.G5260 | 87 | universal stress protein (USP) family protein/early nodulin ENOD18 family protein | EXP | 2000 | | |
| CumMe_WSM_SF19992.G6100 | 88 | unknown protein | EXP | 2000 | | |
| CumMe_WSM_SF20132.G5560 | 89 | peroxidase 21 | EXP | 2000 | Promoter; Leader | 1-1962; 1963-2000 |
| CumMe_WSM_SF20147.G7910 | 90 | CSD1 (COPPER/ZINC SUPEROXIDE DISMUTASE 1) | EXP | 2000 | | |
| CumMe_WSM_SF20355.G5130 | 91 | ATP synthase family | EXP | 2000 | | |
| CumMe_WSM_SF20359.G5870 | 92 | NADH-ubiquinone oxidoreductase 20 kDa subunit, mitochondrial | EXP | 2000 | | |
| CumMe_WSM_SF20368.G5700 | 93 | PGR5 (proton gradient regulation 5) | EXP | 2000 | | |
| CumMe_WSM_SF20409.G5240 | 94 | elongation factor 1B alpha-subunit 1 (eEF1Balpha1) | EXP | 2000 | | |
| CumMe_WSM_SF20431.G6340 | 95 | DHS2 (3-deoxy-d-arabino-heptulosonate 7-phosphate synthase) | EXP | 2000 | | |
| CumMe_WSM_SF20505.G5440 | 96 | THIC (ThiaminC); ADP-ribose pyrophosphohydrolase | EXP | 1373 | | |
| CumMe_WSM_SF20509.G5920 | 97 | Y14; RNA binding/protein binding | EXP | 2000 | | |
| CumMe_WSM_SF206458.G5970 | 98 | FAD2 (FATTY ACID DESATURASE 2) | EXP | 2000 | Promoter | 1-2000 |
| CumMe_WSM_SF206534.G5200 | 99 | unknown protein | EXP | 2000 | | |
| CumMe_WSM_SF20997.G6990 | 100 | ALD1 (AGD2-LIKE DEFENSE RESPONSE PROTEIN1) | EXP | 2000 | | |
| CumMe_WSM_SF21035.G5090 | 101 | sodium/calcium exchanger family protein | EXP | 1078 | | |
| CumMe_WSM_SF21117.G5370 | 102 | 30S ribosomal protein, putative | EXP | 2000 | | |
| CumMe_WSM_SF21141.G5630 | 103 | 40S ribosomal protein S24 (RPS24A) | EXP | 2000 | | |
| CumMe_WSM_SF21198.G5180 | 104 | | EXP | 1974 | | |
| CumMe_WSM_SF21366.G5980 | 105 | GRF12 (GENERAL REGULATORY FACTOR 12) | EXP | 2000 | | |
| CumMe_WSM_SF21828.G5150 | 106 | cpHsc70-1 (chloroplast heat shock protein 70-1) | EXP | 1643 | | |
| CumMe_WSM_SF21886.G5080 | 107 | NPQ4 (NONPHOTOCHEMICAL QUENCHING) | EXP | 2000 | | |
| CumMe_WSM_SF22008.G5670 | 108 | NAP1;2 (NUCLEOSOME | EXP | 2000 | | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| | | ASSEMBLY PROTEIN 1; 2) | | | | |
| CumMe_WSM_SF22070.G5280 | 109 | fructose-bisphosphate aldolase, putative | EXP | 2000 | | |
| CumMe_WSM_SF22097.G5540 | 110 | APX3 (ASCORBATE PEROXIDASE 3) | EXP | 2000 | | |
| CumMe_WSM_SF22254.G5760 | 111 | 40S ribosomal protein S7 (RPS7B) | EXP | 2000 | | |
| CumMe_WSM_SF22275.G5780 | 112 | ribosomal protein L17 family protein | EXP | 1027 | | |
| CumMe_WSM_SF22355.G5310 | 113 | | EXP | 2000 | | |
| CumMe_WSM_SF22531.G5120 | 114 | eukaryotic translation initiation factor 1A, putative | EXP | 2000 | Promoter; Leader; Intron; Leader | 1-759; 760-858; 859-1979; 1980-2000 |
| CumMe_WSM_SF22870.G5370 | 115 | ATSARA1A (*ARABIDOPSIS THALIANA* SECRETION-ASSOCIATED RAS SUPER FAMILY 1) | EXP | 2000 | | |
| CumMe_WSM_SF22934.G5290 | 116 | T-complex protein 1 epsilon subunit, putative | EXP | 2000 | | |
| CumMe_WSM_SF23181.G5100 | 117 | CEV1 (CONSTITUTIVE EXPRESSION OF VSP 1) | EXP | 1025 | | |
| CumMe_WSM_SF23186.G6160 | 118 | ubiquinol-cytochrome C reductase complex 14 kDa protein, putative | EXP | 2000 | | |
| CumMe_WSM_SF23397.G5210 | 119 | RPL27 (RIBOSOMAL PROTEIN LARGE SUBUNIT 27) | EXP | 2000 | | |
| CumMe_WSM_SF23760.G5200 | 120 | NDPK1; ATP binding/ nucleoside diphosphate kinase | EXP | 2000 | Promoter; Leader | 1-1901; 1902-2000 |
| CumMe_WSM_SF23906.G6180 | 121 | PSBX (photosystem II subunit X) | EXP | 2000 | | |
| CumMe_WSM_SF24040.G5450 | 122 | RPS17 (RIBOSOMAL PROTEIN S17) | EXP | 2000 | | |
| CumMe_WSM_SF24045.G5400 | 123 | EXL3 (EXORDIUM LIKE 3) | EXP | 2000 | | |
| CumMe_WSM_SF24117.G5600 | 124 | 60S ribosomal protein L26 (RPL26A) | EXP | 2000 | | |
| CumMe_WSM_SF25084.G5580 | 125 | | EXP | 2000 | | |
| CumMe_WSM_SF25141.G5160 | 126 | isocitrate dehydrogenase, putative | EXP | 1397 | Promoter; Leader | 1-1322; 1323-1397 |
| CumMe_WSM_SF25355.G5000 | 127 | LOS1; copper ion binding translation elongation factor | EXP | 2000 | Promoter; Leader; Intron; Leader; CDS | 1-734; 735-811; 812-1340; 1341-1360; 1361-2000 |
| CumMe_WSM_SF25370.G5000 | 128 | PSBP-1 (PHOTOSYSTEM II SUBUNIT P-1) | EXP | 1657 | | |
| CumMe_WSM_SF25455.G5370 | 129 | GLY3 (GLYOXALASE II 3) | EXP | 2000 | | |
| CumMe_WSM_SF25936.G5450 | 130 | mitochondrial substrate carrier family protein | EXP | 2000 | Promoter; Leader | 1-1878; 1879-2000 |
| CumMe_WSM_SF27080.G5510 | 131 | LIP1 (LIPOIC ACID SYNTHASE 1) | EXP | 2000 | | |
| CumMe_WSM_SF27222.G5150 | 132 | DRT112; copper ion binding/electron carrier | EXP | 2000 | | |
| CumMe_WSM_SF27957.G5450 | 133 | SMAP1 (SMALL ACIDIC PROTEIN 1) | EXP | 2000 | | |
| CumMe_WSM_SF28729.G5340 | 134 | RNA-binding protein cp29, putative | EXP | 1696 | | |
| CumMe_WSM_SF28805.G6200 | 135 | unknown protein | EXP | 2000 | | |
| CumMe_WSM_SF31264.G5380 | 136 | ATPH1 (*ARABIDOPSIS THALIANA* PLECKSTRIN HOMOLOGUE 1) | EXP | 2000 | | |
| CumMe_WSM_SF35856.G5150 | 137 | TIP4; 1 (tonoplast intrinsic protein 4; 1) | EXP | 1575 | | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CumMe_WSM_SF40859.G5250 | 138 | SMT2 (STEROL METHYLTRANSFERASE 2) | EXP | 2000 | | |
| CumMe_WSM_SF41124.G5080 | 139 | 40S ribosomal protein S2 (RPS2C) | EXP | 1006 | Promoter; Leader | 1-883; 884-1006 |
| CumMe_WSM_SF41128.G5410 | 140 | CRY2 (CRYPTOCHROME 2) | EXP | 2000 | | |
| CumMe_WSM_SF41254.G5160 | 141 | GDP-D-glucose Phosphorylase | EXP | 1556 | | |
| CumMe_WSM_SF41588.G5470 | 142 | PRPL11 (PLASTID RIBOSOMAL PROTEIN L11) | EXP | 2000 | | |
| CumMe_WSM_SF41644.G6400 | 143 | SHD (SHEPHERD) | EXP | 2000 | | |
| CumMe_WSM_SF41983.G5000 | 144 | catalytic/coenzyme binding | EXP | 1337 | | |
| CumMe_WSM_SF42075.G5100 | 145 | CPN60B (CHAPERONIN 60 BETA) | EXP | 2000 | | |
| CumMe_WSM_SF42141.G5110 | 146 | cathepsin B-like cysteine protease, putative | EXP | 1212 | | |
| CumMe_WSM_SF44933.G5290 | 147 | EBF1 (EIN3-BINDING F BOX PROTEIN 1) ubiquitin-protein ligase | EXP | 2000 | | |
| CumMe_WSM_SF44977.G5000 | 148 | PAP26 (PURPLE ACID PHOSPHATASE 26) | EXP | 1254 | | |
| CumMe_WSM_SF45441.G5510 | 149 | GAPA-2 (GLYCERALDEHYDE 3-PHOSPHATE DEHYDROGENASE A SUBUNIT 2) | EXP | 2000 | | |
| CumMe_WSM_SF45882.G5120 | 150 | fructose-1,6-bisphosphatase, putative | EXP | 1680 | | |
| CumMe_WSM_SF47806.G5070 | 151 | ATP synthase epsilon chain, mitochondrial | EXP | 1524 | | |
| CumMe_WSM_SF53106.G5190 | 152 | CPN60A (CHAPERONIN-60ALPHA) | EXP | 1851 | | |
| CumMe_WSM_SF65588.G5230 | 153 | vacuolar calcium-binding protein-related | EXP | 2000 | | |
| CumMe_WSM_SF9060.G5120 | 154 | APE2 (ACCLIMATION OF PHOTOSYNTHESIS TO ENVIRONMENT 2) | EXP | 1288 | | |
| P-CUCme.1-1:1:1rc | 155 | Phosphatase 2A | EXP | 2000 | Promoter; Leader; Intron; Leader | 1-1135; 1136-1249; 1250-1990; 1991-2000 |
| EXP-CUCme.4:1:1 | 156 | Ubiquitin 2 | EXP | 2011 | Promoter; Leader; Intron; Leader | 1-1646; 1647-1704; 1705-2005; 2006-2008 |
| P-CUCme.4-1:1:4 | 157 | Ubiquitin 2 | P; L | 1698 | Promoter; Leader | |
| I-CUCme.4-1:1:1 | 158 | Ubiquitin 2 | I; L | 313 | Intron; Leader | |
| EXP-CUCme.5:1:1 | 159 | Ubiquitin 3 | EXP | 2010 | Promoter; Leader; Intron; Leader | 1-748; 749-819; 820-2004; 2005-2007 |
| P-CUCme.5-1:1:3 | 160 | Ubiquitin 3 | P; L | 1107 | Promoter; Leader | |
| I-CUCme.5-1:1:1 | 161 | Ubiquitin 3 | I; L | 903 | Intron; Leader | |
| EXP-CUCme.eEF1a:1:1 | 162 | Elongation Factor 1 alpha | EXP | 1235 | Promoter; Leader; Intron; Leader | 1-617; 618-677; 678-1213; 1214-1235 |
| P-CUCme.eEF1a-1:1:1 | 163 | Elongation Factor 1 alpha | P | 617 | Promoter | |
| L-CUCme.eEF1a-1:1:1 | 164 | Elongation Factor 1 alpha | L | 54 | Leader | |
| I-CUCme.eEF1a-1:1:1 | 165 | Elongation Factor 1 alpha | I | 545 | Intron | |
| L-CUCme.eEF1a-1:1:2 | 166 | Elongation Factor 1 alpha | L | 19 | Leader | |
| P-CUCme.19-1:1:3 | 167 | Chloropyll a/b binding protein | EXP | 2003 | Promoter; Leader | 1-1958; 1959-2003 |
| EXP-CUCme.SAMS2:1:1 | 168 | S-Adenosylmethionine Synthetase | EXP | 2004 | Promoter; Leader; Intron | 1-1067; 1068-1165; 1166-2003 |
| P-CUCme.SAMS2-1:1:1 | 169 | S-Adenosylmethionine Synthetase | P | 1067 | Promoter | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| L-CUCme.SAMS2-1:1:1 | 170 | S-Adenosylmethionine Synthetase | L | 92 | Leader | |
| I-CUCme.SAMS2-1:1:1 | 171 | S-Adenosylmethionine Synthetase | I | 845 | Intron | |
| EXP-CUCme.29:1:1 | 172 | Ribosomal protein S5a | EXP | 2018 | Promoter; Leader; Intron; Leader | 1-490; 491-571; 572-2012; 2013-2018 |
| P-CUCme.29-1:1:4 | 173 | Ribosomal protein S5a | P; L | 565 | Promoter; Leader | |
| I-CUCme.29-1:1:1 | 174 | Ribosomal protein S5a | I; L | 1453 | Intron; Leader | |
| P-CUCme.CumMe_WSM_SF16444.G5140-1:1:1 | 175 | histone H4 | EXP | 1999 | Promoter; Leader; Intron | 1-1946; 947-1999 |
| P-CUCme.CumMe_WSM_SF16563.G5560-1:1:1 | 176 | ATARFB1A (ADP-ribosylation factor B1A) | EXP | 2004 | Promoter; Leader; Intron; Leader | 1-1331; 1332-1429; 1430-1992; 1993-2004 |
| P-CUCme.CumMe_WSM_SF17111.G5790-1:1:1 | 177 | ubiquinol-cytochrome C reductase complex ubiquinone-binding protein | EXP | 2005 | Promoter; Leader | 1-1901; 1902-2005 |
| EXP-CumMe.WSM_SF17252.G7330:1:1 | 178 | nascent polypeptide-associated complex (NAC) domain-containing protein | EXP | 1978 | Promoter; Leader; Intron; Leader | 1-1167; 1168-1269; 1270-1972; 1973-1975 |
| P-CUCme.WSM_SF17252.G7330-1:1:1 | 179 | nascent polypeptide-associated complex (NAC) domain-containing protein | P; L | 1263 | Promoter; Leader | |
| I-CUCme.WSM_SF17252.G7330-1:1:1 | 180 | nascent polypeptide-associated complex (NAC) domain-containing protein | I; L | 715 | Intron; Leader | |
| P-CUCme.CumMe_WSM_SF18488.G5340-1:1:1 | 181 | caffeoyl-CoA 3-O-methyltransferase | EXP | 2000 | Promoter; Leader | 1-923; 1924-2000 |
| P-CUCme.CumMe_WSM_SF18536.G6480-1:1:1 | 182 | MBF1A (MULTIPROTEIN BRIDGING FACTOR 1A) transcription coactivator | EXP | 2000 | Promoter; Leader; Intron | |
| P-CUCme.CumMe_WSM_SF18634.G5190-1:1:1 | 183 | 60S ribosomal protein L23 (RPL23A) | EXP | 1989 | Promoter; Leader | 1-1960; 1961-1989 |
| P-CUCme.CumMe_WSM_SF18716.G5860-1:1:1 | 184 | Auxin-induced prtoein X10A-like | EXP | 1463 | Promoter; Leader | 1-1392; 1393-1463 |
| EXP-CUCme.WSM_SF19064.G5690:1:1 | 185 | histone H3.2 | EXP | 2006 | Promoter; Leader; Intron; Leader | 1-1581; 1582-1670; 1671-2000; 2001-2003 |
| P-CUCme.WSM_SF19064.G5690-1:1:1 | 186 | histone H3.2 | P; L | 1664 | Promoter; Leader | |
| I-CUCme.WSM_SF19064.G5690-1:1:1 | 187 | histone H3.2 | I; L | 342 | Intron; Leader | |
| P-CUCme.CumMe_WSM_SF19647.G5760-1:1:1 | 188 | 6-phosphogluconate dehydrogenase family protein | EXP | 2003 | Promoter; Leader; Intron; Leader | 1-939; 940-1024; 1025-1995; 1996-2003 |
| P-CUCme.CumMe_WSM_SF19839.G5090-1:1:1 | 189 | ATPDX1.1 (pyridoxine biosynthesis 1.1) | EXP | 1024 | Promoter; Leader | 1-904; 905-1024 |
| P-CUCme.CumMe_SF20132.G5560-1:1:1 | 190 | peroxidase 21 | EXP | 2001 | Promoter; Leader | 1-1962; 1963-2001 |
| P-CUCme.CumMe_WSM_SF206458.G5970-1:1:1 | 191 | FAD2 (FATTY ACID DESATURASE 2) | EXP | 4175 | Promoter; Leader; Intron; Leader | 1-2171; 2172-2325; 2326-4155; 4156-4175 |
| P-CUCme.CumMe_WSM_SF22531.G5120-1:1:1 | 192 | eukaryotic translation initiation factor 1A, putative | EXP | 1999 | Promoter; Leader; Intron; Leader | 1-759; 760-858; 859-1978; 1979-1999 |
| P-CUCme.CumMe_WSM_SF23760.G5200-1:1:1 | 193 | NDPK1; ATP binding/ nucleoside diphosphate kinase | EXP | 2000 | Promoter; Leader | 1-1901; 1902-2000 |
| P- | 194 | PSBX (photosystem II | EXP | 2000 | Promoter; Leader | |

TABLE 1-continued

Transcriptional regulatory expression element groups, promoters, leaders and introns isolated from *Cucumis melo*.

| Annotation | SEQ ID NO: | Description | Composition Type | Size (bp) | Composition | Coordinates of Elements within EXP |
|---|---|---|---|---|---|---|
| CUCme.CumMe_WSM_SF23906.G6180-1:1:1 | | subunit X) | | | | |
| P-CUCme.CumMe_WSM_SF25141.G5160-1:1:2 | 195 | isocitrate dehydrogenase, putative | EXP | 1400 | Promoter; Leader | 1-1325; 1326-1400 |
| P-CUCme.CumMe_WSM_SF25355.G5000-1:1:1 | 196 | LOS1; copper ion binding translation elongation factor | EXP | 2019 | Promoter; Leader; Intron; Leader; CDS | 1-734; 735-811; 812-1340; 1341-1360; 1361-2019 |
| P-CUCme.CumMe_WSM_SF25936.G5450-1:1:1 | 197 | mitochondrial substrate carrier family protein | EXP | 1999 | Promoter; Leader | 1-1877; 1878-1999 |
| P-CUCme.CumMe_WSM_SF35856.G5150-1:1:1 | 198 | TIP4; 1 (tonoplast intrinsic protein 4; 1) | EXP | 1578 | | |
| P-CUCme.CumMe_WSM_SF41124.G5080-1:1:1 | 199 | 40S ribosomal protein S2 (RPS2C) | EXP | 1023 | Promoter; Leader | 1-945; 946-1023 |
| P-CUCme.20-1:3 | 211 | Chloropyll a/b binding protein | EXP | 1446 | Promoter; Leader | 1-1390; 1391-1446 |
| EXP-CUCme.29:1:2 | 212 | Ribosomal protein S5a | EXP | 2018 | Promoter; Leader; Intron; Leader | 1-490; 491-571; 572-2011; 2013-2018 |

As shown in Table 1, for example, the transcriptional regulatory expression element group (EXP) designated EXP-CUCme.Ubq1:1:1 (SEQ ID NO: 1), with components isolated from *C. melo*, comprises a 2068 base pair sized (bp) promoter element, P-CUCme.Ubq1-1:1:15 (SEQ ID NO: 2), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:2 (SEQ ID NO: 5), with components isolated from *C. melo*, comprises a 1459 bp promoter element, P-CUCme.Ubq1-1:1:16 (SEQ ID NO: 6), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:3 (SEQ ID NO: 7), with components isolated from *C. melo*, comprises a 964 bp promoter element, P-CUCme.Ubq1-1:1:17 (SEQ ID NO: 8), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:4 (SEQ ID NO: 9), with components isolated from *C. melo*, comprises a 479 bp promoter element, P-CUCme.Ubq1-1:1:18 (SEQ ID NO: 10), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4). The transcriptional regulatory expression element group (EXP) designated EXP-CUCme.Ubq1:1:5 (SEQ ID NO: 11), with components isolated from *C. melo*, comprises a 173 bp promoter element, P-CUCme.Ubq1-1:1:19 (SEQ ID NO: 12), operably linked 5' to a leader element, L-CUCme.Ubq1-1:1:1 (SEQ ID NO: 3), operably linked 5' to an intron element, I-CUCme.Ubq1-1:1:1 (SEQ ID NO: 4).

An alignment of the ubiquitin 1 promoter sequences is provided in FIGS. 1a-1f. The promoter elements, P-CUCme.Ubq1-1:1:16 (SEQ ID NO: 6), P-CUCme.Ubq1-1:1:17 (SEQ ID NO: 8), P-CUCme.Ubq1-1:1:18 (SEQ ID NO: 10) and P-CUCme.Ubq1-1:1:19 (SEQ ID NO: 12) were built by introducing varying lengths of deletions from the 5' end of the promoter, P-CUCme.Ubq1-1:1:15 (SEQ ID NO: 2).

Example 2: Analysis of Regulatory Elements Driving GUS in Soy Cotyledon Protoplasts Soybean cotyledon protoplasts were transformed with plant expression vectors containing a test transcriptional regulatory expression element group driving expression of the ß-glucuronidase (GUS) transgene and compared to GUS expression in leaf protoplasts in which expression of GUS is driven by known constitutive promoters.

Expression of a transgene driven by EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) was compared with expression from known constitutive promoters. Each plant expression vector was comprised of a right border region from *Agrobacterium tumefaciens*, a first transgene cassette comprised of an EXP sequence or known constitutive promoter operably linked 5' to a coding sequence for ß-glucuronidase (GUS, SEQ ID NO: 206) containing a processable intron derived from the potato light-inducible tissue-specific ST-LS1 gene (Genbank Accession: X04753), operably linked 5' to a 3' termination region from the *Gossypium barbadense* E6 gene (T-Gb.E6-3b:1:1, SEQ ID NO: 204), the *Pisum sativum* RbcS2-E9 gene (T-Ps.RbcS2-E9-1:1:6, SEQ ID NO: 203), or the *Gossypium barbadense* FbLate-2 gene (T-Gb.FbL2-1:1:1, SEQ ID NO: 205); a second transgene selection cassette used for selection of transformed plant cells that either confers resistance to the herbicide glyphosate (driven by the *Arabidopsis* Actin 7 promoter) or the antibiotic, kanamycin and a left border region from *A. tumefaciens*. A promoterless control plant expression vector (pMON124912) served as a negative control for expression. The foregoing test and constitutive expression element groups were cloned into plant expression vectors as shown in Table 2 below.

TABLE 2

Plant expression vectors and corresponding expression element group and 3' UTR.

| Expression Vector | Regulatory Element | SEQ ID NO: | 3' UTR |
|---|---|---|---|
| pMON80585 | EXP-At.Atntt1:1:2 | 200 | T-Ps.RbcS2-E9-1:1:6 |
| pMON109584 | EXP-CaMV.35S-enh+Ph.DnaK:1:3 | 201 | T-Gb.E6-3b:1:1 |
| pMON118756 | EXP-At.Act7:1:11 | 202 | T-Gb.E6-3b:1:1 |
| pMON124912 | No promoter | | T-Gb.FbL2-1:1:1 |
| pMON138776 | EXP-CUCme.Ubq1:1:1 | 1 | T-Gb.FbL2-1:1:1 |
| pMON138777 | EXP-CUCme.Ubq1:1:2 | 5 | T-Gb.FbL2-1:1:1 |
| pMON138778 | EXP-CUCme.Ubq1:1:3 | 7 | T-Gb.FbL2-1:1:1 |
| pMON138779 | EXP-CUCme.Ubq1:1:4 | 9 | T-Gb.FbL2-1:1:1 |
| pMON138780 | EXP-CUCme.Ubq1:1:5 | 11 | T-Gb.FbL2-1:1:1 |

Two plasmids, for use in co-transformation and normalization of data, were also constructed. One transformation control plasmid was comprised of a constitutive promoter, driving the expression of the firefly (*Photinus pyralis*) luciferase coding sequence (FLuc, SEQ ID NO: 207), operably linked 5' to a 3' termination region from the *Agrobacterium tumefaciens* nopaline synthase gene (T-AGRtu.nos-1:1:13, SEQ ID NO: 209). The other transformation control plasmid was comprised of a constitutive promoter, driving the expression of the sea pansy (*Renilla reniformis*) luciferase coding sequence (RLuc, SEQ ID NO: 208), operably linked 5' to a 3' termination region from the *Agrobacterium tumefaciens* nopaline synthase gene.

The plant expression vectors, pMON80585, pMON109584, pMON118756, pMON124912, pMON138776, pMON138777, pMON138778, pMON138779 and pMON138780 were used to transform soybean cotyledon protoplast cells using PEG transformation methods. Protoplast cells were transformed with equimolar amounts of each of the two transformation control plasmids and a test plant expression vector. GUS and luciferase activity was assayed. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, WI; see for example, Promega Notes Magazine, No: 57, 1996, p.02). Sample measurements were made using 3 or 4 replicates per transformation. The average GUS and luciferase values are presented in Table 3 below.

TABLE 3

Average GUS and luciferase expression values and GUS/luciferase ratios.

| Construct | Regulatory Element | SEQ ID NO: | Average GUS | Average FLuc | Average RLuc | GUS/FLuc | GUS/RLuc |
|---|---|---|---|---|---|---|---|
| pMON80585 | EXP-At.Atntt1:1:2 | 200 | 55173 | 6498 | 30503 | 8.49 | 1.81 |
| pMON109584 | EXP-CaMV.35S-enh + Ph.DnaK:1:3 | 200 | 24940 | 5050.75 | 35495 | 4.94 | 0.70 |
| pMON118756 | EXP-At.Act7:1:11 | 201 | 9871 | 6880 | 40850 | 1.43 | 0.24 |
| pMON124912 | No promoter | | 2000 | 11670 | 73187 | 0.17 | 0.03 |
| pMON138776 | EXP-CUCme.Ubq1:1:1 | 1 | 26972 | 6467.25 | 37200 | 4.17 | 0.73 |
| pMON138777 | EXP-CUCme.Ubq1:1:2 | 5 | 41307 | 5902.5 | 24396 | 7.00 | 1.69 |
| pMON138778 | EXP-CUCme.Ubq1:1:3 | 7 | 90140 | 10710.5 | 60983 | 8.42 | 1.48 |
| pMON138779 | EXP-CUCme.Ubq1:1:4 | 9 | 35526 | 5590 | 28001 | 6.36 | 1.27 |
| pMON138780 | EXP-CUCme.Ubq1:1:5 | 11 | 23298 | 4483.25 | 19075 | 5.20 | 1.22 |

To compare the relative activity of each promoter in soybean cotyledon protoplasts, GUS values were expressed as a ratio of GUS to luciferase activity and normalized with respect to the expression levels observed for the constitutive expression element groups, EXP-At.Act7:1:11 and EXP-CaMV.35S-enh+Ph.DnaK:1:3. Table 4 below shows the GUS to firefly luciferase (FLuc) ratios normalized with respect to EXP-At.Act7:1:11 and EXP-CaMV.35S-enh+Ph.DnaK:1:3. Table 5 below shows the GUS to renilla luciferase (RLuc) ratios normalized with respect to EXP-At.Act7:1:11 and EXP-CaMV.35S-enh+Ph.DnaK:1:3.

TABLE 4

GUS to firefly luciferase (FLuc) ratios normalized with respect to EXP-At.Act7:1:11 and EXP-CaMV.35S-enh+Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh+Ph.DnaK:1:3 |
|---|---|---|---|---|
| pMON80585 | EXP-At.Atntt1:1:2 | 200 | 5.92 | 1.72 |
| pMON109584 | EXP-CaMV.35S-enh+Ph.DnaK:1:3 | 201 | 3.44 | 1.00 |

TABLE 4-continued

GUS to firefly luciferase (FLuc) ratios normalized with respect to
EXP-At.Act7:1:11 and EXP-CaMV.35S-enh+Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh+Ph.DnaK:1:3 |
| --- | --- | --- | --- | --- |
| pMON118756 | EXP-At.Act7:1:11 | 202 | 1.00 | 0.29 |
| pMON124912 | No promoter | | 0.12 | 0.03 |
| pMON138776 | EXP-CUCme.Ubq1:1:1 | 1 | 2.91 | 0.84 |
| pMON138777 | EXP-CUCme.Ubq1:1:2 | 5 | 4.88 | 1.42 |
| pMON138778 | EXP-CUCme.Ubq1:1:3 | 7 | 5.87 | 1.70 |
| pMON138779 | EXP-CUCme.Ubq1:1:4 | 9 | 4.43 | 1.29 |
| pMON138780 | EXP-CUCme.Ubq1:1:5 | 11 | 3.62 | 1.05 |

TABLE 5

GUS to *renilla* luciferase (RLuc) ratios normalized with respect to
EXP-At.Act7:1:11 and EXP-CaMV.35S-enh+Ph.DnaK:1:3.

| Construct | Regulatory Element | SEQ ID NO: | GUS/RLuc normalized with respect to EXP-At.Act7:1:11 | GUS/RLuc normalized with respect to EXP-CaMV.35S-enh+Ph.DnaK:1:3 |
| --- | --- | --- | --- | --- |
| pMON80585 | EXP-At.Atntt1:1:2 | 200 | 7.49 | 2.57 |
| pMON109584 | EXP-CaMV.35S-enh+Ph.DnaK:1:3 | 201 | 2.91 | 1.00 |
| pMON118756 | EXP-At.Act7:1:11 | 202 | 1.00 | 0.34 |
| pMON124912 | No promoter | | 0.11 | 0.04 |
| pMON138776 | EXP-CUCme.Ubq1:1:1 | 1 | 3.00 | 1.03 |
| pMON138777 | EXP-CUCme.Ubq1:1:2 | 5 | 7.01 | 2.41 |
| pMON138778 | EXP-CUCme.Ubq1:1:3 | 7 | 6.12 | 2.10 |
| pMON138779 | EXP-CUCme.Ubq1:1:4 | 9 | 5.25 | 1.81 |
| pMON138780 | EXP-CUCme.Ubq1:1:5 | 11 | 5.05 | 1.74 |

As can be seen in Tables 4 and 5 above, each of the expression element groups EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) demonstrated the ability of driving transgene expression in soybean cotyledon protoplasts. Expression levels were greater than that of EXP-At.Act7:1:11 and was 2.9 to 5.8 (FLuc) or 3 to 7 (RLuc) fold higher than EXP-At.Act7:1:11 in this assay. Expression was equivalent or higher than expression observed for EXP-CaMV.35S-enh+Ph.DnaK:1:3. Expression levels were 0.8 to 1.7 (FLuc) or 1 to 2.4 (RLuc) fold higher than expression observed for EXP-CaMV.35S-enh+Ph.DnaK:1:3.

Example 3: Analysis of Regulatory Elements Driving GUS in Bombarded Soybean Leaves and Roots Soybean leaves and roots were transformed with plant expression vectors containing a test transcriptional regulatory expression element group driving expression of the ß-glucuronidase (GUS) transgene and compared to GUS expression in roots and leaves in which expression of GUS is driven by known constitutive promoters.

Expression of a transgene driven by EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) was compared with expression from known constitutive promoters in particle bombarded soybean leaves and roots. The plant expression vectors used for transformation of leaves and roots was the same as those presented in Table 2 of Example 2 above.

The plant expression vectors, pMON80585, pMON109584, pMON118756, pMON124912, pMON138776, pMON138777, pMON138778, pMON138779 and pMON138780 were used to transform soybean leaves and roots using particle bombardment transformation methods.

Briefly, A3244 soybean seeds were surface sterilized and allowed to germinate in trays with a photoperiod of 16 hours light and 8 hours of darkness. After approximately 13 days, leaf and root tissue was harvested under sterile conditions from the seedlings and used for bombardment. The tissue samples were randomly placed on a petri dish containing plant culture medium. Ten micrograms of plasmid DNA was used to coat 0.6 micron gold particles (Catalog #165-2262 Bio-Rad, Hercules, CA) for bombardment. Macro-carriers were loaded with the DNA-coated gold particles (Catalog #165-2335 Bio-Rad, Hercules CA). A PDS 1000/He biolistic gun was used for transformation (Catalog #165-2257 Bio-Rad, Hercules CA). The bombarded root and leaf tissues were allowed to incubate in the dark for 24 hours at 26 degrees Celsius. Following this overnight incubation, the tissues were stained in solution for GUS expression overnight at 37 degrees Celsius. After staining overnight, the tissues were soaked in 70% ethanol overnight to remove chlorophyll and reveal the GUS staining. The tissues were then photographed and a rating scale of "0", "+" to "++++++" reflecting the level of GUS expression is assigned to each construct (0—no expression, + to ++++++—low to high, respectively).

Expression of the GUS transgene demonstrated in each tissue is used to infer the relative potential level and specificity of each element's capacity to drive transgene expression in stably transformed corn plants. Average GUS expression ratings are provided in Table 6 below.

TABLE 6

GUS expression ratings for particle bombarded leaf and root.

| Construct | Regulatory Element | SEQ ID NO: | Leaf Expression Rating | Root Expression Rating |
|---|---|---|---|---|
| pMON80585 | EXP-At.Atntt1:1:2 | 200 | ++++ | ++ |
| pMON109584 | EXP-CaMV.35S-enh+Ph.DnaK:1:3 | 201 | +++++ | +++ |
| pMON118756 | EXP-At.Act7:1:11 | 202 | ++++ | ++ |
| pMON124912 | No promoter | | 0 | 0 |
| pMON138776 | EXP-CUCme.Ubq1:1:1 | 1 | ++++ | +++ |
| pMON138777 | EXP-CUCme.Ubq1:1:2 | 5 | +++ | ++ |
| pMON138778 | EXP-CUCme.Ubq1:1:3 | 7 | +++ | ++ |
| pMON138779 | EXP-CUCme.Ubq1:1:4 | 9 | +++ | ++ |
| pMON138780 | EXP-CUCme.Ubq1:1:5 | 11 | ++ | + |

As can be seen in Table 6 above, each of the expression element groups EXP-CUCme.Ubq1:1:1 (SEQ ID NO: 1), EXP-CUCme.Ubq1:1:2 (SEQ ID NO: 5), EXP-CUCme.Ubq1:1:3 (SEQ ID NO: 7), EXP-CUCme.Ubq1:1:4 (SEQ ID NO: 9) and EXP-CUCme.Ubq1:1:5 (SEQ ID NO: 11) demonstrated the ability of driving transgene expression in particle bombarded transformed leaf and root tissues.

Example 4: Analysis of Regulatory Elements Driving GUS in Soy Cotyledon Protoplasts Soybean cotyledon protoplasts were transformed with plant expression vectors containing a test transcriptional regulatory expression element group driving expression of the ß-glucuronidase (GUS) transgene and compared to GUS expression in leaf protoplasts in which expression of GUS is driven by known constitutive promoters.

Expression of a transgene driven by P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a: 1:1 (SEQ ID NO: 162), P-CUCme.15-1:1:2 (SEQ ID NO: 23), P-CUCme.16a-1:1:2 (SEQ ID NO: 24), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), P-CUCme.22-1:1:3 (SEQ ID NO: 31), EXP-CUCme.SAMS2:1:1 (SEQ ID NO: 168), P-CUCme.26-1:1:2 (SEQ ID NO: 33), P-CUCme.28-1:1:2 (SEQ ID NO: 34) and EXP-CUCme.29:1:2 (SEQ ID NO: 212) was compared with expression from known constitutive expression element groups. Each plant expression vector was comprised of a right border region from Agrobacterium tumefaciens, a first transgene cassette comprised of a test promoter or known constitutive promoter operably linked 5' to a coding sequence for ß-glucuronidase (GUS, SEQ ID NO: 206) containing a processable intron derived from the potato light-inducible tissue-specific ST-LSI gene (Genbank Accession: X04753), operably linked 5' to a 3' termination region from the Gossypium barbadense E6 gene (T-Gb.E6-3b:1:1, SEQ ID NO: 204), the Pisum sativum RbcS2-E9 gene (T-Ps.RbcS2-E9-1:1:6, SEQ ID NO: 203), or the Gossypium barbadense FbLate-2 gene (T-Gb.FbL2-1:1:1, SEQ ID NO: 205); a second transgene selection cassette used for selection of transformed plant cells that either confers resistance to the herbicide glyphosate (driven by the Arabidopsis Actin 7 promoter) or the antibiotic, kanamycin and a left border region from A. tumefaciens. A promoterless control plant expression vector (pMON124912) served as a negative control for expression. The foregoing test and constitutive expression element groups were cloned into plant expression vectors as shown in Table 7 below.

TABLE 7

Plant expression vectors and corresponding expression element group and 3' UTR.

| Construct | Regulatory Element | SEQ ID NO: | 3' UTR |
|---|---|---|---|
| pMON80585 | EXP-At.Atntt1:1:2 | 200 | T-Ps.RbcS2-E9-1:1:6 |
| pMON109584 | EXP-CaMV.35S-enh+Ph.DnaK:1:3 | 201 | T-Gb.E6-3b:1:1 |
| pMON118756 | EXP-At.Act7:1:11 | 202 | T-Gb.E6-3b:1:1 |
| pMON124912 | Promoterless | | T-Gb.FbL2-1:1:1 |
| pMON140818 | P-CUCme.1-1:1:1rc | 155 | T-Gb.FbL2-1:1:1 |
| pMON140819 | P-CUCme.2-1:1:1 | 14 | T-Gb.FbL2-1:1:1 |
| pMON140820 | P-CUCme.3-1:1:3 | 15 | T-Gb.FbL2-1:1:1 |
| pMON140821 | EXP-CUCme.4:1:1 | 156 | T-Gb.FbL2-1:1:1 |
| pMON140822 | EXP-CUCme.5:1:1 | 159 | T-Gb.FbL2-1:1:1 |
| pMON140823 | P-CUCme.6-1:1:1 | 18 | T-Gb.FbL2-1:1:1 |
| pMON140824 | P-CUCme.8-1:1:2 | 19 | T-Gb.FbL2-1:1:1 |
| pMON140825 | P-CUCme.9-1:1:2 | 20 | T-Gb.FbL2-1:1:1 |
| pMON140826 | P-CUCme.10-1:1:1 | 21 | T-Gb.FbL2-1:1:1 |
| pMON140827 | EXP-CUCme.eEF1a:1:1 | 162 | T-Gb.FbL2-1:1:1 |
| pMON140828 | P-CUCme.15-1:1:2 | 23 | T-Gb.FbL2-1:1:1 |
| pMON140829 | P-CUCme.16a-1:1:2 | 24 | T-Gb.FbL2-1:1:1 |
| pMON140830 | P-CUCme.17-1:1:2 | 26 | T-Gb.FbL2-1:1:1 |
| pMON140831 | P-CUCme.18-1:1:2 | 27 | T-Gb.FbL2-1:1:1 |
| pMON140832 | P-CUCme.19-1:1:3 | 167 | T-Gb.FbL2-1:1:1 |
| pMON140833 | P-CUCme.20-1:3 | 211 | T-Gb.FbL2-1:1:1 |
| pMON140834 | P-CUCme.21-1:1:1 | 30 | T-Gb.FbL2-1:1:1 |
| pMON140835 | P-CUCme.22-1:1:3 | 31 | T-Gb.FbL2-1:1:1 |
| pMON140836 | EXP-CUCme.SAMS2:1:1 | 168 | T-Gb.FbL2-1:1:1 |
| pMON140837 | P-CUCme.26-1:1:2 | 33 | T-Gb.FbL2-1:1:1 |
| pMON140838 | P-CUCme.28-1:1:2 | 34 | T-Gb.FbL2-1:1:1 |
| pMON140839 | EXP-CUCme.29:1:2 | 212 | T-Gb.FbL2-1:1:1 |

Two plasmids, for use in co-transformation and normalization of data, were also constructed. One transformation control plasmid was comprised of a constitutive promoter, driving the expression of the firefly (Photinus pyralis) luciferase coding sequence (FLuc, SEQ ID NO: 207), operably linked 5' to a 3' termination region from the Agrobacterium tumefaciens nopaline synthase gene (T-AGRtu.nos-1:1:13, SEQ ID NO: 209). The other transformation control plasmid was comprised of a constitutive promoter, driving the expression of the sea pansy (Renilla reniformis) luciferase coding sequence (RLuc, SEQ ID NO: 208), operably linked 5' to a 3' termination region from the Agrobacterium tumefaciens nopaline synthase gene.

The plant expression vectors, pMON80585, pMON109584, pMON118756, pMON124912, pMON140818, pMON140819, pMON140820, pMON140821, pMON140822, pMON140823, pMON140824, pMON140825, pMON140826, pMON140827, pMON140828, pMON140829, pMON140830, pMON140831, pMON140832, pMON140833, pMON140834, pMON140835, pMON140836, pMON140837, pMON140838 and pMON140839 were used to transform soybean cotyledon protoplast cells using PEG transformation methods. Protoplast cells were transformed with equimolar amounts of each of the two transformation control plasmids and a test plant expression vector. GUS and luciferase activity was assayed. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, WI; see for example, Promega Notes Magazine, No: 57, 1996, p.02). Sample measurements were made using 3 or 4 replicates per transformation. The average GUS and luciferase values are presented in Table 8 below.

TABLE 8

Average GUS and luciferase expression values and GUS/luciferase ratios.

| Construct | Regulatory Element | SEQ ID NO: | Average GUS | Average FLuc | Average RLuc | GUS/ FLuc | GUS/RLuc |
|---|---|---|---|---|---|---|---|
| pMON80585 | EXP-At.Atntt1:1:2 | 200 | 586 | 5220.7 | 8323 | 0.1100 | 0.0700 |
| pMON109584 | EXP-CaMV.35S-enh + Ph.DnaK:1:3 | 201 | 5768 | 4275 | 15098 | 1.3500 | 0.3800 |
| pMON118756 | EXP-At.Act7:1:11 | 202 | 773 | 7722 | 10545 | 0.1000 | 0.0700 |
| pMON124912 | Promoterless |  | 48 | 9746.5 | 13905 | 0.0000 | 0.0000 |
| pMON140818 | P-CUCme.1-1:1:1rc | 155 | 194 | 4772 | 6363 | 0.0400 | 0.0300 |
| pMON140819 | P-CUCme.2-1:1:1 | 14 | 171 | 6855 | 10123 | 0.0200 | 0.0200 |
| pMON140820 | P-CUCme.3-1:1:3 | 15 | 37 | 7089.3 | 9593 | 0.0100 | 0.0000 |
| pMON140821 | EXP-CUCme.4:1:1 | 156 | 4211 | 7626.8 | 13935 | 0.5500 | 0.3000 |
| pMON140822 | EXP-CUCme.5:1:1 | 159 | 626 | 15609.3 | 21140 | 0.0400 | 0.0300 |
| pMON140823 | P-CUCme.6-1:1:1 | 18 | 331 | 15178.5 | 22818 | 0.0200 | 0.0100 |
| pMON140824 | P-CUCme.8-1:1:2 | 19 | 238 | 17514.5 | 28429 | 0.0100 | 0.0100 |
| pMON140825 | P-CUCme.9-1:1:2 | 20 | 510 | 13208 | 19567 | 0.0400 | 0.0300 |
| pMON140826 | P-CUCme.10-1:1:1 | 21 | 352 | 14805.3 | 22200 | 0.0200 | 0.0200 |
| pMON140827 | EXP-CUCme.eEF1a:1:1 | 162 | 724 | 9326.8 | 14476 | 0.0800 | 0.0500 |
| pMON140828 | P-CUCme.15-1:1:2 | 23 | 304 | 11798 | 17486 | 0.0300 | 0.0200 |
| pMON140829 | P-CUCme.16a-1:1:2 | 24 | 88 | 5429 | 9596 | 0.0200 | 0.0100 |
| pMON140830 | P-CUCme.17-1:1:2 | 26 | 180 | 10477.8 | 15291 | 0.0200 | 0.0100 |
| pMON140831 | P-CUCme.18-1:1:2 | 27 | 111 | 5059.3 | 6778 | 0.0200 | 0.0200 |
| pMON140832 | P-CUCme.19-1:1:3 | 167 | 121 | 3765 | 6032 | 0.0300 | 0.0200 |
| pMON140833 | P-CUCme.20-1:3 | 211 | 155 | 10458.8 | 14748 | 0.0100 | 0.0100 |
| pMON140834 | P-CUCme.21-1:1:1 | 30 | 582 | 7760 | 11440 | 0.0800 | 0.0500 |
| pMON140835 | P-CUCme.22-1:1:3 | 31 | 400 | 11393.8 | 18654 | 0.0400 | 0.0200 |
| pMON140836 | EXP-CUCme.SAMS2:1:1 | 168 | 568 | 9466.3 | 13962 | 0.0600 | 0.0400 |
| pMON140837 | P-CUCme.26-1:1:2 | 33 | 87 | 6683 | 8494 | 0.0100 | 0.0100 |
| pMON140838 | P-CUCme.28-1:1:2 | 34 | 171 | 19104.8 | 29619 | 0.0100 | 0.0100 |
| pMON140839 | EXP-CUCme.29:1:2 | 212 | 90 | 11247.3 | 15919 | 0.0100 | 0.0057 |

To compare the relative activity of each promoter in soybean cotyledon protoplasts, GUS values were expressed as a ratio of GUS to luciferase activity and normalized with respect to the expression levels observed for the constitutive expression element groups, EXP-At.Act7:1:11 and EXP-CaMV.35S-enh+Ph.DnaK:1:3. Table 9 below shows the GUS to firefly luciferase (FLuc) ratios normalized with respect to EXP-At.Act7:1:11 and EXP-CaMV.35S-enh+Ph.DnaK:1:3. Table 10 below shows the GUS to renilla luciferase (RLuc) ratios normalized with respect to EXP-At.Act7:1:11 and EXP-CaMV.35S-enh+Ph.DnaK:1:3.

TABLE 9

GUS to firefly luciferase (FLuc) ratios normalized with respect to EXP-At.Act7:1:11 and EXP-CaMV.35S-enh+Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh+Ph.DnaK:1:3 |
|---|---|---|---|---|
| pMON80585 | EXP-At.Atntt1:1:2 | 200 | 1.12 | 0.08 |
| pMON109584 | EXP-CaMV.35S-enh+Ph.DnaK:1:3 | 201 | 13.48 | 1.00 |
| pMON118756 | EXP-At.Act7:1:11 | 202 | 1.00 | 0.07 |

TABLE 9-continued

GUS to firefly luciferase (FLuc) ratios normalized with respect to
EXP-At.Act7:1:11 and EXP-CaMV.35S-enh+Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh+Ph.DnaK:1:3 |
|---|---|---|---|---|
| pMON124912 | Promoterless | | 0.05 | 0.00 |
| pMON140818 | P-CUCme.1-1:1:1rc | 155 | 0.41 | 0.03 |
| pMON140819 | P-CUCme.2-1:1:1 | 14 | 0.25 | 0.02 |
| pMON140820 | P-CUCme.3-1:1:3 | 15 | 0.05 | 0.00 |
| pMON140821 | EXP-CUCme.4:1:1 | 156 | 5.52 | 0.41 |
| pMON140822 | EXP-CUCme.5:1:1 | 159 | 0.40 | 0.03 |
| pMON140823 | P-CUCme.6-1:1:1 | 18 | 0.22 | 0.02 |
| pMON140824 | P-CUCme.8-1:1:2 | 19 | 0.14 | 0.01 |
| pMON140825 | P-CUCme.9-1:1:2 | 20 | 0.39 | 0.03 |
| pMON140826 | P-CUCme.10-1:1:1 | 21 | 0.24 | 0.02 |
| pMON140827 | EXP-CUCme.eEF1a:1:1 | 162 | 0.78 | 0.06 |
| pMON140828 | P-CUCme.15-1:1:2 | 23 | 0.26 | 0.02 |
| pMON140829 | P-CUCme.16a-1:1:2 | 24 | 0.16 | 0.01 |
| pMON140830 | P-CUCme.17-1:1:2 | 26 | 0.17 | 0.01 |
| pMON140831 | P-CUCme.18-1:1:2 | 27 | 0.22 | 0.02 |
| pMON140832 | P-CUCme.19-1:1:3 | 167 | 0.32 | 0.02 |
| pMON140833 | P-CUCme.20-1:3 | 211 | 0.15 | 0.01 |
| pMON140834 | P-CUCme.21-1:1:1 | 30 | 0.75 | 0.06 |
| pMON140835 | P-CUCme.22-1:1:3 | 31 | 0.35 | 0.03 |
| pMON140836 | EXP-CUCme.SAMS2:1:1 | 168 | 0.60 | 0.04 |
| pMON140837 | P-CUCme.26-1:1:2 | 33 | 0.13 | 0.01 |
| pMON140838 | P-CUCme.28-1:1:2 | 34 | 0.09 | 0.01 |
| pMON140839 | EXP-CUCme.29:1:2 | 212 | 0.08 | 0.01 |

TABLE 10

GUS to *renilla* luciferase (RLuc) ratios normalized with respect to
EXP-At.Act7:1:11 and EXP-CaMV.35S-enh+Ph.DnaK:1:3.

| Construct | Regulatory Element | SEQ ID NO: | GUS/RLuc normalized with respect to EXP-At.Act7:1:11 | GUS/RLuc normalized with respect to EXP-CaMV.35S-enh+Ph.DnaK:1:3 |
|---|---|---|---|---|
| pMON80585 | EXP-At.Atnttt1:1:2 | 200 | 0.96 | 0.18 |
| pMON109584 | EXP-CaMV.35S-enh+Ph.DnaK:1:3 | 201 | 5.21 | 1.00 |
| pMON118756 | EXP-At.Act7:1:11 | 202 | 1.00 | 0.19 |
| pMON124912 | Promoterless | | 0.05 | 0.01 |
| pMON140818 | P-CUCme.1-1:1:1rc | 155 | 0.42 | 0.08 |
| pMON140819 | P-CUCme.2-1:1:1 | 14 | 0.23 | 0.04 |
| pMON140820 | P-CUCme.3-1:1:3 | 15 | 0.05 | 0.01 |
| pMON140821 | EXP-CUCme.4:1:1 | 156 | 4.12 | 0.79 |
| pMON140822 | EXP-CUCme.5:1:1 | 159 | 0.40 | 0.08 |
| pMON140823 | P-CUCme.6-1:1:1 | 18 | 0.20 | 0.04 |
| pMON140824 | P-CUCme.8-1:1:2 | 19 | 0.11 | 0.02 |
| pMON140825 | P-CUCme.9-1:1:2 | 20 | 0.36 | 0.07 |
| pMON140826 | P-CUCme.10-1:1:1 | 21 | 0.22 | 0.04 |
| pMON140827 | EXP-CUCme.eEF1a:1:1 | 162 | 0.68 | 0.13 |
| pMON140828 | P-CUCme.15-1:1:2 | 23 | 0.24 | 0.05 |
| pMON140829 | P-CUCme.16a-1:1:2 | 24 | 0.13 | 0.02 |
| pMON140830 | P-CUCme.17-1:1:2 | 26 | 0.16 | 0.03 |
| pMON140831 | P-CUCme.18-1:1:2 | 27 | 0.22 | 0.04 |
| pMON140832 | P-CUCme.19-1:1:3 | 167 | 0.27 | 0.05 |
| pMON140833 | P-CUCme.20-1:3 | 211 | 0.14 | 0.03 |
| pMON140834 | P-CUCme.21-1:1:1 | 30 | 0.69 | 0.13 |
| pMON140835 | P-CUCme.22-1:1:3 | 31 | 0.29 | 0.06 |
| pMON140836 | EXP-CUCme.SAMS2:1:1 | 168 | 0.55 | 0.11 |
| pMON140837 | P-CUCme.26-1:1:2 | 33 | 0.14 | 0.03 |
| pMON140838 | P-CUCme.28-1:1:2 | 34 | 0.08 | 0.02 |
| pMON140839 | EXP-CUCme.29:1:2 | 212 | 0.08 | 0.01 |

As can be seen in Tables 9 and 10, most of the expression element groups tested, demonstrated the ability to drive transgene expression in soybean cotyledon protoplast cells. One expression element group, EXP-CUCme.4:1:1 (SEQ ID NO: 156) demonstrated levels of transgene expression higher than that of EXP-At.Act7:1:11 in this assay.

Example 5: Analysis of Regulatory Elements Driving GUS in Bombarded Soybean Leaves and Roots Soybean leaves and roots were transformed with plant expression vectors containing a test transcriptional regulatory expression element group driving expression of the ß-glucuronidase (GUS) transgene and compared to GUS expression in roots and leaves in which expression of GUS is driven by known constitutive promoters.

Expression of a transgene driven by P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a: 1:1 (SEQ ID NO: 162), P-CUCme.15-1:1:2 (SEQ ID NO: 23), P-CUCme.16a-1:1:2 (SEQ ID NO: 24), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), P-CUCme.22-1:1:3 (SEQ ID NO: 31), EXP-CUCme-.SAMS2:1:1 (SEQ ID NO: 168), P-CUCme.26-1:1:2 (SEQ ID NO: 33), P-CUCme.28-1:1:2 (SEQ ID NO: 34) and EXP-CUCme.29:1:2 (SEQ ID NO: 212) was compared with expression from known constitutive expression element groups in particle bombarded soybean leaves and roots. The plant expression vectors used for transformation of leaves and roots was the same as those presented in Table 7 of Example 4 above.

The plant expression vectors, pMON80585, pMON109584, pMON118756, pMON124912, pMON140818, pMON140819, pMON140820, pMON140821, pMON140822, pMON140823, pMON140824, pMON140825, pMON140826, pMON140827, pMON140828, pMON140829, pMON140830, pMON140831, pMON140832, pMON140833, pMON140834, pMON140835, pMON140836, pMON140837, pMON140838 and pMON140839 were used to transform soybean leaves and roots using particle bombardment transformation methods.

Briefly, A3244 soybean seeds were surface sterilized and allowed to germinate in trays with a photoperiod of 16 hours light and 8 hours of darkness. After approximately 13 days, leaf and root tissue was harvested under sterile conditions from the seedlings and used for bombardment. The tissue samples were randomly placed on a petri dish containing plant culture medium. Ten micrograms of plasmid DNA was used to coat 0.6 micron gold particles (Catalog #165-2262 Bio-Rad, Hercules, CA) for bombardment. Macro-carriers were loaded with the DNA-coated gold particles (Catalog #165-2335 Bio-Rad, Hercules CA). A PDS 1000/He biolistic gun was used for transformation (Catalog #165-2257 Bio-Rad, Hercules CA). The bombarded root and leaf tissues were allowed to incubate in the dark for 24 hours at 26 degrees Celsius. Following this overnight incubation, the tissues were stained in solution for GUS expression overnight at 37 degrees Celsius. After staining overnight, the tissues were soaked in 70% ethanol overnight to remove chlorophyll and reveal the GUS staining. The tissues were then photographed and a rating scale of "0", "+" to "++++++" reflecting the level of GUS expression is assigned to each construct (0—no expression, + to ++++++—low to high, respectively).

Expression of the GUS transgene demonstrated in each tissue is used to infer the relative potential level and specificity of each element's capacity to drive transgene expression in stably transformed corn plants. Average GUS expression ratings are provided in Table 11 below.

TABLE 11

GUS expression ratings for particle bombarded leaf and root.

| Construct | Regulatory Element | SEQ ID NO: | Leaf Expression | Root Expression |
|---|---|---|---|---|
| pMON80585 | EXP-At.Atntt1:1:2 | 200 | +++ | +++ |
| pMON109584 | EXP-CaMV.35S-enh+Ph.DnaK:1:3 | 201 | +++++ | ++ |
| pMON118756 | EXP-At.Act7:1:11 | 202 | ++++ | +++ |
| pMON124912 | Promoterless | | 0 | 0 |
| pMON140818 | P-CUCme.1-1:1:1rc | 155 | +++ | + |
| pMON140819 | P-CUCme.2-1:1:1 | 14 | ++ | + |
| pMON140820 | P-CUCme.3-1:1:3 | 15 | 0 | 0 |
| pMON140821 | EXP-CUCme.4:1:1 | 156 | ++++++ | +++ |
| pMON140822 | EXP-CUCme.5:1:1 | 159 | ++ | + |
| pMON140823 | P-CUCme.6-1:1:1 | 18 | ++ | + |
| pMON140824 | P-CUCme.8-1:1:2 | 19 | + | + |
| pMON140825 | P-CUCme.9-1:1:2 | 20 | ++ | + |
| pMON140826 | P-CUCme.10-1:1:1 | 21 | +++ | +++ |
| pMON140827 | EXP-CUCme.eEF1a:1:1 | 162 | ++++ | +++ |
| pMON140828 | P-CUCme.15-1:1:2 | 23 | + | + |
| pMON140829 | P-CUCme.16a-1:1:2 | 24 | + | − |
| pMON140830 | P-CUCme.17-1:1:2 | 26 | ++++ | + |
| pMON140831 | P-CUCme.18-1:1:2 | 27 | +++ | + |
| pMON140832 | P-CUCme.19-1:1:3 | 167 | + | + |
| pMON140833 | P-CUCme.20-1:3 | 211 | + | + |
| pMON140834 | P-CUCme.21-1:1:1 | 30 | + | + |
| pMON140835 | P-CUCme.22-1:1:3 | 31 | ++++ | + |
| pMON140836 | EXP-CUCme.SAMS2:1:1 | 168 | +++++ | +++ |
| pMON140837 | P-CUCme.26-1:1:2 | 33 | + | + |
| pMON140838 | P-CUCme.28-1:1:2 | 34 | + | + |
| pMON140839 | EXP-CUCme.29:1:2 | 212 | + | + |

As can be seen in Table 11 above, all but one of the expression element groups demonstrated the ability to drive transgene expression in particle bombarded soybean leaf and root tissue. Two expression element groups, P-CUCme.28-1:1:2 (SEQ ID NO: 34) and EXP-CUCme.4:1:1 (SEQ ID NO: 156) demonstrated similar or higher levels of expression relative to expression driven by EXP-CaMV.35S-enh+Ph.DnaK:1:3 in this assay.

Example 6: Analysis of Regulatory Elements Driving GUS in Soy Cotyledon Protoplast Using Transgene Cassette Amplicons Soybean cotyledon protoplasts were transformed with transgene cassette amplicons containing a transcriptional regulatory expression element group driving expression of the ß-glucuronidase (GUS) transgene and compared to GUS expression in leaf protoplasts in which expression of GUS is driven by known constitutive promoters. The transgene cassette amplicons were comprised of an EXP sequence, operably linked to a GUS coding sequence (GUS, SEQ ID NO: 206), operably linked to a 3' UTR (T-Gb.FbL2-1:1:1, SEQ ID NO: 205). Average GUS expression was compared to the control EXP elements, P-CaMV.35S-enh-1:1:102/L-CaMV.35S-1:1:2 (SEQ ID NO: 210) and EXP-At.Atntt1:1:2 (SEQ ID NO: 200).

A plasmid, for use in co-transformation and normalization of data was also used in a similar manner as that described above in Example 2. The transformation control plasmid was comprised of a constitutive promoter, driving the expression of the firefly (*Photinus pyralis*) luciferase coding sequence (FLuc, SEQ ID NO: 205), operably linked 5' to a 3' termination region from the *Agrobacterium tumefaciens* nopaline synthase gene (T-AGRtu.nos-1:1:13, SEQ ID NO: 209).

Table 12 below shows the mean GUS expression values conferred by each transgene amplicon. Table 13 below shows the GUS to firefly luciferase (FLuc) ratios normalized with respect to EXP-At.Atntt1:1:2 and P-CaMV.35S-enh-1:1:102/L-CaMV.35S-1:1:2

TABLE 12

Average GUS and luciferase expression values and GUS/luciferase ratios.

| Amplicon ID | Regulatory Element | SEQ ID NO: | Mean GUS | Mean Fluc | GUS/Fluc |
|---|---|---|---|---|---|
| No DNA | | | 0.00 | 0.00 | 0.00 |
| pMON124912 | No promoter | | 54.67 | 34905.00 | 0.00 |
| pMON33449 | P-CaMV.35S-enh-1:1:102/L-CaMV.35S-1:1:2 | 210 | 107064.67 | 21757.67 | 4.92 |
| pMON80585 | EXP-At.Atntt1:1:2 | 200 | 4962.33 | 40778.67 | 0.12 |
| 56969 | CumMe_WSM_SF16429.G5670 | 40 | 283.67 | 53452.00 | 0.01 |
| 56877 | P-CUCme.CumMe_WSM_SF16444.G5140-1:1:1 | 175 | 5297.67 | 46576.67 | 0.11 |
| 56749 | P-CUCme.CumMe_WSM_SF16563.G5560-1:1:1 | 176 | 280.67 | 41958.33 | 0.01 |
| 56918 | CumMe_WSM_SF17051.G5470 | 48 | 1088.00 | 36321.00 | 0.03 |
| 56849 | P-CUCme.CumMe_WSM_SF17111.G5790-1:1:1 | 177 | 196.00 | 48128.00 | 0.00 |
| 56754 | P-CUCme.WSM_SF17252.G7330-1:1:1 | 179 | 175.67 | 45427.00 | 0.00 |
| 56892 | CumMe_WSM_SF17349.G5770 | 56 | 34.00 | 38016.00 | 0.00 |
| 56477 | CumMe_WSM_SF17866.G6050 | 62 | 862.00 | 52203.33 | 0.02 |
| 56842 | P-CUCme.CumMe_WSM_SF18488.G5340-1:1:1 | 181 | 2892.67 | 49144.33 | 0.06 |
| 56852 | P-CUCme.CumMe_WSM_SF18536.G6480-1:1:1 | 182 | 3462.67 | 46549.33 | 0.07 |
| 56497 | CumMe_WSM_SF18575.G6410 | 71 | 92.67 | 47628.33 | 0.00 |
| 56847 | P-CUCme.CumMe_WSM_SF18634.G5190-1:1:1 | 183 | 122.33 | 36815.33 | 0.00 |
| 56746 | P-CUCme.CumMe_WSM_SF18716.G5860-1:1:1 | 184 | 14.33 | 62483.33 | 0.00 |
| 56883 | CumMe_WSM_SF18986.G6110 | 79 | 863.3 | 54379.33 | 0.02 |
| 56734 | EXP-CUCme.WSM_SF19064.G5690:1:1 | 185 | 142.00 | 46962.67 | 0.00 |
| 56912 | P-CUCme.CumMe_WSM_SF19647.G5760-1:1:1 | 188 | 7659.00 | 46935.67 | 0.16 |
| 56482 | P-CUCme.CumMe_WSM_SF19839.G5090-1:1:1 | 189 | 3279.00 | 37070.67 | 0.09 |
| 56963 | CumMe_WSM_SF19902.G5260 | 87 | 1629.00 | 55649.00 | 0.03 |
| 56747 | P-CUCme.CumMe_WSM_SF20132.G5560-1:1:1 | 190 | 340.33 | 40577.00 | 0.01 |
| 56479 | CumMe_WSM_SF20359.G5870 | 92 | 192.00 | 61341.67 | 0.00 |
| 56744 | CumMe_WSM_SF206458.G5970 | 98 | 154.67 | 33139.33 | 0.00 |
| 56948 | CumMe_WSM_SF206534.G5200 | 99 | 62.00 | 52118.00 | 0.00 |
| 56896 | CumMe_WSM_SF22008.G5670 | 108 | 1585.00 | 53540.00 | 0.03 |
| 56919 | CumMe_WSM_SF22275.G5780 | 112 | 8.33 | 48546.33 | 0.00 |
| 56967 | CumMe_WSM_SF22355.G5310 | 113 | 74.33 | 36202.67 | 0.00 |
| 56837 | P-CUCme.CumMe_WSM_SF22531.G5120-1:1:1 | 192 | 1526.67 | 52799.33 | 0.03 |
| 56940 | CumMe_WSM_SF22870.G5370 | 115 | 14.67 | 53663.33 | 0.00 |
| 56495 | P-CUCme.CumMe_WSM_SF23760.G5200-1:1:1 | 193 | 196.33 | 49870.67 | 0.00 |
| 56868 | P-CUCme.CumMe_WSM_SF23906.G6180-1:1:1 | 194 | 1584.33 | 42532.33 | 0.04 |
| 56998 | CumMe_WSM_SF24045.G5400 | 123 | 80.67 | 47553.00 | 0.00 |
| 56976 | P-CUCme.CumMe_WSM_SF25141.G5160-1:1:2 | 195 | 4506.00 | 57213.00 | 0.08 |
| 56742 | P-CUCme.CumMe_WSM_SF25355.G5000-1:1:1 | 196 | 4.00 | 41114.33 | 0.00 |
| 56915 | P-CUCme.CumMe_WSM_SF25936.G5450-1:1:1 | 197 | 965.33 | 34494.67 | 0.03 |
| 56854 | CumMe_WSM_SF28729.G5340 | 134 | 208.33 | 53956.00 | 0.00 |
| 56936 | CumMe_WSM_SF31264.G5380 | 136 | 292.67 | 42320.67 | 0.01 |
| 56863 | P-CUCme.CumMe_WSM_SF35856.G5150-1:1:1 | 198 | 125.00 | 48705.33 | 0.00 |
| 56751 | P-CUCme.CumMe_WSM_SF41124.G5080-1:1:1 | 199 | 31.33 | 53595.00 | 0.00 |
| 56921 | CumMe_WSM_SF41254.G5160 | 141 | 11.67 | 52643.67 | 0.00 |
| 56884 | CumMe_WSM_SF42141.G5110 | 146 | 48.33 | 40556.67 | 0.00 |

TABLE 13

GUS to firefly luciferase (FLuc) ratios normalized with respect to EXP-At.Atntt1:1:2 and P-CaMV.35S-enh-1:1:102/L-CaMV.35S-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| No DNA | | | 0.00 | 0.00 |
| pMON124912 | No promoter | | 0.01 | 0.00 |
| pMON33449 | P-CaMV.35S-enh-1:1:102/L-CaMV.35S-1:1:2 | 210 | 40.44 | 1.00 |
| pMON80585 | EXP-At.Atntt1:1:2 | 200 | 1.00 | 0.02 |
| 56969 | CumMe_WSM_SF16429.G5670 | 40 | 0.04 | 0.00 |
| 56877 | P-CUCme.CumMe_WSM_SF16444.G5140-1:1:1 | 175 | 0.93 | 0.02 |
| 56749 | P-CUCme.CumMe_WSM_SF16563.G5560-1:1:1 | 176 | 0.05 | 0.00 |
| 56918 | CumMe_WSM_SF17051.G5470 | 48 | 0.25 | 0.01 |
| 56849 | P-CUCme.CumMe_WSM_SF17111.G5790-1:1:1 | 177 | 0.03 | 0.00 |
| 56754 | P-CUCme.WSM_SF17252.G7330-1:1:1 | 179 | 0.03 | 0.00 |
| 56892 | CumMe_WSM_SF17349.G5770 | 56 | 0.01 | 0.00 |

TABLE 13-continued

GUS to firefly luciferase (FLuc) ratios normalized with respect to EXP-At.Atntt1:1:2 and P-CaMV.35S-enh-1:1:102/L-CaMV.35S-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| 56477 | CumMe_WSM_SF17866.G6050 | 62 | 0.14 | 0.00 |
| 56842 | P-CUCme.CumMe_WSM_SF18488.G5340-1:1:1 | 181 | 0.48 | 0.01 |
| 56852 | P-CUCme.CumMe_WSM_SF18536.G6480-1:1:1 | 182 | 0.61 | 0.02 |
| 56497 | CumMe_WSM_SF18575.G6410 | 71 | 0.02 | 0.00 |
| 56847 | P-CUCme.CumMe_WSM_SF18634.G5190-1:1:1 | 183 | 0.03 | 0.00 |
| 56746 | P-CUCme.CumMe_WSM_SF18716.G5860-1:1:1 | 184 | 0.00 | 0.00 |
| 56883 | CumMe_WSM_SF18986.G6110 | 79 | 0.13 | 0.00 |
| 56734 | EXP-CUCme.WSM_SF19064.G5690:1:1 | 185 | 0.02 | 0.00 |
| 56912 | P-CUCme.CumMe_WSM_SF19647.G5760-1:1:1 | 188 | 1.34 | 0.03 |
| 56482 | P-CUCme.CumMe_WSM_SF19839.G5090-1:1:1 | 189 | 0.73 | 0.02 |
| 56963 | CumMe_WSM_SF19902.G5260 | 87 | 0.24 | 0.01 |
| 56747 | P-CUCme.CumMe_WSM_SF20132.G5560-1:1:1 | 190 | 0.07 | 0.00 |
| 56479 | CumMe_WSM_SF20359.G5870 | 92 | 0.03 | 0.00 |
| 56744 | CumMe_WSM_SF206458.G5970 | 98 | 0.04 | 0.00 |
| 56948 | CumMe_WSM_SF206534.G5200 | 99 | 0.01 | 0.00 |
| 56896 | CumMe_WSM_SF22008.G5670 | 108 | 0.24 | 0.01 |
| 56919 | CumMe_WSM_SF22275.G5780 | 112 | 0.00 | 0.00 |
| 56967 | CumMe_WSM_SF22355.G5310 | 113 | 0.02 | 0.00 |
| 56837 | P-CUCme.CumMe_WSM_SF22531.G5120-1:1:1 | 192 | 0.24 | 0.01 |
| 56940 | CumMe_WSM_SF22870.G5370 | 115 | 0.00 | 0.00 |
| 56495 | P-CUCme.CumMe_WSM_SF23760.G5200-1:1:1 | 193 | 0.03 | 0.00 |
| 56868 | P-CUCme.CumMe_WSM_SF23906.G6180-1:1:1 | 194 | 0.31 | 0.01 |
| 56998 | CumMe_WSM_SF24045.G5400 | 123 | 0.01 | 0.00 |
| 56976 | P-CUCme.CumMe_WSM_SF25141.G5160-1:1:2 | 195 | 0.65 | 0.02 |
| 56742 | P-CUCme.CumMe_WSM_SF25355.G5000-1:1:1 | 196 | 0.00 | 0.00 |
| 56915 | P-CUCme.CumMe_WSM_SF25936.G5450-1:1:1 | 197 | 0.23 | 0.01 |
| 56854 | CumMe_WSM_SF28729.G5340 | 134 | 0.03 | 0.00 |
| 56936 | CumMe_WSM_SF31264.G5380 | 136 | 0.06 | 0.00 |
| 56863 | P-CUCme.CumMe_WSM_SF35856.G5150-1:1:1 | 198 | 0.02 | 0.00 |
| 56751 | P-CUCme.CumMe_WSM_SF41124.G5080-1:1:1 | 199 | 0.00 | 0.00 |
| 56921 | CumMe_WSM_SF41254.G5160 | 141 | 0.00 | 0.00 |
| 56884 | CumMe_WSM_SF42141.G5110 | 146 | 0.01 | 0.00 |

As can be seen in Table 12 above, not all EXP sequences demonstrated the ability to drive transgene expression when compared to the promoterless control. However, the EXP sequences, CumMe_WSM_SF16429.G5670 (SEQ ID NO: 40), P-CUCme.CumMe_WSM_SF16444.G5140-1:1:1 (SEQ ID NO: 175), P-CUCme.CumMe_WSM_SF16563.G5560-1:1:1 (SEQ ID NO: 176), CumMe_WSM_SF17051.G5470 (SEQ ID NO: 48), P-CUCme.CumMe_WSM_SF17111.65790-1:1:1 (SEQ ID NO: 177), P-CUCme.WSM_SF17252.G7330-1:1:1 (SEQ ID NO: 179), CumMe_WSM_SF17866.G6050 (SEQ ID NO: 62), P-CUCme.CumMe_WSM_SF18488.G5340-1:1:1 (SEQ ID NO: 181), P-CUCme.CumMe_WSM_SF18536.G6480-1:1:1 (SEQ ID NO: 182), CumMe_WSM_SF18575.G6410 (SEQ ID NO: 71), P-CUCme.CumMe_WSM_SF18634.G5190-1:1:1 (SEQ ID NO: 183), CumMe_WSM_SF18986.G6110 (SEQ ID NO: 79), EXP-CUCme.WSM_SF19064.G5690:1:1 (SEQ ID NO: 185), P-CUCme.CumMe_WSM_SF19647.G5760-1:1:1 (SEQ ID NO: 188), P-CUCme.CumMe_WSM_SF19839.G5090-1:1:1 (SEQ ID NO: 189), CumMe_WSM_SF19902.G5260 (SEQ ID NO: 87), P-CUCme.CumMe_WSM_SF20132.G5560-1:1:1 (SEQ ID NO: 190), CumMe_WSM_SF20359.G5870 (SEQ ID NO: 92), CumMe_WSM_SF206458.G5970 (SEQ ID NO: 98), CumMe_WSM_SF206534.G5200 (SEQ ID NO: 99), CumMe_WSM_SF22008.G5670 (SEQ ID NO: 108), CumMe_WSM_SF22355.G5310 (SEQ ID NO: 113), P-CUCme.CumMe_WSM_SF22531.G5120-1:1:1 (SEQ ID NO: 192), EXP-CUCme.WSM_SF19064.G5690:1:1 (SEQ ID NO: 193), P-CUCme.CumMe_WSM_SF23906.G6180-1:1:1 (SEQ ID NO: 194), CumMe_WSM_SF24045.G5400 (SEQ ID NO: 123), P-CUCme.CumMe_WSM_SF25141.G5160-1:1:2 (SEQ ID NO: 195), P-CUCme.CumMe_WSM_SF25936.G5450-1:1:1 (SEQ ID NO: 197), CumMe_WSM_SF28729.G5340 (SEQ ID NO: 134), CumMe_WSM_SF31264.G5380 (SEQ ID NO: 136) and P-CUCme.CumMe_WSM_SF35856.G5150-1:1:1 (SEQ ID NO: 198) demonstrated the ability to drive transgene expression in soybean cotyledon protoplasts at a level similar or greater than EXP-At.Atntt1:1:2. As shown in Table 13 above, the EXP sequence P-CUCme.CumMe_WSM_SF19647.G5760-1:1:1 (SEQ ID NO: 188) demonstrated the ability to drive transgene expression in this assay at a level greater than EXP-At.Atntt1:1:2.

Example 7: Analysis of Regulatory Elements Driving GUS in Cotton Leaf Protoplasts Cotton leaf protoplasts were transformed with plant expression vectors containing a test transcriptional regulatory expression element group driving expression of the β-glucuronidase (GUS) transgene and compared to GUS expression in leaf protoplasts in which expression of GUS is driven by known constitutive promoters.

Expression of a transgene driven by P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.16a-1:1:2 (SEQ ID NO: 24), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), P-CUCme.22-1:1:3 (SEQ ID NO: 31), EXP-CUCme.SAMS2:1:1 (SEQ ID NO: 168), P-CUCme.26-1:1:2 (SEQ ID NO: 33), P-CUCme.28-1:1:2 (SEQ ID NO: 34) and EXP-CUCme.29:1:2 (SEQ ID NO: 212) was compared with expression from known constitutive expression element groups. Each plant expression vector was comprised of a right border region from *Agrobacterium tumefaciens*, a first transgene cassette comprised of a test promoter or known constitutive promoter operably linked 5' to a coding sequence for ß-glucuronidase (GUS, SEQ ID NO: 206) containing a processable intron derived from the potato light-inducible tissue-specific ST-LS1 gene (Genbank Accession: X04753), operably linked 5' to a 3' termination region from the *Gossypium barbadense* E6 gene (T-Gb.E6-3b:1:1, SEQ ID NO: 204), the *Pisum sativum* RbcS2-E9 gene (T-Ps.RbcS2-E9-1:1:6, SEQ ID NO: 203), or the *Gossypium barbadense* FbLate-2 gene (T-Gb.FbL2-1:1:1, SEQ ID NO: 205); a second transgene selection cassette used for selection of transformed plant cells that either confers resistance to the herbicide glyphosate (driven by the *Arabidopsis* Actin 7 promoter) or the antibiotic, kanamycin and a left border region from *A. tumefaciens*. A promoterless control plant expression vector (pMON124912) served as a negative control for expression. The foregoing test and constitutive expression element groups were cloned into plant expression vectors as shown in Table 14 below.

TABLE 14

Plant expression vectors and corresponding expression element group and 3' UTR.

| Construct | Regulatory Element | SEQ ID NO: | 3' UTR |
|---|---|---|---|
| pMON109584 | EXP-CaMV.35S-enh+Ph.DnaK:1:3 | 201 | T-Gb.E6-3b:1:1 |
| pMON118756 | EXP-At.Act7:1:11 | 202 | T-Gb.E6-3b:1:1 |
| pMON124912 | Promoterless | | T-Gb.FbL2-1:1:1 |
| pMON140818 | P-CUCme.1-1:1:1rc | 155 | T-Gb.FbL2-1:1:1 |
| pMON140819 | P-CUCme.2-1:1:1 | 14 | T-Gb.FbL2-1:1:1 |
| pMON140820 | P-CUCme.3-1:1:3 | 15 | T-Gb.FbL2-1:1:1 |
| pMON140821 | EXP-CUCme.4:1:1 | 156 | T-Gb.FbL2-1:1:1 |
| pMON140823 | P-CUCme.6-1:1:1 | 18 | T-Gb.FbL2-1:1:1 |
| pMON140824 | P-CUCme.8-1:1:2 | 19 | T-Gb.FbL2-1:1:1 |
| pMON140825 | P-CUCme.9-1:1:2 | 20 | T-Gb.FbL2-1:1:1 |

TABLE 14-continued

Plant expression vectors and corresponding expression element group and 3' UTR.

| Construct | Regulatory Element | SEQ ID NO: | 3' UTR |
|---|---|---|---|
| pMON140826 | P-CUCme.10-1:1:1 | 21 | T-Gb.FbL2-1:1:1 |
| pMON140827 | EXP-CUCme.eEF1a:1:1 | 162 | T-Gb.FbL2-1:1:1 |
| pMON140828 | P-CUCme.15-1:1:2 | 23 | T-Gb.FbL2-1:1:1 |
| pMON140829 | P-CUCme.16a-1:1:2 | 24 | T-Gb.FbL2-1:1:1 |
| pMON140830 | P-CUCme.17-1:1:2 | 26 | T-Gb.FbL2-1:1:1 |
| pMON140831 | P-CUCme.18-1:1:2 | 27 | T-Gb.FbL2-1:1:1 |
| pMON140832 | P-CUCme.19-1:1:3 | 167 | T-Gb.FbL2-1:1:1 |
| pMON140833 | P-CUCme.20-1:3 | 211 | T-Gb.FbL2-1:1:1 |
| pMON140834 | P-CUCme.21-1:1:1 | 30 | T-Gb.FbL2-1:1:1 |
| pMON140835 | P-CUCme.22-1:1:3 | 31 | T-Gb.FbL2-1:1:1 |
| pMON140836 | EXP-CUCme.SAMS2:1:1 | 168 | T-Gb.FbL2-1:1:1 |
| pMON140837 | P-CUCme.26-1:1:2 | 33 | T-Gb.FbL2-1:1:1 |
| pMON140838 | P-CUCme.28-1:1:2 | 34 | T-Gb.FbL2-1:1:1 |
| pMON140839 | EXP-CUCme.29:1:2 | 212 | T-Gb.FbL2-1:1:1 |

Two plasmids, for use in co-transformation and normalization of data, were also constructed. One transformation control plasmid was comprised of a constitutive promoter, driving the expression of the firefly (*Photinus pyralis*) luciferase coding sequence (FLuc, SEQ ID NO: 205), operably linked 5' to a 3' termination region from the *Agrobacterium tumefaciens* nopaline synthase gene (T-AGRtu.nos-1:1:13, SEQ ID NO: 209). The other transformation control plasmid was comprised of a constitutive promoter, driving the expression of the sea pansy (*Renilla reniformis*) luciferase coding sequence (RLuc, SEQ ID NO: 206), operably linked 5' to a 3' termination region from the *Agrobacterium tumefaciens* nopaline synthase gene.

The plant expression vectors, pMON80585, pMON109584, pMON118756, pMON124912, pMON140818, pMON140819, pMON140820, pMON140821, pMON140823, pMON140824, pMON140825, pMON140826, pMON140827, pMON140828, pMON140829, pMON140830, pMON140831, pMON140832, pMON140833, pMON140834, pMON140835, pMON140836, pMON140837, pMON140838 and pMON140839 were used to transform cotton leaf protoplast cells using PEG transformation methods. Protoplast cells were transformed with equimolar amounts of each of the two transformation control plasmids and a test plant expression vector. GUS and luciferase activity was assayed. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, WI; see for example, Promega Notes Magazine, No: 57, 1996, p.02). Sample measurements were made using 4 replicates per transformation. The average GUS and luciferase values are presented in Table 15 below.

TABLE 15

Average GUS and luciferase expression values and GUS/luciferase ratios.

| Construct | Regulatory Element | SEQ ID NO: | Average GUS | Average FLuc | Average RLuc | GUS/FLuc | GUS/RLuc |
|---|---|---|---|---|---|---|---|
| pMON109584 | EXP-CaMV.35S-enh + Ph.DnaK:1:3 | 201 | 5322.8 | 14842.8 | 27990.5 | 0.3586 | 0.1902 |
| pMON118756 | EXP-At.Act7:1:11 | 202 | 1006.3 | 19746.8 | 25582.3 | 0.0510 | 0.0393 |

TABLE 15-continued

Average GUS and luciferase expression values and GUS/luciferase ratios.

| Construct | Regulatory Element | SEQ ID NO: | Average GUS | Average FLuc | Average RLuc | GUS/FLuc | GUS/RLuc |
|---|---|---|---|---|---|---|---|
| pMON124912 | Promoterless | | 21 | 19248.5 | 25012 | 0.0011 | 0.0008 |
| pMON140818 | P-CUCme.1-1:1:1rc | 155 | 170.3 | 17796.8 | 22026.3 | 0.0096 | 0.0077 |
| pMON140819 | P-CUCme.2-1:1:1 | 14 | 34.8 | 16326.3 | 21407.5 | 0.0021 | 0.0016 |
| pMON140820 | P-CUCme.3-1:1:3 | 15 | 51.5 | 17356.8 | 21523.8 | 0.0030 | 0.0024 |
| pMON140821 | EXP-CUCme.4:1:1 | 156 | 3497.8 | 18745.3 | 26065.3 | 0.1866 | 0.1342 |
| pMON140823 | P-CUCme.6-1:1:1 | 18 | 40.8 | 19533.8 | 26361.5 | 0.0021 | 0.0015 |
| pMON140824 | P-CUCme.8-1:1:2 | 19 | 22 | 19701 | 26278 | 0.0011 | 0.0008 |
| pMON140825 | P-CUCme.9-1:1:2 | 20 | 372.5 | 21972.3 | 28755 | 0.0170 | 0.0130 |
| pMON140826 | P-CUCme.10-1:1:1 | 21 | 198 | 21362.8 | 28902 | 0.0093 | 0.0069 |
| pMON140827 | EXP-CUCme.eEF1a:1:1 | 162 | 725 | 21589 | 27635.3 | 0.0336 | 0.0262 |
| pMON140828 | P-CUCme.15-1:1:2 | 23 | 55.3 | 17706 | 28846 | 0.0031 | 0.0019 |
| pMON140829 | P-CUCme.16a-1:1:2 | 24 | 14 | 23289.5 | 30190 | 0.0006 | 0.0005 |
| pMON140830 | P-CUCme.17-1:1:2 | 26 | 155.5 | 23178.3 | 31602.8 | 0.0067 | 0.0049 |
| pMON140831 | P-CUCme.18-1:1:2 | 27 | 86.8 | 19085.8 | 22396.5 | 0.0045 | 0.0039 |
| pMON140832 | P-CUCme.19-1:1:3 | 167 | 130 | 21520.3 | 27270.5 | 0.0060 | 0.0048 |
| pMON140833 | P-CUCme.20-1:3 | 211 | 88.5 | 22223.8 | 30786 | 0.0040 | 0.0029 |
| pMON140834 | P-CUCme.21-1:1:1 | 30 | 98.5 | 18579 | 20506.3 | 0.0053 | 0.0048 |
| pMON140835 | P-CUCme.22-1:1:3 | 31 | 363 | 21780.3 | 28816.3 | 0.0167 | 0.0126 |
| pMON140836 | EXP-CUCme.SAMS2:1:1 | 168 | 515 | 17906 | 23031 | 0.0288 | 0.0224 |
| pMON140837 | P-CUCme.26-1:1:2 | 33 | 125 | 15529.3 | 15169.3 | 0.0080 | 0.0082 |
| pMON140838 | P-CUCme.28-1:1:2 | 34 | 115.8 | 17013.5 | 22236.5 | 0.0068 | 0.0052 |
| pMON140839 | EXP-CUCme.29:1:2 | 212 | 15.5 | 16370.3 | 20409 | 0.0009 | 0.0008 |

To compare the relative activity of each promoter in cotton leaf protoplasts, GUS values were expressed as a ratio of GUS to luciferase activity and normalized with respect to the expression levels observed for the constitutive expression element groups, EXP-At.Act7:1:11 and EXP-CaMV.35S-enh+Ph.DnaK:1:3. Table 16 below shows the GUS to firefly luciferase (FLuc) ratios normalized with respect to EXP-At.Act7:1:11 and EXP-CaMV.35S-enh+Ph.DnaK:1:3. Table 17 below shows the GUS to renilla luciferase (RLuc) ratios normalized with respect to EXP-At.Act7:1:11 and EXP-CaMV.35S-enh+Ph.DnaK:1:3.

TABLE 16

GUS to firefly luciferase (FLuc) ratios normalized with respect to EXP-At.Act7:1:11 and EXP-CaMV.35S-enh+Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh+Ph.DnaK:1:3 |
|---|---|---|---|---|
| pMON109584 | EXP-CaMV.35S-enh+Ph.DnaK:1:3 | 201 | 7.037 | 1.000 |
| pMON118756 | EXP-At.Act7:1:11 | 202 | 1.000 | 0.142 |
| pMON124912 | Promoterless | | 0.021 | 0.003 |
| pMON140818 | P-CUCme.1-1:1:1rc | 155 | 0.188 | 0.027 |
| pMON140819 | P-CUCme.2-1:1:1 | 14 | 0.042 | 0.006 |
| pMON140820 | P-CUCme.3-1:1:3 | 15 | 0.058 | 0.008 |
| pMON140821 | EXP-CUCme.4:1:1 | 156 | 3.662 | 0.520 |
| pMON140823 | P-CUCme.6-1:1:1 | 18 | 0.041 | 0.006 |
| pMON140824 | P-CUCme.8-1:1:2 | 19 | 0.022 | 0.003 |
| pMON140825 | P-CUCme.9-1:1:2 | 20 | 0.333 | 0.047 |
| pMON140826 | P-CUCme.10-1:1:1 | 21 | 0.182 | 0.026 |
| pMON140827 | EXP-CUCme.eEF1a:1:1 | 162 | 0.659 | 0.094 |
| pMON140828 | P-CUCme.15-1:1:2 | 23 | 0.061 | 0.009 |

TABLE 16-continued

GUS to firefly luciferase (FLuc) ratios normalized with respect to EXP-At.Act7:1:11 and EXP-CaMV.35S-enh+Ph.DnaK:1:3.

| Construct | Regulatory Element | SEQ ID NO: | GUS/FLuc normalized with respect to EXP-At.Act7:1:11 | GUS/FLuc normalized with respect to EXP-CaMV.35S-enh+Ph.DnaK:1:3 |
|---|---|---|---|---|
| pMON140829 | P-CUCme.16a-1:1:2 | 24 | 0.012 | 0.002 |
| pMON140830 | P-CUCme.17-1:1:2 | 26 | 0.132 | 0.019 |
| pMON140831 | P-CUCme.18-1:1:2 | 27 | 0.089 | 0.013 |
| pMON140832 | P-CUCme.19-1:1:3 | 167 | 0.119 | 0.017 |
| pMON140833 | P-CUCme.20-1:3 | 211 | 0.078 | 0.011 |
| pMON140834 | P-CUCme.21-1:1:1 | 30 | 0.104 | 0.015 |
| pMON140835 | P-CUCme.22-1:1:3 | 31 | 0.327 | 0.046 |
| pMON140836 | EXP-CUCme.SAMS2:1:1 | 168 | 0.564 | 0.080 |
| pMON140837 | P-CUCme.26-1:1:2 | 33 | 0.158 | 0.022 |
| pMON140838 | P-CUCme.28-1:1:2 | 34 | 0.134 | 0.019 |
| pMON140839 | EXP-CUCme.29:1:2 | 212 | 0.019 | 0.003 |

TABLE 17

GUS to *renilla* luciferase (RLuc) ratios normalized with respect to EXP-At.Act7:1:11 and EXP-CaMV.35S-enh+Ph.DnaK:1:3.

| Construct | Regulatory Element | SEQ ID NO: | GUS/RLuc normalized with respect to EXP-At.Act7:1:11 | GUS/RLuc normalized with respect to EXP-CaMV.35S-enh+Ph.DnaK:1:3 |
|---|---|---|---|---|
| pMON109584 | EXP-CaMV.35S-enh+Ph.DnaK:1:3 | 201 | 4.83 | 1.00 |
| pMON118756 | EXP-At.Act7:1:11 | 202 | 1.00 | 0.21 |
| pMON124912 | Promoterless | | 0.02 | 0.00 |
| pMON140818 | P-CUCme.1-1:1:1rc | 155 | 0.20 | 0.04 |
| pMON140819 | P-CUCme.2-1:1:1 | 14 | 0.04 | 0.01 |
| pMON140820 | P-CUCme.3-1:1:3 | 15 | 0.06 | 0.01 |
| pMON140821 | EXP-CUCme.4:1:1 | 156 | 3.41 | 0.71 |
| pMON140823 | P-CUCme.6-1:1:1 | 18 | 0.04 | 0.01 |
| pMON140824 | P-CUCme.8-1:1:2 | 19 | 0.02 | 0.00 |
| pMON140825 | P-CUCme.9-1:1:2 | 20 | 0.33 | 0.07 |
| pMON140826 | P-CUCme.10-1:1:1 | 21 | 0.17 | 0.04 |
| pMON140827 | EXP-CUCme.eEF1a:1:1 | 162 | 0.67 | 0.14 |
| pMON140828 | P-CUCme.15-1:1:2 | 23 | 0.05 | 0.01 |
| pMON140829 | P-CUCme.16a-1:1:2 | 24 | 0.01 | 0.00 |
| pMON140830 | P-CUCme.17-1:1:2 | 26 | 0.13 | 0.03 |
| pMON140831 | P-CUCme.18-1:1:2 | 27 | 0.10 | 0.02 |
| pMON140832 | P-CUCme.19-1:1:3 | 167 | 0.12 | 0.03 |
| pMON140833 | P-CUCme.20-1:3 | 211 | 0.07 | 0.02 |
| pMON140834 | P-CUCme.21-1:1:1 | 30 | 0.12 | 0.03 |
| pMON140835 | P-CUCme.22-1:1:3 | 31 | 0.32 | 0.07 |
| pMON140836 | EXP-CUCme.SAMS2:1:1 | 168 | 0.57 | 0.12 |
| pMON140837 | P-CUCme.26-1:1:2 | 33 | 0.21 | 0.04 |
| pMON140838 | P-CUCme.28-1:1:2 | 34 | 0.13 | 0.03 |
| pMON140839 | EXP-CUCme.29:1:2 | 212 | 0.02 | 0.00 |

As can be seen in Tables 16 and 17, most of the expression element groups tested, demonstrated the ability to drive transgene expression in cotton leaf protoplast cells. One expression element group, EXP-CUCme.4:1:1 (SEQ ID NO: 156) demonstrated levels of transgene expression higher than that of EXP-At.Act7:1:11 in this assay.

Example 8: Analysis of Regulatory Elements Driving GUS in Cotton Leaf Protoplasts Using Transgene Cassette Amplicons Cotton leaf protoplasts were transformed with transgene cassette amplicons containing a transcriptional regulatory expression element group driving expression of the ß-glucuronidase (GUS) transgene and compared to GUS expression in leaf protoplasts in which expression of GUS is driven by known constitutive promoters. The transgene cassette amplicons were comprised of an EXP sequence, operably linked to a GUS coding sequence (GUS, SEQ ID NO: 206), operably linked to a 3' UTR (T-Gb.FbL2-1:1:1, SEQ ID NO: 205). Average GUS expression was compared to the control EXP elements, P-CaMV.35S-enh-1:1:102/L-CaMV.35S-1:1:2 (SEQ ID NO: 210) and EXP-At.Atntt1:1:2 (SEQ ID NO: 200).

A plasmid, for use in co-transformation and normalization of data was also used in a similar manner as that described above in Example 2. The transformation control plasmid was comprised of a constitutive promoter, driving the expression of the firefly (*Photinus pyralis*) luciferase coding sequence (FLuc, SEQ ID NO: 205), operably linked 5' to a 3' termination region from the *Agrobacterium tumefaciens* nopaline synthase gene (T-AGRtu.nos-1:1:13, SEQ ID NO: 209).

Table 18 below shows the mean GUS expression values conferred by each transgene amplicon. Table 19 below shows the GUS to firefly luciferase (FLuc) ratios normalized with respect to EXP-At.Atntt1:1:2 and P-CaMV.35S-enh-1:1:102/L-CaMV.35S-1:1:2.

TABLE 18

Average GUS and luciferase expression values and GUS/luciferase ratios.

| Amplicon ID | Regulatory Element | SEQ ID NO: | Mean GUS | Mean Fluc | GUS/Fluc |
|---|---|---|---|---|---|
| Empty Vector | No DNA | | 32.8 | 14087.5 | 0.002 |
| pMON124912 | No promoter | | 12 | 20486.3 | 0.001 |
| pMON80585 | EXP-At.Atntt1:1:2 | 200 | 55.5 | 18811 | 0.003 |
| pMON33449 | P-CaMV.35S-enh-1:1:102/L-CaMV.35S-1:1:2 | 210 | 12472.5 | 19126.3 | 0.652 |
| 56741 | CumMe_WSM_SF143981.G5150 | 36 | 5.8 | 17449.5 | 0.000 |
| 56492 | CumMe_WSM_SF144839.G5080 | 37 | 27.5 | 16674 | 0.002 |
| 56877 | P-CUCme.CumMe_WSM_SF16444.G5140-1:1:1 | 175 | 96.3 | 17237.8 | 0.006 |
| 56485 | CumMe_WSM_SF16530.G6000 | 42 | 27.3 | 17858.5 | 0.002 |
| 56844 | CumMe_WSM_SF16953.G5180 | 47 | 22.3 | 19398.5 | 0.001 |
| 56500 | CumMe_WSM_SF17250.G5910 | 52 | 12.3 | 23980.3 | 0.001 |
| 56754 | P-CUCme.WSM_SF17252.G7330-1:1:1 | 179 | 16 | 13848.8 | 0.001 |
| 56740 | CumMe_WSM_SF17672.G5610 | 60 | 12 | 16646.8 | 0.001 |
| 56870 | CumMe_WSM_SF18287.G5380 | 66 | 39.3 | 13930.5 | 0.003 |
| 56478 | CumMe_WSM_SF18504.G5090 | 68 | 11.8 | 15830.5 | 0.001 |
| 56481 | CumMe_WSM_SF18530.G5750 | 69 | 6.5 | 15211.3 | 0.000 |
| 56498 | CumMe_WSM_SF18645.G5380 | 73 | 36 | 14569.8 | 0.002 |
| 56746 | P-CUCme.CumMe_WSM_SF18716.G5860-1:1:1 | 184 | 11 | 18054.5 | 0.001 |
| 56490 | CumMe_WSM_SF18801.G5040 | 75 | 21.5 | 14147.3 | 0.002 |
| 56488 | CumMe_WSM_SF19323.G5120 | 81 | 15.3 | 11985.3 | 0.001 |
| 56499 | CumMe_WSM_SF19631.G5170 | 83 | 12.5 | 20140.5 | 0.001 |
| 56482 | P-CUCme.CumMe_WSM_SF19839.G5090-1:1:1 | 189 | 75 | 18690.5 | 0.004 |
| 56489 | CumMe_WSM_SF19850.G5130 | 86 | 38.3 | 19756.5 | 0.002 |
| 56476 | CumMe_WSM_SF20355.G5130 | 91 | 10.5 | 27901.8 | 0.000 |
| 56895 | CumMe_WSM_SF20431.G6340 | 95 | 34.8 | 16283.8 | 0.002 |
| 56744 | CumMe_WSM_SF206458.G5970 | 98 | 11 | 19659 | 0.001 |
| 56480 | CumMe_WSM_SF21366.G5980 | 105 | 10.8 | 17367 | 0.001 |
| 56930 | CumMe_WSM_SF22070.G5280 | 109 | 25.3 | 14210.5 | 0.002 |
| 56484 | CumMe_WSM_SF23181.G5100 | 117 | 20.3 | 13506 | 0.002 |
| 56495 | P-CUCme.CumMe_WSM_SF23760.G5200-1:1:1 | 193 | 7.8 | 15138.5 | 0.001 |
| 56971 | CumMe_WSM_SF25084.G5580 | 125 | 16 | 16135.3 | 0.001 |
| 56742 | P-CUCme.CumMe_WSM_SF25355.G5000-1:1:1 | 196 | 18 | 13782.8 | 0.001 |
| 56494 | CumMe_WSM_SF25455.G5370 | 129 | 10.5 | 16089.8 | 0.001 |
| 56751 | P-CUCme.CumMe_WSM_SF41124.G5080-1:1:1 | 199 | 24.3 | 17884.3 | 0.001 |
| 56483 | CumMe_WSM_SF41644.G6400 | 143 | 14.5 | 13130.5 | 0.001 |
| 56904 | CumMe_WSM_SF44933.G5290 | 147 | 33 | 13369 | 0.002 |
| 56743 | CumMe_WSM_SF9060.G5120 | 154 | 11.3 | 15230.8 | 0.001 |

TABLE 19

GUS to firefly luciferase (FLuc) ratios normalized with respect to EXP-At.Atntt1:1:2 and P-CaMV.35S-enh-1:1:102/L-CaMV.35S-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| Empty Vector | No DNA | | | |
| pMON124912 | No promoter | | | |
| pMON80585 | EXP-At.Atntt1:1:2 | 200 | 1.000 | 0.005 |
| pMON33449 | P-CaMV.35S-enh-1:1:102/L-CaMV.35S-1:1:2 | 210 | 221.025 | 1.000 |
| 56741 | CumMe_WSM_SF143981.G5150 | 36 | 0.113 | 0.001 |
| 56492 | CumMe_WSM_SF144839.G5080 | 37 | 0.559 | 0.003 |
| 56877 | P-CUCme.CumMe_WSM_SF16444.G5140-1:1:1 | 175 | 1.893 | 0.009 |
| 56485 | CumMe_WSM_SF16530.G6000 | 42 | 0.518 | 0.002 |
| 56844 | CumMe_WSM_SF16953.G5180 | 47 | 0.390 | 0.002 |
| 56500 | CumMe_WSM_SF17250.G5910 | 52 | 0.174 | 0.001 |
| 56754 | P-CUCme.WSM_SF17252.G7330-1:1:1 | 179 | 0.392 | 0.002 |
| 56740 | CumMe_WSM_SF17672.G5610 | 60 | 0.244 | 0.001 |
| 56870 | CumMe_WSM_SF18287.G5380 | 66 | 0.956 | 0.004 |
| 56478 | CumMe_WSM_SF18504.G5090 | 68 | 0.253 | 0.001 |

TABLE 19-continued

GUS to firefly luciferase (FLuc) ratios normalized with respect to EXP-
At.Atntt1:1:2 and P-CaMV.35S-enh-1:1:102/L-CaMV.35S-1:1:2.

| Amplicon ID | Regulatory Element | SEQ ID NO: | GUS/Fluc normalized with respect to EXP-At.Atntt1:1:2 | GUS/Fluc normalized with respect to P-CaMV.35S-enh-1:1:102/L-CaMV.35S-1:1:2 |
|---|---|---|---|---|
| 56481 | CumMe_WSM_SF18530.G5750 | 69 | 0.145 | 0.001 |
| 56498 | CumMe_WSM_SF18645.G5380 | 73 | 0.837 | 0.004 |
| 56746 | P-CUCme.CumMe_WSM_SF18716.G5860-1:1:1 | 184 | 0.207 | 0.001 |
| 56490 | CumMe_WSM_SF18801.G5040 | 75 | 0.515 | 0.002 |
| 56488 | CumMe_WSM_SF19323.G5120 | 81 | 0.433 | 0.002 |
| 56499 | CumMe_WSM_SF19631.G5170 | 83 | 0.210 | 0.001 |
| 56482 | P-CUCme.CumMe_WSM_SF19839.G5090-1:1:1 | 189 | 1.360 | 0.006 |
| 56489 | CumMe_WSM_SF19850.G5130 | 86 | 0.657 | 0.003 |
| 56476 | CumMe_WSM_SF20355.G5130 | 91 | 0.128 | 0.001 |
| 56895 | CumMe_WSM_SF20431.G6340 | 95 | 0.724 | 0.003 |
| 56744 | CumMe_WSM_SF206458.G5970 | 98 | 0.190 | 0.001 |
| 56480 | CumMe_WSM_SF21366.G5980 | 105 | 0.211 | 0.001 |
| 56930 | CumMe_WSM_SF22070.G5280 | 109 | 0.603 | 0.003 |
| 56484 | CumMe_WSM_SF23181.G5100 | 117 | 0.509 | 0.002 |
| 56495 | P-CUCme.CumMe_WSM_SF23760.G5200-1:1:1 | 193 | 0.175 | 0.001 |
| 56971 | CumMe_WSM_SF25084.G5580 | 125 | 0.336 | 0.002 |
| 56742 | P-CUCme.CumMe_WSM_SF25355.G5000-1:1:1 | 196 | 0.443 | 0.002 |
| 56494 | CumMe_WSM_SF25455.G5370 | 129 | 0.221 | 0.001 |
| 56751 | P-CUCme.CumMe_WSM_SF41124.G5080-1:1:1 | 199 | 0.461 | 0.002 |
| 56483 | CumMe_WSM_SF41644.G6400 | 143 | 0.374 | 0.002 |
| 56904 | CumMe_WSM_SF44933.G5290 | 147 | 0.837 | 0.004 |
| 56743 | CumMe_WSM_SF9060.G5120 | 154 | 0.251 | 0.001 |

As can be seen in Table 18 above, not all EXP sequences demonstrated the ability to drive transgene expression when compared to the promoterless control. However, the EXP sequences, P-CUCme.CumMe_WSM_SF16444.G5140-1:1:1 (SEQ ID NO: 175) and P-CUCme.CumMe_WSM_SF19839.G5090-1:1:1 (SEQ ID NO: 189) demonstrated the ability to drive transgene expression in soybean cotyledon protoplasts at a level similar or greater than EXP-At.Atntt1:1:2. As shown in Table 19 above, the EXP sequence, P-CUCme.CumMe_WSM_SF19839.G5090-1:1:1 (SEQ ID NO: 189) demonstrated the ability to drive transgene expression in this assay at a level greater than EXP-At.Atntt1:1:2.

Example 9: Analysis of Regulatory Elements Driving GUS in Stably Transformed Soybean Soybean plants were transformed with plant expression vectors containing an EXP sequence driving expression of the ß-glucuronidase (GUS) transgene.

Expression of the GUS transgene driven by EXP-CUCme.Ubq1:1:1 (SEQ ID NO: 1), EXP-CUCme.Ubq1:1:3 (SEQ ID NO: 7), P-CUCme.1-1:1:1rc (SEQ ID NO: 155), P-CUCme.2-1:1:1 (SEQ ID NO: 14), P-CUCme.3-1:1:3 (SEQ ID NO: 15), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), EXP-CUCme.SAMS2:1:1 (SEQ ID NO: 168), P-CUCme.26-1:1:2 (SEQ ID NO: 33), EXP-CUCme.29:1:2 (SEQ ID NO: 212), P-CUCme.CumMe_WSM_SF25355.G5000-1:1:1 (SEQ ID NO: 196), P-CUCme.CumMe_WSM_SF17111.G5790-1:1:1 (SEQ ID NO: 177), P-CUCme.CumMe_WSM_SF22531.G5120-1:1:1 (SEQ ID NO: 192), P-CUCme.CumMe_WSM_SF18488.G5340-1:1:1 (SEQ ID NO: 181), P-CUCme.CumMe_WSM_SF23760.G5200-1:1:1 (SEQ ID NO: 193), EXP-CUCme.WSM_SF19064.G5690:1:1 (SEQ ID NO: 185), P-CUCme.WSM_SF17252.G7330-1:1:1 (SEQ ID NO: 179), P-CUCme.CumMe_WSM_SF18634.G5190-1:1:1 (SEQ ID NO: 183), P-CUCme.CumMe_WSM_SF19647.G5760-1:1:1 (SEQ ID NO: 188), P-CUCme.CumMe_WSM_SF25936.G5450-1:1:1 (SEQ ID NO: 197), P-CUCme.CumMe_WSM_SF19839.G5090-1:1:1 (SEQ ID NO: 189), CumMe_WSM_SF206458.G5970 (SEQ ID NO: 98) and P-CUCme.CumMe_WSM_SF18716.G5860-1:1:1 (SEQ ID NO: 184) assayed both qualitatively through inspection of stained tissue sections and quantitatively. Each plant expression vector was comprised of a right border region from Agrobacterium tumefaciens, a first transgene cassette comprised of an EXP sequence operably linked 5' to a coding sequence for ß-glucuronidase (GUS, SEQ ID NO: 206) containing a processable intron derived from the potato light-inducible tissue-specific ST-LS1 gene (Genbank Accession: X04753), operably linked 5' to a 3' termination region from the Gossypium barbadense FbLate-2 gene (T-Gb.FbL2-1:1:1, SEQ ID NO: 205); a second transgene selection cassette used for selection of transformed plant cells that conferred resistance to the herbicide glyphosate (driven by the Arabidopsis Actin 7 promoter) and a left border region from A. tumefaciens.

The foregoing EXP sequences were cloned into plant expression constructs as shown in Tables 20 through 23 below and used to transform soybean plants using an agrobacterium mediated transformation method. Expression of GUS was assayed qualitatively using histological sections of selected tissues and quantitatively.

Histochemical GUS analysis was used for qualitative expression analysis of transformed plants. Whole tissue sections were incubated with GUS staining solution X-Gluc (5-bromo-4-chloro-3-indolyl-b-glucuronide) (1 milligram/milliliter) for an appropriate length of time, rinsed, and visually inspected for blue coloration. GUS activity was qualitatively determined by direct visual inspection or inspection under a microscope using selected plant organs and tissues. The $R_0$ generation plants were inspected for expression in Vn5 Root, R1 Root, Vn5 Sink Leaf, Vn5 Source Leaf, R1 Source Leaf, R1 Petiole, Yellow Pod Embryo, Yellow Pod Cotyledon, R3 Immature Seed, R3 Pod, R5 Cotyledon and R1 Flower.

For quantitative analysis, total protein was extracted from selected tissues of transformed corn plants. One microgram of total protein was used with the fluorogenic substrate 4-methylumbelliferyl-β-D-glucuronide (MUG) in a total reaction volume of 50 microliters. The reaction product, 4-methylumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm using a Fluoromax-3 (Horiba; Kyoto, Japan) with Micromax Reader, with slit width set at excitation 2 nm and emission 3 nm.

Tables 20 and 21 below show the mean quantitative expression levels measured in the $R_0$ generation plant tissues. Those tissued not assayed are shown as blank cells in both tables.

TABLE 20

Mean GUS expression in Vn5 Root, R1 Root, Vn5 Sink Leaf, Vn5 Source Leaf, R1 Source Leaf and R1 Petiole of $R_0$ generation transformed soybean plants

| Construct | Regulatory Element | SEQ ID NO: | Vn5_Root | R1_Root | Vn5_Sink_Leaf | Vn5_Source Leaf | R1_Source_Leaf | R1_Petiole |
|---|---|---|---|---|---|---|---|---|
| pMON138776 | EXP-CUCme.Ubq1:1:1 | 1 | 4 | | | | 4 | 4 |
| pMON138778 | EXP-CUCme.Ubq1:1:3 | 7 | 16 | | 1 | 2 | 13 | 23 |
| pMON140818 | P-CUCme.1-1:1:1rc | 155 | 48.21 | | 22.35 | 20.24 | 33.01 | 78.17 |
| pMON140819 | P-CUCme.2-1:1:1 | 14 | | | | | | |
| pMON140820 | P-CUCme.3-1:1:3 | 15 | | | | | | |
| pMON140821 | EXP-CUCme.4:1:1 | 156 | 96.82 | | 28.32 | 39.17 | 322.98 | 280.03 |
| pMON140822 | EXP-CUCme.5:1:1 | 159 | 28.88 | | | | 41.11 | |
| pMON140823 | P-CUCme.6-1:1:1 | 18 | 23.94 | | | | 32.14 | 30.22 |
| pMON140824 | P-CUCme.8-1:1:2 | 19 | | | | | | |
| pMON140825 | P-CUCme.9-1:1:2 | 20 | 22.06 | | | | 21.22 | 23.08 |
| pMON140826 | P-CUCme.10-1:1:1 | 21 | | | | | | |
| pMON140827 | EXP-CUCme.eEF1a:1:1 | 162 | 189.24 | 153.52 | 59.6 | 37.44 | 103.01 | 130.6 |
| pMON140828 | P-CUCme.15-1:1:2 | 23 | 30.53 | | | | | |
| pMON140830 | P-CUCme.17-1:1:2 | 26 | 51.62 | | 30.07 | 31.08 | 30.49 | 60.14 |
| pMON140831 | P-CUCme.18-1:1:2 | 27 | 57.38 | | | | | 30.03 |
| pMON140832 | P-CUCme. 19-1:1:3 | 167 | 23.07 | | 50.21 | 59.73 | 65.58 | 137.42 |
| pMON140833 | P-CUCme.20-1:3 | 211 | 23.15 | | 61.6 | 118.76 | 502.55 | 119.46 |
| pMON140834 | P-CUCme.21-1:1:1 | 30 | | | | | 25.49 | |
| pMON140836 | EXP-CUCme.SAMS2:1:1 | 168 | 230.89 | 184.88 | 65.44 | 53.36 | 118.82 | 351.49 |
| pMON140837 | P-CUCme.26-1:1:2 | 33 | 56.21 | | 26.81 | 45.07 | 51.61 | 47.42 |
| pMON140839 | EXP-CUCme.29:1:2 | 212 | 82.17 | | 45.2 | 28.27 | 64.96 | 109.9 |
| pMON144926 | P-CUCme.CumMe_WSM_SF25355.G5000-1:1:1 | 196 | 28.53 | | | | | |
| pMON144927 | P-CUCme.CumMe_WSM_SF17111.G5790-1:1:1 | 177 | 23.62 | | | | | |
| pMON144928 | P-CUCme.CumMe_WSM_SF22531.G5120-1:1:1 | 192 | 75.62 | | 23 | 20.46 | 21.78 | 39.77 |
| pMON144931 | P-CUCme.CumMe_WSM_SF18488.G5340-1:1:1 | 181 | 43.2 | | | | | 52.55 |
| pMON144933 | P-CUCme.CumMe_WSM_SF23760.G5200-1:1:1 | 193 | 25.61 | | 20.45 | 0 | 0 | 28.69 |
| pMON146941 | EXP-CUCme.WSM_SF19064.G5690:1:1 | 185 | 33.5 | | 0 | 0 | 24.27 | 47.82 |
| pMON144932 | P-CUCme.WSM_SF17252.G7330-1:1:1 | 179 | 32.54 | | 23.76 | 21.5 | 0 | 22.21 |
| pMON146940 | P-CUCme.CumMe_WSM_SF18634.G5190-1:1:1 | 183 | 0 | | 0 | 0 | 0 | 0 |
| pMON147340 | P-CUCme.CumMe_WSM_SF19647.G5760-1:1:1 | 188 | 28.9 | | 0 | 0 | 29.77 | 25.82 |

TABLE 20-continued

Mean GUS expression in Vn5 Root, R1 Root, Vn5 Sink Leaf, Vn5 Source Leaf, R1 Source Leaf and R1 Petiole of R₀ generation transformed soybean plants

| Construct | Regulatory Element | SEQ ID NO: | Vn5_Root | R1_Root | Vn5_Sink_Leaf | Vn5_Source_Leaf | R1_Source_Leaf | R1_Petiole |
|---|---|---|---|---|---|---|---|---|
| pMON147342 | P-CUCme.CumMe_WSM_SF25936.G5450-1:1:1 | 197 | 50.15 | | 24.26 | 0 | 29.38 | 29.91 |
| pMON147343 | P-CUCme.CumMe_WSM_SF19839.G5090-1:1:1 | 189 | 36.05 | | 25.7 | 27.54 | 22.85 | 37.15 |
| pMON144929 | CumMe_WSM_SF206458.G5970 | 98 | | | | | | |
| pMON147304 | P-CUCme.CumMe_WSM_SF18716.G5860-1:1:1 | 184 | 35.01 | | 21.17 | 21.23 | 22 | 44.57 |

TABLE 21

Mean GUS expression in Yellow Pod Embryo, Yellow Pod Cotyledon, R3 Immature Seed, R3 Pod, R5 Cotyledon and R1 Flower of R₀ generation transformed soybean plants

| Construct | Regulatory Element | SEQ ID NO: | Yellow_Pod_Embryo | Yellow_Pod_Cotyledon | R3_Immature_Seed | R3_Pod | R5_Cotyledon | R1_Flower |
|---|---|---|---|---|---|---|---|---|
| pMON138776 | EXP-CUCme.Ubq1:1:1 | 1 | 12 | 9 | 13 | 11 | 10 | 7 |
| pMON138778 | EXP-CUCme.Ubq1:1:3 | 7 | 3 | 1 | 13 | 9 | 13 | 27 |
| pMON140818 | P-CUCme.1-1:1:1rc | 155 | 100.79 | 117.5 | 38.31 | 84.72 | 132.27 | 66.8 |
| pMON140819 | P-CUCme.2-1:1:1 | 14 | | | | | 20.35 | 36.18 |
| pMON140820 | P-CUCme.3-1:1:3 | 15 | | | | | | |
| pMON140821 | EXP-CUCme.4:1:1 | 156 | 86.68 | 225.53 | 105.62 | 342.07 | 119.08 | 184.92 |
| pMON140822 | EXP-CUCme.5:1:1 | 159 | 21.48 | 32.27 | 21.47 | 21.66 | | 36.88 |
| pMON140823 | P-CUCme.6-1:1:1 | 18 | 38.75 | | 23.03 | | 25.32 | 58.7 |
| pMON140824 | P-CUCme.8-1:1:2 | 19 | | | | | 90.33 | 25.77 |
| pMON140825 | P-CUCme.9-1:1:2 | 20 | 132.04 | | | 20.56 | 34.78 | |
| pMON140826 | P-CUCme.10-1:1:1 | 21 | | | | | 22.34 | |
| pMON140827 | EXP-CUCme.eEF1a:1:1 | 162 | 200.28 | 291.26 | 58.21 | 131.17 | 114.29 | 130.38 |
| pMON140828 | P-CUCme.15-1:1:2 | 23 | | | 142.24 | 26.2 | | |
| pMON140830 | P-CUCme.17-1:1:2 | 26 | 343.34 | 302.94 | 65.55 | 80.94 | 137.02 | 62.7 |
| pMON140831 | P-CUCme.18-1:1:2 | 27 | 103.17 | 135.97 | 30 | 34.62 | 88.14 | 23.73 |
| pMON140832 | P-CUCme.19-1:1:3 | 167 | 30.96 | 64.46 | | 316.66 | | 53.46 |
| pMON140833 | P-CUCme.20-1:3 | 211 | 174.62 | 524.88 | | 222.04 | 59.43 | 124.68 |
| pMON140834 | P-CUCme.21-1:1:1 | 30 | | | 28.15 | 20.52 | 23.89 | |
| pMON140836 | EXP-CUCme.SAMS2:1:1 | 168 | 110.23 | 159.43 | 61.99 | 248.96 | 49.17 | 224.24 |
| pMON140837 | P-CUCme.26-1:1:2 | 33 | 56.73 | 50.06 | 70 | 143.05 | 25.06 | 49.92 |
| pMON140839 | EXP-CUCme.29:1:2 | 212 | 251.76 | 237.2 | 49.16 | 89.28 | 114.92 | 57.84 |
| pMON144926 | P-CUCme.CumMe_WSM_SF25355.G5000-1:1:1 | 196 | | | 21.41 | | 22.23 | |
| pMON144927 | P-CUCme.CumMe_WSM_SF17111.G5790-1:1:1 | 177 | 58.84 | 28.94 | | | 20.97 | |
| pMON144928 | P-CUCme.CumMe_WSM_SF22531.G5120-1:1:1 | 192 | 135.62 | 152.48 | 30.45 | 51.71 | 129.72 | 42.2 |
| pMON144931 | P-CUCme.CumMe_WSM_SF18488.G5340-1:1:1 | 181 | 866.94 | | 23.26 | 21.49 | | |
| pMON144933 | P-CUCme.CumMe_WSM_SF23760.G5200-1:1:1 | 193 | | | 29.03 | 34.9 | 69.63 | 24.42 |
| pMON146941 | EXP-CUCme.WSM_SF19064.G5690:1:1 | 185 | | | 36.69 | 83.08 | 89.81 | 33.99 |
| pMON144932 | P-CUCme.WSM_SF17252.G7330-1:1:1 | 179 | | | 34.29 | 39.89 | 113.83 | 0 |
| pMON146940 | P-CUCme.CumMe_WSM_SF18634.G5190-1:1:1 | 183 | | | 30.25 | 0 | 0 | 0 |
| pMON147340 | P-CUCme.CumMe_WSM_SF19647.G5760-1:1:1 | 88 | | | 25.73 | 28.28 | 24.04 | 23.35 |

TABLE 21-continued

Mean GUS expression in Yellow Pod Embryo, Yellow Pod Cotyledon, R3 Immature Seed, R3 Pod, R5 Cotyledon and R1 Flower of R₀ generation transformed soybean plants

| Construct | Regulatory Element | SEQ ID NO: | Yellow_Pod_ Embryo | Yellow_Pod_ Cotyledon | R3_ Immature_ Seed | R3_Pod | R5_ Cotyledon | R1_ Flower |
|---|---|---|---|---|---|---|---|---|
| pMON147342 | P-CUCme.CumMe_WSM_SF25936.G5450-1:1:1 | 197 | | | 104.02 | 80.27 | 31.06 | 26.8 |
| pMON147343 | P-CUCme.CumMe_WSM_SF19839.G5090-1:1:1 | 189 | | | | | | 29.09 |
| pMON144929 | CumMe_WSM_SF206458.G5970 | 98 | | | 24.42 | 25.33 | | |
| pMON147304 | P-CUCme.CumMe_WSM_SF18716.G5860-1:1:1 | 184 | | | | 283.49 | | 61.43 |

As can be seen in Tables 20 and 21, the EXP sequences, EXP-CUCme.Ubq1:1:1 (SEQ ID NO: 1), EXP-CUCme.Ubq1:1:3 (SEQ ID NO: 7), P-CUCme.1-1:1:1rc (SEQ ID NO: 155), P-CUCme.2-1:1:1 (SEQ ID NO: 14), EXP-CUCme.4:1:1 (SEQ ID NO: 156), EXP-CUCme.5:1:1 (SEQ ID NO: 159), P-CUCme.6-1:1:1 (SEQ ID NO: 18), P-CUCme.8-1:1:2 (SEQ ID NO: 19), P-CUCme.9-1:1:2 (SEQ ID NO: 20), P-CUCme.10-1:1:1 (SEQ ID NO: 21), EXP-CUCme.eEF1a:1:1 (SEQ ID NO: 162), P-CUCme.15-1:1:2 (SEQ ID NO: 23), P-CUCme.17-1:1:2 (SEQ ID NO: 26), P-CUCme.18-1:1:2 (SEQ ID NO: 27), P-CUCme.19-1:1:3 (SEQ ID NO: 167), P-CUCme.20-1:3 (SEQ ID NO: 211), P-CUCme.21-1:1:1 (SEQ ID NO: 30), EXP-CUCme.SAMS2:1:1 (SEQ ID NO: 168), P-CUCme.26-1:1:2 (SEQ ID NO: 33), EXP-CUCme.29:1:2 (SEQ ID NO: 212), P-CUCme.CumMe_WSM_SF25355.G5000-1:1:1 (SEQ ID NO: 196), P-CUCme.CumMe_WSM_SF17111.G5790-1:1:1 (SEQ ID NO: 177), P-CUCme.CumMe_WSM_SF22531.G5120-1:1:1 (SEQ ID NO: 192), P-CUCme.CumMe_WSM_SF18488.G5340-1:1:1 (SEQ ID NO: 181), P-CUCme.CumMe_WSM_SF23760.G5200-1:1:1 (SEQ ID NO: 193), EXP-CUCme.WSM_SF19064.G5690:1:1 (SEQ ID NO: 185), P-CUCme.WSM_SF17252.G7330-1:1:1 (SEQ ID NO: 179), P-CUCme.CumMe_WSM_SF18634.G5190-1:1:1 (SEQ ID NO: 183), P-CUCme.CumMe_WSM_SF19647.G5760-1:1:1 (SEQ ID NO: 188), P-CUCme.CumMe_WSM_SF25936.G5450-1:1:1 (SEQ ID NO: 197), P-CUCme.CumMe_WSM_SF19839.G5090-1:1:1 (SEQ ID NO: 189), CumMe_WSM_SF206458.G5970 (SEQ ID NO: 98) and P-CUCme.CumMe_WSM_SF18716.G5860-1:1:1 (SEQ ID NO: 184) demonstrated quantitatively the capacity to drive transgene expression in some or all tissues assayed, depending upon the EXP sequence used to drive expression.

Histological analysis of selected tissue sections provided further evidence of expression for many of the EXP sequences. EXP-CUCme.Ubq1:1:1 (SEQ ID NO: 1) and EXP-CUCme.Ubq1:1:3 (SEQ ID NO: 7) demonstrated a constitutive expression pattern with staining observed in all tissues, even though quantitative analysis showed fairly low levels of expression. This type of expression pattern can be most adventitious to driving expression of transgenes that require a low level of constitutive expression. Expression driven by P-CUCme.1-1:1:1rc (SEQ ID NO: 155) demonstrated expression in sink and source leaf vascular bundles and xylem and in the root cortex, phloem, xylem, endodermis, stele and tip. Expression driven by EXP-CUCme.4:1:1 (SEQ ID NO: 156) was observed in all tissues with the highest expression observed in the reproductive phase of the plant. Expression driven by P-CUCme.10-1:1:1 (SEQ ID NO: 21) was observed only in in V5 Sink Leaf and R1 Flower anthers. Expression driven by EXP-CUCme.eEF1a:1:1 (SEQ ID NO: 162) demonstrated a constitutive expression pattern with highest expression being observed in yellow pod embryo and cotyledon. The yellow pod embryo activity was 5fold higher in the R1 generation than in the R0 generation (see Table 23 below). Expression driven by P-CUCme.15-1:1:2 (SEQ ID NO: 23), P-CUCme.17-1:1:2 (SEQ ID NO: 26) and P-CUCme.18-1:1:2 (SEQ ID NO: 27) demonstrated a constitutive level of expression histologically. Expression driven by P-CUCme.19-1:1:3 (SEQ ID NO: 167) demonstrated a constitutive pattern of expression histologically with the exception of the V5 root and R1 petiole. R3 pod showed the highest expression.

Expression driven by P-CUCme.20-1:3 (SEQ ID NO: 211) demonstrated a constitutive expression pattern histologically with the exception of expression in V5 root. Expression was highest in the R8 stage cotyledon. Expression driven by EXP-CUCme.SAMS2:1:1 (SEQ ID NO: 168) demonstrated a constitutive pattern of expression with expression observed histologically in all tissues. GUS expression was observed to increase in the R1 generation (see Tables 22 and 23 below). The R1 stage flowers and petioles demonstrated the highest levels of expression in soybean. Expression driven by P-CUCme.CumMe_WSM_SF22531.G5120-1:1:1 (SEQ ID NO: 192) demonstrated a constitutive pattern of expression histologically with highest expression in the R8 stage cotyledon and embryo. Expression driven by P-CUCme.CumMe_WSM_SF18488.G5340-1:1:1 (SEQ ID NO: 181) demonstrated a constitutive level of expression while quantitatively high expression was observed in the yellow pod embryo.

R₀ generation plants transformed with the plasmid constructs comprising EXP-CUCme.eEF1a:1:1 (SEQ ID NO: 162) and EXP-CUCme.SAMS2:1:1 (SEQ ID NO: 168) were allowed to set seed and the R₁ generation plants analyzed for GUS expression. The R₁ generation plants were analyzed for expression in Vn5 Root, Vn5 Sink Leaf, Vn5 Source Leaf, R1 Source Leaf, R1 Petiole Yellow Pod Embryo, Yellow Pod Cotyledon, R3 Immature Seed, R3 Pod, R5 Cotyledon and R1 Flower. Tables 22 and 23 show the mean GUS expression measured in each tissue of the R₁ generation transformed plants.

TABLE 22

Mean GUS expression in Vn5 Root, Vn5 Sink Leaf, Vn5 Source Leaf, R1 Source Leaf, R1 Petiole of R₁ generation transformed soybean plants

| Construct | Regulatory Element | SEQ ID NO: | Vn5_Root | Vn5_Sink_Leaf | Vn5_Source Leaf | R1_Source_Leaf | R1_Petiole |
|---|---|---|---|---|---|---|---|
| pMON140827 | EXP-CUCme.eEF1a:1:1 | 162 | 145.84 | 50.24 | 43.73 | 107.98 | 357.67 |
| pMON140836 | EXP-CUCme.SAMS2:1:1 | 168 | 260.41 | 65.52 | 51.12 | 129.86 | 623.42 |

TABLE 23

Mean GUS expression in Yellow Pod Embryo, Yellow Pod Cotyledon, R3 Immature Seed, R3 Pod, R5 Cotyledon, R1 Flower of R₁ generation transformed soybean plants

| Construct | Regulatory Element | SEQ ID NO: | Yellow_Pod_Embryo | Yellow_Pod_Cotyledon | R3_Immature_Seed | R3_Pod | R5_Cotyledon | R1_Flower |
|---|---|---|---|---|---|---|---|---|
| pMON140827 | EXP-CUCme.eEF1a:1:1 | 162 | 1098.51 | 764.83 | 288.77 | 214.6 | 459.62 | 394.77 |
| pMON140836 | EXP-CUCme.SAMS2:1:1 | 168 | 219.04 | 291.58 | 241.48 | 382.73 | 397.91 | 653.23 |

As can be seen in Tables 22 and 23 above expression driven in R₁ generation by EXP-CUCme.eEF1a:1:1 (SEQ ID NO: 162) and EXP-CUCme.SAMS2:1:1 (SEQ ID NO: 168) shows a constitutive level of expression with increase in expression observed in many tissues at R₁ generation relative to R₀ generation.

Having illustrated and described the principles of the present invention, it should be apparent to persons skilled in the art that the invention can be modified in arrangement and detail without departing from such principles. All modifications that are within the spirit and scope of the claims are intended to be included within the scope of the present invention. All publications and published patent documents cited herein are hereby incorporated by reference to the same extent as if each individual publication or patent application is specifically and individually indicated to be incorporated by reference.

What is claimed is:

1. A DNA molecule exhibiting a gene regulatory functional activity comprising a polynucleotide sequence selected from the group consisting of:
   a) a sequence with at least 95 percent sequence identity to SEQ ID NO:168 or 32 and having promoter activity;
   b) a sequence comprising SEQ ID NO:168 or 32; and
   c) a fragment comprising at least 250 contiguous nucleotides of SEQ ID NO:168 or 32 exhibiting promoter activity;
   wherein said DNA molecule is operably linked to a heterologous transcribable polynucleotide molecule.

2. The DNA molecule of claim 1, wherein said polynucleotide sequence has at least 97 percent sequence identity to the polynucleotide sequence as set forth in SEQ ID NO:168 or 32 and having promoter activity.

3. The DNA molecule of claim 1, wherein said polynucleotide sequence has at least 99 percent sequence identity to the polynucleotide sequence as set forth in SEQ ID NO:168 or 32 and having promoter activity.

4. The DNA molecule of claim 1, wherein the heterologous transcribable polynucleotide molecule comprises a gene of agronomic interest.

5. The DNA molecule of claim 4, wherein the gene of agronomic interest confers herbicide tolerance in plants.

6. The DNA molecule of claim 4, wherein the gene of agronomic interest confers pest resistance in plants.

7. A transgenic plant cell comprising the DNA molecule of claim 1, wherein said DNA molecule is operably linked to a heterologous transcribable polynucleotide molecule.

8. The transgenic plant cell of claim 7, wherein said transgenic plant cell is a monocotyledonous plant cell.

9. The transgenic plant cell of claim 7, wherein said transgenic plant cell is a dicotyledonous plant cell.

10. A transgenic plant, or part thereof, comprising the DNA molecule of claim 1, wherein said DNA molecule is operably linked to a heterologous transcribable polynucleotide molecule.

11. A progeny plant of the transgenic plant of claim 10, or part thereof, wherein the progeny plant or part thereof comprises said DNA molecule exhibiting a gene regulatory functional activity.

12. A transgenic seed comprising the DNA molecule of claim 1, wherein said DNA molecule is operably linked to a heterologous transcribable polynucleotide molecule.

13. A method of producing a commodity product comprising:
   a) obtaining a transgenic plant or part thereof comprising the DNA molecule of claim 1, wherein said DNA molecule is operably linked to a heterologous transcribable polynucleotide molecule; and
   b) producing the commodity product therefrom.

14. The method of claim 13, wherein the commodity product is protein concentrate, protein isolate, grain, starch, seeds, meal, flour, biomass, or seed oil.

15. A commodity product comprising the DNA molecule of claim 1, wherein said DNA molecule is operably linked to a heterologous transcribable polynucleotide molecule.

16. A method of expressing a transcribable polynucleotide molecule comprising:
   a) obtaining a transgenic plant comprising the DNA molecule of claim 1, wherein said DNA molecule is operably linked to a heterologous transcribable polynucleotide molecule; and
   b) cultivating said transgenic plant, wherein the transcribable polynucleotide is expressed.

17. The DNA molecule of claim 1, wherein said polynucleotide sequence comprises a sequence with at least 95 percent sequence identity to SEQ ID NO: 168 or 32 and having promoter activity.

18. The DNA molecule of claim 1, wherein said polynucleotide sequence comprises SEQ ID NO:168 or 32.

19. The DNA molecule of claim 1, wherein said polynucleotide sequence comprises a fragment comprising at least 250 contiguous nucleotides of SEQ ID NO: 168 or 32 exhibiting promoter activity.

* * * * *